US012442003B2

(12) United States Patent
Johnson et al.

(10) Patent No.: US 12,442,003 B2
(45) Date of Patent: Oct. 14, 2025

(54) TRANS-SPLICING MOLECULES

(71) Applicants: Ascidian Therapeutics, Inc., Boston, MA (US); The Trustees of the University of Pennsylvania, Philadelphia, PA (US)

(72) Inventors: Philip R. Johnson, Bryn Mawr, PA (US); Bruce C. Schnepp, Havertown, PA (US); Jean Bennett, Bryn Mawr, PA (US); Scott J. Dooley, Clementon, NJ (US); Krishna Jawaharlal Fisher, Durham, NC (US); Junwei Sun, Philadelphia, PA (US)

(73) Assignees: Ascidian Therapeutics, Inc., Boston, MA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 18/673,713

(22) Filed: May 24, 2024

(65) Prior Publication Data

US 2024/0318186 A1 Sep. 26, 2024

Related U.S. Application Data

(63) Continuation of application No. 17/047,496, filed as application No. PCT/US2019/027981 on Apr. 17, 2019, now Pat. No. 11,993,776.

(60) Provisional application No. 62/658,658, filed on Apr. 17, 2018, provisional application No. 62/658,667, filed on Apr. 17, 2018.

(51) Int. Cl.
*C12N 15/113* (2010.01)
*C07K 14/705* (2006.01)

(52) U.S. Cl.
CPC ........ *C12N 15/1138* (2013.01); *C07K 14/705* (2013.01); *C07K 2319/71* (2013.01); *C07K 2319/85* (2013.01); *C12N 2320/33* (2013.01); *C12N 2320/34* (2013.01)

(58) Field of Classification Search
None
See application file for complete search history.

(56) References Cited

U.S. PATENT DOCUMENTS

| | | | |
|---|---|---|---|
| 6,013,487 | A | 1/2000 | Mitchell |
| 6,280,978 | B1 | 8/2001 | Mitchell et al. |
| 7,943,374 | B2 | 5/2011 | Hildinger |
| 8,053,232 | B2 | 11/2011 | Puttaraju et al. |
| 8,076,461 | B2 | 12/2011 | Pearce et al. |
| 8,173,377 | B2 | 5/2012 | Agris et al. |
| 8,236,557 | B2 | 8/2012 | Dongsheng et al. |
| 8,323,910 | B2 | 12/2012 | Agris et al. |
| 8,697,355 | B2 | 4/2014 | Agris et al. |
| 8,735,366 | B2 | 5/2014 | Bauer et al. |
| 9,249,425 | B2 | 2/2016 | Bennett et al. |
| 9,567,376 | B2 | 2/2017 | Cronin et al. |
| 9,896,665 | B2 | 2/2018 | Bennett et al. |
| 10,155,794 | B2 | 12/2018 | Drivas et al. |
| 10,266,845 | B2 | 4/2019 | Cronin et al. |
| 10,301,366 | B2 | 5/2019 | Drivas et al. |
| 10,987,433 | B2 | 4/2021 | Bennett et al. |
| 11,993,776 | B2 | 5/2024 | Johnson et al. |
| 2013/0059901 | A1 | 3/2013 | Bauer et al. |
| 2013/0071951 | A1 | 3/2013 | Agris et al. |
| 2014/0087444 | A1 | 3/2014 | Bennett et al. |
| 2014/0243388 | A1 | 8/2014 | Hastings |
| 2015/0202269 | A1 | 7/2015 | Beltran et al. |
| 2015/0252358 | A1 | 9/2015 | Maeder et al. |
| 2017/0342414 | A1 | 11/2017 | Collin et al. |
| 2018/0369412 | A1 | 12/2018 | Bennett et al. |
| 2022/0062437 | A1 | 3/2022 | Bennett et al. |
| 2022/0204989 | A1 | 6/2022 | Fisher et al. |
| 2024/0042057 | A1 | 2/2024 | Krumbach et al. |
| 2024/0091381 | A1 | 3/2024 | Krumbach et al. |

FOREIGN PATENT DOCUMENTS

| | | | |
|---|---|---|---|
| EP | 2151248 A1 | 2/2010 | |
| JP | 2016-516424 A | 6/2016 | |
| WO | WO-97/22250 A1 | 6/1997 | |
| WO | WO-98/14275 A1 | 4/1998 | |
| WO | WO-2001/049745 A1 | 7/2001 | |

(Continued)

OTHER PUBLICATIONS

Bennicelli et al., "CEP290 Minigene Model of Common Splice Site Mutation in Leber Congenital Amaurosis," Mol. Ther. Suppl 1:S167-168, Poster presented at American Society of Gene and Cell Therapy, 15th Annual Meeting, Philadelphia, Pennsylvania, USA, May 16-19, 2012.

(Continued)

*Primary Examiner* — Sean McGarry
(74) *Attorney, Agent, or Firm* — Clark & Elbing LLP

(57) ABSTRACT

The present invention features nucleic acid trans-splicing molecules (e.g., pre-mRNA trans-splicing molecules (RTMs)) capable of correcting one or more mutations in the ABCA4 gene or the CEP290 gene. Such molecules are useful in the treatment of disorders associated with mutations in ABCA4, such as Stargardt Disease (e.g., Stargardt Disease 1) and disorders associated with a mutation in CEP290, such as Leber congenital amourosis 10 (LCA 10). Also provided by the invention described herein are methods of using the nucleic acid trans-splicing molecules for correcting mutations in ABCA4 and CEP290 and for treating disorders associated with mutations in ABCA4 and CEP290, such as Stargardt Disease and LCA 10.

21 Claims, 29 Drawing Sheets

Specification includes a Sequence Listing.

(56) References Cited

FOREIGN PATENT DOCUMENTS

| | | | |
|---|---|---|---|
| WO | WO-2003/003014 | A1 | 1/2003 |
| WO | WO-2003/069311 | A2 | 8/2003 |
| WO | WO-2003/072739 | A2 | 9/2003 |
| WO | WO-2003/104412 | A2 | 12/2003 |
| WO | WO-2003/104416 | A2 | 12/2003 |
| WO | WO-2004/006678 | A1 | 1/2004 |
| WO | WO-2004/038380 | A2 | 5/2004 |
| WO | WO-2005/023990 | A2 | 3/2005 |
| WO | WO-2005/070023 | A2 | 8/2005 |
| WO | WO-2005/070948 | A1 | 8/2005 |
| WO | WO-2006/026611 | A2 | 3/2006 |
| WO | WO-2009/103562 | A1 | 8/2009 |
| WO | WO-2010/012472 | A1 | 2/2010 |
| WO | WO-2012/158757 | A1 | 11/2012 |
| WO | WO-2014/062801 | A1 | 4/2014 |
| WO | WO-2014/068063 | A1 | 5/2014 |
| WO | WO-2014/124282 | A1 | 8/2014 |
| WO | WO-2014/170480 | A1 | 10/2014 |
| WO | WO-2015/009575 | A1 | 1/2015 |
| WO | WO-2016/005524 | A1 | 1/2016 |
| WO | WO-2016/139321 | A1 | 9/2016 |
| WO | WO-2017/087900 | A1 | 5/2017 |
| WO | WO-2017/106370 | A1 | 6/2017 |
| WO | WO-2019/025984 | A1 | 2/2019 |
| WO | WO-2019/027869 | A1 | 2/2019 |
| WO | WO-2019/204514 | A1 | 10/2019 |
| WO | WO-2020/214973 | A1 | 10/2020 |
| WO | WO-2020/214990 | A1 | 10/2020 |
| WO | WO-2020/223180 | A1 | 11/2020 |
| WO | WO-2023/220742 | A2 | 11/2023 |

OTHER PUBLICATIONS

Brown, J.A. et al., "Formation of triple-helical structures by the 3'-end sequences of MALAT1 and MEN noncoding RNAs," PNAS, vol. 109 (47):19202-19207 (2012).

Dooley et al., "Spliceosome-Mediated Pre-mRNA trans-Splicing Can Repair CEP290 mRNA," Mol Ther Nucleic Acids. 12:294-308 (Sep. 2018) (17 pages).

Wilusz et al., "A triple helix stabilizes the 3' ends of long noncoding RNAs that lack poly(A) tails," Genes Dev. 26(21):2392-407 (Nov. 2012).

Applicants' Response and Amendment filed Jan. 8, 2020 in European Patent Application No. EP16867296.2 (9 pages).

Bacchi et al., "Splicing-Correcting Therapeutic Approaches for Retinal Dystrophies: Where Endogenous Gene Regulation and Specificity Matter," Invest Ophthalmol Vis Sci. 55(5):3285-3294 (2014).

Colella et al., "Efficient gene delivery to the cone-enriched pig retina by dual AAV vectors," Investigative Ophthalmology and Visual Science. 55(13):3332 (Apr. 2014) (abstract) (2 pages).

Collin et al., "Antisense Oligonucleotide (AON)-based Therapy for Leber Congenital Amaurosis Caused by a Frequent Mutation in CEP290," Mol Ther Nucleic Acids. 1(3):e14 (2012) (7 pages).

Communication pursuant to Article 94(3) EPC issued in European Patent Application No. EP16867296.2, dated Sep. 2, 2020 (4 pages).

Communication pursuant to Rule 164(1) EPC issued in European Patent Application No. EP16867296.2, dated Mar. 1, 2019 (10 pages).

Extended European Search Report for European Patent Application No. 19789043.7, dated Sep. 20, 2022 (10 pages).

Garanto et al., "In Vitro and In Vivo Rescue of Aberrant Splicing in CEP290-associated LCA by Antisense Oligonucleotide Delivery," Hum Mol Genet. 25(12):2552-2563 (2016).

Garanto et al., "Species-Dependent Splice Recognition of a Cryptic Exon Resulting from a Recurrent Intronic CEP290 Mutation that Causes Congenital Blindness," Int J Mol Sci. 16(3):5285-5298 (2015).

Gerard et al., "Intravitreal Injection of Splice-switching Oligonucleotides to Manipulate Splicing in Retinal Cells," Mol Ther Nucleic Acids. 4(9):e250 (2015) (8 pages).

Havens et al., "Targeting RNA Splicing for Disease Therapy," Wiley Interdiscip Rev RNA. 4(3):247-266 (2013).

Helou et al., "Mutation analysis of NPHP6/CEP290 in patients with Joubert syndrome and Senior-Løken syndrome," J Med Genet 44(10):657-63 (2007).

International Search Report and Written Opinion for International Patent Application No. PCT/US2019/027981, dated Aug. 6, 2019 (33 pages).

International Search Report for International Patent Application No. PCT/US2016/062941, dated Feb. 16, 2017 (3 pages).

Koller et al., "A novel screening system improves genetic correction by internal exon replacement," Nucleic Acids Res. 39(16):e108 (2011) (11 pages).

Liemberger et al., "RNA Trans-Splicing Modulation via Antisense Molecule Interference," Int J Mol Sci. 19(3):762 (Mar. 7, 2018) (18 pages).

Maia-Lopes et al., "ABCA4 mutations in Portuguese Stargardt patients: identification of new mutations and their phenotypic analysis," Mol Vis. 15:584-591 (2009).

Supplementary European Search Report issued in related European Patent Application No. EP16867296.2, dated Feb. 15, 2019 (4 pages).

Written Opinion for International Patent Application No. PCT/US2016/062941, dated Feb. 16, 2017 (6 pages).

Zhang et al., "Protein misfolding and the pathogenesis of ABCA4-associated retinal degenerations," Hum Mol Genet. 24(11):3220-3237 (2015).

Target Regions for 3 Different TALENs

FIG. 12A

Guide 1: hABCA4-g1 GGAGCCAGAGGCGCTCTTAA

Guide 2: hABCA4-g2 GTTAAGAGCGCCTCTGGCTC (Guides expressed off plasmid with U6 promoter and Cas9)

5'ARM:

5arm 2F CCTGGGCAAGATAAGCTATTCCTCCC
Puro GT R GAGCTGCAAGAACTCTTCCTCA

3' ARM:

CAG F gcctctgctaaccatgttcatgccttcttc
3arm 1R gcagctcccagggtcctaatc

Cell lines 17+06 AND 17+21 were chosen as representative ABCA4 knock-outs.

FIG. 18

Alleles in 17+06

| | Exon 3 | Exon 4 | Effect of sum mutations |
|---|---|---|---|
| Allele 1 | Mutation A | Mutation a | Early stop – likely NMD |
| Allele 2 | Mutation B | Mutation a | Early stop – likely NMD |
| Allele 3 | Mutation B | Wild type | Early stop – likely NMD |
| Allele 4 – not expressed | Mutation C | Mutation c | No Promoter insertion on this allele, no RNA, no Protein |

Alleles in 17+21

| | Exon 3 | Exon 4 | Effect of sum mutations |
|---|---|---|---|
| Allele 1 | Mutation A | Mutation a | Early stop – likely NMD |
| Allele 2 | Mutation B | Mutation a | Early stop – likely NMD |
| Allele 3 | Mutation B | Wild type | Early stop – likely NMD |
| Allele 4 – not expressed | Mutation C | Mutation c | No Promoter insertion on this allele, no RNA, no Protein |

SEQUENCE LISTING

```
Sequence total quantity: 113
SEQ ID NO: 1            moltype = DNA  length = 25
FEATURE                 Location/Qualifiers
source                  1..25
                        mol_type = other DNA
                        organism = synthetic construct
SEQUENCE: 1
gtaagagagc tcgttgcgat attat                                         25

SEQ ID NO: 2            moltype = DNA  length = 33
FEATURE                 Location/Qualifiers
source                  1..33
                        mol_type = other DNA
                        organism = synthetic construct
SEQUENCE: 2
tactaactgg tacctcttct ttttttctg cag                                 33

SEQ ID NO: 3            moltype = DNA  length = 23
FEATURE                 Location/Qualifiers
source                  1..23
                        mol_type = other DNA
                        organism = synthetic construct
SEQUENCE: 3
tggtacctct tcttttttt ctg                                            23

SEQ ID NO: 4            moltype = DNA  length = 20
FEATURE                 Location/Qualifiers
source                  1..20
                        mol_type = other DNA
                        organism = synthetic construct
SEQUENCE: 4
agatctcgtt gcgatattat                                               20

SEQ ID NO: 5            moltype = DNA  length = 27
FEATURE                 Location/Qualifiers
source                  1..27
                        mol_type = other DNA
                        organism = synthetic construct
SEQUENCE: 5
gagaacatta ttatagcgtt gctcgag                                       27

SEQ ID NO: 6            moltype = RNA  length = 135313
FEATURE                 Location/Qualifiers
source                  1..135313
                        mol_type = other RNA
                        organism = Homo sapiens
SEQUENCE: 6
agtccccagt ctttgcttag gcccctacgt acacaaactg aacctagtga cccagcatgg  60
cctctaattt ctcaacactt ctgtacttct gtaatgatta acccatgctt ctcacagatc  120
catgccccaa atttctgtga ataggccctg actggcccag ctaagatcat gtgactgcac  180
atgaccagtc cactttggca ttaacaagcc tactgcagac tcttcccttg gtgttggagt  240
cactcctaga aaagagcaaa tctttgtgag ccaggcagtc aacctgctgg cagcttccac  300
tcagccttgg agttttttct atgtgtaact ttcataaact gagccttatt tatttatttt  360
ttgcactatc atctcatgaa atattattgc gtaagctgag gaaacatgtt attcatgatg  420
actggagttt caagttttaa ttgtacaatg atttagtttt gagtttggta gaaataaaat  480
caaatttaaa aatcagatat ttttcatctt acattatgat gtcccaaaac tgcctttatg  540
cttgtgacat agattcataa tgtcttctca ttccacctgt aatcactgtt tgaaataaac  600
atatgtctaa tgatatattt ggggacattc tattttcttc agcttgttgc aagtgaattg  660
atggtgatct tttggtattg gtttcattat caaatttatc tccactccaa aattacagta  720
atttcaaagt aatttagtct atatattttt ccatagcttt tcttccaaat agaaactgta  780
aaaagttata aattacttct ctccactact gaatttttgt ttgcagaata actgatgtaa  840
gtagcagaat gcctcttcct agttcaaccc tcaggaatag aagtgagaag atctttaaaa  900
cttcaccatt ttccttgact tgtttataat tctgaatgta aatgtgaatt gatatggtct  960
atcgcttaac accacaactc ttaatctatg tgcagggtcg tagctcaaaa ctactgccag  1020
```

-continued

```
gaccacatca atttcatatt caccctgatc aatgtgtatt aatggtgata actatgagaa  1080
tgaaatgtac agttatcagt atcatttttg actcactagg tatatcctca gaaatatatg  1140
aaaaaactaa acacagcttt tagtttgaca taatttttaa acaactggag ttaccttggg  1200
agaaaaatcc taccaaatat ctataatatt gaaagagtaa aaaagagtta aatgtcctta  1260
acatcattaa tcattaggga catgcaaatc aaaaccacag tgaaatacca tctcacaccc  1320
tttaggatgg tggtgataag aagaaaaaca gagcataaca agtgttggcc aggatgtgga  1380
aaagctggaa ccattgtgca ctgctgattg gaaagtacaa tggtgcagct gctaagggaa  1440
atagtatggt agttcttcaa aaaataaaca gttataccat ttgattcagc agtttcactc  1500
ctaggtatat accccaaaga attgaaagca gaatctcaaa tatttgtaca cctatgttca  1560
tagcagcatt actcacaata gccaaaaggt ggaaacaacc cgaatgaccc tggatggacg  1620
aatggataaa caaaatgagg tctatactga caataggata ttaattgacc ttaaaaagga  1680
aagaaattct ggccgggcac ggtggctcac acctgtaata ccagcacttt gggaggccaa  1740
ggcaggcaga tcacctgagg ttgggagttt gagaccagcc tgaccaacat ggagaaacct  1800
catatctact taaaatacaa aaaaaaaaat tagccaagca tggtggcgcc tgcctgtaat  1860
cccaggtact cagtaggctg aggcaggaga atcgcttgaa caggaagcag aggttgcaat  1920
gagctgagat tgcaccatca cactccagcc tgggcaacaa gagtgaaact gcatctcaaa  1980
aaaaaaaaaa acaaaaaaaa caaaaaaaga aattctgaca catctgctat ggtctaaatt  2040
atgtgttcct ctaaaattca taaattgaaa tcctaacccc caaggtgatg gtattaggag  2100
gtgaggcttt gtggaggtga ttaggtcatg agggtacaac cctcgtgaat gggactagtg  2160
ccctcataaa aagaagccca agagagaccc cttttccctt ccactggatg aggtcacacc  2220
aagaagttac catctacatg tcaggaaata ggccctcacc agacaccaaa tctattggca  2280
ccttgatctt ggacttccca gcctgcaaag ctgtgagaaa taagttcctg ttgtttataa  2340
accacccagt ttatggtatt ttgttatagc agctcaaaca gattaagatg gcttgctaca  2400
acatagatga actttaaaga ttatgctttt ctatgattcc acttagatgg ggtaccaaga  2460
gtagtcaagt tcattgagac agaaaataga gtggttggca ggggctaggg ggagggaact  2520
ctggggagtt agtgtttaat ggatacagag tttcagtttt gcaaaatgaa aaagttctga  2580
agatggatgg tgctgatggc tgcacaatat gaatgtatca acactactca actgtacact  2640
taaaataagg ttcaaatgat acatttttatt tcatgtgtgt gtcaatctca acaaacagat  2700
ttgttcaggc aaggaaactg gttagatgcg aataatacta ttagagcatc atcaattgaa  2760
tattaacaaa gtgctcatag tttaactttc tagctcaagg aagaatggac catttttgaaa  2820
ctatgacaga acattactta tatagctgat gtctttggga attggaagga ggcatattcc  2880
ttcaccagct gtggctcccc ttcagcaacc tcatatactc tccaagcttc tctttcctgg  2940
gtcacctgtt taatcactcc cgggacttaa tcttccacct atatgttgac cactcacaaa  3000
tctatgtctc catctcacaa gcttattctt gactccagac ccaagtattc aactgcctgc  3060
tgaatacgtg tggtcagatg tcatagaact tcagcttcag tatatcaaat gcaaacccct  3120
gttcccccca actgcctcct actccccact ggccttcctc tggcattccc tcctcagtta  3180
tgagcaccac cgtctcacta gccagccagt caagccccaa actccatcta gctgacttct  3240
gcctcttcct caccaccctc ttccagtaac tcatcaggca ctgctgtgtc tcattccttc  3300
ctatccctcc agtccctccc cttctctcca tcatggctgt cactgcatgg ttcaggctct  3360
ctggctcccc ccaaaccacc cccacattgc tgccgaggtg aactgactac tcttggcagc  3420
cactggatta aaatctttca tcatcttcag catgataaaa cccatatcct ttagcatgta  3480
acaaggtctt aatgattctg ccagagcttg cttgggggta gcctgcactt gtgggccact  3540
ccagtcactt cacaggtgct cagtaaatct cagttgaatc agtcatcatc atcatcatca  3600
tcatcatcat catcatcatc atcaattttt cagtctggtt cctgtctcct tttccagcat  3660
cctccattca tagcctcata gccttcactc cagccatgtt tcacttgtgg ttttcctggg  3720
caagataagc tattcctccc tgtctttgca gagtttaaat gactcacttg ttcaagtacc  3780
caccgttgcc atgtgggacc gtgagcaaag tacttaatct cactaagctt cacgttcctc  3840
atctgtaaaa cagcaaatat ggacctcaca aaattgtagt gaggctaaaa tgaaataaca  3900
tatgcaaaag cagtttataa ataataaact tactataaaa tattattttg taattctgca  3960
agcttgtctt aaatgccatc acctccaagg agccttttttg ccatcataag cagaaactat  4020
ctctctcttc ttggaagctc caccatgcac agcctatggg ccctcatcac actccttgag  4080
ttattcgagt tcaagtcccg tgtttacaac cagaccgcaa actctatgaa gtcagcatcc  4140
attcctctct gtggttctcc ctccgcccca tccaggtctc aagggtctag agtctttcaa  4200
agagaacaca ttctgagatt tgaggaggca gagacaaaaa gttccactgc gaagtgccag  4260
ggaggcttct gtttggggtg tcccttggga tcacagatcc cccacctggt gatgagtcaa  4320
cccagcacca ccccattgca gggctggaat gacagtaatg ggcccacctg ctgcctctcc  4380
tcatacccgc accccagtca gacattgcaa gtcagtcacg gctctgtcct gctgggcctg  4440
gagtgttcca gtgccttttc catcacagca ccaagcagcc actactagtc gatcaatttc  4500
agcacaagag ataaacatca ttaccctctg ctaagctcag agataaccca actagctgac  4560
cataatgact tcagtcatta cggagcaaga taaaagacta aaagagggag ggatcacttc  4620
agatctgccg agtgagtcga ttggacttaa agggccagtc aaaccctgac tgccggctca  4680
tggcaggctc ttgccgagga caaatgccca gcctatattt atgcaaagag attttgttcc  4740
aaacttaagg tcaaagatac ctaaagacat ccccctcagg aacccctctc atggaggaga  4800
gtgcctgagg gtcttggttt cccattgcat cccccacctc aatttccctg gtgcccagcc  4860
acttgtgtct ttagggttct ctttctctcc ataaaaggga gccaacacag tgtcggcctc  4920
ctctccccaa ctaagggctt atgtgtaatt aaaagggatt atgctttgaa ggggaaaagt  4980
agcctttaat caccaggaga aggacacagc gtccggagcc agaggcgctc ttaacggcgt  5040
ttatgtcctt tgctgtctga ggggcctcag ctctgaccaa tctggtcttc gtgtggtcat  5100
tagcatgggc ttcgtgagac agatacagct tttgctctgg aagaactgga ccctgcggaa  5160
aaggcaaaag gtaacagtta ctgtctgtgg tttaaaaatg aggtgtggag caaataaaca  5220
ggttggaagt gtggggtggg gtggtggggt agggtggtgg ggcagggtgg ggggttgtga  5280
gcagtcagtg ggcttgtcgc cgattagcac tgaagcagtg tttagctgga cggccttttct  5340
gtgggcccct ctgacagtgc ccttcccagg aagatgtgtt tctctgtcct cagccacatg  5400
aaaatctttt gcctaccgtg cctgtcaatc cattgcctgc ccgcccctcc cccacccccc  5460
gttttacacc tgcctgtcca gtctaccgct ctctagggca tccacgctga gcagtgggaa  5520
gaactttaag ccctgaagag caggccaaag gcaagcaaga accccctcga acagcttccc  5580
agcttagtga ggccttattt cattgattct ctgaggcaca ttgtttttttc acatgttagc  5640
atttctgaaa ttgggatgca gctcacgatc aagtcacagt ttaactggac acattatttt  5700
tctttcttag tggtgcagaa aagtaacagt gtgtcttaca attgactgcg tcctagattc  5760
```

```
tgtgagatgc aatacgttat taaccatcac gcacatttcc tgaactcttt caatgagcag  5820
acaccagcct gggttagact ggagccctaa aagcacgaca cagattccac cctggactgg  5880
cttctgttct gcctgggaaa acccaaagta cgtttggaga ccaagagcaa cataaagtag  5940
cataggtgga atagtccatg agaagtgcga gcaaaaggtg ccggagatca gagaacacca  6000
agactgtact tgtaaatgac aactggcttt gtgcaatttt ttctgggaaa ggataaggag  6060
tgactataga actgtaaaga aagaatgcac tttgctacag ccttgcagag ttgtgcaaat  6120
gccgatgact aaaggagctg aaagaggaag gaggggataa gggatggggg ctgggtaggg  6180
gtgagattag gaccctggga gctgcaagcc actggagaga tcaggaggaa agggagggag  6240
acctgcttta ggcgagaaga gaacagtatt tgttccaaat ctcggttcag aataagttca  6300
tgtaggtgat ggggccaact ggaacaggtg aaggcctatg aatgagtgtc tcagttaggg  6360
tctccttaga gtttaatatg aaaaggtgtt agctaagtac agagctggta cctgagagag  6420
taaaaggaaa ctctaaggta tcatggaggt agcaattgca ggacacagct cccacccccta  6480
gggctgagag aaccaaggga agagacagga attattaaga cttggagcat agatgagagg  6540
tctgtggagc tgacattagg acttgggagg aaggcgtgca tggaggctgc tgctggatct  6600
ctgaacctga cctcgggtct ggacccctga ggagaaagcc ctggcaggtt ggtgcatgtg  6660
gggccgaggg acaatagctt aacaaccagc ataaaagaga gcagcatggg acacgcttca  6720
accatgcgca tggatggctc caaaacctgt gtgtggctgg cccaggacgc agggaggctg  6780
caggggggaag agacaagtta aacctgactt gtctgggaag caccattgtc ctcaggtcac  6840
tttcctctgt caagcctggt gctgaagtta tctgttgtct ccaggggcca agtattaaga  6900
gtaatcagaa actcagtcct ttcttctagg agcttccctt cttgcatgaa aatcctgata  6960
aaactggaaa aaaaaacctc atgattaaat tttttcatgt attcattctt tccttctatc  7020
aaaaaataat ctccaggcac cgtgctaggt tcattggtat acaatggcaa caagacctcc  7080
cagcccctgc ctatgtgagg catctgtgga ctgcggagga aaatccaata tgccattgtt  7140
ctctctttcc cataagaaat tacaattctc agttcatttt attctcactg tgctctttgt  7200
gaccctcaaa gggggtcaca tgataacagg actgtagctg ctggcctaaa atgagcccat  7260
tcctgtggcg ctcatgtcgc tgtgacagag aataaccctg ttttcagaat gctctggtgc  7320
cctccctctc aatctggcct ttcgctggca tgggtgggcg actcctgctc agggactctg  7380
ccttctccac agtgtgctcc cagggagatg gagccactcg ggctgagggc cttggccagg  7440
gcacctccca gggctgggcc tggtctgggc tggcgttcac tggatgccat cctgatggcc  7500
tggaaattga gatttctgtc tggcacgcct cccgatggct ccccacctgc taccacattc  7560
caggagcttc caggatgtct gggtaagaca gaggcacccc caacagattc agtagctctg  7620
agagggatct gtggctcctt cctaagcttg cggttcttct ggaaacttct gcctctagaa  7680
gatggtccct ctaagaaaag tacaaccacc cagcccataa ttcagctccc aggttttccc  7740
tcaaacctcc atgtctcctg taagcagagc aagagtaaaa tcagatacca aatttcctca  7800
ttcctcagct cccaatccct aagggcataa gatgaaaatc ttcagatctc tgctttcctc  7860
cctctttttt tcttcctctg ttaacatttg tcaagtgtta ctaagtgtct ggcactgtac  7920
taagtgcatc acctccctga actctccgaa cagttccacg agagaggcct ctctgtgatc  7980
cccccggtac tgatgaggtc actgaggctc cagagaagga ttagtaactg gtggggttgg  8040
acctgggatt cacacccatg ctgcgtgacc caggacaggc aggcatggcc gttacaccac  8100
actgaccccc gtggatcgag atctatccaa tagtctggtc actgatatca ctaagataga  8160
gtggccatat aatttatcat ccaatcaggg cagttttgca agtgaaaggg agcactatta  8220
ataattgcac tgggacaata aatgtaaacc aacactggac ctggaaaact gggacgtgtg  8280
tttgccctat accaaggtaa gctagacaca gccactgcct tcatggagtt cagaaccagg  8340
caggggcggc tcccacgtat aattactgtg cagcacaacg tggagaccgt ggagtagaag  8400
gaaacacgga tgggaggtga ggaggaggtc tgtgagctca gaggaggcac cggggctgga  8460
gagggtgaga gaagacttcc caaggagttc atcctgataa cgtgcattcc caatgacgag  8520
cgctctctcc actgcacaag acaagtatac atctgcccgt gttggctgtg gacctggcgc  8580
tgtgtcaggg agggtttatg aagatcacta ggtgggtctc ttggtgtcat cccttcatcc  8640
cagcttctgg gttaggatgg atatctgtgg gggggcctga ggactcatga aagtggggcg  8700
ctaatcatgt tttggacacc acaccctgga gcacctggga cagctgtggc ctttgtcctg  8760
ggttcagcat caagccgagg atgtggcaag taaagagagg ctgggcacca actccagtgt  8820
acccaggctc cgggtcatgt ttgtccaggc taagaattct gtcctggttc tcagtgcaga  8880
aggaagaatc atggggctca ttttaggcct tggctgcctt ctgttaaatt gaaaacagag  8940
caggaaggaa gaaaatttaa caggctcagt tctaaaacaa caagcacaac tgtgcccttg  9000
ccagaaaccc ctcctcccca tgttgattga atggtaaaga gaggagggga ggtgagaggg  9060
agagagagag agaggaagag agagagaaag gaaagaaagg aaagaagaag aaagaaagaa  9120
aaggaaagaa agaaagaaag aaagaaagaa agaaagaaag aaagaaagaa agaaagaaag  9180
agaaagaaag aaaggaggga gggagggaag gggaaaagaa aagaaaagaa aaagaaaaaa  9240
agaaaggaaat accagtttgg gaaaaaagaa ttttccacca gcccttctga gccttggctg  9300
ggcttaatta aagttacaga catgtgtaaa gggcagggta gggggagtct gagctgctga  9360
gaaaacatgt ttttaattat actgtggaat ttctccctgg ggtatgcctg tacgcagtta  9420
agcgtcaagg acagggatgc cgctctgggg aggggaagct gagcatgatt ttggaagccg  9480
gcagaagagg ctattgtgaa aaccagacct gtcaggctag gaaaagaatg gctggtggtc  9540
tttgaccagg gagtgacgcg tgaaatgcag caaccgcccc cgcccccgc caaaaacaaa  9600
cacactctca cagagttaga acaacagtga cctctcaaca aatatttttc aaagattacc  9660
aaccaaccat tacctagagc agcggttctc aaccttggct gcacggtgga actacctgag  9720
acgtgttaaa aagaagaacc ctgatgtccc atgccccaag attctgatgt agttgatctg  9780
gggtatgatc tgagaccccg gcatgttttc agcctgcagc cacatgagaa gtgctgacct  9840
aatcaacagg ggtgatgatt tgaggggcgg ggactatagg caaaaaaaaa cagcctaatt  9900
caaggatgag aagagggcac aggtgaggtg ggaacagtcc tagggccaga caaagaagga  9960
agggagaaag gaggtgctga tccctcccct actcctgaga ggaggccttt aagtcaccgt  10020
gccttgtgga gaccagattc ttcaaaaata caagaatgag tgagtgaggg agtgggtgga  10080
tgccaggaga gtgcgtgaca agccttgcaa gggaggatga caatgcacta gcttggtttg  10140
gaaattttac ccctggaaca ggcaggccaa gctggctggt cccctccctg atacacagcc  10200
ctccctcttt atatatggag caggggacgg tgtgtggctg gtttcttagc aagcaccatg  10260
gttccaagtt ggcaactggg gagttctgaa tccaaaaagg agggagatga acgtaagtgg  10320
agggcaggcc tacaaggttg cagataagct taattctgtc tccttactct tctgcctttg  10380
caacaaccct gtgatcttgc gacaaccctg taaggcaata acaaatggct catgtttatt  10440
gagtgttacc tcatgccata ttgtgctttc gtgtttaaca caattgtctc atttcaccct  10500
```

```
cacgactgct ctgggaggta ggtcctggta tcacatccat ttcacagatg agaccatttg  10560
gcacggaaga gttgagtggg ctgcccaagg tcacatagct aagatggaac aggctggata  10620
ggaaccccag taacttgacc tcagagtaac cttctcttaa ccctgagtgt acactgtagg  10680
aaaaatgagc agtcccattt cagagaggac aaaactgaga ctcagaggtt aagcaagccc  10740
caaagtggtt gttaacccag atcttcccac taactcccaa atcagcatca gtgtttaacg  10800
taccagacct ctcccagata gatgttgccg catggaagac agccgatcta cgtgatagaa  10860
agccaatatt gcaagcagtc gtctaaagga gtcaaatgtg ttggatttga actggatgtc  10920
tcatttcttt ggtgaagaca ctggaaacaa cttccaggtt tcatcaattg ctcctatcac  10980
tcaacgttgc tatcttactg aacttgttcc ccagccttac ccactgatgg aatgatccag  11040
aatggaagac aagacaccaa tgtacatgac cctgggggag gctgtttctt aaatctacag  11100
actgttggtg acctgagccc catgtcacca aaggctttcc tggagaagcc tcctagacca  11160
gtcttgacaa aggctcactc attccgtgga tatttattgg gcacctatta tgagttctgc  11220
cccatgtggg gtgctggaat cacagtagtg acaacgacag atgaggttcc tgtcctcagg  11280
aagcttactg cccttgaggg cttcacttac ttggaggagt gatgaacctg aagtgcggtg  11340
tgtgttaaga agcggaagtc cagggccagg cgcggtggct cacgcctgta atcccagcac  11400
tttgggaggc tgaggcaggc ggatcaccag gtcaggagat cgagaccatc ctggctaaca  11460
tggtgaaacc ccgtctctac taaaaataca aaaaaattag ccgggcatgg tggtgggcac  11520
ctgcagtccc agctactcag gaggctgagg caggagagtg gcgtgaacct gggaggcaga  11580
gcttgcagtg agccaagatc gtgccactgc actccagcct gggcaacaga gtgagactcc  11640
gtctcaaaaa gaaaaaaaaa agtgcctcac ggagagtcta ttcttttctt cccatattgt  11700
gtgtgtgtgt gcgcgcttcc tccaacacat cctccctata tatattttga gtaaaacatc  11760
ttgtaaaaag ttacagctac ataatcacca cctgtcccta aatagttttt gctttttctt  11820
tcttcaatgc acgatcattt tcccccatca atttattttt tagtttctta taatcttgtt  11880
gccagtaggc tgttttttaa aaagcagaac atggtttgtt cttactagca ggaaaggagc  11940
atttattgag cctctgctat ggtgtctttt attttgctga gagcctattt acatttcttt  12000
gagaggaaaa caacaaaggg ttacatgaaa gaccatgtga atagccccta gctgatctat  12060
taaacttgct attccccggc cagctgcttc agatctcctt cagatcttat gtgtttcctt  12120
cctaaggtcc ctggagtaag ggttgcatag acctattcta ctctccaact cacatgtccc  12180
tctccctctt cctctccata attccacatc tccaaccccc acccctatgt gcaatgccac  12240
agggtgtgga ctgccacagc cactggatct gcttttggaa tcaagagtcc ttaagctcca  12300
aatggaaccg aaatttaaat accaactttc aaccatatgt taacatcagc agcctcttcc  12360
aatgtaaaaa cccatggcag tgtgccctgc tttgtttctt taagcaatag aaacttgaag  12420
gaagcatgtt ggtaggccag atttttgttg gctttgcaat ggatcacagt catttattca  12480
ctcattcatt cactgattca ttaaatgacc acatttgcaa gggcaaggta atggggaggg  12540
ccagaaagga cactggcccc agaaacagga ggctggattt tggttctgat gctgccactg  12600
ctgatgtgac actgcacagg tcacctgcct cctctgagcc tctttcctta actgcagagt  12660
gagtggctac agagaaatct ttactacctg ttagatcagc attacctggg agcttgttag  12720
aaatgcaagc tctggtgggg ccatactgaa cccaaatctg cattcatgtg catagtgaca  12780
gctaaaatgc actgaagcag atgatcttga tgatccttta tgaaagtctc atgctaatgc  12840
agttttctaa aatagaggca gagtggaacc cagatggaca caaaatctgg ttgatataat  12900
aaaacaaggt agagggtgta tggtggggag ggggtaaagg aaggaaactg tttaggtaaa  12960
gataccacaa ccaaagtcct actgcacaca tgggatctga ggagggctgt gtctgctctg  13020
gttacgtttt ctataatctc ttagcaccac tgaactttct ctctttttgt tttgtttttc  13080
cagattcgct ttgtggtgga actcgtgtgg cctttatctt tatttctggt cttgatctgg  13140
ttaaggaatg ccaacccgct ctacagccat catgaatgta agcatagcag ggtagcttgg  13200
gcaagccctg aagagacttt ggtctgggcc ttttgtctag aaagatcttg gggtgggagt  13260
gtggggatca gatctgctta tcatcatttc atgtctatga tgcatgtaac agatttatca  13320
atgttacaca aattataatt tttaaaaagt ctttagagac agggtctcac tctgttgccg  13380
aggctggagt acagtgttag gaccatggca cactgcagct tctatctctt gggctcaagt  13440
gatcctcctg cctgggcttc caaagtgctg gaattatagg catgagccac tgctcccagc  13500
taattttttt gtttttgtg gagacagagt cactacattg cccgggctgg tcttgaactc  13560
ctggcctcaa gtgatcctcc cacctcagcg ttctaaagca ctgggattac aagcatgagc  13620
caccttgtcc agcccaaatt ttcatgtttt aatcctacac attctaagca aatacttgtg  13680
tgtagttact aagggactgt gcacttattt ttgtttgctt tgttgttgct agtttttatt  13740
tttttatacc taaactctct cgttttaaag agaacagatt tgtagatgag ttctcgaaaa  13800
tatttcagga atcaatatag agaatatgtt atacatggtg ccagagaaaa atgaggacaa  13860
gagatgctat acaatcgtac tgaagaaaaa ttttatttct tggacccctg aggtgtctgc  13920
agacctgaaa ggaacctagt gagagcctct tttacactct gcccctgtgg gaaagccttc  13980
acctggtttc cggccctcta tgtggtgaat gtggaagcct caagcgttat gcaaatctgc  14040
ccagtcctct attcttgatc ttcaccttct cgttcatgag tttcaggccc cagttctgaa  14100
tcagcctcct gtccatcaga ctcttcttta cctctccccg aggagcccat aacctgcagc  14160
cctactgcat gcttggggta ggtgctcagt tcaccgtggt tgaaggaata gacgagcgtc  14220
tgctcaagca gcagcagcaa ctgcgtggag tcttcttgaa ctaacactcc tatgcccctc  14280
tcggcacaaa atgacgtgtc ccccttgct tccccttcac atttccaccc atgcctatta  14340
caacatccgt ctgtctcccc actacaccgg gagcttgaga gaagaggcca tgtctctagc  14400
acccagcaca gggactggca cacatgagat gctcctgctt cttaaatgct gagaatgaag  14460
gaggacatca gaggggcccg ggccccttcc caaaaaggcc aactcctagg tctgcatcct  14520
gcttggtctc catgactaat cccgtcttgt cctcattttc tgttttaaag gccatttccc  14580
caacaaggcg atgccctcag caggaatgct gccgtggctc caggggatct tctgcaatgt  14640
gaacaatccc tgttttcaaa gccccacccc aggagaatct cctggaattg tgtcaaacta  14700
taacaactcc atgtaagtgt tgagatccct accatgcagg ggaggaagtt gcacacccct  14760
tcacgtgctg aaatgcacac gtgcgtgcac ggagcatgga gcactgagtg ttcttgtggc  14820
tttgctgagc ccctaacctc ttaggagcag agcaggtttc ctctctggaa cattctgtta  14880
actgtcaggg cacttgggga gaaatctcca agctaaggcc acgtgcacaa aatttcttgg  14940
tccttatatc cccagaatgt gacctggagt ctgatggcag cccgctgcag agatgtgtcc  15000
actgccttct ggtcattgac ctgcttgggt ggagtgaatc attgtaggag aaaaactcag  15060
ttccctcacc ctgatcaacc tggacagatc tctcttcctt taaaagcttt cttggacatc  15120
taagggctag gaaaaatgtc agggagcatt gggaaggtaa atgaagtcag gtttacaaag  15180
tcaagtttac ttcttgggag aaaaatacaa tttccaaatc ctctgttata attgccatcg  15240
```

-continued

```
gccccctgga gtggtgagat ctcggaatat ggctcgggtg cagtggctct tcactgtggg  15300
cctgcaggct attctgaaaa gctgatgaaa accaatgacc cctcttccaa gaaaaatggc  15360
cacataccaa acattacact gtacatctga tttcagggaa ttgtagatgc caggttagta  15420
gcctcaggtc tagggtcaaa attcaagtcg aatcccacag gaagagggtc tgccttcgga  15480
attccctttc agagcattgg gagaacatca tgggagcata ttctagagac agaggcttag  15540
ggtgtggaca gggccatccc tcacccactg tgctgacctt aagcagcacc ttgtgcagcc  15600
catacctgaa ggccaccagc aaaggcctgt tggggagcag gctttacccg acctgtataa  15660
acaccaggct aggtgaaaac tgagatacct ggttacttta gttttttcct tgggggagct  15720
cagtatgatt cttccaggag aagcctgctt ttagactaaa aagaaaaaaa gtttgatagg  15780
tcaacctaat gattggaggt ggccttcccc actgtgaaca aactatggct gcatgtgccc  15840
tacaatggca gagttgagta gttgtgatag agactgtatg atctgtaagc ctgtaatttt  15900
tatgtttgct gaccccctgga ttaccagatg atagaagagg aaacatctgt cttcctagca  15960
aagtcaagga agtggcattt agcaggactc atattgctgc aagcactgcc ttgcagtttt  16020
agtttacaac tgcactttca gcttaagaaa cacctgccca tccagagaga tcgtgtgggg  16080
tcacatggtg ggatcaggga ggcctgaaga cagctcagtg gaggctgcat ggagctttgg  16140
tgggaacggc cctggcagtg tctatagatg ttattgcgga aaactgaggg gtgggagttg  16200
gagaaggggg ctccagactc tagctgtact tggcatttga acccggaaag ttgggtttca  16260
tgttttgcac tcacattatg agtgaaatat tggcttattc aaggttcttt tgcttgcaag  16320
gcacggaaac ccattcaagc aatcttaaac cccagaagga aatctatgat ttggatacta  16380
gacattctca cagagccaag ggcagcaagg cggggctcag gagaggcagg ccaagacctg  16440
gagagctgtc aggagctgct tcctcaactc tcttccatct gggcctgcca gccctggcct  16500
ctgtatctac tccattcacc tctctccatg gaccagtctc ccctgctcct caatgcctgg  16560
gctgccattg ttcatgcaat tcacaatacc tcggcctggg caatcagaag ctcatctctg  16620
aacaccatcc aaattcctgg gaacaaatcg ggttgaccca gctttattct ccctgtccca  16680
tcagccttgg cagaggcgtg catgtgcatg cgtgccaatg tgtgtgtgca gggaggtcct  16740
tgtggatgaa gcatggctgt cagagcctac ctgcgtgaat gggtggaagg gcaggtctca  16800
gagaattggg taaaaactgg ataaaccctc cagtgatatc caccaatgtc accctgttta  16860
aggcttctct gggcaagaga cacacagagc atggaccgga gaggcgagca gaccctgcca  16920
aaactgggag actgaataga tcgctcacca tccttgtcag ttagcctata tgtacaagga  16980
agtaaaatta tctctttctc ctgccttggc agtattgtaa ggatactcaa tgtagtagct  17040
aggccagaca catagtatct ttaaatatag catgagatgg ccaagcacgg tggctcatgc  17100
ctgtaatccc agcactttgg gaggctgagg cgggtggatc acgaggtcag gagatcgaga  17160
ccatcctggc taacacgatg aagccccgtc tctactaaaa atataaaaaa ttagctgggt  17220
gtggtggcgg gcgcctgtag tcccagctac tcgggaggct gaggcaggag aatagcgtga  17280
acccgggggg cagagcttgc agtgagccga gatcacgcca ctgcactcca gcctgggtga  17340
cagagcgaga taaaaaaaaa aaatagcatg agatattatt actgttataa aaataacagc  17400
tatttcctta ttaatgaggc tttgtcctta cagcttggca agggtatatc gagattttca  17460
agaactcctc atgaatgcac cagagagcca gcaccttggc cgtatttgga cagagctaca  17520
catcttgtcc caattcatgg acaccctccg gactcacccg gagagaattg caggtaagca  17580
tgactgcagt gctctcaagc atcatttccc tcacctatgg agagactgaa gatataggaa  17640
agaacaggga gagttggtga aaaatatact agcggaggca ggaagggatg gggtctggag  17700
gcggcttgaa catcaccttg gtgaagatgc ctcttcctcc acagaagcct ggaaggtagg  17760
aagttgggaa ggaaggcagg aaaggtctca tccacgttaa gtctagagac agaaagaatg  17820
ctaagagaga tggcactatg ggaagtatga ggctaggtca agggctagaa gcaggggaga  17880
cgagtttaca gagtttcgta aagatataga gcaactctca cagagttcta gagcgagagc  17940
taaccaggaa catgaagcag caaggccaac tatcattaag gagccaggga ggtcagagat  18000
catgtattat catgacataa atatgcataa ttgtactatt tctcccagta atatttagca  18060
cccaggcccc gaggcagagc aagtggagag tgggtgatgc agggctgggg gtgtgtatgg  18120
aggcaccaca gaaggtcaac aggcagcggg ctgaaggcag ggactggact acatgcatca  18180
agtccaggct gcacgaggaa ggatgagaag gcagatgagc acggaaatgg actgggggaa  18240
atgaagaggc aagggaatag aagtctcagt gggtgccatg accctgttta agtgattgag  18300
aaaatgaaca agatgaaaag gttaatggct gtggtcagaa agtgaaatat gtgaattcag  18360
gatttcgaag gtagggtggg tgatgactgg cccccagatg cggccatggt gaagtggggc  18420
aaaggtgcag gtgcatggtg aggggaagga ggaaatggga ggtgatgatg ttggccccac  18480
acggacacca cggttgtgca ggaagatggc aggagctggg caccagggtg ggagccacct  18540
ggagtcagga agagtgaaga gaaaggatga agaggctccc tctcctgtgt ctctcctccc  18600
caggagaaga acaagaaaca atccgaaagt aataacacca atgtgccttt acaaagtgtg  18660
agtgggtgtt gtgtgctgtc acgtgtgtag taggctcctc tgtggatggc tagagggact  18720
ggacatggcc actggatccc acttgcaaga gcagaggaaa agagtggtcg tgaggaagta  18780
aagcccccca aaatccaggg gttgctgcag ctttgggtgt ggagcgtgcc ctctgaggaa  18840
aggctgctct gggggagatt gcccaggaaa cggggctcag aggccacgaa agcagctgtt  18900
aggggcttct gggagatgtg tgctcctagg attagggagt tgactctaag gatgacctta  18960
gaggttaaca gggatgagaa aggggtcacc aaggggtcta ccaggggaat gggagaggct  19020
gtattgatag aacagcttct gctgcaggtt ccaaacaaga aatgtgggag aatggttgaa  19080
atcagccccg ggggcacctt cccgtgcatg cgtgcagctc cttcaacatt cagtcgacct  19140
tcagtgcctc ctgtgagcca ggcactgggc tagtctctgg gggtggagag atgagtcagg  19200
caaatgccag ccctcagagg gctcacaggg cagaaggtga gagatgagtg agcagaaaat  19260
gaccacagcg cgtgtggggc ccagtggagg gaaggagggg attcaggagc acaggagagt  19320
caacagggga aacttctccg aggagaatct gatcctcctc ccatctggcc accttctgaa  19380
gccctctctc cccatccaag tgagaaagga caggcgtatg accagattgg tgtatgaaga  19440
tgctgaatta cgttctcatt gtttcaaact agtaaaccat agattttatg tagtaacttc  19500
tacaaactgc attacaaaca ctccattctt tgttgccctg ggtagaagtt tattttagtg  19560
agcccaagtt tgaggaacct tatatggtat gagtacaatt accattttaa tagtaagaaa  19620
tccccccttcc cctgtgtacc aaccagaagg tgtttttttc ctaatttaaa caaacagatg  19680
cagacgtggg ctgtccagct cctggcggga tgacatacct catgcatcca gtgggtttga  19740
tgatgaggca gacatttcac ttaagtgcct gatcatcaga ttgagtcctg ctgggaggaa  19800
gtgtgaagga agtaatttca aaccacagtt tctctgtggc ttttacaatg tggatatgag  19860
aaccaaaatc actacttctt aaccccagag caggactgat tttgaattgg tatgcaggcg  19920
gttccttctg caggcttcgg gctgtgagaa gtccctaaca gagcaaatct ggggacaagg  19980
```

```
gctcaggaaa ggttggccac ggccccctag gaatgggggc tctgcaagat ccctggcctt  20040
agaggctgtg agagggaaca ggggtccatc cccaagtaag ggacacggtc tttgaggaaa  20100
tcccaggcca gggcctgaag ggcactgtca ggaacacagg ctgtttcagt ctgttgagat  20160
tcaccggggc gctgctcact gtgagcacgg actcctcagg ccaatgtggc agaagagccc  20220
acctttgaaa gcgagcgggt gggggtggcg gggctggtgc tggtgcgtgc ttctgcacag  20280
ccacctggga aggtatgccg ctggttgacc caggcagagg ttttctttca tggcaaacct  20340
gcagtactgc attctcagca gggaggatta atggtaaaag accaggcatg gagccccctt  20400
ccctctccct cgaagcaagc tctgtggtct ctcaatcatc tttaaaacac cttcttcccg  20460
ggagcctcct acattctcct ggcttccctc ccacccccac cctcagctcc tggggcctca  20520
gcagccccac ccccaagcct ctaatcttcc cagggaaggg aacaagaaga accacatttt  20580
aaacgaaatt tatttttctt tcctcaggct cccagttcac atttctccct caggagtcta  20640
gggaagcttc tgtctggtat cggcctcctc ttcacctggg cccccgccct cctcaggtgt  20700
accagaagcc agcacactcc cccttccccc ccagagccac agcagccctg tctcctgggt  20760
ggtcttgtgt gccaagcctg ggcaacatca ctcccagctt ttcttgtttt gccccttctc  20820
cccagcaaga tatttgtatg taaggtcagg tgagtgagtt aaagaataac gaagagataa  20880
acagtcaaat ggagtcctga ctgtcaggtc aagacaacag ttatttactg aatgcctcat  20940
gtcattcaac agacatttat tgagactctg attggatgtc agtctttaat gctgggtgtc  21000
agagagaggt gacttcaagg gcttgcatct gtgcacccag cattgctagg tacaatgagg  21060
agtataataa aagcaggagc catagccccc aactctcaag agatctccca tgtgtgtatg  21120
tctgcatatg cgtgcgtgtg catgtgtgcg catgtgtgca tgtgtgtgtg catgtgtgtg  21180
catgcgtgtg tgtgtgcgtg tgttggggat ggtgttggtg gagtgagagt gtacaaggct  21240
gtgtatgaag gggtaattgg gaaaagaaca atggagctgg cacccaggga caggaggaaa  21300
agcaggaggg ctgggtttgg aagacagccg gatttatgtt tttgaagagg gaagactaga  21360
atataaggga gcagcccttc tcagagccct cctcctccct tcgggccctg tgtccagctt  21420
tccccaaagt ccttggatct ttcctatgca aaggggagtg acagtgggca ccactctcag  21480
ggaacccatt actgtgagag aagccactgt gccactgtgt ggtcgaactt caagaccggc  21540
ttcccctgcc ccagctgcat ggacaggcct gtggggttgg cgcaagaccc ttccagagga  21600
aactagctgc aacataaatc cggatatggt gctgttcagg gaaaggcaca acctggggat  21660
gagaagggtg gctgtccagc acacagggc aggcctcttg gccactgggg gaggggagaa  21720
tttggagagg aagaggatgg gatgccgtgg aattgggacc aggaaagaat ggggacatgt  21780
gatggttaaa gctagttaga gaagaactgg gagataaaca gtcacccatg cccctgaagc  21840
actcggggtg aagagattgg cattttcacg caccccagtg ctttcccttt gtgttgaagt  21900
cccttcgtag acatccaggc ccataaggct cttctctggc cagagcctca tgaactatag  21960
cactagcagg gttgaggcca agcattggcc ctggaagcca gccgaggagg agggtgcttg  22020
tgtgaatctc ccaggagggg taagaattat attaattcga tcataataag catttattga  22080
gtgctgtttt gaggcctggg agctaagcac ttcacattcc ttaccccgca tcaacaatcc  22140
tatgaggtag atgtggaaaa tgcagacacg gggacaggct caatcacttg ccccaaggtc  22200
accttaactg ttaggtgttc tttatgcctc cttataaaga aaccctgctt cccacaggtg  22260
ttgagaggag ctggagggag cttgactagg gctcatcagg caagccccgg catgtgcctg  22320
gctctcctct ttctacctgg agcttttcct gcccttaatg gccccaactc atttctctta  22380
gtccatgtca gtgccctgag catctcagcc caagctgaga tgatagaaac acccagaggg  22440
gtcctctacc ctgtgacagc tgcggtgtgg gaagagcacg tgtctcctcc aatcctagac  22500
cagagtttct cagcctcagc atcactgaca cttggggcta gataatcctt tgtgtggggg  22560
agggaggagt gtcttgggcc ttgcaggatg tttagcagca tctctggcct ctacccacca  22620
gcacctcccc agttgtgaca cccagaaatg tctttagatc ttgccaaata tttccaggag  22680
gatgaaattc ccctgtttca gttccccagc cccacctcaa tgagaagcac tgtcctagac  22740
caaccccaca aagcatctga cacccccatc cagccctggc taactttttc caccttctta  22800
ctaaattggg cccagctgct tcagcagtca atgtgttggg ggcagcccac tggcaagagc  22860
ctcacctcta ggggctccca gagaccccaa gaacagaacc ttcctctgag agttgagtta  22920
caagtgtttc caatcgactc tggctgtttt cctttttttg acccatttcc ccttcaacac  22980
cctgttcttt ctcttattca tatgtaggaa gaggaatacg aataagggat atcttgaaag  23040
atgaagaaac actgacacta tttctcatta aaaacatcgg cctgtctgac tcagtggtct  23100
accttctgat caactctcaa gtccgtccag agcaggtagg gggatgtcac tggccagtgg  23160
tccctggagg ggagggaagc acccagcctg agaaaggcaa gaaatatatt ggcttttttc  23220
ttctttcttc cttgtgttca cattcagaat ccatcactta atgccttgta tttagaaaaa  23280
aaccggggga tcacttgaga tcgtgatcat tttcaacata ggattcgaag ctgtacacat  23340
cctggtgacc ttaaaacatc tcaggttttt ataactggaa ggaaccttag agatcatggg  23400
gcacaacctt ctctttatag atgaggaaac agaaatctat tcatttatta ctcaaatatt  23460
tagggacagt tgtaggtact agaacacagt gtgaaccaga caggcaaaac cccaggccag  23520
ggagcttcca ttccagtggg gccacaggcg atgctcaggt aagcagagac tccgctgtgt  23580
gacttctggc tgtgatgggt gctgcaagga aaatccggta gagtcgaggg ttagagaggg  23640
acggaggggc aggtttaagg gggatgctca ggaaggcctt cctgaggagg tggtatttga  23700
gcagagttgt ctgtcagcca cacagtaagt gagaggggag ttccgggctt ggaagctgcc  23760
agcacagtgc tggcaagtgc tggggtggcg tcccgaggct acagaacctg agatgctgca  23820
gaagagccca cttctgcttt cctggaccac ttccttctca gcaccaggca aactccttct  23880
tctatcccct ggcacatttc tgacctgtgt atacgccccc aatttatcta accccttaa  23940
ataatctcct ctatttatgc agagcattct taccactaac tcacgacttg cacatccctt  24000
agctccctta ctcctcacaa caatcctgag atgggtcaga gaaggaggct tgcgcgtctg  24060
gtgatggggt gatttgtgca cagttacagg gctagaaatt gtcagagcca gatggaatcc  24120
aggtcctctc aatcctaatc cagtgtttct tacttcagtc ctgtggctct caaagcccag  24180
agaccagcag catcagcgat gcctgggagc ttgttaggaa tgcaaattat cagggcccac  24240
tccaggtgaa ctgggtccaa agccctggga taaggcctag caatctgtgc ttcacaagcc  24300
ctccaggtga ttccgcaggc tcaggtgtga gagctgcagc tgtcctctgg gccttctggg  24360
ctccccgccc agcttcttca gtgtgatgaa cacagcgaga atgctagatc tgcagcagct  24420
gatatcccag acaccctccc gactccctcc tggctgggtc tgatcctcct ccagactcca  24480
ggagagaacg agacataaac agaacttcag agcctgtgtt aaccctgaga tcaaggtctg  24540
cacagggtgc tgtctgagtc cagaggagtg agggacccca ccccacctgg tcagcaccag  24600
ctcctggaag caggttctca cactggttcc ctgcacaatg aaggagctca tacctgcttt  24660
tctggcttct cagaccctga ggttttcacc gaaactagac aaggggaacc tagggtcagc  24720
```

```
ctggaggcag ggtgagcttg gcgcctgcag tgcccaggcc ctgggtggtg cggctccggc  24780
caggccctgt ttagcttcct ctcccacccc cacagagggg gtgctgtcgg caccgattgc  24840
tcattttccc ctttgctttc tcttcagctc gtaaaactca agtcctgaca atgccttgat  24900
gacttccagt tggtaataaa agggagatga agataaggac aggaatttcg gggaaatttc  24960
tttccagttc cttactaatg tgacatttag atctctagta ctgtgcttct ggcatcagtg  25020
ccaaggcctt tcatgttgga gaatggaggc cggggtcacc aggttgtgcc tttatttcat  25080
gttgctggct ctgatgagct gatgctctgc tgattagcaa acgctgagcc atctgcgctt  25140
cgcagaggca cgttccagcc aacccggccc tccctgccca cttcccagga tgctttgcct  25200
tgtgggctca cctgtcttct agctcctgat ctgtatctcc acctccatcc agttccgggg  25260
ctccttatca gcactgttcc cagaactgtc catcacgatg gcaacgttct ctctgggcgc  25320
tgtccaacat gggagctcgc ctctgtgttg tcactcatgc tcattgaaca tggatttgtg  25380
tcctttacca tcaggactgg ataccccctcc tggtcctttc tgcctggggt cttagcacag  25440
ctcagaagga acctcaccat tccctctctc catctaggga attagaagat gacaggggca  25500
cagttctctg gctcaccccc agcccagtaa actcctggac atgcttcaag gcccagctca  25560
gatgttgcct cctcagtgaa ataatttata aacccaccct tctttgtcct gccttctccc  25620
tcttccctac tcactggaga gttaacaggt gatggttaag ctctgggttc aaatctcaca  25680
aggccacaca cttagctatg tgacttcagg caagttaatt aaccactctg tgcctctcgt  25740
ttcctcattt gtaaaatgga aatagtaaaa gtgcctacca gcatggcagt tgaagttaaa  25800
agaaataata tatgtgaaca cttggaaggg cgcctgacac atagtaaact ctcagtaaat  25860
actagctgct tttagtggct attcttaaca caccctcttc agtgctctgg tttcactatg  25920
ttttatgggt ccctgagatc gaaagtgtcc acaccgactc atggtcagct gtaacctgtg  25980
cctcgtgtgg ggaccaggct gccatgtgta gtctggacag tgtaggaggt ggcagagctc  26040
aggcctgttc tgccctccag cccagagagc cacgtcgtta gatgtcatgg gagactgtgg  26100
tgccccggga atctcacgaa tttgcccacg gtactcagtg tctgtccaat gctatgggag  26160
tccaggactc taggagccag ttaaggtgct gggtggccac aggtccctgg ccaaggtcca  26220
ggcctctccc ctgccacctg atcctcgaga ggccatcacg agggttgtac ttcaagaacc  26280
actatccttg agctacctag gagctgcaga atgtgcactc tgcagggctt agggcctgca  26340
gacaagatag atgcagggtg tctagttaaa ttcgaacttc agataaacaa caaataattt  26400
tttcaaataa ttgtgttcta ttcggtccct atttgggaca tatttgtact aaaaagtatt  26460
catttatctg aaattcagat tcgactgggc atctggtgct tttgtttgct aaatccaaga  26520
gcaaatttgt tctagctact tctcaacccc accttcagag aggaagcctt gatggtactg  26580
taacatcatg ctgtaagaag gggatccctt gaattgtaaa tggcactctg ataagatgag  26640
gtatggggat tgtattggtt tcctgttgct gctgtcataa attaccacaa acttagtggc  26700
ttcaaacaac acagatgcat tatcttacag ttctggaggt cacaagtctg aaagttaggg  26760
catcagcagg actgcattcc ttactgcgga gttctagaga aaaatccatt ttcctgcctc  26820
cttcagcctc cagagacacg ccacattctt tggctagtgg tctgcttcca tctccaaggc  26880
cagtgggggc ttatcaagtc tttctcacat cacatgactc tgtttcttct gcctccctct  26940
tctacattta agggaccctt gtgattacac aggggcccac ctagaaaagc caaaataatc  27000
tccttatttt aaaatcagct aatcagtggc tttaatccca tctgcgatct taattcctgt  27060
cgccatgtaa cacaaggtat tcccaggttc tgtgggttag gacgtgggtg tctttcctac  27120
cacagggcag tttctagtgt tgcctcttct ccctgcagtt cgctcatgga gtcccggacc  27180
tggcgctgaa ggacatcgcc tgcagcgagg ccctcctgga gcgcttcatc atcttcagcc  27240
agagacgcgg ggcaaagacg gtgcgctatg ccctgtgctc cctctcccag ggcaccctac  27300
agtggataga agacactctg tatgccaacg tggacttctt caagctcttc cgtgtggtaa  27360
gggaggggtt tggctgctcg ccaattgcaa ggtgattcct ggggtagcag agcctcacga  27420
attgaccttg gggagggcgt gagcctggtg ttctggacaa tccttgcaaa agctccaggc  27480
tcccagggct caaaaaatca caactgatag tatttctaga acagtggccc agggacccag  27540
aagtcactat gaggttcacc attaggtatg tggctgtggc atgtttgtgt ccactctaaa  27600
tgtggggata atccccttta cctcctctaa cagagtggta aaggaaggag gaggcctggt  27660
ttgactccct gacctgctat ttcctagcca ggtgatcatg gtaagatatt gaaccttttc  27720
tggtcccagt actcatctat aaaacaaata taatacttta cagagtggta ggaattatac  27780
aagaaaagta tacgcaaaac atttcataaa ttttaataaa tgatggcccc atgcttcttc  27840
ctctggaaat ggtctcaacc tcaatggttg gtgtttctag agagaaaaaa cgacagagaa  27900
agtttcatag tctcaaaaat ttggaaagcc ctgatctagc tcaacccttt gttctagaac  27960
tgcatcccag acagactgct tgggacctga aaatatctcc tcctttgcta gaaggataag  28020
atgagaagga attagataaa ggaggtgtag agcagaggtt ttcacactgc aaagtgcata  28080
aaaaccatca gagggccggg cgcagtggct cacgcctgta atcccagcac tttgggaggc  28140
cgaggcgggc ggatcatgag gtcaggagat agagaccatc ctggctaaca cggtgaaacc  28200
ccgtctctac taaaaaacac acacacacaa aaattagcca ggtgtggtgg cgggcgcctg  28260
taatcccagc tactgaggag gctgaggccg gagaatggcg tgaacccggg aggcggagct  28320
tgcagtgagc cgagattgcg ccactgcact ccagcctggg tgacagagca agactccgtc  28380
tcaataaaaa caaacaaaca aacaaaccaa aaaaacccat cagagaagtt ggtaaaagat  28440
gcaagtgcta aatccccacc cccaatcact gtgattcaga agaaccaggc caggcccaga  28500
atctatcctg ttaccttagg cgattctgat gaagaccatt gtaggccaca ctttcagaaa  28560
cactcaaaat tagaatcctt cagagaaggt ggcatatata atatttctag catggaatta  28620
tgtttttttt cttttgccta cattttaatt tctagaactg tgttgtaggg aatgtcagtc  28680
actaagaact tgattgagga actgtgtttt gtctgtttca tgactgctct ctcaagtccc  28740
aggaaactca ctttcagctt gtcttaaaaa gcaagctgaa ggcttttaaa aatgaagcaa  28800
catgaaataa gacaccgcag tttctggcac ggtccacgct taatcccctt caatgtgtga  28860
ctttccgtgg aaagttactc tacgattttc ccagctcgtc agggtggggc cccagagtga  28920
gtatgaaggg tcagagccta gggatgccac catcagtgag agcccaggac cccagaaaag  28980
gtctcttggc tcaccacact gtaggaaaaa taaaaagcaa tgtagtccaa atgtctctat  29040
ccaaagtttc aaaaagaact tgattttaga cacgctcctt gacttgtttt cagaatcaga  29100
cagaagagtg aggcaacaaa ggtcccttat tccaggcagc tgaataccag cacagccagg  29160
agtccagtgc tggtgtttgc agagccacca gaggctccct ctcaggtgtc cagggcccgc  29220
atgctttgta gaatgggcag aatgagcaat gtctgtgcac ctgggctttg caggcagggc  29280
ctgggtaccc aggttcgtgc aatcctctcg tcaccatgaa gggagcagca tcattcttcc  29340
cttcttgaag caccttggcc accagtatag gtaaatttac ctcccaggac atgaccattg  29400
attctgggat gtcaatgcca gagatagtag ggtaaatcgg cacctgggta aaactttcca  29460
```

```
ttggagacta gaaccaaaac tcaggacact ggcttccaaa tgtttcttta tcagacaaga  29520
aagaccaagt ctttccttac gtcttcacat gctgccttgg caaatgctag cattcacaaa  29580
ccctgggcta ccttgacctg tcacccttgc agacctcaga cgggtcctgg gggcttgctt  29640
tctcggtttc tgtatgcagg cactcaaacc tgcatcaggc acctgtgaag ggccgggcac  29700
tgtgctgagg ccaaggctcc aaatgtgaac cttccaccct cactgaactc acagccagac  29760
cagagacaag caaacaggac atttcacagc agtgcagcct agaaagggcc aacaccagca  29820
gcatttgtcc ccccgagcgg tagcttttag aagcttcccc agtgattcaa tgtgtcctac  29880
aaatgcctgg cccccactcc cagagattct gagtcagctg gcctagggtg cagccttgac  29940
ttcactgtgt taaaaagctt cccagataag tccaatgtcc ggccaagatt gagaatcact  30000
gacctagagt ttaatttacc acctcagtct ctatagacca cgcataataa tagtacccca  30060
cacacctctg agggtccaaa gaactttcat ttgatcaccc atgagaccac cgtggtgtgg  30120
agatgctttc tctctcctgt tctcttaaca aagctggtga gcgacagagc ctgcagtgga  30180
ccgggagatg gcccagagga gaaagctctg ccgtagtcgg cctcagttaa ccacggagca  30240
ccacccctac ctgctctcct ctcactcctg cttccgtctc ggtggagaaa gatccaaccg  30300
aagcaggaca catctagtct tctggtgcct ttaaaatgta cttttccatt tgacaaatgg  30360
attacactaa aaacaaaaat ttacaaaaaa aaaaaaaaaa cctgaaagaa attgcaggca  30420
ttaaaatggg actttgcctt tattgctcct gggcccatcc tatttgggtt tttagaaaaa  30480
caagcctgag gcaggcccag aaaggctcag ggcagaccct ccgatcctct gaaaggagca  30540
tcaggcaggc aggggttgct ccggggccag ggaaggggcc ccgctgggac gcggctgtta  30600
ttgcagctgg ttggcgcgca gccatgctta gctgcagtgc gggaatgctg ggccttctgt  30660
tctgggctgt ttctcatacg cacgtaggcc agtgtataaa taaggtttta ttaaatgcca  30720
aatgagttct cattaacaaa gaaagaggga aaatctcagt aaaccaccgt gacggcatct  30780
acccactttg agtcaggagc tgggggtgtg agtgcaacct ccgagacaag ggaacctgtg  30840
gagcccagag aatcggaggg gggcgctggg gttagcaccg actgagacca gctgtgtttt  30900
ctctcggttc cttggagatc agaagtgagt gttgtcatct tcaaacaatc caaaggcagt  30960
acccatggcc ttactacatc cctcccacac catcccaccc atccccgcgc gtacactcac  31020
acgctcattt gcacactatc gcacacgctc acttgcgtgc gcacacacag attggtgacc  31080
taggtggact gggagagaaa taagagccaa atgactggat tttctccaag gaaatttatt  31140
aatagcccct cttggtttca cctgaaggag cttgtcttca cctgcggcct ttgcaggctt  31200
aacgccccca gcttgaaacc cagaagctca gacttgggcc caaggtatta ttagtgccaa  31260
cactacctga aatgtttcgc acctcataaa aatggtgtgt cagtttcggg tgagaggttg  31320
ggacgcttcc catctgattt ggcccaaggc atgcatgccc ctccttctcc ttcccctcct  31380
cctccccctc ttccccctac catccttcct gttttctctc caactctggt gcacagcttt  31440
gaaatcttgc tgagaagcaa atctgtccct tctgctttga atgtttattt gtggaagttc  31500
ggcaggggaa ccgaggcggg tgccaagacc tgccatgctg ctgggaagtc tgagtctccc  31560
tcccttcccc ctcctaaatg cttgttgata gagaaaagtc agcctcctcg gcatttgggc  31620
tcacggtttt cctttgaaaa tgcttccagt gtggcatgat tcagctttct tttctgtccc  31680
ccaaccactg ctctgttgtc atttttactt ttctgattgc atttatccg tgtctctttg  31740
actacggggt ggctggacgt tgagttccag gaagaaaagg gcccaatctt ggggttctga  31800
ctacatgcgc ccatcaatgt cctgtttcat tcttggctct ggctccctga attcctgagt  31860
cactggggag aagcgtgggt ggaccgcccc ctacccagtg agagttgcca cagttgctgc  31920
tctcctgggt cattggttgc agattgttaa acttcaccta tgcatttcaa ctttcgggtg  31980
gatattgcta cgtcaagtgt ctgggaaagc ccccacagct acaggatttt acagtgaggt  32040
cccactaatg acttgatgtc atgacttcct cattctttcc aatttctccc acttctccat  32100
aagggttttg ggaaggggag aagagaaagg agtgattcct gagtgccagt accagggaac  32160
agcagggctg ttgggaggaa acaaaactaa atcaggaagg tttttgttgt tgtttttggg  32220
gggttttatg aaaatattca agccacagca aatatatttg atttatagca ttagtatttt  32280
ttctgcctgc atctacaaaa atctttacct attaccatca aaatatcctc tgggtgaatg  32340
gatttcaaca aagaagaaat aaaaatgaaa tagaagagag gccccttcgt gcacattgag  32400
cctactggct ggattgtcac ttgcctgcct tgatgtcttt tcagctccag gcaggcagta  32460
ggccagggct tattttcatg acagatcaga tgttctttta tggatttaca aagaaagaaa  32520
tactgagaag tcaaaactga agtcacttaa gacaagagca ggcccctggg aaggctgcca  32580
ttgaggataa tgagtcctgg ggtcctggcc tttgttcagt aaatacgcac taggcgccta  32640
caatgtgtgc accaatgtgt gaggcgtcag gttctctcca gggtcagttg gttttaagaa  32700
aggttttggc ttctgatatg ttttatctct acagaacagt agctcttaac ctttcttatg  32760
ggttaggatt accttcgaga atctgactac agctctagac ctgttcccta aagaaaacta  32820
agttcacagg gacacacagg atggggctca tggagcagct gaagccagac cccaggttaa  32880
tagcctttac attaaaatgt ttttctacct accactaata tgcattcttt agtaagcggt  32940
ctcaatatac accgattctt ccttaactct gtttatgaag tattcagcat cctccctgcc  33000
cccttcagca tcctccctgc ccctgagcac aggatccaat ggcgtgagga ccacaggcct  33060
gggcagctgc tggggcatac aggcatctct tagtggctga gagactgggc cctggctcta  33120
tgttggctcc taacttgctg ccatttaaag gaaatcttag cctcccatcc gtaaaatcga  33180
gaaaataaga cttgtcctac acagctcatg aaatagtaat gaaattcaca ttagagaaga  33240
gatggaaaaa cactttgaac aaaaagcatt ttgctcttat aaaagcacag cctcttttga  33300
gaggcccttt gctccccatt tctccttctt cagaccccc cagactagga gaaggtctgt  33360
ctcatggagt gaccttttgg ctgcctctag attccaagct cagttttgct ttcattaacc  33420
acagatactg ggacggacag aaaaagacct agtttctgtt gagccaaaga gtctcataac  33480
ttgtctgttc acatacccaa gagcccaccc tctagttgag acactcagtt ccctctcatt  33540
ctgggagact gcatgtctct gtgacctcct ggtagagacc gtttgacatg tcccccaacc  33600
ccccagtgat tgagtctgaa ttctccactg atgacgcatt tcctagcact cagggtgtcc  33660
cctcctggtt gccccctcac cactgaagcc cgcttcctcc cttttcattt gatgcttaac  33720
aactgtcagt ttgcaagaaa catgcttcaa atccacattc tcccagttgc ctagcaacaa  33780
cttccctccc ggataaatgt gggtttcctg tagctcagcc caggactgaa cacagcagca  33840
cacacttctg tccactgctt caactgcttt tcacctctgg tctgcatgcc ttcaagactg  33900
cagctcatcc ctcccttcag aaccttccat agcctgcaga ggccatgtct gccccaaaaa  33960
gacacattga acctgaggct acttatttac ccttgtgtta ggtatatcct caacttagaa  34020
attaatactg tttccagatt gtcttctttg aatcacagaa agtaaaacaa caaaacattc  34080
aatgcttaag acatttcatg tgcggttggg tgacatctgt ttgatgaaca catttgatcc  34140
aaagcatcag aaatactatg ccaacaagac tttttaggag gtgataaaca tgtctgttct  34200
```

```
accttaagaa aaaaatatta cacagtccca agggagagac atggttttga tcccagacaa  34260
cccaagcaga gacctcttag ggccggaatc atcttggctg ctgcctagga ccttatatca  34320
atttcttaag cacaggatca aggcctaaag gcccccttaga ctgacctcag ttagtagagg  34380
cagatccctt cacagcctta tcttccttag aggtctagtc tgaccttgaa cttcggctgg  34440
cagtgctgtc agttgtgatg tgtgacatgg aagagttatt tgttacttgg aaaattaaga  34500
gaacttattt ggcataggaa attgtgtgtg tgtgtgtgtg tgtgtgtgtg tgtgtgtgtg  34560
tgtgtgtgtg agatgatgtt tgccatttttg atctgtgact tttttttcca gaaatagttt  34620
ctcagttcca ttccaactaa acttacagtc tcttccggtt ctttgacaga aacaattcat  34680
gtgaatttga acagataata gggaaggggg aaccaaaaga agaggagagc cctgggaaag  34740
ttattttata atttatggca acctcagtca ggcaactgtg aacaggtaca tatggagggc  34800
tccctcggga ctaggcagta ttcagagatg taaggtgtga ggaccggacc ctcatcattt  34860
accattccca ctaaaaagag ctgggaagga aattgtagct gtagcaccag gcacgtaact  34920
ggagcttagt aactatttgg tgaaggaata ttattaaatt attaacaaga tggaaaaaag  34980
ggtattaacc acacaaaaat acatctcaag ctattgtttc tctgttccct ttcccccaaa  35040
ttcctagtct tgctcttatc tggctgtctc tctagtcact ctttcttgct gactctcttc  35100
acgttccttt ctccacctgg aattcctggg ccctcccctt ttactgacag acactgtcct  35160
cactctcaca gtcatcagtt tgtctcttta caaacctcag ctcaagtgtc acttccccgt  35220
ccccaggtga aactgactgc tccctccctg taagtcacca tgatgactgc tatatatagc  35280
cctcatggaa cctaaaacct caacagacac agtctctttc ctactctgtt atagtttatt  35340
tactcattaa ttaccacaac acgtattatt gagcacctac tgtgtaccat gcccagaaga  35400
taaaagacaa acaaaataaa acctattcct atgcttaatg agtttacagt ctagtggaga  35460
gatagataca ttaaaaaata acagcaaacc aaaataaaag tggtaaataa atgcactgag  35520
aaagacagga atagctagga ggggcaccta atccctaggg aaggaaagct ggaagagcat  35580
ggtgatgggg gaagaaggct ttctggagaa ggtgaggtag tttgaaatga gttgactctg  35640
gccagtaggg gtagagtgag aatggggtga gacagggtgg gttggtcatt ttgatccatt  35700
agtcctcaaa gtgataggac tagtggctaa ggactgcagg ctttacagaa gcctacaaaa  35760
ctatttgaga tttgaagttt tttttttttt ttaattggct ccaaaagaaa atgaaaaaac  35820
tttagaatta taatgaatga atattaaatg aatatttaag gaaggtaatt ttattcaact  35880
tcattgttaa atttagttaa aacaagccct tgagtttcat tcaacactgt tttatcatac  35940
cgttgatgag agaaaacaaa actgattcct ggccagggcc actgtcagcg tggggtttgc  36000
acatctttcc catgtctgct tgggttagct ccaggtactc ctgtttcccc cacatcccca  36060
agatgtgccc attagtggaa acggtgtgtc tgcatgattc caacgtgagt gagtgtgggt  36120
gtgggagtga gtgcccctgc catgggaggg catcctgtcc aggttagatt cctaccttgt  36180
gccctgagct gctgggatgg aatccagcca cccatgactc tgaactgaaa taattgggtg  36240
aataattatc ttactttta attaatcttt gaaaatgtat gtatagttca catgtatttc  36300
aatatttaat attagaagta ttttagtctt tattttgaag tttggtgatt tattgtaacc  36360
agaaacaagc tatagaaact taattttggg ccaagtgcag tggctcacac ctataatccc  36420
agcattttgg gaggccgagg cagacgcatc acttgaggtc cggagttcaa gatcagcctg  36480
gccaacatgg taaaaccctg tctctactaa aaaatacaaa aattagccag atgtggtggg  36540
cacctgtagt cccagctact tgggtggctg aagcaggaga atcacttgaa cccgggaggc  36600
ggagcagtga gcagagatcg tgccactgca ctcccaccta ggcgacagtg tgacactcca  36660
tctcaaaaaa aaaaaaaaat agaaaagaaa gaaacttaat tctggtttat atcaattagc  36720
ctgtggtaaa attggtttca ttatagccat ttcacttagt tgaagtttcc aataacctgt  36780
ggatgaatta agtgaggatt tactatattc ataaaatctt aaattccaaa gcctgtttgc  36840
agttcaggtt tttccacttt acaaacactt ctaagtattc acaatgattg cttaaaattc  36900
ataccagata aatcattaaa taagttgttc aaagtcaaat aatttcataa gtaaaaatta  36960
ggagctttta gaaaactata cctacataga cctagaccta tagatagaca gagatctgaa  37020
tagatatgga cacagatgct ttccaaagtg ttcatgtgat gtgtggtgga gtttcaagac  37080
cagagtgtgc ctggggcctg cagaagtaaa ggagaggggga tggagagaag attgtccaca  37140
tggccatggg caatctccca cccacactca agtgaggaag acaggaaaca aattcagaaa  37200
gaagagaaaa taatcaaaac tgatgggagc ttgtgactga tttacttatg cgcagcctcc  37260
ctggagacat gagtgtggct gttccttagg ttgtgcctct gggctcctac cccctcttag  37320
atgccttcct attatctagg acctggttgc tttttgtctg catagcttct ttggattcca  37380
gtctttgatg ccagcttcct cctaaagtag cctttcagat gtcccttggt taccctctgc  37440
tatctaaggg ctcatcctac cccacactca ttcccagcac caatttctgg atctccaggc  37500
tggagattta gacaatggga tggaagaac ccatgatggg tcccagacag aaagtggtgc  37560
cagccacaga aagggcacac aggcacagaa gttggtttgg ggtaagacga tgtggtcagt  37620
tcagaacacg ctggatctag gcagatgccc agcagacagt tggatatgta agtctgaagc  37680
tctggggaga ggtctaggtt ggaggtacag atttagaagt catcaacaaa aaggtagcag  37740
attaaatgat aaaggaaatg agactatccg gggagtgtgc agagtgagag gagcaaggga  37800
ggcccttggg aacctcagca cttcagggga aggtagaggt acagttgctg gtgggaaagg  37860
cagagaagta gcaaagcaaa ccaggcaaaa gcagtgtcac agacgaccag ggaggaaaag  37920
gacatgatca aaatgttgag aaaagcagag aggtttgaaa atacaagaag caaaaatgtc  37980
cactagactt aaaaaccagg agaaaactgg ggggttcttg ataaagcatc ttagtaggat  38040
ggtgagggta gaagccaggg aagtgttggt gaggaagtga agtcactgat tacggactat  38100
gcttaaaaga atgtgggaat gaagggtgga agagagaaat tagactgtag ctagggagac  38160
ataagcgatc agaggtagat tctttctctc ctgtgggaga atcttgcacg tatacacagc  38220
atgacgacag tgatggaagg gctggcgaag cctcagggag actcttggag gtaaacccca  38280
tgaagggagg actttgtttc attcactgcc gtgtccccag cacctggcac aatagcagac  38340
actcaataca tatttgtcaa atgtgggatt ttatcattta gaaactgcac ctggctgtga  38400
gtaacaaaag tcagagaaac cgtgggtttc atttttctcc ccaggcagag tctggagctg  38460
ggtcctccaa gaggggtttg gagcaccaca ggtttcctca agacccccag gctgccctgt  38520
gtttccctcc ttcatcccca gcatatgcct gtcatctggt gacctccaaa cacctgtgct  38580
gcctcctcca gcacatccat gttgcaggca gggaccaggc aaagggcaga ggggcctact  38640
tcaaaagacc atttccagaa accccatcct atgacttctc ctggtgtctt ggttaccatt  38700
gtgccatagg ctcaccctgt atgcatggga ggctgggcca ggcattatga cttttagcaa  38760
tattgcatag ataagcatca atctttgtca ctgtgacgaa gcctagtcac tcagtgctag  38820
gcaaggttaa tggaatgggt tggtgtgtgc attattcttg aggtctttct tatgcttcat  38880
gttatacatt tattaggacg tttaggcaac agggggataa aaatgaagag gagatgcatg  38940
```

```
ctatgatctg aatgtttgca tcctccccaa aattcatatg ttgaaatctt catccccaag  39000
atgatggcat taggaggtgg ggcctttcgg aggcaattag gtcatgactg ggattagtgc  39060
ccttgtaaaa ccccagaaag ccagcttgcc gcttccacca tatgaagaca cagagagaag  39120
atgccatcta cgaatcagga aatgagcccg caccatgcaa taaacctgct ggagccttga  39180
tcttagactt cccagctgcc agatctgtgg gaaatagatt tctgttgttt acccagctta  39240
tggtattttg ttgtagcagc cagagtgaac taagacagtg ctgatctcgt attcttggag  39300
ggaaccctta gtctttaggg aaagcaaagc caccatttgg ggcagggtgt tctccaagtg  39360
ctgccacata tgctgatgtg gttaaactgc aaactatggt aaaaatgtgg aggtctgtgg  39420
aattgtcaat caggaaaaag atataaaaag aagttaaagt cttcgtgctt ctggaaggat  39480
atgtgccaaa ttgttaacat tgattatcct tgggtagaga tgtggggaag tttgcagaga  39540
cagttttgcc ttgtacttta tataagtaaa cagctactac ttcgttgtct taaaaaaaaa  39600
aaacagccta tgtgctcttc atgtgactca gaactaccta ggcaatacga ttaattgaat  39660
tagtaaaatt gagtgattat gaattttcag gaagtcatta atttaccact tctttattac  39720
atccacttct aacaggactt caatataggg gaatttgact tcaagataaa aagaccaaat  39780
ttatttaccc ttttaaaaaa agacaactta aaagcagact tgtcttacag aaccttcctt  39840
agttggacat cgatgagtgt acagaaaatg caatggataa aaagcttggt gatacaaaga  39900
taaaaagtgg ggtcctgtcc ttaatgaaca taccatttca tggagtatca ggtgtataaa  39960
caattataat caatctgctt gttattctga taagatcatt tactcacaca tcaaatactg  40020
agtgcccacc acatgcccag catacctaga agtcatccag tatgatttct gtctacatgg  40080
agcatagagt cttacagggg agatagatga caagtaaaca ccagaataat taccaatggt  40140
gaagagcaca aggaaggaaa cagaactcct aaagagagcg tggctgggca ggggtgagca  40200
agaggcatag aaaaaggggc atctaaatct acttgggagg aagctgtttc tcacataggt  40260
catcatgtta ggaatgagac ttgagggatg agtagaagtt tgccaggcaa agaaggaatg  40320
ggggggaata gagagcagag ctaggggcag gagacagctg acgtgtgagc agacataaaa  40380
agaagtccac tgtggcagca gagaagcagg agagaaggca agtgagggag ccaggcacca  40440
gctcacagag gtcatgtgtg tcaaaacgta gtaatggcct tctcttctgg agacagtagg  40500
gagccatgga agatgtttga gcagggaaag cgacatgact ggattggcct gttgggtaac  40560
tcagaccaca atgcattgga agggaggggg ctagaggcaa ggggactggc aagaaggcca  40620
gtcctttttc tatgcctatt ttgatgaaat attctagaag ggaagtgaac aaaggtagtc  40680
ctagagagga agaacaaaac agataggata cttccttagt atttgctcat tcgacaattt  40740
atttttgcat atacactaaa acctttttta ttattaaaac gttttattgt aggaaaaaag  40800
tatgaaagta gagtgaataa taaaatgagc tcccatggat ctatcaccca gcttcaacta  40860
ttatcaatat ttggctgttc ttgttttaac tgttctccac cttttttcc tgaagttttt  40920
ttgaagcaaa tcacagacaa catatcattt caccatatgt acttccctct gtatctctaa  40980
catgtaagaa cttgttttaa caaaatcacc atgctatgat catacccaac aaaatttatc  41040
ataatgtctt aataatacct aatacccatt tcatgtccac tttcccccaa ttgctacagc  41100
tggtttgttc agatcagaat caaaatccac ctgtggccat tttactgcta tgtctctcag  41160
gtctcttttc atctctaata atctcagggg agacaggagg gaggacgggc aggacttggg  41220
gctaacttgc ttatcgacac acagttttgc ctacttgctt cctcccttca cacccactct  41280
tcttctcagc cccacccttg tatggaaaaa acagaaatta aagtgctttg cccagcaccc  41340
actgaagcta tttcgaagga gtttgaagag tactcccggc aagacaaatg cctcggtcca  41400
gtgctcaggt caaagagggg agacgcttct cagtgatgtg gtgtcaatag cagcttagtt  41460
gttctttcct ctggaaaatt ctacccatct gctttgtaac tcccatacct aacaaggcct  41520
tttatttcac aattagaaaa taagcctgaa atatgaatgc tgcctgagtg tacctacatt  41580
tattctagag tttcagggtc aaaaagaata caaggacctc tgcatctaca gccaagagga  41640
gaggggcaaa gacacacagc tacaaatgag aacctggctg gtcaaagcct aactccacct  41700
gtttgtcagc actgatgcaa gttaggtcag cccaatgatc atttaggaga actgtgctgg  41760
caaataaaaa gcagaggctt ttggtcccca gatacttgga tgagaattac aagtccagct  41820
ggttaaaagg cacatgccca gtgctcactt cacacctact caggaagcac acttgagttg  41880
gaaaaccact gtctttacac ttagaactca gtcctacatg actcctctag gatcagtgat  41940
tccatcagtt ttgaaacatg aagcatgaag tcaaacagga catgaccttg gtttccagaa  42000
aaccagatgt tcacatcagt ctctggagct tggaggcagc acacctgggg acttccacat  42060
cccctgccga ggtggcaaaa gcaggagcag tggtgagttc acatgggctg ggggtttcctg  42120
aacactgctg gcaattggag aatctgcaag ggaacttctc cgactcctac cagcagctgc  42180
tttaaaataa aggtgatgta gctggtcaaa tcctccatga gagagcagtg ttgaatggag  42240
gaagagacac aacctgtctg aaaatggcac aaaggaagaa agatgtaaac aatgacgaga  42300
agactgcagt gtctacaaag ctccgaggtg aacagatggg caccccaggc ccgcagcact  42360
tccttcagtc tctgccagct gcactctgtt ttccttcctc caggaatctt gtttggtgtc  42420
actaaaacag caattagaat cactttgaaa tagtgatagt atttaatata actatgaaac  42480
tatctgtgat tgacaagtgc agcaaggagt cttggaatga gagcctttat tttttcaatt  42540
aaataaaaga gttttttgtt tctaaaagta atcttgcaga aaagatcctg cgatcagaaa  42600
gaaggagggg gggagttttc aaacatatag gagatcagac tgtgcctatg tgtgtatata  42660
cctacaaaca tatatatatt taaaaaattg ttttactgtc aattacagct tcccacactc  42720
ctagacagcc gttctcaagg tatcaatctg agatcttggg gaggaatatt atctgatatg  42780
tcaccaagaa ttcaagaggt gagtagcctg atggtagtaa ttataatttc attatgtctt  42840
tccaccattt accccactta tgtcaaataa tttaattgta tttcaaacct gttcaaggaa  42900
aagtacattt gatctttcca tctagcaatt tcaaagcacc tgttcacatc ccaaattatc  42960
tgtgctctta agtaagaggc agaaagaaag gaaccaccct tctgatttca catcaaaaaa  43020
gaaatgccac tggcaataag caacttgcct ggtgtggcat aaatcatcag aagacttaca  43080
gttgaatcta agtcttttca gtactgaggt ggttcattat tctgttacag tcttaaaatt  43140
cacataaata tatactgcca ataataatag catacacctt tatagcttac aggcactctt  43200
cttctaagtg ttttacctat gttggcttat ttcatcataa agaaaacaat ggacttttgt  43260
gttgttttgt aaaaagatgc gcacatttta attaacatct gattgcacaa gtctcctccc  43320
atatagaaat ggattcttcc acgcaataga taagaggtgc tggggatatg atgatgaaca  43380
cacagatttg gtcatgaccc tgtgggaaag agagatggga aaaaaacaat tctcttcaag  43440
tgtgatgagt gttacgaaag ggagggaaaa gttgaaacag gttttttttcc aaactttttct  43500
ccctccatta ttcgcagctg acttgggctc caccaacctg gaaaactgca tggttggaat  43560
ctgtctttat aaaacgcatc tcaacctggg ccgagtatgc acactgatgt gggaaagtta  43620
gagaagagcc cattgtacta atgctcacct gctacagtgg gagtctctgt taaacagtct  43680
```

```
tttcttcata gcattaaaaa aatttatatc actacaataa ggttgaaatt gatagagaat  43740
gtacaaacaa tccccaaagt atatcaacac tcttagttct gagtagaagt tccagaaggc  43800
ttcttgactg tctagatagc aagtctaatc atttgtgaac taagttaaag cagaaggccc  43860
agtttatatg aattggtatt acaccatttg acctgagaac agccccttca tctctgagtg  43920
ctttgactaa atgagcaaca taataatagt aataacccct tacaagatgt cataagactc  43980
actgttgttg aagcaatttg agattttgac tttattgaag catagatggt gattataggc  44040
atgactcact gtgtggattc tccctgggct catcagtttc agagggcaag tgttggcatg  44100
tggacaaaga gagggatgac acgtaaacat ggcttattgc aatggggaaa tattttcagt  44160
ctcactgatt gaatcctaat ggttttataa attccccagt accactgaaa gcaaagcaag  44220
taatcaggtg tgttttagga ataaaagcag cattatttta atttcgtatt ttcccctaaa  44280
gcaaagccaa atggcattat gggagccaag ctactggcag ctccaccagc cttctcctga  44340
gttctcggca ttacagatct accctcaaag gatgaggcca gcaagcacca cagggtgccc  44400
acatggagaa gagaaggcca ccaacctcct cttagctggc acagaattga aaaagtgttt  44460
ttccaggaat ggatacttca tctgttctgt atttgctaga attttaaaac gcacacacag  44520
acacacacag gcgtgcacac acacacgcac acacacacga gaaaaccaca aaccacacat  44580
ttcaaggaaa tggaagaatt cattggtaaa attaagctaa taagattatt ttccaaatat  44640
aagaaactaa attttagact atttagccaa agaaatttgc tctgatcttg cttttctaca  44700
acagaatcat tccccaatca ttttatttcc ctctttttct ccccagtatc cccatcttgg  44760
tgggacaaca gaacccaaga actggcttaa cagtaaaata ttttctgcat ttgcccaagg  44820
acacattccc aacgaattca aataaaggag actagaagaa gagaggctat actacagtgc  44880
tctaggggtc actctgtgat ttgttgttgt tgttgttgtt gttttgagac ggagtattgc  44940
tcagtcgccc aggctggagt gcagtggcac gatgtctact cactgtaagc tctgcccccc  45000
aggttcacgc cattctcctg cctcagcctc ccgaatagct gggagtacag gggcccgcca  45060
ccatgtccgg ctaatttttt tgtattttta atagagacgg ggtttcacca tgttcgccag  45120
gatggtctcg atctcctgac ctcgtgatcc gcccgcctcg gcctcccaaa gtgctaggat  45180
tacaggcatg agccactgcg cccggccact ctgtgatttt ctttaaggct catcctagta  45240
ttctcctagt ccctaagtag atggcagtag gttttgtttt ttgtttttcg cagctggatt  45300
aaggattgct gagaatatat ggatgttttc ttttaaatgt ggaagtcaaa ccaaacgttg  45360
gagcattggc ctcacagcag attatgactc tagctgcctt aaaataacct gaagactttg  45420
ccttgcccta gtttatccat cggccgagta tgcaggactt gctgtgggtg accaggcccc  45480
tcatgcagaa tggtggtcca gagaccttta caaagctgat gggcatcctg tctgacctcc  45540
tgtgtggcta ccccgaggga ggtggctctc gggtgctctc cttcaactgg tatgaagaca  45600
ataactataa ggcctttctg gggattgact ccacaaggaa ggatcctatc tattcttatg  45660
acagaagaac aagtaagttt tctgagtcct gcttataaat tggcctctca tgttggttaa  45720
gttgatggtt taacacttct aggtgaaacc aaacctgggg ttgcatctgt cttgtcttgc  45780
tgagtggcct taggtaaaga gacttctccc agaaagtcca cttccccttg cagaaagggg  45840
gcattgctta taagcaattc tggacatgaa ccacagaaag aactgaggcc cacttggaaa  45900
gggaacagag gggccatttc ccactgatgt aattgaacta gggctaagtt caagaggaag  45960
agaatgatcc gcaaggaagc aacccagagt tccaggtgaa gctcaggtca gaagggccct  46020
ggcaagtaaa cacggctgtg ggatgctttt acaaacacaa tatcgtgaaa atctatgtgt  46080
gtagtactga attacattcc aaatggcaaa ttcctggcaa atcatcttcc ccacctttca  46140
ctattttttt ttttttggtc ttctatgggg taaaggagga tggggtgggg aagaaatgta  46200
actggctgcc cctctagtta aaaactgaaa agaggcagca agggacatgc caaaagtagt  46260
tggactctaa gatagctaca cacaacaaag cagctaagca gctaattgaa gggaaattac  46320
tgaggctcaa gctgagattc caagcggggg ccttgtttgg cctctcagtc cctttcatct  46380
gagaaaggcc tcagttccta gcagtaatca gaggcaggct tctcagcctc cttctcctaa  46440
agcagaataa accacagggc aagtcgcatc ctttgtttct ctgatgaggc cattactgag  46500
agtcactgtg gcattttgct actaatgatg agcttgttat tggtggggta cagcctatta  46560
atttaggtta ttcatcaaat cctccagcat ggagttgaat gagacatgtg atgtggatac  46620
actaatgact atattgagtt acaagcaatg gggagtttct gtaaaatctg tcccttgtct  46680
cctggcagca tccttttgta atgcattgat ccagagcctg gagtcaaatc ctttaaccaa  46740
aatcgcttgg agggcggcaa agcctttgct gatgggaaaa atcctgtaca ctcctgattc  46800
acctgcagca cgaaggatac tgaagaatgt aagatcccag ctgggcttgc cttgtgtacc  46860
ctggacctcc cagaagtgtg tgtgtgtgtg tgtgtgtgtg agagagatgt gccttcctgg  46920
tagcacatct catgtttgtt ttttgctaag tggactcttg cgtttcctcc cccatccaca  46980
gtcatcactg gaatgctttg cttcagtgcc cctgcctggg ccctcccctc tctactgcag  47040
cctacaatga ggtttttcttt cccattgctt gaattatatc cctaatggaa gggttcacaa  47100
ttctctgaat cctggctact cagataaaga cagggaggaa gggaggaagg gtattttctc  47160
ccagggggtc caaatctagc tttaacgagg gaggttctga gaaaataata tcatcaatat  47220
tacatggact tctgagatac taagaaatta gattctgtca gcccaggaag ttgggagatg  47280
gtgaattgtt ctgggaaata gcaatagact gagaaaataa aaacacttcc ttgaaaagcc  47340
tttccctaac actaagtgat aggggcagaa aagacacaac caaaagttct ctctcacttt  47400
tctctctgtt cgtgtctctg tcttgatctc tgtctggttt taggccaact caacttttga  47460
agaactggaa cacgttagga agttggtcaa agcctgggaa gaagtagggc cccagatctg  47520
gtacttcttt gacaacagca cacagatgaa catgatcaga gtaagggggg ttggaggatg  47580
gggaggggag gggaggagga agcggtgggg gcaagaaagt tccacttgtt tccttttccc  47640
aggaaagagt taatcgctat tggagttaga tcaaaataca acaagcaggc cccaaaggcc  47700
ttcattccaa gcagtcacca agtggggtca ctgactttgg atgagaaata tgtttcttga  47760
attctgggag aagtctaaaa gctgccacaa gaccagtggc ttcctggagt ttcctacttt  47820
tatgaattca ctcaagggcc tcaaattcaa agaggcatct ccccaagggg ccagctctgt  47880
aactccaaag atggtggaat gtgtttgtct ggtctcattt tcagctttgc aaaatgaaga  47940
caagagttct atatatcagg gacactcaaa agaaaacaaa aatatccata agcaaaagaa  48000
agctttttat acaccatatt caatgacccc catctggccc ctcctttgcc cctacacatc  48060
ttccctctat tctagagacc catggacttg gggaaatggg atatagatag gtatgtttca  48120
tagtggaaca agctcaccag ctcttcaggg agccttagca tctctatcct caatcactaa  48180
aaattagaaa tggctgaaga acaagaccaa agatcctatg gaatttctaa gcagagcagt  48240
gactgtattt cttcttccca aggataccct ggggaaccca acagtaaaag actttttgaa  48300
taggcagctt ggtgaagaag gtattactgc tgaagccatc ctaaacttcc tctacaaggg  48360
ccctcgggaa agccaggctg acgacatggc caacttcgac tggagggaca tatttaacat  48420
```

-continued

```
cactgatcgc accctccgcc tggtcaatca atacctggag gtaaggggct gcaagcccca  48480
cagtgggccc cttgaagata gccccatgag tggggccaga gctcccttag caagtcaagt  48540
ggtcttgaat ttaagctttc attttcccca ctgaagaaac aagaatccct acatcccctg  48600
tacagttctc attctctaac agcttatcca tacttaaaac ttatctatgc tgaaaacggt  48660
ttcctcttca catctcctac ttctcatgct gggcacctcc tcctgtagcc ccctttaagc  48720
atctgtgtct gtcctcaacc ctcttctgtc tgacattgct tgagtggcca tctatggcca  48780
gtgtcccctc aaccccacag tccattgctt gctggacact cctgccctca agttctacaa  48840
gcacatcagc ctcaacatgt cccctccaaa aactgtatgt tctccttgcc catagaacat  48900
atccttctcc tatatttcct atcctaatta acgtcctcag catttgcccg aattctcaag  48960
tgagggattt cagggtcatc cctaattttc cttcttcacc ctccacacag tagctgtcac  49020
ttactgagtg ttactttatg ccaagtactg tgccaactgc ttttacacac atatgcttca  49080
tttaattctc acagctccat gaggcttgca ccattatcat tgccaatttg cagatgagaa  49140
gccagggctt aaagaggtta aataagatcc cacgcatgac cattaagagg agcgaacagg  49200
atccagctct gggggtgcct gagttcagag cctgcctttc tgatttctct taccaagctt  49260
tgtctcctct ccctcctaaa tatctctcaa ctctgcctct tgcattccag gctctctgag  49320
gactagaggc cttgtcatct ctgcgccagc ccattccaag ggcttccttc ctggaatcca  49380
gggtccagcc tctgttggcc caggcatttc tctacactgg caccagagtt acattccgca  49440
cacctgctta cgttgctctc tcacttaaaa tcttaatgac tcgacccccca aataacacag  49500
gtcccttcca aatctgtcct accccacctt cccagccctt gctcaactct gctacctggc  49560
cctttcacgc ctacaggcat tcccattcca tgacctcttg ggattctacc ctttgcaaat  49620
gctgttttca ttgcccattt attagagcgc ttttggtcac aagcttttttg cttaaccaaa  49680
aagaaagcat ttattggtgg acataaataa tgaagttcag gaggatccaa gagttggaag  49740
ccaccatgag accccctgtgt ccttccacct cacttttcta ctcgcctctg ctcagcttca  49800
tctctggcca ggccctctcc tctgctgatg ccctagctgc ttacagccct tagcagtcat  49860
ctatacacca aaaatccctt tcccatagca gaagcaatgc tcctagagag tttccctgtt  49920
ggtctggctc ctgtacccac ccctgtgtac tctgattggg aggcctgggt cagctgccca  49980
ccatggggcc atttctatga gcaggattac tgtgaagtgg aggaagatgt ttccccaaaa  50040
gaagaaacac aaggtagaaa agtgtatgtc caccaatgcc tgaaatgact gtccctttcc  50100
tcatctgctg agcttctact cattcattct ttgagactca gcactcagct cttaaatgtc  50160
acttctgctt tgatggaggt ttagtcattc actcctctgt gcttcctggc cctctcttca  50220
cacctctctc agacccctct cccagataga ttagagttgg ctgttgacat gtccatctct  50280
ggctgggcag ctaaactgga gttatttaga atcagggagc acatgtcagt cattttcaaa  50340
ttctcaacct catactccca gtaaatgact ccatctaagg gtggaccact cttgcccatg  50400
ggccaggtct gggtctgtgt catctagaac tgttggaagg taggggcttc tgtgagcagt  50460
aggagaggga ataaactcga gggccctcgg gagcatgccc tcttgtctca gacttgtgag  50520
tcctgaggat aacaaactag tgaagaaaag cctcgttcta tctgtcacct ggtgctcttg  50580
aggactttct gttgccctgg tgccaccaca attttccaga gtgtgtgacc ctcgctctcc  50640
aaactctgga agtggcagcc gaggctcccc agtggccttt cagaaggtgc cagtcatgac  50700
agcagcacca aactgcaggc aactactaag cgatcaccaa cttgtctgaa gataagaatg  50760
accttgaatg cattttataa aacaggattt tttttttaat ttttagattt tctttcttta  50820
ttttacctta agttctggga tacaagtgca gaatgtgtag gtttgttaca taggtatatg  50880
tgtgccatgg tggtttgctg cacttgtcaa cccatcatct aggttttaag ccccacatgc  50940
attagctatt tgtcctaatg ctctccctcg cctcgcccct accccacccc aacaggctcc  51000
ggtgtgtgat gttcccctcc ctgtgtccat gtgttctcat tgttcagctt ccacttacaa  51060
gtgagaacat gtggtgttta gttttctgtt cctgtgttag tttgctgagg atgatggctt  51120
ccagcttctt ccatgtccct gcaaaggaca tgatctcatt cctttttatg gctgcatagt  51180
attctatggt gtatatgtac catattttcc ttatccagcc tatcactgat gggcatttgg  51240
attggttcca tgtctttgca attgtaaaca tacatgtgca tgtattttta tagtagaatg  51300
atttatattc ctttggttat atacccagta atgggattgc ctggtcaaat tgtatttctg  51360
gttctagatc cttgaggaat cacactatct tccacaatgg ttgaactaat ttacattccc  51420
accaacagtg taaaagcctt cctatttctc aacagcctca ccagcatcta ttgtttcttg  51480
acattttaat aatcaccatt ctgactggca tgagatgata gatacccatt tgtcagatgg  51540
gtagattaca aaaatttttct ctcattctgc aggttgcctg ttcacgctaa tgatagtttc  51600
ttttgctgtg cagaagctct ttagcctaat tagatccatt tttcaatttt ggcttttgtt  51660
gcaattgctt ttggtgtttt agtcatgaag tctttgccca tgcgtatgtc ctgagtggta  51720
ttgcctaggc tttcttctag ttttcatgat tttagatttt acatttaagt ctttaatcca  51780
gcttgagtta atttttgtat aaggtgtaag gaagggatcc agtttaagtt ttctacatat  51840
ggctagccag ttttcccaac accatttatt aaatagggaa tcctttcccc attgcttgtg  51900
tgtgtcaggt ttggcaaaga tcaggtggtt gtagatgtgt ggtgctattt ctgaagcctc  51960
tgttctgttc cattggtcta tgtgtctgtt tacaaaacag attcttaagc atcaacccag  52020
atcgactggc tcagaatttc cagggaagag gcctggttat ctgcatgttt acagacctat  52080
tagatttgtg ggacctgcag ttcccttgta cagttagtta ctcaattaac atctccctcc  52140
tctcatggtg cctctacctg ctaagccctt attcccagcc aggcccacca ccatccaccc  52200
actgctgtta taacataagc aggacctgtg cgaggggggtg tggacggagg agagaggctc  52260
tgttgcttca tttgtgcagc atggagttca gtggttctca caatgttttt gcaaagtata  52320
taaagaatac tccttgtcta cttgacattc gtatcgtgac ataaatgtct tgttttccag  52380
aaggattatt ttttccaagc agcttgttcc taatgcagcc ccaggcacca aacagatact  52440
taaaatatat taattgctta aatggttaag aattcagtct ctggacccac actgcctggg  52500
ttcaaattcc tattatctgt gcccagtttc caagtctata aaatagggat attaatagca  52560
cttacctaat aggctcgtta tgagaattaa atgagctaat tcatgcaaag cactgacata  52620
tagtaagcac ttaataaata ttagcttttt aacaaaatac aagccaaaaa acactgctta  52680
ggagaggaaa tgatgttagt gcctcctgta aataggccca gcctccaagc tggtgctcct  52740
ctaggaatca caacgctgca aatcacatcc tccggggccg ccaggacttc acgagggcct  52800
ctgagcagag gggtatgatg ggagcagaag cccagcagct gtgatgatgt ggtttctgat  52860
cttcctgccc ttggggtggg ggaggaggaa agcaaggggc aatgaacaga aaggagaaga  52920
tagcggggag gaaatgtgtg aggaagaaac acatcactgt ggcttgtcct ggatttttct  52980
gcttctgttc tcgtgttttg ggaagtctgg aggagacttg aaaatcattc atgtccccac  53040
cctgaggatg gcttagtagc agagaggcca tgaaaactct ttgctgatgg ctctgaaagc  53100
aaggatgttg cttcactggg ctgctgaagg cctgcctggg ggttctgagc agagagtaca  53160
```

```
ggcccctccc aggagggcgg cctaaccacc atgctggcat ttctgtggac catggtctgc  53220
tgtctcagac cccctccaca atagggtctg caatctcatt caccccataa atacattctg  53280
tctttcctct gatcccctcc cattagcagg gggaaataaa tggaagtcag acggcccagt  53340
tagaaggcag gcagtggagt aggaaaatag atgatggtgg tttggggagc ctcacatcac  53400
tcatggggag acattcattc ccatgggcct tccaatcacc cttttctcca aatctaagga  53460
cacaggacaa atgggtcctc atacaggcaa atatcttaaa ctggtatgtg tattcattta  53520
tagttctaat ttatatgtgt ctttattcac atatattttg cttctggaga aaagctcaat  53580
tagaaaaatt aatacattat tcttcttatt gcccttcagc taaaacaagc atacacaccc  53640
ctcccctttg gattttttgt ttagcaaaag gttaggcctg gcacagatga aatactattc  53700
agagttcaca gtgtattttc atttcataat atatttgatt ttcaggtctt gaatttcaca  53760
tcaggaagct gatataggaa gctgaattca gccagatttt aatacgaaaa tacctctgat  53820
caaggcataa aattgtactt taaccagtaa ccactgtatt tctctaagct gtgaaaaaac  53880
atgcattcat taactgcttt ttcctctgct gtcaacacag tcaatacatg tgcataactc  53940
cttattgtct acatggtgat tatcttgctg atgaattctc aaaggccaga gatttggact  54000
attttttctc tgtaaccttg catgttcctg gccacatgcc accaccaccc aaacagaatg  54060
tacgcaggga atgtattttt caggataacc taagaaaaaa taggattaag aagataaagc  54120
tgctgatcat gtaatgtact ttagactcag atatataaat atttgtgaat tatctgtcct  54180
atttctttct tctattaatt cattgactct agatgtgcat tggaaggcta gggagaaatc  54240
aggggatcgt gagaaagagc acagaagtct gcatcacaca aacaatatta tttcaagagc  54300
catgaactag atcctaagca actcataggc aatgacctca tttcatacct ctagtctcta  54360
agaaacatat aactggcctg aggaaggaaa atgtgggcaa ggggtagacc ggggtcatgg  54420
gtggaggtcc aaatagtaat caatggagct catagggtgg actgatattg aagctgctat  54480
gagccagcca catgctgggc actgttacat gtcatctcat gcaatactcc caattacctg  54540
cctagtaagc ataattgtca ttttatagaa ttaaaaacag actcaaagag gttgacagtc  54600
taatgtaaca caacagctaa atgggggatc tggaattata atccagagct gcctggctct  54660
gatgagaaag ctctttctgc tgtcatatgc agcccacatt aatagggggc tcagaaagta  54720
ttctctggat aaattatata atgaatccaa tgaaggaaga cattatttta taatatgcag  54780
cataataggc actattatga ttggattttc ctgcttgaaa gtagctagat tagagtagga  54840
aaccaaaaag atgtgaattc attcagtcat tcatgcattt gcatggattg agctacctac  54900
atttgaataa atgctgttaa tccctgattc cttggaagct cacattggag agataagcat  54960
gtcattaaat aatgccataa tagtggtatc tcagaggact agcagaacat aattcaatct  55020
gacagagtag aaacagattg tacaaatcca attcaaaaca tcataaatcc tctaagcact  55080
gtcaattctt cctccaaatt atctctgaaa ttcctccttc tttcccattt atggcctcca  55140
tttacagaag cgtgtactgt ctctcttagc tgtttgccag gccgccagtc tcttgctgtt  55200
cagctctcaa ctgcttccag caagatcttt ctaaaatccc aggcttgcca agacttagcg  55260
cccacagctc cacagtgact cctcattgct gttaaggtaa aggccttccc agtctagccc  55320
ttcatgcttc ttccatgttc tatgggactg ccccaggctt cccacctggt accactgagc  55380
ctttccatcc ttcccccact cgactgccag gtcaacaccc acacccacgc ttcaggactc  55440
aggtcctatg tttcgggcct tcttctgtgc accattccct tccctgtagc ccttgatcat  55500
gatttgttta tacgcctccg caccttcatg gccctgaacc cctcaagggc cgaaactgcc  55560
ttacttttct ttttgacttc ccaacttacc ttagtggagc tgtagtcaca tagaatagac  55620
gctcataaat gcttctctgg gctgtaaagg ttgaattttc cagctaagca aggaagaaag  55680
acaatttcag gcaggaggaa gggcataagc aaagtgcaga gatgtgaagc tcaagagaaa  55740
tggatgggct gggcagaggt gtggctgcag catcagggga gaagaagtag tgcctggagt  55800
cagcaggcac ggcttgcaaa agcttcacct ataggtgaaa ggacaccatc tcttgcacca  55860
ataggctctg tgattggagg caactttgct gttttactgc cagaaaactg aggatgataa  55920
cccaaactgc agttcaagtg gcattcactg gtgtggctga aatgggtgtt tgtggccaga  55980
atgtggtctg attggtcagt gcccagctct gttgattagc agatgttttg aatatagtag  56040
catccatgtg cccaagttgt tgggatgatt caacaagaaa ctttaagagc tcaagtgccc  56100
tgcagttgtc agccaggtga ttctcttcct ttggacccag ttagacgcag gcattacctc  56160
gtggctttgc cccagtgtga atctttgtcc tccaacttga tctttttatt tgtttcatta  56220
ttgtatttaa gttgtttatt ttagagacag acatttttta acagctgtgc atttcctgtc  56280
cctttgtttt ccagtcgtca tgtgtttcct tactctctgt gggtgaacgt ttcagatgtc  56340
tgtttgcggt gcccagcgtg caagataaaa tttattgcag tgccttcggc ctctaactca  56400
ccattccaac caattcagat agcccaaggc tgttttatcc agtggatttt tccatgtagt  56460
gggaaataaa tcttgaatgt tactgtttag attagccagg aaactcattc tgggatgttt  56520
gcccacatcc attggcattt ctcaaaagga accccaggtg tctaccttga caccagcagg  56580
gccacttgag ccctccgctg gcattcatcg cccgctttgt tctcagcctg agtttaggag  56640
ttacagatgt gagaggcggg attatacagc caacatctct aagcgggcag tggctccctt  56700
accctcgaag acctcactcc tagcacgtcc tggatgtatt cgtcaaaata tgtcctctta  56760
tgccacgtca gcacagggtt gctccccact ttgatcatca agtttaaaca aaaggaaaga  56820
ttttctttct ttctctgcct ctactggaca tcatttccca cctaacagat aatttaatgt  56880
atctgttact gaatgtgttt gaattacaga cagagaggtc acagttaaag aaggaagcct  56940
gctgctactg cagcttgtcc tcccaaggag gtgtttgatt tagctgtgta aacaaatgac  57000
tgcattctcc agaggtcctg aacacagctg cctgcgctgg agagggctca aacctcttcc  57060
gccagggtga actctgcttc ctggtgagtg ccagcaaaac aaccaacaaa gagctgtagg  57120
acttgtgtgg acttcaaatg gtggtggtcc tgccacttgg gctcagccac agcagttagg  57180
aaactaaagg ggaggaggaa agccctttcc ttgctttatt gtcattggct gtcatagggc  57240
attacaatgg ttctctttga gattctgagc tccggctata acatttgccc agaatctgcc  57300
tctgaggcct taagacactg tgtttttatt cagcaaagat gccctttgac tccttttccc  57360
actagtggtg ctaggtttga gcaccttaca ctggcccctt acaatagcca gttcttgtct  57420
acctacattc ttccctaaca ttcatgattg catagttact cttagtgtag aagcagacag  57480
cttttacaca tagactccat ggccgtagcc tcatagaacc tactatattc taacttgcaa  57540
gctaatcaga ccaaatatat caaaatcaaa aacctctgct gagagtttat tcattcatct  57600
ctgtctccca aacgtactta tgtacatacg tgcactaata tacatgtcca ttagccaaga  57660
ttttgatttc agggatcaaa gcaagtacca atagggaatg aggtcacttg ctgcatggca  57720
ggtggcttcc ccatgagaat gcaaggccac ctcatgactc atacttcaga gggtgaccca  57780
ggaacttctg attcatgtcc aaagcagctt ctacaattgc tctaccttga tctagggaag  57840
atgtggggag gatgacattc gggattagct ttataaggcc ttcctgtggg cagagttgtc  57900
```

-continued

```
tgactttcac ctagtgatca acaagcagct agcaagcatc agtgtgtgag gccccacgcc  57960
ctctcagctc ccctactgcc cacctgggac atgggctttg gcatctgtcc atagcattgt  58020
tctaaccaaa tgaggtgtta tggatcagct caggatggga tatgttccca gacatattat  58080
ttaaagaaaa tagctccctt cctcccctga taaacagctg ccatggctaa aaggtaacct  58140
ggctggggct taaaagtctg ttgactttca agatattttg caaaaacagt cataaaaatg  58200
gtatttatca gatcctaact atttgtgaga cggtttggta taccatagtg gttaaaaaca  58260
caggctcttt ccagaggagg tttactttgc ttagtcgtgt ctcctaagtg aacttggacc  58320
tcataaggtt gttgtgagaa tgaaatgggt gaatatgagt aaagtccttg gaccagtttt  58380
ggccgtatag taagccttca gcaagcatct gcttttattc ctacagggag gcaattgtaa  58440
gcccttcaca aacagcgtct aatgtgatcc ttagaacaaa cctatgagat agggcatatc  58500
tcaattttgt aggtagggaa acagaagcca cacaattagg aaatggcaac agatctgtta  58560
gactcttaaa cactatgcta caccaatttg caaggcaagg aagacaaagc acctttgaaa  58620
atgggtcaga tgttttaggg taaatgaacg tttgagaatc ttttaagttt tttttccccc  58680
agagattatc aaggtatcat tgtaggggga tgcatcagga aacatgacta tgaatcagct  58740
gcctgataaa ccagccagga tggagcccac gtcatcacag cagtcagcaa tgccactgaa  58800
aaacatcagc tgcttattcc cgtatagatt tccccttaag acatgaaaag ggagttcaaa  58860
gagaatgggc cagatatctc tgagagtcat attactaaaa tatatttatt tttactagct  58920
tttttgtttt aagaggtata ctgtcattag cactgtagca aaaattcacg ttttattaat  58980
ttctcctagt ttatcatgtg attctagggt aggatgcaga gttatattca aaatacacaa  59040
atcaactcaa ctcagtaaac atatatcgag gccctatcat gacaaaatgc tattctagag  59100
accacggcga acaagccacg gccccagcct caaagaatgt actatctttg gaactgtgct  59160
ggccaataca gtaaccagca gccacgcagg gctatttaaa tttaaattaa ttaaaagtaa  59220
aaacacaatg cctcagatgc attagccaca ttttaagtgt tcaatagata tttgtggctc  59280
ctgcctgcca tattggacag ggcagatata gaacaattcc atcactgcag aaagttctac  59340
tgaacaatgc tgctctggag cagaagatct tcttgttcag ggatgttaca cccccgcttg  59400
tggctagagt gtggcttatc ctcagagcaa ggataggga accatggcac tctgcaggct  59460
cagcactgaa gacacggatg caggctctgc ttctgaccta gattgacctt gggcaaggcc  59520
ctttgctcct ctgatcccaa tttcttcacc agccaagtaa gaacatcaga ccacaagccc  59580
tctagggctc tgtccaaatg ccccatgact gagtgaactg gtagaacatt ctatgtgtgt  59640
gtcacaacat gaagagcaaa gactttcatc tccccaaata attttgtttt tcgttttagg  59700
aattaaattt cagattcact ctaattgcca atactaaaat tctctatatg cagttctaaa  59760
cttgacaaac caataaaaaa agattatttg actacttatc tttgtacaac attgaggtct  59820
ccctaaagca aatttaaatg catattttaa aaatgtattc tagcagttca gttcagaagc  59880
cccctggccc aagcatcaca ctgtcaatcc tttgtcctca agcagcatgg ttgggtgggt  59940
taagtactga caaacactgg gtgtcaggcc catggtcagg gactgtgcta acagtctaca  60000
tattagatgc cacctacccc caccctcaac agacccaaac tatttatcca atagcaaacc  60060
ttgcattatt tctgtccaga agaaacaaac atttattgac aacttttggt gtgtgacctg  60120
tttaagtcct acatctcatt taaggactgg tcaatgttag gctaggcaat gcctgtttgt  60180
gagagaatca ctgcctaaag aaaattctcc atttccctta gctctatggt gggtgactac  60240
acatactggt atttcttaaa gaaataccaa ttccatttcc ttttaacata attattaata  60300
tctcattagc atggtgtcac tgaagcctgg gcccaaagaa ataccaattc catatcattt  60360
taagatcatt attaatatct catcagcgtg gtgtcactta agcctgggcc ctttagaatt  60420
tttcatgtac ctgtgttcct ctgcccatat cagctggaac actaatagtt ttcttccttt  60480
ttatctagaa gactgagaac attacatggg acctgccccc agggcatgga ggctgaggtg  60540
ggacagttta gttcaggagg cccaagaagt gttgggtgtg cagccccttg ttcaaacaca  60600
gcctctgaat cgccagaggc ttccggtgca tactctgagg cgcaggtggg actcgggagt  60660
gagaggtttc ggcgaatgaa ttgggattgc ctacttcttc ccagtgcagt ggagcttggt  60720
tctgtggtca ggtccttacg ccctgtctgc ctttctcgtt tctttatttc tcgggtagta  60780
gttgtggaat caaatgacct ggggtttgat acctactcta ccacgcctct gggggagtca  60840
ctcagactcg ttgaacctaa gttccggggc tgccaagtga ggataagtag taattgctga  60900
tccacctact tgacaagata gtagtgaggg ccctgagcgc caggctgtgg atccagcctt  60960
tcccacggtt cctggtgtgg caggaagaac tctaggcctg aaggtgaaat tggggaggga  61020
gtcccagctc tgccactgtc tctctgggtg acctcaggca ggtctcctca aaaaaataag  61080
atactttata aagctcagtt tcctcttcag taaaatgagg attccaggta actcacagat  61140
agtttgtggg gatgaatctg ttccttaaag cctgcagtac atcaataacc cagtcttcct  61200
gcttgctttc ccccctctcc actaccagtg atcatagtct gatcccatag gtgatatccc  61260
agctcaaaac cctacattag cttctgtggc tgtttaaggc ctgcccagaa ctcccctggt  61320
cttagcactg aaagcacgtg tccggggaag ccctgcattg gtcgttcata ctactgagtc  61380
ccgcagggca aaccgtccgg tcccaccctc ctttctagtg ctgctgtcac actcacctcc  61440
cttcacccta cactcccttc tgtgccttgc aattacctag ggagtttttt acaagatatg  61500
gatgccctgg ccctgccact agagattctg atttaattgc ttggggtagg gcctggcata  61560
ggtatctttt aaagctccgc agtggttcta aagcacagcc acagatggga accactgatc  61620
tattcttgta ggtccccaga tacctcatgt gctgttccct gtgcctgagc tgacctttcc  61680
cccactttcc tctcctcggc taattcctgc ttatcctcct actcaggagg ctcttcctcc  61740
aggcagcctt ccctgatccc tccaggaaga cttagctgcg tccctccgct gggcttcccc  61800
aatacactgg gcttgctttc attagaacct gatccttcca cattatggtt gttggtttgc  61860
tccaatcctc tccctcatta gctctcaact ttctttcagg aagagatgtt tatctttcct  61920
tcttgtattc ctagagtcga ccaggctctg gcacattgca gattctcagt atgcattcag  61980
ggaacaactt aatcaagaca agaccatctg acttcttgtg agttacatgc taagaaagaa  62040
atgtcgacac caatagccct cacaatgata ggaacaggag gttaaagaaa aggaaataga  62100
tgcaaatagc aatataagtg ctttaacaaa tctatacagg aggacaacca tcatattcaa  62160
attttcaaac attcttagtt ctgctctttt gtgggtaatg gttttttttt ttcctcttcc  62220
aggagaagaa aagaggcata ttatagaaat tcctcctccc ccagcattac ttgtcacaga  62280
attgtaattg gaagtgattt ccctgactaa gttattttgg ctgtctgtta ttttctctct  62340
tcctccttgc tcttccctca gctggccatc ctgtgtgttt ggagagagcc agaaaggttc  62400
aaggctagga atgtttctct ctctctttaa agctctttaa tcgtcaggct ttctgatctt  62460
caaagcaggc tgtagccagt gtgaccccac tccctcgcct ccccatgctg gagagtaaaa  62520
gcctggagta tttttgtcat tttgaagact tgcatatttg gacagccttg gacatctgga  62580
aagtgtggtc ctcactagct ctgcagggat aagagcacgt cagcacttcc aagctctctg  62640
```

```
gcgcccctac atctggacac gttgaaaaat taacaccaga ctctggagtt aagcaaacat  62700
taagtttata ggcctccttg catttgacca tttcctggga cagcagccct tatcctgtga  62760
ctttctgtgt gtagagttga gtctttgcag ttggtcctcc tcacactctc tcaactttgt  62820
gactctctgc agtgcttggt cctggataag tttgaaagct acaatgatga aactcagctc  62880
acccaacgtg ccctctctct actggaggaa aacatgttct gggccggagt ggtattccct  62940
gacatgtatc cctggaccag ctctctacca ccccacgtga agtataagat ccgaatggac  63000
atagacgtgg tggagaaaac caataagatt aaagacaggt gatgtttcag gaagggctcg  63060
ctgcatttct ccaaagtcag tgggaaatta catttggtag agagaaaggg attgagactg  63120
gactcataaa tcaataaaat taagttaaat aagaaaaaat aagatatttt ataaagctca  63180
acaaagagtc cttgaatgaa agcaattaca gagtcacatt gtggctaata ttcaaaactg  63240
agatttaaac tgaggactag gaaatagaat tggatccttt tgaagcgttt aggagaaaga  63300
ttttaagaga atgagttccg agtcaccctg tggtcgggag gtgtgagtga gctatccaag  63360
cccgttccca tcctttgtcc ctctgtgtct tctcaggtat tgggattctg gtcccagagc  63420
tgatcccgtg gaagatttcc ggtacatctg gggcgggttt gcctatctgc aggacatggt  63480
tgaacagggg atcacaagga gccaggtgca ggcggaggct ccagttggaa tctacctcca  63540
gcagatgccc taccctgct tcgtggacga ttcgtgagtc tgaagttcgc gatcctcctc  63600
catgacacgc taatgggggt gctggagtgg gctggggtgg gctgggggtg ccctcaaggc  63660
ttccatgtct ttagagagag ccccagggac cagagccaaa ttggagagca tggagctctg  63720
actgaggaac ctgcttctcc caagctccag gcaggcacag atgagtcagt gcagtggtgg  63780
gaaagggaaa agagttgatg ttgtagctgg aaaagggaag gggaaaatta aagcaaggaa  63840
agtgaggctg ggggagggga caaattcccc actatgtagt atgtttggta tgtggaaggg  63900
ttctggtcag aatgtttgcc caatgattgc cacatcagca ttcattttgg actctgtatg  63960
gccagtaggt ctggttcctg ggagccctgg aataatgcag ccccttccct aactaacatt  64020
tccatgatgt atgctcaatg acaaggcaga ggaatgtgtt ggatgagctc aggacctgcc  64080
tccctggaca ctcccatccc aggcctgtat atctgttgac caggaataag ccaagcaagc  64140
agcctactgt ttgactgaat atggatttgg ggggtggtag agaaagggcc ggggtggagg  64200
gttgggaggc tcatttgtca ttatagatgg ggtcagacac actaccaaaa cagcagcaga  64260
gatctacaat tgagttcacc taaaactcag tgtggacaca ggaaaccctc ttttaataac  64320
tgtccaatgg gttttccagc ctcagctcta cagaaaactt gagataacag tggccagtct  64380
gcagttagtt tgggttcgga caataggcag agctgggaaa tggagccagg ggcgaaagcc  64440
caggtccact ttaggatcag gacgggagtg gctggtgggg aagtgaggtg ggtgtgggga  64500
ggcaataggg agctgggtca tttggtatgg gagagtcctc tggtggctag tcccagaagt  64560
gcatgcttta cgaacatatg cttctctccc tagggccacc ttgagtgaaa ccctcccatg  64620
ctggaattgg gccctttcag tgacaacaca caacagtttt caatagataa taatcccaag  64680
ggctttacta gcacatgaaa cacagggaaa acgtgtaaag ttcacaagaa agtcgttcca  64740
gtgtatcaaa tctatcctgt ttgccaggtg gatataccag ggtctcctcc acctgtgcat  64800
ggctggtggt gggtccagtg gctgttggat aactgatgta ttgatggatc attcgccttc  64860
tgaaagtgcc aaactgatta gttattttgt gtgtcttttt gtgtaactag ggtttgacct  64920
tccagggcag actgtgctgg ggcggctgac cccttgggga gccaagttat tgctcttacc  64980
accaccactt gcccttgtca gtcctccacc ctcttgggtt tcagtgtcag catgtagctg  65040
tctactcaga tcccatccac atcatcaagt ctgcagtttt ttccttgcaa ggccttacag  65100
ggaagatctt tgacatagag gatataattt tattgacaca ttttacttgc agagcattca  65160
cccgggctaa ccagaaagcc agcactctgc tataaacaaa aaataatgct tcagggctaa  65220
catggaatgt gttaaaagat tccagcccat taaatgtcca ggggaggttt tcctgttttc  65280
ctttccctcc atctgggctt tgttctcaac acattcattc aacaaacatt tattctgcct  65340
ctaccaggta cagagcactc tactattctg cttctctcct tttgctttag tttcatgatc  65400
atcctgaacc gctgtttccc tatcttcatg gtgctggcat ggatctactc tgtctccatg  65460
actgtgaaga gcatcgtctt ggagaaggag ttgcgactga aggagacctt gaaaaatcag  65520
ggtgtctcca atgcagtgat ttggtgtacc tggttcctgg acagcttctc catcatgtcg  65580
atgagcatct tcctcctgac gatattcatc atggtaagcc aaatggagaa ggcccagaaa  65640
atcttgaata ctttggttcc tttccccttt cctcctgttc atgtgcctgg attagtcatg  65700
tggccaccaa ggagagcgtg acatctagct tcccagccct tccttttagc caacgtggga  65760
gacactcaaa gagacgaaat ctcctgaagg agccactgta tcacagcatc ctcccatctc  65820
ccacttcctg cccaggggtc catggtccac acagacttcc cagtcccatt ccgtgaccat  65880
ctggagaagc tgctattagc agagccctgc acagggtgat agtgtaatta aagtggtctt  65940
ctctttccaa acacagaaaa aatcagttca gggagtgttt tcctgggctt acaattttaa  66000
ctactggcta gagttgaaat ggggaaagcc ttttgccttt tcagtagcag taggggagga  66060
gatctggatt atttacttat catcatcatg gtcacctcct acatggcttc accaaaaaac  66120
attctgctgc ctgaaaaagc tccaacacct ctctctcttt taaaggatgg aatttggagt  66180
ccatccttcc tcagtgataa ggagttttta tagccacagg cagcatctat tggtctgtcc  66240
tctgcaaact tgcaactcct ctgagagcta gacttggaaa tgaaacatta ttttgcaatg  66300
cgctgctatc cttcattttt agctcctcca ccgtagatga tagtttgtac ttgttaaatg  66360
ataaggatat aaatttaggt catttttat attttattgg gtggaatttg gtataatttt  66420
tagacttcag gctttacagg ctcctgagat ggactgattg agcttgttct acttcttccc  66480
catcatgata ggaagtgctg taccacacta ggcagtgtgt gtagtgacca cagactggct  66540
gagtgtctcc catcccatgc tggcccatat ctggtaccca cctgatccac aaatgttcca  66600
tcagatcctg ttcaaacaac acatctccag ttaagccaaa tcttgccctt tctccttacg  66660
gtaaaatgta ctaaatctga aggttttgtc tttttaatgt tgctccatga tccagtgatc  66720
tgtggccttg gttatgctct gtgctagagt cctaacaaga caaatgctaa ggtagaggtc  66780
attctgctca aacaacctga ccccacctgg atgtgggctt acatttgcaa agggcaccaa  66840
agttctaaga gatgagggga ggagctgagc cccttgtcct tatctaggtt tcccttgttc  66900
tttcccatcc ctcagtctgc ttcttttccc agtaccaaca tgtttgtgtc ctcagaatta  66960
aaggagtaaa aatgtgtaaa catctgacta gcaacagcca tgagattttg cctggcttgt  67020
tgataagcag cattgagatc tgccctccta agaatgggcc attaggtctt caaagctttt  67080
acgatgtgag gtaaagaatg ttcaccagga gtttcatgca caaaagggtt tctctttgtg  67140
ggaactagaa cattgttcca gtgatgacgg aaacagggct ttccatacca aaacagggtt  67200
ttcctttgaa tgactctccc acctttccct tgtctcttcc tccccacctc aacaacacag  67260
gaaagaagct ggaagcaggg acaatggaa ggtccctttg ttactcgagc tattagaaac  67320
aaaaagaaaa gtggccatct gaggaagcca cagctggtga aactgtaggg tcacagagtg  67380
```

```
aattacacct ctggcttaag tcagtgaaaa gtcctagaag tttgtggtcc tagaagtcct  67440
aaaagtttat gggactttgt tttgagcaag gataagaaat tgatttcagg ctgggcgtgg  67500
tggctcacgc ctgtaaccct aatactttgg gagacagagg caggtggatc acttcaggtc  67560
aggagttcca gagcagtctg gccaacatgg cgaaaccctg cctctcctaa aaatacaaaa  67620
attagccagg tgcggtggca catgcctgta gtcccggcta ctcaggagac tgagcaagga  67680
gaatcccttg aacccaggag gtggaggtct cagtgagctg atatcatatc actgcactct  67740
agcctgggca acagagcaag actctgtcta aaaaaataaa taaataaaaa agaaattgat  67800
ttcattcttc tgagaactgc aacaactacc ttaaagtgat tccatccaaa acccacatgt  67860
tcagccatgg acttgctttt atggagctgc gtgtgggtga cacacaaaat caggagctct  67920
gagtcctaat ttagactttt atttagattt cctcaaattt gggttccagt taagcgtggg  67980
tctcttctgt gccccgctcc cctttgccat ttgttttatc tgttcttcag tctgttctgt  68040
cagtacccac aggcaggaga gcagaaagga gaaatggcag ccacagcaga caaatggcac  68100
attcgttcca ctcagctctc gcatgcccat cacagataca gctcattggt ctcttttcta  68160
tgagaggaag ccagagctcc agggaactac tgccaactga tcagaactca tttaggacat  68220
ggacctattt gttcctttat gttcctggga agagcacagg atgaattcta tgtactcatt  68280
tacgtgttca gagagtaaag tgcctcatag gatgcctcca gcaaaagata accaagaagg  68340
tctaatacct ttgacaatct cagtttatcc tatagtgtaa ttggatagca gttcccctag  68400
caaaagttgc tagtttggtc ctattttcta catagccaaa gtgattgatt cattggttaa  68460
tgtgaaagtt actgagtact gccagcaggt tctaggaaat atatttgtgt gatattcatg  68520
gatggggagg atcaatccac ttccaagtga tttggattaa ttactggtat tttcacctgt  68580
gtgggtagca aacctcagaa aatcaagtat agatgacggc ataggacagg ccaggcccca  68640
ggcaaaatgt tgaagctcct ctggagttcc ctcccatctc cctcttttgt tttccatata  68700
cctggtttat ccagggccct ggagatgctc caagaccccc tacccaggtc ttcctccctt  68760
gtcccagcta tatttctcca tattaccact cttctcaccg aggatttgct tacttaacac  68820
ataataaata ctattaaaag agaaacttag gcacattaaa atgttagagt tgattccagc  68880
aaacagtgat tcacaggagg ctccagatca caagtggttc agggccccac tgaggggtag  68940
ggaagcaaga caaagaaaaa caaagcaaat atttgattgg ttcaagtgga aagtccctga  69000
ttacaggtta gtgggcagtt tgtgattagt taagtttctc taagttgggt tttggtttgc  69060
tgatgtagga acacagaatg ctggggccgt ttcaacctaa tggtctccca attaattttt  69120
ttaacattac tgatgactgt taggagtcta atgtgctact cctcccaggg aaaatggcat  69180
tcctaggatt aaaggaactc agcacatgga gtgtgcgtag aaatttagac actaactgca  69240
ggctggtggg agagagccct ttagggcaga atgagaaggc gtccggccaa gggcaggagt  69300
tactgacgca tggcctcttg gtttcagcat ggaagaatcc tacattacag cgacccattc  69360
atcctcttcc tgttcttgtt ggctttctcc actgccacca tcatgctgtg ctttctgctc  69420
agcaccttct tctccaaggc cagtctggca gcagcctgta gtggtgtcat ctatttcacc  69480
ctctacctgc cacacatcct gtgcttcgcc tggcaggacc gcatgaccgc tgagctgaag  69540
aaggctgtgg tgaggccctt gggctggccc ctgtcctaca acacgtttcc ttggaagggt  69600
ccgtagcagt cctggaggcc cagcctgccc tctgaggggg tccactttgc ctttgaccta  69660
aggttaaaaa gttcacgtga ggctaaaatg tacaggggca aaagtgggag cagtcctcac  69720
cccgagcgat gcaacagtga ctcctcacca cgcctgcttg attcatctgc cctggaaagt  69780
cattaaaaaa ccagttcaac tcatgggtcc ctttatttac tcacaagaga gagccagcag  69840
cccatttcac tagttttcct ttcctactct ttgagaagaa tcagaaggga gggagcttgc  69900
cactttacta tctgtctaaa gagatgtttc cattaattaa aggtttttgt tttgcttcaa  69960
aaaaacttga attggagtat ttccacaagt atctttaaca tgctctacca atgtttgcag  70020
aaagaagtgc agaaatgaga ctgtccacag agtcaggctc gctggccagg agaggactcc  70080
cgaagctgac ttctgatggc ctgagaaact tcctagttca caattcccag acccagacaa  70140
agagcactgt cttttctcta attgttttca aatgggccat ttccaccctc taatcagcct  70200
ctggccctgg agggtgcagt tccccttgtc ctccggagtc tccctgtctc tgtgctgtag  70260
agtcaagaag ggacaaccac ctgccctcac tgggaaaaga cagaaagtct gacttgttct  70320
cacgactcac acttattagg ctccagaggt gtcagggcat ctgcctttca tttcttaggt  70380
taaataagaa atcaattgct gccatttgta gtacccaatt ttctaaaatg atcacaatgg  70440
ataagtggca agaaatcctt atgactcatc tgtgggcaga gttgggctat tttggtaatc  70500
cttgagtagg cagatggaat ttgaggccat cttcttgggt acatagatca ctaggaagct  70560
ataggtctag caactgtgga ttagggctgg gctgagaatt gtttcatgtt ttttgtgact  70620
gtatagctag agactctctt gtttgcagag agacactctg aactccccct ggccgtcaag  70680
ggaaagactg ccttcaccct cctgagctga ccttacactg agagacaatg gggaccctct  70740
tttggccctc ccctctacct cgagggcatc tgggtgctgt tgcattggat aaaaggcact  70800
gctctttttc tgtgccctct ccgcctcact gcagagctta ctgtctccgg tggcatttgg  70860
atttggcact gagtacctgg ttcgctttga agagcaaggc ctggggctgc agtggagcaa  70920
catcgggaac agtcccacgg aaggggacga attcagcttc ctgctgtcca tgcagatgat  70980
gctccttgat gctgctgtct atggcttact cgcttggtac cttgatcagg tgtttccagg  71040
taagcatcct cctctatagg gtaaaggtaa ttgagttctt cagatcccca gccctctcca  71100
ttcatctagt ttaaatttca tttcttccaa gctctttgtc agaaccagca tttgaagttt  71160
aaatctagaa gttaaaaatc caccagcaaa tcctactggc tctacttgag aaacaaatcc  71220
agaatctgat ctcttgtcac cacctccacc acaaccttcc caatgccagt ctcttccttc  71280
cactaccacc tcccatcagt ccattctgca cactgtattc agggagatcc tttcagaatc  71340
aaggtcatgt ggtgtcagcc ctctctgtca aatgcttgca ctggcttttc ctctctttca  71400
gagtaaaacc cagtgtctca accctggcct ccaagctgct tcattatccg gcctccaact  71460
ctcttcttca tcttacgatt ttccctactc ctccatgttc ctctgctcca gccacgtcgg  71520
cctccttact gactgtttaa tacaccgagc gcatttcctc ttcagggcct ttccacctgc  71580
tgttctcatg ccagaagcac atttctctcc ccacaacctg caacccgccc ctcatatctg  71640
caggcttgct tccttacttt gttaaggtct ctgttcaaat gtcccattat cacagggatc  71700
tttccagact gaagagatct acataactat ggctctgtaa acaacattcc tccagggttc  71760
ctgtcccctt accctacttt attttgggga acattcttca ccatctgata caatgatgta  71820
tcttatgcat gtatttactg actctctgcc cttagtagaa tatgagccca gagagcatgc  71880
atgtggtcta ttttgttaac tgtgacagtc ccagtgccca gaatagtgcc tgacctttgg  71940
tgggcactga ataaatatct aagtaatctg tagcatggaa aatcagcttc tgaaaattgg  72000
ctgtttgcac ggtcgtgtat ttgcttggta gaaaatcaaa ttttccttca aattagcatt  72060
ttctggtaac tagagctgcc ccatcttcct ctgagtggtc tccaagtcag ccaatagcct  72120
```

```
tgtgctgtgg cagccatgcc tggctcttga tgctgtagcc aaaagcaggc aggggatggt  72180
gaggctggtc cagtccatgg ggagggacaa actcacagct ctcagatcat ctcagggcag  72240
cctttgttgg cagaaatagg taggcagcca ccctgaatag gaggaaggct tctagactgg  72300
gtcaggaggc ctgggtttgc atcctagtgg caagcgtgca ttcatttact agggctgcca  72360
taacaaaata ccactaactg ggcagcttag acaacagcca tttatatctc acagctctga  72420
aggctggaag tccaaaatca aggtgttggc agggccatgc tccctctgaa acctgtaggt  72480
gcttgggcac tccttgactt gtagatgctt cctgctgatc cttcgtctgc acatggcatt  72540
ctgcctgtct tacatggcca tcttataagg ataccaactg gattggatta ggtgcctacc  72600
ttgctcccat gtgacctcat ctcaactaat cacatctgca atgaccctgt tcctaaacaa  72660
ggccacatta tgaggtacct ggggttagca ctctggtatc tttttcttg acagcacttc  72720
tgacaccaaa tgtgtgtttt ggttttttgt tgttgttgtt ttggcaccaa ccaattctcc  72780
tatattaatg ggttgtccaa gaattcaatt gaattctgac actatccaga attcacacag  72840
actccacggg ttcagtccca caaggcttcc ccgtcttcag atgccagctg gaaatgtggt  72900
gcccaggcta cccacacttt tgccaaaatc ctgtacttac aatcacagct ttaaaatgaa  72960
ggatgcagct caggaactgc cacatggaag agaagcacag tatggggtcg ggggaagagt  73020
ttctatgctc tctctagacg caccactctc ccagcacctc aaagtgttca gcaacccaaa  73080
agctctccaa atcttgttgt tcgagagttt ttataaccct atctccagct ccatactccc  73140
ccattggagg ttgagggttg ggactgaaag ttccattctt cacatgtgtg gtgtttctgg  73200
tgaccagtcc ccagaaactg cagctatctt ggggctctac cctgagtcac atcattagca  73260
taaactcaga tgtggtagag gaaggggctt attatgaata aaaaaagaca ctcctttctg  73320
ccaggaaatt ccaagggttt taggagatct gtgccctgca caggagctgg ggacaaagac  73380
caagtatatt ttgtgttatg ccacagaccc caacatgtct ttttggaggg agaccaaatt  73440
caacccatga cagtgacttt gaacaagaca tttgaactta gtctgttttt tctatcctac  73500
tagattgttg gaaacagata taatagatga aaattagttg attaaaattg aaatttgtgc  73560
ataattcaaa agttttattt tagccaagct aaagctttca tttattcaac agctatttac  73620
tgagcagcac ctgtgcatga ggctcagcag ggccaggttc tgggaacaga gcggtggaga  73680
taaagatcca gacctgcccc gaggaataga cagtccagtg gcagcaaagg ccatgaaaca  73740
tacggcaact cttaaaaaaa gccgagacca tgattttaca aaatcaacat tttgtaggga  73800
gcagaacttt caaagagaac tggactagaa atttgggagt ctttttcttg gaaccctggt  73860
agatccagta gaatgaggga tgggggtgta gggttaaaaa cactgacatt agaactggat  73920
tacctgtgtt ggaattccta catttctgtt tcactatctg tgacgggggg cagatggctg  73980
aatctcagtg tgcctctgtt tcctttctca caagaataat attactacct atctcctggg  74040
gttgttttga ggtttagatt atttaacaca tggaaagcac tcacagcaat gcctgccaca  74100
gaaagaatat ccagtacatc ttagtgatga tcaccattat tattatctga ctcctggaaa  74160
aggacttgat ttaattctct catgaaacgt tttcttggaa aactgatgtc aaccaagatt  74220
attggtcttg ctgttgctta taacacccca aaaacatgac tgtgtggata aaaatatgtt  74280
ggaaggggta gtctttctgg gagcctgaga atagccatgt aataataact gcaaatatct  74340
atagttacaa tttgaggttc aggtaaataa actctagatc ttatagaact gcggtaaggt  74400
aggataggga gactccttcg actttctctg tttatttgtc tctattttta ggagactatg  74460
gaaccccact tccttggtac tttcttctac aagagtcgta ttggcttggc ggtgaaggtg  74520
agtcctttaa aacacaaatc ttaatgtttg aaatcaactc cttgggctct gtgcaagatg  74580
tatatggatc acagaggtgg ccctctatgt aaacggtgtg attcctgatg agtcagctgc  74640
ctcctggggc tctgcccctt gatgggcatt gcagcgtctg ggggaccacc tttcacaagt  74700
tgctgggccc tgtgtgatca tgaatggctg atcatggatg aagccctggg tcctgtacac  74760
cttgtccagt agactaaatt gccctattta aaaaaggcca agccacttca gggttcaaag  74820
aacttttgca gcttttcagt ataaagcaga aatccaggga atcatgaagg aacctttgca  74880
ttcatctccc attgccttcc ttgtgccttt ttattcttct ctgccttttc aaaatataaa  74940
ttagtttatt ctcccaagat gaagactcct cctggggctg aggcagagct gttatcttca  75000
gggcaatacc tcagattctc ctggtgttga tctttcttag gggtggggaa aaaggctgaa  75060
agggcatttg cccacaacac atcttaggta aaaggcacct ttactactga accaaacagg  75120
aggcctagct agagaaagtt ctagaagcag ggaaaagcac agactctttt gtgaggtctg  75180
agaaagcaaa gaaattccag ggtgaaagcg ggggactccc ctagagctga agtactctcc  75240
catctgtttg ttgctcacct acctattctt tactttgtat tattgggcct gggccaggac  75300
ttatcctgca agcactgaga tggatgtttg ttttctctgg gggattagtc tttttttttc  75360
tttttttctt ttgtttttttg cttttgtttt cactgggtca aacaaacaac actttaacag  75420
ctcaggattt tttcattgta ttgacttgtc tacctgtaaa cttgttaatt ttttactata  75480
ataaaattat catataataa atgaaaaatt tcaacacagg gcttgtgggc attttatttt  75540
tctctacaat cccaacagat actctgcctc ttaagaaaaa aagaaatcat aaggaaaata  75600
tgctccttca aaagtgaatc acaaatatgt ttgccaacgg aaggcaaata tttttcacct  75660
gtctcatagg ctggactgaa atggatttct aaaactctct aaaaccagaa aagagctgag  75720
tgtctccacc caacctccct cctttcacag attaaaaaat aaaaaatgga gcccaggaga  75780
catccagtat cttcccctat tggtcacctg ggacaaaatc tggaacatgc acatgcattg  75840
cctggcagga actcattcca gtgattaaac tcttcaggag gatgtttcct cttgctattt  75900
cattacctat ttgtgcagtt tgatagctag taaagtgatc aaaggaactg tggggcatag  75960
attcaaaagt ccttcaggaa gcagaaatag aagaacagta ctagaggcag caggtccctg  76020
accagcaggc ccactacctg ctgctccagc acacatcctg cacattttca gagggtgggg  76080
gacagagggg ccctgggtgg ctgttgcatt gagaaatctc gccctgctcc tgtatgtgca  76140
cttgaggccg agagcccttg gatgcctggt gacagtggtt tcctcctgcc cctgccttcc  76200
tctctggcag actgactggc ccttctgctc ctcttcccct tccaggatgt cctgatatct  76260
ttttaaacca aatgccaagt ttgccaaaaa gtgtctgttt gtgtgtgtgt gtgtgtgtgt  76320
gttcaatgcg tgtgtttata ccacacttca caatttgtcc aggcttgtat taataccatc  76380
accaggctca accctggtgt taattccaag atacttaaat gcccatctag gtgaatttct  76440
caggtaaacc atatattcaa gctgtagttt aagctggctg cccgtcatag cactttgaat  76500
agactttgtt tttgttttttg tttttgaga cagagtctca ctctgtcggc caggctggag  76560
tgcagtggca ctatctcggc tcactgcaac ctccgcctcc cgggttcaag cgattctcct  76620
gcctcagcct cctaagtagc tgggattaca ggtgagcgcc accccacccg gctaattttt  76680
gtatttttag tagatacggg gtttcaccat gttggtcaga ctggtctcga actcctgacc  76740
tcatgatacg cctacattgg cctcccaaag tgctgggatt acaggcgtga gccaccacat  76800
ccggcccctg aatagacttt tactcaaggt tcaccatgac tttcacatgt tttgtattgg  76860
```

```
agtaaaatgt gccagtggtg ggctaaagaa aattaactca tttcaaattc aaacctggtt  76920
ttcttaattt ttttaaaatc acagtttctg aaactgtggg ctcctcatgg cacattgaga  76980
ggaggaggtg aaactctcca agtctgaagc tcctgttata aatcttcctc tggcaaagat  77040
tgtgtgatca ggcttgagta cctcacagtc ctagagcagg tcaaaggctg gctaggaaac  77100
tcatttgctc cctgtacctc tcccctcctt tcctgccttt gctcgttctc agctcccggt  77160
ggtagagtaa cactggcttc tgattggtgc agggtgttca accagagaag aaagagccct  77220
ggaaaagacc gagcccctaa cagaggaaac ggaggatcca gagcacccag aaggaataca  77280
cggtaaaacc ccgataaaga atacacagca gaggcgagga aaaggctcta agcactgcag  77340
agggccagag caaaacatct catggcaagg gtggaaagaa gcctaggaaa ctgactctct  77400
ctgtggacaa gtgttaaacc agatcccttc tcagaggtcc atctgcatgt gtgtggaatg  77460
aatggttcag cccagacatt agcgcatatt tcctggagaa agcaaatacc aactatgtag  77520
tgtgcctgtg cccttgttag gcaaatccca agtgagttgc acaaatgtgc tgacttccga  77580
ggatttagca agaacaataa ctttggtcac tgggacttaa agcggatatg agctataagg  77640
aaagacaaaa ataaatgctt ctgtgtccag ggggaaagag actccagggg agctgactac  77700
acttcactta cggcttacaa atctagaagg ccattcattg aaaccatcag aagcctttcc  77760
tgacagtgga agttacctaa taatccctaa actgacgacc cagatttaca agttttgttt  77820
tcctggcttt tgctgccctc atcttctctc ttaaactagt tctgtatttc tcccaaggct  77880
tttcattccc taagcatacg catttctctg tggccaaaat gctctgggtt tagacaggca  77940
gcacagcccc tgggctctgc ctgacagggc aggagagggt ctggccttta tccctccagc  78000
ccaccccagg ggccatttca taaaactaaa gccagagacc tgcagcccct cccagagtta  78060
gactgcagta caccatgcct ctggcaagat cctcctccca cagtggaaag tctaagccaa  78120
atcaggaggc tggggactgg ttccacctca gttgcaggca aggccaggag gcacggatag  78180
aagaaacagt ggactttttc cccctaggga aagaaatgct tagagctaca gtattaagat  78240
gacaaattaa gctgtgccat atagggtgaa atgaagcagg gatagatggg aggtcaggga  78300
gaagtgagag cactcggtga gggtctgcac tggagggggc atgggaggaa gaaggagggg  78360
agtggggttt gagggatggt gatgaggaag cgtggactgc cctacccacc tattggaaaa  78420
cctgggagtt ctgaggagca agaagcctta gtcaaagtca actcaaagat tcaagccaag  78480
gtgactaaga gaatggcggt ccagaaaagg tcatgggaga atctgaaggc agatgttgtt  78540
ttgggaagat gaagaaccta agccgcttcc agaaattcat gaggaaatgc cccgtggact  78600
gttggcaatg agggcctagg accaaggttg agcttggggc caactctccc tatagacagt  78660
gagtgcattc tgacaagcat gggctctggg ttcaaatccc aactctgcca ctcatgccta  78720
tgtgtcctta ataggacgct tgatgtctct gtgtctaagg tttcctggac tatggaaatg  78780
agcctaataa atgtctaccc cttaggacca ttgtaagagt acattgaggt aatttgtgta  78840
aagcagtcga agcagtgcct ggcatatagg aggtgctgta taaacgtttg atgctagtat  78900
tactattatt attctggagt cttccttgca acggtgatag ccgaagccac aggggcaggt  78960
gacgttatag gcagaataca agggcctgga gacagagccc tggggccatg taattaggca  79020
ttatgtttac atcatgttca tttttttcc tccaagactc cttctttgaa cgtgagcatc  79080
cagggtgggt tcctggggta tgcgtgaaga atctggtaaa gatttttgag ccctgtggcc  79140
ggccagctgt ggaccgtctg aacatcacct tctacgagaa ccagatcacc gcattcctgg  79200
gccacaatgg agctgggaaa accaccacct tgtgagtctt ccagcagaga agctggctgc  79260
catgctagcc tgtcatttcc tggcttagtc tttccctatc agcggctgtc tactctttcc  79320
cacaaatttt agtgacaaat atttgcggcc ccaaaaatgt gtaaaagctt tctgcagtat  79380
tcaaagatca ctaatatgta ttctcttgat ggggaggtag aatacgttta ttgccccttt  79440
tgtgtgccgg ggaagtggac attcattcag agagttgaag tgactttcct gaagccacca  79500
agttgtcatg gctcagcggg ggcaaaagcc aggcaccaca gttgcctctt gtttctcaca  79560
ccttgagtct ttccccccat ctcaacagtc catggtggtg atcaagtcat ggccactgtc  79620
atcatgtgca tggaagctat agagtcctcc tatttccttt ctcttttctt ttctttttt  79680
ttttttttt ttttgagata gtaaccatta cccatgctgg agggcagtgg tgcgatcttg  79740
gctcactgca acctccgcct cccaggatca agcgattctc ccacctcagc ctcccaagta  79800
ggtgggacta caggtgcata ccaccatgcc cagctaattt ttgtattttt ttttttttt  79860
ttttttttta gtacagacag ggtttcacca tgttggccag gctggtctcg aactcctgac  79920
ctcaggtgat ctgcccgcct cagcttccca aagtgctggg attacaggcg tgagcgaccg  79980
caccaggccg agtcctgcta ttttcaagga acattccttt tcctaccaat cattaggcag  80040
gcttcaacat cagctgatga gggttagtgg tcgttctgga gaaagtgaaa aaagaatcag  80100
tctctagagg ggcttgtgga gtaaccgcct ggtaacagaa ggtcagggca gggaaggcaa  80160
aggggctctg cgcggatctc tcagctccgc aggcgcccca ctctcctcca agggacccga  80220
gcgccatctg ctgagaggag aacacggccc gccatggttt cccaaggagc agcagacacg  80280
gacctcgcag ggggcagcga acccacgtga cacagtcttc aagtcctttg gagagcccca  80340
ggaaggaaca acagcgtgta caccctgtga tggaatgttc tctagggcgg ttcagtgtga  80400
atggaatgtg gggccggtgc cattctaatt ggttctgttt ccctctagtg gttgatcgcg  80460
gagatttcgg cttctccatc aggacaagtt cagatagcct gagatggtat cagaactcag  80520
ggacagagct gggtgtggcg gccctgcatc catctgcttt ctctccatgc taactgatat  80580
ggtcagagag ctggaagcaa attccaggac cccagggctc cgcaaaggca aacacattac  80640
ttcatcggct gctgacatgc aacttccccc aggggttaaa acaatgttta atactaacag  80700
taataatatt tttgagtttt actttatgct ggcgctgttc taatgttgta agtgtattaa  80760
ctcatttaag ccttacaaca acctaaggac atgggagtca tagttcccat ttaaaaaaaa  80820
aaaaaaaaaa agcccaccat tgctctgagg ctttttatgt tttggatcca aagctaatat  80880
tggtggtggt aattcccatg cctggcttcg atcaattaat cagcaaatgc ctaggactgc  80940
ttagggttct ggccttcatc aagaccttac ccgggcttta tgatgatgac acctggcttt  81000
tcaatagcca tgactgctca cccaggaggc aacgcctcga gtcatgcacc gaacaccttt  81060
tattgatcct ctccaacacc aggctccgtg atggctgagc tggggacacc tgtgactgca  81120
cgtgaacatt ttgaggctgg gaatcccaaa ggccctcggc gttggcctgg gagcaccatg  81180
aaacaagtag aagcagagaa ggatggcaga ggtggccctc tgcattaggg cctggatgta  81240
tacactggtg ctaagggggc cccacagcta ataggggttt gagtttgact gacagcccca  81300
ggcaggaatc tgtgagagtt ctcactgaac ctggtgtggg ggtggccctc ctaaggcatg  81360
ttgctaaagg ccatctcttc tgccactgac gcctgtgttc tgcaggtcca tcctgacggg  81420
tctgttgcca ccaacctctg ggactgtgct cgttggggga agggacattg aaaccagcct  81480
ggatgcagtc cggcagagcc ttggcatgtg tccacagcac aacatcctgt tccaccagta  81540
agcgacacag gaactgagac cgccccatcc cctctcctca cctctgcccc cagcacactt  81600
```

```
ctctagagcc cagctcaggg gtgccaggcc tgggcacagg cagagataca gactcttatt  81660
tggtttcccc tatgtttaaa gtcctttgtc ctacttgcag tgagaattgt ccctgagaat  81720
atgggactct gcctctgctg ctcagagctg agggctcctc cctcagaagg gtgaggctgc  81780
cttcgctctg acagagcagc tgatcgatcc ccgagcccct tgtgcagccc tgaagtactt  81840
cctctctggg accaaagaca ggagaaccat tgttcctttt tcctgttgaa gccacggcct  81900
gaaaggcaaa cttttcaggg ggcttttcag ttactttttt tccccaataa gatatctttt  81960
atttcttatc taagaagcta cgcatagtca ttgtgaaaga aaaaaaagga agggaggaag  82020
gaagggagga aggaaggaag gaaggaagga aggaaagaag ggagggaggg aggggagaag  82080
gaagcgaggg agggagggag gggagaagga agggaacagg agggaggaaa agggaagggg  82140
aaggaggaag gaaagggaag gagggaggaa gtaaatatag gtaaacaaaa aattgaaaat  82200
aaaagtcacc tgtaatttca ctactcagag ataaccgctg agttataaca ttggtatata  82260
attttttaga actttctcct atacatgtat agatagataa acacatatac ttcaaaatga  82320
taaagaatag taaaactatg catacaattt tataacctga cttttttttc aaaaaaaagg  82380
attgcttttt taaacataag atatcaggaa catctttcat gtcattacat attcttctat  82440
aaaataatat ttaatgttta cagattattc cattgtatgc atgaactatg taagccatcc  82500
tcttattaga tatttaagca gggtctgcta tttttgtatt gtatcataaa caccaccaca  82560
gtgagcatct tgattgccaa atcaagaata cttgtcctca attatttctg taagatcagc  82620
tgctggaagt ggaagtgcta agccactgct tttctcgttg tcccatcctc ctagcctcac  82680
ggtggctgag cacatgctgt tctatgccca gctgaaagga aagtcccagg aggaggccca  82740
gctggagatg gaagccatgt tggaggacac aggcctccac cacaagcgga atgaagaggc  82800
tcaggaccta tcaggtgctc agagctggat ggagacaggg ccacagatgg caaatccatg  82860
gctccccagt gcacccagga ggcaggggag gcttggagca ggagagcttc taagggtggg  82920
aacacctctg tgaagttaca ccaaaaatct aagagcagcc cccagatcat tttccctgca  82980
gagcactgtc tcacagcagc ctgggtttta tttgtcctga gattgatgtg cttgaacagt  83040
cttcaaaggg tctgatccga ggaggtgagg gttgcccttt ctgcatttac aaagcctgaa  83100
cagtattagg gctttgaacg ctataaacat ctaagaggca gcaccaaacc actgctgggt  83160
taaggtaccc ccacaatgcc acttgccctg ggcctttctc ttcctcaccc tccacagccc  83220
cttaactctc ccgtccttct tgtgcctcca ggtggcatgc agagaaagct gtcggttgcc  83280
attgcctttg tgggagatgc caaggtggtg attctggacg aacccacctc tggggtggac  83340
ccttactcga gacgctcaat ctgggatctg ctcctgaagt atcgctcagg taacagctgc  83400
tgctcagtct cctgggctgg gctctcactg cagccctagc tgtggtcccc actctctcac  83460
ctgccatttt gtagctgagt acaggaacca caatgactac actcagaagg gggtttatca  83520
gtgacttggt gaatctaagt tccagctaaa gcctcctgag gtttttacaa atataaacag  83580
agaatcactg atgatgcaac ctacttccca aaatatttta gaaaattctc ttgacctgca  83640
gcccttctgt ctggaataat ggatgctact ctaggtgaat gtcttctctg accatgggga  83700
cccaggtcac ctgcaaacat acctagaagc tccatagctg tcagatgacc actcaggacc  83760
agtgtgaggg tgacctgctg ggcattcagt gctccagagg gtggccacag atggaagtgg  83820
ctcctctgtc atggcacctc tcagacaagg ggctcagatc agaagagaca gcaagcagag  83880
ctgagtgccc atagaggtaa cagcacggtt caaccccgtg gtcaagccag agctttcccc  83940
cttgctctac tcacacagcg ttgccccgtg cctttctctg agggtttgtc atcctgaaat  84000
cctcattgct attttctttc tttcttttct tttttttttt tttttttttt tgagacagaa  84060
tctcgctctg tcgcgcaggc tggagtgcag tggcgcaatc tccactcact gcaagctccg  84120
cctcctgggt tcgagccatt ctcctgcctc agcctcctga gtagctggga ctacaggtgc  84180
ccgccaccac gcctagctaa ttgtttttgt atttttagta gagacggggt ttcaccgtgt  84240
tagccaggat ggtctcgatc tcccgacctc aggtgatcct cccgccttgt cctcccaaag  84300
tgctgggatt acaggcatga gccaccgtgc ccggcctgct gttttctgtt aatgacatct  84360
ccagttagtg agagtatgca cgtgtgtgtt ctttatgaag agtataaatc cagagcttaa  84420
tgatccagaa aatgtacata tgaaactccc tagatgctga ccataataca tgagccccta  84480
atatagagat ttatttgaat cagatcctat gctggataca gagacactgt gtgtggcaat  84540
gctttacagt atgtaggaag ctatgaaatg ttagttatta ttgtcctaat atgctggaat  84600
ttgctgctga attagttccc ttgggttttt ttttttagtt aactcctgat ttttgcaact  84660
atatagccag gaaattgctg tacacccttt accaacaatg cccaacccag ggcaggcctg  84720
gtgattgccc tggcccctac cttgcaggca gaaccatcat catgtccact caccacatgg  84780
acgaggccga cctccttggg gaccgcattg ccatcattgc ccagggaagg ctctactgct  84840
caggcacccc actcttcctg aagaactgct ttggcacagg cttgtactta accttggtgc  84900
gcaagatgaa aaacatccag agccaaagga aaggcagtga ggtaggtgtc tgcccaggga  84960
aggaccctgg cctgggtgag aaggagcaca cagcacgggg ctgccactcc agacatggct  85020
actcacacag gctctcgcca ccagaatcag tgtctttgtt ctgggaccat ttgcagaaga  85080
tttcgatgaa cacattctga agcctcctcc tacagagatg ctttagccaa aatgaaacaa  85140
ctagctttaa atggtctgca agtattacat gccagattac acaccagttt ggtgcggttt  85200
ggtgcaacat agaagtgagt gtcttattct gtaaggttag gctgttttaa gagcaattgg  85260
ttgagcttca tttcaacatt aatattccct aattaaacct gaatttcagt ggtaagtgaa  85320
aactaagaag aggcctcctt gggtgctata acataaaaat gatgaaggca aaaagtacca  85380
accagcagag accacttcag cacatcagga gacccagttt tatgtctgtg ctgcgaagtg  85440
aacaaactgt gtcatcctag gcaaattatt taattcctcc ttttttttag tatttttttc  85500
ttcttcacat ggaacatgaa gctaatgacc tctgcttcta tttcttaggg atgtgaagat  85560
aagtgagata aagtattata aatgtgctct gggcttctta agaacaggca ttgctcacat  85620
tcaaatggtc atgattatga tatggcagca ttatttatgc ctctggttta agtgtctggc  85680
tgccgctggg gtttcctatg tccatccacg gggagggagg cacagaatgt ctcccacagg  85740
cagaacctac agctgccaca taattgatga caagccaaag ggacccttgg aggttctgct  85800
cctctctgtg tgtgactcac acactctcta ggataaaatc aagcgactac accctcaaaa  85860
tgctcagatg aattaacaga ttaaacagtg aagaaaaaaa tgtgttgact acacttggca  85920
gtgagaaata aataaagcgg gcggtgacag cagctggcat cagggagagg ctgtcatgga  85980
agggatgtgc atcttgtcag tcatcccatc catctgttgc aggggacctg cagctgctcg  86040
tctaagggtt tctccaccac gtgtccagcc cacgtcgatg acctaactcc agaacaagtc  86100
ctggatggta aggactggac gggccatact tgggttccgt ctggcagcca tctcccagta  86160
ttgctgggtg tgtcctgttg tgatgcattt taatgggagc aaagagaaca ctgggtactt  86220
ctgcaggtca cacagttgtt cttttgcttt gagcttcttt ctcctcttcc ttcttccttc  86280
attcccaaag ggattttaaa agtcatgcac ctaaaggccc tctcccttta atgaggaata  86340
```

```
cactctgtgc tcttaccctt agtaagccat cattcctggg gtccccctgc cctggctcca  86400
ggccacattc cttagtgtct ggggagagct tcttctacat gtgtgccgtg gcgccctcta  86460
gtggaagcat ggtgatgcac ggctcttcca gtgaattcgt ggagtcagag attgcacatg  86520
tggatggcaa gtctggaaat agcatacacc cctgttatac tcctgattct cccctcagct  86580
tcccaatttc ccagtgattc tccctttaat taggatgcac tgaagctctc aggggtgccc  86640
ccatctccaa ggagctgcag tggagaggct atcccctctc tatgtgagag aatgtgtgag  86700
aagcgtattc ccacacagga gcaaaactaa acttacgtac tgatgcaggt taatgaatgg  86760
ggaaagtatc tgcttatcaa agaaaaggca tatttttcta tttagcacaa actttttcaa  86820
atgttaagaa tttactaact gaaatctggt gaagcaagag aaccgggcaa tatttgcgtt  86880
gtctgatcat tacaactgga gggaacatgc tcagagaggc atcatcactg ttcatgcacc  86940
tgccctctct ttacactgag agaccctgtg atgaacagaa aacatctttt taggatgaca  87000
tctctgggtc tttctcctag cctgccttgc tgtgggtacc tatctccctg ctctctgaac  87060
cttggtcaag aagtttatat ttgttttaaa ttgatactaa tatgttaagt tactgtgatt  87120
tgccaaaatc agattggaaa cagggcctgc atggctgaat gattcttttt tttaaattac  87180
tttatttcta aataaaggtt ttctttgtat agaatcggga tgctgtgaat ggtgggaaat  87240
gcactaaata gttatgcccc aaataagaaa gggaaaatca tttgaatccc cagttagctc  87300
cttgaaagtc ttttcactta aacacaccca cataccacac acacactcac agacctccct  87360
cccagatgcc caaagccctg ctgacctaca gagctacttc tggaaaggct gacacatgcc  87420
taagacacaa ttcctgggaa tccagcagct ttgggttcaa tttccttcct aaaagaacaa  87480
tgaatatgac ccctggagag ctattagggc agagctgctt ccttaacgta aaggactctc  87540
cagcctccgt atgaagtcat ctcagagcta aagacaatca agtccaactt gcagatttga  87600
cataaagcaa gacttccaat ccggctaggc agaaggattt tggttgaaaa ccatgaaatc  87660
ccttcatatg gatcattttt taaacaacaa aaaaagaaaa gaacctactg ggtgtccaca  87720
actctgagag ctgctttctg aagagtcatg ttttgagtcc tggaatccct ctccctttga  87780
cctgcctctc aagacaatgt gcgagagaac tctctcttca agtgcatgca agtgaggttt  87840
tcacagttag atttttaatt ttaaagtaat acacatttgt acataaaatt caattctgac  87900
tgtatacatg tgtcagataa acagttgata cctgacactt gttcacagtc tatgatacgc  87960
accgcatatc ctaccctctc ccccagcctc tctccatggc ttctcaaccc cccctctgca  88020
tttcctgtga cctgaggatt cagttttgtt tgtggaggca ggtgcaatcc caagagaaac  88080
tgtgcaatct tctgagaagt tagagtaggc atgtgtgtgt gatttaggga aggtacttct  88140
cactcagctt ggtcaccggt tccaggtttg tgtcttgggc aagtccccca tagctggtga  88200
cagaccagaa aaatgaaaac aactttgact tagccctcaa gttttcagtg aatgagaatg  88260
aaaaacaacc atgagtaaga gatttcttac cgagatgatg taaaggataa taatagcagc  88320
cagcactcac ctatgtgcca ggtatttctc taactgcttt gtgtagtttg actcatccag  88380
tcctcaaaaa caacaatgaa gtggatacca gtattttccc cttttcacag atgaggaaag  88440
tctaatgtga cccacccaac ataacatagt ttgaggggac agagcatttc gttgaacaga  88500
ggaggaactg gcacaggaaa gttgcatgac ccccccacca acctccgccc ccaggttgca  88560
cagctagcta gtcgggagga ctttgcttcc gtttccctct gcctctcaat gatgatctca  88620
gggccaacta agctaaaagc agacttgatg gagcatcagt cctctgaaag agtcactgcc  88680
gagatacaaa atacctcttc ttcaaagggg aagtggagag aagtaggaaa tctgggtaac  88740
ctcacagtct tccagtttct ggaaaacaga gctggcatca gtcttttttc ttgtcctagg  88800
ggatgtaaat gagctgatgg atgtagttct ccaccatgtt ccagaggcaa agctggtgga  88860
gtgcattggt caagaactta tcttccttct tccaaataag aacttcaagc acagagcata  88920
tgccagcctt ttcagagagc tggaggagac gctggctgac cttggtctca gcagttttgg  88980
aatttctgac actcccctgg aagaggtaaa gtagagattc cagctggttt ctgtcaagtg  89040
ccagaagtgg cggttctttg aaaaagtcta acattagagc aaagttttgt aaaagcaaaa  89100
agccatcgtt ccccacccaa gcatagcaac tatctttatt tttggcatag ttccccccatc  89160
tctgcatgca tacaaatttt atgtacttgt ggttactgtg tgcttacgtt tttgtattta  89220
tagaagatga tgttctcaga tagagtcgta atggatttc ttcccattat gaagcaatac  89280
ccaacaaaac agagcttggg ttagattttt ctgagaataa gaatgactaa acaaaattct  89340
ctctttttttt cttcttgaca gatttttctg aaggtcacgg aggattctga ttcaggacct  89400
ctgtttgcgg gtatggtgct ggagccagtg gcttgttccc ttccttgcct ccctcccaag  89460
ttccatctcg aaagtctaag ggctgggca cagtggctca tgcctgtaat cccagcaatt  89520
tgggaggcca aggcagatgg accacctgag ttcgagacca gcctggccaa catggtgaaa  89580
ccccatctgt actaaaaata caaaaattag ctaggtgtgg tggcgcgcac ctgtaattcc  89640
agctactcgg gaggctgagg caggagaatc acttgaacct gggaggcaga ggttgcagtg  89700
agcagagatt gtgccactgc actgcagcct gagcgacaag agcaaaatcc atctcaaaaa  89760
aaaaaaaaag tctaaggaaa aagtcatgaa acaacaaagc aggcaaatac tcctccatag  89820
tatctgactc cccagtagta ggcattttgc atcctagatg gctttgagtg acaaaggaat  89880
aacagactga gttaggtcta gatggggaca ctttggatga atgaggattc ttacggaggt  89940
caggttggta gcttcatccc tcagctcctc atgctgtatc cccagtctct cggcctgcca  90000
tgtcatcatc ctcatctcct cctgtcatct ccaccaggcc tctgatccat ctctgtctgc  90060
atgagtgaca gctggcagag tccttaatgt ttatcaaata caactcagac gtcagtctcc  90120
tggcccccttt gagatcaaca taaaatcatt ttgaaccctt atttagtggt ctatgggctt  90180
tgaaaacatg gggaccaaaa ttcctgtgga ttctagaagt ctctcttcta catgtgtcag  90240
cctgggcacc aactagctcc ttccatgaac ttttatcaaa cccacagcca cacaaagcat  90300
gtgtgagtgt agcagagttt acagcagagg gtggagggtg gggagataga tgtgtggaag  90360
ggttacctgc cacacaaaca gaaaccactt ctgatagaac acgaggtgtc cacccacact  90420
gtaaaatcct ctcctggtac aggcaaagct ttgcagcgat tctcctttgc tgcccctggg  90480
ctcctaacac ctcctaaacc accagttacc tccttctttc cagtgtggca tatttcagtg  90540
ttttcctgtt ggagtgtttc ctttctatgt ggattctgga atcagctctt aagataactt  90600
ggttttcatc tttcttcata atgatcccaa acatctatct actatgccta gaactaccaa  90660
tggacacata taccagccca gatatgcttc agcccatccc agtacatcgc atggtgacca  90720
aaagatgtag tcgtcctggc acagtgggtg tggggcagga agcagtcctc tccaggggac  90780
agcagcaatt caccacagaa cccaagtttc tttcaagctc tgctgacaca gaaattgaat  90840
aatctcagct cacccaatgt caaagactca tattaaccaa gaccagaatg aaaatatgct  90900
aatttatatc agaagctttg ctggattcaa gagttagggc cttttacctg tgcagaatat  90960
tccttcttga taaataggcc ctctcaggag aataaattac acatcagagg actgtttagt  91020
cagcataggc atagaacagg atgttccaaa gatacagtca aggggagtgg gtaagagtgt  91080
```

```
agcctctgga gtgaggccga ccaaatatca aacctgagct tcataatttg caaactaact  91140
ggctttgggt aagtacatag cctctttgta cctgtttccc catctgcaaa atggagataa  91200
taatagcatc tacctgtagc attgttgaga gaattaagtg agttaatgct tgccgactta  91260
taacacagta tacgatcact gattaagact tagcaactct aaactaaatg tttacaaacc  91320
atctcttacc tcaaagcact taacatccat tgtcttattt gattatcact gtaatcttat  91380
gaagcaggca gggcaggggt ctgccccatc tggggggaac tgagctcaca gaggttggag  91440
ggtttgccta aagtcaccca ggccactggg tctcactctc tggtcttagc tctgtaatct  91500
aggatgctca atgccacact ctcagccact tttcagatgg ctaagtacat ttgttttgag  91560
ttagctcagt ctcagaggat gacattttct gatcttgtct ccagtgttta aatgaacctg  91620
tagctgtgca ttggggtcac acaatgcgtg gcatggagag ggtctgtggc tgactgccac  91680
ggttactacg tgaaaccatc attacagcag ttactactgt tactgcctga gaacatcatt  91740
acaagactga acgaagggat caacatggaa atgataacaa aaaaaccaaa gtaactgttt  91800
taaggaaagg ctagcatcgg gaagaagaag agagaagaag agaagaagaa aagggctccc  91860
tgcttctaat gagtaaaggc agctccctaa gcttctgcag cccttcatta tttattgggt  91920
aacaggagga aggagcagga ggtaatgatt gggtcagctg cttaaatgat cacgggttca  91980
tgttgttact gacagatttc aattatgcct aatcataaga aacatttgtg cagcctccaa  92040
caagggtcaa tgccacttct gaaggggtga ctcatagtca gtaactagaa agcagcagat  92100
agctagggac aaactggcga ttctgaatag gcctggaacc cttagctctg gccaggtcag  92160
tgggctccag tcaggatgga gccttcaggg agagatcaaa gctcagaggt ttgagatgat  92220
atcagccagc aaagaggagg ggcagtaggg atcctcccag agggagggcc agccatagaa  92280
gacatcaaat ctgagcccgg atcaggagaa ggagcctgca gaactggggc tctggcaccg  92340
agaacctgca gaacttcgcc cctctgagtg caggtgccag ggctggggct gccacccagc  92400
cttcgcatcc caggcctggc acgtcatagg taaatgtagt tgaaaggatg actgagctga  92460
tccaattccc tttacaactg tccttgtcct gggggacttg aggagggtta agaaagcagc  92520
tggggaccaa ccaacagtcc tctaggctct ccatgtccag caatagttgt tcagcaaatg  92580
agcattaatc agtgactata aactgtagct tcaacataac cgacaacttg caatggtttc  92640
tagagcatgc tcccatgtgt tatctcattt aaatttccaa accaatcctg tgaaatgttc  92700
ttttttttt tcttttttt tttttgaga tagagttttg ctctgtcacc caggctggaa  92760
tacagcggct cgatcatagc tcactgcagc cttgacctcc tgggcccaag ggtcctccc  92820
acctcagcct cccaagtagc tgggactaca ggcacacgcc accgtgcctg gctaatttct  92880
tttctagttg tttgtagaga cagggtctcc ctatgttgta caggctgatc tgaaactcct  92940
ggggtcaatc aatcctcctg gcttggcctc ccaaagtgct gggattacag gcatgagcca  93000
ccatgccttc attttacaga taagaagtct gagaaaactc agatttaggc agattgagtc  93060
acttccccaa atttatgtat cttgtaagaa tccatattca aacctcagtc ccctaactct  93120
tagttcatta ctttttctac cacttctcag tatcctctaa gaattcagaa agaaccacat  93180
cgactctgat ttttcatttg tttaagtaca caggtaatag gtgaatgtat tttgttgttt  93240
aaaaattcat ataatacaca aaaggctaaa gtctcgcttc ccacttcctc tcccctttct  93300
acccaactct gcctccccag ggagagcttc tgctgacagt cggtggacat tctttcagag  93360
ttttacaatt atgtgtgtgt gtgtacataa gatgtcagtt tttctttgtg taggatacat  93420
gaacatgaat tttaaacata aatgtgagtg tattacacat attgaccagc accttagttt  93480
ttttgtttgt ttgtttggtt ttctttgtgc tgtttgagaa ggagtcttgc tctgtcaccc  93540
aggctggagt gcagtcttgc aatctcggct tacgcaacct ccacctcctg ggttcaagtg  93600
attctcctgc ctcagcctcc cgagtagttg ggattacagg tgcctgccac catgcctggc  93660
taatttttgt atttttgtag agaggggggtt tcactatgta ggtcaagctg gtctcaaact  93720
gctgacctca aatgatccat ccacctcagc ctcccaaagt gctgagatga caggcgtgag  93780
cctccgtgcc cagccagttt tgttttttta ttaaccaagt tacgtatttt aaacttctcc  93840
atgtcaatgc ttttagagct attttgttct ctttaatgtt aatagagaat tttaaggcaa  93900
tttcaggtga atctatacaa tttctctgta taagtaattt acactagaaa tagattttta  93960
taaagatgat taagctacca gcctggtatt tcattgctga cttaaatgaa gaggaaaatc  94020
aatgctgtaa gggaaaaaaa aaatggcatt agagatccag accttatagg cattttccaa  94080
attattaatt caatctctca aaacaggtgg cgctcagcag aaaagagaaa acgtcaaccc  94140
ccgacacccc tgcttgggtc ccagagagaa ggctggacag acaccccagg actccaatgt  94200
ctgctcccca ggggcgccgg ctgctcaccc agagggccag cctcccccag agccagagtg  94260
cccaggcccg cagctcaaca cggggacaca gctggtcctc cagcatgtgc aggcgctgct  94320
ggtcaagaga ttccaacaca ccatccgcag ccacaaggac ttcctggcgc aggtactatt  94380
gtcggtcggt gtttagctga gctcagtggc tcctctccca gccttcccct cctctcctga  94440
gtgttccttc aggcatgggt tataactcag caaggagcac cctctttaga ttctgctggt  94500
tttgtttcct gctttccaaa cccttatctt gattcttggt aacatgaatc ttctttgtaa  94560
gttggacctc ccctagcaaa gaaaatagaa taatagtgaa aatgttaata ttgtttttat  94620
ttttacagtg agggataaag tcatgttttc attcattttt gcagtgaccc tacatatcaa  94680
aatcattgcc ctcttttttc ttttaatgtt gtttaattta gaaaaagaag ctctggttta  94740
aagaacagtg agtcacgtga cttgctcttt gaaatgccct ttgaagtctg gctgaacact  94800
gggctgcatt cagattcttc agtggccacc agaacattct gttttcttct gcacatctta  94860
cctttgcaca ccctgcttat tatgttcccc cagaagccca accctctcca ccaggggctg  94920
attaggaggc tgcaggataa atgtttaaaa gaatgaagat gtgtgtgcac gcgcacgtgt  94980
gacatctcca tgccacagtc atgtttattc cacgtctatt ctcccacaga tcgtgctccc  95040
ggctaccttt gtgtttttgg ctctgatgct ttctattgtt atccctcctt ttggcgaata  95100
ccccgctttg acccttcacc cctggatata tgggcagcag tacaccttct tcaggtgcgc  95160
ggactcgggg tcaccattct cctctgtggg tttggggcac ctgggtcaca tgctgcttag  95220
aagggccctg accttcccac ttcactggga ccttcaccaa tgagagaggg gaggggtctt  95280
tgggctgcct gcagaaagga acttaatgta tctgccactg cttggaaagg cgatcctagt  95340
ggacaggcag gactgcttgg gaaggccgaa tggggaaagg aatgcaaagc ttaggtgaat  95400
gggttgaagc gccatctttt tgaggcatag gtgacatgcc atcagaccac tgcgagtgtt  95460
caggcagcct accgcactcc caggagagct agcgccatcc caaggcagca ttcggtgcct  95520
ccaatacata cctggcacac agcagctatc cagtaaaggc tctgagttgc atgatgttgg  95580
cacgcgcctg ctctgtccca gtcacatgtc tcactctgtc tagcatggat gaaccaggca  95640
gtgagcagtt cacggtactt gcagacgtcc tcctgaataa gccaggcttt ggcaaccgct  95700
gcctgaagga agggtggctt ccgtaagtgc ctacgcgccc ctgtcctaag aagactagct  95760
cccctgggag gacccaacgg tgggttcaag atggcaggcg ttggggaggc cccactcaat  95820
```

```
cctgctctgc tggtcacttc catgtctctg accagcactc ccccaacctc tccttccaca  95880
cttgtgtgca gggacattca ctacctccta ggaagccccc acaccactgg acagctctat  95940
atttctcagc atagaagttc tatgttgagt tgacagatga ttccccataa cttatttgaa  96000
aggcctctga gcagggaggg agggaaatag ggttatgcta ttgtgtgatt gggccttgaa  96060
tggcgtgagt gacacagtgg ccagtacttt gtgatagttg tgagtctgga gaagggagtt  96120
agcgaaggcc attgacatcc accaggaatc ctaaaagttc aatataattt taacttttct  96180
ccctcagtct ttttcaaagc tgtcaataag gaccaaaaca gactaatttc aaattcctct  96240
tctggttgct gtgtctctca acagctagag ctgctaggaa taaaaaggga gacaaaacga  96300
tccacaagct agagatggtt attccccagc cccacaccta gtcagtcaca aaaccctagt  96360
tttgatattg cttgagcaga aaccagcctc caagagaata agaagaaagg gcctgggtct  96420
aaagaggagg aggaaagggt tgggcacaat ttcttatgcc tagggatttg tcagcaactt  96480
tgaggctgat tatggaatat tttcttgtct tccatgaggg agtacccctg tggcaactca  96540
acaccctgga agactccttc tgtgtcccca aacatcaccc agctgttcca gaagcagaaa  96600
tggacacagg tcaacccttc accatcctgc aggtgcagca ccagggagaa gctcaccatg  96660
ctgccagagt gccccgaggg tgccgggggc ctcccgcccc cccaggtacc tgacctccaa  96720
acaacggggc cccaggtctg cctgccacag agggactagg ggagtccctg gtatctcctg  96780
agtctctcac aaactaacat ttcaaactgg cagttgagta ggggactaaa ccaaactccc  96840
tgcaccctct gggaggggct ccccacaggg cgctgtggct gccaactgga ggaagccact  96900
caccaaaagc ttcattttcc accagatact tcctatttga tctagtagaa aaaatgtgtt  96960
taagcactaa aaaaaattaa gtcatatgtg ctcattatag aaaaattaga aaacacaggt  97020
aagtcagaag gaaaaaaaat catcgcttgg atataaacac agataatgtt tggtttgcag  97080
ccacccaaac agattatatt ccaaatattg tcttaaaatc tgatttactg cataatttac  97140
taggaacatg catccatgtc aataaataga catctgcatc acttttaata tctgtatatt  97200
atcccattgt ttgaatttct tttttttttt tttttttttt tttgagacag agtctctctc  97260
tgtcacccag gttggagtgc agcggtgtga tctcggctca ctgcaacctc tgcctcccag  97320
gttcaattct tgtgcctcag cccccccgag tagtggggat tacaggcatg caccatcatg  97380
cccgcctaat ttttttggta gttttagtac agatggggtt ttaccatgtt ggccaggctg  97440
gtgttgaact cctggcctca agtgatctac ccacttctgc ctaccagagt gctaggatta  97500
caagcgtcag ccactgctcc tggcctaaag ttactttaaa ttaactgatc tcccattatt  97560
cgccacttag gttttttagt tttcaccatt ataagcaatg ctatgatgta cattcaaatg  97620
gaaatgtgtt tacacactta ttaacagtct taattaagaa gctctccatg tgctgtgtct  97680
ctaacatctg caggtatgta cacaaataca tgcacagcca gcatccatct tttgcaggga  97740
cattaatgat cttggctctg agcagcaccc tgtcctggga gttctaaagt ccagaacaga  97800
ttacagtgag catctcctgg gggatttaga gacatcaaag aaggctgtgt ccgtggttga  97860
taatgggcct cccagctgac ttgccagggc tgggccttag acagccctgt ccaatgattt  97920
gtcaatgaat aaactgttcc caaacaggct atgcagttca gtgggaaagc acaggtatgg  97980
gacacggaga gccccaggtg gactacttga cctctctgag ccttaatttt atcacctgtg  98040
aattgggaat aactgcttat ttcataatat tattatgagg atttaatgaa atcatgtggg  98100
caaggaatta tttagaatta gattcaactc aagtgatgac aaccccaaac taacagcaga  98160
taaaacaaga cacaacttgt ttctcactca tctaaaagtc tacgtgggtg gtgcacgatg  98220
ttctattctc tttctcctcc acactaaaca ggcctcagcc tcatcagcca ataaggcagg  98280
agctgccttc caggcagcgg aatggaagaa ggatgaagca aaacagaggg cagagtgtgc  98340
acatgtgcta tgtttaggga aggttttctg aagttcccac atagtacttc cacttacaaa  98400
cccaacaaaa aaggctatgg ctaaggcagc agggaggagc aaataatggg agcaactaga  98460
ttttgccaca gcacctatca cagtctggtt tataaatggt tctaggccaa gaacacccga  98520
tccctgctct tttttatatt ctaaagcatg tatctttata tttctcaagc aatattttct  98580
ctctttgaat cacagctcat ctgctgcatc atagggatcc caaaagaagg acccaaggaa  98640
cttgtctcag tcctctgtgc cccaagagga agctttgctt gtttgctttg ctgtcaatgc  98700
tgagggctcc tgtggctgcc tccactcaaa accctccagc atcaggacgt caaggctgtg  98760
atactgtacc ctgagctctt ggccagggcg agggagggga ggccaagcct acctacatgg  98820
tgtttcattt cctaaacgaa cccttacttc cacgcggtct gtccagctta gaaacttatt  98880
ttcagtagtg ttggtccttg gtccctggac aaaatgtaac agccaaagtc ctagaaaaag  98940
gcaagccagt tcctgccatt ttctttcact tctgcatttc ctcactatta tacgtgcctt  99000
ccattggagc aaaactgaat gccacgcata tgcacaggag ctgtgcgcgc tctgtctctc  99060
tcactcactc tttttctctc tctctctttc tctctcaatc tctctgtctc tatctatctc  99120
ttactcttta tctctcactc tctcactctt tctcactctt tctctcaatc tctttctcat  99180
tctctctcta tctttctctc tctctctctt tctcacacac acacactcac aaacccacac  99240
tcttattcac atctgctcac cctagccact caaacacaat ccctcattca gcctggaata  99300
agtccagagg gcgtgggcct gattcagaga caatcagttg ttctcatctg ggaaatgggg  99360
caatgtggtc atctctaggg accctccctg ctctaacatt ctttgaatgt ggtgggtcct  99420
gaggtggaag cactctgtcc ctgacttcta gtatatgtgg agatagggtt acacaaatat  99480
tttattgggc agaactttta taaaacaatt tatcataagc tatcgcagcc agcagcaatt  99540
tttccaacct ggattccacc aggggagctt ggccggtgtc tgagtgccac tttcagcttg  99600
agaagcaggt gactcagtga aaagagcaag gaggagacag aggcagattc agttcctagg  99660
ccctgggcca cccacctgca agtttgcagc ccagtcagtg caagtcagct aactgttctg  99720
aacctcagtt tctctgtctg taaattaagc taaaaattct tctttcaaag agtgtcagga  99780
tgaagtgaga tcgtgtatgt agggcattta acatagtgcc cgacacacag ggagcattcg  99840
gtaggtgcca gctctcctcc tggcaggaga gagagaaaca aggtgaaaag agtgaattaa  99900
agaagaggaa agtcaaatgg gaaaacaggg ggaggagata gaaagtgtat gaaaaggaaa  99960
gaatggtgcg caataacggc ggtgtaatgc caccaaaatc ccctcaacta cttctgggca  100020
gcacccttga cagagtgaat gcttttatga gaatgtaagc ggaatgtgtt cccagatttg  100080
cagtaatatt gccacctggt ggacaaaccc atgcaccttt gaattttcca aaatatttcg  100140
atgaactagc ttccagtcct agatgtattt tgaaagtgat ttgtaaattg taaggaacta  100200
ttcaaattct ttcattaatg tcacaaatca actgtgtcat ctgtatgcca cccactattc  100260
tgggtgctgg ggacacaaca gctcacaaat caggcaaagt ccctgctctc accaaaatga  100320
tatcctacgg gggattacag atacaaatac gtaaacagat ccatcgggag gaaactctca  100380
gatggaaatg agagctatga agataacaca acagtacatg acaatacaga gtgactggaa  100440
ccaggaacat ttctccgagg aataaaattt gaagcgagcc atgagagggt ctacaggtag  100500
agttcccagg cagagtgaac agccaagcac aaagctgcac caggagagag aggtgctcgc  100560
```

```
cgagagacag ggaggggagt gtggcaggtg agctcagaga ggggcagggc cacacacatc  100620
ggccacatgg gccttggtag tgagtcgaga tttgatccca gggtttattg gagtggataa  100680
gtaagcaagg tgactgaggt gctcgggttt acatttttat agttcaagct ggctgctggg  100740
tggaaaacgg aagttggcag accaaggaca gaatcaggca gacccatgtg gaagtttctc  100800
tagtggtcta ggtggtggct tgggtagcgt ggcagtattg gagctggaga aacgcagatg  100860
gattggagat ttgttttgga gtgacgccat tctgtcttgt caatggattg gcgaaaaaag  100920
aggcatcaaa gatgagttac acatcattga agtgagaact agggagatgc cagtacttta  100980
tttagtattt tctcagcagc tcaatccata aataattttt ggaagacaac aagcagtttc  101040
acaaactact tataagtcct caagttccaa ggtaattaac gtgggtgtct cattgcctca  101100
gagaacacag cgcagcacgg aaattctaca agacctgacg gacaggaaca tctccgactt  101160
cttggtaaaa acgtatcctg ctcttataag aagcaggtaa gaagaaatcc ttttatgctt  101220
tttatcctgg ctccctgtag aagatattaa ctagggacag aagataattt tctctctcaa  101280
tttatgtatg atcagggcag tagatttttt tcttttttat ctgatttgag ggccccattc  101340
aacataaaaa gcaattgagg cacatacaag taaaatgtaa cttaagatta attcttttttt  101400
tgttgtttgt ttgtttgttt ttacatttag ggcaagcagt cttaaatttt aacccacgta  101460
ttattaaaag ttatatcaga agaccataga agttattcaa aaatgcagcc acatatttta  101520
actagttaaa agagagagta aaaatttgga gggaggtgga ggagtatagg ggaaaaggta  101580
gaagaaaaag agaaaataag taagtggcaa aaaagagaaa ggaaaaagat agggtgggaa  101640
agaggcagcg ggacagtgtc tgagtccagc acacgccagg gcgagccagg tcaactgcag  101700
ctgtcatatt ctaactgtga attatcatct ttgatcactg ccctttgaga tgccaatgaa  101760
cttttcaaga aatatctagt tctcttggct ctccagctgt tcttatcagc cccatccagg  101820
atggaacagc tttggcagcc cgtatcagaa caagcagctt gacaggggca tgccatgcca  101880
ggagagagga tcctaaggaa gcgtggtcca gtccgcacag gctctggggc tttaagataa  101940
aacctcctgt ctaactttag taggactttc tgttgcttca cctgccagag ccctgaacga  102000
gggataaatt gacttaatta actagaacac actgcaaatg gtgaaagcat ttagcaaaac  102060
aaagaatgcc atccaagccc caaaataaaa gcagaataaa tagaatgcaa taaacagcaa  102120
ccatcccaaa ctgagttctc agcagcaaat ctccagtatg aaattttgga ttttgtgcgt  102180
gtgtgcttaa aggtggatga caatgacagt tcatgggatt gagctctggg gtccagagtt  102240
ggcatctgtt catttcccat tttgtcattt tacccttgat tgactgaatg tcagtgcctt  102300
aactttgggc tgtggagtga gtcggaactc ccccgaggtg tgcaggtggt tgttagagtc  102360
tcatttttgc agggtggaag acaggagggc tgcagccttc attccacact gacatggtca  102420
ttgccgtgtg ttctgggtcc agatcaggca tattgacctg acatatgacc tgacaacagg  102480
accactcaga aagtccagca tgcgggatat gatttggaga gccagtgggg gaaatcatag  102540
gtcctttctc tgcatgtgta ttcaggcaat gtcccagggc tgggcggctt ccgcattgct  102600
tggatatcgg aaaatgcaaa aatgcccctg aagactgaga cttcagtctt caaaatgaat  102660
gtttgggaaa gaaagttaac ggcactgctg tacttgtggt attcattgca ttattttatt  102720
ttggctttca gcttaaagag caaattctgg gtcaatgaac agaggtaaga aactattttt  102780
atcagaatta aaatctcaga ttgattcatt gttgaaataa ttgcacactt ttaaaaggca  102840
cacctcacag ccatgaggag gggctgttct gtaggtgctc aggaagtcac aagacacgtc  102900
ctgaagaata tgtggctagg gacatcccag actcagaaga cactcagtgg tgcctcttct  102960
tggaggacat aagtgggggt ggcattccct gatgtggcgt ttcagagcat tctcacccaa  103020
aaaaagcttc taaaacctcc aagtatataa cagtttataa tactccaaca agagggcctt  103080
gtagcctaaa cccgggacac tccttggccc attcctttta agcttcaggg agtgtgggcc  103140
agccccagac tcaccccatt cctgaggcat cctggaggtt gaaatatttc cagaggttta  103200
gaacctcacc aagtgggact ctaggagcct gctgcctccc agcctccctc aggaactgca  103260
cctccagaac aggtgcgggg ctgacatgta tgtgctttcc tgggcagatt ctagaccgta  103320
cacatgaaat ctggctttca ggattgctct ccagagggac ctgtggggcc tcggctgaga  103380
cagagagtag gagtgaggca gtgattcaag gccctgagaa agagctcctc ctctgcttgg  103440
tataaccagc taattcattc tgttctgttg actttggctt ctgccctgcc tttgaagggt  103500
ttgaggccag ggagtgatgc actcagactg gtgtttccac acagtcactt cagacttcca  103560
gggcagtaca ggagatagat cccagggcca gtgaagaagc agagcacaag tccaggcagg  103620
agaggctaag ggcctccctg aacaggtgtg aggcacagaa gccccgagag gtagggatga  103680
caggatgaag atgggtcctg tgctgctaga agtacctgca aagcacagag gtggcacaga  103740
aaaggagtcc ttggctggga tgggaggaga tgacatgtga catgtgaaag aggacctgga  103800
gttggctcga tgctcccaaa agggaaaggt gccgaggggga gctagcagcc atgcaaaggc  103860
agagacatgc aggcagtctg ggccatgagg agctctggaa gtgactcgat atgtccagaa  103920
taggccactc cagggaaggg ctgaggaagg atgaagttgg agaggggcac agaccagatg  103980
cagaagggcc tcagaggcca ggatgagggt ttggactcct tcctggaggc agcagcagtg  104040
ggaaaagagt taaaagctgg tttgtaaagt ggagccatgt tgctcgctgg tccaggcaat  104100
tcccccgaaa gttcatgttt ccctacaaaa cccgagagag ctactagtag gcgtgaagtt  104160
cgtggccctg gtctgaggat ttcctgtttc cttgtcaggt atggaggaat ttccattgga  104220
ggaaagctcc cagtcgtccc catcacgggg gaagcacttg ttgggttttt aagcgacctt  104280
ggccggatca tgaatgtgag cggggtatgt aaacagactg gagatttgag taggattttt  104340
gacttgctta actaccatga atgagaaact ctcatgagtg ataacaggaa aaaaaaatta  104400
aaaccgtctt gtttgtttgt ttacatggtt tttagggccc tatcactaga gaggcctcta  104460
aagaaatacc tgatttcctt aaacatctag aaactgaaga caacattaag gtacttgacc  104520
tatgtataat ctgctctgga gctaaaaatt tacctgagct ggttatttta tttttacttt  104580
cctaccttca ttaaattcca tccctcctcc tgctgaaatc tagcaaggaa tgtcttccag  104640
ctaccaaacc cttcctgctt ctcaaatttc ctttccttca ctgatttctg ctttaactag  104700
ctgttagtgc agcgtctcag atgtcctctc caccctctag gtgtggttta ataacaaagg  104760
ctggcatgcc ctggtcagct ttctcaatgt ggcccacaac gccatcttac gggccagcct  104820
gcctaaggac aggagccccg aggagtatgg aatcaccgtc attagccaac ccctgaacct  104880
gaccaaggag cagctctcag agattacagt gtaagccacc acagccccag cctcaccact  104940
ttcttgtcac cttctccact ctttgaacat cctgagagga ttctcaccac cgcgaagtgc  105000
tgatttggat ggtaatgctg tttagtcagg cacatatgaa catccgactt tcaaataagt  105060
gcctcacact tcacatacca gacctcttgg tcattctttc tccccaacat ttatgtggca  105120
agtaagttta catttggttc cattcccttt tggcttttga tagcaagttg ctcctggagc  105180
ttatacaatt attatctttg ctatgtgcaa agcagctgcc aggaactggc aaagttcagt  105240
aaacctttca gctccctcgg agtaattatc ttagattcca ggaatttcct cagaagagca  105300
```

```
tactttggag atgtcgacag agctttgcta ccctcaagct gaggctcttc ttgcacagtt 105360
tcagccagtg gagacagtgg ccttgtgcgt tttgtagtat gttcactcta tttgaggcct 105420
acatggagga ggggttggta ggagcacctt tgttagtgca aacttcagca acgttgtggg 105480
gtcctgattt tactatccta gcacacgctg agtgccagtg aacatgccca gggtcatcca 105540
ctaaaacctg ggccttggct ccttggtgtc ttcctctgga caccctaggg ccctagactg 105600
tcctctgtta attctcactc agccacactt tcgtgtgtct ccttccagtc atttgttcta 105660
agcttactac gtgtatggat gatatgatct gtagttttat caaggtagtg actaccacat 105720
aggatacctt tgtggaaatt agtaaaaatg ctcttttctg caggtggaca ctgtcccatg 105780
ccaggggtta tggcttgtac ataaagttca ggctggcttt agccccaact taccccctcag 105840
ccagatgcct tctatttgtc cgaggaaaga ataaatagag ccaagtccct gtacaacttg 105900
cctgccctct tttcacttaa atttacatca tgaacatttc cttgtgttac gatgtacttc 105960
ttgaaaatgt gatttaacaa gatgattatt aacaaaagat aaatctcaca gaccgtatgt 106020
ctgtcaacat agaaaattca agagactcta tagacagatt attagagcta atgagagcat 106080
tgcagtacat aagattaata taaacatcta tttctataca ccataaaaat aattagagaa 106140
tataataaaa agaaaggttg tctagaaata ttcacatgaa atagaaaggc aacccgcaaa 106200
tacccattta accttggtcc atatggatta agacagttta gtggagtgac agcttcaagg 106260
tagagaagag gaacctggag gccacacctg ggcgggtgta aggccttccc aaagcctgac 106320
tttgtatctt ctcctccttc tgctcttccc tcttcatcgc cctctccctg tgtctctggc 106380
cctgctgcag gctgaccact tcagtggatg ctgtggttgc catctgcgtg attttctcca 106440
tgtccttcgt cccagccagc tttgtccttt atttgatcca ggagcgggtg aacaaatcca 106500
agcacctcca gtttatcagt ggagtgagcc ccaccaccta ctgggtgacc aacttcctct 106560
gggacatcgt aagtgtcagt ttacagcgcc tccctcccct ccgtgggccc aaggtggagc 106620
ttgtgtgtgc tctgaaggac cagaccaaga ggggaggggt tctcacggtg ccagggctgc 106680
tgaaaggcac tgggccaagg gccttgtgta tctgctgtcc cttgacatct tctcagaaag 106740
gcacagaact aggagcccga agctaggaaa ggctgtgggg tgcagcttaa caactggtga 106800
acgggggctc tctatgtcct gcactgaggg gtcttctgac ccatcaaata atcactgcac 106860
cgcaggcatg agtctggcct tcctggcatc agtctggcgc tgagaaggta atatgaaggg 106920
gtctttcacc ccaagtcccc ttctcaaatc ctgccccacc ttcaaaaggg taaaggtaaa 106980
actttccctg tggtagggtc accagataaa tacaggacac ccagttaaat ttaatttcag 107040
atgatgaata atttttagta taagcatatg ctacttcaaa tattgcacag gacatatcta 107100
cactaaaaaa aaaaaaaaaa aaaaaaaaaa cctggttgtt tatctgaaac tcaaatttca 107160
ctaggcatcc tagattttta tttgccaaat ctggcaaccc cagccagtgg ccaaaataat 107220
aagaccttca cttattagat taaccaccgc tacagggaaa aatgaagaaa aaatatttat 107280
taaatcaata gcacactacc accttcctga caaccaaggt tggtgggggt agggaggggt 107340
caggatagcg taccctatta caggctgcag ggtcaaagga attggtagta aaggcctagt 107400
tataatgtaa cagggatcat tatgacatca accccaattt attctaggtg tcttgagtag 107460
taaaatctca acattttaag accaacatga gcctccattt catgtgatga taagatatac 107520
caactgatgg agaccaacac aaatgacctt ctcatccatg gtttttttaaa atgatggtga 107580
atattggaat tcctgaagat atgatttcta tcttactcag cttagtaagc agctatcact 107640
taacaataca aaaccagaga ttatcagtag caactaaatt atttcctctc tcttctgtct 107700
acacgaggaa acactcataa atgcacgggg aggaggtcag aacctgaaag cctttctttg 107760
gataagagca tcaactgcag gtaccacatt ggccctgtga tgctaatata aaaggagcta 107820
ggcccaccgg taccgaaaag ttacttagaa aagtgcggag gcttttaatt ttactttttt 107880
taaaagataa gaaatagaat ttacacactt ggggctggcc cacgtgtttc tgtgtgtgtg 107940
tatgtgtgca cgcacgcgcg tgtgcgctta cagggatctc tgagcctatg gagagagatg 108000
tagctaggat agagtggaca tctgaggtgg gaggtgatac tagctggcag tccaatgaag 108060
gggtagaaga tggtaggcat catgttagca ggctttctga tgctccagaa ttttaaagct 108120
ggcctggaat ctcacctccg cgatccatca ttttggaact taggaccacc attagccagt 108180
ggcaaaaaaa aagttgaatg aaggaacaaa caattattgc ttatgtaatt cacttagcac 108240
atatatgatg ttttaaattc ttatatgtgt catctatttt tctttacttt aaaattttgc 108300
aacagttaca gacttatgga aaagtcacaa gtacagttga aacctttttt tcttagtcat 108360
ttgaaagtaa cttctcagca agatgcccct tctcatttat ttctctcttc ctgtctctct 108420
ctctcacacc cctcagcacg tccgatgtat acttcctaca aacgaggata caccccatac 108480
aaccacaaca caaactgtca acatgaggaa accagcactg atgtgtcatc accacctaat 108540
cctcacaccc cactcctctt tcgcccattg ccccagtgat gtctttcaga aaaaaggatc 108600
tagctcagaa tcatgcatga catttgattg tgctgtttct ttagtctcgt tcagcctgga 108660
agagttccac agtcttttgt taacactcat ggtcttgaca ctttgaggac tgcaggctgg 108720
ttattttgca gaatgtccct tggtctgagc ttgtctgagg tttcctcttg cccaggttga 108780
gggtgtgcat cttggcagca gtatcagcaa acagatgctg tgttctcact gcatcctatc 108840
aggtggcttc tgatttcaat ttgctctgtt actgatgatg ttcaattcgg tcacttaaga 108900
aggtgtctgc tgagcttctt cactgtaaaa ttactctttt ccccttttata ataaatacaa 108960
atttcaggta gaggcacttc aaagatatat aaatatccta ttcattatac aattttccat 109020
ttattcatcc atttatttat ctctgtatgc agtcatggtt catgtgttaa tcaatggact 109080
atgatccaag actatcatta tttattttga tattcacatt atccccactg tggtcagtgg 109140
ggggccgttg aagctggctt ctgtatcgtc ttgacttggg tcctcatgcc cctggacctc 109200
ctccatgctc aatggcacag caagatattc caggctcatc cttccattat ccccattcct 109260
accctctccc caagaagccc tggttcctgc cagtgggaag tggccctcag aagccaaggt 109320
ctgagtgcta gatatgttca ttgcctctgg agcaccattg gtcccaggcc ttctcagtga 109380
tagaactagg gaagatatgg atgtacacac acaggtatgc acacacctct atctatagtt 109440
ctctatctac ctatacagtg aacactatga gctctccaaa accaactcca cagggctcat 109500
tctagttttt tttctttcca catctgtaac tcccttctcc aacagtgaga cgctggcttc 109560
tctcactccc aactcattta tctaccggac ctatacacct gaacagtgcc caactctgcc 109620
accatcccct ccccatgtgg atgccgtcct ctccctgctc cagctgcctc tgctgcatgc 109680
aggtcctcct cgttctgctc tggctctgat accctgcacc agatcagcct cctgtaagga 109740
tatctttctc atcccgttga ggcctccaca ccccacggca ggttgccccc tgaggaagcc 109800
cgtctctggt tcttgccctg ctcctgatca ccatggctcc tcccctaacc ccactgttgc 109860
cgtccccttt ctgtgcccag tatagtggct gtaggactaa attgtttaaa aagggtatca 109920
ttatttattt gagctttgtg aagccaagaa ctaggcttta agtttttctg aattctgaag 109980
acatgcttag aaagaagaat caacaaaact ttatgaccaa atagaaagag tgagagacca 110040
```

```
ggcagaattt tgtaattgat cctttcaaaa gatacaaact aaaggttccc ttggcaggga  110100
ggtagggcat ggggtggggt aggaggacta gtgacagctt aacatatgtt tgccaaccaa  110160
gaactgttta aaaagcaagt cgaatcagaa tcccagaccc tacgagctgg aggagcctgg  110220
ccccacccct cattttgcag agctggcagc aggtctgaga ggttaagtga cttgctctcc  110280
tcttctcttt ccgagatgaa ttattccgtg agtgctgggc tggtggtggg catcttcatc  110340
gggtttcaga agaaagccta cacttctcca gaaaaccttc ctgcccttgt ggcactgctc  110400
ctgctgtatg ggtaagccgt ttgggccatt agctaatgcc tctgaagaga agcctggtgg  110460
tgggggtggg ggatcatctc ctgacagaaa acctgggctg tcctgtggtg gtagcaccca  110520
caagtttagc ttccggcccc aggtagggtc tgaagctgat aaccagggat ctgtctggct  110580
tctgattctg actccactga cagaggtatc tctgaggcct ggtcctgtca gtgacaatga  110640
gagaagtccc acatgatctg aatctcctac tcaaactgag gccttgacca aagcctgggg  110700
gcagccattc cccaacccct cacccagctc tgactctcac tcatctgtgg ccaatctgtc  110760
cacctcagtg tccccatgtg aactggccaa gagttaccgc ccacagtaga agactccggc  110820
caaaaagctc ctcctgagtc agggacagag gatgacacag gggttacatc agcagagtta  110880
cagggcccag catgcaactt tctttcccac gtgtgtaaat ttgaatgagt aattcatcca  110940
tctcggcctc agtttcctca tctgtaaaag aaaatagtga tcctggtcct tcctctgtgg  111000
gccagtagag ccttgccaaa gcattgttct ccacatcttt ctcttggaaa tagagaattt  111060
gggaaccaac ctgactataa gctgtgaaga tgagctcact gggctcatct gagatgacct  111120
cagctgggct ttgctgaccc aggctagagt gggaggtgtt gcaggctgga gaaccctcct  111180
atgaattgta cagggctttg tagtttacag agtatataca cagctagcag cccatttgct  111240
cctcacaaaa ccccatgaag tggtcaaggc aggcatcatt atctccattt aaagttgagg  111300
cacagagacc aacaaatgga gtatctctct ggtcccctgg gactctggcc agttcacaca  111360
catcacctca ggtgtaaggg gagtgcatta tatccagacg tattgtaggt ggaatggaat  111420
gtggaactcc atcactctga gttgtctcat ttcacacaga tgggcggtca ttcccatgat  111480
gtacccagca tccttcctgt ttgatgtccc cagcacagcc tatgtggctt tatcttgtgc  111540
taatctgttc atcggcatca acagcagtgc tattaccttc atcttggaat tatttgagaa  111600
taaccgggtg agcataactt tcttggcttt tttgtttgat tagtaggata gtagagtatg  111660
tgttggtcga gcagagccag gggcaagcat cgtacatgta gcagctgtat gcggatgagt  111720
gccactttct tcctccctac ccccgaccct gcctcctttc cttccttcct tcctcccatc  111780
cttccttcct ctttccttct tctcctccct cctccctcct tcccccgtcc ctccttcctt  111840
cctttttcat tgcttccttc cttccttcgt ccctccttcc cttcctcttt ccttctgccc  111900
tctctccctt tttcctttca tcctccctcc atccctccct ccatccttcc ttctttcttc  111960
cttctttcct tcctataagc accttttttca tttctgtgct ctgaatgaaa tggttttctg  112020
tgtttattct gcaagcaaaa cttgattctt gcaataaact ttaagctttg cttactcttt  112080
cagaaaggtt ttctcaggga ctttgggtgt tgggttttac acacacacac atcaatacat  112140
ttgggtaatt tcaaaatcta aaaggaacaa aaaggcatac aatgaaaaaa tctccttcct  112200
acccctgttt cccactcatg cagttctctt ctccagaggc aaactcttac ttgagtttcc  112260
tgtgtgctct ggagacacat cagcagatcc ctatacggtc tttctcccgc tttcttatgg  112320
aaattgtaac actctgacat atactattcc ttgggcaagt taatcttgat gaagagactg  112380
ggtgttctcc atgctgaatg cctcactttt atgagctgcc aagcccagtt gtcccttcca  112440
cctgacctcc ccctgtccag agacagatgg ccaaactgaa tcataaaaag agggggaaaa  112500
aaagaaggca gtcgctgcag ggctgtcttt actccacact ccacactccc agtccccacc  112560
gctgtgtctg agtcctggct gtggctgtcc ttggaacatt tgcctcacca cgtgcctgtg  112620
tccccaggcg cctcaacctt tcctctcctc attagctctt cccagttcag agggtgggac  112680
cggccagcac atctgcactg ctgccctgcc acacccacct ccacctgcct ctgggcccca  112740
ctggggaaca caggacaaat ctgtgcggag gccccaccat gaaccgccca gacccgtgga  112800
cccctgagac tgactctttc cagatcttgt tagggtttcg tggctgctag gcaagtaacg  112860
aagcctcatc tgtcccatga atgataagaa attcagcatg tcagagtcag actctggaaa  112920
ggcgggggga taagaacaca gccccagcag atggccagag cacccaggtg actgaaagtg  112980
ctgctttgca gagctgtgtt tgccacaggc tcacagccca ctaagtctta agacagtttt  113040
ccttcagaat aattaaatag ccagcttaaa gcaactcaga acattttccc ctctgaggct  113100
gcacccattt agccaacatt tgctaagcac ccgccttcaa aaacctggta ttttcatgta  113160
aattatccga tacacagctg ctatggaaac ccccagtatc ccacaggaag ctccccagct  113220
cccagcagct gccggcccgt gtgagatcag gaggtcttta ccagctgaac accacgtgcc  113280
gggtgtgtgc tgatataaac aagcgtggcc cactcgtcct gccctccaga ggctcccgtt  113340
ccagtcggaa aaggacctgc ccacgaagtt tgcaacgata taagccacag tgtatgatcc  113400
tccataatac agcgtgtgac agagcagcag aggagcgagg cagataacat gctgcaggcc  113460
agaggcagcg ggaagagcca ggctgcaggg gctgggggag ccgtggtgga ggaagttcaa  113520
tttcagcctg tagatttcta ttagcccatt taataaataa tgaagtgcct actctgagct  113580
aatcattgtg caggtattta ggaaggacaa aaaaataatt aggactcagt gcccacccctc  113640
caggggccca ctgactagta gagaaagtag gcagattttt aaaaaattaa tcatgggaat  113700
gtgataagtg ctgggagaga ggaatggata ctttctcatg ggaatcttgg aaggcttgta  113760
agggaaggca ctctctgagc cagctgtcta aagaagaaca ggaatcttta agaaagcaga  113820
agggaaaaga gcattctttc ctgcttggag caataggtaa cagcctgcac atgcccaggc  113880
ctagaggcca aagagcacag tgattccaga aagagtgggg agaaagggta ggcagggaag  113940
gatgaggtaa tgtgggcgca ggtgtggagg ctggagaggg aggaggttgt gggactggga  114000
ggagccagat ggaatggaca gcagtggccc agccaggagc tatgctggcc tcgtacgcct  114060
cgatgtccct tctattttct caggggaggc tctgcccaac atgccaagtc cgaccacttg  114120
aaaacaagtc cctggcttaa cacagaccc agagagagtc tccaaccctc ctctccctag  114180
acaatggtag ttgccctgtg aggggctgaa aagcagagct ggagatggct cagggcctgg  114240
tgttaacaaa tgccttgagg gctcctgttg tttcaaagtg agtctgcagg gagagctccc  114300
taagtggaca gcaggagggc tgcagcttct ctgcacattc ctgctgtcac ccccagagtc  114360
acctagggga ggggtaagga cagtaatgca ggttcctcac agttagcctc ggtgcccaca  114420
tggtactgag catagtaaat gtttagaaga tgctgcctgg ctagacaaag gggaagctcc  114480
cgcccactag aaacttgcag ggagccccag tccttgattg gtcatttaat tgattagctc  114540
cttggcctgg ccttgaggca ctgcttgtaa gtacttcatg acctccattg caaacccatg  114600
atgctctgct ggacaaatcc ctccagtggc cagtctggct gcaaggactc tctgtctgca  114660
ggccttgccc tgtgctgtcc tgtgagagca tctgggcccc acctgctgaa gagagggggg  114720
gtggggtttg ccccgtttcc aacagtccta cttctctgtt tcagacgctg ctcaggttca  114780
```

```
acgccgtgct gaggaagctg ctcattgtct tccccccactt ctgcctgggc cggggcctca  114840
ttgaccttgc actgagccag gctgtgacag atgtctatgc ccggtttggt gggtggtagc  114900
cgaggcccat ggagcatggg ccctgggtcc aaagctggga gggttaccgg gggggctcct  114960
gcatcagact gtggcagggg ctggtgctag gaggggacct tgttgggctg gaggtgtcct  115020
gccagctgga gaggattagg gtgcctctgt ttccatggct ggggagccac aggagggatg  115080
gagggcagcc cttatgaggc gggtgtttgg ctcttgctca gttcccacat aaggcctggt  115140
ctagtgggcc ctgtgctgtg gccaggtctg tggggtgagc tggggcggct gaagtggact  115200
caattcctgt tgatgcccag gtgaggagca ctctgcaaat ccgttccact gggacctgat  115260
tgggaagaac ctgtttgcca tggtggtgga aggggtggtg tacttcctcc tgaccctgct  115320
ggtccagcgc cacttcttcc tctcccaatg gtacgtccat gccacaccct gggccagtgg  115380
gcagctcagg gcatccagaa ctggacctta tacccacatg gtcatttctt tcctcaggag  115440
ccccactcca caatgttttt tctacattct caaagcctgg cttttctcca ataatacaag  115500
tagaggatcg ggttaaaata ggcacattca aatatgtgaa gagcatccac tttaaaatat  115560
ttaaaatgca gtgctattaa tttcaattgc tgatatttaa tccttctcat ttaattacca  115620
aatgtgtatt ttgattagat gatagtattg caaataacaa tggttacagg gtatccaaag  115680
tactaggaaa tagactaatg tatttatgag agaaaggaca cagcaggccc ctttgctaat  115740
tagagatttg ggagcatggg agtaatatgg gagccatgtg gaggggtgcg ggcagtgatc  115800
acgacccccc actcctggag gaaggtgggt agctgccaac cctgactttt gaccagggct  115860
tctcaaatgc caggttagct ggcaattgcc attcttccgc aggctcttcc tgaagctggg  115920
tgggccccctg cctcactccc ctctgcaatc cagtcctacc tttattgtcc tcacccaggg  115980
gcctgaattg ccaagcagca gcccttccta gcaagctttc cccaatagtg ttttgtttct  116040
taacttttcc tcctctcagg ctgagtgtgg tcacctgtaa atagattcca aggacttggt  116100
tttatgtttt gatccacagg gaattgattt attggaaatg aatctgcctt tctactcaca  116160
ggactgtgag aggtgaatga gatcacaggt gtcaacacac gcctgatgaa acaggataca  116220
caagcagttc tagttatggg agacagtgtc aggaattgtt gtccttggca ccctcagccc  116280
ctgcagaccc tttctgcagc cttggccata ccttttagag gcttttgtgt gggagagagc  116340
aggtcaggag gttgactacc caaattgact cattagcttc aaactctgat gtcaacacat  116400
ttgaatgagt cctgcctgct ttagggccta aagaggacca gagaagtaca ccatagtccc  116460
tggcttccag aaggtcaggg agggtttcaa agaagaggct gtgtctttaa gaatggggaa  116520
gattccattt ggtggggcag gaggaggaga acattgaggg actggaaaca catgcggagg  116580
ctgggagacg ggaatgacca ataggactgg gaaccagggg gagatgccaa ttgctgacag  116640
aggagttagt gcaagaggta agtgagaagg gtaggtgggg ctggattgca gggctgtaac  116700
tacagctgca gagggagggc ttcaacctac agctgatggg gaacaacaga aggttttgag  116760
gcatgaggtg gcctgatgac aactctgttt tggaaaggtg gagttggcag ggcagactgg  116820
aggaagtggg aggctcggag gttagtaact acccccttact gagtgcttgc tgtagaggaa  116880
gcattttagt cctgacggtg atcccaggcc ctgagtcttt actctgtgcc aggcactgtg  116940
ctgagttcat cttcagcaca atcctatgag acaggtattg ttaccctcct cctcatcaca  117000
tggttgaagt aggcaaggtt cagagaggtc caatgcccaa gatcacacat gaggaggcca  117060
ggactggaac ccaaggctga ctctggacat gagcacctga cctctctacc taatgcctaa  117120
tgcctctcct gctgggagcc ctttttagaa tttaagtctt aaaggatgga agcccagaag  117180
gaagcagaag caaggaagtg gaagagaggt cccatggaaa ggacagtgcc aaggacactg  117240
tacagccagc ccaatcctga cccctttttct tcatctagga ttgccgagcc cactaaggag  117300
cccattgttg atgaagatga tgatgtggct gaagaaagac aaagaattat tactggtgga  117360
aataaaactg acatcttaag gctacatgaa ctaaccaagg taagggaatg ggtatgagtt  117420
tggaggtgct ggttagatcc acagttggca tgatgttgcc attttccttc tatagaacaa  117480
ttgatatgct tatgcaagca atttggttcc cagttttatg tagggtcatc atccctgtgt  117540
tataactcgt cttccaagag catctaattc caatgtgtgt tccctgctat tcatctcggg  117600
cactgacaca gggcctcagt gagaatcact ccagctgagc atcattccct tttctgtgtt  117660
ctgtttctgc agagcatggg tcagcctcga gatgtctcag tactcaccac acctctgtgc  117720
ctgcccatgt caatatgtaa cctcctagtg ctggtagttt tctcctaaac catcctttgc  117780
tctttgttcc ctcttcccct ccttgctctc accctgtctc agttctcagt ccggtttctt  117840
cgtatcttgc agatttatcc aggcacctcc agcccagcag tggacaggct gtgtgtcgga  117900
gttcgccctg gagaggtggg tactctgcag accacgtgtg aaaggcttcc gaacatcagc  117960
tcttgtgcct gcctctcctc cccataaggc agagctattc aataggaaca taatgccata  118020
atgcaagtca catatgtaat tttaaatctt ccactagcca catgagaaaa gtaaaaagaa  118080
aataggtaaa attaatttca ttagtatttt ttattttact caatataacc aaaatattat  118140
ttcaaaatgt aattaataga aaaccttatt aatgaaatat ttgacaattt ctcgttgttt  118200
ttaagtcttt gaatctttac actcagggcc cgtgtcaact gggacttaga tgtgtttcaa  118260
gtgcttagta gccacatatg gctcgtggcc tctgatggca gcccaggtct aaaattcctc  118320
ccccagctca cacacacact taccctgggg cctgacattt tagaccttct tgatctctag  118380
ggccaggcta gctctgtgtt ttctcctagt gctttggcct cctgggagtg aatggtgccg  118440
gcaaaacaac cacattcaag atgctcactg gggacaccac agtgacctca ggggatgcca  118500
ccgtagcagg caagaggtga gtatcctgct cctcctgtct cagggagtct ctcacaggtc  118560
ctgtgagaag aataggaagg gtgatcatca gaccctatag tagggtggct ctgaggccct  118620
gaaagatctg tacagagaag gaggcctccc agagagcatg gcccaaaaag cccaacacat  118680
agacccaatg gaaaagtgaa ctgaattgtg atagttaaga gattcctctg ttgggatgga  118740
ttcttggaaa gacctgggaa gcactaagtg tgtggttctt aatctcttag aggtcacgga  118800
accttttaag catctgatga atatttgtag cctattccta taaaaatgca ccattgcttc  118860
ccattacctc cctccacaca tttttacaaa acgtttcagg gagtttactg agccccaggt  118920
cacatttatg atcctgcagg agctcttgaa tcccaggtta agaacccctg tgatgaatga  118980
agaatccttc ctctgggttg agtttctaga taggggctca tgcatgggcc tttggggtag  119040
cctaacctgc attggctatt tgtaggctga tatttggctt tgccagacca aggagcatag  119100
agggaaaact ggcgtgtgcc cttggattct ggagggtgac tgctgctctc tgtaataaaa  119160
tgtgtttaaa cagactggtc ccctatgggc aggacagaga ggatgagctc tcactcatct  119220
gcctctttcc tggctgcagg aaaagcttga acagtaaaac ttcagcacac acaatagagg  119280
tgcccagagg aagcctctgc cctggtttat aagtggagtt aggtgctgct gacatctgtc  119340
cagcatctgc ttgactgggg cctcttcctc tctcctgaaa gccatcctca gcatggccca  119400
atgcccagtg ggcaggacga gtcctgagca cgcttcactg gctcagacag gatgaatttg  119460
attctttggc ctccatagcc agccctactg ggtttacaga aaagggacag gcaggggtga  119520
```

```
agccaggtca tggctgagtc catctcaaca gatccagctt cacctgcaag tgaccacgca  119580
ggtgacttcc tcatggtgac aaaaggagtc atggcagggt agagatatca taccatggca  119640
ggggaaagat atcatagaat tttccatgag cacatttatg agacatcaag ttacaactgt  119700
gtccaagtga ggcacagtct gacatccaga aggtaaaact gagctggacg ctagaaagaa  119760
actataggct taagacacag aattgggatt atatggtagg gtagctccca ctaatttgga  119820
aacgtaccct acttgcttcc ctgagtagtt ttaattggcc cagccatgcc tttggtggct  119880
tttgtcattg tggggaactg taatggtctc tctgtaccat cctatatcat ccatccttta  119940
ttcatagacc ctaagctata agaagaaaag gatgagatta gactaaatgt ctatgtatag  120000
tttattttcc atcttggcaa tatatttttt agtgggggtg aatatattag ccaaagggag  120060
ttggtggaac ccaactcact ctacccctgc tccctgcagg cctctcgctg tgggtagtta  120120
tctgactggc tcctctttca ttgctatctt tgccaataaa tacagataga gaagtttact  120180
tccatcggga cacatgcatc ttttctagtt acttcccaaa tgtctgaaaa ttattgataa  120240
atcatgaatc attttcttaa acctgatctt ccctctgttt ttaaactcac atgtgaggtg  120300
atctgatcca aaatgaaagc tgacttttgg cgtaacaggg attcaattaa tcctagacat  120360
ggaaacatgg aagaatctga caggattcag tttctaaccg aagggcccct gttttgattc  120420
ccaaatatcc catgcatttc tgaagccaaa taggagaaga gaagaagcag cttccttttc  120480
ccgttggcag aagcttctcc agccctagct ctatggtcat ccctccactc cttgaaggat  120540
actcagtaat tgcttttttt cttgcagtat tttaaccaat atttctgaag tccatcaaaa  120600
tatgggctac tgtcctcagt ttgatgcaat tgatgagctg ctcacaggac gagaacatct  120660
ttacctttat gcccggcttc gaggtgtacc agcagaagaa atcgaaaagg tgaaaaatgt  120720
tttgttgtgg ccacatagga gtctggttaa ttacaagcct gtttcatgag agtgcattct  120780
cttggagatg agaaactgaa gcgtgctatt cattcattca ttccaacaaa tgtttactat  120840
gtgtctactg tgtgccaagt actgttctag aaaccaggag tatagcagtg aacaagacag  120900
acaaaaaaaa atccccactc tcatatctaa caaaatgttg tatgcattta tcctctgact  120960
cagcaatcac acgtctaaga gtttatcctg aagatgcatc tcccacagtg caaaatgaat  121020
atgtataagg tgatccattg catttgtaat tgcaaaatgc tggaagttac ctaaatgttt  121080
agtcattgta gattggctga ataatttatg gtacagacac acaataaagt cttacgcaac  121140
tataaaaaag aagaagaaaa gtctcagtaa actgatatgg agatatttcc agtaaatact  121200
gttaaatgat aaaaagcaaa gtggaaaaca gaacatagag aacgctactt tgtatgtaag  121260
aaagaaggaa aaacaagaaa gtaaacgtat gtctgcttac ctttgcaaat agaacgtaga  121320
aaggataaac cagaaaacaa tgaatttggt gatcaacaag aagaaaatgg gaagaaagaa  121380
aaatgggagg aaacagtact tctggggata tatttttgta tagttttaat ttttggaagc  121440
atgttaatgt tccacatatt caaaaaaaat cagtaagaat gggaagtagg caaaaatgaa  121500
aacaaaaaga aaacctaaca ctgacagcaa actaaataaa gtaacccaat tttatttcaa  121560
ataaatatca taatcttgca aaagggggat agagctaaca caaacaactg ctgaacacag  121620
tgtttgactc tatatcctca ttcttgggca gggtggagcg ggggagaaga actacaaata  121680
atttctgagt tctttttagt ttgtttttta tagtggtata ggcaaagtga ttctgaaaat  121740
tttagatgtg ttacaggatt aaataaatta ataaatgttt tgatgttatt gggacccaga  121800
attctcaccg tggaagaagg gacttacaaa tatggaaaag ggaaaagcaa gaaagaactg  121860
tgaggtcatg gataggaacc ggaggtagca ctgggaattc aggaatattt atatgcttgt  121920
gtttgtgggt gcatgcagat gtgttcatgt ttcatgcaca taggcatgta tatatagaca  121980
tatatttgca tgtgtgtatc tgtcttccga aaggctcaag aagcaaaaac accccagtag  122040
ccatgagcac acttagcact caggcttttg tcttaataac attcccccact aaaagtaacc  122100
ctgattcctc caataaatga taagttccag ggctggaatg gcataggtat aaaatgaacc  122160
tggaatatct tatgccagaa agtaaggaag tgcttttaaa aaaaaaataa ggggctgggc  122220
atggtggctc acacctgtaa tcgcagcact ttgggaggcc aaggtaggaa gatcgcttga  122280
gcccaggagt tccagattag cctgtgcaac atagggagac cctgtctcta caaaaaaatta  122340
gcaaacaaat tagctgggcc tggtggtgca cgcctatagt cccagctact caggtggctg  122400
aggtgggagg aatgcttgag cccaggaggt tgaggctgca gtgagctgtg atcaagccac  122460
tgctctccag cctgggaaac agagcaagac tctgtctctt aaaataataa taatataatt  122520
ttaaagaaat aaaagtaact ctgtacagat tgcttattgg ttacatggga gaaacataat  122580
aattttacaa tggagaaatt agacagcacc ttaactgggt gatcaaaatt aaccataagg  122640
ggcagatgga catctcatgc cccgagatgt gataccctgt gaaggacaca atttcactta  122700
tgtagaatcc agattggaga tatgtaacct gaatcttatc atgaggaaac atctgacaag  122760
ctccaaagaa ggaatattcc ttaaaaaaaa aaaaaggaga ctgtattctt caaaaacata  122820
agagtcataa aagacaaaga aagagctatg gaaatatctc tgatcgcagg aggctaaaca  122880
ggcataatga ctgaatagca gacaatagac tacatcttgt gcagaagaga aaaaaaatga  122940
tagaaggata ttattggacc aactgacaaa actgaactat gaacagtaga ttaggtaaat  123000
gtatcataac attaagttta ctgacattga taatgtactg tggttatgta agagaagatc  123060
tctattctta ggaaatatgc cctgaagtat ttaggagtga agggctgtga tgagtaattt  123120
accctcaaat gggtcacaaa aaattgtgtg tgagagagag aagggtttta ttagttaata  123180
attctatgaa ctatttttat tcctatatgt ttgtgtgagt ttgaaactat ttccaaataa  123240
aaagttaaaa atggagatta cattctagtg ggagggatag acgatctgta gataaatagg  123300
taaaatatcc agtacattag agagtgaaaa gtcctcaggg aaaagtaacg cagggaggaa  123360
ctgctggggc agggtttgca ttttgaggta gggtggccca gggagagcct gcagaggaga  123420
gaacctgaat gaagaactag aggtgagaga aggagccacg tgcacaccta gggaggaaca  123480
ttccaggcac gggggactag tatagaaggc agaagcatgg tgagcttgtc tccagtggct  123540
tccctagatc ccctcctgcg catgtgcaca cacacctggt gtctctgtca tcgttccctc  123600
acagcactgt cacgatctgc cagtattctg tttattttga ctgccacctc cccgcagtct  123660
gaggatagca gcaatggctg tgttcacatt gttctccagt gcctggttca gtgcctggcg  123720
tatggtcagt gctccatagg tatgtgtcgg atgcacaagg ctttgggtgt aaccctcttg  123780
acgggtggga tcaacaggtc tgggactcac catcttctca aacagagcct tcctcctcca  123840
ctgctagcca tggtccagga cgctgggcga gacccactgt cttgctcttt gtaaggctga  123900
agtccatttc ccaggcggct acacccaaca gatgctgagc aggctgggcc accctgggat  123960
ccaagacaca gagagaaaga gcccctgtct ggcgcctgaa gcacatgcca gaggacagga  124020
gccagcagga gcctgtttca gcctagctgg ggatttcatt ctggaggcgt gagatctggg  124080
agcccaaggc tttgaactgg gggaggtttg gggtgtttgc ttgtcttctc caaatggcat  124140
ttctttctct tccctaggtt gcaaactgga gtattaagag cctgggcctg actgtctacg  124200
ccgactgcct ggctggcacg tacagtgggg gcaacaagcg gaaactctcc acagccatcg  124260
```

cactcattgg ctgcccaccg ctggtgctgc tggtaactgc gggcttgggc cgcaccaagg 124320
gcttaaacca agtgctgggt ctcttgggtt ggggaaatag gttctgggtc ggcagattta 124380
gaaactgcag cagtttggct ttagtctgga ctgtttcctg tgttgctcat tttgagcgat 124440
cagcccagtg tttggttcac acagctccgg agaaaaacaa gtcacggcac agccttgact 124500
tgggactgcg cacatcctgc gttcccagga tgtctcctgt ggggccatcg gctcacagcc 124560
gggaagttca gcccactctg cggcctgtcg gtgtctggtc cccatacagg agcactgagc 124620
tgggtcaaag gctcctgagc tgagccaggc caggcctgag gccatgccca cgcagcccaa 124680
ggatcatgag ggcacaggac atagcgggaa ccaaggaagt gacctgagtg acctccctgc 124740
cttctgacaa atgtatttgc aggattttct ttttttgagg agaattctgt cattgcctta 124800
atccacttta atcccctcgt gggctgaaat gggcccagga tggacgccac gcttctttac 124860
tcttggatcc acctcctgcc ttccctaccc tacaccaggg taccccctgtc ttgctcaagt 124920
gaggggagtg actgtgtgcg ccttctgtca gctcatcctc cacaggggag ccagcccagg 124980
gggaagcagt aatcagaagg gccagctccc agcctgtgcc cccaaccttc tctccacccc 125040
ccaggatgag cccaccacag ggatggaccc ccaggcacgc cgcatgctgt ggaacgtcat 125100
cgtgagcatc atcagagaag ggagggctgt ggtcctcaca tcccacaggc aagagattcc 125160
cagggctggg gaaggtgggt gggaatcctc tcctgctcac ctcctctctc ctgccccaca 125220
gcatggaaga atgtgaggca ctgtgtaccc ggctggccat catggtaaag ggcgcctttc 125280
gatgtatggg caccattcag catctcaagt ccaagtaagc agatggtggg gcgtgcccct 125340
tgttgccttc tgtggatcca cctggatcct gtgttctcca ttgacacttg gaagagtcct 125400
gctgctccgt catcccctgg ggcagaggca ggtggtggct gggcctcatt ctccagcagc 125460
agatggagaa ggccatcatg ctgataagaa actcctctat attggcctaa tttcctgtgg 125520
tcgaagactc gcccaagtct ctggatgggg catctgatca ggatgcatgc agagcctggc 125580
tgggatgagg gagggctgct accactgcct caatatttca ccacttatct caacagatcc 125640
gggacctgtg gcctatttac taagagtcca ctccaatgta ggaatggtta ggagaccaac 125700
tgacttgagg acccatcttt gtttttagaa tattgtatgc ttttgagttt gaaaaaagac 125760
catatgttat atgacaaacc aacaatggca gtaatcttga ataggattat ccttatcctg 125820
tacccacaca ttgtaaacta ttgtagataa ttccttatta ttaagagttt gcatgccaaa 125880
gctaacagtt taagattatc agcatattgc cgtgctcatt cacgttctga tatgctttat 125940
aacctagaaa agagcagagt tacaattact catttattta acaaacactt attaagagct 126000
cagaatataa gtcactaagc tggttggtgg gaggaacagc acataaccca ccttatctat 126060
gctgaggtgc ataatcctga tgcacccaca ggagggtgtt acacagaaga tgtcatcctt 126120
tcatatgtgt cagagcagat aaataattga gagaaaggtc taatagatta gctgcttgtg 126180
gcaagtggac gtttgaccca tgatttattg agcaactaca acttggacac tgcatagata 126240
tctatagaaa tagcagcatg tcaggtcacc agacctgtgt cagcaacttc ctgtgtccaa 126300
ctgctggaga aagggaagtc tcctattcct ttccctccag ctccttaata tctccatgat 126360
agaggggtg agaggggagt gttccctgtg tggagggatg gtgagtttc tggagctgaa 126420
aggtaaacag cctttctcct ctgcatctta ctgcagagga gaacagccct agactgtgga 126480
ggaagctttg gagtcagtta tgactgacac aggataccag ggcatagggt actgacaccc 126540
gctagccgtg cacacactct ctggtggacc atcactcatc caagagaggg taaccagcca 126600
tcctgctgaa ggagaaagaa agcaccaatg gcccaagccc tagcagctcc attgtttcag 126660
gaagcttcct cagggaagtg ctgccttccc gagcctttgc tcccacctgg cccatcagcc 126720
cttaccacca ctcagtatgc actggtccac gtgtctttat gggcagtctt gggatcccca 126780
cactgggcta aaactacctt tgacggccag gtgcagtggc ttacacctgt aatcctatca 126840
ctttgggaag ctgaggcagg tggatcactt gaggtcagga gttcgagacc agcctggcca 126900
acacggtgaa accctgtctc tactaaaaat acaaaaatta gatgggcatg gtggtatgca 126960
cctgtaatcc cacctactcg ggaaactgag gcacaagaat tgcttgaact cagaaggcag 127020
aggttgcagt gaatcgagat cacaccactg cactccagcc tgggtgaaac agcaagactc 127080
tgtctcaaaa aataaaatag gctgggcgtg gtggctcatg cctgtaatcc cagcactttg 127140
ggaggccaag gcgggcggat cacttgaggt caggagttta agaccagcct ggccaacata 127200
gtgaaaccct gtctctacta aaaatacaaa aaaaaaaaaa aaaattagcc gagtgtggtg 127260
gcaggtgcct gtagttccag cctctcagga gactgaggca ggagaattgc ttgaacccag 127320
gaggcggagg ttgcagtgag ccaagatcat gccactgtac tccagcctgg gcaacggtga 127380
gactgtctca aataaaataa aataaaataa aataaaataa aataaaataa aataaataaa 127440
ataaaataaa taaaactacc tttgacttca gcaagtacga ttatcccaca ttaccatgca 127500
gacatttgat ctctaaaaac tggtatcaaa tgatttctcc agggactacc atggtttttc 127560
tctcctagtt ttcagtatgt acacaggtct atggtatggg cctttaatcc ccagtatttc 127620
tttttttgtt gttcttgttt gggtttgttt cttgttttc ggttttttg agacagggtc 127680
tcactctgtc acccaggctg gagtgcagtg gcatgatcat ggctcactgt agccttgacc 127740
tcctatgctc aagtgatcct cccgcctcag cctcccaagt agctgggacc acaggcatgt 127800
gccaccatgc cctgctaatt ttcgtagaga cagggtcttt cttgttgccc aggcttatct 127860
tacattcctg agctcaagtg atcctcccac ctctacctcc caaattgctg ggatttcagg 127920
tgtgagccac caagctgagc ttaatcccca aaatttctga tgagtctact ccttattttg 127980
ggattacctt aggcccaacc actaacagag gcctgtcctg cactgtgtgc atcccctaga 128040
tttggagatg gctatatcgt cacaatgaag atcaaatccc cgaaggacga cctgcttcct 128100
gacctgaacc ctgtggagca gttcttccag gggaacttcc caggcagtgt gcagagggag 128160
aggcactaca acatgctcca gttccaggtc tcctcctcct ccctggcgag gatcttccag 128220
ctcctcctct cccacaagga cagcctgctc atcgaggagt actcagtcac acagaccaca 128280
ctggaccagg caagttggcc ctggggcacc gagagctgag caaagactgg tccagaacac 128340
ccagtgtggg ttggaattgc cataagaggg aggcataaca ttcccgattt ttaacaaact 128400
cttgccctct gtttattggg gtaaaagctg atatatcaga aattgttttc taacaatatt 128460
ttttagtcat caggaaactt cattgattct ttttttaca ttttccttcc ctgtgatgct 128520
atggtgtgtt atttcattct tgctcgtttg tggtggtggt ttttccttca aatcagcttt 128580
attgatgtgt aattaacata cgatgaaaca caggttcttt gggaggccaa ggcaggagga 128640
tcacttgagc ccaggagttt aagacaggcc catgtaacaa agtgagactt tgtctctaca 128700
gaaaaaaaaa aaaaaaatca gaaaattagc caggcgtggt ggtgcatgcc tgtggtccca 128760
tctacatggg aggttgagga aggaagattg ctggagccca ggaggtcaag gctgcaatga 128820
gctgtgttca taccactgca ctctagtctg ggtgacagag caagcccctg tctcaaaaaa 128880
gcaaaacaaa acaaaaacac ctattttaaa tgtacagttt agtgagtttt gataaacgtg 128940
cattccatgt gtggttttta aaaatgtaat cacatttttt attgcggtaa aatataataa 129000

```
cataaaattg accatgccaa ccatgtttaa gtgcacagtg cagtggcact aagtacattt  129060
acattgttgt gcaaccgtta ccaccatccc cgatagaact ctttcatctt gcttcagtga  129120
aaatctgtgc ccattaaaca ctaactcacc acttactgcc cccctcgccc ttggcaacta  129180
ctgttctact ttctgtctct aaggctctga ctactataga tacctcatat aagtggaatc  129240
atacagtgtt tgtccttttg tgtctggctt attatgcgag gacttagcat aatgtcctca  129300
aggttcatcc gtgttgtatc atgtgccaga atttccttcc tttttcaggc cgaataatat  129360
tcctttgtac gtatatgtgc tacattttgt tcatccatct attcattcat tgatagacat  129420
ttgggttgtt tctgggtttt gtgtttttat atatgttttt ttaaaaaataa acatctttag  129480
agacagttca gtaaagcagt ggaaacaggg aagtctccat ttaacccctg aggatctggc  129540
tcacctgcac cttctcatca gcattaagca gagggaggca cgagcaggag ccacctgcac  129600
actcaatgag gagctgaaca gggatcaatt acctttttt ttagttatta ggatgctgct  129660
agctgagaat ctgccttgcc ttgattaccc caatgtctgg tgcccaagtc ccttgagtcc  129720
tccagcagga actcctgtgg catcactcag gagtctagtc taagaagcta gctctgacca  129780
gggcagtggt ggccaggctt ctgtgagtgg gccagcctcc cccgggtagg acacaagcca  129840
taccagcagg gctgtatgtg aactgtggaa aatagagagc aaagtgggta ggtgggtgta  129900
gggtgctgtt ttcctggaaa tatctaccta atctcgctct tctcttacct ctaggtgttt  129960
gtaaattttg ctaaacagca gactgaaagt catgacctcc ctctgcaccc tcgagctgct  130020
ggagccagtc gacaagccca ggtacccctg ctgcttatgc agtccacagc ttgaggcagt  130080
tccttggctc agagcccagc tggttcactg ggcttgagtt gctccaaggc tcagatatgc  130140
ctcctacaga gagccccacc cacaccacgg tccctaccaa gtccccacca catcctcatc  130200
acatccttgc taagtccctg ccactgtgtg ttctgtgctg aagaactttt cattcagtag  130260
ttgtaggggt tcctattgta atcaggaaac catctggata gcatgggaga gcatttttga  130320
aaagaacttt cccatgtttt tgcttacagc aaaaaagctt ggatttgggg aataaggagc  130380
agagaaggta atagagaata ttagaatgtt ttgggtgctt gacatctatg tctggacatg  130440
tgtttgagtt tcaagggaag ggacttaact ggcacatcat ttcagtgtca gacacatttg  130500
gttagatcaa ggaatagcat ctgttgtagg aagagggctc tttgttcttt ataaaaatta  130560
caagaagatg gagaaagaag caataggagg tatgtctcct ggcttgtgat aactcttgga  130620
ataggtgctt gtaggttcct gccctggcac agtgccccat gtaaggagca caccacccaa  130680
gaaggagaga gctagagcaa gtactggagg aggcaccagc atcccaatgc cttggcttaa  130740
gcctgggatt gtagagggat gaattagcca ctctcttctg acttacctgg agagtaaatc  130800
aaatcaaatc aagaagcaag gatatgcaaa aaccttattt ccccataaag tttttattct  130860
gcccagtttc tggattgcaa gaaaaaccaa atacagctaa tgattgaaac actgctgtct  130920
aaagcagtgc ttgtgatgaa ttttttccct tcctcttgac cagcagagac ctaatggcta  130980
cttggcaaaa ctgactttgt cttcccaccc cttacctgcc agagggccca gaaatgccta  131040
aggctccttt agttacagaa agtttgcttt tactgagatc ttccagccac tgattcccat  131100
ttatagatct ggtgattgct gttgacatca gttgaaaatt atttttaaaa accacttgca  131160
gttgcaaatc ctttttataa ctctgtaact cagaatatag aattgggtag caaaattgtt  131220
tcccagaatt accaatggtc tccccacccc tgcctggcat gttccctctt aaaggactaa  131280
tcccaccaca tcacctctgg gccaggcaga acatcagggg tgctgatgtt ctgtgatcta  131340
cagcagttaa ttccaaactt ttctccctta ttggatgaga tcatttttct attgtgtttt  131400
ttacattttt gttcacaaag attagaaaac ctgcaacaca cttattggca tatttttctg  131460
ataattttca tccaaaacct aattctgact ttacaacata ctatctttac aaaggtttgc  131520
aaaaattctt tcatatagca ttgtatatgt ctgtcatgaa ataatagtaa gtatattatt  131580
gtttacatta taccacttca aaataatttc ctttaaagta ttcttcaaac aagaaaaagg  131640
caatttctct caagaagttt tagagagaat ttacaacttg ctcctaagca aatgtgagaa  131700
cttcaggagg ttcatctggc cattggcttt acaactccaa attgtgagcc aggaccacac  131760
agatatttct ctagaaatca gcgtttgctt accaagaaca tttttactct ccaaaggact  131820
ccatcctgga aaacatgttt tgggataagg tcttatgcaa tcttatactc tgttattaaa  131880
accagtgagg gtcaaggtgt taatagatta agtagtgaca gatgatcaga caacttagaa  131940
acatcctaaa taggttaata attatgtgac catcgcatgt gcattcccaa attaggaaca  132000
actcagatca atttctaatc cttattctta cactgttcca gttcccccat ataactcgta  132060
tctttgtgtt agtttcagaa gtttctgaag taccctcagc cttgatgggg atcctcgcac  132120
cacctcaaat cctgttctca gccctaagaa ctgtgttagt catcctctta agaggatgtg  132180
tgattttaaa tcagataatg ggataaacca catttcgtct agactggtca ggcctttgtc  132240
cagtcccctc ctcgcccaca ctaccccagc tccacagcgg gcattggttc aggaattcaa  132300
cccacacttt ataactggag acagtatctc tccagttaaa aaggtcacct tggtgtccgc  132360
ttctcaagga acatggacat ctttattaat caaagcccaa gctttgatct ggagcctaat  132420
atcctgcact ccagctctca tctctcccct cccccagtca cactttcatg cttcccagag  132480
ccacccctac aggaagtggt caagggaatt ctatacctca gggctgacct aaattaggat  132540
ttcttggctt ttaagataat ggtaactttc ttaagctaaa aaagccccaa aagaccctgt  132600
aagagccctt ggaaacagca ccatgggtgt agcttccccc caggatgtaa gcatgtatgc  132660
acacatctcg tatgtgtgtc tttgtaacaa atgcctggat cttagtacca gggagacctg  132720
attcatagat ttcatagaga aggagagaaa gatggcccat aacctgggtg atctgacaga  132780
atcacagtgc cctcagctga gtgcccttca gaaattgatt gacaactgtt tagcttttga  132840
aatctaaaag tagtacagca tctcagaaaa ccaagatgac gcgagtccat gtgatctcct  132900
tccacaggac tgatctttca caccgctcgt tcctgcagcc agaaaggaac tctgggcagc  132960
tggaggcgca ggagcctgtg cccatatggt catccaaatg gactggccag cgtaaatgac  133020
cccactgcag cagaaaacaa acacacgagg agcatgcagc gaattcagaa agaggtcttt  133080
cagaaggaaa ccgaaactga cttgctcacc tggaacacct gatggtgaaa ccaaacaaat  133140
acaaaatcct tctccagacc ccagaactag aaaccccggg ccatcccact agcagctttg  133200
gcctccatat tgctctcatt tcaagcagat ctgcttttct gcatgtttgt ctgtgtgtct  133260
gcgttgtgtg tgattttcat ggaaaaataa aatgcaaatg cactcatcac aaactatcct  133320
aattcacagt ctccctggtg tgcaccacct agtatagttt tagacattct ttagatgggt  133380
gcatagctcc ttgtcagtcc catgcacttc tgtgagtgtt actgcctcag gactgctcgt  133440
tctggcaaga ttctgcaaca ctaggttgga agtgaatgga ctagtcttaa tgttccatgt  133500
caagtctttg tagagtttga agaaaacacc caactagtaa tgcctgtaaa cattatccat  133560
tgtcagctgg gtattactga ctttaagttt cgtgtctgtt tgcccagctt atttgagtgt  133620
ttacctcaca agtgtaatta ggacaggaga caaagaggca tgcacaggcg agagttggtc  133680
cttggttgga cgtgagaccc gacaggactt tgtaaccatt tgaagaggtc aggacctcat  133740
```

```
tctcatgctg ctgtgccttt tctgcagtgc taccatgtgc atcttctgca gtggtgttag  133800
aagggaatga aggccgggcg cagtagctca cgcctgtaat cccagcactt tgggagcctg  133860
aggtgggcag atcacaagat cagaagatca agaccatcct gactaacaca gtgagacccc  133920
gtgtctacta aaactatgaa aaattagctg agcatggtgg cacatgcctg tagtcccagc  133980
tactcaggag gctgaggcag gagaatcgct tgaacccagg aggcagaggt tgcagtgagc  134040
tgagattgtg ccactgcaca ccagcctggc gacagagcaa gactccatct aaaaataaat  134100
aaataaataa aaaggaatga agatggacat ctagttcaca taaatgctca tcaagattca  134160
gaaaataata attttaaacc aaacatttcc agagactgtg gatgaggaga acaagtgggt  134220
ttccttgtca gggcagtctc ccctccatga cctagagatg ggcttcgtcg taaacatgct  134280
ttcattatac tgaggataga ctccagagtc ggggtgaggc aagaggaaaa ggggagagat  134340
gctgaggccc aggaactgtt gctgagaaga ggatgagaaa gaaagtgagc acaaggtgct  134400
aaaatttttg tttcagctgt gcttgtttag aggcagacag agggcaaggg ctacacaact  134460
ttaagtcctg cacacctcct ggcttgccac tttgcacctt ctagatgcta ggcaaacaac  134520
tgcccataga gactataaaa ctactttggt aaccccgcag cttcatctgg tgttgacttt  134580
ttctttttaag ttaccaagga ccaaaactgt aagaccattt tagctagggc taggatagag  134640
gttgggaaag cccagcacac tgcttgcatc acactgctgc accctggctg gtttcataat  134700
ttaaattagc aactgcaata tcacaggaaa gaagactaca ctcttcgggg ctgcttagga  134760
aaagaaaact aaaaaaagac tatgtagggg aggtggttta gcagccattc tgtttggctg  134820
tgagggtttc ggaaaggcat catgaactgg gaagagtcga tgcaggtaaa atctgcacac  134880
ccccttaagg aaaaatctca gtttaccttt tgtctccact acacctgagg tctgtgtctt  134940
ttcatcctgt tttttccagc tcctggcaca cagaaaatgt tcaactaata cccaccaaac  135000
tgaaaaccca gcaaactatg aaaactcagc aagaaaaata gacagaaaag aagtgggtcc  135060
aagaaaatga tgcctccaaa aagcagcaaa gggcaagtgg agcaggagga tgccgtgctt  135120
taaaaacagc cacaggccgg gtgtggtggc tcacgtctaa tcctagcact ttgggaggcc  135180
gaggcgggcg gattgcctga gctcaggagt tcgagaccag ctggccaatg tggtgaaagc  135240
ccgtctctat taaaatacaa aaaaaaaaaa aagaaagaaa gaaaattagc caggcgtggt  135300
ggtgggtgcc tgt                                                     135313

SEQ ID NO: 7            moltype = RNA  length = 7913
FEATURE                 Location/Qualifiers
source                  1..7913
                        mol_type = other RNA
                        organism = Homo sapiens
SEQUENCE: 7
gtaacagtta ctgtctgtgg tttaaaaatg aggtgtggag caaataaaca ggttggaagt  60
gtggggtggg gtggtggggt agggtggtgg ggcagggtgg ggggttgtga gcagtcagtg  120
ggcttgtcgc cgattagcac tgaagcagtg tttagctgga cggcctttct gtgggcccct  180
ctgacagtgc ccttcccagg aagatgtgtt tctctgtcct cagccacatg aaaatctttt  240
gcctaccgtg cctgtcaatc cattgcctgc ccgcccctcc cccacccccc gttttacacc  300
tgcctgtcca gtctaccgct ctctaggca tccacgctga gcagtgggaa gaactttaag  360
ccctgaagag caggccaaag gcaagcaaga accccctcga acagcttccc agcttagtga  420
ggccttattt cattgattct ctgaggcaca ttgtttttttc acatgttagc atttctgaaa  480
ttgggatgca gctcacgatc aagtcacagt ttaactggac acattatttt tctttcttag  540
tggtgcagaa aagtaacagt gtgtcttaca attgactgcg tcctagattc tgtgagatgc  600
aatacgttat taaccatcac gcacatttcc tgaactcttt caatgagcag acaccagcct  660
gggttagact ggagccctaa aagcacgaca cagattccac cctggactgg cttctgttct  720
gcctgggaaa acccaaagta cgtttggaga ccaagagcaa cataaagtag cataggtgga  780
atagtccatg agaagtgcga gcaaaaggtg ccggagatca gagaacacca agactgtact  840
tgtaaatgac aactggcttt gtgcaatttt ttctgggaaa ggataaggag tgactataga  900
actgtaaaga aagaatgcac tttgctacag ccttgcagag ttgtgcaaat gccgatgact  960
aaaggagctg aaagaggaag gaggggataa gggatggggg ctgggtaggg gtgagattag  1020
gaccctggga gctgcaagcc actggagaga tcaggaggaa agggagggag acctgcttta  1080
ggcgagaaga gaacagtatt tgttccaaat ctcggttcag aataagttca tgtaggtgat  1140
ggggccaact ggaacaggtg aaggcctatg aatgagtgtc tcagttaggg tctccttaga  1200
gtttaatatg aaaaggtgtt agctaagtac agagctggta cctgagagag taaaaggaaa  1260
ctctaaggta tcatggaggt agcaattgca ggacacagct cccaccccta gggctgagag  1320
aaccaaggga agagacagga attattaaga cttggagcat agatgagagg tctgtggagc  1380
tgacattagg acttgggagg aaggcgtgca tggaggctgc tgctggatct ctgaacctga  1440
cctcgggtct ggacccctga ggagaaagcc ctggcaggtt ggtgcatgtg gggccgaggg  1500
acaatagctt aacaaccagc ataaaagaga gcagcatggg acacgcttca accatgcgca  1560
tggatggctc caaaacctgt gtgtggctgg cccaggacgc agggaggctg caggggggaag  1620
agacaagtta aacctgactt gtctgggaag caccattgtc ctcaggtcac tttcctctgt  1680
caagcctggt gctgaagtta tctgttgtct ccaggggcca agtattaaga gtaatcagaa  1740
actcagtcct ttcttctagg agcttccctt cttgcatgaa aatcctgata aaactggaaa  1800
aaaaaacctc atgattaaat tttttcatgt attcattctt tccttctatc aaaaaataat  1860
ctccaggcac cgtgctaggt tcattggtat acaatggcaa caagacctcc cagcccctgc  1920
ctatgtgagg catctgtgga ctgcggagga aaatccaata tgccattgtt ctctctttcc  1980
cataagaaat tacaattctc agttcatttt attctcactg tgctctttgt gaccctcaaa  2040
gggggtcaca tgataacagg actgtagctg ctggcctaaa atgagcccat tcctgtggcg  2100
ctcatgtcgc tgtgacagag aataaccctg ttttcagaat gctctggtgc cctccctctc  2160
aatctggcct ttcgctggca tgggtgggcg actcctgctc agggactctg ccttctccac  2220
agtgtgctcc cagggagatg gagccactcg ggctgagggc cttggccagg gcacctccca  2280
gggctgggcc tggtctgggc tggcgttcac tggatgccat cctgatggcc tggaaattga  2340
gatttctgtc tggcacgcct cccgatggct ccccacctgc taccacattc caggagcttc  2400
caggatgtct gggtaagaca gaggcacccc caacagattc agtagctctg agagggatct  2460
gtggctcctt cctaagcttg cggttcttct ggaaacttct gcctctagaa gatggtccct  2520
ctaagaaaag tacaaccacc cagcccataa ttcagctccc aggttttccc tcaaacctcc  2580
atgtctcctg taagcagagc aagagtaaaa tcagatacca aatttcctca ttcctcagct  2640
cccaatccct aagggcataa gatgaaaatc ttcagatctc tgctttcctc cctctttttt  2700
```

-continued tcttcctctg ttaacatttg tcaagtgtta ctaagtgtct ggcactgtac taagtgcatc 2760
acctccctga actctccgaa cagttccacg agagaggcct ctctgtgatc cccccggtac 2820
tgatgaggtc actgaggctc cagagaagga ttagtaactg gtggggttgg acctgggatt 2880
cacacccatg ctgcgtgacc caggacaggc aggcatggcc gttacaccac actgaccccc 2940
gtggatcgag atctatccaa tagtctggtc actgatatca ctaagataga gtggccatat 3000
aatttatcat ccaatcaggg cagttttgca agtgaaaggg agcactatta ataattgcac 3060
tgggacaata aatgtaaacc aacactggac ctggaaaact gggacgtgtg tttgccctat 3120
accaaggtaa gctagacaca gccactgcct tcatggagtt cagaaccagg caggggcggc 3180
tcccacgtat aattactgtg cagcacaacg tggagaccgt ggagtagaag gaaacacgga 3240
tgggaggtga ggaggaggtc tgtgagctca gaggaggcac cggggctgga gagggtgaga 3300
gaagacttcc caaggagttc atcctgataa cgtgcattcc caatgacgag cgctctctcc 3360
actgcacaag acaagtatac atctgcccgt gttggctgtg gacctggcgc tgtgtcaggg 3420
agggtttatg aagatcacta ggtgggtctc ttggtgtcat cccttcatcc cagcttctgg 3480
gttaggatgg atatctgtgg gggggcctga ggactcatga aagtggggcg ctaatcatgt 3540
tttggacacc acaccctgga gcacctggga cagctgtggc ctttgtcctg ggttcagcat 3600
caagccgagg atgtggcaag taaagagagg ctgggcacca actccagtgt acccaggctc 3660
cgggtcatgt ttgtccaggc taagaattct gtcctggttc tcagtgcaga aggaagaatc 3720
atggggctca ttttaggcct tggctgcctt ctgttaaatt gaaaacagag caggaaggaa 3780
gaaaatttaa caggctcagt tctaaaacaa caagcacaac tgtgcccttg ccagaaaccc 3840
ctcctcccca tgttgattga atggtaaaga gaggaggga ggtgagaggg agagagagag 3900
agaggaagag agagagaaag gaaagaaagg aaagaagaag aaagaaagaa aaggaaagaa 3960
agaaagaaag aaagaaagaa agaaagaaag aaagaaagaa agaaagaaag agaaagaaag 4020
aaaggaggga gggagggaag gggaaaagaa aagaaaagaa aaagaaaaaa agaaggaaat 4080
accagtttgg gaaaaaagaa ttttccacca gcccttctga gccttggctg ggcttaatta 4140
aagttacaga catgtgtaaa gggcagggta gggggagtct gagctgctga gaaaacatgt 4200
ttttaattat actgtggaat ttctccctgg ggtatgcctg tacgcagtta agcgtcaagg 4260
acagggatgc cgctctgggg aggggaagct gagcatgatt ttggaagccg gcagaagagg 4320
ctattgtgaa aaccagacct gtcaggctag gaaaagaatg gctggtggtc tttgaccagg 4380
gagtgacgcg tgaaatgcag caaccgcccc cgccccccgc caaaaacaaa cacactctca 4440
cagagttaga acaacagtga cctctcaaca aatatttttc aaagattacc aaccaaccat 4500
tacctagagc agcggttctc aaccttggct gcacggtgga actacctgag acgtgttaaa 4560
aagaagaacc ctgatgtccc atgccccaag attctgatgt agttgatctg gggtatgatc 4620
tgagaccccg gcatgttttc agcctgcagc cacatgagaa gtgctgacct aatcaacagg 4680
ggtgatgatt tgaggggcgg ggactatagg caaaaaaaaa cagcctaatt caaggatgag 4740
aagagggcac aggtgaggtg ggaacagtcc tagggccaga caaagaagga agggagaaag 4800
gaggtgctga tccctcccct actcctgaga ggaggccttt aagtcaccgt gccttgtgga 4860
gaccagattc ttcaaaaata caagaatgag tgagtgaggg agtgggtgga tgccaggaga 4920
gtgcgtgaca agccttgcaa gggaggatga caatgcacta gcttggtttg gaaattttac 4980
ccctggaaca ggcaggccaa gctggctggt cccctccctg atacacagcc ctccctcttt 5040
atatatggag caggggacgg tgtgtggctg gtttcttagc aagcaccatg gttccaagtt 5100
ggcaactggg gagttctgaa tccaaaaagg agggagatga acgtaagtgg agggcaggcc 5160
tacaaggttg cagataagct taattctgtc tccttactct tctgcctttg caacaaccct 5220
gtgatcttgc gacaaccctg taaggcaata acaaatggct catgtttatt gagtgttacc 5280
tcatgccata ttgtgctttc gtgtttaaca caattgtctc atttcaccct cacgactgct 5340
ctgggaggta ggtcctggta tcacatccat ttcacagatg agaccatttg gcacggaaga 5400
gttgagtggg ctgcccaagg tcacatagct aagatggaac aggctggata ggaaccccag 5460
taacttgacc tcagagtaac cttctcttaa ccctgagtgt acactgtagg aaaaatgagc 5520
agtcccattt cagagaggac aaaactgaga ctcagaggtt aagcaagccc caaagtggtt 5580
gttaacccag atcttcccac taactcccaa atcagcatca gtgtttaacg taccagacct 5640
ctcccagata gatgttgccg catggaagac agccgatcta cgtgatagaa agccaatatt 5700
gcaagcagtc gtctaaagga gtcaaatgtg ttggatttga actggatgtc tcatttcttt 5760
ggtgaagaca ctggaaacaa cttccaggtt tcatcaattg ctcctatcac tcaacgttgc 5820
tatcttactg aacttgttcc ccagccttac ccactgatgg aatgatccag aatggaagac 5880
aagacaccaa tgtacatgac cctgggggag gctgtttctt aaatctacag actgttggtg 5940
acctgagccc catgtcacca aaggctttcc tggagaagcc tcctagacca gtcttgacaa 6000
aggctcactc attccgtgga tatttattgg gcacctatta tgagttctgc cccatgtggg 6060
gtgctggaat cacagtagtg acaacgacag atgaggttcc tgtcctcagg aagcttactg 6120
cccttgaggg cttcacttac ttggaggagt gatgaacctg aagtgcggtg tgtgttaaga 6180
agcggaagtc cagggccagg cgcggtggct cacgcctgta atcccagcac tttgggaggc 6240
tgaggcaggc ggatcaccag gtcaggagat cgagaccatc ctggctaaca tggtgaaacc 6300
ccgtctctac taaaaataca aaaaaattag ccgggcatgg tggtgggcac ctgcagtccc 6360
agctactcag gaggctgagg caggagagtg gcgtgaacct gggaggcaga gcttgcagtg 6420
agccaagatc gtgccactgc actccagcct gggcaacaga gtgagactcc gtctcaaaaa 6480
gaaaaaaaaa agtgcctcac ggagagtcta ttcttttctt cccatattgt gtgtgtgtgt 6540
gcgcgcttcc tccaacacat cctccctata tatattttga gtaaaacatc ttgtaaaaag 6600
ttacagctac ataatcacca cctgtcccta aatagttttt gctttttctt tcttcaatgc 6660
acgatcattt tcccccatca atttattttt tagtttctta taatcttgtt gccagtaggc 6720
tgttttttaa aaagcagaac atggtttgtt cttactagca ggaaaggagc atttattgag 6780
cctctgctat ggtgtctttt attttgctga gagcctattt acatttcttt gagaggaaaa 6840
caacaaaggg ttacatgaaa gaccatgtga atagccccta gctgatctat taaacttgct 6900
attccccggc cagctgcttc agatctcctt cagatcttat gtgtttcctt cctaaggtcc 6960
ctggagtaag ggttgcatag acctattcta ctctccaact cacatgtccc tctccctctt 7020
cctctccata attccacatc tccaaccccc acccctatgt gcaatgccac agggtgtgga 7080
ctgccacagc cactggatct gcttttggaa tcaagagtcc ttaagctcca aatggaaccg 7140
aaatttaaat accaactttc aaccatatgt taacatcagc agcctcttcc aatgtaaaaa 7200
cccatggcag tgtgccctgc tttgtttctt taagcaatag aaacttgaag gaagcatgtt 7260
ggtaggccag atttttgttg gctttgcaat ggatcacagt catttattca ctcattcatt 7320
cactgattca ttaaatgacc acatttgcaa gggcaaggta atggggaggg ccagaaagga 7380
cactggcccc agaaacagga ggctggattt tggttctgat gctgccactg ctgatgtgac 7440

-continued

```
actgcacagg tcacctgcct cctctgagcc tctttcctta actgcagagt gagtggctac  7500
agagaaatct ttactacctg ttagatcagc attacctggg agcttgttag aaatgcaagc  7560
tctggtgggg ccatactgaa cccaaatctg cattcatgtg catagtgaca gctaaaatgc  7620
actgaagcag atgatcttga tgatccttta tgaaagtctc atgctaatgc agttttctaa  7680
aatagaggca gagtggaacc cagatggaca caaaatctgg ttgatataat aaaacaaggt  7740
agagggtgta tggtggggag ggggtaaagg aaggaaactg tttaggtaaa gataccacaa  7800
ccaaagtcct actgcacaca tgggatctga ggagggctgt gtctgctctg gttacgtttt  7860
ctataatctc ttagcaccac tgaactttct ctctttttgt tttgtttttc cag         7913

SEQ ID NO: 8            moltype = RNA  length = 1393
FEATURE                 Location/Qualifiers
source                  1..1393
                        mol_type = other RNA
                        organism = Homo sapiens
SEQUENCE: 8
gtaagcatag cagggtagct tgggcaagcc ctgaagagac tttggtctgg gccttttgtc  60
tagaaagatc ttggggtggg agtgtgggga tcagatctgc ttatcatcat ttcatgtcta  120
tgatgcatgt aacagattta tcaatgttac acaaattata atttttaaaa agtctttaga  180
gacagggtct cactctgttg ccgaggctgg agtacagtgt taggaccatg gcacactgca  240
gcttctatct cttgggctca agtgatcctc ctgcctgggc ttccaaagtg ctggaattat  300
aggcatgagc cactgctccc agctaatttt tttgtttttt gtggagacag agtcactaca  360
ttgcccgggc tggtcttgaa ctcctggcct caagtgatcc tcccacctca gcgttctaaa  420
gcactgggat tacaagcatg agccaccttg tccagcccaa attttcatgt tttaatccta  480
cacattctaa gcaaatactt gtgtgtagtt actaagggac tgtgcactta tttttgtttg  540
ctttgttgtt gctagttttt atttttttat acctaaactc tctcgtttta aagagaacag  600
atttgtagat gagttctcga aaatatttca ggaatcaata tagagaatat gttatacatg  660
gtgccagaga aaaatgagga caagagatgc tatacaatcg tactgaagaa aaattttatt  720
tcttggaccc ctgaggtgtc tgcagacctg aaaggaacct agtgagagcc tcttttacac  780
tctgcccctg tgggaaagcc ttcacctggt ttccggccct ctatgtggtg aatgtggaag  840
cctcaagcgt tatgcaaatc tgcccagtcc tctattcttg atcttcacct tctcgttcat  900
gagtttcagg ccccagttct gaatcagcct cctgtccatc agactcttct ttacctctcc  960
ccgaggagcc cataacctgc agccctactg catgcttggg gtaggtgctc agttcaccgt  1020
ggttgaagga atagacgagc gtctgctcaa gcagcagcag caactgcgtg gagtcttctt  1080
gaactaacac tcctatgccc ctctcggcac aaaatgacgt gtcccccctt gcttcccctt  1140
cacatttcca cccatgccta ttacaacatc cgtctgtctc cccactacac cgggagcttg  1200
agagaagagg ccatgtctct agcacccagc acagggactg gcacacatga gatgctcctg  1260
cttcttaaat gctgagaatg aaggaggaca tcagaggggc ccgggcccct tcccaaaaag  1320
gccaactcct aggtctgcat cctgcttggt ctccatgact aatcccgtct tgtcctcatt  1380
ttctgtttta aag                                                     1393

SEQ ID NO: 9            moltype = RNA  length = 2721
FEATURE                 Location/Qualifiers
source                  1..2721
                        mol_type = other RNA
                        organism = Homo sapiens
SEQUENCE: 9
gtaagtgttg agatccctac catgcagggg aggaagttgc acaccccttc acgtgctgaa  60
atgcacacgt gcgtgcacgg agcatggagc actgagtgtt cttgtggctt tgctgagccc  120
ctaacctctt aggagcagag caggtttcct ctctggaaca ttctgttaac tgtcagggca  180
cttggggaga aatctccaag ctaaggccac gtgcacaaaa tttcttggtc cttatatccc  240
cagaatgtga cctggagtct gatggcagcc cgctgcagag atgtgtccac tgccttctgg  300
tcattgacct gcttgggtgg agtgaatcat tgtaggagaa aaactcagtt ccctcaccct  360
gatcaacctg gacagatctc tcttccttta aaagcttttct tggacatcta agggctagga  420
aaaatgtcag ggagcattgg gaaggtaaat gaagtcaggt ttacaaagtc aagtttactt  480
cttgggagaa aaatacaatt tccaaatcct ctgttataat tgccatcggc cccctggagt  540
ggtgagatct cggaatatgg ctcgggtgca gtggctcttc actgtgggcc tgcaggctat  600
tctgaaaagc tgatgaaaac caatgacccc tcttccaaga aaaatggcca cataccaaac  660
attacactgt acatctgatt tcagggaatt gtagatgcca ggttagtagc ctcaggtcta  720
gggtcaaaat tcaagtcgaa tcccacagga agagggtctg ccttcggaat tccctttcag  780
agcattggga gaacatcatg ggagcatatt ctagagacag aggcttaggg tgtggacagg  840
gccatccctc acccactgtg ctgaccttaa gcagcacctt gtgcagccca tacctgaagg  900
ccaccagcaa aggcctgttg gggagcaggc tttacccgac ctgtataaac accaggctag  960
gtgaaaactg agatacctgg ttactttagt tttttccttg ggggagctca gtatgattct  1020
tccaggagaa gcctgctttt agactaaaaa gaaaaaaagt ttgataggtc aacctaatga  1080
ttggaggtgg ccttccccac tgtgaacaaa ctatggctgc atgtgcccta caatggcaga  1140
gttgagtagt tgtgatagag actgtatgat ctgtaagcct gtaattttta tgtttgctga  1200
cccctggatt accagatgat agaagaggaa acatctgtct tcctagcaaa gtcaaggaag  1260
tggcatttag caggactcat attgctgcaa gcactgcctt gcagttttag tttacaactg  1320
cactttcagc ttaagaaaca cctgcccatc cagagagatc gtgtggggtc acatggtggg  1380
atcagggagg cctgaagaca gctcagtgga ggctgcatgg agctttggtg ggaacggccc  1440
tggcagtgtc tatagatgtt attgcggaaa actgaggggt gggagttgga gaagggggct  1500
ccagactcta gctgtacttg gcatttgaac ccggaaagtt gggtttcatg ttttgcactc  1560
acattatgag tgaaatattg gcttattcaa ggttcttttg cttgcaaggc acggaaaccc  1620
attcaagcaa tcttaaaccc cagaaggaaa tctatgattt ggatactaga cattctcaca  1680
gagccaaggg cagcaaggcg gggctcagga gaggcaggcc aagacctgga gagctgtcag  1740
gagctgcttc ctcaactctc ttccatctgg gcctgccagc cctggcctct gtatctactc  1800
cattcacctc tctccatgga ccagtctccc ctgctcctca atgcctgggc tgccattgtt  1860
catgcaattc acaatacctc ggcctgggca atcagaagct catctctgaa caccatccaa  1920
attcctggga acaaatcggg ttgacccagc tttattctcc ctgtcccatc agccttggca  1980
```

```
gaggcgtgca tgtgcatgcg tgccaatgtg tgtgtgcagg gaggtccttg tggatgaagc  2040
atggctgtca gagcctacct gcgtgaatgg gtggaagggc aggtctcaga gaattgggta  2100
aaaactggat aaaccctcca gtgatatcca ccaatgtcac cctgtttaag gcttctctgg  2160
gcaagagaca cacagagcat gggaccgaga ggcgagcaga ccctgccaaa actgggagac  2220
tgaatagatc gctcaccatc cttgtcagtt agcctatatg tacaaggaag taaaattatc  2280
tctttctcct gccttggcag tattgtaagg atactcaatg tagtagctag gccagacaca  2340
tagtatcttt aaatatagca tgagatggcc aagcacggtg gctcatgcct gtaatcccag  2400
cactttggga ggctgaggcg ggtggatcac gaggtcagga gatcgagacc atcctggcta  2460
acacgatgaa gccccgtctc tactaaaaat ataaaaaatt agctgggtgt ggtggcgggc  2520
gcctgtagtc ccagctactc gggaggctga ggcaggagaa tagcgtgaac ccgggggggca  2580
gagcttgcag tgagccgaga tcacgccact gcactccagc ctgggtgaca gagcgagata  2640
aaaaaaaaaa atagcatgag atattattac tgttataaaa ataacagcta tttccttatt  2700
aatgaggctt tgtccttaca g                                            2721

SEQ ID NO: 10          moltype = RNA  length = 5434
FEATURE                Location/Qualifiers
source                 1..5434
                       mol_type = other RNA
                       organism = Homo sapiens
SEQUENCE: 10
gtaagcatga ctgcagtgct ctcaagcatc atttccctca cctatggaga gactgaagat  60
ataggaaaga acagggagag ttggtgaaaa atatactagc ggaggcagga agggatgggg  120
tctggaggcg gcttgaacat caccttggtg aagatgcctc ttcctccaca gaagcctgga  180
aggtaggaag ttgggaagga aggcaggaaa ggtctcatcc acgttaagtc tagagacaga  240
aagaatgcta agagagatgg cactatggga agtatgaggc taggtcaagg gctagaagca  300
ggggagacga gtttacagag tttcgtaaag atatagagca actctcacag agttctagag  360
cgagagctaa ccaggaacat gaagcagcaa ggccaactat cattaaggag ccagggaggt  420
cagagatcat gtattatcat gacataaata tgcataattg tactatttct cccagtaata  480
tttagcaccc aggccccgag gcagagcaag tggagagtgg gtgatgcagg gctgggggtg  540
tgtatggagg caccacagaa ggtcaacagg cagcgggctg aaggcaggga ctggactaca  600
tgcatcaagt ccaggctgca cgaggaagga tgagaaggca gatgagcacg gaaatggact  660
gggggaaatg aagaggcaag ggaatagaag tctcagtggg tgccatgacc ctgtttaagt  720
gattgagaaa atgaacaaga tgaaaaggtt aatggctgtg gtcagaaagt gaaatatgtg  780
aattcaggat ttcgaaggta gggtgggtga tgactggccc ccagatgcgg ccatggtgaa  840
gtggggcaaa ggtgcaggtg catggtgagg ggaaggagga aatgggaggt gatgatgttg  900
gccccacacg gacaccacgg ttgtgcagga agatggcagg agctgggcac cagggtggga  960
gccacctgga gtcaggaaga gtgaagagaa aggatgaaga ggctccctct cctgtgtctc  1020
tcctccccag gagaagaaca agaaacaatc cgaaagtaat aacaccaatg tgcctttaca  1080
aagtgtgagt gggtgttgtg tgctgtcacg tgtgtagtag gctcctctgt ggatggctag  1140
agggactgga catggccact ggatcccact tgcaagagca gaggaaaaga gtggtcgtga  1200
ggaagtaaag ccccccaaaa tccaggggtt gctgcagctt tgggtgtgga gcgtgccctc  1260
tgaggaaagg ctgctctggg ggagattgcc caggaaacgg ggctcagagg ccacgaaagc  1320
agctgttagg ggcttctggg agatgtgtgc tcctaggatt agggagttga ctctaaggat  1380
gaccttagag gttaacaggg atgagaaagg ggtcaccaag gggtctacca ggggaatggg  1440
agaggctgta ttgatagaac agcttctgct gcaggttcca aacaagaaat gtgggagaat  1500
ggttgaaatc agccccgggg gcaccttccc gtgcatgcgt gcagctcctt caacattcag  1560
tcgaccttca gtgcctcctg tgagccaggc actgggctag tctctggggg tggagagatg  1620
agtcaggcaa atgccagccc tcagagggct cacagggcag aaggtgagag atgagtgagc  1680
agaaaatgac cacagcgcgt gtggggccca gtggagggaa ggaggggatt caggagcaca  1740
ggagagtcaa caggggaaac ttctccgagg agaatctgat cctcctccca tctggccacc  1800
ttctgaagcc ctctctcccc atccaagtga gaaaggacag gcgtatgacc agattggtgt  1860
atgaagatgc tgaattacgt tctcattgtt tcaaactagt aaaccataga ttttatgtag  1920
taacttctac aaactgcatt acaaacactc cattctttgt tgccctgggt agaagtttat  1980
tttagtgagc ccaagtttga ggaaccttat atggtatgag tacaattacc attttaatag  2040
taagaaatcc cccttcccct gtgtaccaac cagaaggtgt ttttttccta atttaaacaa  2100
acagatgcag acgtgggctg tccagctcct ggcgggatga catacctcat gcatccagtg  2160
ggtttgatga tgaggcagac atttcactta agtgcctgat catcagattg agtcctgctg  2220
ggaggaagtg tgaaggaagt aatttcaaac cacagtttct ctgtggcttt tacaatgtgg  2280
atatgagaac caaaatcact acttcttaac cccagagcag gactgatttt gaattggtat  2340
gcaggcggtt ccttctgcag gcttcgggct gtgagaagtc cctaacagag caaatctggg  2400
gacaagggct caggaaaggt tggccacggc cccctaggaa tgggggctct gcaagatccc  2460
tggccttaga ggctgtgaga gggaacaggg gtccatcccc aagtaaggga cacggtcttt  2520
gaggaaatcc caggccaggg cctgaagggc actgtcagga acacaggctg tttcagtctg  2580
ttgagattca ccggggcgct gctcactgtg agcacggact cctcaggcca atgtggcaga  2640
agagcccacc tttgaaagcg agcgggtggg ggtggcgggg ctggtgctgg tgcgtgcttc  2700
tgcacagcca cctgggaagg tatgccgctg gttgacccag gcagaggttt tctttcatgg  2760
caaacctgca gtactgcatt ctcagcaggg aggattaatg gtaaaagacc aggcatggag  2820
ccccttccc tctccctcga agcaagctct gtggtctctc aatcatcttt aaaacacctt  2880
cttcccggga gcctcctaca ttctcctggc ttccctccca cccccaccct cagctcctgg  2940
ggcctcagca gccccacccc caagcctcta atcttcccag ggaagggaac aagaagaacc  3000
acattttaaa cgaaatttat ttttctttcc tcaggctccc agttcacatt tctccctcag  3060
gagtctaggg aagcttctgt ctggtatcgg cctcctcttc acctgggccc ccgccctcct  3120
caggtgtacc agaagccagc acactccccc ttcccccca gagccacagc agccctgtct  3180
cctgggtggt cttgtgtgcc aagcctgggc aacatcactc ccagcttttc ttgttttgcc  3240
ccttctcccc agcaagatat ttgtatgtaa ggtcaggtga gtgagttaaa gaataacgaa  3300
gagataaaca gtcaaatgga gtcctgactg tcaggtcaag acaacagtta tttactgaat  3360
gcctcatgtc attcaacaga catttattga gactctgatt ggatgtcagt ctttaatgct  3420
gggtgtcaga gagaggtgac ttcaagggct tgcatctgtg cacccagcat tgctaggtac  3480
aatgaggagt ataataaaag caggagccat agcccccaac tctcaagaga tctcccatgt  3540
```

```
gtgtatgtct gcatatgcgt gcgtgtgcat gtgtgcgcat gtgtgcatgt gtgtgtgcat  3600
gtgtgtgcat gcgtgtgtgt gtgcgtgtgt tggggatggt gttggtggag tgagagtgta  3660
caaggctgtg tatgaagggg taattgggaa aagaacaatg gagctggcac ccagggacag  3720
gaggaaaagc aggagggctg ggtttggaag acagccggat ttatgttttt gaagagggaa  3780
gactagaata taagggagca gcccttctca gagccctcct cctcccttcg ggccctgtgt  3840
ccagctttcc ccaaagtcct tggatctttc ctatgcaaag gggagtgaca gtgggcacca  3900
ctctcaggga acccattact gtgagagaag ccactgtgcc actgtgtggt cgaacttcaa  3960
gaccggcttc ccctgcccca gctgcatgga caggcctgtg gggttggcgc aagacccttc  4020
cagaggaaac tagctgcaac ataaatccgg atatggtgct gttcagggaa aggcacaacc  4080
tggggatgag aagggtggct gtccagcaca caggggcagg cctcttggcc actgggggag  4140
gggagaattt ggagaggaag aggatgggat gccgtggaat tgggaccagg aaagaatggg  4200
gacatgtgat ggttaaagct agttagagaa gaactgggag ataaacagtc acccatgccc  4260
ctgaagcact cggggtgaag agattggcat tttcacgcac cccagtgctt tccctttgtg  4320
ttgaagtccc ttcgtagaca tccaggccca taaggctctt ctctggccag agcctcatga  4380
actatagcac tagcagggtt gaggccaagc attggccctg gaagccagcc gaggaggagg  4440
gtgcttgtgt gaatctccca ggaggggtaa gaattatatt aattcgatca taataagcat  4500
ttattgagtg ctgttttgag gcctgggagc taagcacttc acattcctta ccccgcatca  4560
acaatcctat gaggtagatg tggaaaatgc agacacgggg acaggctcaa tcacttgccc  4620
caaggtcacc ttaactgtta ggtgttcttt atgcctcctt ataaagaaac cctgcttccc  4680
acaggtgttg agaggagctg gagggagctt gactagggct catcaggcaa gccccggcat  4740
gtgcctggct ctcctctttc tacctggagc ttttcctgcc cttaatggcc ccaactcatt  4800
tctcttagtc catgtcagtg ccctgagcat ctcagcccaa gctgagatga tagaaacacc  4860
cagaggggtc ctctaccctg tgacagctgc ggtgtgggaa gagcacgtgt ctcctccaat  4920
cctagaccag agtttctcag cctcagcatc actgacactt ggggctagat aatcctttgt  4980
gtgggggagg gaggagtgtc ttgggccttg caggatgttt agcagcatct ctggcctcta  5040
cccaccagca cctccccagt tgtgacaccc agaaatgtct ttagatcttg ccaaatattt  5100
ccaggaggat gaaattcccc tgtttcagtt ccccagcccc acctcaatga gaagcactgt  5160
cctagaccaa ccccacaaag catctgacac ccccatccag ccctggctaa ctttttccac  5220
cttcttacta aattgggccc agctgcttca gcagtcaatg tgttgggggc agcccactgg  5280
caagagcctc acctctaggg gctcccagag accccaagaa cagaaccttc ctctgagagt  5340
tgagttacaa gtgtttccaa tcgactctgg ctgttttcct ttttttgacc catttcccct  5400
tcaacaccct gttctttctc ttattcatat gtag                               5434

SEQ ID NO: 11          moltype = RNA  length = 4023
FEATURE                Location/Qualifiers
source                 1..4023
                       mol_type = other RNA
                       organism = Homo sapiens
SEQUENCE: 11
gtagggggat gtcactggcc agtggtccct ggagggggagg gaagcaccca gcctgagaaa  60
ggcaagaaat atattggctt ttttcttctt tcttccttgt gttcacattc agaatccatc  120
acttaatgcc ttgtatttag aaaaaaaccg ggggatcact tgagatcgtg atcattttca  180
acataggatt cgaagctgta cacatcctgg tgaccttaaa acatctcagg tttttataac  240
tggaaggaac cttagagatc atggggcaca accttctctt tatagatgag gaaacagaaa  300
tctattcatt tattactcaa atatttaggg acagttgtag gtactagaac acagtgtgaa  360
ccagacaggc aaaaccccag gccagggagc ttccattcca gtggggccac aggcgatgct  420
caggtaagca gagactccgc tgtgtgactt ctggctgtga tgggtgctgc aaggaaaatc  480
cggtagagtc gagggttaga gagggacgga ggggcaggtt taagggggat gctcaggaag  540
gccttcctga ggaggtggta tttgagcaga gttgtctgtc agccacacag taagtgagag  600
gggagttccg ggcttggaag ctgccagcac agtgctggca agtgctgggg tggcgtcccg  660
aggctacaga acctgagatg ctgcagaaga gcccacttct gctttcctgg accacttcct  720
tctcagcacc aggcaaactc cttcttctat cccctggcac atttctgacc tgtgtatacg  780
cccccaattt atctaacccc tttaaataat ctcctctatt tatgcagagc attcttacca  840
ctaactcacg acttgcacat cccttagctc ccttactcct cacaacaatc ctgagatggg  900
tcagagaagg aggcttgcgc gtctggtgat ggggtgattt gtgcacagtt acagggctag  960
aaattgtcag agccagatgg aatccaggtc ctctcaatcc taatccagtg tttcttactt  1020
cagtcctgtg gctctcaaag cccagagacc agcagcatca gcgatgcctg ggagcttgtt  1080
aggaatgcaa attatcaggg cccactccag gtgaactggg tccaaagccc tgggataagg  1140
cctagcaatc tgtgcttcac aagccctcca ggtgattccg caggctcagg tgtgagagct  1200
gcagctgtcc tctgggcctt ctgggctccc cgcccagctt cttcagtgtg atgaacacag  1260
cgagaatgct agatctgcag cagctgatat cccagacacc ctcccgactc cctcctggct  1320
gggtctgatc ctcctccaga ctccaggaga gaacgagaca taaacagaac ttcagagcct  1380
gtgttaaccc tgagatcaag gtctgcacag ggtgctgtct gagtccagag gagtgaggga  1440
ccccacccca cctggtcagc accagctcct ggaagcaggt tctcacactg gttccctgca  1500
caatgaagga gctcatacct gcttttctgg cttctcagac cctgaggttt tcaccgaaac  1560
tagacaaggg gaacctaggg tcagcctgga ggcagggtga gcttggcgcc tgcagtgccc  1620
aggccctggg tggtgcggct ccggccaggc cctgtttagc ttcctctccc acccccacag  1680
agggggtgct gtcggcaccg attgctcatt ttccccttg ctttctcttc agctcgtaaa  1740
actcaagtcc tgacaatgcc ttgatgactt ccagttggta ataaaaggga gatgaagata  1800
aggacaggaa tttcggggaa atttctttcc agttccttac taatgtgaca tttagatctc  1860
tagtactgtg cttctggcat cagtgccaag gcctttcatg ttggagaatg gaggccgggg  1920
tcaccaggtt gtgcctttat ttcatgttgc tggctctgat gagctgatgc tctgctgatt  1980
agcaaacgct gagccatctg cgcttcgcag aggcacgttc cagccaaccc ggccctccct  2040
gcccacttcc caggatgctt tgccttgtgg gctcacctgt cttctagctc ctgatctgta  2100
tctccacctc catccagttc cggggctcct tatcagcact gttcccagaa ctgtccatca  2160
cgatggcaac gttctctctg ggcgctgtcc aacatgggag ctcgcctctg tgttgtcact  2220
catgctcatt gaacatggat ttgtgtcctt taccatcagg actggatacc cctcctggtc  2280
ctttctgcct ggggtcttag cacagctcag aaggaacctc accattccct ctctccatct  2340
agggaattag aagatgacag gggcacagtt ctctggctca cccccagccc agtaaactcc  2400
```

```
tggacatgct tcaaggccca gctcagatgt tgcctcctca gtgaaataat ttataaaccc  2460
acccttcttt gtcctgcctt ctccctcttc cctactcact ggagagttaa caggtgatgg  2520
ttaagctctg ggttcaaatc tcacaaggcc acacacttag ctatgtgact tcaggcaagt  2580
taattaacca ctctgtgcct ctcgtttcct catttgtaaa atggaaatag taaaagtgcc  2640
taccagcatg gcagttgaag ttaaaagaaa taatatatgt gaacacttgg aagggcgcct  2700
gacacatagt aaactctcag taaatactag ctgcttttag tggctattct taacacaccc  2760
tcttcagtgc tctggtttca ctatgtttta tgggtccctg agatcgaaag tgtccacacc  2820
gactcatggt cagctgtaac ctgtgcctcg tgtggggacc aggctgccat gtgtagtctg  2880
gacagtgtag gaggtggcag agctcaggcc tgttctgccc tccagcccag agagccacgt  2940
cgttagatgt catgggagac tgtggtgccc cgggaatctc acgaatttgc ccacggtact  3000
cagtgtctgt ccaatgctat gggagtccag gactctagga gccagttaag gtgctgggtg  3060
gccacaggtc cctggccaag gtccaggcct ctcccctgcc acctgatcct cgagaggcca  3120
tcacgagggt tgtacttcaa gaaccactat ccttgagcta cctaggagct gcagaatgtg  3180
cactctgcag ggcttagggc ctgcagacaa gatagatgca gggtgtctag ttaaattcga  3240
acttcagata aacaacaaat aatttttca aataattgtg ttctattcgg tccctatttg  3300
ggacatattt gtactaaaaa gtattcattt atctgaaatt cagattcgac tgggcatctg  3360
gtgcttttgt ttgctaaatc caagagcaaa tttgttctag ctacttctca accccacctt  3420
cagagaggaa gccttgatgg tactgtaaca tcatgctgta agaaggggat cccttgaatt  3480
gtaaatggca ctctgataag atgaggtatg gggattgtat tggtttcctg ttgctgctgt  3540
cataaattac cacaaactta gtggcttcaa acaacacaga tgcattatct tacagttctg  3600
gaggtcacaa gtctgaaagt tagggcatca gcaggactgc attccttact gcggagttct  3660
agagaaaaat ccattttcct gcctccttca gcctccagag acacgccaca ttctttggct  3720
agtggtctgc ttccatctcc aaggccagtg gggcttatc aagtctttct cacatcacat  3780
gactctgttt cttctgcctc cctcttctac atttaaggga cccttgtgat tacacagggg  3840
cccacctaga aaagccaaaa taatctcctt attttaaaat cagctaatca gtggctttaa  3900
tcccatctgc gatcttaatt cctgtcgcca tgtaacacaa ggtattccca ggttctgtgg  3960
gttaggacgt gggtgtcttt cctaccacag ggcagtttct agtgttgcct cttctccctg  4020
cag                                                                4023
```

```
SEQ ID NO: 12          moltype = RNA  length = 15352
FEATURE                Location/Qualifiers
source                 1..15352
                       mol_type = other RNA
                       organism = Homo sapiens
SEQUENCE: 12
gtaagggagg ggtttggctg ctcgccaatt gcaaggtgat tcctggggta gcagagcctc  60
acgaattgac cttggggagg gcgtgagcct ggtgttctgg acaatccttg caaaagctcc  120
aggctcccag ggctcaaaaa atcacaactg atagtatttc tagaacagtg gcccagggac  180
ccagaagtca ctatgaggtt caccattagg tatgtggctg tggcatgttt gtgtccactc  240
taaatgtggg gataatcccc tttacctcct ctaacagagt ggtaaaggaa ggaggaggcc  300
tggtttgact ccctgacctg ctatttccta gccaggtgat catggtaaga tattgaacct  360
tttctggtcc cagtactcat ctataaaaca aatataatac tttacagagt ggtaggaatt  420
atacaagaaa agtatacgca aaacatttca taaattttaa taaatgatgg ccccatgctt  480
cttcctctgg aaatggtctc aacctcaatg gttggtgttt ctagagagaa aaaacgacag  540
agaaagtttc atagtctcaa aaatttggaa agccctgatc tagctcaacc ctttgttcta  600
gaactgcatc ccagacagac tgcttgggac ctgaaaatat ctcctccttt gctagaagga  660
taagatgaga aggaattaga taaaggaggt gtagagcaga ggttttcaca ctgcaaagtg  720
cataaaaacc atcagagggc cgggcgcagt ggctcacgcc tgtaatccca gcactttggg  780
aggccgaggc gggcggatca tgaggtcagg agatagagac catcctggct aacacggtga  840
aaccccgtct ctactaaaaa acacacacac acaaaaatta gccaggtgtg gtggcgggcg  900
cctgtaatcc cagctactga ggaggctgag gccggagaat ggcgtgaacc cgggaggcgg  960
agcttgcagt gagccgagat tgcgccactg cactccagcc tgggtgacag agcaagactc  1020
cgtctcaata aaaacaaaca aacaaacaaa ccaaaaaaac ccatcagaga agttggtaaa  1080
agatgcaagt gctaaatccc cacccccaat cactgtgatt cagaagaacc aggccaggcc  1140
cagaatctat cctgttacct taggcgattc tgatgaagac cattgtaggc cacactttca  1200
gaaacactca aaattagaat ccttcagaga aggtggcata tataatattt ctagcatgga  1260
attatgtttt ttttcttttg cctacatttt aatttctaga actgtgttgt agggaatgtc  1320
agtcactaag aacttgattg aggaactgtg ttttgtctgt ttcatgactg ctctctcaag  1380
tcccaggaaa ctcactttca gcttgtctta aaaagcaagc tgaaggcttt taaaaatgaa  1440
gcaacatgaa ataagacacc gcagtttctg gcacggtcca cgcttaatcc ccttcaatgt  1500
gtgactttcc gtggaaagtt actctacgat tttcccagct cgtcagggtg gggccccaga  1560
gtgagtatga agggtcagag cctagggatg ccaccatcag tgagagccca ggaccccaga  1620
aaaggtctct tggctcacca cactgtagga aaaataaaaa gcaatgtagt ccaaatgtct  1680
ctatccaaag tttcaaaaag aacttgattt tagacacgct ccttgacttg ttttcagaat  1740
cagacagaag agtgaggcaa caaaggtccc ttattccagg cagctgaata ccagcacagc  1800
caggagtcca gtgctggtgt ttgcagagcc accagaggct ccctctcagg tgtccagggc  1860
ccgcatgctt tgtagaatgg gcagaatgag caatgtctgt gcacctgggc tttgcaggca  1920
gggcctgggt acccaggttc gtgcaatcct ctcgtcacca tgaagggagc agcatcattc  1980
ttcccttctt gaagcacctt ggccaccagt ataggtaaat ttacctccca ggacatgacc  2040
attgattctg ggatgtcaat gccagagata gtagggtaaa tcggcacctg ggtaaaactt  2100
tccattggag actagaacca aaactcagga cactggcttc caaatgtttc tttatcagac  2160
aagaaagacc aagtctttcc ttacgtcttc acatgctgcc ttggcaaatg ctagcattca  2220
caaaccctgg gctaccttga cctgtcaccc ttgcagacct cagacgggtc ctgggggctt  2280
gctttctcgg tttctgtatg caggcactca aacctgcatc aggcacctgt gaagggccgg  2340
gcactgtgct gaggccaagg ctccaaatgt gaaccttcca ccctcactga actcacagcc  2400
agaccagaga caagcaaaca ggacatttca cagcagtgca gcctagaaag ggccaacacc  2460
agcagcattt gtccccccga gcggtagctt ttagaagctt ccccagtgat tcaatgtgtc  2520
ctacaaatgc ctggccccca ctcccagaga ttctgagtca gctggcctag ggtgcagcct  2580
tgacttcact gtgttaaaaa gcttcccaga taagtccaat gtccggccaa gattgagaat  2640
```

cactgaccta gagtttaatt taccacctca gtctctatag accacgcata ataatagtac 2700
cccacacacc tctgagggtc caaagaactt tcatttgatc acccatgaga ccaccgtggt 2760
gtggagatgc tttctctctc ctgttctctt aacaaagctg gtgagcgaca gagcctgcag 2820
tggaccggga gatggcccag aggagaaagc tctgccgtag tcggcctcag ttaaccacgg 2880
agcaccaccc ctacctgctc tcctctcact cctgcttccg tctcggtgga gaaagatcca 2940
accgaagcag gacacatcta gtcttctggt gcctttaaaa tgtacttttc catttgacaa 3000
atggattaca ctaaaaacaa aaatttacaa aaaaaaaaaa aaaacctgaa agaaattgca 3060
ggcattaaaa tgggactttg cctttattgc tcctgggccc atcctatttg ggtttttaga 3120
aaaacaagcc tgaggcaggc ccagaaaggc tcagggcaga ccctccgatc ctctgaaagg 3180
agcatcaggc aggcaggggt tgctccgggg ccagggaagg ggccccgctg ggacgcggct 3240
gttattgcag ctggttggcg cgcagccatg cttagctgca gtgcgggaat gctgggcctt 3300
ctgttctggg ctgtttctca tacgcacgta ggccagtgta taaataaggt tttattaaat 3360
gccaaatgag ttctcattaa caaagaaaga gggaaaatct cagtaaacca ccgtgacggc 3420
atctacccac tttgagtcag gagctggggg tgtgagtgca acctccgaga caagggaacc 3480
tgtggagccc agagaatcgg aggggggcgc tggggttagc accgactgag accagctgtg 3540
ttttctctcg gttccttgga gatcagaagt gagtgttgtc atcttcaaac aatccaaagg 3600
cagtacccat ggccttacta catccctccc acaccatccc acccatcccc gcgcgtacac 3660
tcacacgctc atttgcacac tatcgcacac gctcacttgc gtgcgcacac acagattggt 3720
gacctaggtg gactgggaga gaaataagag ccaaatgact ggattttctc caaggaaatt 3780
tattaatagc ccctcttggt ttcacctgaa ggagcttgtc ttcacctgcg gcctttgcag 3840
gcttaacgcc cccagcttga aacccagaag ctcagacttg ggcccaaggt attattagtg 3900
ccaacactac ctgaaatgtt tcgcacctca taaaaatggt gtgtcagttt cgggtgagag 3960
gttgggacgc ttcccatctg atttggccca aggcatgcat gcccctcctt ctccttcccc 4020
tcctcctccc cctcttcccc ctaccatcct tcctgttttc tctccaactc tggtgcacag 4080
ctttgaaatc ttgctgagaa gcaaatctgt cccttctgct ttgaatgttt atttgtggaa 4140
gttcggcagg ggaaccgagg cgggtgccaa gacctgccat gctgctggga agtctgagtc 4200
tccctccctt cccccteccta aatgcttgtt gatagagaaa agtcagcctc ctcggcattt 4260
gggctcacgg ttttcctttg aaaatgcttc cagtgtggca tgattcagct ttcttttctg 4320
tcccccaacc actgctctgt tgtcattttt actttctga ttgcatttta tccgtgtctc 4380
tttgactacg gggtggctgg acgttgagtt ccaggaagaa aagggcccaa tcttggggtt 4440
ctgactacat gcgcccatca atgtcctgtt tcattcttgg ctctggctcc ctgaattcct 4500
gagtcactgg ggagaagcgt gggtggaccg ccccctaccc agtgagagtt gccacagttg 4560
ctgctctcct gggtcattgg ttgcagattg ttaaacttca cctatgcatt tcaactttcg 4620
ggtggatatt gctacgtcaa gtgtctggga aagcccccac agctacagga ttttacagtg 4680
aggtcccact aatgacttga tgtcatgact tcctcattct ttccaatttc tcccacttct 4740
ccataagggt tttgggaagg ggagaagaga aaggagtgat tcctgagtgc cagtaccagg 4800
gaacagcagg gctgttggga ggaaacaaaa ctaaatcagg aaggtttttg ttgttgtttt 4860
tgggggggttt tatgaaaata ttcaagccac agcaaatata tttgatttat agcattagta 4920
ttttttctgc ctgcatctac aaaaatcttt acctattacc atcaaaatat cctctgggtg 4980
aatggatttc aacaaagaag aaataaaaat gaaatagaag agaggcccct tcgtgcacat 5040
tgagcctact ggctggattg tcacttgcct gccttgatgt cttttcagct ccaggcaggc 5100
agtaggccag ggcttatttt catgacagat cagatgttct tttatggatt tacaaagaaa 5160
gaaatactga gaagtcaaaa ctgaagtcac ttaagacaag agcaggcccc tgggaaggct 5220
gccattgagg ataatgagtc ctggggtcct ggcctttgtt cagtaaatac gcactaggcg 5280
cctacaatgt gtgcaccaat gtgtgaggcg tcaggttctc tccagggtca gttggtttta 5340
agaaaggttt tggcttctga tatgttttat ctctacagaa cagtagctct taacctttct 5400
tatgggttag gattaccttc gagaatctga ctacagctct agacctgttc cctaaagaaa 5460
actaagttca cagggacaca caggatgggg ctcatggagc agctgaagcc agaccccagg 5520
ttaatagcct ttacattaaa atgtttttct acctaccact aatatgcatt ctttagtaag 5580
cggtctcaat atacaccgat tcttccttaa ctctgtttat gaagtattca gcatcctccc 5640
tgccccttc agcatcctcc ctgcccctga gcacaggatc caatggcgtg aggaccacag 5700
gcctgggcag ctgctggggc atacaggcat ctcttagtgg ctgagagact gggccctggc 5760
tctatgttgg ctcctaactt gctgccattt aaaggaaatc ttagcctccc atccgtaaaa 5820
tcgagaaaat aagacttgtc ctacacagct catgaaatag taatgaaatt cacattagag 5880
aagagatgga aaaacacttt gaacaaaaag cattttgctc ttataaaagc acagcctctt 5940
ttgagaggcc ctttgctccc catttctcct tcttcagacc cccccagact aggagaaggt 6000
ctgtctcatg gagtgacctt ttggctgcct ctagattcca agctcagttt tgctttcatt 6060
aaccacagat actgggacgg acagaaaaag acctagtttc tgttgagcca aagagtctca 6120
taacttgtct gttcacatac ccaagagccc accctctagt tgagacactc agttccctct 6180
cattctggga gactgcatgt ctctgtgacc tcctggtaga gaccgtttga catgtccccc 6240
aaccccccag tgattgagtc tgaattctcc actgatgacg catttcctag cactcagggt 6300
gtcccctcct ggttgccccc tcaccactga agcccgcttc ctcccttttc atttgatgct 6360
taacaactgt cagtttgcaa gaaacatgct tcaaatccac attctcccag ttgcctagca 6420
acaacttccc tcccggataa atgtgggttt cctgtagctc agcccaggac tgaacacagc 6480
agcacacact tctgtccact gcttcaactg cttttcacct ctggtctgca tgccttcaag 6540
actgcagctc atccctccct tcagaacctt ccatagcctg cagaggccat gtctgcccca 6600
aaaagacaca ttgaacctga ggctacttat ttacccttgt gttaggtata tcctcaactt 6660
agaaattaat actgtttcca gattgtcttc tttgaatcac agaaagtaaa acaacaaaac 6720
attcaatgct taagacattt catgtgcggt tgggtgacat ctgtttgatg aacacatttg 6780
atccaaagca tcagaaatac tatgccaaca agacttttta ggaggtgata aacatgtctg 6840
ttctacctta agaaaaaaat attacacagt cccaagggag agacatggtt ttgatcccag 6900
acaacccaag cagagacctc ttagggccgg aatcatcttg gctgctgcct aggaccttat 6960
atcaatttct taagcacagg atcaaggcct aaaggcccct tagactgacc tcagttagta 7020
gaggcagatc ccttcacagc cttatcttcc ttagaggtct agtctgacct tgaacttcgg 7080
ctggcagtgc tgtcagttgt gatgtgtgac atggaagagt tatttgttac ttggaaaatt 7140
aagagaactt atttggcata ggaaattgtg tgtgtgtgtg tgtgtgtgtg tgtgtgtgtg 7200
tgtgtgtgtg tgtgagatga tgtttgccat tttgatctgt gacttttttt tccagaaata 7260
gtttctcagt tccattccaa ctaaacttac agtctcttcc ggttctttga cagaaacaat 7320
tcatgtgaat ttgaacagat aatagggaag ggggaaccaa aagaagagga gagccctggg 7380

```
aaagttattt tataatttat ggcaacctca gtcaggcaac tgtgaacagg tacatatgga  7440
gggctccctc gggactaggc agtattcaga gatgtaaggt gtgaggaccg gaccctcatc  7500
atttaccatt cccactaaaa agagctggga aggaaattgt agctgtagca ccaggcacgt  7560
aactggagct tagtaactat ttggtgaagg aatattatta aattattaac aagatggaaa  7620
aaagggtatt aaccacacaa aaatacatct caagctattg tttctctgtt ccctttcccc  7680
caaattccta gtcttgctct tatctggctg tctctctagt cactctttct tgctgactct  7740
cttcacgttc ctttctccac ctggaattcc tgggccctcc ccttttactg acagacactg  7800
tcctcactct cacagtcatc agtttgtctc tttacaaacc tcagctcaag tgtcacttcc  7860
ccgtccccag gtgaaactga ctgctccctc cctgtaagtc accatgatga ctgctatata  7920
tagccctcat ggaacctaaa acctcaacag acacagtctc tttcctactc tgttatagtt  7980
tatttactca ttaattacca caacacgtat tattgagcac ctactgtgta ccatgcccag  8040
aagataaaag acaaacaaaa taaaacctat tcctatgctt aatgagttta cagtctagtg  8100
gagagataga tacattaaaa aataacagca aaccaaaata aaagtggtaa ataaatgcac  8160
tgagaaagac aggaatagct aggaggggca cctaatccct agggaaggaa agctggaaga  8220
gcatggtgat gggggaagaa ggctttctgg agaaggtgag gtagtttgaa atgagttgac  8280
tctggccagt aggggtagag tgagaatggg gtgagacagg gtgggttggt catttttgatc  8340
cattagtcct caaagtgata ggactagtgg ctaaggactg caggctttac agaagcctac  8400
aaaactattt gagatttgaa gttttttttt ttttttaatt ggctccaaaa gaaaatgaaa  8460
aaactttaga attataatga atgaatatta aatgaatatt taaggaaggt aattttattc  8520
aacttcattg ttaaatttag ttaaaacaag cccttgagtt tcattcaaca ctgttttatc  8580
ataccgttga tgagagaaaa caaaactgat tcctggccag ggccactgtc agcgtggggt  8640
ttgcacatct ttcccatgtc tgcttgggtt agctccaggt actcctgttt cccccacatc  8700
cccaagatgt gcccattagt ggaaacggtg tgtctgcatg attccaacgt gagtgagtgt  8760
gggtgtggga gtgagtgccc ctgccatggg agggcatcct gtccaggtta gattcctacc  8820
ttgtgccctg agctgctggg atggaatcca gccacccatg actctgaact gaaataattg  8880
ggtgaataat tatcttactt tttaattaat ctttgaaaat gtatgtatag ttcacatgta  8940
tttcaatatt taatattaga agtattttag tctttatttt gaagtttggt gatttattgt  9000
aaccagaaac aagctataga aacttaattt tgggccaagt gcagtggctc acacctataa  9060
tcccagcatt ttgggaggcc gaggcagacg catcacttga ggtccggagt tcaagatcag  9120
cctggccaac atggtaaaac cctgtctcta ctaaaaaata caaaaattag ccagatgtgg  9180
tgggcacctg tagtcccagc tacttgggtg gctgaagcag gagaatcact tgaacccggg  9240
aggcggagca gtgagcagag atcgtgccac tgcactccca cctaggcgac agtgtgacac  9300
tccatctcaa aaaaaaaaaa aaatagaaaa gaaagaaact taattctggt ttatatcaat  9360
tagcctgtgg taaaattggt ttcattatag ccatttcact tagttgaagt ttccaataac  9420
ctgtggatga attaagtgag gatttactat attcataaaa tcttaaattc caaagcctgt  9480
ttgcagttca ggtttttcca ctttacaaac acttctaagt attcacaatg attgcttaaa  9540
attcatacca gataaatcat taaataagtt gttcaaagtc aaataatttc ataagtaaaa  9600
attaggagct tttagaaaac tatacctaca tagacctaga cctatagata gacagagatc  9660
tgaatagata tggacacaga tgctttccaa agtgttcatg tgatgtgtgg tggagtttca  9720
agaccagagt gtgcctgggg cctgcagaag taaaggagag gggatggaga gaagattgtc  9780
cacatggcca tgggcaatct cccacccaca ctcaagtgag gaagacagga aacaaattca  9840
gaaagaagag aaaataatca aaactgatgg gagcttgtga ctgatttact tatgcgcagc  9900
ctccctggag acatgagtgt ggctgttcct taggttgtgc ctctgggctc ctaccccctc  9960
ttagatgcct tcctattatc taggacctgg ttgctttttg tctgcatagc ttctttggat  10020
tccagtcttt gatgccagct tcctcctaaa gtagcctttc agatgtccct tggttaccct  10080
ctgctatcta agggctcatc ctaccccaca ctcattccca gcaccaattt ctggatctcc  10140
aggctggaga tttagacaat gggatgggaa gaacccatga tgggtcccag acagaaagtg  10200
gtgccagcca cagaaagggc acacaggcac agaagttggt ttggggtaag acgatgtggt  10260
cagttcagaa cacgctggat ctaggcagat gcccagcaga cagttggata tgtaagtctg  10320
aagctctggg gagaggtcta ggttggaggt acagatttag aagtcatcaa caaaaaggta  10380
gcagattaaa tgataaagga aatgagacta tccggggagt gtgcagagtg agaggagcaa  10440
gggaggccct tgggaacctc agcacttcag gggaaggtag aggtacagtt gctggtggga  10500
aaggcagaga agtagcaaag caaaccaggc aaaagcagtg tcacagacga ccagggagga  10560
aaaggacatg atcaaaatgt tgagaaaagc agagaggttt gaaaatacaa gaagcaaaaa  10620
tgtccactag acttaaaaac caggagaaaa ctggggggtt cttgataaag catcttagta  10680
ggatggtgag ggtagaagcc agggaagtgt tggtgaggaa gtgaagtcac tgattacgga  10740
ctatgcttaa aagaatgtgg gaatgaaggg tggaagagag aaattagact gtagctaggg  10800
agacataagc gatcagaggt agattctttc tctcctgtgg gagaatcttg cacgtataca  10860
cagcatgacg acagtgatgg aagggctggc gaagcctcag ggagactctt ggaggtaaac  10920
cccatgaagg gaggactttg tttcattcac tgccgtgtcc ccagcacctg gcacaatagc  10980
agacactcaa tacatatttg tcaaatgtgg gattttatca tttagaaact gcacctggct  11040
gtgagtaaca aaagtcagag aaaccgtggg tttcattttt ctccccaggc agagtctgga  11100
gctgggtcct ccaagagggg tttggagcac cacaggtttc ctcaagaccc ccaggctgcc  11160
ctgtgtttcc ctccttcatc cccagcatat gcctgtcatc tggtgacctc caaacacctg  11220
tgctgcctcc tccagcacat ccatgttgca ggcagggacc aggcaaaggg cagaggggcc  11280
tacttcaaaa gaccatttcc agaaacccca tcctatgact tctcctggtg tcttggttac  11340
cattgtgcca taggctcacc ctgtatgcat gggaggctgg gccaggcatt atgactttta  11400
gcaatattgc atagataagc atcaatcttt gtcactgtga cgaagcctag tcactcagtg  11460
ctaggcaagg ttaatggaat gggttggtgt gtgcattatt cttgaggtct ttcttatgct  11520
tcatgttata catttattag gacgtttagg caacaggggg ataaaaatga agaggagatg  11580
catgctatga tctgaatgtt tgcatcctcc ccaaaattca tatgttgaaa tcttcatccc  11640
caagatgatg gcattaggag gtggggcctt tcggaggcaa ttaggtcatg actgggatta  11700
gtgcccttgt aaaaccccag aaagccagct tgccgcttcc accatatgaa gacacagaga  11760
gaagatgcca tctacgaatc aggaaatgag cccgcaccat gcaataaacc tgctggagcc  11820
ttgatcttag acttcccagc tgccagatct gtgggaaata gatttctgtt gtttacccag  11880
cttatggtat tttgttgtag cagccagagt gaactaagac agtgctgatc tcgtattctt  11940
ggagggaacc cttagtcttt agggaaagca aagccaccat ttggggcagg gtgttctcca  12000
agtgctgcca catatgctga tgtggttaaa ctgcaaacta tggtaaaaat gtggaggtct  12060
gtggaattgt caatcaggaa aaagatataa aaagaagtta aagtcttcgt gcttctggaa  12120
```

```
ggatatgtgc caaattgtta acattgatta tccttgggta gagatgtggg gaagtttgca  12180
gagacagttt tgccttgtac tttatataag taaacagcta ctacttcgtt gtcttaaaaa  12240
aaaaaaacag cctatgtgct cttcatgtga ctcagaacta cctaggcaat acgattaatt  12300
gaattagtaa aattgagtga ttatgaattt tcaggaagtc attaatttac cacttcttta  12360
ttacatccac ttctaacagg acttcaatat aggggaattt gacttcaaga taaaaagacc  12420
aaatttattt accctttttaa aaaaagacaa cttaaaagca gacttgtctt acagaacctt  12480
ccttagttgg acatcgatga gtgtacagaa aatgcaatgg ataaaaagct tggtgataca  12540
aagataaaaa gtggggtcct gtccttaatg aacataccat ttcatggagt atcaggtgta  12600
taaacaatta taatcaatct gcttgttatt ctgataagat catttactca cacatcaaat  12660
actgagtgcc caccacatgc ccagcatacc tagaagtcat ccagtatgat ttctgtctac  12720
atggagcata gagtcttaca ggggagatag atgacaagta aacaccagaa taattaccaa  12780
tggtgaagag cacaaggaag gaaacagaac tcctaaagag agcgtggctg ggcaggggtg  12840
agcaagaggc atagaaaaag gggcatctaa atctacttgg gaggaagctg tttctcacat  12900
aggtcatcat gttaggaatg agacttgagg gatgagtaga agtttgccag gcaaagaagg  12960
aatggggggg aatagagagc agagctaggg gcaggagaca gctgacgtgt gagcagacat  13020
aaaaagaagt ccactgtggc agcagagaag caggagagaa ggcaagtgag ggagccaggc  13080
accagctcac agaggtcatg tgtgtcaaaa cgtagtaatg gccttctctt ctggagacag  13140
tagggagcca tggaagatgt ttgagcaggg aaagcgacat gactggattg gcctgttggg  13200
taactcagac cacaatgcat tggaagggag ggggctagag gcaaggggac tggcaagaag  13260
gccagtcctt tttctatgcc tattttgatg aaatattcta gaagggaagt gaacaaaggt  13320
agtcctagag aggaagaaca aaacagatag gatacttcct tagtatttgc tcattcgaca  13380
atttattttt gcatatacac taaaaccttt tttattatta aaacgtttta ttgtaggaaa  13440
aaagtatgaa agtagagtga ataataaaat gagctcccat ggatctatca cccagcttca  13500
actattatca atatttggct gttcttgttt taactgttct ccaccttttt ttcctgaagt  13560
ttttttgaag caaatcacag acaacatatc atttcaccat atgtacttcc ctctgtatct  13620
ctaacatgta agaacttgtt ttaacaaaat caccatgcta tgatcatacc caacaaaatt  13680
tatcataatg tcttaataat acctaatacc catttcatgt ccactttccc ccaattgcta  13740
cagctggttt gttcagatca gaatcaaaat ccacctgtgg ccattttact gctatgtctc  13800
tcaggtctct tttcatctct aataatctca ggggagacag gagggaggac gggcaggact  13860
tggggctaac ttgcttatcg acacacagtt ttgcctactt gcttcctccc ttcacaccca  13920
ctcttcttct cagccccacc cttgtatgga aaaaacagaa attaaagtgc tttgcccagc  13980
acccactgaa gctatttcga aggagtttga agagtactcc cggcaagaca aatgcctcgg  14040
tccagtgctc aggtcaaaga ggggagacgc ttctcagtga tgtggtgtca atagcagctt  14100
agttgttctt tcctctggaa aattctaccc atctgctttg taactcccat acctaacaag  14160
gccttttatt tcacaattag aaaataagcc tgaaatatga atgctgcctg agtgtaccta  14220
catttattct agagtttcag ggtcaaaaag aatacaagga cctctgcatc tacagccaag  14280
aggagagggg caaagacaca cagctacaaa tgagaacctg gctggtcaaa gcctaactcc  14340
acctgtttgt cagcactgat gcaagttagg tcagcccaat gatcatttag gagaactgtg  14400
ctggcaaata aaaagcagag gcttttggtc cccagatact tggatgagaa ttacaagtcc  14460
agctggttaa aaggcacatg cccagtgctc acttcacacc tactcaggaa gcacacttga  14520
gttggaaaac cactgtcttt acacttagaa ctcagtccta catgactcct ctaggatcag  14580
tgattccatc agttttgaaa catgaagcat gaagtcaaac aggacatgac cttggtttcc  14640
agaaaaccag atgttcacat cagtctctgg agcttggagg cagcacacct ggggacttcc  14700
acatcccctg ccgaggtggc aaaagcagga gcagtggtga gttcacatgg gctggggttt  14760
cctgaacact gctggcaatt ggagaatctg caagggaact tctccgactc ctaccagcag  14820
ctgctttaaa ataaaggtga tgtagctggt caaatcctcc atgagagagc agtgttgaat  14880
ggaggaagag acacaacctg tctgaaaatg gcacaaagga agaaagatgt aaacaatgac  14940
gagaagactg cagtgtctac aaagctccga ggtgaacaga tgggcacccc aggcccgcag  15000
cacttccttc agtctctgcc agctgcactc tgttttcctt cctccaggaa tcttgtttgg  15060
tgtcactaaa acagcaatta gaatcacttt gaaatagtga tagtatttaa tataactatg  15120
aaactatctg tgattgacaa gtgcagcaag gagtcttgga atgagagcct ttattttttc  15180
aattaaataa aagagttttt tgtttctaaa agtaatcttg cagaaaagat cctgcgatca  15240
gaaagaagga ggggggagt tttcaaacat ataggagatc agactgtgcc tatgtgtgta  15300
tatacctaca aacatatata tatttaaaaa attgttttac tgtcaattac ag          15352

SEQ ID NO: 13           moltype = RNA  length = 2633
FEATURE                 Location/Qualifiers
source                  1..2633
                        mol_type = other RNA
                        organism = Homo sapiens
SEQUENCE: 13
gtgagtagcc tgatggtagt aattataatt tcattatgtc tttccaccat ttaccccact  60
tatgtcaaat aatttaattg tatttcaaac ctgttcaagg aaaagtacat ttgatctttc  120
catctagcaa tttcaaagca cctgttcaca tcccaaatta tctgtgctct taagtaagag  180
gcagaaagaa aggaaccacc cttctgattt cacatcaaaa aagaaatgcc actggcaata  240
agcaacttgc ctggtgtggc ataaatcatc agaagactta cagttgaatc taagtctttt  300
cagtactgag gtggttcatt attctgttac agtcttaaaa ttcacataaa tatatactgc  360
caataataat agcatacacc tttatagctt acaggcactc ttcttctaag tgttttacct  420
atgttggctt atttcatcat aaagaaaaca atggactttt gtgttgtttt gtaaaaagat  480
gcgcacattt taattaacat ctgattgcac aagtctcctc ccatatagaa atggattctt  540
ccacgcaata gataagaggt gctggggata tgatgatgaa cacacagatt tggtcatgac  600
cctgtgggaa agagagatgg gaaaaaaaca attctcttca agtgtgatga gtgttacgaa  660
agggagggaa aagttgaaac aggttttttt ccaaactttt ctccctccat tattcgcagc  720
tgacttgggc tccaccaacc tggaaaactg catggttgga atctgtcttt ataaaacgca  780
tctcaacctg ggccgagtat gcacactgat gtgggaaagt tagagaagag cccattgtac  840
taatgctcac ctgctacagt gggagtctct gttaaacagt cttttcttca tagcattaaa  900
aaaatttata tcactacaat aaggttgaaa ttgatagaga atgtacaaac aatccccaaa  960
gtatatcaac actcttagtt ctgagtagaa gttccagaag gcttcttgac tgtctagata  1020
gcaagtctaa tcatttgtga actaagttaa agcagaaggc ccagtttata tgaattggta  1080
```

```
ttacaccatt tgacctgaga acagcccctt catctctgag tgctttgact aaatgagcaa  1140
cataataata gtaataaccc cttacaagat gtcataagac tcactgttgt tgaagcaatt  1200
tgagattttg actttattga agcatagatg gtgattatag gcatgactca ctgtgtggat  1260
tctccctggg ctcatcagtt tcagagggca agtgttggca tgtggacaaa gagagggatg  1320
acacgtaaac atggcttatt gcaatgggga aatattttca gtctcactga ttgaatccta  1380
atggttttat aaattcccca gtaccactga aagcaaagca agtaatcagg tgtgttttag  1440
gaataaaagc agcattattt taatttcgta ttttccccta aagcaaagcc aaatggcatt  1500
atgggagcca agctactggc agctccacca gccttctcct gagttctcgg cattacagat  1560
ctaccctcaa aggatgaggc cagcaagcac cacagggtgc ccacatggag aagagaaggc  1620
caccaacctc ctcttagctg gcacagaatt gaaaaagtgt ttttccagga atggatactt  1680
catctgttct gtatttgcta gaattttaaa acgcacacac agacacacac aggcgtgcac  1740
acacacacgc acacacacac gagaaaacca caaaccacac atttcaagga aatggaagaa  1800
ttcattggta aaattaagct aataagatta ttttccaaat ataagaaact aaattttaga  1860
ctatttagcc aaagaaattt gctctgatct tgcttttcta caacagaatc attccccaat  1920
cattttattt ccctcttttt ctccccagta tccccatctt ggtgggacaa cagaacccaa  1980
gaactggctt aacagtaaaa tattttctgc atttgcccaa ggacacattc ccaacgaatt  2040
caaataaagg agactagaag aagagaggct atactacagt gctctagggg tcactctgtg  2100
atttgttgtt gttgttgttg ttgttttgag acggagtatt gctcagtcgc ccaggctgga  2160
gtgcagtggc acgatgtcta ctcactgtaa gctctgcccc ccaggttcac gccattctcc  2220
tgcctcagcc tcccgaatag ctgggagtac aggggcccgc caccatgtcc ggctaatttt  2280
tttgtatttt taatagagac ggggtttcac catgttcgcc aggatggtct cgatctcctg  2340
acctcgtgat ccgcccgcct cggcctccca aagtgctagg attacaggca tgagccactg  2400
cgcccggcca ctctgtgatt ttctttaagg ctcatcctag tattctccta gtccctaagt  2460
agatggcagt aggttttgtt ttttgttttt cgcagctgga ttaaggattg ctgagaatat  2520
atggatgttt tcttttaaat gtggaagtca aaccaaacgt tggagcattg gcctcacagc  2580
agattatgac tctagctgcc ttaaaataac ctgaagactt tgccttgccc tag         2633

SEQ ID NO: 14          moltype = RNA  length = 1016
FEATURE                Location/Qualifiers
source                 1..1016
                       mol_type = other RNA
                       organism = Homo sapiens
SEQUENCE: 14
gtaagttttc tgagtcctgc ttataaattg gcctctcatg ttggttaagt tgatggttta  60
acacttctag gtgaaaccaa acctggggtt gcatctgtct tgtcttgctg agtggcctta  120
ggtaaagaga cttctcccag aaagtccact tccccttgca gaaagggggc attgcttata  180
agcaattctg gacatgaacc acagaaagaa ctgaggccca cttggaaagg gaacagaggg  240
gccatttccc actgatgtaa ttgaactagg gctaagttca agaggaagag aatgatccgc  300
aaggaagcaa cccagagttc caggtgaagc tcaggtcaga agggccctgg caagtaaaca  360
cggctgtggg atgcttttac aaacacaata tcgtgaaaat ctatgtgtgt agtactgaat  420
tacattccaa atggcaaatt cctggcaaat catcttcccc acctttcact attttttttt  480
ttttggtctt ctatggggta aaggaggatg gggtggggaa gaaatgtaac tggctgcccc  540
tctagttaaa aactgaaaag aggcagcaag ggacatgcca aaagtagttg gactctaaga  600
tagctacaca caacaaagca gctaagcagc taattgaagg gaaattactg aggctcaagc  660
tgagattcca agcgggggcc ttgtttggcc tctcagtccc tttcatctga gaaaggcctc  720
agttcctagc agtaatcaga ggcaggcttc tcagcctcct tctcctaaag cagaataaac  780
cacagggcaa gtcgcatcct ttgtttctct gatgaggcca ttactgagag tcactgtggc  840
attttgctac taatgatgag cttgttattg gtggggtaca gcctattaat ttaggttatt  900
catcaaatcc tccagcatgg agttgaatga gacatgtgat gtggatacac taatgactat  960
attgagttac aagcaatggg gagtttctgt aaaatctgtc ccttgtctcc tggcag      1016

SEQ ID NO: 15          moltype = RNA  length = 615
FEATURE                Location/Qualifiers
source                 1..615
                       mol_type = other RNA
                       organism = Homo sapiens
SEQUENCE: 15
gtaagatccc agctgggctt gccttgtgta ccctggacct cccagaagtg tgtgtgtgtg  60
tgtgtgtgtg tgagagagat gtgccttcct ggtagcacat ctcatgtttg ttttttgcta  120
agtggactct tgcgtttcct cccccatcca cagtcatcac tggaatgctt tgcttcagtg  180
cccctgcctg ggccctcccc tctctactgc agcctacaat gaggttttct ttcccattgc  240
ttgaattata tccctaatgg aagggttcac aattctctga atcctggcta ctcagataaa  300
gacagggagg aagggaggaa gggtattttc tcccaggggg tccaaatcta gctttaacga  360
gggaggttct gagaaaataa tatcatcaat attacatgga cttctgagat actaagaaat  420
tagattctgt cagcccagga agttgggaga tggtgaattg ttctgggaaa tagcaataga  480
ctgagaaaat aaaaacactt ccttgaaaag cctttcccta acactaagtg atagggggcag  540
aaaagacaca accaaaagtt ctctctcact tttctctctg ttcgtgtctc tgtcttgatc  600
tctgtctggt tttag                                                   615

SEQ ID NO: 16          moltype = RNA  length = 702
FEATURE                Location/Qualifiers
source                 1..702
                       mol_type = other RNA
                       organism = Homo sapiens
SEQUENCE: 16
gtaagggggg ttggaggatg gggaggggag gggaggagga agcggtgggg gcaagaaagt  60
tccacttgtt tccttttccc aggaaagagt taatcgctat tggagttaga tcaaaataca  120
acaagcaggc cccaaaggcc ttcattccaa gcagtcacca agtggggtca ctgactttgg  180
atgagaaata tgtttcttga attctgggag aagtctaaaa gctgccacaa gaccagtggc  240
```

```
ttcctggagt ttcctacttt tatgaattca ctcaagggcc tcaaattcaa agaggcatct  300
ccccaagggg ccagctctgt aactccaaag atggtggaat gtgtttgtct ggtctcattt  360
tcagctttgc aaaatgaaga caagagttct atatatcagg gacactcaaa agaaaacaaa  420
aatatccata agcaaaagaa agctttttat acaccatatt caatgacccc catctggccc  480
ctcctttgcc cctacacatc ttccctctat tctagagacc catggacttg gggaaatggg  540
atatagatag gtatgtttca tagtggaaca agctcaccag ctcttcaggg agccttagca  600
tctctatcct caatcactaa aaattagaaa tggctgaaga acaagaccaa agatcctatg  660
gaatttctaa gcagagcagt gactgtattt cttcttccca ag                     702

SEQ ID NO: 17          moltype = RNA  length = 14372
FEATURE                Location/Qualifiers
source                 1..14372
                       mol_type = other RNA
                       organism = Homo sapiens
SEQUENCE: 17
gtaaggggct gcaagcccca cagtgggccc cttgaagata gccccatgag tggggccaga  60
gctcccttag caagtcaagt ggtcttgaat ttaagctttc attttcccca ctgaagaaac  120
aagaatccct acatcccctg tacagttctc attctctaac agcttatcca tacttaaaac  180
ttatctatgc tgaaaacggt ttcctcttca catctcctac ttctcatgct gggcacctcc  240
tcctgtagcc ccctttaagc atctgtgtct gtcctcaacc ctcttctgtc tgacattgct  300
tgagtggcca tctatggcca gtgtcccctc aaccccacag tccattgctt gctggacact  360
cctgccctca agttctacaa gcacatcagc ctcaacatgt cccctccaaa aactgtatgt  420
tctccttgcc catagaacat atccttctcc tatatttcct atcctaatta acgtcctcag  480
catttgcccg aattctcaag tgagggattt cagggtcatc cctaattttc cttcttcacc  540
ctccacacag tagctgtcac ttactgagtg ttactttatg ccaagtactg tgccaactgc  600
ttttacacac atatgcttca tttaattctc acagctccat gaggcttgca ccattatcat  660
tgccaatttg cagatgagaa gccagggctt aaagaggtta aataagatcc cacgcatgac  720
cattaagagg agcgaacagg atccagctct gggggtgcct gagttcagag cctgcctttc  780
tgatttctct taccaagctt tgtctcctct ccctcctaaa tatctctcaa ctctgcctct  840
tgcattccag gctctctgag gactagaggc cttgtcatct ctgcgccagc ccattccaag  900
ggcttccttc ctggaatcca gggtccagcc tctgttggcc caggcatttc tctacactgg  960
caccagagtt acattccgca cacctgctta cgttgctctc tcacttaaaa tcttaatgac  1020
tcgaccccca aataacacag gtcccttcca aatctgtcct accccacctt cccagccctt  1080
gctcaactct gctacctggc cctttcacgc ctacaggcat tcccattcca tgacctcttg  1140
ggattctacc ctttgcaaat gctgttttca ttgcccattt attagagcgc ttttggtcac  1200
aagctttttg cttaaccaaa aagaaagcat ttattggtgg acataaataa tgaagttcag  1260
gaggatccaa gagttggaag ccaccatgag accccctgtgt ccttccacct cacttttcta  1320
ctcgcctctg ctcagcttca tctctggcca ggccctctcc tctgctgatg ccctagctgc  1380
ttacagccct tagcagtcat ctatacacca aaaatccctt tcccatagca gaagcaatgc  1440
tcctagagag tttccctgtt ggtctggctc ctgtacccac ccctgtgtac tctgattggg  1500
aggcctgggt cagctgccca ccatggggcc atttctatga gcaggattac tgtgaagtgg  1560
aggaagatgt ttccccaaaa gaagaaacac aaggtagaaa agtgtatgtc caccaatgcc  1620
tgaaatgact gtccctttcc tcatctgctg agcttctact cattcattct ttgagactca  1680
gcactcagct cttaaatgtc acttctgctt tgatggaggt ttagtcattc actcctctgt  1740
gcttcctggc cctctcttca cacctctctc agacccctct cccagataga ttagagttgg  1800
ctgttgacat gtccatctct ggctgggcag ctaaactgga gttatttaga atcagggagc  1860
acatgtcagt cattttcaaa ttctcaacct catactccca gtaaatgact ccatctaagg  1920
gtggaccact cttgcccatg ggccaggtct gggtctgtgt catctagaac tgttggaagg  1980
taggggcttc tgtgagcagt aggagaggga ataaactcga gggccctcgg gagcatgccc  2040
tcttgtctca gacttgtgag tcctgaggat aacaaactag tgaagaaaag cctcgttcta  2100
tctgtcacct ggtgctcttg aggactttct gttgccctgg tgccaccaca attttccaga  2160
gtgtgtgacc ctcgctctcc aaactctgga agtggcagcc gaggctcccc agtggccttt  2220
cagaaggtgc cagtcatgac agcagcacca aactgcaggc aactactaag cgatcaccaa  2280
cttgtctgaa gataagaatg accttgaatg cattttataa aacaggattt ttttttaat   2340
ttttagattt tctttcttta ttttacctta agttctggga tacaagtgca gaatgtgtag  2400
gtttgttaca taggtatatg tgtgccatgg tggtttgctg cacttgtcaa cccatcatct  2460
aggttttaag ccccacatgc attagctatt tgtcctaatg ctctccctcg cctcgcccct  2520
accccacccc aacaggctcc ggtgtgtgat gttcccctcc ctgtgtccat gtgttctcat  2580
tgttcagctt ccacttacaa gtgagaacat gtggtgttta gttttctgtt cctgtgttag  2640
tttgctgagg atgatggctt ccagcttctt ccatgtccct gcaaaggaca tgatctcatt  2700
cctttttatg gctgcatagt attctatggt gtatatgtac catattttcc ttatccagcc  2760
tatcactgat gggcatttgg attggttcca tgtctttgca attgtaaaca tacatgtgca  2820
tgtattttta tagtagaatg atttatattc ctttggttat atacccagta atgggattgc  2880
ctggtcaaat tgtatttctg gttctagatc cttgaggaat cacactatct tccacaatgg  2940
ttgaactaat ttacattccc accaacagtg taaaagcctt cctatttctc aacagcctca  3000
ccagcatcta ttgtttcttg acattttaat aatcaccatt ctgactggca tgagatgata  3060
gatacccatt tgtcagatgg gtagattaca aaaatttttct ctcattctgc aggttgcctg  3120
ttcacgctaa tgatagtttc ttttgctgtg cagaagctct ttagcctaat tagatccatt  3180
tttcaatttt ggcttttgtt gcaattgctt ttggtgtttt agtcatgaag tctttgccca  3240
tgcgtatgtc ctgagtggta ttgcctaggc tttcttctag ttttcatgat tttagatttt  3300
acatttaagt ctttaatcca gcttgagtta atttttgtat aaggtgtaag gaagggatcc  3360
agtttaagtt ttctacatat ggctagccag ttttcccaac accatttatt aaatagggaa  3420
tcctttcccc attgcttgtg tgtgtcaggt ttggcaaaga tcaggtggtt gtagatgtgt  3480
ggtgctattt ctgaagcctc tgttctgttc cattggtcta tgtgtctgtt tacaaaacag  3540
attcttaagc atcaacccag atcgactggc tcagaatttc cagggaagag gcctggttat  3600
ctgcatgttt acagacctat tagatttgtg ggacctgcag ttcccttgta cagttagtta  3660
ctcaattaac atctccctcc tctcatggtg cctctacctg ctaagccctt attcccagcc  3720
aggcccacca ccatccaccc actgctgtta taacataagc aggacctgtg cgaggggggtg  3780
tggacggagg agagaggctc tgttgcttca tttgtgcagc atggagttca gtggttctca  3840
```

```
caatgttttt gcaaagtata taaagaatac tccttgtcta cttgacattc gtatcgtgac  3900
ataaatgtct tgttttccag aaggattatt ttttccaagc agcttgttcc taatgcagcc  3960
ccaggcacca aacagatact taaaatatat taattgctta aatggttaag aattcagtct  4020
ctggacccac actgcctggg ttcaaattcc tattatctgt gcccagtttc caagtctata  4080
aaatagggat attaatagca cttacctaat aggctcgtta tgagaattaa atgagctaat  4140
tcatgcaaag cactgacata tagtaagcac ttaataaata ttagcttttt aacaaaatac  4200
aagccaaaaa acactgctta ggagaggaaa tgatgttagt gcctcctgta aataggccca  4260
gcctccaagc tggtgctcct ctaggaatca caacgctgca aatcacatcc tccggggccg  4320
ccaggacttc acgagggcct ctgagcagag gggtatgatg ggagcagaag cccagcagct  4380
gtgatgatgt ggtttctgat cttcctgccc ttggggtggg ggaggaggaa agcaaggggc  4440
aatgaacaga aaggagaaga tagcggggag gaaatgtgtg aggaagaaac acatcactgt  4500
ggcttgtcct ggatttttct gcttctgttc tcgtgttttg ggaagtctgg aggagacttg  4560
aaaatcattc atgtccccac cctgaggatg gcttagtagc agagaggcca tgaaaactct  4620
ttgctgatgg ctctgaaagc aaggatgttg cttcactggg ctgctgaagg cctgcctggg  4680
ggttctgagc agagagtaca ggcccctccc aggagggcgg cctaaccacc atgctggcat  4740
ttctgtggac catggtctgc tgtctcagac cccctccaca atagggtctg caatctcatt  4800
caccccataa atacattctg tctttcctct gatcccctcc cattagcagg gggaaataaa  4860
tggaagtcag acggcccagt tagaaggcag gcagtggagt aggaaaatag atgatggtgg  4920
tttggggagc ctcacatcac tcatggggag acattcattc ccatgggcct tccaatcacc  4980
cttttctcca aatctaagga cacaggacaa atgggtcctc atacaggcaa atatcttaaa  5040
ctggtatgtg tattcattta tagttctaat ttatatgtgt ctttattcac atatattttg  5100
cttctggaga aaagctcaat tagaaaaatt aatacattat tcttcttatt gcccttcagc  5160
taaaacaagc atacacaccc ctcccctttg gattttttgt ttagcaaaag gttaggcctg  5220
gcacagatga aatactattc agagttcaca gtgtattttc atttcataat atatttgatt  5280
ttcaggtctt gaatttcaca tcaggaagct gatataggaa gctgaattca gccagatttt  5340
aatacgaaaa tacctctgat caaggcataa aattgtactt taaccagtaa ccactgtatt  5400
tctctaagct gtgaaaaaac atgcattcat taactgcttt ttcctctgct gtcaacacag  5460
tcaatacatg tgcataactc cttattgtct acatggtgat tatcttgctg atgaattctc  5520
aaaggccaga gatttggact attttttctc tgtaaccttg catgttcctg gccacatgcc  5580
accaccaccc aaacagaatg tacgcaggga atgtattttt caggataacc taagaaaaaa  5640
taggattaag aagataaagc tgctgatcat gtaatgtact ttagactcag atatataaat  5700
atttgtgaat tatctgtcct atttctttct tctattaatt cattgactct agatgtgcat  5760
tggaaggcta gggagaaatc aggggatcgt gagaaagagc acagaagtct gcatcacaca  5820
aacaatatta tttcaagagc catgaactag atcctaagca actcataggc aatgacctca  5880
tttcatacct ctagtctcta agaaacatat aactggctct aggaaggaaa atgtgggcaa  5940
ggggtagacc ggggtcatgg gtggaggtcc aaatagtaat caatggagct catagggtgg  6000
actgatattg aagctgctat gagccagcca catgctgggc actgttacat gtcatctcat  6060
gcaatactcc caattacctg cctagtaagc ataattgtca ttttatagaa ttaaaaacag  6120
actcaaagag gttgacagtc taatgtaaca caacagctaa atgggggatc tggaattata  6180
atccagagct gcctggctct gatgagaaag ctctttctgc tgtcatatgc agcccacatt  6240
aataggggggc tcagaaagta ttctctggat aaattatata atgaatccaa tgaaggaaga  6300
cattatttta taatatgcag cataataggc actattatga ttggattttc ctgcttgaaa  6360
gtagctagat tagagtagga aaccaaaaag atgtgaattc attcagtcat tcatgcattt  6420
gcatggattg agctacctac atttgaataa atgctgttaa tccctgattc cttggaagct  6480
cacattggag agataagcat gtcattaaat aatgccataa tagtggtatc tcagaggact  6540
agcagaacat aattcaatct gacagagtag aaacagattg tacaaatcca attcaaaaca  6600
tcataaatcc tctaagcact gtcaattctt cctccaaatt atctctgaaa ttcctccttc  6660
tttcccattt atggcctcca tttacagaag cgtgtactgt ctctcttagc tgtttgccag  6720
gccgccagtc tcttgctgtt cagctctcaa ctgcttccag caagatcttt ctaaaatccc  6780
aggcttgcca agacttagcg cccacagctc cacagtgact cctcattgct gttaaggtaa  6840
aggccttccc agtctagccc ttcatgcttc ttccatgttc tatgggactg ccccaggctt  6900
cccacctggt accactgagc ctttccatcc ttcccccact cgactgccag gtcaacaccc  6960
acacccacgc ttcaggactc aggtcctatg tttcgggcct tcttctgtgc accattccct  7020
tccctgtagc ccttgatcat gatttgttta tacgcctccg caccttcatg gccctgaacc  7080
cctcaagggc cgaaactgcc ttacttttct ttttgacttc ccaacttacc ttagtggagc  7140
tgtagtcaca tagaatagac gctcataaat gcttctctgg gctgtaaagg ttgaattttc  7200
cagctaagca aggaagaaag acaatttcag gcaggaggaa gggcataagc aaagtgcaga  7260
gatgtgaagc tcaagagaaa tggatgggct gggcagaggt gtggctgcag catcagggga  7320
gaagaagtag tgcctggagt cagcaggcac ggcttgcaaa agcttcacct ataggtgaaa  7380
ggacaccatc tcttgcacca ataggctctg tgattggagg caactttgct gttttactgc  7440
cagaaaactg aggatgataa cccaaactgc agttcaagtg gcattcactg gtgtggctga  7500
aatgggtgtt tgtggccaga atgtggtctg attggtcagt gcccagctct gttgattagc  7560
agatgttttg aatatagtag catccatgtg cccaagttgt tgggatgatt caacaagaaa  7620
ctttaagagc tcaagtgccc tgcagttgtc agccaggtga ttctcttcct ttggacccag  7680
ttagacgcag gcattacctc gtggctttgc cccagtgtga atctttgtcc tccaacttga  7740
tctttttatt tgtttcatta ttgtatttaa gttgtttatt ttagagacag acatttttta  7800
acagctgtgc atttcctgtc cctttgtttt ccagtcgtca tgtgtttcct tactctctgt  7860
gggtgaacgt ttcagatgtc tgtttgcggt gcccagcgtg caagataaaa tttattgcag  7920
tgccttcggc ctctaactca ccattccaac caattcagat agcccaaggc tgttttatcc  7980
agtggatttt tccatgtagt gggaaataaa tcttgaatgt tactgtttag attagccagg  8040
aaactcattc tgggatgttt gcccacatcc attggcattt ctcaaaagga accccaggtg  8100
tctaccttga caccagcagg gccacttgag ccctccgctg gcattcatcg cccgctttgt  8160
tctcagcctg agtttaggag ttacagatgt gagaggcggg attatacagc caacatctct  8220
aagcgggcag tggctccctt accctcgaag acctcactcc tagcacgtcc tggatgtatt  8280
cgtcaaaata tgtcctctta tgccacgtca gcacagggtt gctccccact ttgatcatca  8340
agtttaaaca aaaggaaaga ttttctttct ttctctgcct ctactggaca tcatttccca  8400
cctaacagat aatttaatgt atctgttact gaatgtgttt gaattacaga cagagaggtc  8460
acagttaaag aaggaagcct gctgctactg cagcttgtcc tcccaaggag gtgtttgatt  8520
tagctgtgta aacaaatgac tgcattctcc agaggtcctg aacacagctg cctgcgctgg  8580
```

-continued

```
agagggctca aacctcttcc gccagggtga actctgcttc ctggtgagtg ccagcaaaac  8640
aaccaacaaa gagctgtagg acttgtgtgg acttcaaatg gtggtggtcc tgccacttgg  8700
gctcagccac agcagttagg aaactaaagg ggaggaggaa agccctttcc ttgctttatt  8760
gtcattggct gtcatagggc attacaatgg ttctctttga gattctgagc tccggctata  8820
acatttgccc agaatctgcc tctgaggcct taagacactg tgtttttatt cagcaaagat  8880
gcccttttgac tccttttccc actagtggtg ctaggtttga gcaccttaca ctggcccctt  8940
acaatagcca gttcttgtct acctacattc ttccctaaca ttcatgattg catagttact  9000
cttagtgtag aagcagacag cttttacaca tagactccat ggccgtagcc tcatagaacc  9060
tactatattc taacttgcaa gctaatcaga ccaaatatat caaaatcaaa aacctctgct  9120
gagagtttat tcattcatct ctgtctccca aacgtactta tgtacatacg tgcactaata  9180
tacatgtcca ttagccaaga ttttgatttc agggatcaaa gcaagtacca atagggaatg  9240
aggtcacttg ctgcatggca ggtggcttcc ccatgagaat gcaaggccac ctcatgactc  9300
atacttcaga gggtgaccca ggaacttctg attcatgtcc aaagcagctt ctacaattgc  9360
tctaccttga tctagggaag atgtggggag gatgacattc gggattagct ttataaggcc  9420
ttcctgtggg cagagttgtc tgactttcac ctagtgatca acaagcagct agcaagcatc  9480
agtgtgtgag gccccacgcc ctctcagctc ccctactgcc cacctgggac atgggctttg  9540
gcatctgtcc atagcattgt tctaaccaaa tgaggtgtta tggatcagct caggatggga  9600
tatgttccca gacatattat ttaaagaaaa tagctccctt cctcccctga taaacagctg  9660
ccatggctaa aaggtaacct ggctggggct taaaagtctg ttgactttca agatattttg  9720
caaaaacagt cataaaaatg gtatttatca gatcctaact atttgtgaga cggtttggta  9780
taccatagtg gttaaaaaca caggctcttt ccagaggagg tttactttgc ttagtcgtgt  9840
ctcctaagtg aacttggacc tcataaggtt gttgtgagaa tgaaatgggt gaatatgagt  9900
aaagtccttg gaccagtttt ggccgtatag taagccttca gcaagcatct gcttttattc  9960
ctacagggag gcaattgtaa gcccttcaca aacagcgtct aatgtgatcc ttagaacaaa  10020
cctatgagat agggcatatc tcaattttgt aggtagggaa acagaagcca cacaattagg  10080
aaatggcaac agatctgtta gactcttaaa cactatgcta caccaatttg caaggcaagg  10140
aagacaaagc acctttgaaa atgggtcaga tgttttaggg taaatgaacg tttgagaatc  10200
ttttaagttt tttttccccc agagattatc aaggtatcat tgtaggggga tgcatcagga  10260
aacatgacta tgaatcagct gcctgataaa ccagccagga tggagcccac gtcatcacag  10320
cagtcagcaa tgccactgaa aaacatcagc tgcttattcc cgtatagatt tccccttaag  10380
acatgaaaag ggagttcaaa gagaatgggc cagatatctc tgagagtcat attactaaaa  10440
tatatttatt tttactagct tttttgtttt aagaggtata ctgtcattag cactgtagca  10500
aaaattcacg ttttattaat ttctcctagt ttatcatgtg attctagggt aggatgcaga  10560
gttatattca aaatacacaa atcaactcaa ctcagtaaac atatatcgag gccctatcat  10620
gacaaaatgc tattctagag accacggcga acaagccacg gccccagcct caaagaatgt  10680
actatctttg gaactgtgct ggccaataca gtaaccagca gccacgcagg gctatttaaa  10740
tttaaattaa ttaaaagtaa aaacacaatg cctcagatgc attagccaca ttttaagtgt  10800
tcaatagata tttgtggctc ctgcctgcca tattggacag ggcagatata gaacaattcc  10860
atcactgcag aaagttctac tgaacaatgc tgctctggag cagaagatct tcttgttcag  10920
ggatgttaca cccccgcttg tggctagagt gtggcttatc ctcagagcaa ggatagggga  10980
accatggcac tctgcaggct cagcactgaa gacacggatg caggctctgc ttctgaccta  11040
gattgacctt gggcaaggcc ctttgctcct ctgatcccaa tttcttcacc agccaagtaa  11100
gaacatcaga ccacaagccc tctagggctc tgtccaaatg ccccatgact gagtgaactg  11160
gtagaacatt ctatgtgtgt gtcacaacat gaagagcaaa gactttcatc tccccaaata  11220
attttgtttt tcgttttagg aattaaattt cagattcact ctaattgcca atactaaaat  11280
tctctatatg cagttctaaa cttgacaaac caataaaaaa agattatttg actacttatc  11340
tttgtacaac attgaggtct ccctaaagca aatttaaatg catattttaa aaatgtattc  11400
tagcagttca gttcagaagc cccctggccc aagcatcaca ctgtcaatcc tttgtcctca  11460
agcagcatgg ttgggtgggt taagtactga caaacactgg gtgtcaggcc catggtcagg  11520
gactgtgcta acagtctaca tattagatgc cacctacccc caccctcaac agacccaaac  11580
tatttatcca atagcaaacc ttgcattatt tctgtccaga agaaacaaac atttattgac  11640
aacttttggt gtgtgacctg tttaagtcct acatctcatt taaggactgg tcaatgttag  11700
gctaggcaat gcctgtttgt gagagaatca ctgcctaaag aaaattctcc atttccctta  11760
gctctatggt gggtgactac acatactggt atttcttaaa gaaataccaa ttccatttcc  11820
ttttaacata attattaata tctcattagc atggtgtcac tgaagcctgg gcccaaagaa  11880
ataccaattc catatcattt taagatcatt attaatatct catcagcgtg gtgtcactta  11940
agcctgggcc ctttagaatt tttcatgtac ctgtgttcct ctgcccatat cagctggaac  12000
actaatagtt ttcttccttt ttatctagaa gactgagaac attacatggg acctgccccc  12060
agggcatgga ggctgaggtg ggacagttta gttcaggagg cccaagaagt gttgggtgtg  12120
cagccccttg ttcaaacaca gcctctgaat cgccagaggc ttccggtgca tactctgagg  12180
cgcaggtggg actcgggagt gagaggtttc ggcgaatgaa ttgggattgc ctacttcttc  12240
ccagtgcagt ggagcttggt tctgtggtca ggtccttacg ccctgtctgc ctttctcgtt  12300
tctttatttc tcgggtagta gttgtggaat caaatgacct ggggtttgat acctactcta  12360
ccacgcctct ggggagtcca ctcagactcg ttgaacctaa gttccggggc tgccaagtga  12420
ggataagtag taattgctga tccacctact tgacaagata gtagtgaggg ccctgagcgc  12480
caggctgtgg atccagcctt tcccacggtt cctggtgtgg caggaagaac tctaggcctg  12540
aaggtgaaat tggggaggga gtcccagctc tgccactgtc tctctgggtg acctcaggca  12600
ggtctcctca aaaaaataag atactttata aagctcagtt tcctcttcag taaaatgagg  12660
attccaggta actcacagat agtttgtggg gatgaatctg ttccttaaag cctgcagtac  12720
atcaataacc cagtcttcct gcttgctttc ccccctctcc actaccagtg atcatagtct  12780
gatcccatag gtgatatccc agctcaaaac cctacattag cttctgtggc tgtttaaggc  12840
ctgcccagaa ctcccctggt cttagcactg aaagcacgtg tccggggaag ccctgcattg  12900
gtcgttcata ctactgagtc ccgcagggca aaccgtccgg tcccaccctc ctttctagtg  12960
ctgctgtcac actcacctcc cttcacccta cactcccttc tgtgccttgc aattacctag  13020
ggagtttttt acaagatatg gatgccctgg ccctgccact agagattctg atttaattgc  13080
ttggggtagg gcctggcata ggtatctttt aaagctccgc agtggttcta aagcacagcc  13140
acagatggga accactgatc tattcttgta ggtccccaga tacctcatgt gctgttccct  13200
gtgcctgagc tgacctttcc cccactttcc tctcctcggc taattcctgc ttatcctcct  13260
actcaggagg ctcttcctcc aggcagcctt ccctgatccc tccaggaaga cttagctgcg  13320
```

```
tccctccgct gggcttcccc aatacactgg gcttgctttc attagaacct gatccttcca  13380
cattatggtt gttggtttgc tccaatcctc tccctcatta gctctcaact ttctttcagg  13440
aagagatgtt tatctttcct tcttgtattc ctagagtcga ccaggctctg gcacattgca  13500
gattctcagt atgcattcag ggaacaactt aatcaagaca agaccatctg acttcttgtg  13560
agttacatgc taagaaagaa atgtcgacac caatagccct cacaatgata ggaacaggag  13620
gttaaagaaa aggaaataga tgcaaatagc aatataagtg ctttaacaaa tctatacagg  13680
aggacaacca tcatattcaa attttcaaac attcttagtt ctgctctttt gtgggtaatg  13740
gttttttttt ttcctcttcc aggagaagaa aagaggcata ttatagaaat tcctcctccc  13800
ccagcattac ttgtcacaga attgtaattg gaagtgattt ccctgactaa gttattttgg  13860
ctgtctgtta ttttctctct tcctccttgc tcttccctca gctggccatc ctgtgtgttt  13920
ggagagagcc agaaaggttc aaggctagga atgtttctct ctctctttaa agctctttaa  13980
tcgtcaggct ttctgatctt caaagcaggc tgtagccagt gtgaccccac tccctcgcct  14040
ccccatgctg gagagtaaaa gcctggagta tttttgtcat tttgaagact tgcatatttg  14100
gacagccttg gacatctgga aagtgtggtc ctcactagct ctgcagggat aagagcacgt  14160
cagcacttcc aagctctctg gcgcccctac atctggacac gttgaaaaat taacaccaga  14220
ctctggagtt aagcaaacat taagtttata ggcctccttg catttgacca tttcctggga  14280
cagcagccct tatcctgtga ctttctgtgt gtagagttga gtctttgcag ttggtcctcc  14340
tcacactctc tcaactttgt gactctctgc ag                                14372

SEQ ID NO: 18          moltype = RNA  length = 358
FEATURE                Location/Qualifiers
source                 1..358
                       mol_type = other RNA
                       organism = Homo sapiens
SEQUENCE: 18
gtgatgtttc aggaagggct cgctgcattt ctccaaagtc agtgggaaat tacatttggt  60
agagagaaag ggattgagac tggactcata aatcaataaa attaagttaa ataagaaaaa  120
ataagatatt ttataaagct caacaaagag tccttgaatg aaagcaatta cagagtcaca  180
ttgtggctaa tattcaaaac tgagatttaa actgaggact aggaaataga attggatcct  240
tttgaagcgt ttaggagaaa gattttaaga gaatgagttc cgagtcaccc tgtggtcggg  300
aggtgtgagt gagctatcca agcccgttcc catcctttgt ccctctgtgt cttctcag    358

SEQ ID NO: 19          moltype = RNA  length = 1817
FEATURE                Location/Qualifiers
source                 1..1817
                       mol_type = other RNA
                       organism = Homo sapiens
SEQUENCE: 19
gtgagtctga agttcgcgat cctcctccat gacacgctaa tgggggtgct ggagtgggct  60
ggggtgggct gggggtgccc tcaaggcttc catgtcttta gagagagccc cagggaccag  120
agccaaattg gagagcatgg agctctgact gaggaacctg cttctcccaa gctccaggca  180
ggcacagatg agtcagtgca gtggtgggaa agggaaaaga gttgatgttg tagctggaaa  240
agggaagggg aaaattaaag caaggaaagt gaggctgggg gaggggacaa attccccact  300
atgtagtatg tttggtatgt ggaagggttc tggtcagaat gtttgcccaa tgattgccac  360
atcagcattc attttggact ctgtatggcc agtaggtctg gttcctggga gccctggaat  420
aatgcagccc cttccctaac taacatttcc atgatgtatg ctcaatgaca aggcagagga  480
atgtgttgga tgagctcagg acctgcctcc ctggacactc ccatcccagg cctgtatatc  540
tgttgaccag gaataagcca agcaagcagc ctactgtttg actgaatatg gatttggggg  600
gtggtagaga aagggccggg gtggagggtt gggaggctca tttgtcatta tagatggggt  660
cagacacact accaaaacag cagcagagat ctacaattga gttcacctaa aactcagtgt  720
ggacacagga aaccctcttt taataactgt ccaatgggtt ttccagcctc agctctacag  780
aaaacttgag ataacagtgg ccagtctgca gttagtttgg gttcggacaa taggcagagc  840
tgggaaatgg agccaggggc gaaagcccag gtccacttta ggatcaggac gggagtggct  900
ggtggggaag tgaggtgggt gtggggaggc aatagggagc tgggtcattt ggtatgggag  960
agtcctctgg tggctagtcc cagaagtgca tgctttacga acatatgctt ctctccctag  1020
ggccaccttg agtgaaaccc tcccatgctg gaattgggcc ctttcagtga caacacacaa  1080
cagttttcaa tagataataa tcccaagggc tttactagca catgaaacac agggaaaacg  1140
tgtaaagttc acaagaaagt cgttccagtg tatcaaatct atcctgtttg ccaggtggat  1200
ataccagggt ctcctccacc tgtgcatggc tggtggtggg tccagtggct gttggataac  1260
tgatgtattg atggatcatt cgccttctga aagtgccaaa ctgattagtt attttgtgtg  1320
tctttttgtg taactagggt ttgaccttcc agggcagact gtgctggggc ggctgacccc  1380
ttggggagcc aagttattgc tcttaccacc accacttgcc cttgtcagtc ctccaccctc  1440
ttgggtttca gtgtcagcat gtagctgtct actcagatcc catccacatc atcaagtctg  1500
cagtttttc cttgcaaggc cttacaggga agatctttga catagaggat ataattttat  1560
tgacacattt tacttgcaga gcattcaccc gggctaacca gaaagccagc actctgctat  1620
aaacaaaaaa taatgcttca gggctaacat ggaatgtgtt aaaagattcc agcccattaa  1680
atgtccaggg gaggttttcc tgttttcctt tccctccatc tgggctttgt tctcaacaca  1740
ttcattcaac aaacatttat tctgcctcta ccaggtacag agcactctac tattctgctt  1800
ctctcctttt gctttag                                                 1817

SEQ ID NO: 20          moltype = RNA  length = 3714
FEATURE                Location/Qualifiers
source                 1..3714
                       mol_type = other RNA
                       organism = Homo sapiens
SEQUENCE: 20
gtaagccaaa tggagaaggc ccagaaaatc ttgaatactt tggttccttt cccctttcct  60
cctgttcatg tgcctggatt agtcatgtgg ccaccaagga gagcgtgaca tctagcttcc  120
cagcccttcc ttttagccaa cgtgggagac actcaaagag acgaaatctc ctgaaggagc  180
```

```
cactgtatca cagcatcctc ccatctccca cttcctgccc aggggtccat ggtccacaca  240
gacttcccag tcccattccg tgaccatctg gagaagctgc tattagcaga gccctgcaca  300
gggtgatagt gtaattaaag tggtcttctc tttccaaaca cagaaaaaat cagttcaggg  360
agtgttttcc tgggcttaca attttaacta ctggctagag ttgaaatggg gaaagccttt  420
tgccttttca gtagcagtag gggaggagat ctggattatt tacttatcat catcatggtc  480
acctcctaca tggcttcacc aaaaaacatt ctgctgcctg aaaaagctcc aacacctctc  540
tctcttttaa aggatggaat ttggagtcca tccttcctca gtgataagga gtttttatag  600
ccacaggcag catctattgg tctgtcctct gcaaacttgc aactcctctg agagctagac  660
ttggaaatga aacattattt tgcaatgcgc tgctatcctt catttttagc tcctccaccg  720
tagatgatag tttgtacttg ttaaatgata aggatataaa tttaggtcat tttttatatt  780
ttattgggtg gaatttggta taatttttag acttcaggct ttacaggctc ctgagatgga  840
ctgattgagc ttgttctact tcttccccat catgatagga agtgctgtac cacactaggc  900
agtgtgtgta gtgaccacag actggctgag tgtctcccat cccatgctgg cccatatctg  960
gtacccacct gatccacaaa tgttccatca gatcctgttc aaacaacaca tctccagtta  1020
agccaaatct tgccctttct ccttacggta aaatgtacta aatctgaagg ttttgtcttt  1080
ttaatgttgc tccatgatcc agtgatctgt ggccttggtt atgctctgtg ctagagtcct  1140
aacaagacaa atgctaaggt agaggtcatt ctgctcaaac aacctgaccc cacctggatg  1200
tgggcttaca tttgcaaagg gcaccaaagt tctaagagat gaggggagga gctgagcccc  1260
ttgtccttat ctaggtttcc cttgttcttt cccatccctc agtctgcttc ttttcccagt  1320
accaacatgt ttgtgtcctc agaattaaag gagtaaaaat gtgtaaacat ctgactagca  1380
acagccatga gattttgcct ggcttgttga taagcagcat tgagatctgc cctcctaaga  1440
atgggccatt aggtcttcaa agcttttacg atgtgaggta aagaatgttc accaggagtt  1500
tcatgcacaa aagggtttct ctttgtggga actagaacat tgttccagtg atgacggaaa  1560
cagggctttc cataccaaaa cagggttttc ctttgaatga ctctcccacc tttcccttgt  1620
ctcttcctcc cccacctcaac aacacaggaa agaagctgga agcagggaca atgggaaggt  1680
ccctttgtta ctcgagctat tagaaacaaa aagaaaagtg gccatctgag gaagccacag  1740
ctggtgaaac tgtagggtca cagagtgaat tacacctctg gcttaagtca gtgaaaagtc  1800
ctagaagttt gtggtcctag aagtcctaaa agtttatggg actttgtttt gagcaaggat  1860
aagaaattga tttcaggctg ggcgtggtgg ctcacgcctg taaccctaat actttgggag  1920
acagaggcag gtggatcact tcaggtcagg agttccagag cagtctggcc aacatggcga  1980
aaccctgcct ctcctaaaaa tacaaaaatt agccaggtgc ggtggcacat gcctgtagtc  2040
ccggctactc aggagactga gcaaggagaa tcccttgaac ccaggaggtg gaggtctcag  2100
tgagctgata tcatatcact gcactctagc ctgggcaaca gagcaagact ctgtctaaaa  2160
aaataaataa ataaaaaaga aattgatttc attcttctga gaactgcaac aactacctta  2220
aagtgattcc atccaaaacc cacatgttca gccatggact tgcttttatg gagctgcgtg  2280
tgggtgacac acaaaatcag gagctctgag tcctaattta gacttttatt tagatttcct  2340
caaatttggg ttccagttaa gcgtgggtct cttctgtgcc ccgctcccct ttgccatttg  2400
ttttatctgt tcttcagtct gttctgtcag tacccacagg caggagagca gaaaggagaa  2460
atggcagcca cagcagacaa atggcacatt cgttccactc agctctcgca tgcccatcac  2520
agatacagct cattggtctc ttttctatga gaggaagcca gagctccagg gaactactgc  2580
caactgatca gaactcattt aggacatgga cctatttgtt cctttatgtt cctgggaaga  2640
gcacaggatg aattctatgt actcatttac gtgttcagag agtaaagtgc ctcataggat  2700
gcctccagca aaagataacc aagaaggtct aatacctttg acaatctcag tttatcctat  2760
agtgtaattg gatagcagtt cccctagcaa aagttgctag tttggtccta ttttctacat  2820
agccaaagtg attgattcat tggttaatgt gaaagttact gagtactgcc agcaggttct  2880
aggaaatata tttgtgtgat attcatggat ggggaggatc aatccacttc caagtgattt  2940
ggattaatta ctggtatttt cacctgtgtg ggtagcaaac ctcagaaaat caagtataga  3000
tgacggcata ggacaggcca ggccccaggc aaaatgttga agctcctctg gagttccctc  3060
ccatctccct cttttgtttt ccatatacct ggtttatcca gggccctgga gatgctccaa  3120
gaccccctac ccaggtcttc ctcccttgtc ccagctatat ttctccatat taccactctt  3180
ctcaccgagg atttgcttac ttaacacata ataaatacta ttaaaagaga aacttaggca  3240
cattaaaatg ttagagttga ttccagcaaa cagtgattca caggaggctc cagatcacaa  3300
gtggttcagg gccccactga ggggtaggga agcaagacaa agaaaaacaa agcaaatatt  3360
tgattggttc aagtggaaag tccctgatta caggttagtg ggcagtttgt gattagttaa  3420
gtttctctaa gttgggtttt ggtttgctga tgtaggaaca cagaatgctg gggccgtttc  3480
aacctaatgg tctcccaatt aatttttttta acattactga tgactgttag gagtctaatg  3540
tgctactcct cccagggaaa atggcattcc taggattaaa ggaactcagc acatggagtg  3600
tgcgtagaaa tttagacact aactgcaggc tggtgggaga gagcccttta gggcagaatg  3660
agaaggcgtc cggccaaggg caggagttac tgacgcatgg cctcttggtt tcag        3714

SEQ ID NO: 21          moltype = RNA  length = 1285
FEATURE                Location/Qualifiers
source                 1..1285
                       mol_type = other RNA
                       organism = Homo sapiens
SEQUENCE: 21
gtgaggccct tgggctggcc cctgtcctac aacacgtttc cttggaaggg tccgtagcag  60
tcctggaggc ccagcctgcc ctctgagggg gtccactttg cctttgacct aaggttaaaa  120
agttcacgtg aggctaaaat gtacaggggc aaaagtggga gcagtcctca ccccgagcga  180
tgcaacagtg actcctcacc acgcctgctt gattcatctg ccctggaaag tcattaaaaa  240
accagttcaa ctcatgggtc cctttattta ctcacaagag agagccagca gcccatttca  300
ctagttttcc tttcctactc tttgagaaga atcagaaggg agggagcttg ccactttact  360
atctgtctaa agagatgttt ccattaatta aaggtttttg ttttgcttca aaaaaacttg  420
aattggagta tttccacaag tatctttaac atgctctacc aatgtttgca gaaagaagtg  480
cagaaatgag actgtccaca gagtcaggct cgctggccag gagaggactc ccgaagctga  540
cttctgatgg cctgagaaac ttcctagttc acaattccca gacccagaca aagagcactg  600
tcttttctct aattgttttc aaatgggcca tttccaccct ctaatcagcc tctggccctg  660
gagggtgcag ttccccttgt cctccggagt ctccctgtct ctgtgctgta gagtcaagaa  720
gggacaacca cctgccctca ctgggaaaag acagaaagtc tgacttgttc tcacgactca  780
```

```
cacttattag gctccagagg tgtcagggca tctgcctttc atttcttagg ttaaataaga  840
aatcaattgc tgccatttgt agtacccaat tttctaaaat gatcacaatg gataagtggc  900
aagaaatcct tatgactcat ctgtgggcag agttgggcta ttttggtaat ccttgagtag  960
gcagatggaa tttgaggcca tcttcttggg tacatagatc actaggaagc tataggtcta  1020
gcaactgtgg attagggctg ggctgagaat tgtttcatgt tttttgtgac tgtatagcta  1080
gagactctct tgtttgcaga gagacactct gaactccccc tggccgtcaa gggaaagact  1140
gccttcaccc tcctgagctg accttacact gagagacaat ggggaccctc ttttggccct  1200
cccctctacc tcgagggcat ctgggtgctg ttgcattgga taaaaggcac tgctcttttt  1260
ctgtgccctc tccgcctcac tgcag                                        1285

SEQ ID NO: 22          moltype = RNA  length = 3412
FEATURE                Location/Qualifiers
source                 1..3412
                       mol_type = other RNA
                       organism = Homo sapiens
SEQUENCE: 22
gtaagcatcc tcctctatag ggtaaaggta attgagttct tcagatcccc agccctctcc  60
attcatctag tttaaatttc atttcttcca agctctttgt cagaaccagc atttgaagtt  120
taaatctaga agttaaaaat ccaccagcaa atcctactgg ctctacttga gaaacaaatc  180
cagaatctga tctcttgtca ccacctccac cacaaccttc ccaatgccag tctcttcctt  240
ccactaccac ctcccatcag tccattctgc acactgtatt cagggagatc ctttcagaat  300
caaggtcatg tggtgtcagc cctctctgtc aaatgcttgc actggctttt cctctctttc  360
agagtaaaac ccagtgtctc aaccctggcc tccaagctgc ttcattatcc ggcctccaac  420
tctcttcttc atcttacgat tttccctact cctccatgtt cctctgctcc agccacgtcg  480
gcctccttac tgactgttta atacaccgag cgcatttcct cttcagggcc tttccacctg  540
ctgttctcat gccagaagca catttctctc cccacaacct gcaacccgcc cctcatatct  600
gcaggcttgc ttccttactt tgttaaggtc tctgttcaaa tgtcccatta tcacagggat  660
ctttccagac tgaagagatc tacataacta tggctctgta aacaacattc ctccagggtt  720
cctgtcccct taccctactt tattttgggg aacattcttc accatctgat acaatgatgt  780
atcttatgca tgtatttact gactctctgc ccttagtaga atatgagccc agagagcatg  840
catgtggtct attttgttaa ctgtgacagt cccagtgccc agaatagtgc ctgacctttg  900
gtgggcactg aataaatatc taagtaatct gtagcatgga aaatcagctt ctgaaaattg  960
gctgtttgca cggtcgtgta tttgcttggt agaaaatcaa attttccttc aaattagcat  1020
tttctggtaa ctagagctgc cccatcttcc tctgagtggt ctccaagtca gccaatagcc  1080
ttgtgctgtg gcagccatgc ctggctcttg atgctgtagc caaaagcagg caggggatgg  1140
tgaggctggt ccagtccatg gggagggaca aactcacagc tctcagatca tctcagggca  1200
gcctttgttg gcagaaatag gtaggcagcc accctgaata ggaggaaggc ttctagactg  1260
ggtcaggagg cctgggtttg catcctagtg gcaagcgtgc attcatttac tagggctgcc  1320
ataacaaaat accactaact gggcagctta gacaacagcc atttatatct cacagctctg  1380
aaggctggaa gtccaaaatc aaggtgttgg cagggccatg ctccctctga aacctgtagg  1440
tgcttgggca ctccttgact tgtagatgct tcctgctgat ccttcgtctg cacatggcat  1500
tctgcctgtc ttacatggcc atcttataag gataccaact ggattggatt aggtgcctac  1560
cttgctccca tgtgacctca tctcaactaa tcacatctgc aatgaccctg ttcctaaaca  1620
aggccacatt atgaggtacc tggggttagc actctggtat ctttttttctt gacagcactt  1680
ctgacaccaa atgtgtgttt tggttttttg ttgttgttgt tttggcacca accaattctc  1740
ctatattaat gggttgtcca agaattcaat tgaattctga cactatccag aattcacaca  1800
gactccacgg gttcagtccc acaaggcttc cccgtcttca gatgccagct ggaaatgtgg  1860
tgcccaggct acccacactt ttgccaaaat cctgtactta caatcacagc tttaaaatga  1920
aggatgcagc tcaggaactg ccacatggaa gagaagcaca gtatggggtc gggggaagag  1980
tttctatgct ctctctagac gcaccactct cccagcacct caaagtgttc agcaacccaa  2040
aagctctcca aatcttgttg ttcgagagtt tttataaccc tatctccagc tccatactcc  2100
cccattggag gttgagggtt gggactgaaa gttccattct tcacatgtgt ggtgtttctg  2160
gtgaccagtc cccagaaact gcagctatct tggggctcta ccctgagtca catcattagc  2220
ataaactcag atgtggtaga ggaaggggct tattatgaat aaaaaaagac actcctttct  2280
gccaggaaat tccaagggtt ttaggagatc tgtgccctgc acaggagctg gggacaaaga  2340
ccaagtatat tttgtgttat gccacagacc ccaacatgtc tttttggagg gagaccaaat  2400
tcaacccatg acagtgactt tgaacaagac atttgaactt agtctgtttt ttctatccta  2460
ctagattgtt ggaaacagat ataatagatg aaaattagtt gattaaaatt gaaatttgtg  2520
cataattcaa aagttttatt ttagccaagc taaagctttc atttattcaa cagctattta  2580
ctgagcagca cctgtgcatg aggctcagca gggccaggtt ctgggaacag agcggtggag  2640
ataaagatcc agacctgccc cgaggaatag acagtccagt ggcagcaaag gccatgaaac  2700
atacggcaac tcttaaaaaa agccgagacc atgattttac aaaatcaaca ttttgtaggg  2760
agcagaactt tcaaagagaa ctggactaga aatttgggag tctttttctt ggaaccctgg  2820
tagatccagt agaatgaggg atgggggtgt agggttaaaa acactgacat tagaactgga  2880
ttacctgtgt tggaattcct acatttctgt ttcactatct gtgacggggg gcagatggct  2940
gaatctcagt gtgcctctgt ttcctttctc acaagaataa tattactacc tatctcctgg  3000
ggttgttttg aggtttagat tatttaacac atggaaagca ctcacagcaa tgcctgccac  3060
agaaagaata tccagtacat cttagtgatg atcaccatta ttattatctg actcctggaa  3120
aaggacttga tttaattctc tcatgaaacg ttttcttgga aaactgatgt caaccaagat  3180
tattggtctt gctgttgctt ataacacccc aaaaacatga ctgtgtggat aaaaatatgt  3240
tggaaggggt agtctttctg ggagcctgag aatagccatg taataataac tgcaaatatc  3300
tatagttaca atttgaggtt caggtaaata aactctagat cttatagaac tgcggtaagg  3360
taggataggg agactccttc gactttctct gtttatttgt ctctattttt ag          3412

SEQ ID NO: 23          moltype = RNA  length = 2675
FEATURE                Location/Qualifiers
source                 1..2675
                       mol_type = other RNA
                       organism = Homo sapiens
```

SEQUENCE: 23
gtgagtcctt taaaacacaa atcttaatgt ttgaaatcaa ctccttgggc tctgtgcaag 60
atgtatatgg atcacagagg tggccctcta tgtaaacggt gtgattcctg atgagtcagc 120
tgcctcctgg ggctctgccc cttgatgggc attgcagcgt ctgggggacc acctttcaca 180
agttgctggg ccctgtgtga tcatgaatgg ctgatcatgg atgaagccct gggtcctgta 240
caccttgtcc agtagactaa attgccctat ttaaaaaagg ccaagccact tcagggttca 300
aagaactttt gcagcttttc agtataaagc agaaatccag ggaatcatga aggaaccttt 360
gcattcatct cccattgcct tccttgtgcc tttttattct tctctgcctt ttcaaaatat 420
aaattagttt attctcccaa gatgaagact cctcctgggg ctgaggcaga gctgttatct 480
tcagggcaat acctcagatt ctcctggtgt tgatctttct taggggtggg gaaaaaggct 540
gaaagggcat ttgcccacaa cacatcttag gtaaaaggca cctttactac tgaaccaaac 600
aggaggccta gctagagaaa gttctagaag cagggaaaag cacagactct tttgtgaggt 660
ctgagaaagc aaagaaattc cagggtgaaa gcgggggact cccctagagc tgaagtactc 720
tcccatctgt ttgttgctca cctacctatt ctttactttg tattattggg cctgggccag 780
gacttatcct gcaagcactg agatggatgt ttgttttctc tgggggatta gtcttttttt 840
ttcttttttt cttttgtttt ttgcttttgt tttcactggg tcaaacaaac aacactttaa 900
cagctcagga ttttttcatt gtattgactt gtctacctgt aaacttgtta atttttttact 960
ataataaaat tatcatataa taaatgaaaa atttcaacac agggcttgtg ggcattttat 1020
ttttctctac aatcccaaca gatactctgc ctcttaagaa aaaaagaaat cataaggaaa 1080
atatgctcct tcaaaagtga atcacaaata tgtttgccaa cggaaggcaa atatttttca 1140
cctgtctcat aggctggact gaaatggatt tctaaaactc tctaaaacca gaaaagagct 1200
gagtgtctcc acccaacctc cctcctttca cagattaaaa aataaaaaat ggagcccagg 1260
agacatccag tatcttcccc tattggtcac ctgggacaaa atctggaaca tgcacatgca 1320
ttgcctggca ggaactcatt ccagtgatta aactcttcag gaggatgttt cctcttgcta 1380
tttcattacc tatttgtgca gtttgatagc tagtaaagtg atcaaaggaa ctgtggggca 1440
tagattcaaa agtccttcag gaagcagaaa tagaagaaca gtactagagg cagcaggtcc 1500
ctgaccagca ggcccactac ctgctgctcc agcacacatc ctgcacattt tcagagggtg 1560
ggggacagag gggccctggg tggctgttgc attgagaaat ctcgccctgc tcctgtatgt 1620
gcacttgagg ccgagagccc ttggatgcct ggtgacagtg gtttcctcct gcccctgcct 1680
tcctctctgg cagactgact ggcccttctg ctcctcttcc ccttccagga tgtcctgata 1740
tctttttaaa ccaaatgcca agtttgccaa aaagtgtctg tttgtgtgtg tgtgtgtgtg 1800
tgtgttcaat gcgtgtgttt ataccacact tcacaatttg tccaggcttg tattaatacc 1860
atcaccaggc tcaaccctgg tgttaattcc aagatactta aatgcccatc taggtgaatt 1920
tctcaggtaa accatatatt caagctgtag tttaagctgg ctgcccgtca tagcactttg 1980
aatagacttt gtttttgttt ttgtttttttg agacagagtc tcactctgtc ggccaggctg 2040
gagtgcagtg gcactatctc ggctcactgc aacctccgcc tcccgggttc aagcgattct 2100
cctgcctcag cctcctaagt agctgggatt acaggtgagc gccaccccac ccggctaatt 2160
tttgtatttt tagtagatac ggggtttcac catgttggtc agactggtct cgaactcctg 2220
acctcatgat acgcctacat tggcctccca aagtgctggg attacaggcg tgagccacca 2280
catccggccc ctgaatagac ttttactcaa ggttcaccat gactttcaca tgttttgtat 2340
tggagtaaaa tgtgccagtg gtgggctaaa gaaaattaac tcatttcaaa ttcaaacctg 2400
gttttcttaa tttttttaaa atcacagttt ctgaaactgt gggctcctca tggcacattg 2460
agaggaggag gtgaaactct ccaagtctga agctcctgtt ataaatcttc ctctggcaaa 2520
gattgtgtga tcaggcttga gtacctcaca gtcctagagc aggtcaaagg ctggctagga 2580
aactcatttg ctccctgtac ctctcccctc ctttcctgcc tttgctcgtt ctcagctccc 2640
ggtggtagag taacactggc ttctgattgg tgcag 2675

SEQ ID NO: 24 moltype = RNA length = 1774
FEATURE Location/Qualifiers
source 1..1774
mol_type = other RNA
organism = Homo sapiens
SEQUENCE: 24
gtaaaacccc gataaagaat acacagcaga ggcgaggaaa aggctctaag cactgcagag 60
ggccagagca aaacatctca tggcaagggt ggaaagaagc ctaggaaact gactctctct 120
gtggacaagt gttaaaccag atcccttctc agaggtccat ctgcatgtgt gtggaatgaa 180
tggttcagcc cagacattag cgcatatttc ctggagaaag caaataccaa ctatgtagtg 240
tgcctgtgcc cttgttaggc aaatcccaag tgagttgcac aaatgtgctg acttccgagg 300
atttagcaag aacaataact ttggtcactg ggacttaaag cggatatgag ctataaggaa 360
agacaaaaat aaatgcttct gtgtccaggg ggaaagagac tccaggggag ctgactacac 420
ttcacttacg gcttacaaat ctagaaggcc attcattgaa accatcagaa gcctttcctg 480
acagtggaag ttacctaata atccctaaac tgacgaccca gatttacaag ttttgttttc 540
ctggcttttg ctgccctcat cttctctctt aaactagttc tgtatttctc ccaaggcttt 600
tcattcccta agcatacgca tttctctgtg gccaaaatgc tctgggttta gacaggcagc 660
acagcccctg ggctctgcct gacagggcag gagagggtct ggcctttatc cctccagccc 720
accccagggg ccatttcata aaactaaagc cagagacctg cagcccctcc cagagttaga 780
ctgcagtaca ccatgcctct ggcaagatcc tcctcccaca gtggaaagtc taagccaaat 840
caggaggctg gggactggtt ccacctcagt tgcaggcaag gccaggaggc acggatagaa 900
gaaacagtgg actttttccc cctagggaaa gaaatgctta gagctacagt attaagatga 960
caaattaagc tgtgccatat agggtgaaat gaagcaggga tagatgggag gtcagggaga 1020
agtgagagca ctcggtgagg gtctgcactg gagggggcat gggaggaaga aggaggggag 1080
tggggtttga gggatggtga tgaggaagcg tggactgccc tacccaccta ttggaaaacc 1140
tgggagttct gaggagcaag aagccttagt caaagtcaac tcaaagattc aagccaaggt 1200
gactaagaga atggcggtcc agaaaaggtc atgggagaat ctgaaggcag atgttgtttt 1260
gggaagatga agaacctaag ccgcttccag aaattcatga ggaaatgccc cgtggactgt 1320
tggcaatgag ggcctaggac caaggttgag cttggggcca actctcccta tagacagtga 1380
gtgcattctg acaagcatgg gctctgggtt caaatcccaa ctctgccact catgcctatg 1440
tgtccttaat aggacgcttg atgtctctgt gtctaaggtt tcctggacta tggaaatgag 1500
cctaataaat gtctacccct taggaccatt gtaagagtac attgaggtaa tttgtgtaaa 1560

```
gcagtcgaag cagtgcctgg catataggag gtgctgtata aacgtttgat gctagtatta  1620
ctattattat tctggagtct tccttgcaac ggtgatagcc gaagccacag gggcaggtga  1680
cgttataggc agaatacaag ggcctggaga cagagccctg gggccatgta attaggcatt  1740
atgtttacat catgttcatt ttttttcctc caag                              1774

SEQ ID NO: 25          moltype = RNA  length = 2174
FEATURE                Location/Qualifiers
source                 1..2174
                       mol_type = other RNA
                       organism = Homo sapiens
SEQUENCE: 25
gtgagtcttc cagcagagaa gctggctgcc atgctagcct gtcatttcct ggcttagtct  60
ttccctatca gcggctgtct actctttccc acaaatttta gtgacaaata tttgcggccc  120
caaaaatgtg taaaagcttt ctgcagtatt caaagatcac taatatgtat tctcttgatg  180
gggaggtaga atacgtttat tgcccctttt gtgtgccggg gaagtggaca ttcattcaga  240
gagttgaagt gactttcctg aagccaccaa gttgtcatgg ctcagcgggg gcaaaagcca  300
ggcaccacag ttgcctcttg tttctcacac cttgagtctt tccccccatc tcaacagtcc  360
atggtggtga tcaagtcatg gccactgtca tcatgtgcat ggaagctata gagtcctcct  420
atttcctttc tcttttcttt tcttttttttt ttttttttt tttgagatag taaccattac  480
ccatgctgga gggcagtggt gcgatcttgg ctcactgcaa cctccgcctc ccaggatcaa  540
gcgattctcc cacctcagcc tcccaagtag gtgggactac aggtgcatac caccatgccc  600
agctaatttt tgtatttttt tttttttttt tttttttag tacagacagg gtttcaccat  660
gttggccagg ctggtctcga actcctgacc tcaggtgatc tgcccgcctc agcttcccaa  720
agtgctggga ttacaggcgt gagcgaccgc accaggccga gtcctgctat tttcaaggaa  780
cattcctttt cctaccaatc attaggcagg cttcaacatc agctgatgag ggttagtggt  840
cgttctggag aaagtgaaaa aagaatcagt ctctagaggg gcttgtggag taaccgcctg  900
gtaacagaag gtcagggcag ggaaggcaaa ggggctctgc gcggatctct cagctccgca  960
ggcgccccac tctcctccaa gggacccgag cgccatctgc tgagaggaga acacggcccg  1020
ccatggtttc ccaaggagca gcagacacgg acctcgcagg gggcagcgaa cccacgtgac  1080
acagtcttca agtcctttgg agagccccag gaaggaacaa cagcgtgtac accctgtgat  1140
ggaatgttct ctagggcggt tcagtgtgaa tggaatgtgg ggccggtgcc attctaattg  1200
gttctgtttc cctctagtgg ttgatcgcgg agatttcggc ttctccatca ggacaagttc  1260
agatagcctg agatggtatc agaactcagg gacagagctg ggtgtggcgg ccctgcatcc  1320
atctgctttc tctccatgct aactgatatg gtcagagagc tggaagcaaa ttccaggacc  1380
ccagggctcc gcaaaggcaa acacattact tcatcggctg ctgacatgca acttccccca  1440
ggggttaaaa caatgtttaa tactaacagt aataatattt ttgagtttta ctttatgctg  1500
gcgctgttct aatgttgtaa gtgtattaac tcatttaagc cttacaacaa cctaaggaca  1560
tgggagtcat agttcccatt taaaaaaaaa aaaaaaaaaa gcccaccatt gctctgaggc  1620
tttttatgtt ttggatccaa agctaatatt ggtggtggta attcccatgc ctggcttcga  1680
tcaattaatc agcaaatgcc taggactgct tagggttctg gccttcatca agaccttacc  1740
cgggctttat gatgatgaca cctggctttt caatagccat gactgctcac ccaggaggca  1800
acgcctcgag tcatgcaccg aacacctttt attgatcctc tccaacacca ggctccgtga  1860
tggctgagct ggggacacct gtgactgcac gtgaacattt tgaggctggg aatcccaaag  1920
gccctcggcg ttggcctggg agcaccatga aacaagtaga agcagagaag gatggcagag  1980
gtggccctct gcattagggc ctggatgtat acactggtgc taagggggcc ccacagctaa  2040
taggggtttg agtttgactg acagccccag gcaggaatct gtgagagttc tcactgaacc  2100
tggtgtgggg gtggccctcc taaggcatgt tgctaaaggc catctcttct gccactgacg  2160
cctgtgttct gcag                                                    2174

SEQ ID NO: 26          moltype = RNA  length = 1137
FEATURE                Location/Qualifiers
source                 1..1137
                       mol_type = other RNA
                       organism = Homo sapiens
SEQUENCE: 26
gtaagcgaca caggaactga gaccgcccca tcccctctcc tcacctctgc ccccagcaca  60
cttctctaga gcccagctca ggggtgccag gcctgggcac aggcagagat acagactctt  120
atttggtttc ccctatgttt aaagtccttt gtcctacttg cagtgagaat tgtccctgag  180
aatatgggac tctgcctctg ctgctcagag ctgagggctc ctccctcaga agggtgaggc  240
tgccttcgct ctgacagagc agctgatcga tccccgagcc ccttgtgcag ccctgaagta  300
cttcctctct gggaccaaag acaggagaac cattgttcct ttttcctgtt gaagccacgg  360
cctgaaaggc aaactttca gggggctttt cagttacttt ttttccccaa taagatatct  420
tttatttctt atctaagaag ctacgcatag tcattgtgaa agaaaaaaaa ggaagggagg  480
aaggaaggga ggaaggaagg aaggaaggaa ggaaggaaag aagggaggga gggaggggag  540
aaggaagcga gggagggagg gaggggagaa ggaagggaac aggagggagg aaaagggaag  600
gggaaggagg aaggaaaggg aaggagggag gaagtaaata taggtaaaca aaaaattgaa  660
aataaaagtc acctgtaatt tcactactca gagataaccg ctgagttata acattggtat  720
ataatttttt agaactttct cctatacatg tatagataga taaacacata tacttcaaaa  780
tgataaagaa tagtaaaact atgcatacaa ttttataacc tgactttttt ttcaaaaaaa  840
aggattgctt ttttaaacat aagatatcag gaacatcttt catgtcatta catattcttc  900
tataaaataa tatttaatgt ttacagatta ttccattgta tgcatgaact atgtaagcca  960
tcctcttatt agatatttaa gcagggtctg ctatttttgt attgtatcat aaacaccacc  1020
acagtgagca tcttgattgc caaatcaaga atacttgtcc tcaattattt ctgtaagatc  1080
agctgctgga agtggaagtg ctaagccact gcttttctcg ttgtcccatc ctcctag     1137

SEQ ID NO: 27          moltype = RNA  length = 437
FEATURE                Location/Qualifiers
source                 1..437
                       mol_type = other RNA
```

```
                        organism = Homo sapiens
SEQUENCE: 27
gtgctcagag ctggatggag acagggccac agatggcaaa tccatggctc cccagtgcac  60
ccaggaggca ggggaggctt ggagcaggag agcttctaag ggtgggaaca cctctgtgaa  120
gttacaccaa aaatctaaga gcagccccca gatcattttc cctgcagagc actgtctcac  180
agcagcctgg gttttatttg tcctgagatt gatgtgcttg aacagtcttc aaagggtctg  240
atccgaggag gtgagggttg ccctttctgc atttacaaag cctgaacagt attagggctt  300
tgaacgctat aaacatctaa gaggcagcac caaaccactg ctgggttaag gtaccccccac  360
aatgccactt gccctgggcc tttctcttcc tcaccctcca cagcccctta actctcccgt  420
ccttcttgtg cctccag                                                 437

SEQ ID NO: 28           moltype = RNA  length = 1358
FEATURE                 Location/Qualifiers
source                  1..1358
                        mol_type = other RNA
                        organism = Homo sapiens
SEQUENCE: 28
gtaacagctg ctgctcagtc tcctgggctg ggctctcact gcagccctag ctgtggtccc  60
cactctctca cctgccattt tgtagctgag tacaggaacc acaatgacta cactcagaag  120
ggggtttatc agtgacttgg tgaatctaag ttccagctaa agcctcctga ggtttttaca  180
aatataaaca gagaatcact gatgatgcaa cctacttccc aaaatatttt agaaaattct  240
cttgacctgc agcccttctg tctggaataa tggatgctac tctaggtgaa tgtcttctct  300
gaccatgggg acccaggtca cctgcaaaca tacctagaag ctccatagct gtcagatgac  360
cactcaggac cagtgtgagg gtgacctgct gggcattcag tgctccagag ggtggccaca  420
gatggaagtg gctcctctgt catggcacct ctcagacaag ggctcagat cagaagagac  480
agcaagcaga gctgagtgcc catagaggta acagcacggt tcaaccccgt ggtcaagcca  540
gagctttccc ccttgctcta ctcacacagc gttgccccgt gcctttctct gagggtttgt  600
catcctgaaa tcctcattgc tattttcttt ctttcttttc ttttttttt ttttttttt  660
ttgagacaga atctcgctct gtcgcgcagg ctggagtgca gtggcgcaat ctccactcac  720
tgcaagctcc gcctcctggg ttcgagccat tctcctgcct cagcctcctg agtagctggg  780
actacaggtg cccgccacca cgcctagcta attgtttttg tatttttagt agagacgggg  840
tttcaccgtg ttagccagga tggtctcgat ctcccgacct caggtgatcc tcccgccttg  900
tcctcccaaa gtgctgggat tacaggcatg agccaccgtg cccggcctgc tgtttctgt  960
taatgacatc tccagttagt gagagtatgc acgtgtgtgt tctttatgaa gagtataaat  1020
ccagagctta atgatccaga aaatgtacat atgaaactcc ctagatgctg accataatac  1080
atgagcccct aatatagaga tttatttgaa tcagatccta tgctggatac agagacactg  1140
tgtgtggcaa tgctttacag tatgtaggaa gctatgaaat gttagttatt attgtcctaa  1200
tatgctggaa tttgctgctg aattagttcc cttgggtttt tttttttagt taactcctga  1260
tttttgcaac tatatagcca ggaaattgct gtacaccctt taccaacaat gcccaaccca  1320
gggcaggcct ggtgattgcc ctggccccta ccttgcag                           1358

SEQ ID NO: 29           moltype = RNA  length = 1081
FEATURE                 Location/Qualifiers
source                  1..1081
                        mol_type = other RNA
                        organism = Homo sapiens
SEQUENCE: 29
gtaggtgtct gcccagggaa ggaccctggc ctgggtgaga aggagcacac agcacggggc  60
tgccactcca gacatggcta ctcacacagg ctctcgccac cagaatcagt gtctttgttc  120
tgggaccatt tgcagaagat ttcgatgaac acattctgaa gcctcctcct acagagatgc  180
tttagccaaa atgaaacaac tagctttaaa tggtctgcaa gtattacatg ccagattaca  240
caccagtttg gtgcggtttg gtgcaacata gaagtgagtg tcttattctg taaggttagg  300
ctgttttaag agcaattggt tgagcttcat ttcaacatta atattcccta attaaacctg  360
aatttcagtg gtaagtgaaa actaagaaga ggcctccttg ggtgctataa cataaaaatg  420
atgaaggcaa aaagtaccaa ccagcagaga ccacttcagc acatcaggag acccagtttt  480
atgtctgtgc tgcgaagtga acaaactgtg tcatcctagg caaattattt aattcctcct  540
ttttttagt atttttttct tcttcacatg gaacatgaag ctaatgacct ctgcttctat  600
ttcttaggga tgtgaagata agtgagataa agtattataa atgtgctctg ggcttcttaa  660
gaacaggcat tgctcacatt caaatggtca tgattatgat atggcagcat tatttatgcc  720
tctggtttaa gtgtctggct gccgctgggg tttcctatgt ccatccacgg ggagggaggc  780
acagaatgtc tcccacaggc agaacctaca gctgccacat aattgatgac aagccaaagg  840
gacccttgga ggttctgctc ctctctgtgt gtgactcaca cactctctag gataaaatca  900
agcgactaca ccctcaaaat gctcagatga attaacagat taaacagtga agaaaaaaat  960
gtgttgacta cacttggcag tgagaaataa ataaagcggg cggtgacagc agctggcatc  1020
agggagaggc tgtcatggaa gggatgtgca tcttgtcagt catcccatcc atctgttgca  1080
g                                                                  1081

SEQ ID NO: 30           moltype = RNA  length = 2692
FEATURE                 Location/Qualifiers
source                  1..2692
                        mol_type = other RNA
                        organism = Homo sapiens
SEQUENCE: 30
gtaaggactg gacgggccat acttgggttc cgtctggcag ccatctccca gtattgctgg  60
gtgtgtcctg ttgtgatgca ttttaatggg agcaaagaga acactgggta cttctgcagg  120
tcacacagtt gttcttttgc tttgagcttc tttctcctct tccttcttcc ttcattccca  180
aagggatttt aaaagtcatg cacctaaagg ccctctccct ttaatgagga atacactctg  240
tgctcttacc cttagtaagc catcattcct ggggtccccc tgccctggct ccaggccaca  300
ttccttagtg tctggggaga gcttcttcta catgtgtgcc gtggcgccct ctagtggaag  360
```

```
catggtgatg cacggctctt ccagtgaatt cgtggagtca gagattgcac atgtggatgg  420
caagtctgga aatagcatac acccctgtta tactcctgat tctcccctca gcttcccaat  480
ttcccagtga ttctcccttt aattaggatg cactgaagct ctcaggggtg cccccatctc  540
caaggagctg cagtggagag gctatcccct ctctatgtga gagaatgtgt gagaagcgta  600
ttcccacaca ggagcaaaac taaacttacg tactgatgca ggttaatgaa tggggaaagt  660
atctgcttat caaagaaaag gcatattttt ctatttagca caaacttttt caaatgttaa  720
gaatttacta actgaaatct ggtgaagcaa gagaaccggg caatatttgc gttgtctgat  780
cattacaact ggagggaaca tgctcagaga ggcatcatca ctgttcatgc acctgccctc  840
tctttacact gagagaccct gtgatgaaca gaaaacatct ttttaggatg acatctctgg  900
gtctttctcc tagcctgcct tgctgtgggt acctatctcc ctgctctctg aaccttggtc  960
aagaagttta tatttgtttt aaattgatac taatatgtta agttactgtg atttgccaaa  1020
atcagattgg aaacagggcc tgcatggctg aatgattctt ttttttaaat tactttattt  1080
ctaaataaag gttttctttg tatagaatcg ggatgctgtg aatggtggga aatgcactaa  1140
atagttatgc cccaaataag aaagggaaaa tcatttgaat ccccagttag ctccttgaaa  1200
gtcttttcac ttaaacacac ccacatacca cacacacact cacagacctc cctcccagat  1260
gcccaaagcc ctgctgacct acagagctac ttctggaaag gctgacacat gcctaagaca  1320
caattcctgg gaatccagca gctttgggtt caatttcctt cctaaaagaa caatgaatat  1380
gacccctgga gagctattag ggcagagctg cttccttaac gtaaaggact ctccagcctc  1440
cgtatgaagt catctcagag ctaaagacaa tcaagtccaa cttgcagatt tgacataaag  1500
caagacttcc aatccggcta ggcagaagga ttttggttga aaaccatgaa atcccttcat  1560
atggatcatt ttttaaacaa caaaaaaaga aaagaaccta ctgggtgtcc acaactctga  1620
gagctgcttt ctgaagagtc atgttttgag tcctggaatc cctctccctt tgacctgcct  1680
ctcaagacaa tgtgcgagag aactctctct tcaagtgcat gcaagtgagg ttttcacagt  1740
tagattttta attttaaagt aatacacatt tgtacataaa attcaattct gactgtatac  1800
atgtgtcaga taaacagttg atacctgaca cttgttcaca gtctatgata cgcaccgcat  1860
atcctaccct ctcccccagc ctctctccat ggcttctcaa cccccccctct gcatttcctg  1920
tgacctgagg attcagtttt gtttgtggag gcaggtgcaa tcccaagaga aactgtgcaa  1980
tcttctgaga agttagagta ggcatgtgtg tgtgatttag ggaaggtact tctcactcag  2040
cttggtcacc ggttccaggt ttgtgtcttg ggcaagtccc ccatagctgg tgacagacca  2100
gaaaaatgaa aacaactttg acttagccct caagttttca gtgaatgaga atgaaaaaca  2160
accatgagta agagatttct taccgagatg atgtaaagga taataatagc agccagcact  2220
cacctatgtg ccaggtattt ctctaactgc tttgtgtagt ttgactcatc cagtcctcaa  2280
aaacaacaat gaagtggata ccagtatttt ccccttttca cagatgagga aagtctaatg  2340
tgacccaccc aacataacat agtttgaggg gacagagcat ttcgttgaac agaggaggaa  2400
ctggcacagg aaagttgcat gacccccccca ccaacctccg cccccaggtt gcacagctag  2460
ctagtcggga ggactttgct tccgtttccc tctgcctctc aatgatgatc tcagggccaa  2520
ctaagctaaa agcagacttg atggagcatc agtcctctga aagagtcact gccgagatac  2580
aaaatacctc ttcttcaaag gggaagtgga gagaagtagg aaatctgggt aacctcacag  2640
tcttccagtt tctggaaaac agagctggca tcagtctttt ttcttgtcct ag          2692

SEQ ID NO: 31           moltype = RNA  length = 356
FEATURE                 Location/Qualifiers
source                  1..356
                        mol_type = other RNA
                        organism = Homo sapiens
SEQUENCE: 31
gtaaagtaga gattccagct ggtttctgtc aagtgccaga agtggcggtt ctttgaaaaa  60
gtctaacatt agagcaaagt tttgtaaaag caaaaagcca tcgttcccca cccaagcata  120
gcaactatct ttatttttgg catagttccc ccatctctgc atgcatacaa attttatgta  180
cttgtggtta ctgtgtgctt acgtttttgt atttatagaa gatgatgttc tcagatagag  240
tcgtaatgga ttttcttccc attatgaagc aatacccaac aaaacagagc ttgggttaga  300
tttttctgag aataagaatg actaaacaaa attctctctt tttttcttct tgacag      356

SEQ ID NO: 32           moltype = RNA  length = 4696
FEATURE                 Location/Qualifiers
source                  1..4696
                        mol_type = other RNA
                        organism = Homo sapiens
SEQUENCE: 32
gtatggtgct ggagccagtg gcttgttccc ttccttgcct ccctcccaag ttccatctcg  60
aaagtctaag gggctgggca cagtggctca tgcctgtaat cccagcaatt tgggaggcca  120
aggcagatgg accacctgag ttcgagacca gcctggccaa catggtgaaa ccccatctgt  180
actaaaaata caaaaattag ctaggtgtgg tggcgcgcac ctgtaattcc agctactcgg  240
gaggctgagg caggagaatc acttgaacct gggaggcaga ggttgcagtg agcagagatt  300
gtgccactgc actgcagcct gagcgacaag agcaaaatcc atctcaaaaa aaaaaaaaag  360
tctaaggaaa aagtcatgaa acaacaaagc aggcaaatac tcctccatag tatctgactc  420
cccagtagta ggcattttgc atcctagatg gctttgagtg acaaaggaat aacagactga  480
gttaggtcta gatggggaca ctttggatga atgaggattc ttacggaggt caggttggta  540
gcttcatccc tcagctcctc atgctgtatc cccagtctct cggcctgcca tgtcatcatc  600
ctcatctcct cctgtcatct ccaccaggcc tctgatccat ctctgtctgc atgagtgaca  660
gctggcagag tccttaatgt ttatcaaata caactcagac gtcagtctcc tggccccttt  720
gagatcaaca taaaatcatt ttgaaccctt atttagtggt ctatgggctt tgaaaacatg  780
gggaccaaaa ttcctgtgga ttctagaagt ctctcttcta catgtgtcag cctgggcacc  840
aactagctcc ttccatgaac ttttatcaaa ccccacagcca cacaaagcat gtgtgagtgt  900
agcagagttt acagcagagg gtggagggtg gggagataga tgtgtggaag ggttacctgc  960
cacacaaaca gaaaccactt ctgatagaac acgaggtgtc cacccacact gtaaaatcct  1020
ctcctggtac aggcaaagct ttgcagcgat tctcctttgc tgcccctggg ctcctaacac  1080
ctcctaaacc accagttacc tccttctttc cagtgtggca tatttcagtg ttttcctgtt  1140
ggagtgtttc ctttctatgt ggattctgga atcagctctt aagataactt ggttttcatc  1200
```

-continued

```
tttcttcata atgatcccaa acatctatct actatgccta gaactaccaa tggacacata  1260
taccagccca gatatgcttc agcccatccc agtacatcgc atggtgacca aaagatgtag  1320
tcgtcctggc acagtgggtg tggggcagga agcagtcctc tccaggggac agcagcaatt  1380
caccacagaa cccaagtttc tttcaagctc tgctgacaca gaaattgaat aatctcagct  1440
caccccaatgt caaagactca tattaaccaa gaccagaatg aaaatatgct aatttatatc  1500
agaagctttg ctggattcaa gagttagggc cttttacctg tgcagaatat tccttcttga  1560
taaataggcc ctctcaggag aataaattac acatcagagg actgtttagt cagcataggc  1620
atagaacagg atgttccaaa gatacagtca aggggagtgg gtaagagtgt agcctctgga  1680
gtgaggccga ccaaatatca aacctgagct tcataatttg caaactaact ggctttgggt  1740
aagtacatag cctctttgta cctgtttccc catctgcaaa atggagataa taatagcatc  1800
tacctgtagc attgttgaga gaattaagtg agttaatgct tgccgactta taacacagta  1860
tacgatcact gattaagact tagcaactct aaactaaatg tttacaaacc atctcttacc  1920
tcaaagcact taacatccat tgtcttattt gattatcact gtaatcttat gaagcaggca  1980
gggcaggggt ctgccccatc tgggggggaac tgagctcaca gaggttggag ggtttgccta  2040
aagtcaccca ggccactggg tctcactctc tggtcttagc tctgtaatct aggatgctca  2100
atgccacact ctcagccact tttcagatgg ctaagtacat ttgttttgag ttagctcagt  2160
ctcagaggat gacattttct gatcttgtct ccagtgttta aatgaacctg tagctgtgca  2220
ttggggtcac acaatgcgtg gcatggagag ggtctgtggc tgactgccac ggttactacg  2280
tgaaaccatc attacagcag ttactactgt tactgcctga gaacatcatt acaagactga  2340
acgaagggat caacatggaa atgataacaa aaaaaccaaa gtaactgttt taaggaaagg  2400
ctagcatcgg gaagaagaag agagaagaag agaagaagaa aagggctccc tgcttctaat  2460
gagtaaaggc agctccctaa gcttctgcag cccttcatta tttattgggt aacaggagga  2520
aggagcagga ggtaatgatt gggtcagctg cttaaatgat cacgggttca tgttgttact  2580
gacagatttc aattatgcct aatcataaga aacatttgtg cagcctccaa caagggtcaa  2640
tgccacttct gaaggggtga ctcatagtca gtaactagaa agcagcagat agctagggac  2700
aaactggcga ttctgaatag gcctggaacc cttagctctg gccaggtcag tgggctccag  2760
tcaggatgga gccttcaggg agagatcaaa gctcagaggt ttgagatgat atcagccagc  2820
aaagaggagg ggcagtaggg atcctcccag agggagggcc agccatagaa gacatcaaat  2880
ctgagcccgg atcaggagaa ggagcctgca gaactggggc tctggcaccg agaacctgca  2940
gaacttcgcc cctctgagtg caggtgccag ggctggggct gccacccagc cttcgcatcc  3000
caggcctggc acgtcatagg taaatgtagt tgaaaggatg actgagctga tccaattccc  3060
tttacaactg tccttgtcct gggggacttg aggagggtta agaaagcagc tggggaccaa  3120
ccaacagtcc tctaggctct ccatgtccag caatagttgt tcagcaaatg agcattaatc  3180
agtgactata aactgtagct tcaacataac cgacaacttg caatggtttc tagagcatgc  3240
tcccatgtgt tatctcattt aaatttccaa accaatcctg tgaaatgttc tttttttttt  3300
tctttttttt tttttgaga tagagttttg ctctgtcacc caggctggaa tacagcggct  3360
cgatcatagc tcactgcagc cttgacctcc tgggcccaag ggtcctcccc acctcagcct  3420
cccaagtagc tgggactaca ggcacacgcc accgtgcctg gctaatttct tttctagttg  3480
tttgtagaga cagggtctcc ctatgttgta caggctgatc tgaaactcct ggggtcaatc  3540
aatcctcctg gcttggcctc ccaaagtgct gggattacag gcatgagcca ccatgccttc  3600
attttacaga taagaagtct gagaaaactc agatttaggc agattgagtc acttccccaa  3660
atttatgtat cttgtaagaa tccatattca aacctcagtc ccctaactct tagttcatta  3720
ctttttctac cacttctcag tatcctctaa gaattcagaa agaaccacat cgactctgat  3780
ttttcatttg tttaagtaca caggtaatag gtgaatgtat tttgttgttt aaaaattcat  3840
ataatacaca aaaggctaaa gtctcgcttc ccacttcctc tccccttttct acccaactct  3900
gcctccccag ggagagcttc tgctgacagt cggtggacat tctttcagag ttttacaatt  3960
atgtgtgtgt gtgtacataa gatgtcagtt tttctttgtg taggatacat gaacatgaat  4020
tttaaacata aatgtgagtg tattacacat attgaccagc accttagttt ttttgtttgt  4080
ttgtttggtt ttctttgtgc tgtttgagaa ggagtcttgc tctgtcaccc aggctggagt  4140
gcagtcttgc aatctcggct tacgcaacct ccacctcctg ggttcaagtg attctcctgc  4200
ctcagcctcc cgagtagttg ggattacagg tgcctgccac catgcctggc taatttttgt  4260
atttttgtag agaggggggtt tcactatgta ggtcaagctg gtctcaaact gctgacctca  4320
aatgatccat ccacctcagc ctcccaaagt gctgagatga caggcgtgag cctccgtgcc  4380
cagccagttt tgttttttta ttaaccaagt tacgtatttt aaacttctcc atgtcaatgc  4440
ttttagagct attttgttct ctttaatgtt aatagagaat tttaaggcaa tttcaggtga  4500
atctatacaa tttctctgta taagtaattt acactagaaa tagattttta taaagatgat  4560
taagctacca gcctggtatt tcattgctga cttaaatgaa gaggaaaatc aatgctgtaa  4620
gggaaaaaaa aaatggcatt agagatccag accttatagg cattttccaa attattaatt  4680
caatctctca aaacag                                                 4696
```

```
SEQ ID NO: 33          moltype = RNA  length = 657
FEATURE                Location/Qualifiers
source                 1..657
                       mol_type = other RNA
                       organism = Homo sapiens
SEQUENCE: 33
gtactattgt cggtcggtgt ttagctgagc tcagtggctc ctctcccagc cttcccctcc  60
tctcctgagt gttccttcag gcatgggtta taactcagca aggagcaccc tctttagatt  120
ctgctggttt tgtttcctgc tttccaaacc cttatcttga ttcttggtaa catgaatctt  180
ctttgtaagt tggacctccc ctagcaaaga aaatagaata atagtgaaaa tgttaatatt  240
gtttttattt ttacagtgag ggataaagtc atgttttcat tcatttttgc agtgacccta  300
catatcaaaa tcattgccct cttttttctt ttaatgttgt ttaatttaga aaaagaagct  360
ctggtttaaa gaacagtgag tcacgtgact tgctctttga aatgcccttt gaagtctggc  420
tgaacactgg gctgcattca gattcttcag tggccaccag aacattctgt tttcttctgc  480
acatcttacc tttgcacacc ctgcttatta tgttccccca gaagcccaac cctctccacc  540
aggggctgat taggaggctg caggataaat gtttaaaaga atgaagatgt gtgtgcacgc  600
gcacgtgtga catctccatg ccacagtcat gtttattcca cgtctattct cccacag     657

SEQ ID NO: 34          moltype = RNA  length = 469
```

```
FEATURE                Location/Qualifiers
source                 1..469
                       mol_type = other RNA
                       organism = Homo sapiens
SEQUENCE: 34
gtgcgcggac tcggggtcac cattctcctc tgtgggtttg gggcacctgg gtcacatgct  60
gcttagaagg gccctgacct tcccacttca ctgggacctt caccaatgag agaggggagg  120
ggtctttggg ctgcctgcag aaaggaactt aatgtatctg ccactgcttg gaaaggcgat  180
cctagtggac aggcaggact gcttgggaag gccgaatggg gaaaggaatg caaagcttag  240
gtgaatgggt tgaagcgcca tctttttgag gcataggtga catgccatca gaccactgcg  300
agtgttcagg cagcctaccg cactcccagg agagctagcg ccatcccaag gcagcattcg  360
gtgcctccaa tacatacctg gcacacagca gctatccagt aaaggctctg agttgcatga  420
tgttggcacg cgcctgctct gtcccagtca catgtctcac tctgtctag             469

SEQ ID NO: 35          moltype = RNA  length = 796
FEATURE                Location/Qualifiers
source                 1..796
                       mol_type = other RNA
                       organism = Homo sapiens
SEQUENCE: 35
gtaagtgcct acgcgcccct gtcctaagaa gactagctcc cctgggagga cccaacggtg  60
ggttcaagat ggcaggcgtt ggggaggccc cactcaatcc tgctctgctg gtcacttcca  120
tgtctctgac cagcactccc ccaacctctc cttccacact tgtgtgcagg gacattcact  180
acctcctagg aagcccccac accactggac agctctatat ttctcagcat agaagttcta  240
tgttgagttg acagatgatt ccccataact tatttgaaag gcctctgagc agggagggag  300
ggaaataggg ttatgctatt gtgtgattgg gccttgaatg gcgtgagtga cacagtggcc  360
agtactttgt gatagttgtg agtctggaga agggagttag cgaaggccat tgacatccac  420
caggaatcct aaaagttcaa tataatttta actttctcc ctcagtcttt ttcaaagctg  480
tcaataagga ccaaaacaga ctaatttcaa attcctcttc tggttgctgt gtctctcaac  540
agctagagct gctaggaata aaaagggaga caaaacgatc cacaagctag agatggttat  600
tccccagccc cacacctagt cagtcacaaa accctagttt tgatattgct tgagcagaaa  660
ccagcctcca agagaataag aagaaagggc ctgggtctaa agaggaggag gaaagggttg  720
ggcacaattt cttatgccta gggatttgtc agcaactttg aggctgatta tggaatattt  780
tcttgtcttc catgag                                                 796

SEQ ID NO: 36          moltype = RNA  length = 4396
FEATURE                Location/Qualifiers
source                 1..4396
                       mol_type = other RNA
                       organism = Homo sapiens
SEQUENCE: 36
gtacctgacc tccaaacaac ggggccccag gtctgcctgc cacagaggga ctaggggagt  60
ccctggtatc tcctgagtct ctcacaaact aacatttcaa actggcagtt gagtagggga  120
ctaaaccaaa ctccctgcac cctctgggag gggctcccca cagggcgctg tggctgccaa  180
ctggaggaag ccactcacca aaagcttcat tttccaccag atacttccta tttgatctag  240
tagaaaaaat gtgtttaagc actaaaaaaa attaagtcat atgtgctcat tatagaaaaa  300
ttagaaaaca caggtaagtc agaaggaaaa aaaatcatcg cttggatata aacacagata  360
atgtttggtt tgcagccacc caaacagatt atattccaaa tattgtctta aaatctgatt  420
tactgcataa tttactagga acatgcatcc atgtcaataa atagacatct gcatcacttt  480
taatatctgt atattatccc attgtttgaa tttcttttt tttttttttt ttttttttga  540
gacagagtct ctctctgtca cccaggttgg agtgcagcgg tgtgatctcg gctcactgca  600
acctctgcct cccaggttca attcttgtgc ctcagccccc ccgagtagtg ggattacag  660
gcatgcacca tcatgcccgc ctaatttttt tggtagtttt agtacagatg gggttttacc  720
atgttggcca ggctggtgtt gaactcctgg cctcaagtga tctacccact tctgcctacc  780
agagtgctag gattacaagc gtcagccact gctcctggcc taaagttact ttaaattaac  840
tgatctccca ttattcgcca cttaggtttt ttagttttca ccattataag caatgctatg  900
atgtacattc aaatggaaat gtgtttacac acttattaac agtcttaatt aagaagctct  960
ccatgtgctg tgtctctaac atctgcaggt atgtacacaa atacatgcac agccagcatc  1020
catcttttgc agggacatta atgatcttgg ctctgagcag caccctgtcc tgggagttct  1080
aaagtccaga acagattaca gtgagcatct cctgggggat ttagagacat caaagaaggc  1140
tgtgtccgtg gttgataatg ggcctcccag ctgacttgcc agggctgggc cttagacagc  1200
cctgtccaat gatttgtcaa tgaataaact gttcccaaac aggctatgca gttcagtggg  1260
aaagcacagg tatgggacac ggagagcccc aggtggacta cttgacctct ctgagcctta  1320
attttatcac ctgtgaattg ggaataactg cttatttcat aatattatta tgaggattta  1380
atgaaatcat gtgggcaagg aattatttag aattagattc aactcaagtg atgacaaccc  1440
caaactaaca gcagataaaa caagacacaa cttgtttctc actcatctaa aagtctacgt  1500
gggtggtgca cgatgttcta ttctctttct cctccacact aaacaggcct cagcctcatc  1560
agccaataag gcaggagctg ccttccaggc agcggaatgg aagaaggatg aagcaaaaca  1620
gagggcagag tgtgcacatg tgctatgttt agggaaggtt ttctgaagtt cccacatagt  1680
acttccactt acaaacccaa caaaaaaggc tatggctaag gcagcaggga ggagcaaata  1740
atgggagcaa ctagattttg ccacagcacc tatcacagtc tggtttataa atggttctag  1800
gccaagaaca cccgatccct gctctttttt atattctaaa gcatgtatct ttatatttct  1860
caagcaatat tttctctctt tgaatcacag ctcatctgct gcatcatagg gatcccaaaa  1920
gaaggaccca aggaacttgt ctcagtcctc tgtgccccaa gaggaagctt tgcttgtttg  1980
ctttgctgtc aatgctgagg gctcctgtgg ctgcctccac tcaaaaccct ccagcatcag  2040
gacgtcaagg ctgtgatact gtaccctgag ctcttggcca gggcgaggga ggggaggcca  2100
agcctaccta catggtgttt catttcctaa acgaaccctt acttccacgc ggtctgtcca  2160
gcttagaaac ttattttcag tagtgttggt ccttggtccc tggacaaaat gtaacagcca  2220
aagtcctaga aaaaggcaag ccagttcctg ccattttctt tcacttctgc atttcctcac  2280
```

```
tattatacgt gccttccatt ggagcaaaac tgaatgccac gcatatgcac aggagctgtg  2340
cgcgctctgt ctctctcact cactcttttt ctctctctct ctttctctct caatctctct  2400
gtctctatct atctcttact ctttatctct cactctctca ctctttctca ctctttctct  2460
caatctcttt ctcattctct ctctatcttt ctctctctct ctctttctca cacacacaca  2520
ctcacaaacc cacactctta ttcacatctg ctcaccctag ccactcaaac acaatccctc  2580
attcagcctg gaataagtcc agagggcgtg ggcctgattc agagacaatc agttgttctc  2640
atctgggaaa tggggcaatg tggtcatctc tagggaccct ccctgctcta acattctttg  2700
aatgtggtgg gtcctgaggt ggaagcactc tgtccctgac ttctagtata tgtggagata  2760
gggttacaca aatattttat tgggcagaac ttttataaaa caatttatca taagctatcg  2820
cagccagcag caatttttcc aacctggatt ccaccagggg agcttggccg gtgtctgagt  2880
gccactttca gcttgagaag caggtgactc agtgaaaaga gcaaggagga gacagaggca  2940
gattcagttc ctaggccctg ggccacccac ctgcaagttt gcagcccagt cagtgcaagt  3000
cagctaactg ttctgaacct cagtttctct gtctgtaaat taagctaaaa attcttcttt  3060
caaagagtgt caggatgaag tgagatcgtg tatgtagggc atttaacata gtgcccgaca  3120
cacagggagc attcggtagg tgccagctct cctcctggca ggagagagag aaacaaggtg  3180
aaaagagtga attaaagaag aggaaagtca aatgggaaaa caggggggagg agatagaaag  3240
tgtatgaaaa ggaaagaatg gtgcgcaata acggcggtgt aatgccacca aaatcccctc  3300
aactacttct gggcagcacc cttgacagag tgaatgcttt tatgagaatg taagcggaat  3360
gtgttcccag atttgcagta atattgccac ctggtggaca aacccatgca cctttgaatt  3420
ttccaaaata tttcgatgaa ctagcttcca gtcctagatg tattttgaaa gtgatttgta  3480
aattgtaagg aactattcaa attctttcat taatgtcaca aatcaactgt gtcatctgta  3540
tgccacccac tattctgggt gctggggaca caacagctca caaatcaggc aaagtccctg  3600
ctctcaccaa aatgatatcc tacgggggat tacagataca aatacgtaaa cagatccatc  3660
gggaggaaac tctcagatgg aaatgagagc tatgaagata acacaacagt acatgacaat  3720
acagagtgac tggaaccagg aacatttctc cgaggaataa aatttgaagc gagccatgag  3780
agggtctaca ggtagagttc ccaggcagag tgaacagcca agcacaaagc tgcaccagga  3840
gagagaggtg ctcgccgaga gacagggagg ggagtgtggc aggtgagctc agagaggggc  3900
agggccacac acatcggcca catgggcctt ggtagtgagt cgagatttga tcccagggtt  3960
tattggagtg gataagtaag caaggtgact gaggtgctcg ggtttacatt tttatagttc  4020
aagctggctg ctgggtggaa aacggaagtt ggcagaccaa ggacagaatc aggcagaccc  4080
atgtggaagt ttctctagtg gtctaggtgg tggcttgggt agcgtggcag tattggagct  4140
ggagaaacgc agatggattg gagatttgtt ttggagtgac gccattctgt cttgtcaatg  4200
gattggcgaa aaaagaggca tcaaagatga gttacacatc attgaagtga gaactaggga  4260
gatgccagta ctttatttag tattttctca gcagctcaat ccataaataa tttttggaag  4320
acaacaagca gtttcacaaa ctacttataa gtcctcaagt tccaaggtaa ttaacgtggg  4380
tgtctcattg cctcag                                                  4396

SEQ ID NO: 37          moltype = RNA  length = 1535
FEATURE                Location/Qualifiers
source                 1..1535
                       mol_type = other RNA
                       organism = Homo sapiens
SEQUENCE: 37
gtaagaagaa atccttttat gctttttatc ctggctccct gtagaagata ttaactaggg  60
acagaagata attttctctc tcaatttatg tatgatcagg gcagtagatt tttttctttt  120
ttatctgatt tgagggcccc attcaacata aaaagcaatt gaggcacata caagtaaaat  180
gtaacttaag attaattctt tttttgttgt ttgtttgttt gtttttacat ttagggcaag  240
cagtcttaaa ttttaaccca cgtattatta aaagttatat cagaagacca tagaagttat  300
tcaaaaatgc agccacatat tttaactagt taaaagagag agtaaaaatt tggagggagg  360
tggaggagta taggggaaaa ggtagaagaa aaagagaaaa taagtaagtg gcaaaaaaga  420
gaaaggaaaa agatagggtg ggaaagaggc agcgggacag tgtctgagtc cagcacacgc  480
cagggcgagc caggtcaact gcagctgtca tattctaact gtgaattatc atctttgatc  540
actgcccttt gagatgccaa tgaacttttc aagaaatatc tagttctctt ggctctccag  600
ctgttcttat cagccccatc caggatggaa cagctttggc agcccgtatc agaacaagca  660
gcttgacagg ggcatgccat gccaggagag aggatcctaa ggaagcgtgg tccagtccgc  720
acaggctctg gggctttaag ataaaacctc ctgtctaact ttagtaggac tttctgttgc  780
ttcacctgcc agagccctga acgagggata aattgactta attaactaga acacactgca  840
aatggtgaaa gcatttagca aaacaaagaa tgccatccaa gccccaaaat aaaagcagaa  900
taaatagaat gcaataaaca gcaaccatcc caaactgagt tctcagcagc aaatctccag  960
tatgaaattt tggattttgt gcgtgtgtgc ttaaaggtgg atgacaatga cagttcatgg  1020
gattgagctc tggggtccag agttggcatc tgttcatttc ccattttgtc attttaccct  1080
tgattgactg aatgtcagtg ccttaacttt gggctgtgga gtgagtcgga actcccccga  1140
ggtgtgcagg tggttgttag agtctcattt ttgcagggtg gaagacagga gggctgcagc  1200
cttcattcca cactgacatg gtcattgccg tgtgttctgg gtccagatca ggcatattga  1260
cctgacatat gacctgacaa caggaccact cagaaagtcc agcatgcggg atatgatttg  1320
gagagccagt gggggaaatc ataggtcctt tctctgcatg tgtattcagg caatgtccca  1380
gggctgggcg gcttccgcat tgcttggata tcggaaaatg caaaaatgcc cctgaagact  1440
gagacttcag tcttcaaaat gaatgtttgg gaaagaaagt taacggcact gctgtacttg  1500
tggtattcat tgcattattt tattttggct ttcag                             1535

SEQ ID NO: 38          moltype = RNA  length = 1434
FEATURE                Location/Qualifiers
source                 1..1434
                       mol_type = other RNA
                       organism = Homo sapiens
SEQUENCE: 38
gtaagaaact atttttatca gaattaaaat ctcagattga ttcattgttg aaataattgc  60
acacttttaa aaggcacacc tcacagccat gaggaggggc tgttctgtag gtgctcagga  120
agtcacaaga cacgtcctga agaatatgtg gctagggaca tcccagactc agaagacact  180
```

```
cagtggtgcc tcttcttgga ggacataagt gggggtggca ttccctgatg tggcgtttca  240
gagcattctc acccaaaaaa agcttctaaa acctccaagt atataacagt ttataatact  300
ccaacaagag ggccttgtag cctaaacccg ggacactcct tggcccattc cttttaagct  360
tcagggagtg tgggccagcc ccagactcac cccattcctg aggcatcctg gaggttgaaa  420
tatttccaga ggtttagaac ctcaccaagt gggactctag gagcctgctg cctcccagcc  480
tccctcagga actgcacctc cagaacaggt gcggggctga catgtatgtg ctttcctggg  540
cagattctag accgtacaca tgaaatctgg ctttcaggat tgctctccag agggacctgt  600
ggggcctcgg ctgagacaga gagtaggagt gaggcagtga ttcaaggccc tgagaaagag  660
ctcctcctct gcttggtata accagctaat tcattctgtt ctgttgactt tggcttctgc  720
cctgcctttg aagggtttga ggccagggag tgatgcactc agactggtgt ttccacacag  780
tcacttcaga cttccagggc agtacaggag atagatccca gggccagtga agaagcagag  840
cacaagtcca ggcaggagag gctaagggcc tccctgaaca ggtgtgaggc acagaagccc  900
cgagaggtag ggatgacagg atgaagatgg gtcctgtgct gctagaagta cctgcaaagc  960
acagaggtgg cacagaaaag gagtccttgg ctgggatggg aggagatgac atgtgacatg  1020
tgaaagagga cctggagttg gctcgatgct cccaaaaggg aaaggtgccg aggggagcta  1080
gcagccatgc aaaggcagag acatgcaggc agtctgggcc atgaggagct ctggaagtga  1140
ctcgatatgt ccagaatagg ccactccagg gaagggctga ggaaggatga agttggagag  1200
gggcacagac cagatgcaga agggcctcag aggccaggat gagggtttgg actccttcct  1260
ggaggcagca gcagtgggaa aagagttaaa agctggtttg taaagtggag ccatgttgct  1320
cgctggtcca ggcaattccc ccgaaagttc atgtttccct acaaaacccg agagagctac  1380
tagtaggcgt gaagttcgtg gccctggtct gaggatttcc tgtttccttg tcag        1434
```

```
SEQ ID NO: 39          moltype = RNA  length = 131
FEATURE                Location/Qualifiers
source                 1..131
                       mol_type = other RNA
                       organism = Homo sapiens
SEQUENCE: 39
gtatgtaaac agactggaga tttgagtagg atttttgact tgcttaacta ccatgaatga  60
gaaactctca tgagtgataa caggaaaaaa aaattaaaac cgtcttgttt gtttgtttac  120
atggttttta g                                                      131
```

```
SEQ ID NO: 40          moltype = RNA  length = 230
FEATURE                Location/Qualifiers
source                 1..230
                       mol_type = other RNA
                       organism = Homo sapiens
SEQUENCE: 40
gtacttgacc tatgtataat ctgctctgga gctaaaaatt tacctgagct ggttatttta  60
tttttacttt cctaccttca ttaaattcca tccctcctcc tgctgaaatc tagcaaggaa  120
tgtcttccag ctaccaaacc cttcctgctt ctcaaatttc ctttccttca ctgatttctg  180
ctttaactag ctgttagtgc agcgtctcag atgtcctctc caccctctag            230
```

```
SEQ ID NO: 41          moltype = RNA  length = 1480
FEATURE                Location/Qualifiers
source                 1..1480
                       mol_type = other RNA
                       organism = Homo sapiens
SEQUENCE: 41
gtaagccacc acagccccag cctcaccact ttcttgtcac cttctccact ctttgaacat  60
cctgagagga ttctcaccac cgcgaagtgc tgatttggat ggtaatgctg tttagtcagg  120
cacatatgaa catccgactt tcaaataagt gcctcacact tcacatacca gacctcttgg  180
tcattctttc tccccaacat ttatgtggca agtaagttta catttggttc cattcccttt  240
tggcttttga tagcaagttg ctcctggagc ttatacaatt attatctttg ctatgtgcaa  300
agcagctgcc aggaactggc aaagttcagt aaacctttca gctccctcgg agtaattatc  360
ttagattcca ggaatttcct cagaagagca tactttggag atgtcgacag agctttgcta  420
ccctcaagct gaggctcttc ttgcacagtt tcagccagtg gagacagtgg ccttgtgcgt  480
tttgtagtat gttcactcta tttgaggcct acatggagga ggggttggta ggagcacctt  540
tgttagtgca aacttcagca acgttgtggg gtcctgattt tactatccta gcacacgctg  600
agtgccagtg aacatgccca gggtcatcca ctaaaacctg ggccttggct ccttggtgtc  660
ttcctctgga caccctaggg ccctagactg tcctctgtta attctcactc agccacactt  720
tcgtgtgtct ccttccagtc atttgttcta agcttactac gtgtatggat gatatgatct  780
gtagttttat caaggtagtg actaccacat aggatacctt tgtggaaatt agtaaaaatg  840
ctcttttctg caggtggaca ctgtcccatg ccaggggtta tggcttgtac ataaagttca  900
ggctggcttt agccccaact taccccctcag ccagatgcct tctatttgtc cgaggaaaga  960
ataaatagag ccaagtccct gtacaacttg cctgccctct tttcacttaa atttacatca  1020
tgaacatttc cttgtgttac gatgtacttc ttgaaaatgt gatttaacaa gatgattatt  1080
aacaaaagat aaatctcaca gaccgtatgt ctgtcaacat agaaaattca agagactcta  1140
tagacagatt attagagcta atgagagcat tgcagtacat aagattaata taaacatcta  1200
tttctataca ccataaaaat aattagagaa tataataaaa agaaaggttg tctagaaata  1260
ttcacatgaa atagaaaggc aacccgcaaa tacccattta accttggtcc atatggatta  1320
agacagttta gtggagtgac agcttcaagg tagagaagag gaacctggag gccacacctg  1380
ggcgggtgta aggccttccc aaagcctgac tttgtatctt ctcctccttc tgctcttccc  1440
tcttcatcgc cctctccctg tgtctctggc cctgctgcag                        1480
```

```
SEQ ID NO: 42          moltype = RNA  length = 3727
FEATURE                Location/Qualifiers
source                 1..3727
                       mol_type = other RNA
```

```
                        organism = Homo sapiens
SEQUENCE: 42
gtaagtgtca gtttacagcg cctccctccc ctccgtgggc ccaaggtgga gcttgtgtgt  60
gctctgaagg accagaccaa gaggggaggg gttctcacgg tgccagggct gctgaaaggc  120
actgggccaa gggccttgtg tatctgctgt cccttgacat cttctcagaa aggcacagaa  180
ctaggagccc gaagctagga aaggctgtgg ggtgcagctt aacaactggt gaacgggggc  240
tctctatgtc ctgcactgag gggtcttctg acccatcaaa taatcactgc accgcaggca  300
tgagtctggc cttcctggca tcagtctggc gctgagaagg taatatgaag gggtctttca  360
ccccaagtcc ccttctcaaa tcctgcccca ccttcaaaag ggtaaaggta aaactttccc  420
tgtggtaggg tcaccagata aatacaggac acccagttaa atttaatttc agatgatgaa  480
taatttttag tataagcata tgctacttca aatattgcac aggacatatc tacactaaaa  540
aaaaaaaaaa aaaaaaaaaa aacctggttg tttatctgaa actcaaattt cactaggcat  600
cctagatttt tatttgccaa atctggcaac cccagccagt ggccaaaata ataagacctt  660
cacttattag attaaccacc gctacaggga aaaatgaaga aaaaatattt attaaatcaa  720
tagcacacta ccaccttcct gacaaccaag gttggtgggg gtagggaggg gtcaggatag  780
cgtaccctat tacaggctgc agggtcaaag gaattggtag taaaggccta gttataatgt  840
aacagggatc attatgacat caaccccaat ttattctagg tgtcttgagt agtaaaatct  900
caacatttta agaccaacat gagcctccat ttcatgtgat gataagatat accaactgat  960
ggagaccaac acaaatgacc ttctcatcca tggtttttta aaatgatggt gaatattgga  1020
attcctgaag atatgatttc tatcttactc agcttagtaa gcagctatca cttaacaata  1080
caaaaccaga gattatcagt agcaactaaa ttatttcctc tctcttctgt ctacacgagg  1140
aaacactcat aaatgcacgg ggaggaggtc agaacctgaa agcctttctt tggataagag  1200
catcaactgc aggtaccaca ttggccctgt gatgctaata taaaaggagc taggcccacc  1260
ggtaccgaaa agttacttag aaaagtgcgg aggcttttaa ttttactttt tttaaaagat  1320
aagaaataga atttacacac ttggggctgg cccacgtgtt tctgtgtgtg tgtatgtgtg  1380
cacgcacgcg cgtgtgcgct tacagggatc tctgagccta tggagagaga tgtagctagg  1440
atagagtgga catctgaggt gggaggtgat actagctggc agtccaatga aggggtagaa  1500
gatggtaggc atcatgttag caggctttct gatgctccag aattttaaag ctggcctgga  1560
atctcacctc cgcgatccat cattttggaa cttaggacca ccattagcca gtggcaaaaa  1620
aaaagttgaa tgaaggaaca aacaattatt gcttatgtaa ttcacttagc acatatatga  1680
tgttttaaat tcttatatgt gtcatctatt tttctttact ttaaaatttt gcaacagtta  1740
cagacttatg gaaaagtcac aagtacagtt gaaacctttt tttcttagtc atttgaaagt  1800
aacttctcag caagatgccc cttctcattt atttctctct tcctgtctct ctctctcaca  1860
cccctcagca cgtccgatgt atacttccta caaacgagga tacaccccat acaaccacaa  1920
cacaaactgt caacatgagg aaaccagcac tgatgtgtca tcaccaccta atcctcacac  1980
cccactcctc tttcgcccat tgccccagtg atgtctttca gaaaaaagga tctagctcag  2040
aatcatgcat gacatttgat tgtgctgttt ctttagtctc gttcagcctg gaagagttcc  2100
acagtctttt gttaacactc atggtcttga cactttgagg actgcaggct ggttattttg  2160
cagaatgtcc cttggtctga gcttgtctga ggtttcctct tgcccaggtt gagggtgtgc  2220
atcttggcag cagtatcagc aaacagatgc tgtgttctca ctgcatccta tcaggtggct  2280
tctgatttca atttgctctg ttactgatga tgttcaattc ggtcacttaa gaaggtgtct  2340
gctgagcttc ttcactgtaa aattactctt ttccccttta taataaatac aaatttcagg  2400
tagaggcact tcaaagatat ataaatatcc tattcattat acaattttcc atttattcat  2460
ccatttattt atctctgtat gcagtcatgg ttcatgtgtt aatcaatgga ctatgatcca  2520
agactatcat tatttatttt gatattcaca ttatccccac tgtggtcagt ggggggccgt  2580
tgaagctggc ttctgtatcg tcttgacttg ggtcctcatg cccctggacc tcctccatgc  2640
tcaatggcac agcaagatat tccaggctca tccttccatt atccccattc ctaccctctc  2700
cccaagaagc cctggttcct gccagtggga agtggccctc agaagccaag gtctgagtgc  2760
tagatatgtt cattgcctct ggagcaccat tggtcccagg ccttctcagt gatagaacta  2820
gggaagatat ggatgtacac acacaggtat gcacacacct ctatctatag ttctctatct  2880
acctatacag tgaacactat gagctctcca aaaccaactc cacagggctc attctagttt  2940
tttttctttc cacatctgta actcccttct ccaacagtga gacgctggct tctctcactc  3000
ccaactcatt tatctaccgg acctatacac ctgaacagtg cccaactctg ccaccatccc  3060
ctccccatgt ggatgccgtc ctctccctgc tccagctgcc tctgctgcat gcaggtcctc  3120
ctcgttctgc tctggctctg ataccctgca ccagatcagc ctcctgtaag gatatctttc  3180
tcatcccgtt gaggcctcca caccccacgg caggttgccc cctgaggaag cccgtctctg  3240
gttcttgccc tgctcctgat caccatggct cctcccctaa ccccactgtt gccgtcccct  3300
ttctgtgccc agtatagtgg ctgtaggact aaattgttta aaaagggtat cattatttat  3360
ttgagctttg tgaagccaag aactaggctt taagtttttc tgaattctga agacatgctt  3420
agaaagaaga atcaacaaaa ctttatgacc aaatagaaag agtgagagac caggcagaat  3480
tttgtaattg atcctttcaa aagatacaaa ctaaaggttc ccttggcagg gaggtagggc  3540
atggggtggg gtaggaggac tagtgacagc ttaacatatg tttgccaacc aagaactgtt  3600
taaaaagcaa gtcgaatcag aatcccagac cctacgagct ggaggagcct ggccccaccc  3660
ctcattttgc agagctggca gcaggtctga gaggttaagt gacttgctct cctcttctct  3720
ttccgag                                                            3727

SEQ ID NO: 43           moltype = RNA  length = 1048
FEATURE                 Location/Qualifiers
source                  1..1048
                        mol_type = other RNA
                        organism = Homo sapiens
SEQUENCE: 43
gtaagccgtt tgggccatta gctaatgcct ctgaagagaa gcctggtggt gggggtgggg  60
gatcatctcc tgacagaaaa cctgggctgt cctgtggtgg tagcacccac aagtttagct  120
tccggcccca ggtagggtct gaagctgata accagggatc tgtctggctt ctgattctga  180
ctccactgac agaggtatct ctgaggcctg gtcctgtcag tgacaatgag agaagtccca  240
catgatctga atctcctact caaactgagg ccttgaccaa agcctggggg cagccattcc  300
ccaacccctc acccagctct gactctcact catctgtggc caatctgtcc acctcagtgt  360
ccccatgtga actggccaag agttaccgcc cacagtagaa gactccggcc aaaaagctcc  420
```

```
tcctgagtca gggacagagg atgacacagg ggttacatca gcagagttac agggcccagc  480
atgcaacttt ctttcccacg tgtgtaaatt tgaatgagta attcatccat ctcggcctca  540
gtttcctcat ctgtaaaaga aaatagtgat cctggtcctt cctctgtggg ccagtagagc  600
cttgccaaag cattgttctc cacatctttc tcttggaaat agagaatttg ggaaccaacc  660
tgactataag ctgtgaagat gagctcactg ggctcatctg agatgacctc agctgggctt  720
tgctgaccca ggctagagtg ggaggtgttg caggctggag aaccctccta tgaattgtac  780
agggctttgt agtttacaga gtatatacac agctagcagc ccatttgctc ctcacaaaac  840
cccatgaagt ggtcaaggca ggcatcatta tctccattta aagttgaggc acagagacca  900
acaaatggag tatctctctg gtcccctggg actctggcca gttcacacac atcacctcag  960
gtgtaagggg agtgcattat atccagacgt attgtaggtg gaatggaatg tggaactcca  1020
tcactctgag ttgtctcatt tcacacag                                     1048

SEQ ID NO: 44          moltype = RNA  length = 3157
FEATURE                Location/Qualifiers
source                 1..3157
                       mol_type = other RNA
                       organism = Homo sapiens
SEQUENCE: 44
gtgagcataa ctttcttggc ttttttgttt gattagtagg atagtagagt atgtgttggt  60
cgagcagagc caggggcaag catcgtacat gtagcagctg tatgcggatg agtgccactt  120
tcttcctccc tacccccgac cctgcctcct ttccttcctt ccttcctccc atccttcctt  180
cctctttcct tcttctcctc cctcctccct ccttcccccg tccctccttc cttccttttt  240
cattgcttcc ttccttcctt cgtccctcct tcccttcctc tttccttctg ccctctctcc  300
ctttttcctt tcatcctccc tccatccctc cctccatcct tccttctttc ttccttcttt  360
ccttcctata agcacctttt tcatttctgt gctctgaatg aaatggtttt ctgtgtttat  420
tctgcaagca aaacttgatt cttgcaataa actttaagct ttgcttactc tttcagaaag  480
gttttctcag ggactttggg tgttgggttt tacacacaca cacatcaata catttgggta  540
atttcaaaat ctaaaaggaa caaaaaggca tacaatgaaa aaatctcctt cctacccctg  600
tttcccactc atgcagttct cttctccaga ggcaaactct tacttgagtt tcctgtgtgc  660
tctggagaca catcagcaga tccctatacg gtctttctcc cgctttctta tggaaattgt  720
aacactctga catatactat tccttgggca agttaatctt gatgaagaga ctgggtgttc  780
tccatgctga atgcctcact tttatgagct gccaagccca gttgtccctt ccacctgacc  840
tccccctgtc cagagacaga tggccaaact gaatcataaa aagaggggga aaaaaagaag  900
gcagtcgctg cagggctgtc tttactccac actccacact cccagtcccc accgctgtgt  960
ctgagtcctg gctgtggctg tccttggaac atttgcctca ccacgtgcct gtgtccccag  1020
gcgcctcaac ctttcctctc ctcattagct cttcccagtt cagagggtgg gaccggccag  1080
cacatctgca ctgctgccct gccacaccca cctccacctg cctctgggcc ccactgggga  1140
acacaggaca aatctgtgcg gaggccccac catgaaccgc ccagacccgt ggacccctga  1200
gactgactct ttccagatct tgttagggtt tcgtggctgc taggcaagta acgaagcctc  1260
atctgtccca tgaatgataa gaaattcagc atgtcagagt cagactctgg aaaggcgggg  1320
ggataagaac acagccccag cagatggcca gagcacccag gtgactgaaa gtgctgcttt  1380
gcagagctgt gtttgccaca ggctcacagc ccactaagtc ttaagacagt tttccttcag  1440
aataattaaa tagccagctt aaagcaactc agaacatttt cccctctgag gctgcaccca  1500
tttagccaac atttgctaag cacccgcctt caaaaacctg gtattttcat gtaaattatc  1560
cgatacacag ctgctatgga aacccccagt atcccacagg aagctcccca gctcccagca  1620
gctgccggcc cgtgtgagat caggaggtct ttaccagctg aacaccacgt gccgggtgtg  1680
tgctgatata aacaagcgtg gcccactcgt cctgccctcc agaggctccc gttccagtcg  1740
gaaaaggacc tgcccacgaa gtttgcaacg atataagcca cagtgtatga tcctccataa  1800
tacagcgtgt gacagagcag cagaggagcg aggcagataa catgctgcag gccagaggca  1860
gcgggaagag ccaggctgca ggggctgggg gagccgtggt ggaggaagtt caatttcagc  1920
ctgtagattt ctattagccc atttaataaa taatgaagtg cctactctga gctaatcatt  1980
gtgcaggtat ttaggaagga caaaaaaata attaggactc agtgcccacc ctccaggggc  2040
ccactgacta gtagagaaag taggcagatt tttaaaaaat taatcatggg aatgtgataa  2100
gtgctgggag agaggaatgg atactttctc atgggaatct tggaaggctt gtaagggaag  2160
gcactctctg agccagctgt ctaaagaaga acaggaatct ttaagaaagc agaagggaaa  2220
agagcattct ttcctgcttg gagcaatagg taacagcctg cacatgccca ggcctagagg  2280
ccaaagagca cagtgattcc agaaagagtg gggagaaagg gtaggcaggg aaggatgagg  2340
taatgtgggc gcaggtgtgg aggctggaga gggaggaggt tgtgggactg ggaggagcca  2400
gatggaatgg acagcagtgg cccagccagg agctatgctg gcctcgtacg cctcgatgtc  2460
ccttctattt tctcagggga ggctctgccc aacatgccaa gtccgaccac ttgaaaacaa  2520
gtccctggct taacacagac cccagagaga gtctccaacc ctcctctccc tagacaatgg  2580
tagttgccct gtgaggggct gaaaagcaga gctggagatg gctcagggcc tggtgttaac  2640
aaatgccttg agggctcctg ttgtttcaaa gtgagtctgc agggagagct ccctaagtgg  2700
acagcaggag ggctgcagct tctctgcaca ttcctgctgt cacccccaga gtcacctagg  2760
ggaggggtaa ggacagtaat gcaggttcct cacagttagc ctcggtgccc acatggtact  2820
gagcatagta aatgtttaga agatgctgcc tggctagaca aaggggaagc tcccgcccac  2880
tagaaacttg cagggagccc cagtccttga ttggtcattt aattgattag ctccttggcc  2940
tggccttgag gcactgcttg taagtacttc atgacctcca ttgcaaaccc atgatgctct  3000
gctggacaaa tccctccagt ggccagtctg gctgcaagga ctctctgtct gcaggccttg  3060
ccctgtgctg tcctgtgaga gcatctgggc cccacctgct gaagagaggg ggggtggggt  3120
ttgccccgtt tccaacagtc ctacttctct gtttcag                            3157

SEQ ID NO: 45          moltype = RNA  length = 332
FEATURE                Location/Qualifiers
source                 1..332
                       mol_type = other RNA
                       organism = Homo sapiens
SEQUENCE: 45
gtgggtggta gccgaggccc atggagcatg ggccctgggt ccaaagctgg gagggttacc  60
```

```
ggggggcctc ctgcatcaga ctgtggcagg ggctggtgct aggaggggac cttgttgggc  120
tggaggtgtc ctgccagctg gagaggatta gggtgcctct gtttccatgg ctggggagcc  180
acaggaggga tggagggcag cccttatgag gcgggtgttt ggctcttgct cagttcccac  240
ataaggcctg gtctagtggg ccctgtgctg tggccaggtc tgtggggtga gctggggcgg  300
ctgaagtgga ctcaattcct gttgatgccc ag                                332

SEQ ID NO: 46          moltype = RNA  length = 1928
FEATURE                Location/Qualifiers
source                 1..1928
                       mol_type = other RNA
                       organism = Homo sapiens
SEQUENCE: 46
gtacgtccat gccacaccct gggccagtgg gcagctcagg gcatccagaa ctggacctta  60
tacccacatg gtcatttctt tcctcaggag ccccactcca caatgttttt tctacattct  120
caaagcctgg cttttctcca ataatacaag tagaggatcg ggttaaaata ggcacattca  180
aatatgtgaa gagcatccac tttaaaatat ttaaaatgca gtgctattaa tttcaattgc  240
tgatatttaa tccttctcat ttaattacca aatgtgtatt ttgattagat gatagtattg  300
caaataacaa tggttacagg gtatccaaag tactaggaaa tagactaatg tatttatgag  360
agaaaggaca cagcaggccc ctttgctaat tagagatttg ggagcatggg agtaatatgg  420
gagccatgtg gaggggtgcg ggcagtgatc acgacccccc actcctggag gaaggtgggt  480
agctgccaac cctgactttt gaccagggct tctcaaatgc caggttagct ggcaattgcc  540
attcttccgc aggctcttcc tgaagctggg tgggcccctg cctcactccc ctctgcaatc  600
cagtcctacc tttattgtcc tcacccaggg gcctgaattg ccaagcagca gcccttccta  660
gcaagctttc cccaatagtg ttttgtttct taacttttcc tcctctcagg ctgagtgtgg  720
tcacctgtaa atagattcca aggacttggt tttatgtttt gatccacagg gaattgattt  780
attggaaatg aatctgcctt tctactcaca ggactgtgag aggtgaatga gatcacaggt  840
gtcaacacac gcctgatgaa acaggataca caagcagttc tagttatggg agacagtgtc  900
aggaattgtt gtccttggca ccctcagccc ctgcagaccc tttctgcagc cttggccata  960
ccttttagag gcttttgtgt gggagagagc aggtcaggag gttgactacc caaattgact  1020
cattagcttc aaactctgat gtcaacacat ttgaatgagt cctgcctgct ttagggccta  1080
aagaggacca gagaagtaca ccatagtccc tggcttccag aaggtcaggg agggtttcaa  1140
agaagaggct gtgtctttaa gaatggggaa gattccattt ggtggggcag gaggaggaga  1200
acattgaggg actggaaaca catgcggagg ctgggagacg ggaatgacca ataggactgg  1260
gaaccagggg gagatgccaa ttgctgacag aggagttagt gcaagaggta agtgagaagg  1320
gtaggtgggg ctggattgca gggctgtaac tacagctgca gagggagggc ttcaacctac  1380
agctgatggg gaacaacaga aggttttgag gcatgaggtg gcctgatgac aactctgttt  1440
tggaaaggtg gagttggcag ggcagactgg aggaagtggg aggctcggag gttagtaact  1500
acccccttact gagtgcttgc tgtagaggaa gcattttagt cctgacggtg atcccaggcc  1560
ctgagtcttt actctgtgcc aggcactgtg ctgagttcat cttcagcaca atcctatgag  1620
acaggtattg ttaccctcct cctcatcaca tggttgaagt aggcaaggtt cagagaggtc  1680
caatgcccaa gatcacacat gaggaggcca ggactggaac ccaaggctga ctctggacat  1740
gagcacctga cctctctacc taatgcctaa tgcctctcct gctgggagcc ctttttagaa  1800
tttaagtctt aaaggatgga agcccagaag gaagcagaag caaggaagtg gaagagaggt  1860
cccatggaaa ggacagtgcc aaggacactg tacagccagc ccaatcctga cccctttttct  1920
tcatctag                                                           1928

SEQ ID NO: 47          moltype = RNA  length = 453
FEATURE                Location/Qualifiers
source                 1..453
                       mol_type = other RNA
                       organism = Homo sapiens
SEQUENCE: 47
gtaagggaat gggtatgagt ttggaggtgc tggttagatc cacagttggc atgatgttgc  60
cattttcctt ctatagaaca attgatatgc ttatgcaagc aatttggttc ccagttttat  120
gtagggtcat catccctgtg ttataactcg tcttccaaga gcatctaatt ccaatgtgtg  180
ttccctgcta ttcatctcgg gcactgacac agggcctcag tgagaatcac tccagctgag  240
catcattccc ttttctgtgt tctgtttctg cagagcatgg gtcagcctcg agatgtctca  300
gtactcacca cacctctgtg cctgcccatg tcaatatgta acctcctagt gctggtagtt  360
ttctcctaaa ccatcctttg ctctttgttc cctcttcccc tccttgctct caccctgtct  420
cagttctcag tccggtttct tcgtatcttg cag                               453

SEQ ID NO: 48          moltype = RNA  length = 494
FEATURE                Location/Qualifiers
source                 1..494
                       mol_type = other RNA
                       organism = Homo sapiens
SEQUENCE: 48
gtgggtactc tgcagaccac gtgtgaaagg cttccgaaca tcagctcttg tgcctgcctc  60
tcctccccat aaggcagagc tattcaatag gaacataatg ccataatgca agtcacatat  120
gtaattttaa atcttccact agccacatga gaaaagtaaa aagaaaatag gtaaaattaa  180
tttcattagt atttttttatt ttactcaata taaccaaaat attatttcaa aatgtaatta  240
atagaaaacc ttattaatga aatatttgac aatttctcgt tgtttttaag tctttgaatc  300
tttacactca gggcccgtgt caactgggac ttagatgtgt ttcaagtgct tagtagccac  360
atatggctcg tggcctctga tggcagccca ggtctaaaat tcctcccccca gctcacacac  420
acacttaccc tggggcctga cattttagac cttcttgatc tctagggcca ggctagctct  480
gtgttttctc ctag                                                    494

SEQ ID NO: 49          moltype = RNA  length = 2051
FEATURE                Location/Qualifiers
```

```
source                  1..2051
                        mol_type = other RNA
                        organism = Homo sapiens
SEQUENCE: 49
gtgagtatcc tgctcctcct gtctcaggga gtctctcaca ggtcctgtga gaagaatagg  60
aagggtgatc atcagaccct atagtagggt ggctctgagg ccctgaaaga tctgtacaga  120
gaaggaggcc tcccagagag catggcccaa aaagcccaac acatagaccc aatggaaaag  180
tgaactgaat tgtgatagtt aagagattcc tctgttggga tggattcttg gaaagacctg  240
ggaagcacta agtgtgtggt tcttaatctc ttagaggtca cggaaccttt taagcatctg  300
atgaatattt gtagcctatt cctataaaaa tgcaccattg cttcccatta cctccctcca  360
cacattttta caaaacgttt cagggagttt actgagcccc aggtcacatt tatgatcctg  420
caggagctct tgaatcccag gttaagaacc cctgtgatga atgaagaatc cttcctctgg  480
gttgagtttc tagatagggg ctcatgcatg ggcctttggg gtagcctaac ctgcattggc  540
tatttgtagg ctgatatttg gctttgccag accaaggagc atagagggaa aactggcgtg  600
tgcccttgga ttctggaggg tgactgctgc tctctgtaat aaaatgtgtt taaacagact  660
ggtcccctat gggcaggaca gagaggatga gctctcactc atctgcctct ttcctggctg  720
caggaaaagc ttgaacagta aaacttcagc acacacaata gaggtgccca gaggaagcct  780
ctgccctggt ttataagtgg agttaggtgc tgctgacatc tgtccagcat ctgcttgact  840
ggggcctctt cctctctcct gaaagccatc ctcagcatgg cccaatgccc agtgggcagg  900
acgagtcctg agcacgcttc actggctcag acaggatgaa tttgattctt tggcctccat  960
agccagccct actgggttta cagaaaaggg acaggcaggg gtgaagccag gtcatggctg  1020
agtccatctc aacagatcca gcttcacctg caagtgacca cgcaggtgac ttcctcatgg  1080
tgacaaaagg agtcatggca gggtagagat atcataccat ggcaggggaa agatatcata  1140
gaattttcca tgagcacatt tatgagacat caagttacaa ctgtgtccaa gtgaggcaca  1200
gtctgacatc cagaaggtaa aactgagctg gacgctagaa agaaactata ggcttaagac  1260
acagaattgg gattatatgg tagggtagct cccactaatt tggaaacgta ccctacttgc  1320
ttccctgagt agttttaatt ggcccagcca tgcctttggt ggcttttgtc attgtgggga  1380
actgtaatgg tctctctgta ccatcctata tcatccatcc tttattcata gaccctaagc  1440
tataagaaga aaaggatgag attagactaa atgtctatgt atagtttatt ttccatcttg  1500
gcaatatatt ttttagtggg ggtgaatata ttagccaaag ggagttggtg gaacccaact  1560
cactctaccc ctgctccctg caggcctctc gctgtgggta gttatctgac tggctcctct  1620
ttcattgcta tctttgccaa taaatacaga tagagaagtt tacttccatc gggacacatg  1680
catcttttct agttacttcc caaatgtctg aaaattattg ataaatcatg aatcattttc  1740
ttaaacctga tcttccctct gtttttaaac tcacatgtga ggtgatctga tccaaaatga  1800
aagctgactt ttggcgtaac agggattcaa ttaatcctag acatggaaac atggaagaat  1860
ctgacaggat tcagtttcta accgaagggc ccctgttttg attcccaaat atcccatgca  1920
tttctgaagc caaataggag aagagaagaa gcagcttcct tttcccgttg gcagaagctt  1980
ctccagccct agctctatgg tcatccctcc actccttgaa ggatactcag taattgcttt  2040
ttttcttgca g                                                     2051

SEQ ID NO: 50           moltype = RNA  length = 3448
FEATURE                 Location/Qualifiers
source                  1..3448
                        mol_type = other RNA
                        organism = Homo sapiens
SEQUENCE: 50
gtgaaaaatg ttttgttgtg gccacatagg agtctggtta attacaagcc tgtttcatga  60
gagtgcattc tcttggagat gagaaactga agcgtgctat tcattcattc attccaacaa  120
atgtttacta tgtgtctact gtgtgccaag tactgttcta gaaaccagga gtatagcagt  180
gaacaagaca gacaaaaaaa aatccccact ctcatatcta acaaaatgtt gtatgcattt  240
atcctctgac tcagcaatca cacgtctaag agtttatcct gaagatgcat ctcccacagt  300
gcaaaatgaa tatgtataag gtgatccatt gcatttgtaa ttgcaaaatg ctggaagtta  360
cctaaatgtt tagtcattgt agattggctg aataatttat ggtacagaca cacaataaag  420
tcttacgcaa ctataaaaaa gaagaagaaa agtctcagta aactgatatg gagatatttc  480
cagtaaatac tgttaaatga taaaaagcaa agtggaaaac agaacataga gaacgctact  540
ttgtatgtaa gaaagaagga aaaacaagaa agtaaacgta tgtctgctta cctttgcaaa  600
tagaacgtag aaaggataaa ccagaaaaca atgaatttgg tgatcaacaa gaagaaaatg  660
ggaagaaaga aaaatgggag gaaacagtac ttctggggat atatttttgt atagttttaa  720
tttttggaag catgttaatg ttccacatat tcaaaaaaaa tcagtaagaa tgggaagtag  780
gcaaaaatga aaacaaaaag aaaacctaac actgacagca aactaaataa agtaacccaa  840
ttttatttca aataaatatc ataatcttgc aaaaggggga tagagctaac acaaacaact  900
gctgaacaca gtgtttgact ctatatcctc attcttgggc agggtggagc gggggagaag  960
aactacaaat aatttctgag ttctttttag tttgtttttt atagtggtat aggcaaagtg  1020
attctgaaaa ttttagatgt gttacaggat taaataaatt aataaatgtt ttgatgttat  1080
tgggacccag aattctcacc gtggaagaag ggacttacaa atatggaaaa gggaaaagca  1140
agaaagaact gtgaggtcat ggataggaac cggaggtagc actgggaatt caggaatatt  1200
tatatgcttg tgtttgtggg tgcatgcaga tgtgttcatg tttcatgcac ataggcatgt  1260
atatatagac atatatttgc atgtgtgtat ctgtcttccg aaaggctcaa gaagcaaaaa  1320
caccccagta gccatgagca cacttagcac tcaggctttt gtcttaataa cattccccac  1380
taaaagtaac cctgattcct ccaataaatg ataagttcca gggctggaat ggcataggta  1440
taaaatgaac ctggaatatc ttatgccaga aagtaaggaa gtgcttttaa aaaaaaaata  1500
aggggctggg catggtggct cacacctgta atcgcagcac tttgggaggc caaggtagga  1560
agatcgcttg agcccaggag ttccagatta gcctgtgcaa catagggaga ccctgtctct  1620
acaaaaaatt agcaaacaaa ttagctgggc ctggtggtgc acgcctatag tcccagctac  1680
tcaggtggct gaggtgggag gaatgcttga gcccaggagg ttgaggctgc agtgagctgt  1740
gatcaagcca ctgctctcca gcctgggaaa cagagcaaga ctctgtctct taaaataata  1800
ataatataat tttaaagaaa taaaagtaac tctgtacaga ttgcttattg gttacatggg  1860
agaaacataa taattttaca atggagaaat tagacagcac cttaactggg tgatcaaaat  1920
taaccataag ggcagatggg acatctcatg ccccgagatg tgataccctg tgaaggacac  1980
```

```
aatttcactt atgtagaatc cagattggag atatgtaacc tgaatcttat catgaggaaa  2040
catctgacaa gctccaaaga aggaatattc cttaaaaaaa aaaaaaggag actgtattct  2100
tcaaaaacat aagagtcata aaagacaaag aaagagctat ggaaatatct ctgatcgcag  2160
gaggctaaac aggcataatg actgaatagc agacaataga ctacatcttg tgcagaagag  2220
aaaaaaaatg atagaaggat attattggac caactgacaa aactgaacta tgaacagtag  2280
attaggtaaa tgtatcataa cattaagttt actgacattg ataatgtact gtggttatgt  2340
aagagaagat ctctattctt aggaaatatg ccctgaagta tttaggagtg aagggctgtg  2400
atgagtaatt taccctcaaa tgggtcacaa aaaattgtgt gtgagagaga gaagggtttt  2460
attagttaat aattctatga actattttta ttcctatatg tttgtgtgag tttgaaacta  2520
tttccaaata aaaagttaaa aatggagatt acattctagt gggagggata gacgatctgt  2580
agataaatag gtaaaatatc cagtacatta gagagtgaaa agtcctcagg gaaaagtaac  2640
gcagggagga actgctgggg cagggtttgc attttgaggt agggtggccc agggagagcc  2700
tgcagaggag agaacctgaa tgaagaacta gaggtgagag aaggagccac gtgcacacct  2760
agggaggaac attccaggca cgggggacta gtatagaagg cagaagcatg gtgagcttgt  2820
ctccagtggc ttccctagat cccctcctgc gcatgtgcac acacacctgg tgtctctgtc  2880
atcgttccct cacagcactg tcacgatctg ccagtattct gtttattttg actgccacct  2940
ccccgcagtc tgaggatagc agcaatggct gtgttcacat tgttctccag tgcctggttc  3000
agtgcctggc gtatggtcag tgctccatag gtatgtgtcg gatgcacaag gctttgggtg  3060
taaccctctt gacgggtggg atcaacaggt ctgggactca ccatcttctc aaacagagcc  3120
ttcctcctcc actgctagcc atggtccagg acgctgggcg agacccactg tcttgctctt  3180
tgtaaggctg aagtccattt cccaggcggc tacacccaac agatgctgag caggctgggc  3240
caccctggga tccaagacac agagagaaag agcccctgtc tggcgcctga agcacatgcc  3300
agaggacagg agccagcagg agcctgtttc agcctagctg ggatttcat tctggaggcg  3360
tgagatctgg gagcccaagg ctttgaactg ggggaggttt ggggtgtttg cttgtcttct  3420
ccaaatggca tttctttctc ttccctag                                     3448

SEQ ID NO: 51          moltype = RNA  length = 752
FEATURE                Location/Qualifiers
source                 1..752
                       mol_type = other RNA
                       organism = Homo sapiens
SEQUENCE: 51
gtaactgcgg gcttgggccg caccaagggc ttaaaccaag tgctgggtct cttgggttgg  60
ggaaataggt tctgggtcgg cagatttaga aactgcagca gtttggcttt agtctggact  120
gtttcctgtg ttgctcattt tgagcgatca gcccagtgtt tggttcacac agctccggag  180
aaaaacaagt cacggcacag ccttgacttg ggactgcgca catcctgcgt tcccaggatg  240
tctcctgtgg ggccatcggc tcacagccgg gaagttcagc ccactctgcg gcctgtcggt  300
gtctggtccc catacaggag cactgagctg ggtcaaaggc tcctgagctg agccaggcca  360
ggcctgaggc catgcccacg cagcccaagg atcatgaggg cacaggacat agcgggaacc  420
aaggaagtga cctgagtgac ctccctgcct tctgacaaat gtatttgcag gattttcttt  480
ttttgaggag aattctgtca ttgccttaat ccactttaat cccctcgtgg gctgaaatgg  540
gcccaggatg gacgccacgc ttctttactc ttggatccac ctcctgcctt ccctacccta  600
caccagggta cccctgtctt gctcaagtga ggggagtgac tgtgtgcgcc ttctgtcagc  660
tcatcctcca caggggagcc agcccagggg gaagcagtaa tcagaagggc cagctcccag  720
cctgtgcccc caaccttctc tccacccccc ag                                752

SEQ ID NO: 52          moltype = RNA  length = 73
FEATURE                Location/Qualifiers
source                 1..73
                       mol_type = other RNA
                       organism = Homo sapiens
SEQUENCE: 52
gcaagagatt cccagggctg gggaaggtgg gtgggaatcc tctcctgctc acctcctctc  60
tcctgcccca cag                                                     73

SEQ ID NO: 53          moltype = RNA  length = 2725
FEATURE                Location/Qualifiers
source                 1..2725
                       mol_type = other RNA
                       organism = Homo sapiens
SEQUENCE: 53
gtaagcagat ggtggggcgt gccccttgtt gccttctgtg gatccacctg gatcctgtgt  60
tctccattga cacttggaag agtcctgctg ctccgtcatc ccctggggca gaggcaggtg  120
gtggctgggc ctcattctcc agcagcagat ggagaaggcc atcatgctga taagaaactc  180
ctctatattg gcctaatttc ctgtggtcga agactcgccc aagtctctgg atggggcatc  240
tgatcaggat gcatgcagag cctggctggg atgagggagg gctgctacca ctgcctcaat  300
atttcaccac ttatctcaac agatccggga cctgtggcct atttactaag agtccactcc  360
aatgtaggaa tggttaggag accaactgac ttgaggaccc atctttgttt ttagaatatt  420
gtatgctttt gagtttgaaa aaagaccata tgttatatga caaaccaaca atggcagtaa  480
tcttgaatag gattatcctt atcctgtacc cacacattgt aaactattgt agataattcc  540
ttattattaa gagtttgcat gccaaagcta acagtttaag attatcagca tattgccgtg  600
ctcattcacg ttctgatatg ctttataacc tagaaaagag cagagttaca attactcatt  660
tatttaacaa acacttatta agagctcaga atataagtca ctaagctggt tggtgggagg  720
aacagcacat aacccacctt atctatgctg aggtgcataa tcctgatgca cccacaggag  780
ggtgttacac agaagatgtc atcctttcat atgtgtcaga gcagataaat aattgagaga  840
aaggtctaat agattagctg cttgtggcaa gtggacgttt gacccatgat ttattgagca  900
actacaactt ggacactgca tagatatcta tagaaatagc agcatgtcag gtcaccagac  960
ctgtgtcagc aacttcctgt gtccaactgc tggagaaagg gaagtctcct attcctttcc  1020
ctccagctcc ttaatatctc catgatagag ggggtgagag gggagtgttc cctgtgtgga  1080
```

```
gggatggtga gttttctgga gctgaaaggt aaacagcctt tctcctctgc atcttactgc  1140
agaggagaac agccctagac tgtggaggaa gctttggagt cagttatgac tgacacagga  1200
taccagggca tagggtactg acacccgcta gccgtgcaca cactctctgg tggaccatca  1260
ctcatccaag agagggtaac cagccatcct gctgaaggag aaagaaagca ccaatggccc  1320
aagccctagc agctccattg tttcaggaag cttcctcagg gaagtgctgc cttcccgagc  1380
ctttgctccc acctggccca tcagccctta ccaccactca gtatgcactg gtccacgtgt  1440
ctttatgggc agtcttggga tccccacact gggctaaaac tacctttgac ggccaggtgc  1500
agtggcttac acctgtaatc ctatcacttt gggaagctga ggcaggtgga tcacttgagg  1560
tcaggagttc gagaccagcc tggccaacac ggtgaaaccc tgtctctact aaaaatacaa  1620
aaattagatg ggcatggtgg tatgcacctg taatcccacc tactcgggaa actgaggcac  1680
aagaattgct tgaactcaga aggcagaggt tgcagtgaat cgagatcaca ccactgcact  1740
ccagcctggg tgaaacagca agactctgtc tcaaaaaata aaataggctg ggcgtggtgg  1800
ctcatgcctg taatcccagc actttgggag gccaaggcgg gcggatcact tgaggtcagg  1860
agtttaagac cagcctggcc aacatagtga aaccctgtct ctactaaaaa tacaaaaaaa  1920
aaaaaaaaaa ttagccgagt gtggtggcag gtgcctgtag ttccagcctc tcaggagact  1980
gaggcaggag aattgcttga acccaggagg cggaggttgc agtgagccaa gatcatgcca  2040
ctgtactcca gcctgggcaa cggtgagact gtctcaaata aaataaaata aaataaaata  2100
aaataaaata aaataaaata aataaaataa aataaataaa actacctttg acttcagcaa  2160
gtacgattat cccacattac catgcagaca tttgatctct aaaaactggt atcaaatgat  2220
ttctccaggg actaccatgg tttttctctc ctagttttca gtatgtacac aggtctatgg  2280
tatgggcctt taatccccag tatttctttt tttgttgttc ttgtttgggt ttgtttcttg  2340
tttttcggtt tttttgagac agggtctcac tctgtcaccc aggctggagt gcagtggcat  2400
gatcatggct cactgtagcc ttgacctcct atgctcaagt gatcctcccg cctcagcctc  2460
ccaagtagct gggaccacag gcatgtgcca ccatgccctg ctaattttcg tagagacagg  2520
gtctttcttg ttgcccaggc ttatcttaca ttcctgagct caagtgatcc tcccacctct  2580
acctcccaaa ttgctgggat ttcaggtgtg agccaccaag ctgagcttaa tccccaaaat  2640
ttctgatgag tctactcctt attttgggat taccttaggc ccaaccacta acagaggcct  2700
gtcctgcact gtgtgcatcc cctag                                        2725

SEQ ID NO: 54           moltype = RNA  length = 1665
FEATURE                 Location/Qualifiers
source                  1..1665
                        mol_type = other RNA
                        organism = Homo sapiens
SEQUENCE: 54
gcaagttggc cctggggcac cgagagctga gcaaagactg gtccagaaca cccagtgtgg  60
gttggaattg ccataagagg gaggcataac attcccgatt tttaacaaac tcttgccctc  120
tgtttattgg ggtaaaagct gatatatcag aaattgtttt ctaacaatat tttttagtca  180
tcaggaaact tcattgattc tttttttttac attttccttc cctgtgatgc tatggtgtgt  240
tatttcattc ttgctcgttt gtggtggtgg tttttccttc aaatcagctt tattgatgtg  300
taattaacat acgatgaaac acaggttctt tgggaggcca aggcaggagg atcacttgag  360
cccaggagtt taagacaggc ccatgtaaca aagtgagact ttgtctctac agaaaaaaaa  420
aaaaaaaatc agaaaattag ccaggcgtgg tggtgcatgc ctgtggtccc atctacatgg  480
gaggttgagg aaggaagatt gctggagccc aggaggtcaa ggctgcaatg agctgtgttc  540
ataccactgc actctagtct gggtgacaga gcaagcccct gtctcaaaaa agcaaaacaa  600
aacaaaaaca cctattttaa atgtacagtt tagtgagttt tgataaacgt gcattccatg  660
tgtggttttt aaaaatgtaa tcacattttt tattgcggta aaatataata acataaaatt  720
gaccatgcca accatgttta agtgcacagt gcagtggcac taagtacatt tacattgttg  780
tgcaaccgtt accaccatcc ccgatagaac tctttcatct tgcttcagtg aaaatctgtg  840
cccattaaac actaactcac cacttactgc ccccctcgcc cttggcaact actgttctac  900
tttctgtctc taaggctctg actactatag atacctcata taagtggaat catacagtgt  960
ttgtcctttt gtgtctggct tattatgcga ggacttagca taatgtcctc aaggttcatc  1020
cgtgttgtat catgtgccag aatttccttc ctttttcagg ccgaataata ttcctttgta  1080
cgtatatgtg ctacattttg ttcatccatc tattcattca ttgatagaca tttgggttgt  1140
ttctgggttt tgtgttttta tatatgtttt tttaaaaata aacatcttta gagacagttc  1200
agtaaagcag tggaaacagg gaagtctcca tttaacccct gaggatctgg ctcacctgca  1260
ccttctcatc agcattaagc agagggaggc acgagcagga gccacctgca cactcaatga  1320
ggagctgaac agggatcaat taccttttttt tttagttatt aggatgctgc tagctgagaa  1380
tctgccttgc cttgattacc ccaatgtctg gtgcccaagt cccttgagtc ctccagcagg  1440
aactcctgtg gcatcactca ggagtctagt ctaagaagct agctctgacc agggcagtgg  1500
tggccaggct tctgtgagtg ggccagcctc ccccgggtag gacacaagcc ataccagcag  1560
ggctgtatgt gaactgtgga aaatagagag caaagtgggt aggtgggtgt agggtgctgt  1620
tttcctggaa atatctacct aatctcgctc ttctcttacc tctag                  1665

SEQ ID NO: 55           moltype = RNA  length = 2866
FEATURE                 Location/Qualifiers
source                  1..2866
                        mol_type = other RNA
                        organism = Homo sapiens
SEQUENCE: 55
gtacccctgc tgcttatgca gtccacagct tgaggcagtt ccttggctca gagcccagct  60
ggttcactgg gcttgagttg ctccaaggct cagatatgcc tcctacagag agccccaccc  120
acaccacggt ccctaccaag tccccaccac atcctcatca catccttgct aagtccctgc  180
cactgtgtgt tctgtgctga agaacttttc attcagtagt tgtaggggtt cctattgtaa  240
tcaggaaacc atctggatag catgggagag catttttgaa aagaactttc ccatgttttt  300
gcttacagca aaaaagcttg gatttgggga ataaggagca gagaaggtaa tagagaatat  360
tagaatgttt tgggtgcttg acatctatgt ctggacatgt gtttgagttt caagggaagg  420
gacttaactg gcacatcatt tcagtgtcag acacatttgg ttagatcaag gaatagcatc  480
tgttgtagga agagggctct ttgttcttta taaaaattac aagaagatgg agaaagaagc  540
```

```
aataggaggt atgtctcctg gcttgtgata actcttggaa taggtgcttg taggttcctg  600
ccctggcaca gtgccccatg taaggagcac accacccaag aaggagagag ctagagcaag  660
tactggagga ggcaccagca tcccaatgcc ttggcttaag cctgggattg tagagggatg  720
aattagccac tctcttctga cttacctgga gagtaaatca aatcaaatca agaagcaagg  780
atatgcaaaa accttatttc cccataaagt tttattctg cccagtttct ggattgcaag  840
aaaaaccaaa tacagctaat gattgaaaca ctgctgtcta aagcagtgct tgtgatgaat  900
tttttccctt cctcttgacc agcagagacc taatggctac ttggcaaaac tgactttgtc  960
ttcccacccc ttacctgcca gagggcccag aaatgcctaa ggctccttta gttacagaaa  1020
gtttgctttt actgagatct tccagccact gattcccatt tatagatctg gtgattgctg  1080
ttgacatcag ttgaaaatta tttttaaaaa ccacttgcag ttgcaaatcc tttttataac  1140
tctgtaactc agaatataga attgggtagc aaaattgttt cccagaatta ccaatggtct  1200
ccccacccct gcctggcatg ttccctctta aaggactaat cccaccacat cacctctggg  1260
ccaggcagaa catcaggggt gctgatgttc tgtgatctac agcagttaat tccaaacttt  1320
tctcccttat tggatgagat cattttteta ttgtgttttt tacatttttg ttcacaaaga  1380
ttagaaaacc tgcaacacac ttattggcat atttttctga taattttcat ccaaaaccta  1440
attctgactt tacaacatac tatctttaca aaggtttgca aaaattcttt catatagcat  1500
tgtatatgtc tgtcatgaaa taatagtaag tatattattg tttacattat accacttcaa  1560
aataatttcc tttaaagtat tcttcaaaca agaaaaaggc aatttctctc aagaagtttt  1620
agagagaatt tacaacttgc tcctaagcaa atgtgagaac ttcaggaggt tcatctggcc  1680
attggcttta caactccaaa ttgtgagcca ggaccacaca gatatttctc tagaaatcag  1740
cgtttgctta ccaagaacat ttttactctc caaaggactc catcctggaa aacatgtttt  1800
gggataaggt cttatgcaat cttatactct gttattaaaa ccagtgaggg tcaaggtgtt  1860
aatagattaa gtagtgacag atgatcagac aacttagaaa catcctaaat aggttaataa  1920
ttatgtgacc atcgcatgtg cattcccaaa ttaggaacaa ctcagatcaa tttctaatcc  1980
ttattcttac actgttccag ttccccata taactcgtat ctttgtgtta gtttcagaag  2040
tttctgaagt accctcagcc ttgatgggga tcctcgcacc acctcaaatc ctgttctcag  2100
ccctaagaac tgtgttagtc atcctcttaa gaggatgtgt gattttaaat cagataatgg  2160
gataaaccac atttcgtcta gactggtcag gcctttgtcc agtcccctcc tcgcccacac  2220
taccccagct ccacagcggg cattggttca ggaattcaac ccacacttta taactggaga  2280
cagtatctct ccagttaaaa aggtcacctt ggtgtccgct tctcaaggaa catggacatc  2340
tttattaatc aaagcccaag ctttgatctg gagcctaata tcctgcactc cagctctcat  2400
ctctcccctc ccccagtcac actttcatgc ttcccagagc cacccctaca ggaagtggtc  2460
aagggaattc tatacctcag ggctgaccta aattaggatt tcttggcttt taagataatg  2520
gtaactttct taagctaaaa aagccccaaa agaccctgta agagcccttg gaaacagcac  2580
catgggtgta gcttcccccc aggatgtaag catgtatgca cacatctcgt atgtgtgtct  2640
ttgtaacaaa tgcctggatc ttagtaccag ggagacctga ttcatagatt tcatagagaa  2700
ggagagaaag atggcccata acctgggtga tctgacagaa tcacagtgcc ctcagctgag  2760
tgcccttcag aaattgattg acaactgttt agcttttgaa atctaaaagt agtacagcat  2820
ctcagaaaac caagatgacg cgagtccatg tgatctcctt ccacag                 2866

SEQ ID NO: 56          moltype = AA  length = 738
FEATURE                Location/Qualifiers
source                 1..738
                       mol_type = protein
                       organism = synthetic construct
SEQUENCE: 56
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                                 738

SEQ ID NO: 57          moltype = DNA  length = 4393
FEATURE                Location/Qualifiers
source                 1..4393
                       mol_type = other DNA
                       organism = synthetic construct
SEQUENCE: 57
cagagaggga gtggccaact ccatcactag gggtagcgcg aagcgcctcc cacgctgccg  60
cgtcagcgct gacgtaaatt acgtcatagg ggagtggtcc tgtattagct gtcacgtgag  120
tgcttttgcg gcattttgcg acaccacgtg gccatttgag gtatatatgg ccgagtgagc  180
gagcaggatc tccattttga ccgcgaaatt tgaacgagca gcagccatgc cgggcttcta  240
cgagatcgtg atcaaggtgc cgagcgacct ggacgagcac ctgccgggca tttctgactc  300
gtttgtgaac tgggtggccg agaaggaatg ggagctgccc ccggattctg acatggatcg  360
gaatctgatc gagcaggcac ccctgaccgt ggccgagaag ctgcagcgcg acttcctggt  420
ccaatggcgc cgcgtgagta aggccccgga ggccctcttc tttgttcagt tcgagaaggg  480
cgagagctac tttcacctgc acgttctggt cgagaccacg gggtcaagt ccatggtgct  540
aggccgcttc ctgagtcaga ttcgggaaaa gcttggtcca gaccatctac ccgcggggtc  600
gagccccacc ttgcccaact ggttcgcggt gaccaaagac gcggtaatgg cgccggcggg  660
ggggaacaag gtggtggacg agtgctacat ccccaactac ctcctgccca agactcagcc  720
cgagctgcag tgggcgtgga ctaacatgga ggagtatata agcgcgtgct tgaacctggc  780
```

```
cgagcgcaaa cggctcgtgg cgcagcacct gacccacgtc agccagacgc aggagcagaa  840
caaggagaat ctgaacccca attctgacgc gcccgtgatc aggtcaaaaa cctccgcgcg  900
ctatatggag ctggtcgggt ggctggtgga ccggggcatc acctccgaga agcagtggat  960
ccaggaggac caggcctcgt acatctcctt caacgccgcc tccaactcgc ggtcccagat  1020
caaggccgcg ctggacaatg ccggcaagat catggcgctg accaaatccg cgcccgacta  1080
cctggtgggg ccctcgctgc ccgcggacat tacccagaac cgcatctacc gcatcctcgc  1140
tctcaacggc tacgaccctg cctacgccgg ctccgtcttt ctcggctggg ctcagaaaaa  1200
gttcgggaaa cgcaacacca tctggctgtt tggacccgcc accaccggca agaccaacat  1260
tgcggaagcc atcgcccacg ccgtgccctt ctacggctgc gtcaactgga ccaatgagaa  1320
ctttcccttc aatgattgcg tcgacaagat ggtgatctgg tgggaggagg gcaagatgac  1380
ggccaaggtc gtggagtccg ccaaggccat tctcggcggc agcaaggtgc gcgtggacca  1440
aaagtgcaag tcgtccgccc agatcgaccc caccccgtg atcgtcacct ccaacaccaa  1500
catgtgcgcc gtgattgacg ggaacagcac caccttcgag caccagcagc ctctccagga  1560
ccggatgttt aagttcgaac tcacccgccg tctggagcac gactttggca aggtgacaaa  1620
gcaggaagtc aaagagttct tccgctgggc cagtgatcac gtgaccgagg tggcgcatga  1680
gttttacgtc agaaagggcg gagccagcaa aagacccgcc cccgatgacg cggataaaag  1740
cgagcccaag cgggcctgcc cctcagtcgc ggatccatcg acgtcagacg cggaaggagc  1800
tccggtggac tttgccgaca ggtaccaaaa caaatgttct cgtcacgcgg gcatgcttca  1860
gatgctgttt ccctgcaaaa cgtgcgagag aatgaatcag aatttcaaca tttgcttcac  1920
acacggggtc agagactgct cagagtgttt ccccggcgtg tcagaatctc aaccggtcgt  1980
cagaaagagg acgtatcgga aactctgtgc gattcatcat ctgctggggc gggctcccga  2040
gattgcttgc tcggcctgcg atctggtcaa cgtggacctg gatgactgtg tttctgagca  2100
ataaatgact taaaccaggt atggctgccg atggttatct tccagattgg ctcgaggaca  2160
acctctctga gggcattcgc gagtggtggg cgctgaaacc tggagccccg aagcccaaag  2220
ccaaccagca aaagcaggac gacggccggg gtctggtgct tcctggctac aagtacctcg  2280
gacccttcaa cggactcgac aaggggggagc ccgtcaacgc ggcggacgca gcggccctcg  2340
agcacgacaa ggcctacgac cagcagctgc aggcgggtga caatccgtac ctgcggtata  2400
accacgccga cgccgagttt caggagcgtc tgcaagaaga tacgtctttt gggggcaacc  2460
tcgggcgagc agtcttccag gccaagaagc gggttctcga acctctcggt ctggttgagg  2520
aaggcgctaa gacggctcct ggaaagaaga gaccggtaga gccatcaccc cagcgttctc  2580
cagactcctc tacgggcatc ggcaagaaag gccaacagcc cgccagaaaa agactcaatt  2640
ttggtcagac tggcgactca gagtcagttc cagaccctca acctctcgga gaacctccag  2700
cagcgccctc tggtgtggga cctaatacaa tggctgcagg cggtggcgca ccaatggcag  2760
acaataacga aggcgccgac ggagtgggta gttcctcggg aaattggcat tgcgattcca  2820
catggctggg cgacagagtc atcaccacca gcacccgaac ctgggccctg cccacctaca  2880
acaaccacct ctacaagcaa atctccaacg ggacatcggg aggagccacc aacgacaaca  2940
cctacttcgg ctacagcacc ccctgggggt attttgactt taacagattc cactgccact  3000
tttcaccacg tgactggcag cgactcatca acaacaactg gggattccgg cccaagagac  3060
tcagcttcaa gctcttcaac atccaggtca aggaggtcac gcagaatgaa ggcaccaaga  3120
ccatcgccaa taacctcacc agcaccatcc aggtgtttac ggactcggag taccagctgc  3180
cgtacgttct cggctctgcc caccagggct gcctgcctcc gttcccggcg gacgtgttca  3240
tgattcccca gtacggctac ctaacactca acaacggtag tcaggccgtg ggacgctcct  3300
ccttctactg cctggaatac tttccttcgc agatgctgag aaccggcaac aacttccagt  3360
ttacttacac cttcgaggac gtgcctttcc acagcagcta cgcccacagc cagagcttgg  3420
accggctgat gaatcctctg attgaccagt acctgtacta cttgtctcgg actcaaacaa  3480
caggaggcac ggcaaatacg cagactctgg gcttcagcca aggtgggcct aatacaatgg  3540
ccaatcaggc aaagaactgg ctgccaggac cctgttaccg ccaacaacgc gtctcaacga  3600
caaccgggca aaacaacaat agcaactttg cctggactgc tgggaccaaa taccatctga  3660
atggaagaaa ttcattggct aatcctggca tcgctatggc aacacacaaa gacgacgagg  3720
agcgtttttt tcccagtaac gggatcctga tttttggcaa acaaaatgct gccagagaca  3780
atgcggatta cagcgatgtc atgctcacca gcgaggaaga aatcaaaacc actaaccctg  3840
tggctacaga ggaatacggt atcgtggcag ataacttgca gcagcaaaac acggctcctc  3900
aaattggaac tgtcaacagc caggggggcct tacccggtat ggtctggcag aaccgggacg  3960
tgtacctgca gggtcccatc tgggccaaga ttcctcacac ggacggcaac ttccacccgt  4020
ctccgctgat gggcggcttt ggcctgaaac atcctccgcc tcagatcctg atcaagaaca  4080
cgcctgtacc tgcggatcct ccgaccacct tcaaccagtc aaagctgaac tctttcatca  4140
cgcaatacag caccggacag gtcagcgtgg aaattgaatg ggagctgcag aaggaaaaca  4200
gcaagcgctg gaaccccgag atccagtaca cctccaacta ctacaaatct acaagtgtgg  4260
actttgctgt taatacagaa ggcgtgtact ctgaaccccg ccccattggc acccgttacc  4320
tcacccgtaa tctgtaattg cctgttaatc aataaaccgg ttgattcgtt tcagttgaac  4380
tttggtctct gcg                                                    4393
```

```
SEQ ID NO: 58          moltype = AA  length = 738
FEATURE                Location/Qualifiers
source                 1..738
                       mol_type = protein
                       organism = synthetic construct
SEQUENCE: 58
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLPERT AMSLPGTVNS  600
QGALPGMVWQ NRDVYLQGPI WAKIPHTDGN FHPSPLMGGF GLKHPPPQIL IKNTPVPADP  660
```

-continued

```
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 59          moltype = DNA  length = 2214
FEATURE                Location/Qualifiers
source                 1..2214
                       mol_type = other DNA
                       organism = synthetic construct
SEQUENCE: 59
atggctgccg atggttatct tccagattgg ctcgaggaca acctctctga gggcattcgc  60
gagtggtggg cgctgaaacc tggagccccg aagcccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctgc aggcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccaacagcc cgccagaaaa agactcaatt ttggtcagac tggcgactca  540
gagtcagttc cagaccctca acctctcgga gaacctccag cagcgccctc tggtgtggga  600
cctaatacaa tggctgcagg cggtggcgca ccaatggcag acaataacga aggcgccgac  660
ggagtgggta gttcctcggg aaattggcat tgcgattcca catggctggg cgacagagtc  720
atcaccacca gcacccgaac ctgggccctg cccacctaca acaaccacct ctacaagcaa  780
atctccaacg ggacatcggg aggagccacc aacgacaaca cctacttcgg ctacagcacc  840
ccctgggggt attttgactt taacagattc cactgccact tttcaccacg tgactggcag  900
cgactcatca acaacaactg gggattccgg cccaagagac tcagcttcaa gctcttcaac  960
atccaggtca aggaggtcac gcagaatgaa ggcaccaaga ccatcgccaa taacctcacc  1020
agcaccatcc aggtgtttac ggactcggag taccagctgc cgtacgttct cggctctgcc  1080
caccagggct gcctgcctcc gttcccggcg gacgtgttca tgattcccca gtacggctac  1140
ctaacactca acaacggtag tcaggccgtg ggacgctcct ccttctactg cctggaatac  1200
tttccttcgc agatgctgag aaccggcaac aacttccagt ttacttacac cttcgaggac  1260
gtgccttttcc acagcagcta cgcccacagc cagagcttgg accggctgat gaatcctctg  1320
attgaccagt acctgtacta cttgtctcgg actcaaacaa caggaggcac ggcaaatacg  1380
cagactctgg gcttcagcca aggtgggcct aatacaatgg ccaatcaggc aaagaactgg  1440
ctgccaggac cctgttaccg ccaacaacgc gtctcaacga caaccgggca aaacaacaat  1500
agcaactttg cctggactgc tgggaccaaa taccatctga atggaagaaa ttcattggct  1560
aatcctggca tcgctatggc aacacacaaa gacgacgagg agcgtttttt tcccagtaac  1620
gggatcctga tttttggcaa acaaaatgct gccagagaca atgcggatta cagcgatgtc  1680
atgctcacca gcgaggaaga aatcaaaacc actaaccctg tggctacaga ggaatacggt  1740
atcgtggcag ataacttgcc tgagcggacg gcgatgagtc ttccgggaac tgtcaacagc  1800
cagggggcct tacccggtat ggtctggcag aaccgggacg tgtacctgca gggtcccatc  1860
tgggccaaga ttcctcacac ggacggcaac ttccacccgt ctccgctgat gggcggcttt  1920
ggcctgaaac atcctccgcc tcagatcctg atcaagaaca cgcctgtacc tgcggatcct  1980
ccgaccacct tcaaccagtc aaagctgaac tctttcatca cgcaatacag caccggacag  2040
gtcagcgtgg aaattgaatg ggagctgcag aaggaaaaca gcaagcgctg gaaccccgag  2100
atccagtaca cctccaacta ctacaaatct acaagtgtgg actttgctgt taatacagaa  2160
ggcgtgtact ctgaaccccg ccccattggc acccgttacc tcacccgtaa tctg        2214

SEQ ID NO: 60          moltype = RNA  length = 565
FEATURE                Location/Qualifiers
source                 1..565
                       mol_type = other RNA
                       organism = Homo sapiens
SEQUENCE: 60
gtgggtggat ccttgtaagc aggattagcg agtcactcca cgctcaggtt ctttagcctg  60
agggcccgtg tgccacagca tagctacccc gcccttccag cctcgggtcc ctaatactgc  120
cttgcttcgg ttccagtttc cgccgcacaa cttcactcat tccaaatgtt aatttctgcg  180
tttttttca gccccaattc tgtttctcca aatcagggat gattgtcggc cttccacaga  240
ccctcgcgct tgccaggatt agggtgttcg cgcgcattgt gggtaggggt gtggaggaag  300
ggatccagaa atcttaagta ttaacttaga ttagtgttag caaggaagcc gtcacatttt  360
atttagccgg gacactctga cagtttgtgc cgactgctat ttttgatcaa ggctattttg  420
cccacttgtc tattttgtgg cccaattgtc tgttttgcta acatcagaaa gttataatga  480
aataatctgc aaaaaatgta aggtgctaga aaaccaataa tactgtgtac cttgaaaatg  540
ctaatataca cctgttttgt tacag                                        565

SEQ ID NO: 61          moltype = RNA  length = 172
FEATURE                Location/Qualifiers
source                 1..172
                       mol_type = other RNA
                       organism = Homo sapiens
SEQUENCE: 61
gtgcttaatt ggtcaataat aatagatata tacattaact tatgattaat ttattaataa  60
aatatgaatt tattttttc agggacaact ataattgtca caatctggaa gtgttcttat  120
attttgcttg aaggttataa aatataaaac agttgctttt ctgtttactt ag          172

SEQ ID NO: 62          moltype = RNA  length = 1391
FEATURE                Location/Qualifiers
source                 1..1391
                       mol_type = other RNA
                       organism = Homo sapiens
```

```
SEQUENCE: 62
gtttgtatgt agtaggtttt aactataggt ttggctatta gtggaactat aaaaatctgt  60
tcttatataa ggtaatcttt gtgaaaatac ctggtaatat ctacatcacc actaaaaaat  120
gcaatatatt taaatgtgaa ttaagtattt tagtgtataa aacattgcta gtttctactt  180
aaagtttcta aaagggtgtg taggggaaat agaatgagta tgttgaaaag taacataagg  240
aaatatatct tgaggtccaa atgacaaatg cagacaatga ctgctatagg gatttgttaa  300
gaggggaaat gatttaagag atgtcagaag acttcacaaa ggatcaatac tgaggagtag  360
tgttagataa gtggaaggca atgcagtggt aagatagtaa gggaattcta gagctgttgg  420
ttaccataaa taaatactga gaacaggaaa tatgtttatt ctttatattt gaggaaacaa  480
ggtgcagcaa gtttgtagca gactgtagag aaaacaaatc ttgggtaagt actttgagat  540
aggttgttga gggccttaaa ggtgtatttt atgctatcag caattgagaa ggcagtaaag  600
gttttcgaaa cacaattgat aggtacaaaa atacacctta agaaggcaaa actgagtata  660
ttatgtagga caaactgaag gaaattggag ctttgtagac atcacattat agcggagttt  720
aaacctgaaa ttatggatta gaataatagc aattggaaca gaaaaaaagt agtggaaaga  780
cattacaaag ggagatgttg cattactgga tataagactt gaggacttga ggtaaaaagg  840
agaatcaaaa atgtttcatg ctattaaaaa tctagaaatt gtagtcttaa gtaagaaaat  900
tgcctggcat ggtggctcac gtctgtaatc ccagcacttt gggaggccaa ggcaggagga  960
ttgcttgagc ctgggagttc aagactagcc tggataatat agtgagtcct tgcctgtacg  1020
aaaaaatttg ccgagcatga tggcacacca agcatgatgg cacgccaagc atgatggcat  1080
gcacctgtag tcccagctac tcaggagact gagatgggaa gattgcttga gcccaggagg  1140
caggaggttg cagtgagctg agattgtgcc actgcactcc agcctgggtg acaaagtgag  1200
gccctatctc aaaagcaaaa aaaacaaaaa caaaaaccaa aaactattta ttcagcaaat  1260
atttactgaa cgtctccatg tgccagccat tgctggcact aaggatcata acaaataaaa  1320
cagaattttt attttcagtg cttacattcc agtataaagg catattgaaa taaccttttt  1380
ttaatgttta g                                                        1391

SEQ ID NO: 63           moltype = RNA  length = 303
FEATURE                 Location/Qualifiers
source                  1..303
                        mol_type = other RNA
                        organism = Homo sapiens
SEQUENCE: 63
gtaagcacct tggaaaaagt ttattatggt attaaataat gaattccatt tgttcattaa  60
actgtagaaa attaaattat attctataaa atatatatat tcagtttatt tttaatatat  120
aacatttaat aataaatatt tctagactcc tattttatgg atctgccata taatactttt  180
tgttacctta taatcatgat ggactctttt aaaagaatta attttgttat tgaaatttat  240
ttaaaagttt gttttgtggt aactaatcaa ttaaaacgtt tttctttttt tttaaaaaaa  300
tag                                                                 303

SEQ ID NO: 64           moltype = RNA  length = 2358
FEATURE                 Location/Qualifiers
source                  1..2358
                        mol_type = other RNA
                        organism = Homo sapiens
SEQUENCE: 64
gtatgtcttt ttgtattccc taggatgtaa ttgtcattaa ttttattttg aattgttttc  60
aaattttaaa attattgttg gctggaaaaa ttataaggat gattgtaatc atggttattt  120
gtttattctg tatatgttct acatgcctat tatgtgcctt atatagtact aaggactgag  180
catatggttg tgaacaaaat aagaagttaa ctgctggatg gagcttatag tcttgggaaa  240
tatacagaaa gattactagt aactgaggtg gagggtgggt ggggatttga ggaatagtga  300
cgaaagggtg ttatagaagt aatttttgac aaagctgaag gctaaaatat gaatgtattg  360
ttgaagaaca aaatacattg agattcctga gaaggtagga atgtgataca aatggatcag  420
cctttgaaag gaggaatacc cttttccttt gtgttaggag aggaggatga gtggatgagc  480
gtgggaagag tggatgtgta tagaggcttt tatgtttgta ggcataatgc ttggaagttg  540
aggggttggt gatgacatct tctgttaaaa agagtgggaa atggtgtggt cacattttaa  600
ggaaattagg taaaatttga aatatattgg agacaggact ggagagttgg ggatctggag  660
tcagacagat ttgagttcta gtcctgattc ttctactcgt taactctctg aacttggatg  720
acctattgtt tttgattgta tatccagctc ctgggaaaat gccaagcact ttcaataaat  780
actaaatgaa ttatggagtt ggatcagttc tgtgttagtg tttagctagg tagctgctgt  840
agaatagaag ggtagcacag ttgaagatat tggtaggaaa gtggttgaag tgatgattat  900
gaagtcttaa ctgaatagat aaaatcaaga ttggggttgg gtgggcagaa gggtagggat  960
atggagggag aagatgaggg gttagagtgt cctgtgaggt cgaaggacag gcatagtggg  1020
aataattgaa agaatgttct ggttggacaa ggatctgatg tgggtgtggg agtgagagac  1080
tatagtgaat tcaagaaaaa aatagactag aacaaaagtt atgtggagat tgcttagtgg  1140
gcatttgata gacatctgtg ggccacatgc ttaaattccc agtgcatttt gcggagttac  1200
tggaaggttg gtggcttgtt tctaccatga gtaggtaaag atggagagca ggatattttg  1260
tgagaaagca gctgaagttt ctataggatg atggaggaat gataggaatg atcacctgaa  1320
gttgcagggt ggggtaaacc tagaagcacc aacaccttct tctgaccctc atgtatttgg  1380
aatctgaaag aatgagcacc ttccaattga aagagttcca agggcattag tatactaaag  1440
gatccaaatt gcagctaagc caaggagatg gaaaggagga ttcagtaaag aatctgagga  1500
tgtgaaatat taatttatct tggaagagaa ttttagagag cacaatggaa tgctttttgg  1560
aggagagaaa gagtaagaac aatttggtta aggtagagga ataacagaac tataaggtga  1620
agaaatgaat gtgagacaca ttagatgacc aaatgatttg atgttcttgg ccatgacctg  1680
aattaacaag actgtgaggt aaaatggatt taatcggcta caaatcttaa gataaccaaa  1740
acctgagctg tttaatatgg tagcactagc actaaccact tgtagctatt tatatttaca  1800
ttggttaaaa ttaaaatgaa aaatttagtt cttcagttgc actagccaca cttcaaatgc  1860
ccgaacatag ctacatgtag cgagtggcta ttgaactgga cagcactgac agcatgtcca  1920
ttatgctaga aagtcctatg ggacagcact ggtctaaaca gtgcatggta tgagagaaag  1980
ggcaggttaa ggcactcagc ttcactgact ggggtggaga ttctgatggt ttgtactcag  2040
```

gttccagatc cctgaggctc aggaaccttt gcagtttagt ctggttacct gtggcccagt 2100
ggttacaaca gaatgattaa cagtcaattc tttgcatctc tgggtggctc aggaaaaatt 2160
taaggagtta ttagctgtga actaacctta agtaagttaa attaaaaaaa aaaaagttct 2220
taagctaata tgattttaaa tatctgcact gaagtataat gcaaatttaa attcagcata 2280
attatttgct tgttgttgac tcatttgaac ctcaaaatat aatgggatta atttatactt 2340
tgggtttatt actttaag 2358

SEQ ID NO: 65 moltype = RNA length = 5424
FEATURE Location/Qualifiers
source 1..5424
mol_type = other RNA
organism = Homo sapiens
SEQUENCE: 65
gtaaagcact tttttttcc atgaatcttc actgttcaag ttacctggct ttttattatt 60
attggtaaca atatcaattt ttatattgta tgttatattt gaaaaatgat gtacacttat 120
ctctaaggtt ttatatcact gttcattttg tcatcaccaa ttttaaaata taatggtact 180
tctagtgaat atgacttgaa gattaattct ttatatttgg aagtacattt ttctcaggac 240
atcaaacttg ttacctaaaa ttaatgcttt tgtctggaag attggtatca agtaactaat 300
agattttcat aaagaagtga tctttctagt gccatagttt attttgggta aaagttatat 360
ttgttcattt caatgtattt atatgattag tagattcgca aatgaatctt tcgatatatt 420
caataatggt taattaaata tcttgttttt ggttgtacct tattttatgt gagatatata 480
tatatatgta tagtttttga aaagttgtgt tcatgtcagc agtttataaa tcacatattt 540
aaaataacat ttttaatgca tagtttttat tacctcgtta ttccttgtta taaactaata 600
attcttgcag tgttcacttg aatttagttt taggaaaaaa gtttttttgca gatcaacttg 660
tatttcctgg aagaaaattt cctattttac ctcagcttcc tatttaatgt attatttatt 720
tatttactta acatttattt gtttttttatt tcacctgaac tgttagtaaa cttagtaaaa 780
tttggtgcct acatgtggta actgtcctgt cccttatact cagaaacgtt ttccaccttt 840
gtgtccttta ggtcattgtt gtgttatatt ccatttattt tattttgtcc attgttctct 900
cagaaattga gggtcataca ttttaagaaa acaatgatat gctatttaag agaatgtatc 960
ataaattgat ttgtaaggaa aagtatcccc attcttcatg tatgtatttt actctaaaat 1020
gttgaagaat catatagaag ttagctatga aaacaatgtg gtagagaaag tatggatcga 1080
tgccacttaa atgttaggaa gaagctctta gagcattatc tgtttagcta actgcaaaac 1140
atagcagaca tgtggatttt ttaatagtca tcaaggatct aacttataat atacactggt 1200
agaattgctt agggggatgt ctgtggtttt ctggactttt gttcttctat atagacctgt 1260
atcagttgac ttatcattca taccacacac ccttagctaa tcagaactac cttgtccatt 1320
tatatcttag actattgtct tttttcatag tcacacacag agaaaacttg aatatatggc 1380
ctgtgttcct ttttggctgc tcaattcctt gagatgaaat atgggtatgg gttgctttgg 1440
caattacttc tttgccgtta accagtcatt cagttttatt gagtctttac agcataccag 1500
aggctgctag ttactagtga tatagtgggc aactatgttc tggttctcaa gaatattcat 1560
agtcaataat aagcataaca tagtgataat atgatactta gggagataca taaggtcata 1620
ttctggcata ctctggagag agataccgta atcagccttg aggtgcagga tgtgatctgt 1680
aaactgagac ctgaagtata gttagactgg taagaggaat gaggatatat atggtggtta 1740
ataaaagaac attctgggta gaagatatag catttgctaa gacctagagg taagagatgt 1800
tatggagtat ttaggaaact acagttattc attttgactg aaatataagt gaaaatagct 1860
ttcatagagt ccttactatg tgccaggcac ttcatatgca ttaattcatt attgcttatt 1920
tgatacttgt catatgagat agttgtcatt tctgccatga tacagatgaa gaaatggaga 1980
cacagaaaga gtaattgccc atggttgcac agcttataaa tggtaaaggt aggatttgaa 2040
aacagtctta ctcaagagtc tgtgctatct tgccttccca gttttatttt ttatgatcct 2100
ctggagagat aagcaagggc cagttcctaa tgaatttggt tcttttcctg aaaggagcca 2160
gtgaagagtt ttgagcacag gatatcatga tcagatctat actttaaaag tttactgtac 2220
tttgtagaga gtggattgaa aagggccaag actagtaagg aaacatttgt gttaattcag 2280
ggaagtgcta atgatggcat ttgcctgaga aagacaagtg tgagagaagt agatgtaatt 2340
ggatgtggtg aatgtaattg gttgttggag gagagggagg atggagagtc tgcctaattt 2400
tgtgggttgg gccactaaat aggtagatag tgccattcat taaggaggaa cacaagagga 2460
atttggaaag cttgagatta tttcagtttt gtagatgttg agtttgaggt tcttctgggc 2520
atattcaaaa agggtatctg tggatatgga attcacaaga gaccctgtac agatgatgag 2580
gatttatgaa tcatcaatgt agacattatt gaagccagag aagtgattgt aaggcacgtc 2640
tctgagaaat gtctaataaa gcaatgaaat aggaagagtg cttcaaggaa aagctcaaga 2700
aaggagaaac agagtgtgat gtttgagaag acaagggaaa aaaacattaa tagcattaaa 2760
tgctttagca ttaagttctt ggcttctctt cttgtaaaaa tttcccaatt cagaacacag 2820
tgggattatt aactttcaat tgataataat aatgataggc aaacttctaa aatttgtatt 2880
gtagtttgca ttttattata aactttcttt aaatttttat tttgaaaaat gtcatatctt 2940
cataaagatt gtaagaaaca cactgttggt gttaatgtaa attagttcaa ccattgtggg 3000
agacagtgtg gcaattcctc gaagatctag aagcagaaat accacttgac ccagcaatcc 3060
cattactggg tatataccca aaagaatata aatcattttc ttataaagat acttgcacac 3120
atatgttcat tgcagcacta ttcacaatag caaagacatg gaatcaaccc aaatgctcat 3180
caatgataga ctggataatg aaaatgtgga acatatacat catagaatac tatgcagcca 3240
tcaaaagaga atgagaggtc aagcgtggtg actcatgcct acagtcccag cactttggga 3300
ggccgaggca ggcagatcac ttgaggtcag gagttcaaga ccagcctggc cagtatggtg 3360
aaaccccatc tctacaaaaa caaaacaaaa caaacaaaaa ttaactggtc atggtactgt 3420
atgcctgcag tcccagctac ttgggaggct gaggcaggag aatgacttga acccagaagg 3480
cagaggttgc agtgagctga gatcgcacca ctggactcta gccttagcaa caaaactaga 3540
gtttgtctca aaaaaaaaaa aaaaaaaaaa ccggaacaag atcatgtcct ttgcagggac 3600
atgggatgga ggtggaagcc attatcctca gcaaactcac acaggaacag aaaaccaaac 3660
actgcatgtt ctcacttata agtgggagct gaacaatgag aacacatgga cacatggtgg 3720
ggaacaacac acactgggac ccgtcaaggg gtcggggtgg gagaacatca ggaagaatag 3780
ctaatggatg ctgggcttaa tatctaggtt atgggttgat ctgtgcagca agccaccatt 3840
gtacacattt acctaagtaa caaacctgca catcttacac atgtacccca gaacttaaaa 3900
gttgatggga aaaagaaaaa caataaccac ccacataccc ttcatataga ttcaccagtt 3960

```
cttaatgttg tgccaacttt gctttatctt tttgtcagta tttttacaca cacatgtatt  4020
tctctgtctc ttgtttgttc aatcacattt tttgctgagt catttaagag ctaattgcag  4080
atatgatact ttgcacttaa atatttcagc ttgtctgttt gaaaaagaaa gatgttctcc  4140
tacaatgaac acaatataat tgtcatgctc aggaatttta atattgattc aacaccatta  4200
tctagtccat aatgagattt cttctaatgg cccaataata tccttcagtc tccccacctc  4260
caatatccaa agttctgtca aggatcacat actacatttg gttctttatt atagactttt  4320
taaatatcgt tgtataccat tgtgattcta tcgtctcctt taataaagag gagaaccaga  4380
aaaatgaaag gtcataagag gaatgaggtt tggagaatag gtgaaaaaag gcatcataat  4440
gtttataata atgtttgcct gttcagagaa acaagaatca cagataaagt cacttatatg  4500
tagataagag aatgctgtat tactttttgc tattctattc actgatcatt tttctaagaa  4560
ctctgtatgc ttcttgttta actcttatgt cagcatgtat gagaaaactg agttaaagag  4620
atgttaagta actcattcat gctttactag aaattggttg atgagggaca taaacctagg  4680
ccggtgtgat tttagattgc ttcttttaac cattgtgttg tattgcctta tatttctaag  4740
taatttatgt tcactgagag caaataatag tctagctatg acttagaaaa gtaaaataaa  4800
gatgttgggc agaaaaccat tttattaggg gttttttgg aggagcagat taatttgttt  4860
ctgtattctt tggttagttt gtgtgtgtgt tctttttaat tctttaaaat gaaactgttt  4920
aatccttaaa tccttaagtt ttgaaaattt tggcctatta tttatgtgtt aggttgatat  4980
taaatcctta atagctttaa cattttctac tttgttagag aggatttaaa atttaagtag  5040
ataagctgaa tatctggctt tatattaaat tactgctgat ggccaggcac agtggctcat  5100
gtctgaaatc ctagcacttt gggaggttga ggcagatgga tcacttgagg ccaggagttc  5160
aagaccagcc tggctaacac agtgaaaccc cgtctctact aaaaatacaa aaattagcca  5220
gttatggtaa tgcatgccag taattccagc tactcggtag gctgaggtgg gagaattgct  5280
tgaaccggga ggcagaggtt gcagtgagcc gagatcgcac cactgtactc cagcctaggc  5340
gacaaagact ttgtctcaaa aaaaaaaaaa attactgctg aattttatct tcttcttatt  5400
tatttttttt ttttactatt ttag                                         5424

SEQ ID NO: 66          moltype = RNA  length = 599
FEATURE                Location/Qualifiers
source                 1..599
                       mol_type = other RNA
                       organism = Homo sapiens
SEQUENCE: 66
gtaaaaaatt ttagtagttg tggtggttca acaaaggtac ttattaaaat aagtacctaa  60
gtttacataa atttatattt taaccaggac tggagtcttc taagtaactg atgttttcag  120
actgatttta tggtatgact ttgtctcagg gaaatagaaa acaaagcaaa atgtgaggcc  180
attaagtatt acattcatct caggtctatg cgggtaaatc ttttttgtt gttttataag  240
ccattctttg ctagtttctt aattgaatag atgactggat ttctattctt atttctctta  300
cccagaatcc tttaaaattt tttgttactt gtggaatctt ataaattctg attatcattt  360
ggttctactg agccaaataa tgtttgtaca ttgtttattc tgatagaagt tcttaagttt  420
ctaacataat tgaaatatta tttgttttgg tagataatta gtattctttc tttggttatt  480
caagataata tgcatcattt tcccaaaatt tttttgtttt ctttagtttc tgattattat  540
ttttaattat gtattacctt tctcatttct aattaccgtt ttcctgtcct tttctgtag   599

SEQ ID NO: 67          moltype = RNA  length = 124
FEATURE                Location/Qualifiers
source                 1..124
                       mol_type = other RNA
                       organism = Homo sapiens
SEQUENCE: 67
gtgaggcttt aagtgtggtg aaatcttggg aatttaaaat atgttgtgag agcactattt  60
agaggatatg attttgttat tctgaatagt tttgtaattg aatgttgtgt ttggttacct  120
tcag                                                               124

SEQ ID NO: 68          moltype = RNA  length = 391
FEATURE                Location/Qualifiers
source                 1..391
                       mol_type = other RNA
                       organism = Homo sapiens
SEQUENCE: 68
gtaaaatggc tagaagtcaa ttcagagcaa tggttcctaa aaactttaat ttcattacaa  60
tgtaaatata atatttagcc ctacatgtaa attccctggt ataaatctgt cactatgtac  120
ttgtaaaatg tgaaataaat tacatctttg aagttgcaac tttttagcca tttttatatt  180
tgcctgtctt ggtcattaag aacaattgag gtccttatgt actattttct tgattcaatt  240
tgatttaatt ggtcaatgcc aattagtaaa ggtctataaa gaattctctt tttttctaga  300
ggacacttat ggctgcgttt aattttaatt tggtttaaat ttcagttttt ttaaaattac  360
tttttaatta tagtgtcttt aacttttttta g                                391

SEQ ID NO: 69          moltype = RNA  length = 658
FEATURE                Location/Qualifiers
source                 1..658
                       mol_type = other RNA
                       organism = Homo sapiens
SEQUENCE: 69
gtaagaatta cttttagaat aacttattta ttcagacttc atattatctc attactattt  60
atttgacact agaaagtact ttttctagga tgtgaatttt tgtctgtctt tttaatagtg  120
taatatcttg tcatgttggt atatttgtcc atatgtgttt ctccaatcac ctcacaaaca  180
ctaatttttg caatttagga tatataaatg atacttgaat gaatgtgtag atagcagtca  240
ttatggggtt ttctataaaa gactactgaa aatcctgtgg atcataacat ttcattttat  300
cttaaaataa atacattata aatgtattag aaaccaatac attgttcagt atttatgtgg  360
```

```
attaaatttg tttaaaaggt agaataatgt ttaaaaataa aattttctag taatgaaaga  420
taattatgca attataagat gcagaaacta ttaaatgtca cctataattc caggatgact  480
tcaatgataa atacacatat gtaatgtaat gtatccgtat gtatgtgtat ataagtatga  540
atacgtatgt gtgtgtatgt agatatattt atatatataa tgtatatgta aatatgcaca  600
ggtgtaaata tatgttacat cagtttgcaa caactcttga aataactttg tcttttag    658

SEQ ID NO: 70          moltype = RNA  length = 2507
FEATURE                Location/Qualifiers
source                 1..2507
                       mol_type = other RNA
                       organism = Homo sapiens
SEQUENCE: 70
gtattttttt tcaattgaca taataacttt ttctttttgt attttagatt taaattttag  60
tcttattttt ctttaaatgt cttatactgg tttataacac gtttattagg gtttttaaac  120
ataagtttat tttatttatt ggttagaaaa gctctagaac tgtccttttt gatctctagc  180
taatttgtta ttgaatgacc tctttcacat caatgagttt aactttaaac tttttgatag  240
aagtctaact ccaaaatata tttggcatct aaaatatata attcgaaata taatttaaat  300
tttttttactt aactcatagt taccttatat acattagtta aatagttgca ggtttaattt  360
tagtttttct aactaaatgt caggttcatc agtgggaatg ggaataagca aagggatcag  420
aataacttgg gaagcctttt caaaatacac ttttcttcct caccaccact ctccaacctt  480
aaccaaattg tcaggcctta ccatattaga agctgggatt atgatggttg tatacttgaa  540
aaacatcaga gattattctg aatgaataat tctaatttta aaaactatca cttctagagt  600
cattgctttc tagtatggtt cacataaatc ttgtgggcag tttggaactg gttagcatct  660
agggagctca gataacctat attttaaaca aaagcattag caatggaaat aaggcctata  720
gaatcagtca tgtctccata aactttatat aaagggccag acagtgaata ttttagacca  780
cctggtctct gctataacta aactctgctt atagcatgaa agcagccatt gacaatacgt  840
aaatgagtga gcaaggtggt tttccggtaa aattttattt acaaaagcag atgggaggcc  900
agatttgacc tttgggccat agtctaccaa cccctggaaa aaacagttgt ctttaccaga  960
ttgaatgttg gcagggtaaa tggtgacatg ttatatgtat tctgtacttt gttttgactt  1020
aataccattt cataattatt ttatatcagt acgtatagta ttgctgttct ttttaaaggc  1080
tatgtaattt ttctttttat acaggtgtta atttgataat ttgtgaagtt tatgaagttt  1140
ccaattttgg ggttgtaaac tgttttaatg aatatcctta tatatgttat tttgcaaatg  1200
tacaagtata tctgtggaat aaattgctgc aagtgttgta attgtcatgt atgttgcaaa  1260
tacattctaa cagtttgtca cttttttttgc tttatggcat tttttgctgt gaaatatttc  1320
tttttatgct tagttaaatt tattattttt taatgacttt tgacatttgt tataatgaga  1380
aaggcttctg agtataaact tgttttctca tcttttctcc taatatcttg ttttgttttt  1440
gtttttgttt ttgtttttga gacagagtct cactcagttg cttaggctgg agtgcaatgg  1500
tacaatctca gctcactgca aatgccacct cctgggttca ggtggttctt gtgcctcagc  1560
ctcctgagta gctgggatta caggcatgtg ccgccatgcg cagctaattt ttgtagtttt  1620
agtagacatg gggtcacact gtgttggcca ggctggtctt gaacccctgg cctcaagtga  1680
tcctcctgcc tgggcctccc aaagtgctgg aattacaggt gtgactctgc ctggcctttt  1740
tttacattta aatcttcgaa acatataatt cattttgatg taaggagtat catgtggatt  1800
caacagagct actctgttgt ccaaacatct tttattgatt atttcatctt ttattgaatt  1860
gattgatcta ttttctagca gtgtatactt gttttaattt gtgtatgttt taatatctaa  1920
aaacgttatt atttttctgc ttttagactt ctttatgaat atttttaatg tgaattatag  1980
aactggcttg tccagttctt aaaaaaatatc ttgtggattt ttattgggta tgtgttaaag  2040
ttataaattg ttttatagat tgatttagga taaacctttt tatgttattt ggtccttcta  2100
gctaaagaac acaagatacc ttttctttca ttcattcaag atattttatg cctcttggtt  2160
gcattttaat gcatacttca taaagatcaa ttgtataaaa cttttcacag ttgtatggaa  2220
gtacttcttg tttataaatg agttttgaaa ggttgaaata tttttaaaga ttgaattata  2280
aaaaaagaaa attcggtata tattttaaaa tcattttcta tttgaatttc aggttgtata  2340
tacaaaagga acagagatta tgccagtagt tgctcatact ttctcatttc aaataatttt  2400
tattttctgt atcataaatc tactaacggt gtttattatt tatgataatg aagaatgttt  2460
tattaacttt ccttttgcat aacagattct attgtgttta tttctag                2507

SEQ ID NO: 71          moltype = RNA  length = 946
FEATURE                Location/Qualifiers
source                 1..946
                       mol_type = other RNA
                       organism = Homo sapiens
SEQUENCE: 71
gtaaaatctt aacagaattt tgtttatcaa ccagttttat tacagttgga actctgaacg  60
atgtctttta tttattatat catcagtgcc tagtgtagcg gctggtacta ccaagtgtat  120
aataatgtct tttgaaattt cttctaccac ctggtcccaa taaaaaaatta gaattaagtt  180
tagatcacgg attagactta gaactagagt tactgtgttt atttttctat gtttatgtgg  240
atagtacaca cattgttttg gttagaaatt atttaacaag aaatgattaa aaacttttag  300
aaatttaaaa taattttata ctcttttaag gtttatttta ctgtatctta gtcctaacat  360
accctataca atgtgaaata agctaaaagc atggttataa tttgactgtg ctacctattt  420
tatttttagt gaaaataacc caaataaaag gaagtaatac ttttattatt tgtgctgtag  480
ttatagtcca caagtaagaa gatgatttga aaagtgtatg ctgaataaga acaattacag  540
gggacaacat tttttaataa agtacgaaag gggaaaaagc taagttgaat aaaagagaaa  600
gcacagagca aaacagaaac atacaaaatg gtaaaaaggt ggaattgaat ggaggatgag  660
gaaagtaaca tataaggaag tatagaagcc ataaacatta gggagttctg gaaatcctat  720
tttccagagt gttagccatt atatccatct ttcagtattg gagtaacagc agtgtaccta  780
tcattgtgta ttacagttga agtgtacaaa atggtaaaag gcatacttgt acccacaaga  840
aaatatgttc tacagtcttg ttgaaaaaaa tcagacgtac ttttttcctt accttttttag  900
gttaatattc atgaagggat atatattgtt ttaaaatatt ttatag                 946

SEQ ID NO: 72          moltype = RNA  length = 4079
```

```
FEATURE                Location/Qualifiers
source                 1..4079
                       mol_type = other RNA
                       organism = Homo sapiens
SEQUENCE: 72
gtatttttat aaatatatag ttattttata tacaattatg tttttaacga ctttattttt  60
attaaaataa aatgtcaagt caatattgag ttttctccat ttgaatttta tattttcaaa  120
aaattgtaca agatatttat tattatactt atattactag tgcttacatt tgtaaatgat  180
ggatgcattt tctattattt ttctcctctg gtgaaaatta cattaacgtt tattaccagg  240
tcactggtat gaaagaaatg aaaaattgtg atacaattat ttttatttaa ctttttataa  300
ttaacaaaga atggaagata ataaaatttt gaccagtgta acagcattgc agatagtttt  360
cagaggtaat ttcacattaa tcttacccaa attaatgttt catcatattc tccttaccct  420
gagccatatt acctttttta acacatcaaa ttctatgaat ataagttctt acaatatctg  480
tgttgttata tttccatagc actacatact atagttatgc cagggcacac tagtgcgaac  540
tgttcatggg aaattcatgg acatgtttat tataattggt gactatgtat atatgtatac  600
actacattta tacacacgcg catggaatca ctatttcttc ttcatgtcat atatatatac  660
atatatacac atatatatac atgtcatatg tgtgtgtgta tatatatata tttgtatata  720
tgacatgaag aagaaatagt gattccgtgc acatatgtgt gtgtaagtgt agtgatgtgt  780
ttgcaggtac ggttgtaatt tcaaaaatga agcaaaagcc ttgctcagga gataattgaa  840
ccaatactta aaggaagtaa aggagtgaaa catgcagatg gctctaagca gtgggaataa  900
gttcaaaggc agtaaagcag gagtgtacca atcatgtctg agaacaacaa agaagtcttt  960
ttggctggag tagagtcagc aagtgaggca gtgataagac cagagaggta aacagaggcc  1020
atatcatatg gggccttata gttcattgtg cagacttggc ttttaagtga gaagggacac  1080
cggggaaagt ttctgaagat agaaatgata taatttgact taggctgtgt ttgcagtaga  1140
ctgtaggagt ggtaaataag aatcagggag acctgttaga agactattgc aataatctgg  1200
agaaaagtga tggtggtttg gggcatggtg gtagcagtgg agttactgga tgcagcagtt  1260
ctggatgtat tttgaaagtg ataaaaatgg aatttgctaa cagatcagat gtaggatgtg  1320
agagagagag aactcttggt ctgaaccaaa agttttggtc atggtggggt tgtgggaaga  1380
gcaggttgag agataatcag gtacttaatt ttagacatgt taggtttgag atgcttatta  1440
gacattcaag tgaaggtgtt aagtaggcac ttgtatataa aagtttaagg tttaggacaa  1500
caatctaggc taaagatatg tttggtaact gtctctgtaa aagtaattga aataatgagg  1560
ctggctaaga tcaccaaggg agtaaatgta ggttaagaag aaaaatctaa agagcttcta  1620
ctttagcagc tggggagata aaaaggagct accaaaggag actgaaaagg aaagcccaga  1680
gagctaggag gaaaagcagg agtatggaga gccctgaaaa ccacatgagg aatgtaacca  1740
aggaagaaga aacaactgct ttcagagctg tgttcattgc tgctgatagg tcaagatgat  1800
cactaaaagt tgactattgg acttagcaat ggtcattttt ggttcaagag aaaatgggta  1860
gagaggaaat gtaataaaga aatataggaa cccttttcca ggactgtttc tataaagaga  1920
aggagaaaac aaggtggtag cttgagggga aagagggatt aagaaaacat ttttctcttt  1980
aagatggaag aaataactca tgattttagg ttaataggag agctccatta aagaagaaac  2040
attaatgaat caatgaagtg gagagagaga acttctggaa caataatatt tttaagaatg  2100
caatgggatg ggatcctagt gtgccagtga agaggttggc cttaactagg aacacagagt  2160
tcatccataa ttgtagaaaa gaaggtagag tgtatagata tcgatgtagg tggcttggta  2220
gacatcctgg taatgggaat ttgtggaagt tctaaactgg ttgctgcttt tttctcagtg  2280
aacaagggag caaggttctt agctgaaggt gaggatagga gaagatgttt cataagtttg  2340
aggagaaaga agagaagtga aagtataaaa tggtcatctg aaagattgaa gacgtggaga  2400
atgtggtatg actgttgagt aacttcaaga gcccacgata tatatatgta tttctattta  2460
tgtgtttatt atatttgtat cagaacactt tgaaagtagt ttaaactgct ttaaaaggat  2520
gactaatagt atggattgtg cgtattctaa ttactaggag aaaaagtggc aattgatctc  2580
tgctgtcaaa taaggaaaag gacttatctg ataacacttt agtcagtccg tagttatata  2640
atccctaaag ctcacagaag gtgtgtgtac tagactgtac tctacatctt gaacttaact  2700
tgtaaaacgt aatggctaat ggtattcttc cttcataaga ttaggattag gtttagttat  2760
caggaacaga gagctgaaga ataatggcaa aatcaagata gacatttatt tctcatctat  2820
gtaatggcct agaattaagc attccagggt gttgccttca tctgccccat ccaaaatgga  2880
tggaatgcag ctttatctca tgtctgtgtc ccaaacagca agacagagga agaggggcaa  2940
gagttaaaag catgtgctga aggataggca ggtaaatata gtgtttattg tgtagggcca  3000
tgtggaagaa tgataggaga atagatatgt ggatggaagg gagaatagat actgggggac  3060
aactcagcct gtgtcatgtt ccacagctta gatgttagct ccagacagct gtgctcattt  3120
cttaaaaact tttgtgatct caaacgtact agttttatgc ctaagtccaa tattaaatat  3180
ataacctata tattagtaaa tgcttataat gaatgagtgt gagaatgatc tgtcaatcaa  3240
ttttggaatg atagcaatat tatgttttgg tcttttaaca atttagtaag atattacaag  3300
taggcattta ggaagttttt agcttagttt ggattaaatt tagctgcaag tgacagaaaa  3360
atcaagcata atacaataat ttaaacaaga tagaaattta tttctctata atatagacaa  3420
agttgaagca actagggcag gatttgtgtg acagatgctc aaatatcccc tatcaggaac  3480
cctgtctctt gttgctgtgc ctatctcaac atgtggtttc taactcatgt gaagttgcca  3540
ccctcatatc catgtggatt tcagctagca ggaaggagga aagagaagag agattactcc  3600
tttattttaa aaacattttt tttttttttt ttgaaattca catatgaact ttgcgtttat  3660
attccattac tgacatgacc acacatagct gcttgtgtgt aagtggaaat ttagttcttt  3720
atttcaaatg gccacgtgtc aagctaaaaa tccatagttt tagtacagtg gacaaaaggg  3780
aggttaaata ttaggaacag ctagcagtct gtatcacaat gatcattttt tgtaaagcag  3840
tattttgcaa ccttttaaaa tccatacccc ttcagctaag aaggttttac tgaacttcag  3900
ttttttagta aattgtatta gtaaaaccaa aacaaaactt tcatcttaca aatataaaat  3960
gacaacttta aaggattttt ttttaatggc ataccacttt tcttgccacc atgttgggat  4020
cactgatttg aaggaataag tagtcaattc aattcatgat ttttgttttt actctgtag   4079

SEQ ID NO: 73          moltype = RNA  length = 720
FEATURE                Location/Qualifiers
source                 1..720
                       mol_type = other RNA
                       organism = Homo sapiens
```

```
SEQUENCE: 73
gtatgtattt ttatcttgtc attcaaggag cttagaatta ttcttgccat tcacagacta  60
ttctgtgcta tttactgcat accatttaaa aaacattcca taagtatctt ttgataaaga  120
ttatcctcat taatttatac taaactattg aaacctttga gcatttactt tttgccagaa  180
ttgttttcaa acttttgatc acagtgattt gtccaaataa tcagttttgg tgaagcagca  240
ggattacttt tttttattat ctgtgttcat tgggccacca tgtagatgtg acaccactgg  300
ccaatttgac agaatttatg acaggaacat actgtgtcaa tacaacctgc tctccacttt  360
ttatactttt tcattggtta caactaattc aagcaactaa tgacttactt attctactgg  420
tattgctgat ttgcttttac taattctttt agtattttgg taagtgtttt ttatatgtaa  480
tgcatattca gagtcacttt gcctttagga tattatactg gaaagtttta actgttgcat  540
attacatcat tattattact ggatttggtt tataaaagca caataaaaaa ccagtgtaat  600
gatataaatt ataggcatat gtacattttc ctttagactt agtaaaaaaa aaatcatgaa  660
cttgataaat ttattcaagt aaaccatgtt atattttaaa ttaaattgga tatttttcag  720

SEQ ID NO: 74          moltype = RNA  length = 1370
FEATURE                Location/Qualifiers
source                 1..1370
                       mol_type = other RNA
                       organism = Homo sapiens
SEQUENCE: 74
gtaagccatg ttttaagtta catagtttgc gcaacctgat ttacaagtct ttttttttaa  60
tttaaatttt gtttattatt atttattaag tagtttaatg ctttttttcaa atgcttttat  120
aaaacattta atacaaataa aagtggagct aacctgattg aagtggaatc agattttatg  180
gggttggagt ggtgggtggg cagggctgga acattgcttt atttggtcta gcatctcctc  240
agtaatagct gcttgtttaa aaagatgaaa gtttattaat accacatatc agagattaac  300
cttttttttt cccaacaaaa gtagggtctg tattacccat gtttgtttgc aaaatgctct  360
tgtaacagat gagatattta aacttcttgc tctgtgttgt gattctcctg cctctgcctc  420
ctgagtagct gggattacag gtgtgcacca ctatgcccgg ctaatttttg tatttttggt  480
agagatggga tttcaccatg ttggctaggc tggtctccaa ctcctgacct taagtgatcc  540
acccgccttg gcctcccaaa gtgctgggat aataggcatg agccaccgcg cctggcctgt  600
taaaatcttt taaagatttt taagtacttg atttttataa tttagactac ttacgtttta  660
ctttgttcga gtattttaag gagtaattag taatatagct tgagagttta tatatttatt  720
ttaataaata gcctattagt taatattact aatttgagtg ttatgatagt gcagactaag  780
ttgctgcttt aaaatgaaaa taaatatcta aatatcaatt tcattattgc taaatttcat  840
ttaatgcttt cttagttaaa aatgatcatt tgtaaaaact attatctaaa gaaaagacaa  900
atagacaaat aagtatttta tacagatata tatgtgtgaa aagtatctaa cttggatccg  960
tagttgtgct aggaccccaa attagacttc tgatcaactt ggactatcag atcacagcct  1020
tctgatcaac ttggactatc agatcacagc caagaatctg gaagttccta aagatgactt  1080
ctggcccgtc taggtagctg tcatagacat catattttct gtgcttaaaa agctccaaat  1140
cttggtttat aatttcattt aggtttttgt taggatttcc attaataatt gtgataaaat  1200
tttaacttgg gttacagttt aaatatctgg aaaattcttt cacagaaagt tacctcattc  1260
ttcagtgata ctggctaagt gaattataac cagttgcttg atggtatatg acatttttgc  1320
agcttatttg aatgttttta agtttttaat tatattgctt tctattgtag            1370

SEQ ID NO: 75          moltype = RNA  length = 72
FEATURE                Location/Qualifiers
source                 1..72
                       mol_type = other RNA
                       organism = Homo sapiens
SEQUENCE: 75
gcaagtgtgg tagtcagttg attattttct tggctgaact atagagaaat actaataatt  60
tatactttgc ag                                                     72

SEQ ID NO: 76          moltype = RNA  length = 1337
FEATURE                Location/Qualifiers
source                 1..1337
                       mol_type = other RNA
                       organism = Homo sapiens
SEQUENCE: 76
gtatactcag ttattctaaa cctttaaaaa gaattattga taagtgagtt gtctggatat  60
gaaattattt gtgtcttagc tgtttttgct gttctattgt ggatctgcta caaatttaat  120
aaatgacaat aataacctga aggagataag tgagtgtcag tgggttcagt cctgaatctg  180
aaatagacaa aaacaaaaca aaacaaaata acaaaaacca agcaaacaaa aaagaaaaaa  240
accttagaat tatggaattt ttgaaaagtt ttatagtata gtattttaat ttctagacag  300
caccaatatg ttgttattaa taataataaa acttagtagt ttttatgtta atatatgtta  360
ctcaacattt tccctttcct taaggactat gcattgaaaa gcttttcttg taagttatta  420
ttattattat tattattaat atttgagatg gagtctgtct tgttctattg cccaggctgg  480
agtgcactgg tgcgatcttg ctcattgcaa cctccgcctc ccgggttcta gtgattcttg  540
tgcttcagcc tcctgagtag ttgagactac aggcgtgagc caccacgcct gacttatttt  600
tgtatttttta gtagaaacag ggtttcacca tgttggccca ggctggtctt gaactcctga  660
cctcaagtga tccatccact ttggctcccc aaagtgctgg aattataggc gtgagccacc  720
atgcctggcc ttaaattatt cttttctaag tgaaagtaat gttttattga atataaatta  780
acatctttct tgggtttatt ttacttgagc taaagagaac agttggttaa gttttataat  840
agccattgca gtgcttttttt gtaagaagac cacacagaag gactgtcttt ttcacttgcc  900
ccaaatcccc aagcacgtat atgagtaata gcagagtggt tctttttagc attatgattt  960
ctataataca tccaaaactt tctcaagaaa aaacttcatg atttattagt acaataatca  1020
gtttactcat tactcatcat ttatatttac tttatatgtc ttttaactgg tgcttattaa  1080
gtagcacttt aatatagaat aggcaaagaa tggtagagaa gatgaaattc aaaaattagg  1140
ttctcacatt attaatagtt cattaaaagt gagctaaatg agaagcttgt attggctatg  1200
```

```
tagaatttg gagggatttt ggaaacaatt attctacctt tgcattaaaa cttgattgta  1260
ggttttaaga attaaagtgt tggaatagta ggagggttat tttaatgttt ttagtttgtt  1320
aattctctta tatatag                                                1337

SEQ ID NO: 77          moltype = RNA  length = 1850
FEATURE                Location/Qualifiers
source                 1..1850
                       mol_type = other RNA
                       organism = Homo sapiens
SEQUENCE: 77
gtaatagtaa agtattgcaa agagagtaaa ggaaaatatt tttttttttt tttttttttg  60
agacggagtc tcgctctgtc tcccaggctg gagtgcagtg gcgcgatctc ggctcactgc  120
aagctccgcc tcccgggttc atgccattct cctgcctcag cctcccaagt agctgggact  180
acaggcgccc gccaccacgc ccggctaatt ttttgtattt ttagtagaga cggggtttca  240
ccgttttagc cgggatggtc tcgatcttct gacctcgtga tccgcccgcc tcggcctccc  300
aaagtgctgg gattacaggc gtgagccacc gcgcccggcc aggaaaatat ttttattgtg  360
ttttcatttc ttccccctt atctcattct tgaacatcta atcttattat tgttgttaaa  420
taagtagagg gaaatatttg cttatttaac ctgttgattc aaagattgat taatgagaca  480
ttatttactc tgaatacaga ttaggagttc agataaagca gagctgctgc ataggagatc  540
atcattcaat accccacagt cagatcagaa tgagacagaa gagaatatga ccataggatc  600
attatcaaga atgttatctg aaattcacca tagtgtagaa agtggaatgc atccttttgt  660
ccctttaact agactttctt catccatgca agttaaagag aattcaactc cagaaactat  720
tacaataaga gagattttta aagcaccatg tctgcagtct tcaagaaatc tagaatcgtt  780
agtcagcacc tttagtaggg aaagccatga agaaataaat gacatatgcc tttttttctga  840
tgactgtatg aagaaggtgt caagaagcca tcaagcacta gagaagacta gttttgtaca  900
aaaaagcaat tcatctttc atggcttatc aacagcttca gacataatgc agaagttatc  960
acttaggcaa aaatctgcaa tattttgtca acaaattcat gaaaatagag ctgacatgga  1020
taaatcacaa gtagcaacat tagaagaaga acaggttcat tcccaagtaa agtatgctga  1080
tatcaatttg aaagaagata taataaaaag tgaagtaccc ttacagacag agatattgaa  1140
aaataagctt aaggttaatc ttccagaccc tgtgtctatt actgcacaat caaaattatc  1200
tcagataaat tctcttgaaa atcttataga acagttacgg agagagctag tatttcttag  1260
atctcaggtg agtttttctc caaattatat ttctgtggtt gttcttttat gacgtctcta  1320
acaaagttct gtaacaatta tagttagaat atttttgttt gcactttaac atcagttata  1380
cacattgtac tttttaaaat ctaaaatgca gtacattgat atgaactcat tgacttgtct  1440
aatttattaa atttttcttt agaatgaaat catagcacag gaattcttga tcaaagaagc  1500
agagtgtaga aatgcagata tagagcttga acatcacaga agccaggcag aacaggtagt  1560
gtaaaggcag aacattaaaa gagatgattg tggtactaaa gacaaaaacc gttatatctt  1620
tttgcctctt accatggatg ttgggagagg gagaaagtgg gattaagatc accatctgct  1680
ttactgttta gattttagtt tatttttatg attgctgcta tgtcttcata gctcgttttt  1740
tttgttttgt tttgttatac ttaattgatc aaacttttct taacttgaaa attatagact  1800
tgtgatattt tgttgaaaaa aatcaatttt attctctctg cttttttcag              1850

SEQ ID NO: 78          moltype = RNA  length = 535
FEATURE                Location/Qualifiers
source                 1..535
                       mol_type = other RNA
                       organism = Homo sapiens
SEQUENCE: 78
gtaagttaca attatctttt acttttctgt tcttattttt cctatactta aaatcatggg  60
cctaaaaggg cgttaacaca ttctctgttt tctaatctgc tttactccta attacctctg  120
tactgtatat acttcagtct gtcactatcc agttgatttg ccttgctgtt ttcattgtga  180
gagaatgtta ctaatatgaa ttttttgtga gaatatataa ctccttttttc ttgtgtgttc  240
ttcaatcaaa atgaagttag aacaccaaat ttaaaatact ttaatataaa gcatagttta  300
agttaaggca gaagtatgcc ttatatacgt gtgtatatgc acgtgatata aataggtctg  360
tcatttaact caactattca cgttggattt atagttgaat ttttttgtat gtttatttac  420
atttggattt ttccaatgat gtctttggta tatgtgaaat atttgtcatc tgtatagcat  480
agtgtaaatt gtgaaaaaga tctgatcatc caatgagaaa actgtgtaat tacag        535

SEQ ID NO: 79          moltype = RNA  length = 2561
FEATURE                Location/Qualifiers
source                 1..2561
                       mol_type = other RNA
                       organism = Homo sapiens
SEQUENCE: 79
gtaagttatt tttttcatgt taatgttttt cccctatcac tttagagaga ttttctgctg  60
tgtacagatc tccatagttt ctgatgagat atttttagtc atttgaatca ttgtttccct  120
gtatgtaaag tgtagttttt cttgagctgc tttcaatact tttcttctac caattggata  180
attgttatta atctgtcttc aagttcactg acattttcct ctttatctgt gttcttttgg  240
ttcaagggtc agcttgagac cttgaggagt tttttacacc gactttggag ctcgtttttg  300
ctgactcttt tcttattggg attttccttt cacttatccc atggctttgg gctgtatcct  360
gtggttttct agatgagaaa gatgatagat ctctgcaatt gcaccctgcc ctatgactaa  420
atctttaaaa atggcaaagt caatctttgc tggtcctgtc ttccgtattt gaggggtttt  480
ttcccaaaat ctgcttgctt ttgttcattt tctagaacat ctaggtagtt ttttttcatt  540
catttttttat ttatgggagt gtagatctct taggaactta tgccatcaga agtattatga  600
aatggcttta ttctaaatgt ttaaagattt actcattgct acaagaaaga tttagccatc  660
actaatattc tatatatatt taccatatag ggacttgaga atttcacagg attcagtatc  720
tgtatataaa cttgaataat atacacattt tagattgtta atatttaagt atatgtcatt  780
tatgttatct gaacatattt agcgtacatt gtcatattat ttcccaaatt tgtgcttgat  840
ttcaaatggg aaaaaaattc ttattattta ttgaattgtt tttttaaaaa aatcatgatt  900
```

```
aatcagtaat tggatacttt ttaaaataac actataattg ttaacagaga atgagagtga  960
tactggtatg ttaaaaactt cctgaggcaa gaaaataatt tgattcccat tatatctttc  1020
tcatactgac tttccttctc tgattggtga ttttgttttg cctctgccac tttgaatgtc  1080
taaaatgatt ctttatgctt tttttatgtg aacatctttt gtccgtgatg atgcccacta  1140
ctgatactgt gtcccagatc aaacttaatt ttccaagggc agctctactt agtgaccaaa  1200
tgaaaacaca gtgaatagcc caagaaatcc taacttctat ttatgttgac aatctctgga  1260
ccttcctgaa gccactgttt gcatagactt catttacttt tatccgggat tgtcattgtt  1320
ttttcagatt cataggccct atctgaaatt cacaaatcac ctagcaatac ttctctaaga  1380
aatcttcaga atccatgaca atttagacca gacaatgctg gattatgcac ttcagttcac  1440
tttttgttac tacaaggtat ttttcagtgc ccccaacagc tatcttaact cattctcatt  1500
ttaccaaagt ccatgtagac acggcactat tcctcaatga gacaactaac tagaccacct  1560
tgttgtcagt cagagtacct tcctctacct acttttatct tccttatatc ctctttgagt  1620
tagtataagt tattactctg catgacctgc tctaatctcc ttcaggggaa ggcttttaca  1680
aatctactac ctagagttaa accccagatc accttcctga gtaggagatt gcatttggtt  1740
ctattcattt taccttattt ggcttctacc ttcacttttt aagacttact ttgcctttaa  1800
cagttttttc catacagttc atctaaagtc caaatatatt tattagatgt gtgcattgtg  1860
tgtatatact tagatatgcc actgttggag atttcgggcc agtgatgcca ctctgataat  1920
atttaatatt ttgacatatt atttttgctt actcattatt cttagataat atcatgttat  1980
gataccttgc ctttattttt atttatgctt caactatgtg gagaggaagc actgaaaaat  2040
tcacttaatt gaatgttgta ttgatcaatt gttcaatatt gtattccatt cctttgcgca  2100
tgctttgaat gcaggtgcta tataatttca gagaaaaata cctcatttttg actgtacaaa  2160
aaccccatgt agggagcaga gctcacattg ttttcccctt ttagagacaa gaaaactaag  2220
atacagagaa tttaagtcac ttgcccagct gttaagtgac tgattaaaat ttgaaccctg  2280
gtcatcttat tcccgtctgg ttgtttttct agtctaccag tctattaaga ttagctaggt  2340
gtttttttaat tgttttaatg aagtaattac tatgcttggt aatgtaaatg aaagttttat  2400
agattcataa ataagaattt gaattggcat actttattat catgcttggc aatgaaaata  2460
ggaaaatgct taaatgtcca ttttatttaa agacagactg ttttttacta tgattttact  2520
gtttttctcc acatttctaa tatataatat aaatttgcta g                    2561

SEQ ID NO: 80          moltype = RNA  length = 342
FEATURE                Location/Qualifiers
source                 1..342
                       mol_type = other RNA
                       organism = Homo sapiens
SEQUENCE: 80
gtgagaattt tattaaataa aagaaaatgc taaacataag aatgtagatt taataggaaa  60
tttttaattt tttaaaaaga atgctttatg agaaaatgcc ccttgaatta attctttcaa  120
tattaagaaa ctggatttct cttataaaat tataagtgga aaataagtgc cttataagat  180
tgaaaagaat acaaaaattc taaatctcat acctaggcat ttctaagcag aaactgaagt  240
atggttgagg taaaattcct ggcagggcat tcacatatct gtcaatttgt ctttctttgg  300
gtgtaagagt tgtgattctc attgctggat tttttttcc ag                     342

SEQ ID NO: 81          moltype = RNA  length = 2020
FEATURE                Location/Qualifiers
source                 1..2020
                       mol_type = other RNA
                       organism = Homo sapiens
SEQUENCE: 81
gtattgaaaa ttttgttaca ggtattgaaa attttacatg tgaataacaa aaatcattgg  60
tagtatgttt ctttatgttt ttatttttat tttactttat tttaattttt ccatcaccaa  120
agcatgcaga tagtactttt ctcaatattt agtcttcatg tattcctgag ttctcaaaat  180
agtaacagtg aaatatattt tttatggatt ttgatgttag atggattata aataaaagca  240
atttatacca ttcattccat tcatctgcat gagcagcatg ttcatacatc ttgttcgcac  300
acctgtcatt catgtgaaat atatggttca caagcagaac aacaagcagc tattataaag  360
cagtgttaag taaatgagca cttttatttc ttgctgggtg gaaaacaaaa gaataaagtc  420
tgtcaaggct ttttagtgtc atgatagaat tgttcccctt tttgcattca caagtaaaaa  480
ctactttttt tttgagacag agcctcactc tgtcactcag gctggagtgc agttgcgcta  540
tcttggctca ctgcaacttc cacctcctga gtttaagtga ttctcatgcc tcagcctcct  600
gagtagctgg gactacaggc atgcatccct ggctaatttt tgtatttttt tttagtagag  660
atggtgtgtc gtcatattgg ccaggctggt ctcaaactcc tggtctcaag tgattcgcct  720
gccttggcct cccaaggtgc tagggttaca gacgtgagcc actgcacaca gccataagca  780
aaaacttcta aaccaaatta ttcttcatct ttgtcttccc tttacgcaat aaaatgttaa  840
tctaccacca aagaggaaag ggtactctac tatactacct gccctgggtt tctcagtttt  900
gctgtctata taatggtcgt tatgaatgtc ctaatgacag atccttttca ttattttatt  960
tgaaatttga ctatctataa catcacatac attataaata taattacaaa tatatgttca  1020
gaatcaatga aaatatattt ttgattatat gggccactat ttctctctgc taggtgatcc  1080
atttgtgagt atacttgagt tataattatt aagtactcat ttttattttg gaaattacag  1140
taattcatct ttttctcaat attgggattt ttattattat tttatgttgt ctaaggacag  1200
ccttaactac ttattagaat attgctttgt atgtgatatt attattttta aatgtataat  1260
tttaacatta ttatttctct tatttacctg aggtatagga acactatcag caaatattgg  1320
tagtatggca ttgtcgtatt ttttgagata aaattcatga tttttaatct ttgtataaga  1380
aatatatcag aagtttgtag tagattagag agtaccaact gggagtctga aaagctgtcc  1440
aaagtggcaa aacaggtact tagactctca atcctaaggc tgtatagagc tataaacgtg  1500
gcaagacctt tggagtcaga cagacccaaa ctcaaatgtt ggatccatgt atatggaaag  1560
cacctgacaa caagcctagc atatgtactt ggtaaaaatg attgccaagt gtagtgttaa  1620
tgagtttttg gatattgagt aagttattta aatttcaatt tcatctttaa aatgaaataa  1680
ttggaaagga taatttgagt gagggtatga aattatgtgt tcataagaga gggtatgtgg  1740
ccgagtgact agaggcgagt ttataactat tctatctaat aaaactttgt aatctggtaa  1800
tttgtgtgct aaaaataact ttacctgttg tatagtactc ttttttatg ccttaaacta  1860
```

```
aagtgttcaa aatatcatgg aaaaatgatc tgtgttgctt acagatttgg tgacttttaa  1920
ctttcctata atgttgtcag aatatgaatt tatactttca aattcagcat ttattctatt  1980
gtgttttttt ttgcattctt atttctaaac cacttttcag                        2020

SEQ ID NO: 82          moltype = RNA  length = 1967
FEATURE                Location/Qualifiers
source                 1..1967
                       mol_type = other RNA
                       organism = Homo sapiens
SEQUENCE: 82
gtataggtat tagcaaaact ataaatataa ttgcagtata ttcttgttaa ttgtgaaagt  60
aacgtaagaa taatttatgt tttgttcttc ccttcttctt cttcctttgc aattgtattt  120
ttttttactc tggtaactac tgttaggaac ttatttatgg agacagtgta gcttaatgat  180
tacattaagc ctgggattat cctgcctggg tttgagtcat ttaacgtttg ctttttgtaa  240
gagcttgagc aagtcatctt acctatctgt gtctcagttt ccttatctgt aagttacttt  300
gtaagtaata cccttttcat aggattattg taaaacgtaa atgaattatt agatgaaaat  360
gctcggacta gtgtgtggca catatgaaca gtttgtaaat gttagctgtt gttagcatca  420
ttcatcatca tcacaatcat cattgttcat atatgtttat agggaactaa catatttctc  480
cttatttctg tcatctcatc taaatcaata gaatgatttc cttaatagga attagaatac  540
ctaatcaaag gtgatttaaa cactaagaat aattattatc tgacctaacc agaaccacaa  600
agctagttgt agggcaggtc atatttgaag gttgttgtta tcgcctatga tggttgtaaa  660
atagctgcat gaattcaaga aagatgatgt gcccattgaa gaagaggagc atttttttct  720
acatagcttt tatttttaaa taaacatttt tttctggtga tacctggcag acattgactc  780
cgatctcatt tgctagaatt ggatcacatg tccaagtctg aaccattcag ttgcaaagag  840
aatgataccg ctatactggg tttatgccaa gaacattaca catgtttgtg gaatgctcat  900
gtgtagacaa cagtgtctta cacaacttca aaaaaataat ttatatataa atatgtttta  960
aattactttt taaattcaca agaatttatg gtatacaaca tggtgttcta tatatgtata  1020
tactatgcta tacaacatgg tgttctatat atgtatatac tatgctatac aacatggtgt  1080
tctatatatg tatatactgt ggaatggcta aatcaagcta cttaacatat gtattacctc  1140
gcatactttt tttttttttt ccttgagaca gagtcttgct ctgtcaccca ggctggagtg  1200
cagtggcgct atcttggctc actgcaacct ctgcctcctg ggtccaagtt attttcttgc  1260
ctcagcctcc caagtagctg agattacagg catgtgccac cacgcctggc taatttttgt  1320
atttttggta aagacggagt tttgccatat tgtccacgct agtctcaaaa ttcctagcct  1380
caagcaatct gcccaccttg gcctcccaaa gtgctgggat tacagcatac ttcttcttat  1440
tttttttttt ttttgcacta agaacactta aaatttactc tcttagcaat tttaaagtat  1500
ataatatact gttattaact ttggtcacta ttttaattag acttaagatg tgtttgtatt  1560
caaattattt tgtaagcatt taacacccaa atttgagagt ggggtcagaa tgttggaatt  1620
tgatttctag aattagtata gggtattatt ttcctacttt ttttctgtgt tcaataaaat  1680
gtttataaga ttcagcttca attatattat aacccattta gtggtgaatc agggaagaat  1740
gaaaataatt tgataacttt gttgccttgc atttatttaa aaaattttta attctaggct  1800
aaaccctttt taaatgaaag tttaacttct tgtgttttca gatactgaat agctatgata  1860
cctcttgtgt tgagaaaact ttaaatttgc ataatctgaa gttatctttt cttataaaca  1920
ttttattagg tttacagtat tgtctttttg ttttgttttg tttttag                1967

SEQ ID NO: 83          moltype = RNA  length = 90
FEATURE                Location/Qualifiers
source                 1..90
                       mol_type = other RNA
                       organism = Homo sapiens
SEQUENCE: 83
gtaagtaaaa catttttaac attagtatgc aatattgtac aaagtaggat agctagattc  60
aacaagtaat atggatgtgt ctttgtgcag                                   90

SEQ ID NO: 84          moltype = RNA  length = 3663
FEATURE                Location/Qualifiers
source                 1..3663
                       mol_type = other RNA
                       organism = Homo sapiens
SEQUENCE: 84
gtacatctga ttcttatttt gctttttctg actatgaaaa atttcaaata tgcagaagat  60
aggatggtat caataatgct catcacctga attaatagtt aacatttatt aacattttgt  120
cataattgct tcttctgatt tttgtgggat gtttgaattg cagacattcc tcccctaaat  180
atttaatgta ccctttgaa aaaggctttt ttctttaact aaccatagta actttattat  240
acctaacaaa atgacagtaa ttttctaata tcgcctaata ccctgattat agtcacattt  300
tttacatttt ttgatcaaag aataagcatt tggatgttac atctcataaa tctttttaat  360
atagaatccc cttggtttc tttttctcca aaaaatgttt gaagatgtat ctaacttttg  420
tgtgtgtgtc attttacttg ttcctgtgtc ccttgtatta ctaaaagtta ggtcagaacc  480
ctaagttaca ttcaggttta aacattttg gcaagaatac ttcataagta gtgttctata  540
ctttatattg catcacttca agagtatctg gttgttccat gttttgtaat tgattactct  600
gttaaggaaa agacaagcag accaagtatg gtggctcatg cctataattc caacattttg  660
gaaggcccag gcaggaaaat ttcctgagcc cagaccagcc taggcaatat agtgagactc  720
cgtctctaca aaaaatgttt tttttttgt ttgtttgttt ttaattagct tggtgtagtg  780
gcacatgctt gtaatcccag ctacctggga cattgaggtg ggaggatcgc ttgagcccag  840
gaagttgggg gctgcagtga gctgtgatca tgtgccactg atctccagcc tatgtgcctg  900
tataacagag cgagtctctc tcttaaaaga aaaaaagaag aagaagaaga agaaaagata  960
accatatacc tccattatta agcaatttag ctaactggtg atattttggt accatacaaa  1020
taacaaatta tttgtcagtc ctaatgattt tagcatctgc tgatgattgt tgcctaaccc  1080
aattattaaa agttgcaaac atcataattt tctagttata ttatgcactt acatttatta  1140
acagacatgc ttttgtaaaa taaatagcgt ttcctcatta gcccaggcta tttgtttatc  1200
```

```
ttgaagttta gctcctacta caaaggcaag ataaatgctt ttctctttaa ttaccagttt  1260
tcagaataca cacttggtgt actctgcact acctgctttt tttgtcccct ccgctttctc  1320
ttttttaagt atcagattag actcacagat ttttaaatat tccatgtgtt ttagttggag  1380
tcatattctt ttgtctcaac tttagccaaa gagagtcctt taaagttgac tcttatattg  1440
tcttgacaaa aattcattag tcttttgaac gaagcctcaa agcttgactt gttttctagc  1500
ataagatgtc ttagacttac ctacatactt catgcccata cttggaataa accatttctt  1560
taaagagccc aggttccttt tagtggggaa ggcatttaga taccaaaaac tggccactgg  1620
gcatcattgc tctcagagta tcattgccac tagtctctca gtagacaagt tagaaaaata  1680
tgtatatatt taaaccatga gttcatattg ttatttccag tttaattata acattatggg  1740
gtaagtaaat agtatcggat ttttactaag cttctttgat tttgcacttg tattttttc   1800
ttacatagaa aacctttatt attaacatta aaatatttgt tttatcctac aatatacata  1860
caataatttg aaaaataata cttgaattga tattaatagt aacaacaaca gcactgctgc  1920
caaacatagt ttaaagtttt atttcaggtc ttattttctt cagaatatat cttgctgaga  1980
atgtataggc aaagtattct acacttactt gaaataattg tcttcatgcg gttatgttat  2040
acatttgata tatagttagg ctcatttgtt tttcattttt tttattttag ggattttttt  2100
cctttattga attttaatat atacaatatt tatatatgca aaatatttaa tcagagaaat  2160
cttaattctg gtcttacgcc tttcatatta ttctgctcca ccctctgtag gtaacttatt  2220
atctttctca tgtttccttt ttggaaacat aaacaaagac aagacaggtt acatgacatg  2280
tatacccttc tgcacctagt tttatacctt accttgtagt ttatttttaa gcatgtaaat  2340
gttcaatgtt catgactaaa tttggacagg atcataggaa cacagaattc aaagtgaaat  2400
taaaatgggc ttgggttctt tactttccac tttaaaggtt gtaatgggtg atgtcaggct  2460
aataaaccta ttttcagctt gatctaaagc ttaatactga gcatcaagaa attctttaat  2520
aaatataagt gatatttatt cagacatgta ataaggaaat gttcatgtct tatttttgtg  2580
ttagattttt ttagaatcta cttttgttag agttttataa atacagttag tgtttgagat  2640
agaaagagaa aagaattagt tttcttcctc ttctacctgc tcatgaactt gatttttttc  2700
tcccaacaat tgaagagcca agaaaaaggg agattcttaa gagatgggaa atagaatctc  2760
atctacccct gtttccccca gaacagtgaa actgaatctt aagggtaaga tagaatagtg  2820
tgtacttaac ttagatggag aagaaaggct gccaaaatga gatctgaagc gctattacaa  2880
atatttccat cgttactgta cttcagaatg aattacaacc gtaagttttt ttacttcctc  2940
attcataaat ttgattattc cttataccac ttctcagctt tcatcattct ttattgtact  3000
tttctatgta atgtttgcct attatacagc aacttaagag aactgtaagt ttggacattt  3060
cattttggtg ttgataatag aatatctttg aatagttcta tagttgatga gtagaaccat  3120
gaaccaagta acttaaagtc cttgatgtta tttattacag agaactataa tagaagctct  3180
cccgctaatg tttccatcat gtgtacaaaa agtttttcttg ttattaaagc tagtccgttt  3240
aacttacaat aagcataaat agctaagctg tgaaagttac ctgtgataat gctaatttc   3300
ccatttatta aaaggcaagt tgttttccga tcataagaaa tttagaaaag ccatccaaag  3360
ataaattccg agtgatatat tcctgctgtt tgttatgttt tctcaaatta attgagtttt  3420
attttacaat gacaggagtt attaaagtat tttattttta ttatgattaa gatttcaaa   3480
gtaacatttc ttatatgaaa gaaattatgt taatgcatgt ttttcttaca tgggaaatca  3540
tatattttaa aaatgatttt aaaattcgtt ttactttaag ttgtattatc tttctcaaaa  3600
gtggctagtg cttgaccaga aaaaaagaca ccagcataac tcagtgtatc tttatttaca  3660
tag                                                                3663

SEQ ID NO: 85          moltype = RNA  length = 5838
FEATURE                Location/Qualifiers
source                 1..5838
                       mol_type = other RNA
                       organism = Homo sapiens
SEQUENCE: 85
gtaagtttgt gtgattcttg aaccttgtga aattagccat ttttcttcaa tatttttgtg  60
tttgggggga tttggcagat tttaattaaa gtttgcctgc atttatataa atttaacaga  120
gatataatta tccatattat tcattcagtt tagttataaa tattttgttc ccacataaca  180
cacacacaca cacacaatat attatctatt tatagtggct gaatgacttc tgaatgatta  240
tctagatcat tctccttagg tcacttgcat gatttagctg aatcaaacct cttttaacca  300
gacatctaag agaaaaagga gcatgaaaca ggtagaatat tgtaatcaaa ggagggaagc  360
actcattaag tgcccatccc tttctcttac ccctgtaccc agaacaaact attctcccat  420
ggtccctggc ttttgttcct tggaatggat gtagccaaca gtagctgaaa tattaagggc  480
tcttcctgga ccatggatgc actctgtaaa ttctcatcat tttttattgt agaataaatg  540
tagaatttta atgtagaata aatttattta atgtagaata aaaaataaaa aaactagagt  600
agaatatcat aagttacaat ctgtgaatat ggaccagacc ctttgtagtt atcttacagc  660
cacttgaact ctataccttt tactgaggac agaacaagct cctgatttgt tcatcttcct  720
catcagaaat agaggcttat ggattttgga ttattcttat ctaagatcct ttcacaggag  780
tagaataaga tctaattcta ttagctcaaa agcttttgct ggctcataga gacacattca  840
gtaaatgaaa acgttgttct gagtagcttt caggattcct actaaattat gagtcatgtt  900
tatcaatatt atttagaagt aatcataatc agtttgcttt ctgctgcttt tgccaaagag  960
aggtgattat gttacttttt atagaaaatt atgcctattt agtgtggtga taatttattt  1020
ttttccattc tccatgtcct ctgtcctatc ctctccagca ttagaaagtc ctaggcaaga  1080
gacatcttgt ggataatgta tcaatgagtg atgtttaacg ttatcatttt cccaaagagt  1140
atttttcatc tttcctaaag attttttttt tttttttttg agatggagtt tcattctgtc  1200
acccaggctg agtgcagtgg cacgatctcg gcttaacgct tactgcatcc tctgcctccc  1260
agattcaagc agttctcctg cctcagcctc tgagtagctg ggattacagg tgtgcaccac  1320
cacaccagct aatttttttt tttttttttt ttttttgag gcagagtctc gctctgtcac   1380
ccaggctgga gtgcagtggc gccatcttgg ctcactgcaa gctccacctc ccgggttcag  1440
gccgttctcc tgcctcagcc tcctgagtag ctggtaccac aggcacccac catcatgccc  1500
ggctaatttt ttgtattttt agtagagatg gggtttcacc ttgttagcca ggatggtgtc  1560
gatctcctga actcgtgatc cacccgcctc ggcctcctaa agtgctggga ttacagatgt  1620
gagccaccgc acctggcccc agttgtaatt gtgaatatct catacctatc cctattggca  1680
gtgtcttagt tttatttttt attatcttta ttgtggcagc cattattcct gtctctatct  1740
ccagtcttac atcctcctta ctgccacaag aatgatcatt ctaaacatga atcctaccct  1800
```

```
gtgactccca tgtgactccc cgccttaaaa actgtcaaaa gctaccggtt acctgaaggg  1860
taaaagtcaa gtcccctact tacctcatgt catctagagc aagagatgaa ctagctgagt  1920
tttctgacca cagtgttctt tcttatgtat gttcttttgt acgtgctctt ttctatatat  1980
agggaaccat ttctctcttc cagttgtttt gctcagtgaa tttctattcc tgtttcaaaa  2040
cttgttcagg cattaccttt tttttcttaa gcatactttt tttaatggaa caaagtcact  2100
cctgtctaca ctagttctgc atcttataca taggttttgt acatagtaca tatttatatc  2160
acatcaaatt atatgtgttt acatatctgt cttccttaat ggaatataag tcttttgata  2220
taaggaacta tttaatttgt ttctgtgtgt tgagtatctc ctgtttggca cagagttcaa  2280
gctaatacat gagagtgatt agtggtggag agccacagtg catgtggtgt caaatatggt  2340
gcttaggaaa ttattgttgc tttttgagag gtaaaggttc atgagactag aggtcacgaa  2400
aatcagattt catgtgtgaa gaatggaata gataataagg aaatacaaaa actggatggg  2460
taataaagca aaagaaaaac ttgaaatttg atagtagaag aaaaaagaaa tagatgtaga  2520
ttgaggtaga atcaagaaga ggattctttt tttgttgttt ttttttttga aacagagtct  2580
cactgtgttg cccaggctgg agtgcagtgg agtgatcttg gcttactgca acctctgcct  2640
cccaggttca agcgattctt ctgcttcagt ctcccgagta gctggaatta caggtgccca  2700
ccagcacggc cggctaattt agtagagaca gggttttgcc atgttggccg ggctggtctc  2760
aaactttgga tctcaggtaa tccgccagcc tcaacttccc aaagtgctgg gattacaggc  2820
atgagccact gtgcccagcc tgtttttttt tttttaaagg agaccagtga agtttcagga  2880
ggagggaaag aaaatttaga gttactaggg agagagtgat gaagataaga gatgaaagtg  2940
gtaataaggg aaatagcaaa atatcagggt aggtgggaga aaaagagatt tgtaacaaac  3000
aataggatta tcctgtgaaa aaggatgaaa ggaagaaaaa aatggataga aagatattta  3060
aaacaccctc agcctcctgt tttccctcct gtgtattcat agtatataaa actataatta  3120
tgtactttac ttaaaaaata tattattatt accttatcgt gcttatttaa tcatagcatg  3180
tcctcttttt agtctcatta ccctgtttgt attattcttc ataacactta atacctgaca  3240
ttgtattata tattggctta ttttccaggt actccactca aatataagtt ctaggatata  3300
atttatttat cactgaaatc cattgcttag agtacctggc atgtagtaaa taggcattct  3360
gtttttttcaa ataaaaaata aaggaactta agatatatat ttatgttata tcgccagcct  3420
ttttcctcac agctctattc tgttgtacag aattacctac tttacaattc ctgtgtttca  3480
aggggatctc aaatttaacg tgtccacaat gaactcctga tttctgtttc tctcctagtc  3540
attcttattt caatatatgt tcagttacct aaccagctag tcaaggcaga tactttagag  3600
ttattctgta gtcattcttt ttccctacca tttttgtttt ccaaatgtaa tttatgtgtg  3660
tcttcttcat cctcgcagct ctaacccttg tccaaaccag catcatcact catctggagt  3720
tccacaatgt ctttctggct agtttccctg atttctctat tgaccccttt attctccaca  3780
gtgcagccag aatgattgtt taaaacttcc tccttaaaat ctttaaattg ttttctttta  3840
tacgttaagt taaattccag ttccttgtct tggcatgcca tgccctgcct ggtgtggccc  3900
ctgatggtct ctccaacttc atgttttact actattgact cttatttttg cttactctgc  3960
ttgggtgctc cagtcctcca aatcatttcc tgctccaatc atttcaatca tttttttcctc  4020
tcagatctta tagtattcca aatgctttct tcctttggag catctgggtt tactaataaa  4080
tacttcgtac ctcacagttc agcttaaata tcaattattt ggtggttaag acatccttca  4140
accgctctat ctaaatgttc ctttctatta ttcactggct cagtactctg tttttatttt  4200
ctttctaaat gtcaactttt ttttttttga gtcagggtct cactgttgcc caggctcgag  4260
tgcagttgca caatcatagc tcattgcagc cttgccctcc tgggatcaag taattctccc  4320
acctcagcct ccaaaatagc tgggattaca ggtatgcatc accatgctca gctaattttt  4380
tgtgtttttt tgtagagatg aggtctcact ttgttgccca ggctggtctc aaactcctgg  4440
actcaagtga ttctcccacc tcagcctccc aaagtgctgg ggttacaggt gtgagccact  4500
gcacctggtc gatactgact tttttttttt tttgagatgg agttttgctc tgttgcccag  4560
gctagagcgc agtggtgtga tctcagctca ctgcaacctc cacctcccag gttaaaggga  4620
ttcttctgcc tcagtctcct gagtagctgg gattacaggc aagtgccatc atgactggct  4680
aatttttgta tttttagcac tatgtttagt actgtgttgg ccaggcttgt ctcgaactcc  4740
tgacctcaag tgatccaccc acctcagcct cccaaagtgc tgggattaca ggtgtgagcc  4800
accgtaatcg gccaacattg acatttttag tagactttt gtttgtttac ttgcttatta  4860
tctgctgcct tccacactct ggcgaaatcc tgccacccac ccacacacac ataggcactg  4920
aatgggcaga actctgaagg ccagaatttt atatttcttt tcactgtaaa catcatcatc  4980
tgtcactgat ggcacactag gatgctcagc aactgtgtgc atgaaggaag taagcactag  5040
tttgtgaagg ctgcaaaact cttgagtatt ctaagagttt tggccaaaat gaatgtacag  5100
ctttagtggc agaagctaat actcagaaat tgaggccgta tattggataa cacaggattt  5160
ggatgattat tttaaaataa tattttacat tgtatatatg tgtgtgtgtg tgtgtgtgtg  5220
tgtgtgtatg tgtgtgtgtg tgtatatata tatgtatgta tgtgtattag tccgttctca  5280
tgctgctatg aagaaatacc tgagactggg taatttataa aggaaagagg tttaattgac  5340
tcacagttcc acagagctgg ggaggcctca gaaaacttaa cagttatggc agaaggggaa  5400
gcaaacacat ttttcttcac atggtggccg gaattagaag aatgtgagcc gagcaaaggg  5460
gaaagcccct tataaaacca tcagacatcg tgagaactta ctattatgag aatagcgtgg  5520
gggaaaccac ccccacgatt caattacctc ccaccaaatc cctcccatga catatgagga  5580
ttatgggaac tatgattcaa gatgagattt gggtagggac acagccaaac catatcagta  5640
tgtatatgta tacaagtatt atatatatat gtatgtgttt gtatgcatac atgtattata  5700
tatggaggaa attctaattt tgtaaaaaac tggattgtga gttttaagga gatgttatat  5760
aaagttaaga caatgtcatt ttgtggtatt ggtctgaatt acaatgtagt ttcttagtga  5820
tatttttcct ttattcag                                                5838
```

```
SEQ ID NO: 86          moltype = RNA  length = 2912
FEATURE                Location/Qualifiers
source                 1..2912
                       mol_type = other RNA
                       organism = Homo sapiens
SEQUENCE: 86
gtaagtttta tgactctgat aatataaaat gattaacatc taataatgaa tatttcttat  60
ttaaagttcc tttttatgc tagattaaaa ggaagtattt tgactaaaaa aagaaagaac  120
tttctgccta ataatttaac ttaggcagat gaataatcct gtacttaacc ccaccaaagt  180
ttagttttca gtccttaagt tagatttgtt tctaatgaaa tcatatatgt taaaaattta  240
```

```
tgactaagta ttagctactt tgaaccgttt aacaattaaa actgatgata ttttattaat  300
ggtattatga gttctttcac tgagtgcaag ttatattagt tatatatcac ttgatatttt  360
taaattaaaa gataccagga aacagcaaag aaaatgtgaa aagaagttgt atttctcata  420
gttttactac tatattactg tatatttttg ctcctatatg cttacatatt ttatatattt  480
taaattatta taaacatggt tttatactgt atttagatag taatatcaaa aatattttta  540
tggccggcgc agtggctcac acctgtaatt ccagcacttg ggaggctgag gagagcagat  600
cccctggggt caggagttcg agaccagcct ggccaacatg gcaaaacccc atctctacta  660
aaagtacaaa aattagccag gcgtggtggc agttgcctgt aattccatct actcaggagg  720
ctgaggcagg agaattgctt gaacctagga gtcagaggtt gcagtgagcc aagatcatac  780
cacagcactc cagcctaggc gataagagtg agactccgtc tcaaaaaaaa aaaaaaattt  840
gttttattca tcatacttat aaatacttat acaatagcct aatgtgtttg agtgattaaa  900
tcactagctt tttatatttt tgctattgct tatagtgcca cagtgaacat tttcatgtat  960
atctaacaga gatattactg tctcagaagg tattgaaatc tttgttgctc tcattagagt  1020
tttccatatt aatttttcaa acagttatat agtttataag attttcataa ttttatctca  1080
tatattgtgc ttcataattt tcaaataaat ttgctgcttt cgataatgta ttttcatgta  1140
tttgtttcct agacgttaga gctattcaag gtttttatta ctaaatagag ctgttctctt  1200
aaattggtaa tgagatactt ggtttagaga agcctaacac tgggaaatct tacataagct  1260
acttttagaa atgtaatttt tagctcaata agagattaaa tatgaattga cttttgtgta  1320
gtatttgcat ggaagaaggt accatttaaa tgaagacatg agagtattac gtacaatttt  1380
agtaggttct ttttatttta tcatctttat ttttaataaa tgctgaattc cctacagaaa  1440
ttctttaatt tttacatatc ttgatctctt tcatatatgg atttatatca ccgaagtttt  1500
aagagtgttt ccctattccc tgttgccctt atatctttgt ttaaaaaatgt cacatcatta  1560
gctttttttc atctaggaat ttgttagtgt tgggctgttg tgctctaccc tctctttaag  1620
aaaactccaa acccaaaaac atacaagatg gctagtctgc ttcagccttt gtgatgtgct  1680
tttctcttct aatcagagtt tagcacaata cagaatggag aaggactcct ttatatattg  1740
gtatttattg cagtattttt ctacatggtg cctaaggtta cttgaatgag tctttattcc  1800
ataatgaact gatttactaa tgcttttagc acctgttagt gatccattat tgttagttac  1860
ttgattactg cttgccacag ctattctaaa ataatacatt ttaaagataa atacagaaca  1920
taatgaagta ctttttaaaa ctgagataga gaccaatttt tttttcagga aatgtatatt  1980
actttgagaa aactcagtta taaaacttga acttatgaag ctggaaaaac aggagggggc  2040
attattggta ttgtaaaagg ctgtttacaa agtgagttgc tgcttagttc ctttaagtaa  2100
ttggctaccc taaacacatc agttttaagt tgctgaaaag caaaacactc taccaaattt  2160
tgtttttttt ctagaccatg tttacaaagc aaaagtatgt tttcttcccc ccccctcaaa  2220
aaatgactaa tgacactcct atgcgatgcc tttttatggt aaattgaggc ttttagttct  2280
ctttccattt agccacagac ttttgtgtcc aaagacaagc tgcgtaactg catatataag  2340
gttaaggcat aactactaat aaaagaatgt aaaatatttg atattaggtc tgtacaaaga  2400
ccaaataata ctcatgatta gacaagatta tatttggtag aatctatcca tcatatggct  2460
tcagatttta cttttcagct tggctttgtg agactttaaa aatcaagtca ttgcacttat  2520
attcacaaag tcacattgct ttactgcatt gcttctcata cagtttatct cctttcagta  2580
aaatgtttac ttgccatttt taaaatttct tatatgtgac acttctacac taagtccttt  2640
atgttgttag ttccacaatt ctgtgaggaa taggtttttt tttttaatca tttgattgat  2700
gaagaacatt aagttccaca gagattaaat ggtacaggca tcacacaggc aggaagtaac  2760
agagctaaga ttagagtcca ggtctgatgg aattcagaaa gctaatgtgc tttccatgga  2820
actataatgc tttctaatat acagcatcta aaatatctga ggtaatttta atataaacag  2880
catgagattg acttaaatat tattgcatgt ag                                2912

SEQ ID NO: 87          moltype = RNA  length = 937
FEATURE                Location/Qualifiers
source                 1..937
                       mol_type = other RNA
                       organism = Homo sapiens
SEQUENCE: 87
gtttgatatt ataagtttta tcatacaatt atagaataaa gaattagttt tggtagacat  60
tgtattattg ttaagtggtt tgtctggatc tctgaaatat cttattaata tagtgcctat  120
gttttgtgta ataaataaat aaaagattta aatctgaatt gtttaaaagg aaagcagata  180
tttctgtaag tttttctcac caatgttata ttattagatt taatttatga aatgttattt  240
actaaacaat ggaattgcct ttcaccacca tcccttcatt taacaaatat ttattcattg  300
cctattacat gtcagaccct gtgttgggac tggcagtata gcaagaaaca aaatagacaa  360
taatctctac tttcagggac tttacattct aattggtggt tttatatatt tttgatgtgg  420
tcagaatcat taaactgtgt ggcagtaaat atagtttgca agtatttaac aatttatgat  480
taaacacaac tcttacagtg tttgcttacc ttgagattta atatattttc aaagcattta  540
tatcattttt gttttaacta tgtcactaaa tctatatgag taagatttta ttaactcatt  600
tggatttatt tatagatgat acaattgaag taaaatataa tgagcagatt gcattctaag  660
caaagtaaga atattgcaag ttcagatatt attagataat gagttgccta ataaaaatga  720
cttttggtgg attggaatat aaccagagtt tccatagttt gtttctgatt ctttcatatt  780
ttttaccctc cttcagtctg ttcttaacac ttcacactta atataatatg tgaactaagg  840
ccaagtaaag aggattgcag tactttaaaa gctaaattac aaagaaaacc tcaccaaaaa  900
ttgatgtatc tgaacatttt ttgttacatt tccttag                           937

SEQ ID NO: 88          moltype = RNA  length = 1841
FEATURE                Location/Qualifiers
source                 1..1841
                       mol_type = other RNA
                       organism = Homo sapiens
SEQUENCE: 88
gtaagtgcat ataagcattt tagccatttg actagatgta tcttctttaa tttgtcttta  60
agaaacccaa ttacaggtat acaattctta gtagtaattg atactgattt ctttttataa  120
gaacaggatt aagtaatatt aagatcggtt ttaacagggt taaataataa tattgacgag  180
aataatattg ttaaagagga agtgacctct caagatttgc attttttaga gttcaggaat  240
```

```
attattgcag aaaggtccag ttcctccaca tattgatttt ttggggaagg ggtgatggag  300
gaggaatggt tgtttattgt atttaaactt aagtttcttc attttaataa gggagtaata  360
gtacctcttc tacctgtttc ataaggttgc tgtaagaata taataaaaaa ttcagatttt  420
gatttagttt acatttatcg ggcatctact atgtactagt cacggtgcaa ggtattaaac  480
atatattgac ttgtacaatt atacttaacc ttgaggttat atttttgttt tcattttaca  540
tgaagaaata tgcccagcta gtttagaaca caaaatatat ataaggagta aatactgcgt  600
gctggctggg cgtggtgaca tgtgcctgta gccccagcta ctcgggaggc agaggcagga  660
gaatcgcttg atcccgggag gtggaggttg cagtgagccg agatcgcgcc actgcactcc  720
tgcctggtga cagagcgaga ctctgtcaaa caaacaaaca aacaaagaaa aacaaaacaa  780
aaaaaccgtg tgccagctat atgctgtatt ttcattctct tttgtaatta ggtgatattt  840
cagtagaaaa gtataaggag cacttagtta atctgtcaag cataaatagt aaaaatattt  900
tatggcctac tcataaaaat ataaccattc ctttggagcc ttgatagttc tcttgggaat  960
atcagttttt gacatctttt tcactatgaa agaccctttt ttttaaaaaa attgatcctt  1020
tcttctcatg gacctctttt gatataaact aacttataat agttcatttt aatcatattt  1080
tgttaatcat gcaactggca atgagagcct ctcatcagta tgaggaaacc tgccttatct  1140
ataatactga actaaaatta ttctaaccca aagcaaagaa actttacatt ttgctttgcc  1200
tgtattagct tatcacagta ttcatgaggg aatttgaagg acttattacc attaggctat  1260
ctcttttttt tttttttgt aattttatta aatgcatgtt ttgtttcttt tcacattact  1320
gataacttgt agattaaaac aaatcaaaac atgcattaat ccatctaagg atcctagaaa  1380
ttttacattt ctgtgttctt aactgtgtga tggtcttaga taaatgtact aaatacctta  1440
tcctagcata ttccaaatta tgacaataaa tgttttatgg aaaaaagtat gggaacagaa  1500
gttctttggc tatatacatt tggaaaatac tatatagtaa gtatgatttg agataattat  1560
atatgataga acctctggga gcactgaata tatgttagga atattcaaga gggaggaggg  1620
atgttgagaa tgaagttttt tttatatagc aaacatgata acctctgatg gaattatgtt  1680
tcatgaaaca gtttaggaaa tcctgtttta atatttcata caaagaagag atagatgctg  1740
aaaacgaatg gctttttgaa aaagggtcta gaaattttga attttggcat ttacttagaa  1800
agtgtactta attgttcctg aaatacctta tcatttccta g                    1841

SEQ ID NO: 89          moltype = RNA  length = 1240
FEATURE                Location/Qualifiers
source                 1..1240
                       mol_type = other RNA
                       organism = Homo sapiens
SEQUENCE: 89
gtatgtgcag tattggctct tctacataga atccactttt ttccctaaat ttacattaga  60
tgttgggagt gggatatgtt atactttttg tttgtttcga gatagggtct cattctgttg  120
cccagggtgg agtgcagtgg tacattcaag gctcattgca gccttcacca cctgggttca  180
ggtgatcctc ccacctcagc ctcttagaca gctgggacta caggcacgtg ccaccacacc  240
taattttttt gcatttttg tagagacagg gtttcaccat gttgcctagg ctggtcccaa  300
actcctgggt taaaatgatc tgcccacctt gacttcccag aatgctggga ttacaggtat  360
gagccaccat gctgggccat tgttacattt ttaatcaaaa gatataccaa ccagaggctg  420
ttattcttgt tagttggaac ctgattagaa agctctttaa tttgaaatat tgttcagtaa  480
tccagtacag catttaaatg cctatagatg aattatgctg ctgatcaaaa ttaggacact  540
gagaattgta gttagtaaat ctttaataac aatattttct cttgtattta tatgtaactt  600
tttacatatt cttacgttat atatgttggg aattataaaa acatacacat tgtcctgatc  660
agtattatgt tacttgcaat ggaggttaaa aaaaaactgt aacagtcagg catggtggct  720
cacgcctgta atcccagcac tctgggaggc cgaggcaggc ggatcacgag gtcaggagtt  780
cgagaccagc ctgaccaata tggtgaaacc ccgtccctac taaaaataca aaagttagcc  840
aggcgtggtg gcatgtgcct gtaatcccag ctacccagga ggctgaggca ggagaattgc  900
ttgaacccgg gaggtggagg ttgcagtgag ccaaaatcac gccattgcac tccagcttgg  960
gtgacagagt gaaactctgt ctcaaaaaaa aaaaaaaaaa acaccagtaa catacccact  1020
gttattcagt tacatttgga ttttaagttt gtttgattct aggtttttttc ttttacagtt  1080
ctttggtaat tatttgtatt aaagcaaagt tacatttttg tagatctcat gtgccactgt  1140
gttaaaactt tgcttagtaa attgtgaatt ttaaatctgt gataactttc actggaaaaa  1200
tttgaaactt actacaaata tatatttttt ttaatatcag                      1240

SEQ ID NO: 90          moltype = RNA  length = 1087
FEATURE                Location/Qualifiers
source                 1..1087
                       mol_type = other RNA
                       organism = Homo sapiens
SEQUENCE: 90
gtaaacattt aaacttgatt ttttttttta agagacagta tcttgatctg tttcccaggc  60
tggagttcag tggtgcaaac atagctggaa ctcctgggct caagggactc tctagcctca  120
gcctcctgag tagttgtagc tggcagtaca ggtgcacacc accataccta cctaattttt  180
taaaattttt aaatttttttt gtagagacaa ggtctcactt tgtcacccag gctggccttg  240
aactcctggc ttcaagtaat cctcctgctt tggtctctca aaagtgctga gattacaggc  300
atgagccact gtgcccagcc aattttaaat tcattatctt caaaagagtt acatgataat  360
ttcttaatat atgcctatat gaaaaatgct taagatacaa attccaatta tgattcatta  420
atttagattt tataacttag cagtgttggc tatttgaatg tctattatac gtaaaaataa  480
aattaggctt ttctaaccaa agattttagt gggaatgttc agattgtata atagcaaaga  540
attttaatta ctataggaaa atttatatta attaaacact aattattata tttaaacatt  600
gtagtagtta tcagttgatt tctactgttc ataattatct ttgatctaca agtagtgggc  660
ccacatttac ttttaatatg gtttaatctt catttagaaa gaattaaatg aaaaataatt  720
atcttgcaac tacatcctgt tctctaggct agaaacattt aggatttctg tttttgaaag  780
taataccaaa gttccaatga cctgcttata gtcagtgttc aataaacgta taacaaatga  840
aagtgaatat tagtgatgtc cattccaaca taatttgaag atttttattg taaaatccca  900
catatttgta gaaaagtcta tggaaatcct aaataagatt ttgtcatgta gtttgacaaa  960
agataacatt gtgtcttatt ttattttaga atggccatta ctttcaatta aaatcattat  1020
```

```
catcaatgga ggaatgttat ttgttaatat agcatttata tttgtgtata taaattgtaa  1080
atcttag                                                            1087

SEQ ID NO: 91          moltype = RNA  length = 1281
FEATURE                Location/Qualifiers
source                 1..1281
                       mol_type = other RNA
                       organism = Homo sapiens
SEQUENCE: 91
gttttatttt atatttattt cattttttc cctaagtttt ttttttttt ttttttttt  60
gagatggagt ctcactctgt cgcccagact ggagtgcagt ggcgtgatct cggctcactg  120
caagctctgc ctcccgggtt catgccattc tcctgcctca gcctcccaag tagctgggac  180
tacaggcacc cgccaccgtg cctggctaat tttttgtatt tttagtagag acggggtttc  240
accatattag ccaggatggt cttgatctcc tgacctcatg atccgcccgc ctcggcctcc  300
caaagtgctg ggattacagg cgtgagcccc taagatttta aacaagaata ttgcacaaat  360
gactatgtta tccttctaat taagtgcacc ttccattact aattgattat ataataattt  420
gtttttttatt ttctaaacta ttctaaaaat tcatatttat ttagctttta taacagtagt  480
cttaatctta aaaacggcaa tacataagca acctcatttg gtaagttaat ttttattttg  540
atattggtta tttgactttt cacagttcca cgtttctact ggctctcact gatagagtaa  600
gaagtcagct tcttatagaa taaagtatat acttcagaga cagatgaaat tcgtcaaaca  660
tatgactgtc tcagagattg ttccccctgc ttaaattgtt cttaccctag atacctttgg  720
tatttacact gtcagtgcct gcaggtctta gctcaaatgt cttaccttat cagtgtatcc  780
ttcaccagcc acctaatata caacagtaaa tcctactatc cagattccta aatagagatt  840
aattaactta atttttctcc aaagtgcttg taaccttctg acgtattaca tacttactgg  900
tttattattg actgtctttc cttcgccaga atgcaagttc cgtggtgaca cggacttggt  960
tttgtttact gccatgtttg tatttcctag aatgatgctt ggcacataat atatgtcatc  1020
aaatatcttt cgtatagctg aacggatgga tggatggatg gatggatgga tggatagact  1080
gaaatcctta cttcacatct gcctttgtga tcttacacaa gttacttcac ctctctgagt  1140
ttgtattttt ttccataaaa ggaaaataat tacagtttct tcaatgtgtt gtgaggatta  1200
gataagaaaa tatatataaa atgcctgtta tgtgcctgat gtcttcgtgt atgtgtctga  1260
cacaaattgt cctttttta g                                             1281

SEQ ID NO: 92          moltype = RNA  length = 217
FEATURE                Location/Qualifiers
source                 1..217
                       mol_type = other RNA
                       organism = Homo sapiens
SEQUENCE: 92
gtatgaatga ttaatcttgt ttgttactct gtagcatagt ctagagtgtt aactcacaga  60
aatatttcct gtatcagatg taattttaat tgatgttata ttgtatattt aaaatataag  120
aggggtttaa tctatgtttt atcatacagc tgtaaaaatt aatagttact ctcaatgctg  180
caactgcttt tttaaaaaac atactatttc ttaatag                            217

SEQ ID NO: 93          moltype = RNA  length = 1186
FEATURE                Location/Qualifiers
source                 1..1186
                       mol_type = other RNA
                       organism = Homo sapiens
SEQUENCE: 93
gtaattagaa gaatttgcat tttgattagt gtattatttg gtatgtttgg ggggctttct  60
aaataatatt tctttatgag ggcaatgcat agaatgatga atctattgct aatttcacta  120
tttttctatt ctcctataat gtttctaata gccaataatg aacagcagat atagttaatt  180
tgaattcact atttaattat tagttggtac ctttcggtac actgaatatg aaaggaaata  240
aaaagcattt aattgtagtt ctatgagcaa tatattctct tatatgatct ctttattctt  300
actttttttgg ttttattttg aagtgcatgt tacataatct atgaatcaat tttcagttca  360
ttgcctttaa tgcatggtta aagggttgaa ggtaaattag aaattacttt ctgttttaac  420
ctagatcttg aatttgatta gtaggtgatc aaatctgtca tcttcattaa attattcaga  480
aaataatgta aactgaatgt gttttcattt tagttttcat ctaaataaac tgcaaataca  540
tttaaaatat acataaagaa gtttttcaag taaaactgta catttttaat catttcagga  600
aacgtagatt ttcttcagta attttaagat ttgtcattta tgtgaattgc cattgaatta  660
cttaatttaa aatactcacc ttaatcctct tgaagagtaa aaatttttct gtttttttct  720
ctttgtttta ataagctgcg gattttatat tcgtaattta ttgagttggg cctctaaaat  780
tccagttttg tacttaactg acttatagat tagtctccta atgctctgct agtcaatgga  840
ccaaaataaa agaaataatt tattacatat tcttcctaaa tctagtacca ccatacatgt  900
ataattctaa actgtaatat ctcaataaag taccttaatt aaattttatg ttcatcataa  960
caatgaagtt tctagcatat gtaatagtct tataaataag catgcaaata actgctgtca  1020
attagaatta gtcagtttaa ccttattaag tatcaaatgg ctattgtaca tatgatgtga  1080
aaaataaagt gaattttttt tggctaataa ctaatctaaa attcagatga agcattttaa  1140
agggaaaaag atactttaat gatttattat aatttaatca ttgcag                  1186

SEQ ID NO: 94          moltype = RNA  length = 631
FEATURE                Location/Qualifiers
source                 1..631
                       mol_type = other RNA
                       organism = Homo sapiens
SEQUENCE: 94
gtattttatt atattatgag ttatgctgtt atccattagt ttttttaagc aaatgctaaa  60
tattatttta ccctaaagtg gtatttcttt tcttgctttc aaatgattct atttaagaat  120
tgttacttgc atgtgattgg attacacctc tgtcagtaaa actggaagtt tgtgtacatg  180
```

```
tatctttcta ttatacactg actaaaccac gagtagctat catggtgaaa tcatatgatt  240
ttgaaaaata ttttaattga gtttataggt gaggattgag gcaatagggt ggaatgaaat  300
atatcacacc ggtaatcagt agaaatcaga tttgttagaa cttcgtgggg gaaagctaac  360
atttaatttt ttctagaagt aagttaaaag atgatagata catgtcattc taatgttaag  420
aataaattat gaactgaggc tggcttgtc aacttgaaca ttgtctgagg ggacatgcat  480
accagtctag atacatacat atatggagat actgtttctt cctcatctca aaggaatttt  540
agaagattga agagaaaata tataaggtct tcaaaatgtg aatttgtttt aatcacaatt  600
taagatatag tttcgatttt ctgtaaaaca g                                631

SEQ ID NO: 95          moltype = RNA  length = 616
FEATURE                Location/Qualifiers
source                 1..616
                       mol_type = other RNA
                       organism = Homo sapiens
SEQUENCE: 95
gtaagattct aagaactttg ttccattctt tattgatttt tgtgaccatg taaattaaaa  60
ttcagctctc ttcttttttg gaatggaagt tacccttttt gttgccaaaa taatcttctg  120
aaaacatagc tctgatcatt cttcctcctg tagctcaccg ctgttcacaa aattatattt  180
ataattctta gccatgtact caatctgcta tgaacctacc tgcctttctt ttcaaattct  240
actcactgtg agtttagcta tatctaactt ccagaattca gctcatattt gcctcttttg  300
accattctgt tccatatgta tgaaatgaca tgtctttcat cttttaatgt gtaaccttag  360
catatttgag cattacctcg ttaattcggt caacacttat tgatctcctg ctacgtgcag  420
acattttgct agctattgta aatacaaata ataaagtctg catttcctgt cttctttaag  480
ccttcattgc ctattaaatc attacatttt agattagata ttatattttg atcatttgag  540
gaaccaaatt aaaaatatgg aataagtatg gcattgaatt atacatgcct attgctaata  600
tattcatatt ttatag                                                 616

SEQ ID NO: 96          moltype = RNA  length = 2635
FEATURE                Location/Qualifiers
source                 1..2635
                       mol_type = other RNA
                       organism = Homo sapiens
SEQUENCE: 96
gtaagtcttc gaaatgtatt gtaaaaatag gcaaatgata agtgatataa tgaagataaa  60
cataagtgtt tgctatgcca ggcactgttc taagactttt aagtatattg tctcattttt  120
atcctcagga ctgctggtta catatgttat cattttcccc attttaaaga gaggatatgg  180
cctcaggaat gcttaatagc atgtctgggg gtagatggga aagccataat ttgaaactag  240
tcagtctgac tcaaaagcca atacaaattc ttttccagaa tctcattttt accttctttg  300
agcctcagtt tcatcttatt tatttatttt tatttttgag acaaggtctg gctctatttc  360
ctaggctgga gtgcagtgac ataatctcag ctcactgcaa ccttgacctt ccaggctcaa  420
accatcttcc cacctcagcc tgcagagtag ctggcactac aggcaggtgc caccacacct  480
gggtagtttt tttgtatttt tgtagagaca aggtttctcc atgttgccca ggctggtctt  540
gaactcgtga gctcaagtga tccgcccact tcggcctccc aaagtgctgg gattacaggc  600
ctgagccatt gcacccagcc tcatcatctt taaaatggaa ataataatac ttaccctggc  660
cctttcaggg tggttatatg aaggtcaaat tataccgtgt atgaaagtaa tttgaaaact  720
gtaaaataac atacagatag aaaacttttg attacacact tataagagtg tctgtcatat  780
aatagagatt ctaaacattg ttcaaccact ttatcagaac gtagatttta aactcaaaat  840
aggtttatag ttaggtagtt tctaatcatt ataatattat ctctatgggc ctaaatttta  900
ttatctgaaa aaacatgaga aaattgaact gcttgactta taattccatt tcagctctca  960
agcccctgct agagtctttg attctttact cacttattca aatgcctctg acagaattaa  1020
cactattttt gctttgctaa ggagctgcca ctgttaagaa attactctct aaaagaaaga  1080
aaattggcaa cagcatatgt gtattttcag tctcttttcc tcactctatt aaattttgta  1140
caagagatgt tatttttggt ctagtaaatt tctgtcatgt tttggagtat aaaattactt  1200
gtgcttttgc atctaatttg tgggtgtaga aaatcataat cttttgaaat accttatata  1260
atacattttt ttgccacagg aaatacttga agttattgtt gtgtacctta cgtcatttta  1320
gtccaaaatt atacttgtgt tctctgtgtg catattttga tatgtattag gagattatgg  1380
atctgtgtga tttcttaagt aaatcctgat attttcacaa tttgatgatg actctttaaa  1440
gttagactta agttttgcca aaagcaagaa gcctcaaaga gtaacatttg ttcatgtctt  1500
aacactatct ccctcttatt ggtcagaatc tcagtatgga tgcagtgtcc atatgcacaa  1560
caatatatta attcagttta acagacttaa tgctgaataa gcaataagat taattgaatt  1620
aactaaatct tttgatagta tccacttcca tatatatagt tatagatata atgctagtga  1680
atttgaacca taaacaaatt aataatacat gtgatttctg tgaaaattta tattagtctt  1740
ttcaatatgt caatataggg cagtatttct caaatataga ggatcagttt ttcaccattg  1800
tccctcttgg ggacatttgg cgatgtctgg agacattttt gattgtcatg gctcgggggt  1860
gctactggta tccagtgggt agaatcaaaa gatgctgcta aacatcctat catgcacaag  1920
gcagccccac caccaacaaa gaattatcca gtcaaaaatg ttactagtag tatggttagg  1980
aaactatcat atagaggaag caatcacatt ttacaagagc cataatattt aaaatgcctt  2040
tttgttcatt ctctgtatat ttgactagag tcacaaaata acttgataag attgttgcca  2100
aaaatattag aaactagaag aaaaatgtgt tgttaagtct aagagtagtt aaatgaaata  2160
aagaattatt cttctttgga tttggatgcc tgcatcaaga tttagattgt aaggatactt  2220
aggactgaac atttgctcta tatgaaattt gtattaatca aggtatgaat tgcagcaacc  2280
actctattaa ttacatatgt ttggccaggt gtggtggctc acacctgtaa tcccagcaat  2340
ttgggatgcc aaagcgggct tatcacctga ggtcatgcgt tcaaactggc ctggccaaca  2400
tggtgaaacc ccatctctac taaaaataca aaaattagct gggcctgatg gtgcacgccc  2460
gtagtcccag ctactcagga agttgaggca aaaaaatcac ttgaatctgg gaggcagagg  2520
ttgcagtcag ccgagattgc gctgctgcac tccagcctgg gtgacagagt gagactgggt  2580
ctcaaaaaaa ttaaaaatta aaaaacacac acacacatat gtttatttac atcag       2635

SEQ ID NO: 97          moltype = RNA  length = 952
```

```
FEATURE               Location/Qualifiers
source                1..952
                      mol_type = other RNA
                      organism = Homo sapiens
SEQUENCE: 97
gtaagtaaca acagaaaatt atcaacattt aggaaaaata tgtggtagat tgcttttaga  60
gaagatttgt aaatttataa aagatggtag tataaatctc cgtgttgtaa taaaaagtat  120
gagctttatc ttatgctgtt aaacaaggta ttttagacaa tgctgttttt gtgggcagat  180
atagtccaat ttatcttttt atgttttcgt caatctgatt tgtgaattat ctatatgaag  240
ttaggaaaaa tcttaatgta cattacaaaa atataatata tattacattg tattttcttt  300
ttttctactg gaattttatg ctactgaggc tatttttaac aaatgaacaa ttttgaacaa  360
tttgagggat tgagggaagt atgataatga caaaaaggga tgaaaaaagg gggtcataga  420
gatgtttttg tgagaaggag ttggtcagtg tattctgatt tattagggtt ttttttagtt  480
tatctcagat ttgatctatt taaattgttt tagaagatgc tggtgttttt ctgtgctagc  540
tatgaaattt atgggtaaac tttaagcctt tcctagtcct tttgttgtct acctaaattc  600
aattaatttc atatggaagg atgtagtaag tgagtaatat aaatatctaa aattggatgt  660
ttgaaaacaa aacatacctg ttttttgtaa tagcttgatt taatgctgag ttctcaaaat  720
cattattaag attttgaact ttcacattca atgtggaaag aattgagtgt aattacaaaa  780
gatttatttg aaaaagttga gttgttaatt tgtgaaatat gttccattaa actcataata  840
ttttagaaaa atagtaggaa gtaataaagc ttgtttattt tttatatcat atattcatat  900
aaaatgtcag ttttccttta aaaattacat tttttttttg gttaattttt ag          952

SEQ ID NO: 98         moltype = RNA  length = 1173
FEATURE               Location/Qualifiers
source                1..1173
                      mol_type = other RNA
                      organism = Homo sapiens
SEQUENCE: 98
gtgaacatca acacgtgtta atgtaacaaa atttctgata attcctattg gaagagaatt  60
cactatgata tatagtaatt ttgttgatga atagggaatt tataatgcac tgttggtggc  120
tagacataga cacacacatg catttttcaa caataagtct ctttatgata ctcatttact  180
gattatcatc ttggggatta ggaaaggata ggccattatg aactactgtt tctaatgaaa  240
ttaaatttaa gaaatatttt acttaggatt ttttttaaga ctttattatt tttttagagc  300
aattttaggt tcacagcaaa attgagagga aggtacagag atttcctgta tatctcctac  360
cctgaaagtg gtacatttgt taaaattgat gaacctatat tgatacatca taatcaccca  420
aagtccaagt ttacctctat tttagctctt ggtattttac actctgtgtg tttagacaaa  480
tgtataatga tatgtatcca tcattatagt attatacagg gtattttcac tgccctaaaa  540
atcttctgtg cctctcttct tcattccttc ctctgcacct caccaaaccc ctggcaacca  600
gtgatctttt tactgtctcc atagtttcac cttttccaga atatgttata gatggaaaca  660
tacagtgtgt ccccatcatt ctcaccatag gacagctagg aactcctttc tagtggcata  720
catattgtct agtattgtaa gttacccttt tatatcttat ctttgtaaac taggttagaa  780
attacttcaa gtcagagatt tgttctgtac tactcttatg cttcatagtg tttaaaacgt  840
tgtcatatat attgttatat acttgtttgt ttaattaatt cagccaaaat gaaacgtgca  900
tatttgataa aattttgttt gtgggtgttt gttgaagatg aattgcttta cactagtttt  960
tttttttttt ctcaaagtcg actttttttcc tcaaggtaga cttgacatga atatggaaaa  1020
atatatgtag tttgtggtta tttttttttct cttgtgtact taaaaattca gactgaattt  1080
ttcttataat ggtatatttt ctgttttatg ttccttttat cattgatact tcttgaagag  1140
tcatgaataa tacctttctt tttctcttat tag                               1173

SEQ ID NO: 99         moltype = RNA  length = 352
FEATURE               Location/Qualifiers
source                1..352
                      mol_type = other RNA
                      organism = Homo sapiens
SEQUENCE: 99
gtaattttat atttaactct gataatgtct gatttacaat atagaggtag tagtttattt  60
ctactttatc attttatcta tggtatttgt taaaactgac tttcaaatca ctttgattaa  120
tgtaattaat ttcttttgtg acttctattg tgtttatagt tctagagtag catattagta  180
tgttgtatta aaatgcagaa gcagctacca gattatctta tgtattaagt gtcatttaga  240
aagtatggtc agtgatagct tcagaaagtt gctattatat aattgaaata tttactgtct  300
attttgtttt acatttattt gtaaaaatat aaagttacat tttatttttt ag          352

SEQ ID NO: 100        moltype = RNA  length = 5295
FEATURE               Location/Qualifiers
source                1..5295
                      mol_type = other RNA
                      organism = Homo sapiens
SEQUENCE: 100
gtatgtgaag aaacatactg acttatatgc ttaaggtagt gacagagtaa gttaaataca  60
tagctgatta acagttaata tactgcctta atttgatgac ctggctgtat taattctgta  120
ttaattttga ggactataag cagtattgaa taacgtagaa aagtctaagt ttctgttctg  180
taggaattta gagtctactt gaggagatac ctataatgta actcttattt ggaaattact  240
acatcaattt cattcatctt tctgacatta gagtacctct gaagttcctt cacaccttaa  300
catattcaac tgtgtatcat ttctctccaa agtaatcatt tacacaggtt ggtgcttttg  360
acttttggga cagaaagata gacattttaa gataccccac tttgacccaa ataggtcctt  420
tttaatcctt caggagacta ggctgttatt tcagatagca aagttatttg gaatatcttc  480
agtatttgca gtaataatca gtaaccaatc tgctcataga ttaattctgt gggagaaatt  540
gcttaaaatt ttatagttca tagtaaactg ttttgtaata aaaattactg attgaaataa  600
ccccaaaaaa aactaaaatt ggctaaaatg cgtgtaatta aatttgttat ggacaataaa  660
```

```
ttggagataa cttgttggta acattcaaaa tatcgaaagt gaactgggaa atgttgatgt  720
tagcagtaat atttgccatt gaagaaaatc agtatggagg agctatggtt aggaaaattt  780
ttattataaa atttacccag aaaatattta atgtctataa aataatttca atcacatgaa  840
aatggaaaag aaaattctgt ctttaaaggc attgaataga aaataggtaa tggaattcaa  900
atttcttaat agagtatgct cccaaaatta ttttctatga aaattcatta atgtcagtgt  960
aatttattga cactatttgc gtggagtcac aacatgcttg ctgtcagaag ctttgctggt  1020
gaaaactgta agatcaaagt gtccttaatc ttttggattt ccatctttct aactccctaa  1080
ttggggatag gcctgatctt atccctaaat ggggataggt tagaaactgg tatgtttgtt  1140
cctaactggt gtgtttctat accagtttct aacctgattc ctatcagaat gttttaagag  1200
ccttgtggct ttgcctggac tcttctatgc tacagtttat ttagtttatt tattcagttt  1260
attcctcctt aaagtgggaa taatactatc tgtattgcca gtttctcagg attattttac  1320
ataaaatgat atgatatgcg gaagtctttt gtaagccatc acatccatag cagtataaga  1380
tattactact aactagaaag agaaaacagg ggtctatgcc cagtattaaa attggcattc  1440
aggaatctag tgagaatatt ttttcaggtt cattgcttgg gcatttctaa tttatactca  1500
agaaatgctt tcatattgtt tggaaatttt agtacccttt tctctgtaaa cagaatttgt  1560
agtctaccta tgtaacaaaa cccacccctg tgccttgcat ttcattctcc ttagcattta  1620
ttactatctt aacatactag acatgtactt gtcttttgtt catctttttt ttttcttttt  1680
ttattagacc ataaactttg atggcaggaa ctttgcctat tttatttatt attgtattcc  1740
cagcacctag aacaatcgct ggcacatagt agatgctcag tatttgttga atgaatataa  1800
atttttaaat gttataataa tattattctg aaatctatgc atacgaagct tttggtacag  1860
aaaacatgaa aagagaacta ctgccttatc atccagtctt cttccctctt ctcattcagt  1920
ctagaacata acctgtttg gaaaaagttc tcaaaccata tgtttatctt gccctcaaac  1980
cataacaaca atcaatgcaa aagacttctg tgacccccag aatatgtggg gatttctcca  2040
catcagcaag caagcagttg gttttgtagc agacaccaac tgggtgtcgt ccaattcaat  2100
tcatcatcta cctggagata gtgtcagatc ccacagatat cttacttcga tcaaatcaca  2160
agtccaggcc tccgtgactt ccgaagttcc cacatcccca gcccccagct ttgggtttga  2220
ttaatttcct ggagtggctc acagaactca gggaaacatt tacttacatt taccagttta  2280
taataaaggt tattacaaag gatacaggtt aagagatgtg taagaagaga tatgggggaa  2340
ggggtgtgga ccttccatgc ctttctgggg tgccaccttc ctctagaaac ctccacatgt  2400
tcagttctcc agaacctctc tgaacccagt cctcttggtt tttagggaag cttcatgaca  2460
tcagtatttc ttctcctagg gtatggggca ggaccccctc gtattagggt tttaagaccc  2520
acagtcagaa aggcagggga agattacagt cctgccttag ggcaggtgaa aggaggatgg  2580
gagaaggtca gagagactct tttctgaggt gtgctcggaa ggcctaacac actcaatatt  2640
ataactaaag atgaggacaa gggctatgag agttataagc caggaaccat ggaaaaaagc  2700
ctatatgtaa taacaccaca atacccatgg taccattcac gtttgttgtt tttctgtttt  2760
tcaattgttc tttcagtctt ggttccctta atcttaattt agcaagtaat gccaggtggg  2820
ataaaattgc ccaaacccaa caaagtactg tgtgctgcag gattatttaa tgacatacct  2880
tatgtccccc actagtattt acatttctgg gagtacagaa aaattcttgt acatatttca  2940
gaaaaaatga aattaataac tatcaaccac ttagtgaagt ttttactttt ttttttgaga  3000
tggagtttta ttcttgtcac ccaggctgga gtgcaatggc gcaatctcag ctcactgcaa  3060
cctccgcctc ctgggttcaa gtgattctcc tgcatcaacc tcccaagtag ctgggattac  3120
aggtgcctgg caccacgact ggctaatttt tgaattttta gtaaagatgg ggtttcacca  3180
tgttggccag gctagtctca aactcctgac ctcaggtgat ctgcccgcct tggcccccca  3240
aagtgctgga ttacaggtat gagccaccac acccagactg aagtttttac atttttttaaa  3300
gggcacttat tagctgaatt aaataaggta aaaaattgac tagtattaga gacaagaatt  3360
ggagaatata gttctctagt attcgagaaa gtcgttttga taggacaact aatcttagtg  3420
agaatttggc tttatttcat attttttaa tttttgaga tgacgtctta ctatgttgcc  3480
ctggctggtc tttgaactct gggctcaaac aatcttcctg cctcggcctc ccaaagtgct  3540
gagattataa gcatgagcca tctccccagg aatttgactt taaaccatgg ttctcaaccc  3600
tttcagattc aacattccct ttaataaaaa atataatgtt tcataatttc ccctttacta  3660
ttataattga aatgcatagt taacataaac tctacctact tacataattt caaaaatgtc  3720
attatgaatg tcctaaatga aatatatagg gggaacataa aaggaatatt catatttcaa  3780
catgtaaatg ctttggcatg actccattgg aaaatataat gaactagtca tgtgcttgca  3840
ccttcattaa tgtgagttca aagctacgat tgcagactga cacaaatgtg ttctattggc  3900
aactgatggg tcatgatggt attgccattt gtaatttgat ttccaaaatg gtaaacaaat  3960
tgttggtgca gttctcagca aaacaatgtc tataatctta ccttttataa gactgttgta  4020
ttcctagaaa acttagtgta tagtaaaacc attaaaaaat tacttagtgt gaatatgtta  4080
gttggagata aattcttagc tcagaccagt gtaagcagaa ttttttactg tattaatatc  4140
cagtagaaca tttgaaagtt gttcagtgca tgagactatt ctgcattgga taggctttct  4200
ttggctcctt tatcatagtt ataataaacc atgacaccta cccctgaaat gccctaattc  4260
ccttccgttt ctttttcttt tttcttttta gcacttaaaa ctagctaact tactacaaaa  4320
tagatttaga tttatttctt gttttgttat ctgtatcgtt tgctcccttc tccccaatct  4380
atctaaccaa ctagtataaa ctagatagta agattcatga agatacactt ttttatctga  4440
ttttattcat ttgttctatt cctattgcct ctagagtagt acttggcaca tggttagcac  4500
taaataagta cctgtcaaat gagtgaagta atgtgcattg aagacttgaa ggggctctga  4560
tgctaggaaa ttgtcatggg ataatagatg aggttggtcg tttgtacaga ggattcttgt  4620
tagaagctta ctctagtcat gattgtatta gaatcttcat ttaaaggctc ctgaagggtg  4680
ttggcattag tcagaactgt ctcccagaat tttatttgtc ttgtgataga ataaagcata  4740
gttagcctaa agagcagttt tcctaatagc tcggcatgcc caaagattct aggagttata  4800
caggttgaac atctaatcca aaaatctgaa atgctccaag atacaaaatt ttttgagcac  4860
caatatgatg ccacaagtgg aaaattctga tgtgacctca tatgatgagt cacagtcaaa  4920
acacagtcaa aactttgttt catgtacaaa attattaaaa aatattgtat aatactacct  4980
ccaagctatg tgtagaaggt gtatgtgaaa cataagtgaa ttttgtgttt ggacttggga  5040
cccatcccta agatatctca ttatgtatat gcaaatattc caaaaatatt ttttaaaaaa  5100
atccaaattc taaaacacgg ctggttccaa gcgtttcgta agggatactc aacctgtata  5160
gcaaaatgaa catatttaca tattctctag gaaatattag tttacaattt ttctaggcaa  5220
attataattg ataaatcata aagaaaattt aaaataacac tggtaatttt cctacctcct  5280
tcgttattgt tacag                                                   5295
```

```
SEQ ID NO: 101          moltype = RNA  length = 331
FEATURE                 Location/Qualifiers
source                  1..331
                        mol_type = other RNA
                        organism = Homo sapiens
SEQUENCE: 101
gtgagtttaa atatcattat aaaactaatt atgtgtaaaa tcctttagtg acctggaaat  60
tatatagctt tatcatagtt gataatatga gaaatggtct agtttaaatg atcatttatt  120
atctatgatt tacttacttt ttattttctt taaaatctgt tttaaatata ttgtaacaat  180
tatagatgga ttttcctgtg atctcgttgt aaattagctt atgacaaata tagggtgtta  240
caattattgt aatttggttt ggtaatgagt atgcaattga aaagccaaac actgaatggt  300
atatttcatg attctatatt aaattccaca g                                 331

SEQ ID NO: 102          moltype = RNA  length = 2648
FEATURE                 Location/Qualifiers
source                  1..2648
                        mol_type = other RNA
                        organism = Homo sapiens
SEQUENCE: 102
gtaagctatt atgtggaaat gtgccaccca ttgtaatgaa aaactggttg acccctagaa  60
attgaaataa taaatgtgtg ttgtcttaag cttgggttat gttttctttt cccatgtgaa  120
ttgagatatt cctggttctt catatgccac ataatttggg tgtattttg atcttttgaa  180
tattatattg tgagactctg gttcttgttt aaattctatg ggaaaatgta gatacttttg  240
ttttagcatg caatcggtct aattaggttc aggccacaag ttccaacctc atttcttggg  300
ctgtggttcc atttttcaaa gccttttcaa tactcttcag atctgtcctg cctgtgtacc  360
tcacaatagg tgatctggta tgtgagctat gtaccattag ttcagttctt agaaactttg  420
gtattctgat taggatcgat ccatacattt gcagctcaag agtgagccca gaagttcata  480
aacaacttta tagggtccct ttcttgagct cctccctctt tgccatctct ctgatacttt  540
gtttccctag ggatttccat ttggggcttt agttacccag tgatgccatg tacttcagga  600
attgcacact tctgcagcca agcaagcaag aggagagtag aaagaggaag aaaaaaacga  660
cttttacctt accctcttag tatcatagct ctaccaattg gagatttccc tcccaaaaaa  720
tattagcttc tgtgagttcc cattgcagcc tctattacca ctgctatggg atggcttaag  780
ggttggggca tgaaagaaca gatagaagaa aaaaaaagtg aggtgttttc atattgtctc  840
ttgagtgtta aaagattccc tttctcttta ctcgagctag aattagaagg tttacctgga  900
gctctctctg tcagtgcaga cacccatctt caggtttcaa ataatgttgt cttcagggca  960
ggcagtaaca gaataaaaga aaaggtaaat tcatcacctg tttgctgcta ctttaagtcc  1020
tggtattcta ttgtaatctg ccttctactc ctttgcaaag tcctcaaatg gttgctccat  1080
gcatttagga gagagaagat tgaatgtatt tactccattg tacctggaac cagatgccct  1140
tgccctgcat caccccatgt catttcttag cagagccttt gagatttttg tgtgtgtgtg  1200
ctttacaatc tctttccaag ttatatcttc tgatacagtc atggtcgtga aaagcaaaat  1260
aaaatcatgt gttaacattt aaaacttttt aattttattc tgacaacagc taaaactatt  1320
taatcttctg tttcgctcat ttcttccaag gtaaacttca gttggtttta cgtgatttgc  1380
tatttcttct tctttgcatt tacaaatgat ctgtgatcat attactgatc tttgtaaagg  1440
gctaatatct acctgcaaca tttggatatg acagtattta ccctttgtaa atacacattt  1500
tctatttatc ttcaaaaatt accattcatt agtctgtgtt aatgtctgtt tactattgtg  1560
tcattatgaa tgtgatgtga acatacgaag ttgaacttat ttaaacgaac actctcatga  1620
gcttctaatc cacattcctt ccttttcctt ctaagttacc atttcttaaa aatcttttag  1680
aagtttcctt gatagggaaa acacaaatta ttgaggaatt tttctttctc ttgacatctg  1740
tttatagtta ctctcttgtt ccagcagtgg atatttcccc tccatgtttt tctttgtcta  1800
aacatatgtt caaaacaaaa cacttttatt cttctttgca ggttttacaa ggatcaactt  1860
ttagttttga aacctgctat tacttttaga ggccattttt tttttctcta ataatgtgag  1920
ttcatgcggg ctgaagtaat tggaatactt tatagaaaag attgaatttg tcttctctct  1980
gaactctagt ttgaatttct aaattttatg aatcatctag atattaaaga ggaggggcat  2040
atcaaagagg agaaccctag cagagataag aggcaagagt aaatgtttca tgtatgggta  2100
agagtggatt tgtatttacc taagtaaagg tagaccctgg acaataaggt tggatagatg  2160
tggaggtggc aaaccatgga gggtcttgta ggtcaagtgg atgtttttag acttgaagtg  2220
ttaaattatt atctgaaatc attaagagtc tttttagatc cttgagcttc ttgagaagac  2280
catggatatt atgcagttat tatataatgt tttaaaatag taagtatttt agtttaactg  2340
tcttatgtaa ttccatataa atggatgcat gttctttaaa aatgttaatg tatttcagta  2400
aatcaaaata tactttttga ctcatcattt aaaggaggcc ttcagtgaat gctctgtaga  2460
ggattatttt ataatactaa ttttgatatc ctaatttatt tgttataaag tttagaaggt  2520
ttgaagaatt taaaatatag tgttaataaa cacactgaac ttttcttttt ttatcttgta  2580
tttttatata gtacaacaga aaaaagatga aatgtgaata gtaaagagtc tgtgattgtt  2640
gttcatag                                                           2648

SEQ ID NO: 103          moltype = RNA  length = 4406
FEATURE                 Location/Qualifiers
source                  1..4406
                        mol_type = other RNA
                        organism = Homo sapiens
SEQUENCE: 103
gtaagtgtat atcttttatt attttttctt tttttccatg ttaaaatgca tgaaagtgaa  60
atcaacttct ttcttaatct ggccaaaagc attacatctt tctcattaat agtaatacag  120
taaattcaac ttttattttt aacaggtagt gatgtgtaat aatttattta atccttttta  180
acataataac agtaaactta agattcttaa gcttttcata aagctcataa atgatttcta  240
gaaattttaa atatgtagtt atcattatgt attttgctgt agcagcagta tacagttaaa  300
taaaatagga aaacatgttc caagactgtt ttcattcaaa tatttatgct atatttttag  360
cttataaaaa ctcattaatc attaatgtaa aattatttgt tggatttttt aaatatttag  420
tgtattattt ttgtttcttt tttctttcca tgtttcttca ttcttccacc ttaagcagaa  480
```

```
tcaggtgtgt gacacaacta tgttttctat ccttgttacc attattaata aatacaaggg  540
catgatattt ttcacaaaag aaacactttg ttcagaacca aaaaagatca tggcaacagt  600
cagaattaaa aatggtaaaa gactaggtgc caaagatgac ttacataatt gggtacctag  660
aaatattcta tggtattaca gtaatgatga aaaatacaaa ttagaacaca ttttagatcc  720
tattgagtta aataaatcag agtcaagacc aaacaataaa taaagtcaat ttacgtcaac  780
aaatggtaag ttggcagatt ttaactccct ttttgaaaat gaaccatgat cctaaggttg  840
gtaaaattaa tcaagaatgt tgtcaaaatg ataaagataa aaatgaggaa gagaataaga  900
taggcaagag tgagaaagga aagagacaca tagctgaaaa tgtgagtcac aacaactaca  960
tagatccgta gaatctgcta tggaggactg tgattatgtg acagttgctg atgccgtggc  1020
ttagtgagct gagggtgatg cacaggcagg cgatgtaact gatgcgtcag tccagccaag  1080
aaaggacgcg tccctggttt ggctacgtgg ccgtccttta tttctttgtt aactgaattt  1140
tcttatagta agtagcttac gtacatatat agtgcaaatg ggaaagtgtg taagatttag  1200
aaaaagcatt aactattagt aaactttatc ttaagctcta acttttgatt agttcctaca  1260
aaaattagtg aatatgcatt ttctaattta gtgctttttt ttttttaca attggtgttc  1320
acttaatgtt atattagata aatgaatagc aaaaataagg tactttagag ttgattgttt  1380
tgccttacaa acttctaatc catccagctg tatttagaag taagatctca ctacagcgaa  1440
ttatatcagt aaaattttgt tacagtgttg tgcagtgtcc taagatgtat actaagttcc  1500
ttcagtggct ttttttgcca tgttttataa cagataattt tgttataatg agaaaaggaa  1560
acttggatgt gttgctgtct atattgtgtt aggctcaggc aggatgctgt ggcttactca  1620
tttaatcact ttgggaggca ggggcaggaa gattgcttga ggccaagagt ttgagatcag  1680
cttgggcagc atagccagac cctgtctcta caaaaaattt agacagatgt ggtggaacac  1740
atttgtagtc ctagctatta gggaggctgt ggtgggagga tcatttgagc ccaggagttt  1800
gatgttacat tgccctattg cactccagac tgggcaacag agtgagacct gtctctaaaa  1860
taataataat gataatgata aatggtgtta ggctctgtgc ctaagtatat ttttcacata  1920
ggctgggtaa agtggctcat gcctgcaatc ccagcacttt gggaggccaa ggcagcagga  1980
gcatttgagg ccaggagtca aagaccagcc ttgagagacc ccatctctac cagaaaaaaa  2040
aaaaaaaaga aacaattagc tgggtgtgat tgtgcacacc tgtagtccta gctactcggg  2100
aggcagaggt gggcagatca cttgagccca ggagtttgag gttatagtga gctaagattg  2160
tgccactgca ctccagactg ggcaacagag caagactgtc tcaaacaaaa acaaacaaac  2220
aaaaagcact ttgcagaata tcagtctaac tctacagttt atggactttt tatgtacgta  2280
ctacttttgg ctagcttaca ttgagataca gaataaaagt ttgttcatag catttatcgt  2340
ttttttcttt atactgtcca cctgagatat tccagtcacc taagtcatgg aaacatcaac  2400
taaaattaaa tatctatgtt aagagaaaat ggctgaaagt gatttaattc ataacacttt  2460
ttttcacatg ctaataaata agagtttgag acttccacta ggcattatct ctaactccta  2520
tccactaaga atttgatttt aagtagttga tggcttttaa ccggattatt cttctgtaag  2580
agtttggaag tctcgtgaag ttcgttatac aagaattctg tttacaagag agcattacat  2640
tagaatttgt ttttcagaaa tttggactat ctcaacgaat acctttagtt ttattatttc  2700
aaaatgcaag ggaaaaaatg agccataatc actaatagta actgcatcat attttagtga  2760
gaaatgtgtt aaaaatatcc tcatgtgaga tcttccttag atagaattac cctctactct  2820
aatatttaat atattttata tctaccaatc agtgatatta ataggtgttt atcatttgct  2880
gaatcaaata ggtacaacag aagacaggaa gtttgggaga tagaagagct cagggacagg  2940
aaatcacaga tgtccatatc tgaaataacc ttaaaagtta tcctgtctaa tgccttcact  3000
tataaactgt agtggtagaa tttgcctagt attaacctaa tagtggtaga tttgaatgta  3060
tacttgggct ttcttattaa gtggaaatgt attcctgtga tttacatata tcaacaaaaa  3120
tgtttgtctt cttttttttg ctacgacata tgtgcatgtg cacacacatc tcctcaaaca  3180
aaaatcagat ggacacatgc agtcattgga tctaaaagat gttataaagt tgtgtataat  3240
aggtatttta taataatata ttttaagacc cataatgtcg gtggagtaac tgactttaca  3300
gcccatcaag ccaatagaga gagaaaggag aaaaaaatga aagttgtgct gaataattaa  3360
aaaaaattat ttcctatgat gcttataaca gtcctatgag gtaggtggta ttctaattta  3420
tagaaaaaat gcatagaaaa atataattaa gcacagttaa aaaaaataaa gtttagaatg  3480
agaagtaaca acataaataa tgacccaatg tagattcagg tcaaaagaaa tgaaaatata  3540
atattaatgg ttttcaaaga gggaaccatt actttagctc aaagaatgaa ggagggcttt  3600
ccgaaggagt aaagaattat ggcagttctt ttgtagccta gtgtattcat ttgctaaggt  3660
ggctgtaaca gactactaca gatttggtgg cttaaacaat agaaatttat ggtcttagtt  3720
ctggagacct agaagtccaa aatcaagaca tcagcagggt tgatttcctc tgcacaatca  3780
gagggaaaga tctttcccaa tcctctctcc ttggcttata aatgtccatg ttttccctgt  3840
ttctttttat catcttcctt ctgtacatgt ctctgtgtct aaatccccaa attttctctt  3900
ttcataagga taccagtcac agtcgaatag ggtttaccct gaaatctcat tttaacttga  3960
atacctctgt aaagacccag tctccaaata aagtcacatt ctgaggtact ggaaattatg  4020
actttaatat ataaatgtgg agggtaaggg gaacacagtt caacccataa cggttagata  4080
acaatcgtgc tttattttgg actagtaaaa ccaccataga tcagtttaac cattatgaaa  4140
ttatacatga aggcattata tgtatggaca ttattaagtc atacttgctt tgcttccatt  4200
gtaattaaaa caaaccatac tacctttgtt ctgcaagttt tgtattctaa cttatttatt  4260
tttggctttc accagaacac tccgattttc tcatattcct ttgaggaaaa aaagttacct  4320
tttgacagta ttttcttatc cagtatgtct tttatggctt ttatttatta aactttaaaa  4380
atattcctaa tttcatttcc ctgaag                                       4406
```

```
SEQ ID NO: 104          moltype = RNA  length = 1202
FEATURE                 Location/Qualifiers
source                  1..1202
                        mol_type = other RNA
                        organism = Homo sapiens
SEQUENCE: 104
gtgaatttaa tgttttttat taggaaatct aatgcctaaa actccttcct tagttgttat  60
gtttactttt attagcttat taagaagtca aaaatgcata ttcctaatat atcatggtga  120
tggtatactt tatacatttg ctctttagca tttatttgtt gaaggcctac tttatattaa  180
acactcctcc agatgctggg aaacagcagt caaaaaattc cttatactca taggacttac  240
gttctagtgg agaagactga caataaacaa gtcactaaat agtatgtcat ctgatgttag  300
tgctaaggag agaaataaag catgattggt gtaaagagta tggggagaga gaaggggtgt  360
```

```
aactgaaaat agagtagtaa gggaggtctt ccttaataag atgatatatg aacagagagc  420
taaggagggg taaaggaagt gagtcataca gatactagaa aaataattac agacaacaga  480
aatagcaagt tcagatgtcc taaggtggga ggatgcgtgg tatatttcat taaaaattat  540
cacactgtaa aatataagaa taatttgttt cttttagaaa ttttacttta ttctgatatt  600
aataatgatt ttttaatctt tggttttcca agtcttaccc tatttatggg aatctttttt  660
ttcttttggc tagctaattg cttcagtttt gttttctaat ctagaatgtt agcaatctgt  720
taattccact ggtaatgata tagttaagct atgtcttgct tctcacactt tatttattta  780
tttactcagg gcactaatct gccatttttt cgcacttttt ttcctttttt tttttttgg  840
tactgcttct tattctggtt tttacattga tagaaccaat gttagacgtt catttgcctt  900
ttgctgtgta tatttgggta aggatctata tgtgcaatat atgggacagt taaaatcaga  960
attctaaatt tgtattattg catcaggcaa taatgtggga aataccttga catttcatat  1020
acacaatatt cttgtattaa tttaacgtct tagttcaaaa tcttccttgt taatatagag  1080
accctattat ttggtttggc aatacagttg aagagattga tggttcttat gaattgtttg  1140
cctttttcttt tcaatggctg tagctatgtt aaattattac atgtttgctt gttatctttc  1200
ag                                                                 1202

SEQ ID NO: 105         moltype = RNA  length = 1697
FEATURE                Location/Qualifiers
source                 1..1697
                       mol_type = other RNA
                       organism = Homo sapiens
SEQUENCE: 105
gtatgtgaga atttaccata catttgtttt ggtttcagca gtgataagcc agaaatgaaa  60
agtttagata tgttgtaaaa gtactgatat gcctctacaa gtgccctgta gtttcagtgt  120
ttattctgca tctgtaatat aaaacagtaa gcatttctat gtgtctcaaa gtattttatc  180
atctgttata ccttacatac tttcatctct ctttttattg aatatgcctc cataccttga  240
aaacatttaa cttccaggaa tccttttgtt tatggaggta actgctaact ggtccttggt  300
ccaatgctgc cattttgtaa ccatttgtta tgatatcttc ccagcttggt ataatgtttt  360
ataattacat tgttcctccc cctctttttt tgtgttcttg taattttctc cctatgttat  420
tttgtattca ttttatataa tgaataaatg ttgcttatga ggtcaaggcc aaagacttaa  480
gctcctgttg atttcatgtt gctgagtgtc ataaatggaa gcaatcataa tgcagagtca  540
ttctggtagt aatattaaat atatgatgga ttcagtgaaa atattatgtg ttattagaaa  600
aatattcaga acaggccggg ggcagtggct cacacctgta atcccagcaa tttgggaggc  660
cgaggcgggc agatcactgg aagtcaggag ttcaagacca gcctggccga catggtgaaa  720
ccccatctct actaaaaata tgaaaattag ctgggcatgg tggctcatgc ctgtaatcct  780
agctactcag gaggttgagg caggagaatt gcttgaacct ggcaggcgga ggttacagtg  840
agccatggtc acacaactgt actccagcct gggcgacaga gcgagactcc atcttttaaa  900
acaaaaaaaa aaaaggaaaa atattcagaa cagtatcttg ctggcagcaa catttgtttc  960
atcaatgaaa atatgtgtta atttgacctt ttctatctaa gttaattatg aaagtgcata  1020
ctaaaatgat gtaaaagttt atatttcagg attattctta ttcatggatg attaactaaa  1080
atgcaaaaag aaattaagca tactgtttgg ctaaactgtt aaaaattatt tttattttaa  1140
atgataagca gttaaactta ttaagtgatg actcatctct gctgatatat ttatgcaagg  1200
ttttttattt cagataactc ttctatttat attaaacaga aactgtattt ctaagcaata  1260
gcatttctta gagaaaattg cctctattat gttgcaatta aaatttaatt actcatgagc  1320
tctttaaaga cacaatttct cttgtgtggt tttatttcat ataaagaaaa actctgatat  1380
actggagaga acattagcta aatagactat ttagacttaa tcattttgat cagacatcaa  1440
ggctagacta tttaagctgt tacttattag ctgcatgatt ttaggaatgt caaatttcct  1500
aagtcttggt tttcttgtat ttaaaatgga aattataatt cctatctcat agaattgttt  1560
taaggatgaa ttgaattaat acagttttga cttcaaatat taggaattat tgagtataat  1620
aagcctgttg tattgttggt acttcgtatt atacttacta aaatatttga ttaaagattt  1680
aacatattct ttcgtag                                                 1697

SEQ ID NO: 106         moltype = RNA  length = 809
FEATURE                Location/Qualifiers
source                 1..809
                       mol_type = other RNA
                       organism = Homo sapiens
SEQUENCE: 106
gtaatttttt ttaatgtgat catttttagg ggaatatttt acgttttgtt actatttagg  60
aaaatttcaa atatgctcat tactatataa aatggcttta atgaatacaa tacatatttt  120
ataaatatag aaaaaaactt atgagaggca aggctaaggg ttatagagta ggtctacctg  180
atctttcttg ttatttcaag accaatactt ttcacttttc tctctgacag catagattaa  240
ttacctgtgt ctctcttttt tttttctttt gagatggagt actgctttgt cacccaggct  300
ggaatgcagt ggtgcaatct tgactcactg caagctctgc ctcccgggtt catgccattc  360
tcctgcctca gcctccccca gtagctggga ctacaggtgc ccaccaccac gcctggctaa  420
cttttcgtat ttttagtaga gatggggttt caccatgtta accaggactg tctcgatctc  480
ctgacctcgt gatccgccca ctgcggcctc tgtgtctctt tgtgaaaata cagatgccca  540
agctcccatc cctgaaattg atttaattat tttagggtgg gtcctgacac agatatgtat  600
gttgttgtta ttttaagtca tcaatttatt ctaatatgta gccaacgttg ggaacttcgt  660
tctcactaat attcaaatga agactttaat tctaatcata tcaaatatgg tttctaaaac  720
tactttgaag atttatgagt ttataagatt atcttttatt tccttgtttt gataatgtat  780
actttttatt ttgtttgttt ttttactag                                    809

SEQ ID NO: 107         moltype = RNA  length = 877
FEATURE                Location/Qualifiers
source                 1..877
                       mol_type = other RNA
                       organism = Homo sapiens
SEQUENCE: 107
```

```
gtatgacttt tatgactgat tataactttt gatttttatt ttacttaata cctcttggaa  60
aaactggaag tagatccttg atgagagtgt ctgtaaaggt agatattaag agattgagga  120
attgtgtttc tatgcctgct gtcatcacat tccaccatga aaaacattga taataaaagt  180
taatacattt aggctgggca cggtggctca cgcctgtaat cccagcactt tgggaggcca  240
aggcgggtgg atcacgaggt caggagatcg agaccatcct ggctaacacg gtgaaacccc  300
gtctctacta aaaatacaaa aaattagccg ggcgtggtgg cgggcgcctg tagtcccagc  360
tactcgggaa gctgaggcag gagaatcgct tgaacccggg aggcagaggt tgcagtgagc  420
cgagatcgca ccactacact ccagcctggg caacagagcg agactccatc tcaaacaaac  480
aaaaaaaaga aatgatctac gttgcttaca cataccttat gcttatagct aggtctcgta  540
agcattagga agtcaaaaca aagaatcttt tacatgtgta aaggtataaa ctatcccatt  600
tttctaaaaa tatagaggaa caaagtgtca aatttaaagt aatcactagt aactaaatat  660
attcctctga cctcattttc gtgatctgtt gttctaatta ttattggcca tattgctgct  720
ttaaaggaga gatgttgaat ttgttgaaat tttaatcagc atttagagcc ccaggttatt  780
tttgttttcc aatttgtaat gataattttg aatacactga atctatgaga acagtattat  840
gttttctcat aaaatactaa ttagcattta atgatag                            877

SEQ ID NO: 108         moltype = RNA  length = 3130
FEATURE                Location/Qualifiers
source                 1..3130
                       mol_type = other RNA
                       organism = Homo sapiens
SEQUENCE: 108
gtaggaacag agttttaaac ttgtacaaag tttaatcatt tcaaattttg gcattgtttt  60
aaaagacaac actattctgg ataacctggt ttcttcctga tgaacagttt gtttggttgt  120
tgttttaaca taatactttt tttctgttgt agtattgttg gagacttttt cttccttgaa  180
atgtttaact tgtttaacct tgtttgggtg gcagggcatg gaacagtgta gagctggggc  240
tgggcgaagg agttggagct gtgtgtgcgt catgaagctg tcatcagcta tgagcctggg  300
ctgaggctgc tcagcttctc ctgggtgcta tttttctcca actgcagctt cagcttcttg  360
attgtataat ttgcttcctc aagtatgagc caggaataat tgagctgtct tgtcacaatg  420
tgtggcatac tggatctagg ctgtgctgca atgcttttag agttatatcc tgggcaactt  480
tctcttcaga tagccccaag agatgaattc agcaccagct ttgatgtttt actagcttct  540
gctttctggt acttgatttt ctcccacccc gaacacatgg gattccaacc tgtgaaacta  600
atttttgtgg ctatgaaaga ggtagtggta gtttatgagt aaacattcag tctgttgcca  660
ctatcatcat gtgtggttca tcatgactgt gatgagtagg taaaaggctc tttgtgtcat  720
tctcatttcc aattttaagc agctgcttca aggagtctgg aagtcattga ccagtgggat  780
cctgcctgtg tcttttccca ttaaagccat cctgtatgaa gtggtatcct ttaccatcta  840
gcacatctgc cgcccccatt tcaaaaggca tactcatctt tatctcaaca ttctcataca  900
gttccttatg tccatgcacc tccaatgtcc cctttgatgt ctttgaggtt ttcatcttcc  960
atgtctgcta tttggaatgg tcttgatggg aggcaagata gtgatcacta caactaggat  1020
gggagtctta gtaccgtgag gctacagcaa gtcccacaga gggcctgctg cactgtactt  1080
gcctctgtca accaagtcta aggagaaaga ttaagcaggc atattaaagg acagcccaga  1140
tggacatgaa gtcctggagg aggccttggt tcctgtccta atactaaacc tagagtaccc  1200
agaatccaca cttctccact ctagctctca cttttcccat ctacacactg ggaaaaatta  1260
ttctgtcaga aagccagtgt caaggtgaga acaaataaca aatgtgatga tatggagtgg  1320
gagaaggggt ctcttctact gtcttattgg accctagcag tggctctgag ccagcagtcc  1380
tgtcagttga tttcttggtc gttcctttgt tttcttctat aatcacatgt ggactcagaa  1440
tgaattttga gttactctga aatctattta ttcaacagat atttacttag tacctcctat  1500
tgccagactc tgctttatgt tggatattat tttttaaaag cccaccttgc ctagatttcc  1560
tcaaaggacc aggtggcttc cctggttttg aaagacccta attcttacta tgatcttaag  1620
taaattatat cctttctgtg ggctcaagtt ctttctaaga gggctctttg gggctacaaa  1680
agaaattgtt agtgcaaaaa gagtttataa ggtttataaa tggttagtag aggtgatgat  1740
gatatttaac cataattgaa gatgactttg cattttagat catatacgtg tttttcgtct  1800
gagaacgata caggtcactg agcataccat aagccttcag taaatcattt gcagaagaca  1860
ttgcagaaga cataagtcta agtagaaatc tcttgacaga gagaaggctc gttttgatcc  1920
ttgacctcaa atttaggttc cctaaatcca ttaaaaaaga gaaagaaaaa gaaaaaaagt  1980
tactaaagtt taaatctggg aggattatat acccttctca ataaagcagt ttagagagat  2040
ctcttttggg acccatgaca caggtcttgc tcatgctgac atctttatag ttgctttatt  2100
atttattcaa caaacttagt aacacgtatt ctatgtcagg ccttttcctg actactggga  2160
caaaccaggg tgatgtgggg gctgttttag ataggtgat cagaggaggc ctctctgttt  2220
gggtggcttt tgaatagaaa attagatgaa gtgaaggagt aagcttctga tatttcactg  2280
tttacttgtg gtagatctgt gataatctct gtcaggttaa aaacattccc ttctaatcta  2340
agtttctaag atctatcaaa agctgtttga atatatttag acaatcataa ttttcctttc  2400
ttgtattatc ctagcagatt ttgttgccaa agctatactg gccattttaa cttagaatgc  2460
agtctttcta ttcatttctc tggaaaagtt tggatattgt aagcattatt tttctttagg  2520
tatgatgaac ctgcagaact gtttggttca attatgaatt tttttttct ggagtctgta  2580
ttttttgaa ctattaatca tttctttaat gattataaat ctattcagat ttttacaagc  2640
tttatccctc tcccatcata cactattttt cttacccatg cttttgcaca attttttcct  2700
ctcccttagt gttttcctac ctagatacct cctatgtgtg tctgtgtatg tgagaaaagc  2760
tttttatttg ccatctttat atttctaaga atatctagta atacagaatt ttatattctg  2820
aagaatttta ctttgcattt tcttattttg tgattgaaaa aaggtattaa ttttaaaatg  2880
gtcaaatcag gctccatcct tggaaaatac ccaaatcctt tattttgatt gggccatctg  2940
ttaattaggg ataccttatc tcttgccacc actttttaat gctaaataaa tatgtagcta  3000
aaactttgac tagaagaaac agtaaaataa gatattcttg cttattttta gtacagttat  3060
ttgaactgac ttttaaatca gtgacataaa ttatttgcca tgtctatact ttttttcctt  3120
atacttttag                                                      3130

SEQ ID NO: 109         moltype = RNA  length = 1162
FEATURE                Location/Qualifiers
source                 1..1162
```

```
                         mol_type = other RNA
                         organism = Homo sapiens
SEQUENCE: 109
gtaagtaacg taatttttct ttacatgata aaataatgca taatatcgca agatgttcct  60
tgcattgtct tatatagata aaaatggact ctattaagaa gacccatcta actgaagggc  120
accccattca cccatttgct taagccagaa actttggatc atcaacgact tcattctttt  180
cattctccac attttctatc attaaatcat gtcagctcta ttttcaaact atatcctaaa  240
tatgaccact tcttggtatc ttgagacatc actaccagtc ttgtccaagc tattgtttta  300
tacctgaata actgcaataa tttccaagct ggtatctcag cttccactct tggattattt  360
caccctattt ctatttctgg gctgtctcca cacagttgcc aggtaaccct tttaaaacat  420
aaagcacatc acaaagcaca aagtcctatc ctcagaatct tccagtggtt ctccatcacc  480
ctaaaataaa acttaaaagt tcttttcata tcccaaaaca acatatgagg tctggcaccc  540
agttttcttc ccaatctcat cttctactac ttttcccttc atttcattca caatgtttta  600
accacagtaa ccttctttca gtactttaaa caatccaaac tcgtttaagc gtcaagtcct  660
tatacttgtt tcctttgttt agaatactgt tcacccaaat attctcatag cttgctccca  720
gacttcatgt ctctgctgaa atagaggctc cttagagaga ccttccctaa ccctaaccct  780
aaccctatac tacttgccat cactctttat cctcttaccc tggattattt tttcttgata  840
gctcttccta ccatctggca ctatattaca tcatatcata ttaaacacac attctttgtg  900
cttccccact aaacaaggac catgcaagat ggaacattgc cattttgttc actgctgtta  960
gcctctgtgc ctaggacaat gccagttatg cagtagttac tcaatacttg ttgaatgaat  1020
ggtgaataga acatagaaat ttgcctatgc gtgcttttga aaaccatatt ttaatattac  1080
gctttgttaa aaatgtgtat ctttataaat cctcatattt ccatggcaaa ccttatcttc  1140
taacttttca ttgtcctcaa ag                                          1162

SEQ ID NO: 110           moltype = RNA  length = 593
FEATURE                  Location/Qualifiers
source                   1..593
                         mol_type = other RNA
                         organism = Homo sapiens
SEQUENCE: 110
gtacatcatg tattcatatg actactttgt ttttttcttt aaaaaaaaaa ttattagttt  60
ttatatactc cgaattgcta caactagaga caagcatttt tcgactttac tgcctaacag  120
gcttattagg tccttatttc ttccctctaa tgctaatcac tctttttcat aatacacact  180
agaaaaaaag gataaaccca actctaagtt tccagtttgt aatttagttt aaacttttct  240
aagagcatag aatgagttaa accttagctt cccagaggaa aatactaatg aaagagaaca  300
agtaattttt ttactttcag gggtctctgt agcctgcttt cattaagctc ctcttataac  360
gaaaccacac ttgcaaatgc catcaggtca gatattaaga aaaacgtgaa ggcttttgta  420
ttccaggctt tttgtttgag aatggtgaca ttgtagcatt gagagtaaat gtttacttcg  480
ataaaggcta gcttgttctg attactgtac atcactagtt cataagaaat gcccatatat  540
tttatgaagc aatatctgct ttattttttt aacacattat cattgtgttc tag         593

SEQ ID NO: 111           moltype = RNA  length = 3218
FEATURE                  Location/Qualifiers
source                   1..3218
                         mol_type = other RNA
                         organism = Homo sapiens
SEQUENCE: 111
gtaatgtatt ttaaaaaaca tgttagctac ccccaagttt ttgaatttgg gtttgccttt  60
tttttttttt tttggctcag atttctgatc attgtctccc tgtaaaatcg aattcctgat  120
aagctttggg tcttttgtct ctctgtgcta ttaatataaa aatattccca tttttctctt  180
tgtgttgttt atactataga gtagcaagta cccaagtgtt cttctctttg ttctccatct  240
gggtgttaca gatttaatca caatacagtg ctaagcaatg aatactaaat ctgttgcttc  300
cagtttctaa gtataggctc tttcaagtcc tctgaacatt tttaaaaact gcaaataagt  360
aaatactgcc tatatttttt tccgtttaca aagtaaaaag aaaatctttc tgctcccttc  420
cattcccatt caaaagtgat tactaatcat tcctcattcc tgcatataca tacacacata  480
ttttgtatac atatatatca cacatatgca tacatgtgtt tgtatgttca tatgtacaat  540
gtacatatcc tcattatttg tggattctgt attttctaaa tcacctcctc actaaagtgt  600
gtatgtaatc ccaaatcaac actcgcagca catttgcaaa catccacaga gccttggaaa  660
gtttgaataa tccaacctac atgtccccag cagaagtcca acaaggcagt gctcagtatc  720
ctcatttcag ttttcataga gaaatgagca gaggatggag acagtagagg gcagcacagc  780
atagtgcaag aagctgtggc tctggggcct ggtggaaggg atttgaatcc caattctgag  840
gcttgttact gctctagcct taggagagtc atgtaacact tctgaatctt gttttcttat  900
gtaaataaat agaatttacc aggatgagtt atctttagga tttaagatta tcatctgtgt  960
gagatatgta ggtgtatgta tatatatgcg tgtatgtata tatatgcgtg tatgtatata  1020
tatgcatgtc tgtacatatt tcccgtagca gcagtggttt gatattcact aattgggcta  1080
actttataga ccaaaactac tatggataga gaatactttg tttgcattta cgtatatata  1140
ttttcttggc aagtaacata aaattgaact aatactatac acatttctag catatttgcc  1200
tttaacagtt tatcatggac atcttttgag gtctgttcat aaattatctc atccatttaa  1260
taattccata gtgtattatt gcatgtataa gcacatcgaa ccatttatgt tttgatggat  1320
atttagtttg cttccaagtt tctgcttcta taaaatatga ttaatctatt gacctaatta  1380
tgccattgtg ataggatgat agagatgcca ttctctccaa aggattatac caatttatat  1440
ctgaactatc tttgactatc tcttgtagct ttttcagtat gctatgtagt cctattacta  1500
atttgtaata aaagccatca tgtgtgagtt gtactagaca ctatgctaat tgccttacaa  1560
gcattctata tttacaacca tatatgatag gtattactgt ctccatttta tgtgataaac  1620
aaattcaaag tggttaagta accattccct aagccagcta ggaaatagag gcaggattaa  1680
aatctaaatg tatgaaactc cacagctcct tggcattcct agtccttaac ccgctatgct  1740
atgctacgtc ttggtaacta aaagtacata ttaaatactc tcaaaatatg tctcatagca  1800
gccagcttgg tatgtacact agacacagta ttaatgctgt tgatgtgagg aaaattttat  1860
aattttcctt ccatccatat actaaccagg cccaacagtg cttagcttct gagatcagag  1920
```

```
atcaggtgca tgtgcattaa gggtcatatg gccatagata gttctctaat ctttccattc  1980
ctcagtttct taagggaatt tctgaaccct caaaattcct tatttcctaa gtagacagat  2040
tacctgtcat ttttcaaaga ttaaggctta agatcaaacc agaactgttt tggaaattct  2100
aaatcactgt ctatataaat ggcaagataa cttttaagat atttatacca agcccagtac  2160
agtagcacac cacacctgta atcccagcac tttgggaggc tgaagtgggt ggatcacatg  2220
aggtcaggag ttcgagacca ctctggccaa catggtgaaa ccctgtctct actaaaaata  2280
taaaaattag ccaggcatgg tggcacttgc ctgttatccc agctacaagg gaggctaagg  2340
caggagaatc gctttaacct gggaggcagt ggttgttgca gtgagccaag attgcaccac  2400
tgcactctag cctgggcgac agagtgagac tgtctcaaaa aaaaaaaaaa aaaaaaagat  2460
acttgtccca gccatgaaaa tgtttgctgc cccttacttt cgcaaacttt tagtatttta  2520
ttatttttca atggctgtaa aatatgactt attaaatgta gtataatata aagaaaagag  2580
atatctagca aagatagcat taaagcaaaa atcctatttg cctgctgata aagttagagg  2640
tgttaacttg gagggtgaat ccaataaatt agaacttttg tgctatattt ggagactttt  2700
gttttcctac caaagtatca gggctatgtc ttacttatct ttgtattaca cagcctgcat  2760
gacacgtttt gcacatagta attgcacagt aaatgtgtaa taacctacat ggaatagcca  2820
gtgttgtgtt ggatagcggg agcatttggc tagcttatgg ttatagtccc ttacccaaca  2880
gtctgctttt cttctgttgt acttttagta cctaacaagt ttccctggct ttaggatttt  2940
ttccatgtaa aatttctatc atgtgaagaa aaaataactt ggcctacact tctaatacct  3000
agcacatacc tctttctgcc tgctatgaaa ttataatact tgatggaggg aggcagcatt  3060
aagtgtttac atcctgaagt atttcagcca taacatccag tgttttccag gttctaggtt  3120
tcataaaatg tatctctgtt ctctagaaca aatccattac cttgaactca ttcgtagtgg  3180
gaaaaagctg agtctaattt gtatgacttt ttcaacag                          3218

SEQ ID NO: 112         moltype = RNA  length = 939
FEATURE                Location/Qualifiers
source                 1..939
                       mol_type = other RNA
                       organism = Homo sapiens
SEQUENCE: 112
gtaatattta attatatttt agtatcgttt tgtgaaaaca gctgttgaaa actattttca  60
ttaccatctt taactacgta tcctaaaaaa ttcagtaata acatcttata tttgaccttt  120
atattgcaaa gttaattatg ttcatctgac tattcctaac atattagagt taacaaaaaa  180
ttcagactca acataggatt aagtagtaaa tttatttttt aattgtaaca aatatatgcc  240
attagtatgt tcttaagttt tgggtcacat tggcaacagt gtctttattt tttttttgaa  300
attcttttca ggaatcctaa ggttatagtt cccttaaaaa aatatttgct gttttacctc  360
ttttaagact gtaaacagga caaaaaggca tggatatgag aattagctag tgatcactgg  420
ctattctaaa tagtcactaa ggcttgaatt gtctcttcac cagatgcctg tcagaagtcc  480
caaaggtttc cctgatcata ttaataactt tataaaaaat tgatcattat tcattaaata  540
ttagatatta gtaaggaaaa tataaatgaa gtctaaacca aaactcttaa ccagactaac  600
ttcaatgtta tgaatcacaa aatctttttg attgattgct ctattgacaa gctcttatat  660
gcttttagag aaagattaag tcccattata agagatgata aattttagtc aaagactaga  720
acacaactta cagaatacat aactggactt gacagttaac aacttagtta tttacactgt  780
acaatggaac aaagaaaaat cttaattctt ctgcctttat tgctgtattt gaccattcag  840
gaatactttg gctttcatat ttacaattaa atctccttgt tcaaacgtaa aatatgtata  900
tttcctatat gcaactttta aagataatgt ttccattag                         939

SEQ ID NO: 113         moltype = RNA  length = 100204
FEATURE                Location/Qualifiers
source                 1..100204
                       mol_type = other RNA
                       organism = Homo sapiens
SEQUENCE: 113
atacttggga acaacttatg tatctaattt ttagagtact tgcaatgttt aagagaatct  60
aacatcctgg agacttgata cattagctgt taaattattg ttaaattaaa taatttaaaa  120
taaattaaat aatttaaaaa tatataaaaa tatacaataa tatgcataat aaacaatatt  180
aaattatgca tctgattttt tagagtaact gcaaccttta agagaatctg acatcctgga  240
gactttgata tattagctgc ataactataa ttttaaaata tacaataata cgtataataa  300
acatattaaa cataataaac atattaaact actgactatg tagtttctgg attcacaact  360
atagttgaaa agtataataa ttagctaaat acacaaatag tattggaatt tttataagaa  420
cttgggattt gctatagttt caagttttat ttcctaaatt taatcagtta tttaagtact  480
gagaaagttt tctttgttaa gttaggcatc tgaagtactt aaaaatgaat acattcaaaa  540
taattcaatt cttcaatata tctttatttt acatatatat acatatatat gtatatatat  600
atatacacac acacacacac acacaaatat ataggtatgt atatggttct tctgttagtt  660
gtgcctgggg tcactcatgt gcttatagtt atccagtggc ttgattaggg ctggatggct  720
tttaaagggt agatttctca gctttgaaaa ctagtctctg ctacttatta acacatcctc  780
taataggtta tcttaggctt cttaaatgat gatctcagga caacaggagg gcaaggttca  840
atgcacaagc tctttataag gctctattta gtgcgtattt taaaaattat tattcaagca  900
aggtacatcc tgaatcaatg gggaagaagt tataaaaggg ccaagataac agaattttta  960
agattcccca agggagcata gtatgagaga aagggagaga gagcatgtta cgagctcagt  1020
tgtggagtca tcttaggtta cttccaagag ccacctgcaa agtagaggtt gcagggaagg  1080
gacagattta cacaaaggca taggcagacg gggacctgac tcactggggg ccattattgc  1140
aaacatgtaa cacactattc ttgttagttg tgagaacttc taatttttcc taggcacaga  1200
agcagactta cagatgcagt ttaagtggat gggatgactg atttctgttt gcttacaaaa  1260
atggggtgtt actatatatg tgcacaaaat ccaagtgcaa ttggaaatgt gaaaggaaaa  1320
taaaacttgg gatctcaatt cattatgtct ataagaaaaa attagggtga aagctgagtc  1380
atgcaagaaa ctgctctcct tttgttctta gcagacagct acacatcaaa tgttaaatat  1440
ctccacaggt agctacttta ggacattcat cttatctcac gtaaagtgct gatttaccac  1500
cccacgtgaa tacataatat ctatttccct ctctgctctt tttctcttgc aacacataga  1560
ttaccatatc taccctttttt ctcttccaat ggatttttcc cctttaaata ctgaagccct  1620
```

```
caaaatcatc ttagagaaag gaagagacta cagactgttt ctgtgattca gtgtttattt  1680
cttttcggca tgtccctaac cttggcaaaa taaacttcta aattgattga gacccgtctt  1740
agacactttt tggttcacaa agacttctca tgagctacat tatagatata caaaactaaa  1800
tacaatccct tcaataaaac tgtaaattgt attaaggcaa attgttttgc cttaatttca  1860
tggacaagaa tgagtgtgca gcaagcagat acttgtcttc cttcaacatg aggaaactgg  1920
aaagatcagt agggagtcag tgtgaattaa gccattaacc atggcttaat ttgccatgaa  1980
gataaggcaa aacaaaatgt ttaggacaca caatggatac aaaatggcca tgctttgttt  2040
tagagatcgg agaagtaagc tactatgact tttcttggta agtcagcaaa aaggaactag  2100
aagtaacatc caaggaatat aaattcattg ctacagagaa caaaggtaag caataataaa  2160
aggtgaggcc ttcttgtgaa gtgattttgg tcagataaaa ctgttcacaa aagcctaggg  2220
cagaaagaag gcaggtccag acaagtgttc ttataacaag gccacttaca acattgtcac  2280
ataagtccca tttcttgatg aaaactgaca ggtgcagaaa atctgacgaa aaataatagt  2340
tttgccaatt ttcctcaaaa atatacagtg agttattgaa ctagaacctg agttaaattt  2400
cctgactcac acttaggtac agacgacaat gcataaaaac ttagttgact tgttcaagcc  2460
agagctgact tgttcactgc tgtatcccca gtgcctagca caggaaacag gataaaaaat  2520
actgttagaa tgagttaaag aataaaattt aggtaagatt ttgcttttag ttacaattgt  2580
cactgagatc taggttacaa tcttagcttc atcaattatt acttaacttc tatgaacttg  2640
ttctcacttc tgaaaaatta gaataaaatt taccattaga gaccaggcac cttgagttta  2700
tgaatgtgag caagagggtg gtggcagaag ggtagaaaag agtaatacag acaaacgaaa  2760
cttgtaagtg aatacataaa aataagttat aacgaatgaa aaaaaaaaca gaagaaaagg  2820
tgttagagaa aacagacttc tattatgaaa acaaacacgc agtagtcagc atagtgtatg  2880
acataacatg tgctcagtaa ctattaaatt tcattcctac cattgtcaga ggtatttgaa  2940
tcacaacaac tccatcttga atagggggctg ggtaaaataa gggtgagacc tactgggctg  3000
cattctcagg atgtctgtca gtcattctaa gtcacaggat gagataggag gtgggcacaa  3060
gatactgatc ataaagactt tgctgataaa acagcatgca gtaaagaagc cagccaaatc  3120
ccaccaaatc caagatggcg agaaaggtgg gacgtctgct cgttctcact gctcattata  3180
cactaattat aatgcattag catcctaaaa gacactccca ccagtgctat gacagtttac  3240
agatgccatg gcaatgtgaa gaagttactc tatatagtct aaaaagggga ggaacactca  3300
gatctaggaa tggcctaccc tcttcccaga aaactcatga ataacccacc ccttgtttag  3360
catataatca agaaataact ataacaatcc ttagtctacc acctccaatg gggtgtatg  3420
cacctccaat tctttcttgg cgagatccag gagccctctc ctggggtcca gatcagaaca  3480
cctttccaga aacaccatcc catgttaaat tatgaattaa gaacactgaa catgaagaat  3540
gtttaattca aattattgag taaacactta caaaattaaa atataacatt taataaaaat  3600
agcaagattg aggaacaagc acttcacaaa tattggtttc ccagaatgtc tgaggaggtg  3660
tatagaagtt aagaatatgt cctccagcca gagagatctg tgttcaatca cactatttaa  3720
gttacttagc ttctccaagc ctcagtttct taactcagat ggaaaatgag gacaatgtaa  3780
gcacctattt cactggattg taaggaagaa taaacaagat aatgaatagt atttggcata  3840
taatctttca gaaaagtagt aaaattgtca ttcctataaa tctaactaat gtctttaaaa  3900
ttcatctcac aaaatcagta tctttttatt ttgtactgag ctacttattt tacccaaatt  3960
gggggtttaa aaagaaactc attacttatt ttcgaaagga aaatttactg tcaagtacag  4020
taattttttt tttaaagcag cgtttaaaaa aaaaaaaaga caaagcactg gtccagatag  4080
ttggaaatgt catttagatt taagtctaca gcttcttagg aaagttaggt agagatgtat  4140
catactccag catgattgtg agcagacgag caggatgagc aaaacttgca cgagtaagag  4200
tggtaaacac cagagaaggc gctttcatgg aagggcaccc taggtaacca agcaagtggc  4260
aacaatagta caggtgagtc cttggatccc ttctctctcc acccccggca gtggtccgga  4320
caagtactaa cctctcctct ctagagcctt gactttatac tagctccaca accatcaagc  4380
cccacgatcc gcgaaaggaa tggtgctaca ggtaaggcgg gcggggtcgg gatgccgaga  4440
cctcttgtca attcttcgct cgcccccaaa cgaggatcac ggctgcgcgg ctctcactct  4500
aactatcaag acagattctg atactaaaca aggctaaaac tttttgtttt ttccttctta  4560
cagaaggcac taccctggac gccgcttgca aacgcctgaa gagaaggcag ggtgttccca  4620
ctttttcaga atgggaccag gccctacggc cccaatagca gaagcttctc taacccagga  4680
ctgctcccct caattcctcc caatatgctg accgacagct cgacctcacc tgggggcggt  4740
tccgccaggg gatggcttag gaaaacctca ggaagagcag cccagcgagt gacgccactg  4800
aaaccacagt catggtctac ctcgttcagg ccaccagttt gcaggcgcct gagccgctgc  4860
tcctcccgcc tctcggtcct tccccgccgc cccggtaccg tcgcagtctt acgcgttgca  4920
tgccgggagc gccttacctc ctcttctcag ggacttcagt tcccagcatg cagaagcctc  4980
aggcagaact gcactctggg atttgaagtc ctcgttccac gccttctcat catcctgaac  5040
accgagctct gggactccgg cggagaatct aaacgtaaag catcacccac ggtcgtgaac  5100
tgtaggctct cctggcatcc gggatcttat tctggccttg gcggagttgg ggatggtgtc  5160
gcctagcagc cgctgccgct ttggcttgct cgggaccatt tggctggacc cagagtccgc  5220
gtggaaccgc gatagggatc tgtcagggcc cgcggccggg tccagcttgg tggttgcggt  5280
agtgagaggc ctccgctggt tgccaggctt ggtctaggtg ggtggatcct tgtaagcagg  5340
attagcgagt cactccacgc tcaggttctt tagcctgagg gcccgtgtgc cacagcatag  5400
ctaccccgcc cttccagcct cgggtcccta atactgcctt gcttcggttc cagtttccgc  5460
cgcacaactt cactcattcc aaatgttaat ttctgcgttt tttttcagcc ccaattctgt  5520
ttctccaaat cagggatgat tgtcggcctt ccacagaccc tcgcgcttgc caggattagg  5580
gtgttcgcgc gcattgtggg taggggtgtg gaggaaggga tccagaaatc ttaagtatta  5640
acttagatta gtgttagcaa ggaagccgtc acattttatt tagccgggac actctgacag  5700
tttgtgccga ctgctatttt tgatcaaggc tattttgccc acttgtctat tttgtggccc  5760
aattgtctgt tttgctaaca tcagaaagtt ataatgaaat aatctgcaaa aaatgtaagg  5820
tgctagaaaa ccaataatac tgtgtacctt gaaaatgcta atatacacct gttttgttac  5880
agaggtggag cacagtgaaa gaattcaaga tgccacctaa tataaactgg aaagaaataa  5940
tgaaagttga cccagatgac ctgccccgtc aagaagaact ggcagataat ttattgattt  6000
ccttatccaa ggtgcttaat tggtcaataa taatagatat atacattaac ttatgattaa  6060
tttattaata aaatatgaat ttattttttt cagggacaac tataattgtc acaatctgga  6120
agtgttctta tattttgctt gaaggttata aaatataaaa cagttgcttt tctgtttact  6180
taggtggaag taaatgagct aaaaagtgaa aagcaagaaa atgtgataca ccttttcaga  6240
attactcagt cactaatgaa ggtttgtatg tagtaggttt taactatagg tttggctatt  6300
agtggaacta taaaaatctg ttcttatata aggtaatctt tgtgaaaata cctggtaata  6360
```

```
tctacatcac cactaaaaaa tgcaatatat ttaaatgtga attaagtatt ttagtgtata  6420
aaacattgct agtttctact taaagtttct aaaagggtgt gtaggggaaa tagaatgagt  6480
atgttgaaaa gtaacataag gaaatatatc ttgaggtcca aatgacaaat gcagacaatg  6540
actgctatag ggatttgtta agaggggaaa tgatttaaga gatgtcagaa gacttcacaa  6600
aggatcaata ctgaggagta gtgttagata agtggaaggc aatgcagtgg taagatagta  6660
agggaattct agagctgttg gttaccataa ataaatactg agaacaggaa atatgtttat  6720
tctttatatt tgaggaaaca aggtgcagca agtttgtagc agactgtaga gaaaacaaat  6780
cttgggtaag tactttgaga taggttgttg agggccttaa aggtgtattt tatgctatca  6840
gcaattgaga aggcagtaaa ggttttcgaa acacaattga taggtacaaa aatacacctt  6900
aagaaggcaa aactgagtat attatgtagg acaaactgaa ggaaattgga gctttgtaga  6960
catcacatta tagcggagtt taaacctgaa attatggatt agaataatag caattggaac  7020
agaaaaaaag tagtggaaag acattacaaa gggagatgtt gcattactgg atataagact  7080
tgaggacttg aggtaaaaag gagaatcaaa aatgtttcat gctattaaaa atctagaaat  7140
tgtagtctta agtaagaaaa ttgcctggca tggtggctca cgtctgtaat cccagcactt  7200
tgggaggcca aggcaggagg attgcttgag cctgggagtt caagactagc ctggataata  7260
tagtgagtcc ttgcctgtac gaaaaaattt gccgagcatg atggcacacc aagcatgatg  7320
gcacgccaag catgatggca tgcacctgta gtcccagcta ctcaggagac tgagatggga  7380
agattgcttg agcccaggag gcaggaggtt gcagtgagct gagattgtgc cactgcactc  7440
cagcctgggt gacaaagtga ggccctatct caaaagcaaa aaaaacaaaa acaaaaacca  7500
aaaactattt attcagcaaa tatttactga acgtctccat gtgccagcca ttgctggcac  7560
taaggatcat aacaaataaa acagaatttt tattttcagt gcttacattc cagtataaag  7620
gcatattgaa ataacctttt tttaatgttt agatgaaagc tcaagaagtg gagctggctt  7680
tggaagaagt agaaaaagct ggagaagaac aagcaaaatt tggtaagcac cttggaaaaa  7740
gtttattatg gtattaaata atgaattcca tttgttcatt aaactgtaga aaattaaatt  7800
atattctata aaatatatat attcagttta tttttaatat ataacattta ataataaata  7860
tttctagact cctattttat ggatctgcca tataatactt tttgttacct tataatcatg  7920
atggactctt ttaaaagaat taattttgtt attgaaattt atttaaaagt ttgttttgtg  7980
gtaactaatc aattaaaacg tttttctttt tttttaaaaa aatagaaaat caattaaaaa  8040
ctaaagtaat gaaactggaa aatgaactgg aggtatgtct ttttgtattc cctaggatgt  8100
aattgtcatt aattttattt tgaattgttt tcaaatttta aaattattgt tggctggaaa  8160
aattataagg atgattgtaa tcatggttat ttgtttattc tgtatatgtt ctacatgcct  8220
attatgtgcc ttatatagta ctaaggactg agcatatggt tgtgaacaaa ataagaagtt  8280
aactgctgga tggagcttat agtcttggga aatatacaga aagattacta gtaactgagg  8340
tggagggtgg gtggggattt gaggaatagt gacgaaaggg tgttatagaa gtaatttttg  8400
acaaagctga aggctaaaat atgaatgtat tgttgaagaa caaaatacat tgagattcct  8460
gagaaggtag gaatgtgata caaatggatc agcctttgaa aggaggaata ccctttttcct  8520
ttgtgttagg agaggaggat gagtggatga gcgtgggaag agtggatgtg tatagaggct  8580
tttatgtttg taggcataat gcttggaagt tgaggggttg gtgatgacat cttctgttaa  8640
aaagagtggg aaatggtgtg gtcacatttt aaggaaatta ggtaaaattt gaaatatatt  8700
ggagacagga ctggagagtt ggggatctgg agtcagacag atttgagttc tagtcctgat  8760
tcttctactc gttaactctc tgaacttgga tgacctattg tttttgattg tatatccagc  8820
tcctgggaaa atgccaagca ctttcaataa atactaaatg aattatggag ttggatcagt  8880
tctgtgttag tgtttagcta ggtagctgct gtagaataga agggtagcac agttgaagat  8940
attggtagga aagtggttga agtgatgatt atgaagtctt aactgaatag ataaaatcaa  9000
gattggggtt gggtgggcag aagggtaggg atatggaggg agaagatgag gggttagagt  9060
gtcctgtgag gtcgaaggac aggcatagtg ggaataattg aaagaatgtt ctggttggac  9120
aaggatctga tgtgggtgtg ggagtgagag actatagtga attcaagaaa aaaatagact  9180
agaacaaaag ttatgtggag attgcttagt gggcatttga tagacatctg tgggccacat  9240
gcttaaattc ccagtgcatt ttgcggagtt actggaaggt tggtggcttg tttctaccat  9300
gagtaggtaa agatggagag caggatattt tgtgagaaag cagctgaagt ttctatagga  9360
tgatggagga atgataggaa tgatcacctg aagttgcagg gtggggtaaa cctagaagca  9420
ccaacacctt cttctgaccc tcatgtattt ggaatctgaa agaatgagca ccttccaatt  9480
gaaagagttc caagggcatt agtatactaa aggatccaaa ttgcagctaa gccaaggaga  9540
tggaaaggag gattcagtaa agaatctgag gatgtgaaat attaatttat cttggaagag  9600
aattttagag agcacaatgg aatgcttttt ggaggagaga aagagtaaga acaatttggt  9660
taaggtagag gaataacaga actataaggt gaagaaatga atgtgagaca cattagatga  9720
ccaaatgatt tgatgttctt ggccatgacc tgaattaaca agactgtgag gtaaaatgga  9780
tttaatcggc tacaaatctt aagataacca aaacctgagc tgtttaatat ggtagcacta  9840
gcactaacca cttgtagcta tttatattta cattggttaa aattaaaatg aaaaatttag  9900
ttcttcagtt gcactagcca cacttcaaat gcccgaacat agctacatgt agcgagtggc  9960
tattgaactg gacagcactg acagcatgtc cattatgcta gaaagtccta tgggacagca  10020
ctggtctaaa cagtgcatgg tatgagagaa agggcaggtt aaggcactca gcttcactga  10080
ctggggtgga gattctgatg gtttgtactc aggttccaga tccctgaggc tcaggaacct  10140
ttgcagttta gtctggttac ctgtggccca gtggttacaa cagaatgatt aacagtcaat  10200
tctttgcatc tctgggtggc tcaggaaaaa tttaaggagt tattagctgt gaactaacct  10260
taagtaagtt aaattaaaaa aaaaaaagtt cttaagctaa tatgatttta aatatctgca  10320
ctgaagtata atgcaaattt aaattcagca taattatttg cttgttgttg actcatttga  10380
acctcaaaat ataatgggat taatttatac tttgggttta ttactttaag atggctcagc  10440
agtctgcagg tggacgagat actcggtttt tacgtaatga aatttgccaa cttgaaaaac  10500
aattagaaca aaaagataga gaattggagg acatggaaaa ggagttggag aaagagaaga  10560
aagttaatga gcaagtaaag cacttttttt ttccatgaat cttcactgtt caagttacct  10620
ggctttttat tattattggt aacaatatca atttttatat tgtatgttat atttgaaaaa  10680
tgatgtacac ttatctctaa ggttttatat cactgttcat tttgtcatca ccaattttaa  10740
aatataatgg tacttctagt gaatatgact tgaagattaa ttctttatat ttggaagtac  10800
atttttctca ggacatcaaa cttgttacct aaaattaatg cttttgtctg gaagattggt  10860
atcaagtaac taatagattt tcataaagaa gtgatctttc tagtgccata gtttattttg  10920
ggtaaaagtt atatttgttc atttcaatgt atttatatga ttagtagatt cgcaaatgaa  10980
tctttcgata tattcaataa tggttaatta aatatcttgt ttttggttgt accttatttt  11040
atgtgagata tatatatata tgtatagttt ttgaaaagtt gtgttcatgt cagcagttta  11100
```

```
taaatcacat atttaaaata acatttttaa tgcatagttt ttattacctc gttattcctt 11160
gttataaact aataattctt gcagtgttca cttgaattta gttttaggaa aaaagttttt 11220
tgcagatcaa cttgtatttc ctggaagaaa atttcctatt ttacctcagc ttcctattta 11280
atgtattatt tatttattta cttaacattt atttgttttt tatttcacct gaactgttag 11340
taaacttagt aaaatttggt gcctacatgt ggtaactgtc ctgtccctta tactcagaaa 11400
cgttttccac ctttgtgtcc tttaggtcat tgttgtgtta tattccattt attttatttt 11460
gtccattgtt ctctcagaaa ttgagggtca tacattttaa gaaaacaatg atatgctatt 11520
taagagaatg tatcataaat tgatttgtaa ggaaaagtat ccccattctt catgtatgta 11580
ttttactcta aaatgttgaa gaatcatata gaagttagct atgaaaacaa tgtggtagag 11640
aaagtatgga tcgatgccac ttaaatgtta ggaagaagct cttagagcat tatctgttta 11700
gctaactgca aaacatagca gacatgtgga ttttttaata gtcatcaagg atctaactta 11760
taatatacac tggtagaatt gcttaggggg atgtctgtgg ttttctggac ttttgttctt 11820
ctatatagac ctgtatcagt tgacttatca ttcataccac acacccttag ctaatcagaa 11880
ctaccttgtc catttatatc ttagactatt gtctttttc atagtcacac acagagaaaa 11940
cttgaatata tggcctgtgt tcctttttgg ctgctcaatt ccttgagatg aaatatgggt 12000
atgggttgct ttggcaatta cttctttgcc gttaaccagt cattcagttt tattgagtct 12060
ttacagcata ccagaggctg ctagttacta gtgatatagt gggcaactat gttctggttc 12120
tcaagaatat tcatagtcaa taataagcat aacatagtga taatatgata cttagggaga 12180
tacataaggt catattctgg catactctgg agagagatac cgtaatcagc cttgaggtgc 12240
aggatgtgat ctgtaaactg agacctgaag tatagttaga ctggtaagag gaatgaggat 12300
atatatggtg gttaataaaa gaacattctg ggtagaagat atagcatttg ctaagaccta 12360
gaggtaagag atgttatgga gtatttagga aactacagtt attcatttg actgaaatat 12420
aagtgaaaat agctttcata gagtccttac tatgtgccag gcacttcata tgcattaatt 12480
cattattgct tatttgatac ttgtcatatg agatagttgt catttctgcc atgatacaga 12540
tgaagaaatg gagacacaga aagagtaatt gcccatggtt gcacagctta taaatggtaa 12600
aggtaggatt tgaaaacagt cttactcaag agtctgtgct atcttgcctt cccagtttta 12660
tttttatga tcctctggag agataagcaa gggccagttc ctaatgaatt tggttctttt 12720
cctgaaagga gccagtgaag agttttgagc acaggatatc atgatcagat ctatacttta 12780
aaagtttact gtactttgta gagagtggat tgaaaagggc caagactagt aaggaaacat 12840
ttgtgttaat tcagggaagt gctaatgatg gcatttgcct gagaaagaca agtgtgagag 12900
aagtagatgt aattggatgt ggtgaatgta attggttgtt ggaggagagg gaggatggag 12960
agtctgccta attttgtggg ttgggccact aaataggtag atagtgccat tcattaagga 13020
ggaacacaag aggaatttgg aaagcttgag attatttcag ttttgtagat gttgagtttg 13080
aggttcttct gggcatattc aaaaagggta tctgtggata tggaattcac aagagaccct 13140
gtacagatga tgaggattta tgaatcatca atgtagacat tattgaagcc agagaagtga 13200
ttgtaaggca cgtctctgag aaatgtctaa taaagcaatg aaataggaag agtgcttcaa 13260
ggaaaagctc aagaaaggag aaacagagtg tgatgtttga gaagacaagg gaaaaaaaca 13320
ttaatagcat taaatgcttt agcattaagt tcttggcttc tcttcttgta aaaatttccc 13380
aattcagaac acagtgggat tattaacttt caattgataa taataatgat aggcaaactt 13440
ctaaaatttg tattgtagtt tgcattttat tataaacttt ctttaaattt ttattttgaa 13500
aaatgtcata tcttcataaa gattgtaaga aacacactgt tggtgttaat gtaaattagt 13560
tcaaccattg tgggagacag tgtggcaatt cctcgaagat ctagaagcag aaataccact 13620
tgacccagca atcccattac tgggtatata cccaaaagaa tataaatcat tttcttataa 13680
agatacttgc acacatatgt tcattgcagc actattcaca atagcaaaga catggaatca 13740
acccaaatgc tcatcaatga tagactggat aatgaaaatg tggaacatat acatcataga 13800
atactatgca gccatcaaaa gagaatgaga ggtcaagcgt ggtgactcat gcctacagtc 13860
ccagcacttt gggaggccga ggcaggcaga tcacttgagg tcaggagttc aagaccagcc 13920
tggccagtat ggtgaaaccc catctctaca aaaacaaaac aaaacaaaca aaaattaact 13980
ggtcatggta ctgtatgcct gcagtcccag ctacttggga ggctgaggca ggagaatgac 14040
ttgaacccag aaggcagagg ttgcagtgag ctgagatcgc accactggac tctagcctta 14100
gcaacaaaac tagagtttgt ctcaaaaaaa aaaaaaaaaa aaaaccggaa caagatcatg 14160
tcctttgcag ggacatggga tggaggtgga agccattatc ctcagcaaac tcacacagga 14220
acagaaaacc aaacactgca tgttctcact tataagtggg agctgaacaa tgagaacaca 14280
tggacacatg gtggggaaca acacacactg ggacccgtca aggggtcggg gtgggagaac 14340
atcaggaaga atagctaatg gatgctgggc ttaatatcta ggttatgggt tgatctgtgc 14400
agcaagccac cattgtacac atttacctaa gtaacaaacc tgcacatctt acacatgtac 14460
cccagaactt aaaagttgat gggaaaaaga aaaacaataa ccacccacat acccttcata 14520
tagattcacc agttcttaat gttgtgccaa ctttgcttta tctttttgtc agtattttta 14580
cacacacatg tatttctctg tctcttgttt gttcaatcac attttttgct gagtcattta 14640
agagctaatt gcagatatga tactttgcac ttaaatattt cagcttgtct gtttgaaaaa 14700
gaaagatgtt ctcctacaat gaacacaata taattgtcat gctcaggaat tttaatattg 14760
attcaacacc attatctagt ccataatgag atttcttcta atggcccaat aatatccttc 14820
agtctcccca cctccaatat ccaaagttct gtcaaggatc acatactaca tttggttctt 14880
tattatagac tttttaaata tcgttgtata ccattgtgat tctatcgtct cctttaataa 14940
agaggagaac cagaaaaatg aaaggtcata agaggaatga ggtttggaga ataggtgaaa 15000
aaaggcatca taatgtttat aataatgttt gcctgttcag agaaacaaga atcacagata 15060
aagtcactta tatgtagata agagaatgct gtattacttt ttgctattct attcactgat 15120
catttttcta agaactctgt atgcttcttg tttaactctt atgtcagcat gtatgagaaa 15180
actgagttaa agagatgtta agtaactcat tcatgcttta ctagaaattg gttgatgagg 15240
gacataaacc taggccggtg tgattttaga ttgcttcttt taaccattgt gttgtattgc 15300
cttatatttc taagtaattt atgttcactg agagcaaata atagtctagc tatgacttag 15360
aaaagtaaaa taaagatgtt gggcagaaaa ccattttatt aggggttttt ttggaggagc 15420
agattaattt gtttctgtat tctttggtta gtttgtgtgt gtgttctttt taattcttta 15480
aaatgaaact gtttaatcct taaatcctta agttttgaaa attttggcct attatttatg 15540
tgttaggttg atattaaatc cttaatagct ttaacatttt ctactttgtt agagaggatt 15600
taaaatttaa gtagataagc tgaatatctg gctttatatt aaattactgc tgatggccag 15660
gcacagtggc tcatgtctga aatcctagca ctttgggagg ttgaggcaga tggatcactt 15720
gaggccagga gttcaagacc agcctggcta acacagtgaa accccgtctc tactaaaaat 15780
acaaaaatta gccagttatg gtaatgcatg ccagtaattc cagctactcg gtaggctgag 15840
```

```
gtgggagaat tgcttgaacc gggaggcaga ggttgcagtg agccgagatc gcaccactgt  15900
actccagcct aggcgacaaa gactttgtct caaaaaaaaa aaaaattact gctgaatttt  15960
atcttcttct tatttatttt tttttttac tattttagtt ggctcttcga aatgaggagg  16020
cagaaaatga aaacagcaaa ttaagaagag aggtaaaaaa ttttagtagt tgtggtggtt  16080
caacaaaggt acttattaaa ataagtacct aagtttacat aaatttatat tttaaccagg  16140
actggagtct tctaagtaac tgatgttttc agactgattt tatggtatga ctttgtctca  16200
gggaaataga aaacaaagca aaatgtgagg ccattaagta ttacattcat ctcaggtcta  16260
tgcgggtaaa tcttttttttg ttgttttata agccattctt tgctagtttt ctaattgaat  16320
agatgactgg atttctattc ttatttctct tacccagaat cctttaaaat tttttgttac  16380
ttgtggaatc ttataaattc tgattatcat ttggttctac tgagccaaat aatgtttgta  16440
cattgtttat tctgatagaa gttcttaagt ttctaacata attgaaatat tatttgtttt  16500
ggtagataat tagtattctt tctttggtta ttcaagataa tatgcatcat tttcccaaaa  16560
tttttttgtt ttctttagtt tctgattatt atttttaatt atgtattacc tttctcattt  16620
ctaattaccg ttttcctgtc cttttctgta gaacaaacgt ctaaagaaaa aggtgaggct  16680
ttaagtgtgg tgaaatcttg ggaatttaaa atatgttgtg agagcactat ttagaggata  16740
tgattttgtt attctgaata gttttgtaat tgaatgttgt gtttggttac cttcagaatg  16800
aacaactttg tcaggatatt attgactacc agaaacaaat agattcacag aaagaaacac  16860
ttttatcaag aagaggggaa gacagtgact accgatcaca gttgtctaaa aaaaactatg  16920
agcttatcca atatcttgat gaaattcagg taaaatggct agaagtcaat tcagagcaat  16980
ggttcctaaa aactttaatt tcattacaat gtaaatataa tatttagccc tacatgtaaa  17040
ttccctggta taaatctgtc actatgtact tgtaaaatgt gaaataaatt acatctttga  17100
agttgcaact ttttagccat ttttatattt gcctgtcttg gtcattaaga acaattgagg  17160
tccttatgta ctattttctt gattcaattt gatttaattg gtcaatgcca attagtaaag  17220
gtctataaag aattctcttt ttttctagag gacacttatg gctgcgttta attttaattt  17280
ggtttaaatt tcagtttttt taaaattact ttttaattat agtgtcttta actttttttag  17340
actttaacag aagctaatga gaaaattgaa gttcagaatc aagaaatgag aaaaaattta  17400
gaagagtctg tacaggaaat ggagaagatg actgatgaat ataatagaat gaaagctatt  17460
gtgcatcaga cagataatgt aatagatcag ttaaaaaaag aaaacgatca ttatcaactt  17520
caagtaagaa ttacttttag aataacttat ttattcagac ttcatattat ctcattacta  17580
tttatttgac actagaaagt actttttcta ggatgtgaat ttttgtctgt ctttttaata  17640
gtgtaatatc ttgtcatgtt ggtatatttg tccatatgtg tttctccaat cacctcacaa  17700
acactaattt ttgcaattta ggatatataa atgatacttg aatgaatgtg tagatagcag  17760
tcattatggg gttttctata aaagactact gaaaatcctg tggatcataa catttcattt  17820
tatcttaaaa taaatacatt ataaatgtat tagaaaccaa tacattgttc agtatttatg  17880
tggattaaat ttgtttaaaa ggtagaataa tgtttaaaaa taaaattttc tagtaatgaa  17940
agataattat gcaattataa gatgcagaaa ctattaaatg tcacctataa ttccaggatg  18000
acttcaatga taaatacaca tatgtaatgt aatgtatccg tatgtatgtg tatataagta  18060
tgaatacgta tgtgtgtgta tgtagatata tttatatata taatgtatat gtaaatatgc  18120
acaggtgtaa atatatgtta catcagtttg caacaactct tgaaataact ttgtctttta  18180
ggtgcaggag cttacagatc ttctgaaatc aaaaaatgaa gaagatgatc caattatggt  18240
agctgtcaat gcaaaagtag aagaatggaa ggtatttttt ttcaattgac ataataactt  18300
tttcttttttg tattttagat ttaaatttta gtcttatttt tctttaaatg tcttatactg  18360
gtttataaca cgtttattag ggtttttaaa cataagttta ttttatttat tggttagaaa  18420
agctctagaa ctgtcctttt tgatctctag ctaatttgtt attgaatgac ctctttcaca  18480
tcaatgagtt taactttaaa ctttttgata gaagtctaac tccaaaatat atttggcatc  18540
taaaatatat aattcgaaat ataatttaaa ttttttttact taactcatag ttaccttata  18600
tacattagtt aaatagttgc aggtttaatt ttagttttc taactaaatg tcaggttcat  18660
cagtgggaat gggaataagc aaagggatca gaataacttg ggaagccttt tcaaaataca  18720
cttttcttcc tcaccaccac tctccaacct taaccaaatt gtcaggcctt accatattag  18780
aagctgggat tatgatggtt gtatacttga aaaacatcag agattattct gaatgaataa  18840
ttctaatttt aaaaactatc acttctagag tcattgcttt ctagtatggt tcacataaat  18900
cttgtgggca gtttggaact ggttagcatc tagggagctc agataaccta tattttaaac  18960
aaaagcatta gcaatggaaa taaggcctat agaatcagtc atgtctccat aaactttata  19020
taaagggcca gacagtgaat attttagacc acctggtctc tgctataact aaactctgct  19080
tatagcatga aagcagccat tgacaatacg taaatgagtg agcaaggtgg ttttccggta  19140
aaattttatt tacaaaagca gatgggaggc cagatttgac ctttgggcca tagtctacca  19200
acccctggaa aaaacagttg tctttaccag attgaatgtt ggcagggtaa atggtgacat  19260
gttatatgta ttctgtactt tgttttgact taataccatt tcataattat tttatatcag  19320
tacgtatagt attgctgttc tttttaaagg ctatgtaatt tttcttttta tacaggtgtt  19380
aatttgataa tttgtgaagt ttatgaagtt tccaattttg gggttgtaaa ctgttttaat  19440
gaatatcctt atatatgtta ttttgcaaat gtacaagtat atctgtggaa taaattgctg  19500
caagtgttgt aattgtcatg tatgttgcaa atacattcta acagtttgtc actttttttg  19560
ctttatggca ttttttgctg tgaaatattt ctttttatgc ttagttaaat ttattatttt  19620
ttaatgactt ttgacatttg ttataatgag aaaggcttct gagtataaac ttgttttctc  19680
atcttttctc ctaatatctt gttttgtttt tgtttttgtt tttgtttttg agacagagtc  19740
tcactcagtt gcttaggctg gagtgcaatg gtacaatctc agctcactgc aaatgccacc  19800
tcctgggttc aggtggttct tgtgcctcag cctcctgagt agctgggatt acaggcatgt  19860
gccgccatgc gcagctaatt tttgtagttt tagtagacat ggggtcacac tgtgttggcc  19920
aggctggtct tgaacccctg gcctcaagtg atcctcctgc ctgggcctcc caaagtgctg  19980
gaattacagg tgtgactctg cctggccttt ttttacattt aaatcttcga aacatataat  20040
tcattttgat gtaaggagta tcatgtggat tcaacagagc tactctgttg tccaaacatc  20100
ttttattgat tatttcatct tttattgaat tgattgatct attttctagc agtgtatact  20160
tgttttaatt tgtgtatgtt ttaatatcta aaaacgttat tatttttctg cttttagact  20220
tctttatgaa tatttttaat gtgaattata gaactggctt gtccagttct taaaaaatat  20280
cttgtggatt tttattgggt atgtgttaaa gttataaatt gttttataga ttgatttagg  20340
ataaaccttt ttatgttatt tggtccttct agctaaagaa cacaagatac cttttctttc  20400
attcattcaa gatattttat gcctcttggt tgcattttaa tgcatacttc ataaagatca  20460
attgtataaa acttttcaca gttgtatgga agtacttctt gtttataaat gagttttgaa  20520
aggttgaaat atttttaaag attgaattat aaaaaaagaa aattcggtat atattttaaa  20580
```

```
atcattttct atttgaattt caggttgtat atacaaaagg aacagagatt atgccagtag  20640
ttgctcatac tttctcattt caaataattt ttattttctg tatcataaat ctactaacgg  20700
tgtttattat ttatgataat gaagaatgtt ttattaactt tccttttgca taacagattc  20760
tattgtgttt atttctagct aattttgtct tctaaagatg atgaaattat tgagtatcag  20820
caaatgttac ataacctaag ggagaaactt aagaatgctc agcttgatgc tgataaaagt  20880
aatgttatgg ctctacagca ggtaaaatct taacagaatt ttgtttatca accagtttta  20940
ttacagttgg aactctgaac gatgtctttt atttattata tcatcagtgc ctagtgtagc  21000
ggctggtact accaagtgta taataatgtc ttttgaaatt tcttctacca cctggtccca  21060
ataaaaaatt agaattaagt ttagatcacg gattagactt agaactagag ttactgtgtt  21120
tatttttcta tgtttatgtg gatagtacac acattgtttt ggttagaaat tatttaacaa  21180
gaaatgatta aaaactttta gaaatttaaa ataattttat actcttttaa ggtttatttt  21240
actgtatctt agtcctaaca taccctatac aatgtgaaat aagctaaaag catggttata  21300
atttgactgt gctacctatt ttatttttag tgaaaataac ccaaataaaa ggaagtaata  21360
cttttattat ttgtgctgta gttatagtcc acaagtaaga agatgatttg aaaagtgtat  21420
gctgaataag aacaattaca ggggacaaca ttttttaata aagtacgaaa ggggaaaaag  21480
ctaagttgaa taaaagagaa agcacagagc aaaacagaaa catacaaaat ggtaaaaagg  21540
tggaattgaa tggaggatga ggaaagtaac atataaggaa gtatagaagc cataaacatt  21600
agggagttct ggaaatccta ttttccagag tgttagccat tatatccatc tttcagtatt  21660
ggagtaacag cagtgtacct atcattgtgt attacagttg aagtgtacaa aatggtaaaa  21720
ggcatacttg tacccacaag aaaatatgtt ctacagtctt gttgaaaaaa atcagacgta  21780
ctttttttcct taccttttta ggttaatatt catgaaggga tatatattgt tttaaaatat  21840
tttatagggt atacaggaac gagacagtca aattaagatg ctcaccgaac aagtagaaca  21900
atatacaaaa gaaatggaaa agaatacttg tattattgaa gatttgaaaa atgagctcca  21960
aagaaacaaa ggtattttta taaatatata gttattttat atacaattat gtttttaacg  22020
actttatttt tattaaaata aaatgtcaag tcaatattga gttttctcca tttgaatttt  22080
atattttcaa aaaattgtac aagatattta ttattatact tatattacta gtgcttacat  22140
ttgtaaatga tggatgcatt ttctattatt tttctcctct ggtgaaaatt acattaacgt  22200
ttattaccag gtcactggta tgaaagaaat gaaaaattgt gatacaatta tttttattta  22260
actttttata attaacaaag aatggaagat aataaaattt tgaccagtgt aacagcattg  22320
cagatagttt tcagaggtaa tttcacatta atcttaccca aattaatgtt tcatcatatt  22380
ctccttaccc tgagccatat tacctttttt aacacatcaa attctatgaa tataagttct  22440
tacaatatct gtgttgttat atttccatag cactacatac tatagttatg ccagggcaca  22500
ctagtgcgaa ctgttcatgg gaaattcatg gacatgttta ttataattgg tgactatgta  22560
tatatgtata cactacattt atacacacgc gcatggaatc actatttctt cttcatgtca  22620
tatatatata catatataca catatatata catgtcatat gtgtgtgtgt atatatatat  22680
atttgtatat atgacatgaa gaagaaatag tgattccgtg cacatatgtg tgtgtaagtg  22740
tagtgatgtg tttgcaggta cggttgtaat ttcaaaaatg aagcaaaagc cttgctcagg  22800
agataattga accaatactt aaaggaagta aaggagtgaa acatgcagat ggctctaagc  22860
agtgggaata agttcaaagg cagtaaagca ggagtgtacc aatcatgtct gagaacaaca  22920
aagaagtctt tttggctgga gtagagtcag caagtgaggc agtgataaga ccagagaggt  22980
aaacagaggc catatcatat ggggccttat agttcattgt gcagacttgg cttttaagtg  23040
agaagggaca ccggggaaag tttctgaaga tagaaatgat ataatttgac ttaggctgtg  23100
tttgcagtag actgtaggag tggtaaataa gaatcaggga gacctgttag aagactattg  23160
caataatctg gagaaaagtg atggtggttt ggggcatggt ggtagcagtg gagttactgg  23220
atgcagcagt tctggatgta ttttgaaagt gataaaaatg gaatttgcta acagatcaga  23280
tgtaggatgt gagagagaga gaactcttgg tctgaaccaa aagttttggt catggtgggg  23340
ttgtgggaag agcaggttga gagataatca ggtacttaat tttagacatg ttaggtttga  23400
gatgcttatt agacattcaa gtgaaggtgt taagtaggca cttgtatata aaagtttaag  23460
gtttaggaca acaatctagg ctaaagatat gtttggtaac tgtctctgta aaagtaattg  23520
aaataatgag gctggctaag atcaccaagg gagtaaatgt aggttaagaa gaaaaatcta  23580
aagagcttct actttagcag ctggggagat aaaaaggagc taccaaagga gactgaaaag  23640
gaaagcccag agagctagga ggaaaagcag gagtatggag agccctgaaa accacatgag  23700
gaatgtaacc aaggaagaag aaacaactgc tttcagagct gtgttcattg ctgctgatag  23760
gtcaagatga tcactaaaag ttgactattg gacttagcaa tggtcatttt tggttcaaga  23820
gaaaatgggt agagaggaaa tgtaataaag aaatatagga accctttcc aggactgttt  23880
ctataaagag aaggagaaaa caaggtggta gcttgagggg aaagagggat taagaaaaca  23940
tttttctctt taagatggaa gaaataactc atgattttag gttaatagga gagctccatt  24000
aaagaagaaa cattaatgaa tcaatgaagt ggagagagag aacttctgga acaataaat  24060
ttttaagaat gcaatgggat gggatcctag tgtgccagtg aagaggttgg ccttaactag  24120
gaacacagag ttcatccata attgtagaaa agaaggtaga gtgtatagat atcgatgtag  24180
gtggcttggt agacatcctg gtaatgggaa tttgtggaag ttctaaactg gttgctgctt  24240
ttttctcagt gaacaaggga gcaaggttct tagctgaagg tgaggatagg agaagatgtt  24300
tcataagttt gaggagaaag aagagaagtg aaagtataaa atggtcatct gaaagattga  24360
agacgtggag aatgtggtat gactgttgag taacttcaag agcccacgat atatatatgt  24420
atttctattt atgtgtttat tatatttgta tcagaacact ttgaaagtag tttaaactgc  24480
tttaaaagga tgactaatag tatggattgt gcgtattcta attactagga gaaaaagtgg  24540
caattgatct ctgctgtcaa ataaggaaaa ggacttatct gataacactt tagtcagtcc  24600
gtagttatat aatccctaaa gctcacagaa ggtgtgtgta ctagactgta ctctacatct  24660
tgaacttaac ttgtaaaacg taatggctaa tggtattctt ccttcataag attaggatta  24720
ggtttagtta tcaggaacag agagctgaag aataatggca aaatcaagat agacatttat  24780
ttctcatcta tgtaatggcc tagaattaag cattccaggg tgttgccttc atctgcccca  24840
tccaaaatgg atggaatgca gctttatctc atgtctgtgt cccaaacagc aagacagagg  24900
aagaggggca agagttaaaa gcatgtgctg aaggataggc aggtaaatat agtgtttatt  24960
gtgtagggcc atgtggaaga atgataggag aatagatatg tggatggaag ggagaataga  25020
tactggggga caactcagcc tgtgtcatgt tccacagctt agatgttagc tccagacagc  25080
tgtgctcatt tcttaaaaac ttttgtgatc tcaaacgtac tagttttatg cctaagtcca  25140
atattaaata tataacctat atattagtaa atgcttataa tgaatgagtg tgagaatgat  25200
ctgtcaatca attttggaat gatagcaata ttatgttttg gtcttttaac aatttagtaa  25260
gatattacaa gtaggcattt aggaagtttt tagcttagtt tggattaaat ttagctgcaa  25320
```

```
gtgacagaaa aatcaagcat aatacaataa tttaaacaag atagaaattt atttctctat  25380
aatatagaca aagttgaagc aactagggca ggatttgtgt gacagatgct caaatatccc  25440
ctatcaggaa ccctgtctct tgttgctgtg cctatctcaa catgtggttt ctaactcatg  25500
tgaagttgcc accctcatat ccatgtggat ttcagctagc aggaaggagg aaagagaaga  25560
gagattactc ctttatttta aaaacatttt tttttttttt tttgaaattc acatatgaac  25620
tttgcgttta tattccatta ctgacatgac cacacatagc tgcttgtgtg taagtggaaa  25680
tttagttctt tatttcaaat ggccacgtgt caagctaaaa atccatagtt ttagtacagt  25740
ggacaaaagg gaggttaaat attaggaaca gctagcagtc tgtatcacaa tgatcatttt  25800
ttgtaaagca gtattttgca accttttaaa atccataccc cttcagctaa gaaggtttta  25860
ctgaacttca gtttttagt aaattgtatt agtaaaacca aaacaaaact ttcatcttac  25920
aaatataaaa tgacaacttt aaaggatttt tttttaatgg cataccactt ttcttgccac  25980
catgttggga tcactgattt gaaggaataa gtagtcaatt caattcatga tttttgtttt  26040
tactctgtag gtgcttcaac cctttctcaa cagactcata tgaaaattca gtcaacgtta  26100
gacattttaa aagagaaaac taaagaggct gagagaacag ctgaactggc tgaggctgat  26160
gctagggaaa aggataaaga attagttgag gctctgaaga ggttaaaaga ttatgaatcg  26220
gtatgtattt ttatcttgtc attcaaggag cttagaatta ttcttgccat tcacagacta  26280
ttctgtgcta tttactgcat accatttaaa aaacattcca taagtatctt ttgataaaga  26340
ttatcctcat taatttatac taaactattg aaacctttga gcatttactt tttgccagaa  26400
ttgttttcaa acttttgatc acagtgattt gtccaaataa tcagttttgg tgaagcagca  26460
ggattacttt tttttattat ctgtgttcat tgggccacca tgtagatgtg acaccactgg  26520
ccaatttgac agaatttatg acaggaacat actgtgtcaa tacaacctgc tctccacttt  26580
ttatactttt tcattggtta caactaattc aagcaactaa tgacttactt attctactgg  26640
tattgctgat ttgcttttac taattctttt agtattttgg taagtgtttt ttatatgtaa  26700
tgcatattca gagtcacttt gcctttagga tattatactg gaaagtttta actgttgcat  26760
attacatcat tattattact ggatttggtt tataaaagca caataaaaaa ccagtgtaat  26820
gatataaatt ataggcatat gtacatttc ctttagactt agtaaaaaaa aaatcatgaa  26880
cttgataaat ttattcaagt aaaccatgtt atattttaaa ttaaattgga tatttttcag  26940
ggagtatatg gtttagaaga tgctgtcgtt gaaataaaga attgtaaaaa ccaaattaaa  27000
ataagagatc gagagattga aatattaaca aaggaaatca ataaacttga attgaagatc  27060
agtgatttcc ttgatgaaaa tgaggcactt agagagcgtg tgggtaagcc atgttttaag  27120
ttacatagtt tgcgcaacct gatttacaag tcttttttt taatttaaat tttgtttatt  27180
attatttatt aagtagttta atgcttttt caaatgcttt tataaaacat ttaatacaaa  27240
taaaagtgga gctaacctga ttgaagtgga atcagatttt atggggtgg agtggtgggt  27300
gggcagggct ggaacattgc tttatttggt ctagcatctc ctcagtaata gctgcttgtt  27360
taaaaagatg aaagtttatt aataccacat atcagagatt aacctttttt tttcccaaca  27420
aaagtagggt ctgtattacc catgtttgtt tgcaaaatgc tcttgtaaca gatgagatat  27480
ttaaacttct tgctctgtgt tgtgattctc ctgcctctgc ctcctgagta gctgggatta  27540
caggtgtgca ccactatgcc cggctaattt ttgtattttt ggtagagatg ggatttcacc  27600
atgttggcta ggctggtctc caactcctga ccttaagtga tccacccgcc ttggcctccc  27660
aaagtgctgg gataataggc atgagccacc gcgcctggcc tgttaaaatc ttttaaagat  27720
ttttaagtac ttgattttta taatttagac tacttacgtt ttactttgtt cgagtatttt  27780
aaggagtaat tagtaatata gcttgagagt ttatatattt attttaataa atagcctatt  27840
agttaatatt actaatttga gtgttatgat agtgcagact aagttgctgc tttaaaatga  27900
aaataaatat ctaaatatca atttcattat tgctaaattt catttaatgc tttcttagtt  27960
aaaaatgatc atttgtaaaa actattatct aaagaaaaga caaatagaca aataagtatt  28020
ttatacagat atatatgtgt gaaaagtatc taacttggat ccgtagttgt gctaggaccc  28080
caaattagac ttctgatcaa cttggactat cagatcacag ccttctgatc aacttggact  28140
atcagatcac agccaagaat ctggaagttc ctaaagatga cttctggccc gtctaggtag  28200
ctgtcataga catcatattt tctgtgctta aaaagctcca aatcttggtt tataatttca  28260
tttaggtttt tgttaggatt tccattaata attgtgataa aattttaact tgggttacag  28320
tttaaatatc tggaaaattc tttcacagaa agttacctca ttcttcagtg atactggcta  28380
agtgaattat aaccagttgc ttgatggtat atgacatttt tgcagcttat ttgaatgttt  28440
ttaagttttt aattatattg ctttctattg taggccttga accaaagaca atgattgatt  28500
taactgaatt tagaaatagc aaacacttaa aacagcagca gtacagagct gaaaaccaga  28560
ttcttttgaa agaggcaagt gtggtagtca gttgattatt ttcttggctg aactatagag  28620
aaatactaat aatttatact ttgcagattg aaagtctaga ggaagaacga cttgatctga  28680
aaaaaaaaat tcgtcaaatg gctcaagaaa gaggaaaaag aagtgcaact tcaggtatac  28740
tcagttattc taaaccttta aaaagaatta ttgataagtg agttgtctgg atatgaaatt  28800
atttgtgtct tagctgtttt tgctgttcta ttgtggatct gctacaaatt taataaatga  28860
caataataac ctgaaggaga taagtgagtg tcagtgggtt cagtcctgaa tctgaaatag  28920
acaaaaacaa aacaaaacaa aataacaaaa accaagcaaa caaaaaagaa aaaaacctta  28980
gaattatgga atttttgaaa agttttatag tatagtattt taatttctag acagcaccaa  29040
tatgttgtta ttaataataa taaaacttag tagtttttat gttaatatat gttactcaac  29100
attttccctt tccttaagga ctatgcattg aaaagctttt cttgtaagtt attattatta  29160
ttattattat taatatttga gatggagtct gtcttgttct attgcccagg ctggagtgca  29220
ctggtgcgat cttgctcatt gcaacctccg cctcccgggt tctagtgatt cttgtgcttc  29280
agcctcctga gtagttgaga ctacaggcgt gagccaccac gcctgactta tttttgtatt  29340
tttagtagaa acagggtttc accatgttgg cccaggctgg tcttgaactc ctgacctcaa  29400
gtgatccatc cactttggct ccccaaagtg ctggaattat aggcgtgagc caccatgcct  29460
ggccttaaat tattctttc taagtgaaag taatgtttta ttgaatataa attaacatct  29520
ttcttgggtt tattttactt gagctaaaga gaacagttgg ttaagtttta taatagccat  29580
tgcagtgctt ttttgtaaga agaccacaca gaaggactgt ctttttcact tgccccaaat  29640
ccccaagcac gtatatgagt aatagcagag tggttctttt tagcattatg atttctataa  29700
tacatccaaa actttctcaa gaaaaaactt catgatttat tagtacaata atcagtttac  29760
tcattactca tcatttatat ttactttata tgtcttttaa ctggtgctta ttaagtagca  29820
ctttaatata gaataggcaa agaatggtag agaagatgaa attcaaaaat taggttctca  29880
cattattaat agttcattaa aagtgagcta aatgagaagc ttgtattggc tatgtagaat  29940
tttggaggga ttttggaaac aattattcta cctttgcatt aaaacttgat tgtaggtttt  30000
aagaattaaa gtgttggaat agtaggaggg ttattttaat gtttttagtt tgttaattct  30060
```

```
cttatatata ggattaacca ctgaggacct gaacctaact gaaaacattt ctcaaggaga  30120
tagaataagt gaaagaaaat tggatttatt gagcctcaaa aatatgagtg aagcacaatc  30180
aaaggtaata gtaaagtatt gcaaagagag taaaggaaaa tattttttt ttttttttt  30240
tttgagacgg agtctcgctc tgtctcccag gctggagtgc agtggcgcga tctcggctca  30300
ctgcaagctc cgcctcccgg gttcatgcca ttctcctgcc tcagcctccc aagtagctgg  30360
gactacaggc gcccgccacc acgcccggct aatttttgt atttttagta gagacggggt  30420
ttcaccgttt tagccgggat ggtctcgatc ttctgacctc gtgatccgcc cgcctcggcc  30480
tcccaaagtg ctgggattac aggcgtgagc caccgcgccc ggccaggaaa atattttat  30540
tgtgttttca tttcttcccc ctttatctca ttcttgaaca tctaatctta ttattgttgt  30600
taaataagta gagggaaata tttgcttatt taacctgttg attcaaagat tgattaatga  30660
gacattattt actctgaata cagattagga gttcagataa agcagagctg ctgcatagga  30720
gatcatcatt caatacccca cagtcagatc agaatgagac agaagagaat atgaccatag  30780
gatcattatc aagaatgtta tctgaaattc accatagtgt agaaagtgga atgcatcctt  30840
ttgtcccttt aactagactt tcttcatcca tgcaagttaa agagaattca actccagaaa  30900
ctattacaat aagagagatt tttaaagcac catgtctgca gtcttcaaga aatctagaat  30960
cgttagtcag cacctttagt agggaaagcc atgaagaaat aaatgacata tgcctttttt  31020
ctgatgactg tatgaagaag gtgtcaagaa gccatcaagc actagagaag actagttttg  31080
tacaaaaaag caattcatct tttcatggct tatcaacagc ttcagacata atgcagaagt  31140
tatcacttag gcaaaaatct gcaatatttt gtcaacaaat tcatgaaaat agagctgaca  31200
tggataaatc acaagtagca acattagaag aagaacaggt tcattcccaa gtaaagtatg  31260
ctgatatcaa tttgaaagaa gatataataa aaagtgaagt acccttacag acagagatat  31320
tgaaaaataa gcttaaggtt aatcttccag accctgtgtc tattactgca caatcaaaat  31380
tatctcagat aaattctctt gaaaatctta tagaacagtt acggagagag ctagtatttc  31440
ttagatctca ggtgagtttt tctccaaatt atatttctgt ggttgttctt ttatgacgtc  31500
tctaacaaag ttctgtaaca attatagtta gaatattttt gtttgcactt taacatcagt  31560
tatacacatt gtacttttta aaatctaaaa tgcagtacat tgatatgaac tcattgactt  31620
gtctaattta ttaaattttt ctttagaatg aaatcatagc acaggaattc ttgatcaaag  31680
aagcagagtg tagaaatgca gatatagagc ttgaacatca cagaagccag gcagaacagg  31740
tagtgtaaag gcagaacatt aaaagagatg attgtggtac taaagacaaa aaccgttata  31800
tctttttgcc tcttaccatg gatgttggga gagggagaaa gtgggattaa gatcaccatc  31860
tgctttactg tttagatttt agtttatttt tatgattgct gctatgtctt catagctcgt  31920
tttttttgtt ttgttttgtt atacttaatt gatcaaactt ttcttaactt gaaaattata  31980
gacttgtgat attttgttga aaaaaatcaa ttttattctc tctgcttttt tcagaatgaa  32040
tttctttcaa gagaactaat tgaaaaagaa agagatttag aaaggagtag gacagtgata  32100
gccaaatttc agaataaatg taagttacaa ttatctttta cttttctgtt cttatttttc  32160
ctatacttaa aatcatgggc ctaaaagggc gttaacacat tctctgtttt ctaatctgct  32220
ttactcctaa ttacctctgt actgtatata cttcagtctg tcactatcca gttgatttgc  32280
cttgctgttt tcattgtgag agaatgttac taatatgaat tttttgtgag aatatataac  32340
tcctttttct tgtgtgttct tcaatcaaaa tgaagttaga acaccaaatt taaaatactt  32400
taatataaag catagtttaa gttaaggcag aagtatgcct tatatacgtg tgtatatgca  32460
cgtgatataa ataggtctgt catttaactc aactattcac gttggattta tagttgaatt  32520
tttttgtatg tttatttaca tttggatttt tccaatgatg tctttggtat atgtgaaata  32580
tttgtcatct gtatagcata gtgtaaattg tgaaaaagat ctgatcatcc aatgagaaaa  32640
ctgtgtaatt acagtaaaag aattagttga agaaaaataag caacttgaag aaggtatgaa  32700
agaaatattg caagcaatta aggaaatgca gaaagatcct gatgttaaag gaggagaaac  32760
atctctaatt atccctagcc ttgaaagact agttaatgta agttattttt ttcatgttaa  32820
tgtttttccc ctatcacttt agagagattt tctgctgtgt acagatctcc atagtttctg  32880
atgagatatt tttagtcatt tgaatcattg tttccctgta tgtaaagtgt agtttttctt  32940
gagctgcttt caatactttt cttctaccaa ttggataatt gttattaatc tgtcttcaag  33000
ttcactgaca ttttcctctt tatctgtgtt cttttggttc aagggtcagc ttgagacctt  33060
gaggagtttt ttacaccgac tttggagctc gtttttgctg actcttttct tattgggatt  33120
ttcctttcac ttatcccatg gctttgggct gtatcctgtg gtttctaga tgagaaagat  33180
gatagatctc tgcaattgca ccctgcccta tgactaaatc tttaaaaatg gcaaagtcaa  33240
tctttgctgg tcctgtcttc cgtatttgag gggttttttc ccaaaatctg cttgcttttg  33300
ttcattttct agaacatcta ggtagttttt tttcattcat tttttattta tgggagtgta  33360
gatctcttag gaacttatgc catcagaagt attatgaaat ggctttattc taaatgttta  33420
aagatttact cattgctaca agaaagattt agccatcact aatattctat atatatttac  33480
catataggga cttgagaatt tcacaggatt cagtatctgt atataaactt gaataatata  33540
cacattttag attgttaata tttaagtata tgtcatttat gttatctgaa catatttagc  33600
gtacattgtc atattatttc ccaaatttgt gcttgatttc aaatgggaaa aaaattctta  33660
ttatttattg aattgttttt ttaaaaaaat catgattaat cagtaattgg atacttttta  33720
aaataacact ataattgtta acagagaatg agagtgatac tggtatgtta aaaacttcct  33780
gaggcaagaa aataatttga ttcccattat atctttctca tactgacttt ccttctctga  33840
ttggtgattt tgttttgcct ctgccacttt gaatgtctaa aatgattctt tatgcttttt  33900
ttatgtgaac atcttttgtc cgtgatgatg cccactactg atactgtgtc ccagatcaaa  33960
cttaattttc caagggcagc tctacttagt gaccaaatga aaacacagtg aatagcccaa  34020
gaaatcctaa cttctattta tgttgacaat ctctggacct tcctgaagcc actgtttgca  34080
tagacttcat ttacttttat ccgggattgt cattgttttt tcagattcat aggccctatc  34140
tgaaattcac aaatcaccta gcaatacttc tctaagaaat cttcagaatc catgacaatt  34200
tagaccagac aatgctggat tatgcacttc agttcacttt ttgttactac aaggtatttt  34260
tcagtgcccc caacagctat cttaactcat tctcatttta ccaaagtcca tgtagacacg  34320
gcactattcc tcaatgagac aactaactag accaccttgt tgtcagtcag agtaccttcc  34380
tctacctact tttatcttcc ttatatcctc tttgagttag tataagttat tactctgcat  34440
gacctgctct aatctccttc aggggaaggc ttttacaaat ctactaccta gagttaaacc  34500
ccagatcacc ttcctgagta ggagattgca tttggttcta ttcattttac cttatttggc  34560
ttctaccttc actttttaag acttactttg cctttaacag ttttttccat acagttcatc  34620
taaagtccaa atatatttat tagatgtgtg cattgtgtgt atatacttag atatgccact  34680
gttggagatt tcgggccagt gatgccactc tgataatatt ttaatatttg acatattatt  34740
tttgcttact cattattctt agataaatatc atgttatgat accttgcctt tatttttatt  34800
```

```
tatgcttcaa ctatgtggag aggaagcact gaaaaattca cttaattgaa tgttgtattg  34860
atcaattgtt caatattgta ttccattcct ttgcgcatgc tttgaatgca ggtgctatat  34920
aatttcagag aaaaatacct cattttgact gtacaaaaac cccatgtagg gagcagagct  34980
cacattgttt tcccctttta gagacaagaa aactaagata cagagaattt aagtcacttg  35040
cccagctgtt aagtgactga ttaaaatttg aaccctggtc atcttattcc cgtctggttg  35100
tttttctagt ctaccagtct attaagatta gctaggtgtt ttttaattgt tttaatgaag  35160
taattactat gcttggtaat gtaaatgaaa gttttataga ttcataaata agaatttgaa  35220
ttggcatact ttattatcat gcttggcaat gaaaatagga aaatgcttaa atgtccattt  35280
tatttaaaga cagactgttt tttactatga ttttactgtt tttctccaca tttctaatat  35340
ataatataaa tttgctaggc tatagaatca aagaatgcag aaggaatctt tgatgcgagt  35400
ctgcatttga aagcccaagt tgatcagctt accggaagaa atgaagaatt aagacaggag  35460
ctcagggaat ctcggaaaga ggctataaat tattcacagc agttggcaaa agctaattta  35520
aaggtgagaa ttttattaaa taaaagaaaa tgctaaacat aagaatgtag atttaatagg  35580
aaatttttaa tttttaaaa agaatgcttt atgagaaaat gcccccttgaa ttaattcttt  35640
caatattaag aaactggatt tctcttataa aattataagt ggaaaataag tgccttataa  35700
gattgaaaag aatacaaaaa ttctaaatct catacctagg catttctaag cagaaactga  35760
agtatggttg aggtaaaatt cctggcaggg cattcacata tctgtcaatt tgtctttctt  35820
tgggtgtaag agttgtgatt ctcattgctg gatttttttt tccagataga ccatcttgaa  35880
aaagaaacta gtcttttacg acaatcagaa ggatcgaatg ttgtttttaa aggaattgac  35940
ttacctgatg ggatagcacc atctagtgcc agtatcatta attctcagaa tgaatattta  36000
atacatttgt tacaggtatt gaaaattttg ttacaggtat tgaaaatttt acatgtgaat  36060
aacaaaaatc attggtagta tgtttcttta tgtttttatt tttattttac tttattttaa  36120
tttttccatc accaaagcat gcagatagta cttttctcaa tatttagtct tcatgtattc  36180
ctgagttctc aaaatagtaa cagtgaaata tattttttat ggattttgat gttagatgga  36240
ttataaataa aagcaattta taccattcat tccattcatc tgcatgagca gcatgttcat  36300
acatcttgtt cgcacacctg tcattcatgt gaaatatatg gttcacaagc agaacaacaa  36360
gcagctatta taaagcagtg ttaagtaaat gagcactttt atttcttgct gggtggaaaa  36420
caaaagaata aagtctgtca aggcttttta gtgtcatgat agaattgttc cccttttttgc  36480
attcacaagt aaaaactact ttttttttga gacagagcct cactctgtca ctcaggctgg  36540
agtgcagttg cgctatcttg gctcactgca acttccacct cctgagttta agtgattctc  36600
atgcctcagc ctcctgagta gctgggacta caggcatgca tccctggcta atttttgtat  36660
ttttttttag tagagatggt gtgtcgtcat attggccagg ctggtctcaa actcctggtc  36720
tcaagtgatt cgcctgcctt ggcctcccaa ggtgctaggg ttacagacgt gagccactgc  36780
acacagccat aagcaaaaac ttctaaacca aattattctt catctttgtc ttccctttac  36840
gcaataaaat gttaatctac caccaaagag gaaagggtac tctactatac tacctgccct  36900
gggtttctca gttttgctgt ctatataatg gtcgttatga atgtcctaat gacagatcct  36960
tttcattatt ttatttgaaa tttgactatc tataacatca catacattat aaatataatt  37020
acaaatatat gttcagaatc aatgaaaata tatttttgat tatatgggcc actatttctc  37080
tctgctaggt gatccattg tgagtatact tgagttataa ttattaagta ctcattttta  37140
ttttggaaat tacagtaatt catctttttc tcaatattgg gatttttatt attattttat  37200
gttgtctaag gacagcctta actacttatt agaatattgc tttgtatgtg atattattat  37260
ttttaaatgt ataattttaa cattattatt tctcttattt acctgaggta taggaacact  37320
atcagcaaat attggtagta tggcattgtc gtatttttttg agataaaatt catgattttt  37380
aatctttgta taagaaatat atcagaagtt tgtagtagat tagagagtac caactgggag  37440
tctgaaaagc tgtccaaagt ggcaaaacag gtacttagac tctcaatcct aaggctgtat  37500
agagctataa acgtggcaag acctttggag tcagacagac ccaaactcaa atgttggatc  37560
catgtatatg gaaagcacct gacaacaagc ctagcatatg tacttggtaa aaatgattgc  37620
caagtgtagt gttaatgagt ttttggatat tgagtaagtt atttaaattt caatttcatc  37680
tttaaaatga aataattgga aaggataatt tgagtgaggg tatgaaatta tgtgttcata  37740
agagagggta tgtggccgag tgactagagg cgagtttata actattctat ctaataaaac  37800
tttgtaatct ggtaatttgt gtgctaaaaa taactttacc tgttgtatag tactcttttt  37860
ttatgcctta aactaaagtg ttcaaaatat catggaaaaa tgatctgtgt tgcttacaga  37920
tttggtgact tttaactttc ctataatgtt gtcagaatat gaatttatac tttcaaattc  37980
agcatttatt ctattgtgtt ttttttgca ttcttatttc taaaccactt ttcaggaact  38040
agaaaataaa gaaaaaaagt taaagaattt agaagattct cttgaagatt acaacagaaa  38100
atttgctgta attcgtcatc aacaaagttt gttgtataaa gaatacctaa ggtataggta  38160
ttagcaaaac tataaatata attgcagtat attcttgtta attgtgaaag taacgtaaga  38220
ataatttatg ttttgttctt cccttcttct tcttcctttg caattgtatt ttttttttact  38280
ctggtaacta ctgttaggaa cttatttatg gagacagtgt agcttaatga ttacattaag  38340
cctgggatta tcctgcctgg gtttgagtca tttaacgttt gctttttgta agagcttgag  38400
caagtcatct tacctatctg tgtctcagtt tccttatctg taagttactt tgtaagtaat  38460
acccttttca taggattatt gtaaaacgta aatgaattat tagatgaaaa tgctcggact  38520
agtgtgtggc acatatgaac agtttgtaaa tgttagctgt tgttagcatc attcatcatc  38580
atcacaatca tcattgttca tatatgttta tagggaacta acatatttct ccttatttct  38640
gtcatctcat ctaaatcaat agaatgattt ccttaatagg aattagaata cctaatcaaa  38700
ggtgatttaa acactaagaa taattattat ctgacctaac cagaaccaca aagctagttg  38760
tagggcaggt catatttgaa ggttgttgtt atcgcctatg atggttgtaa aatagctgca  38820
tgaattcaag aaagatgatg tgcccattga agaagaggag cattttttttc tacatagctt  38880
ttatttttaa ataaacattt ttttctggtg atacctggca gacattgact ccgatctcat  38940
ttgctagaat tggatcacat gtccaagtct gaaccattca gttgcaaaga gaatgatacc  39000
gctatactgg gtttatgcca agaacattac acatgtttgt ggaatgctca tgtgtagaca  39060
acagtgtctt acacaacttc aaaaaaataa tttatatata aatatgtttt aaattacttt  39120
ttaaattcac aagaatttat ggtatacaac atggtgttct atatatgtat atactatgct  39180
atacaacatg gtgttctata tatgtatata ctatgctata caacatggtg ttctatatat  39240
gtatatactg tggaatggct aaatcaagct acttaacata tgtattacct cgcatacttt  39300
ttttttttt tccttgagac agagtcttgc tctgtcaccc aggctggagt gcagtggcgc  39360
tatcttggct cactgcaacc tctgcctcct gggtccaagt tattttcttg cctcagcctc  39420
ccaagtagct gagattacag gcatgtgcca ccacgcctgg ctaattttttg tatttttggt  39480
aaagacggag ttttgccata ttgtccacgc tagtctcaaa attcctagcc tcaagcaatc  39540
```

```
tgcccacctt ggcctcccaa agtgctggga ttacagcata cttcttctta ttttttttt  39600
tttttgcact aagaacactt aaaatttact ctcttagcaa ttttaaagta tataatatac  39660
tgttattaac tttggtcact attttaatta gacttaagat gtgtttgtat tcaaattatt  39720
ttgtaagcat ttaacaccca aatttgagag tggggtcaga atgttggaat ttgatttcta  39780
gaattagtat agggtattat tttcctactt tttttctgtg ttcaataaaa tgtttataag  39840
attcagcttc aattatatta taacccattt agtggtgaat cagggaagaa tgaaaataat  39900
ttgataactt tgttgccttg catttattta aaaaattttt aattctaggc taaacccttt  39960
ttaaatgaaa gtttaacttc ttgtgttttc agatactgaa tagctatgat acctcttgtg  40020
ttgagaaaac tttaaatttg cataatctga agttatcttt tcttataaac attttattag  40080
gtttacagta ttgtcttttt gttttgtttt gtttttagtg aaaaggagac ctggaaaaca  40140
gaatctaaaa caataaaaga ggaaaagaga aaacttgagg atcaagtcca acaagatgct  40200
ataaaagtaa aagaatataa tgtaagtaaa acatttttaa cattagtatg caatattgta  40260
caaagtagga tagctagatt caacaagtaa tatggatgtg tctttgtgca gaatttgctc  40320
aatgctcttc agatggattc ggatgaaatg aaaaaaatac ttgcagaaaa tagtaggaaa  40380
attactgttt tgcaagtgaa tgaaaaatca cttataaggc aatatacaac cttagtagaa  40440
ttggagcgac aacttagaaa agaaaatgag aagcaaaaga atgaattgtt gtcaatggag  40500
gctgaagttt gtgaaaaaat tgggtgtttg caaagattta aggtacatct gattcttatt  40560
ttgctttttc tgactatgaa aaatttcaaa tatgcagaag ataggatggt atcaataatg  40620
ctcatcacct gaattaatag ttaacattta ttaacatttt gtcataattg cttcttctga  40680
tttttgtggg atgtttgaat tgcagacatt cctcccctaa atatttaatg taccctttttg  40740
aaaaaggctt ttttctttaa ctaaccatag taactttatt atacctaaca aaatgacagt  40800
aattttctaa tatcgcctaa taccctgatt atagtcacat tttttacatt ttttgatcaa  40860
agaataagca tttggatgtt acatctcata aatcttttta atatagaatc cccttggttt  40920
tctttttctc caaaaaatgt ttgaagatgt atctaacttt tgtgtgtgtg tcattttact  40980
tgttcctgtg tcccttgtat tactaaaagt taggtcagaa ccctaagtta cattcaggtt  41040
taaacatttt tggcaagaat acttcataag tagtgttcta tactttatat tgcatcactt  41100
caagagtatc tggttgttcc atgttttgta attgattact ctgttaagga aaagacaagc  41160
agaccaagta tggtggctca tgcctataat tccaacattt tggaaggccc aggcaggaaa  41220
atttcctgag cccagaccag cctaggcaat atagtgagac tccgtctcta caaaaaatgt  41280
ttttttttt gtttgtttgt ttttaattag cttggtgtag tggcacatgc ttgtaatccc  41340
agctacctgg gacattgagg tgggaggatc gcttgagccc aggaagttgg gggctgcagt  41400
gagctgtgat catgtgccac tgatctccag cctatgtgcc tgtataacag agcgagtctc  41460
tctcttaaaa gaaaaaaaga agaagaagaa gaagaaaaga taaccatata cctccattat  41520
taagcaattt agctaactgg tgatattttg gtaccataca aataacaaat tatttgtcag  41580
tcctaatgat tttagcatct gctgatgatt gttgcctaac ccaattatta aaagttgcaa  41640
acatcataat tttctagtta tattatgcac ttacatttat taacagacat gcttttgtaa  41700
aataaatagc gtttcctcat tagcccaggc tatttgttta tcttgaagtt tagctcctac  41760
tacaaaggca agataaatgc ttttctcttt aattaccagt tttcagaata cacacttggt  41820
gtactctgca ctacctgctt tttttgtccc ctccgctttc tctttttaa gtatcagatt  41880
agactcacag atttttaaat attccatgtg ttttagttgg agtcatattc ttttgtctca  41940
actttagcca aagagagtcc tttaaagttg actcttatat tgtcttgaca aaaattcatt  42000
agtcttttga acgaagcctc aaagcttgac ttgttttcta gcataagatg tcttagactt  42060
acctacatac ttcatgccca tacttggaat aaaccatttc tttaaagagc ccaggttcct  42120
tttagtgggg aaggcattta gataccaaaa actggccact gggcatcatt gctctcagag  42180
tatcattgcc actagtctct cagtagacaa gttagaaaaa tatgtatata tttaaaccat  42240
gagttcatat tgttatttcc agtttaatta taacattatg gggtaagtaa atagtatcgg  42300
atttttacta agcttctttg attttgcact tgtatttttt tcttacatag aaaaccttta  42360
ttattaacat taaaatattt gttttatcct acaatataca tacaataatt tgaaaaataa  42420
tacttgaatt gatattaata gtaacaacaa cagcactgct gccaaacata gtttaaagtt  42480
ttatttcagg tcttattttc ttcagaatat atcttgctga gaatgtatag gcaaagtatt  42540
ctacacttac ttgaaataat tgtcttcatg cggttatgtt atacatttga tatatagtta  42600
ggctcatttg tttttcattt tttttatttt agggattttt ttcctttatt gaattttaat  42660
atatacaata tttatatatg caaaatattt aatcagagaa atcttaattc tggtcttacg  42720
cctttcatat tattctgctc caccctctgt aggtaactta ttatctttct catgtttcct  42780
ttttggaaac ataaacaaag acaagacagg ttacatgaca tgtataccct tctgcaccta  42840
gttttatacc ttaccttgta gtttattttt aagcatgtaa atgttcaatg ttcatgacta  42900
aatttggaca ggatcatagg aacacagaat tcaaagtgaa attaaaatgg gcttgggttc  42960
tttactttcc actttaaagg ttgtaatggg tgatgtcagg ctaataaacc tattttcagc  43020
ttgatctaaa gcttaatact gagcatcaag aaattcttta ataaatataa gtgatattta  43080
ttcagacatg taataaggaa atgttcatgt cttatttttg tgttagattt ttttagaatc  43140
tacttttgtt agagttttat aaatacagtt agtgtttgag atagaaagag aaaagaatta  43200
gttttcttcc tcttctacct gctcatgaac ttgatttttt tctcccaaca attgaagagc  43260
caagaaaaag ggagattctt aagagatggg aaatagaatc tcatctaccc ctgtttcccc  43320
cagaacagtg aaactgaatc ttaagggtaa gatagaatag tgtgtactta acttagatgg  43380
agaagaaagg ctgccaaaat gagatctgaa gcgctattac aaatatttcc atcgttactg  43440
tacttcagaa tgaattacaa ccgtaagttt ttttacttcc tcattcataa atttgattat  43500
tccttatacc acttctcagc tttcatcatt ctttattgta cttttctatg taatgtttgc  43560
ctattataca gcaacttaag agaactgtaa gtttggacat ttcattttgg tgttgataat  43620
agaatatctt tgaatagttc tatagttgat gagtagaacc atgaaccaag taacttaaag  43680
tccttgatgt tatttattac agagaactat aatagaagct ctcccgctaa tgtttccatc  43740
atgtgtacaa aaagtttctt tgttattaaa gctagtccgt ttaacttaca ataagcataa  43800
atagctaagc tgtgaaagtt acctgtgata atgctaattt tcccatttat taaaaggcaa  43860
gttgttttcc gatcataaga aatttagaaa agccatccaa agataaattc cgagtgatat  43920
attcctgctg tttgttatgt tttctcaaat taattgagtt ttattttaca atgacaggag  43980
ttattaaagt attttatttt tattatgatt aagattttca aagtaacatt tcttatatga  44040
aagaaattat gttaatgcat gtttttctta catgggaaat catatatttt aaaaatgatt  44100
ttaaaattcg ttttacttta agttgtatta tctttctcaa aagtggctag tgcttgacca  44160
gaaaaaaaga caccagcata actcagtgta tctttattta cataggaaat ggccatttc  44220
aagattgcag ctctccaaaa agttgtagat aatagtgttt ctttgtctga actagaactg  44280
```

gctaataaac agtacaatga actgactgct aagtacaggg acatcttgca aaaagataat 44340
atgcttgttc aaagaacaag taacttggaa cacctggagg taagtttgtg tgattcttga 44400
accttgtgaa attagccatt tttcttcaat atttttgtgt ttggggggat ttggcagatt 44460
ttaattaaag tttgcctgca tttatataaa tttaacagag atataattat ccatattatt 44520
cattcagttt agttataaat attttgttcc cacataacac acacacacac acacaatata 44580
ttatctattt atagtggctg aatgacttct gaatgattat ctagatcatt ctccttaggt 44640
cacttgcatg atttagctga atcaaacctc ttttaaccag acatctaaga gaaaaaggag 44700
catgaaacag gtagaatatt gtaatcaaag gagggaagca ctcattaagt gcccatccct 44760
ttctcttacc cctgtaccca gaacaaacta ttctcccatg gtccctggct tttgttcctt 44820
ggaatggatg tagccaacag tagctgaaat attaagggct cttcctggac catggatgca 44880
ctctgtaaat tctcatcatt ttttattgta gaataaatgt agaattttaa tgtagaataa 44940
atttatttaa tgtagaataa aaaataaaaa aactagagta gaatatcata agttacaatc 45000
tgtgaatatg gaccagaccc tttgtagtta tcttacagcc acttgaactc tataccttt 45060
actgaggaca gaacaagctc ctgatttgtt catcttcctc atcagaaata gaggcttatg 45120
gattttggat tattcttatc taagatcctt tcacaggagt agaataagat ctaattctat 45180
tagctcaaaa gcttttgctg gctcatagag acacattcag taaatgaaaa cgttgttctg 45240
agtagctttc aggattccta ctaaattatg agtcatgttt atcaatatta tttagaagta 45300
atcataatca gtttgctttc tgctgctttt gccaaagaga ggtgattatg ttacttttta 45360
tagaaaatta tgcctattta gtgtggtgat aatttatttt tttccattct ccatgtcctc 45420
tgtcctatcc tctccagcat tagaaagtcc taggcaagag acatcttgtg gataatgtat 45480
caatgagtga tgtttaacgt tatcattttc ccaaagagta tttttcatct ttcctaaaga 45540
tttttttttt tttttttga gatggagttt cattctgtca cccaggctga gtgcagtggc 45600
acgatctcgg cttaacgctt actgcatcct ctgcctccca gattcaagca gttctcctgc 45660
ctcagcctct gagtagctgg gattacaggt gtgcaccacc acaccagcta attttttttt 45720
tttttttttt ttttttgagg cagagtctcg ctctgtcacc caggctggag tgcagtggcg 45780
ccatcttggc tcactgcaag ctccacctcc cgggttcagg ccgttctcct gcctcagcct 45840
cctgagtagc tggtaccaca ggcacccacc atcatgcccg gctaattttt tgtattttta 45900
gtagagatgg ggtttcacct tgttagccag gatggtgtcg atctcctgaa ctcgtgatcc 45960
acccgcctcg gcctcctaaa gtgctgggat tacagatgtg agccaccgca cctggcccca 46020
gttgtaattg tgaatatctc atacctatcc ctattggcag tgtcttagtt ttatttttta 46080
ttatctttat tgtggcagcc attattcctg tctctatctc cagtcttaca tcctccttac 46140
tgccacaaga atgatcattc taaacatgaa tcctaccctg tgactcccat gtgactcccc 46200
gccttaaaaa ctgtcaaaag ctaccggtta cctgaagggt aaaagtcaag tcccctactt 46260
acctcatgtc atctagagca agagatgaac tagctgagtt ttctgaccac agtgttcttt 46320
cttatgtatg ttcttttgta cgtgctcttt tctatatata gggaaccatt tctctcttcc 46380
agttgttttg ctcagtgaat ttctattcct gtttcaaaac ttgttcaggc attacctttt 46440
ttttcttaag catacttttt ttaatggaac aaagtcactc ctgtctacac tagttctgca 46500
tcttatacat aggttttgta catagtacat atttatatca catcaaatta tatgtgttta 46560
catatctgtc ttccttaatg gaatataagt cttttgatat aaggaactat ttaatttgtt 46620
tctgtgtgtt gagtatctcc tgtttggcac agagttcaag ctaatacatg agagtgatta 46680
gtggtggaga gccacagtgc atgtggtgtc aaatatggtg cttaggaaat tattgttgct 46740
ttttgagagg taaaggttca tgagactaga ggtcacgaaa atcagatttc atgtgtgaag 46800
aatggaatag ataataagga aatacaaaaa ctggatgggt aataaagcaa aagaaaaact 46860
tgaaatttga tagtagaaga aaaaagaaat agatgtagat tgaggtagaa tcaagaagag 46920
gattcttttt ttgttgtttt tttttttgaa acagagtctc actgtgttgc ccaggctgga 46980
gtgcagtgga gtgatcttgg cttactgcaa cctctgcctc ccaggttcaa gcgattcttc 47040
tgcttcagtc tcccgagtag ctggaattac aggtgcccac cagcacggcc ggctaattta 47100
gtagagacag ggttttgcca tgttggccgg gctggtctca aactttggat ctcaggtaat 47160
ccgccagcct caacttccca aagtgctggg attacaggca tgagccactg tgcccagcct 47220
gttttttttt ttttaaagga gaccagtgaa gtttcaggag gagggaaaga aaatttagag 47280
ttactaggga gagagtgatg aagataagag atgaaagtgg taataaggga aatagcaaaa 47340
tatcagggta ggtgggagaa aaagagattt gtaacaaaca ataggattat cctgtgaaaa 47400
aggatgaaag gaagaaaaaa atggatagaa agatatttaa aacaccctca gcctcctgtt 47460
ttccctcctg tgtattcata gtatataaaa ctataattat gtactttact taaaaaatat 47520
attattatta ccttatcgtg cttatttaat catagcatgt cctcttttta gtctcattac 47580
cctgtttgta ttattcttca taacacttaa tacctgacat tgtattatat attggcttat 47640
tttccaggta ctccactcaa atataagttc taggatataa tttatttatc actgaaatcc 47700
attgcttaga gtacctggca tgtagtaaat aggcattctg tttttttcaaa taaaaaataa 47760
aggaacttaa gatatatatt tatgttatat cgccagcctt tttcctcaca gctctattct 47820
gttgtacaga attacctact ttacaattcc tgtgtttcaa ggggatctca aatttaacgt 47880
gtccacaatg aactcctgat ttctgtttct ctcctagtca ttcttatttc aatatatgtt 47940
cagttaccta accagctagt caaggcagat actttagagt tattctgtag tcattctttt 48000
tccctaccat ttttgttttc caaatgtaat ttatgtgtgt cttcttcatc ctcgcagctc 48060
taacccttgt ccaaaccagc atcatcactc atctggagtt ccacaatgtc tttctggcta 48120
gtttccctga tttctctatt gaccccttta ttctccacag tgcagccaga atgattgttt 48180
aaaacttcct ccttaaaatc tttaaattgt tttcttttat acgttaagtt aaattccagt 48240
tccttgtctt ggcatgccat gccctgcctg gtgtggcccc tgatggtctc tccaacttca 48300
tgttttacta ctattgactc ttatttttgc ttactctgct tgggtgctcc agtcctccaa 48360
atcatttcct gctccaatca tttcaatcat tttttcctct cagatcttat agtattccaa 48420
atgctttctt cctttggagc atctgggttt actaataaat acttcgtacc tcacagttca 48480
gcttaaatat caattatttg gtggttaaga catccttcaa ccgctctatc taaatgttcc 48540
tttctattat tcactggctc agtactctgt ttttattttc tttctaaatg tcaacttttt 48600
ttttttgag tcagggtctc actgttgccc aggctcgagt gcagttgcac aatcatagct 48660
cattgcagcc ttgccctcct gggatcaagt aattctccca cctcagcctc caaaatagct 48720
gggattacag gtatgcatca ccatgctcag ctaatttttt gtgttttttt gtagagatga 48780
ggtctcactt tgttgcccag gctggtctca aactcctgga ctcaagtgat tctcccacct 48840
cagcctccca aagtgctggg gttacaggtg tgagccactg cacctggtcg atactgactt 48900
tttttttttt ttgagatgga gttttgctct gttgcccagg ctagagcgca gtggtgtgat 48960
ctcagctcac tgcaacctcc acctcccagg ttaaagggat tcttctgcct cagtctcctg 49020

```
agtagctggg attacaggca agtgccatca tgactggcta atttttgtat ttttagcact  49080
atgtttagta ctgtgttggc caggcttgtc tcgaactcct gacctcaagt gatccaccca  49140
cctcagcctc ccaaagtgct gggattacag gtgtgagcca ccgtaatcgg ccaacattga  49200
catttttagt agactttttg tttgtttact tgcttattat ctgctgcctt ccacactctg  49260
gcgaaatcct gccacccacc cacacacaca taggcactga atgggcagaa ctctgaaggc  49320
cagaatttta tatttctttt cactgtaaac atcatcatct gtcactgatg gcacactagg  49380
atgctcagca actgtgtgca tgaaggaagt aagcactagt ttgtgaaggc tgcaaaactc  49440
ttgagtattc taagagtttt ggccaaaatg aatgtacagc tttagtggca gaagctaata  49500
ctcagaaatt gaggccgtat attggataac acaggatttg gatgattatt ttaaaataat  49560
attttacatt gtatatatgt gtgtgtgtgt gtgtgtgtgt gtgtgtatgt gtgtgtgtgt  49620
gtatatatat atgtatgtat gtgtattagt ccgttctcat gctgctatga agaaatacct  49680
gagactgggt aatttataaa ggaaagaggt ttaattgact cacagttcca cagagctggg  49740
gaggcctcag aaaacttaac agttatggca gaaggggaag caaacacatt tttcttcaca  49800
tggtggccgg aattagaaga atgtgagccg agcaaagggg aaagcccctt ataaaaccat  49860
cagacatcgt gagaacttac tattatgaga atagcgtggg ggaaaccacc cccacgattc  49920
aattacctcc caccaaatcc ctcccatgac atatgaggat tatgggaact atgattcaag  49980
atgagatttg ggtagggaca cagccaaacc atatcagtat gtatatgtat acaagtatta  50040
tatatatatg tatgtgtttg tatgcataca tgtattatat atggaggaaa ttctaatttt  50100
gtaaaaaact ggattgtgag ttttaaggag atgttatata aagttaagac aatgtcattt  50160
tgtggtattg gtctgaatta caatgtagtt tcttagtgat atttttcctt tattcagtgt  50220
gaaaacatct ccttaaaaga acaagtggag tctataaata aagaactgga gattaccaag  50280
gaaaaacttc acactattga acaagcctgg gaacaggaaa ctaaattagg taagttttat  50340
gactctgata atataaaatg attaacatct aataatgaat atttcttatt taaagttcct  50400
tttttatgct agattaaaag gaagtatttt gactaaaaaa agaaagaact ttctgcctaa  50460
taatttaact taggcagatg aataatcctg tacttaaccc caccaaagtt tagttttcag  50520
tccttaagtt agatttgttt ctaatgaaat catatatgtt aaaaatttat gactaagtat  50580
tagctacttt gaaccgttta acaattaaaa ctgatgatat tttattaatg gtattatgag  50640
ttctttcact gagtgcaagt tatattagtt atatatcact tgatattttt aaattaaaag  50700
ataccaggaa acagcaaaga aaatgtgaaa agaagttgta tttctcatag ttttactact  50760
atattactgt atatttttgc tcctatatgc ttacatattt tatatatttt aaattattat  50820
aaacatggtt ttatactgta tttagatagt aatatcaaaa atatttttat ggccggcgca  50880
gtggctcaca cctgtaattc cagcacttgg gaggctgagg agagcagatc ccctggggtc  50940
aggagttcga gaccagcctg gccaacatgg caaaacccca tctctactaa aagtacaaaa  51000
attagccagg cgtggtggca gttgcctgta attccatcta ctcaggaggc tgaggcagga  51060
gaattgcttg aacctaggag tcagaggttg cagtgagcca agatcatacc acagcactcc  51120
agcctaggcg ataagagtga gactccgtct caaaaaaaaa aaaaaatttg ttttattcat  51180
catacttata aatacttata caatagccta atgtgtttga gtgattaaat cactagcttt  51240
ttatattttt gctattgctt atagtgccac agtgaacatt ttcatgtata tctaacagag  51300
atattactgt ctcagaaggt attgaaatct ttgttgctct cattagagtt ttccatatta  51360
atttttcaaa cagttatata gtttataaga ttttcataat tttatctcat atattgtgct  51420
tcataatttt caaataaatt tgctgctttc gataatgtat tttcatgtat ttgtttccta  51480
gacgttagag ctattcaagg tttttattac taaatagagc tgttctctta aattggtaat  51540
gagatacttg gtttagagaa gcctaacact gggaaatctt acataagcta cttttagaaa  51600
tgtaattttt agctcaataa gagattaaat atgaattgac ttttgtgtag tatttgcatg  51660
gaagaaggta ccatttaaat gaagacatga gagtattacg tacaatttta gtaggttctt  51720
tttattttat catctttatt tttaataaat gctgaattcc ctacagaaat tctttaattt  51780
ttacatatct tgatctcttt catatatgga tttatatcac cgaagtttta agagtgtttc  51840
cctattccct gttgccctta tatctttgtt taaaaatgtc acatcattag ctttttttca  51900
tctaggaatt tgttagtgtt gggctgttgt gctctaccct ctctttaaga aaactccaaa  51960
cccaaaaaca tacaagatgg ctagtctgct tcagcctttg tgatgtgctt ttctcttcta  52020
atcagagttt agcacaatac agaatggaga aggactcctt tatatattgg tatttattgc  52080
agtatttttc tacatggtgc ctaaggttac ttgaatgagt ctttattcca taatgaactg  52140
atttactaat gcttttagca cctgttagtg atccattatt gttagttact tgattactgc  52200
ttgccacagc tattctaaaa taatacattt taaagataaa tacagaacat aatgaagtac  52260
tttttaaaac tgagatagag accaattttt ttttcaggaa atgtatatta ctttgagaaa  52320
actcagttat aaaacttgaa cttatgaagc tggaaaaaca ggagggggca ttattggtat  52380
tgtaaaaggc tgtttacaaa gtgagttgct gcttagttcc tttaagtaat tggctaccct  52440
aaacacatca gttttaagtt gctgaaaagc aaaacactct accaaatttt gttttttttc  52500
tagaccatgt ttacaaagca aaagtatgtt ttcttccccc cccctcaaaa aatgactaat  52560
gacactccta tgcgatgcct ttttatggta aattgaggct tttagttctc tttccattta  52620
gccacagact tttgtgtcca aagacaagct gcgtaactgc atatataagg ttaaggcata  52680
actactaata aaagaatgta aaatatttga tattaggtct gtacaaagac caaataatac  52740
tcatgattag acaagattat atttggtaga atctatccat catatggctt cagattttac  52800
ttttcagctt ggctttgtga gactttaaaa atcaagtcat tgcacttata ttcacaaagt  52860
cacattgctt tactgcattg cttctcatac agtttatctc ctttcagtaa aatgtttact  52920
tgccattttt aaaatttctt atatgtgaca cttctacact aagtccttta tgttgttagt  52980
tccacaattc tgtgaggaat aggttttttt ttttaatcat ttgattgatg aagaacatta  53040
agttccacag agattaaatg gtacaggcat cacacaggca ggaagtaaca gagctaagat  53100
tagagtccag gtctgatgga attcagaaag ctaatgtgct ttccatggaa ctataatgct  53160
ttctaatata cagcatctaa aatatctgag gtaattttaa tataaacagc atgagattga  53220
cttaaatatt attgcatgta ggtaatgaat ctagcatgga taaggcaaag aaatcaataa  53280
ccaacagtga cattgtttcc atttcaaaaa aaataactat gctggaaatg aaggaattaa  53340
atgaaaggca gcgggctgaa cattgtcaaa aaatgtatga acacttacgg acttcgttaa  53400
agcaaatgga ggaacgtaat tttgaattgg aaaccaaatt tgctgaggtt tgatattata  53460
agttttatca tacaattata gaataaagaa ttagttttgg tagacattgt attattgtta  53520
agtggtttgt ctggatctct gaaatatctt attaatatag tgcctatgtt ttgtgtaata  53580
aataaataaa agatttaaat ctgaattgtt taaaaggaaa gcagatattt ctgtaagttt  53640
ttctcaccaa tgttatatta ttagatttaa tttatgaaat gttatttact aaacaatgga  53700
attgcctttc accaccatcc cttcatttaa caaatattta ttcattgcct attacatgtc  53760
```

```
agaccctgtg ttgggactgg cagtatagca agaaacaaaa tagacaataa tctctacttt  53820
cagggacttt acattctaat tggtggtttt atatattttt gatgtggtca gaatcattaa  53880
actgtgtggc agtaaatata gtttgcaagt atttaacaat ttatgattaa acacaactct  53940
tacagtgttt gcttaccttg agatttaata tattttcaaa gcatttatat catttttgtt  54000
ttaactatgt cactaaatct atatgagtaa gattttatta actcatttgg atttatttat  54060
agatgataca attgaagtaa aatataatga gcagattgca ttctaagcaa agtaagaata  54120
ttgcaagttc agatattatt agataatgag ttgcctaata aaaatgactt ttggtggatt  54180
ggaatataac cagagtttcc atagtttgtt tctgattctt tcatattttt taccctcctt  54240
cagtctgttc ttaacacttc acacttaata taatatgtga actaaggcca agtaaagagg  54300
attgcagtac tttaaaagct aaattacaaa gaaaacctca ccaaaaattg atgtatctga  54360
acattttttg ttacatttcc ttagcttacc aaaatcaatt tggatgcaca gaaggtggaa  54420
cagatgttaa gagatgaatt agctgatagt gtgagcaagg cagtaagtga tgctgatagg  54480
caacggattc tagaattaga gaagaatgaa atggaactaa aagttgaagt gtcaaagtaa  54540
gtgcatataa gcattttagc catttgacta gatgtatctt ctttaatttg tctttaagaa  54600
acccaattac aggtatacaa ttcttagtag taattgatac tgatttcttt ttataagaac  54660
aggattaagt aatattaaga tcggttttaa cagggttaaa taataatatt gacgagaata  54720
atattgttaa agaggaagtg acctctcaag atttgcattt tttagagttc aggaatatta  54780
ttgcagaaag gtccagttcc tccacatatt gattttttgg ggaaggggtg atggaggagg  54840
aatggttgtt tattgtattt aaacttaagt ttcttcattt taataaggga gtaatagtac  54900
ctcttctacc tgtttcataa ggttgctgta agaatataat aaaaaattca gattttgatt  54960
tagtttacat ttatcgggca tctactatgt actagtcacg gtgcaaggta ttaaacatat  55020
attgacttgt acaattatac ttaaccttga ggttatattt ttgttttcat tttacatgaa  55080
gaaatatgcc cagctagttt agaacacaaa atatatataa ggagtaaata ctgcgtgctg  55140
gctgggcgtg gtgacatgtg cctgtagccc cagctactcg ggaggcagag gcaggagaat  55200
cgcttgatcc cgggaggtgg aggttgcagt gagccgagat cgcgccactg cactcctgcc  55260
tggtgacaga gcgagactct gtcaaacaaa caaacaaaca aagaaaaaca aaacaaaaaa  55320
accgtgtgcc agctatatgc tgtattttca ttctcttttg taattaggtg atatttcagt  55380
agaaaagtat aaggagcact tagttaatct gtcaagcata aatagtaaaa atattttatg  55440
gcctactcat aaaaatataa ccattccttt ggagccttga tagttctctt gggaatatca  55500
gtttttgaca tctttttcac tatgaaagac cctttttttt aaaaaaattg atcctttctt  55560
ctcatggacc tcttttgata taaactaact tataatagtt cattttaatc atattttgtt  55620
aatcatgcaa ctggcaatga gagcctctca tcagtatgag gaaacctgcc ttatctataa  55680
tactgaacta aaattattct aacccaaagc aaagaaactt tacattttgc tttgcctgta  55740
ttagcttatc acagtattca tgagggaatt tgaaggactt attaccatta ggctatctct  55800
tttttttttt ttttgtaatt ttattaaatg catgttttgt ttcttttcac attactgata  55860
acttgtagat taaaacaaat caaaacatgc attaatccat ctaaggatcc tagaaatttt  55920
acatttctgt gttcttaact gtgtgatggt cttagataaa tgtactaaat accttatcct  55980
agcatattcc aaattatgac aataaatgtt ttatggaaaa aagtatggga acagaagttc  56040
tttggctata tacatttgga aaatactata tagtaagtat gatttgagat aattatatat  56100
gatagaacct ctgggagcac tgaatatatg ttaggaatat tcaagaggga ggagggatgt  56160
tgagaatgaa gtttttttta tatagcaaac atgataacct ctgatggaat tatgtttcat  56220
gaaacagttt aggaaatcct gttttaatat ttcatacaaa gaagagatag atgctgaaaa  56280
cgaatggctt tttgaaaaag ggtctagaaa ttttgaattt tggcatttac ttagaaagtg  56340
tacttaattg ttcctgaaat accttatcat ttcctagact gagagagatt tctgatattg  56400
ccagaagaca agttgaaatt ttgaatgcac aacaacaatc tagggacaag gaagtagagt  56460
ccctcagaat gcaactgcta gactatcagg tatgtgcagt attggctctt ctacatagaa  56520
tccacttttt tccctaaatt tacattagat gttgggagtg ggatatgtta tactttttgt  56580
ttgtttcgag atagggtctc attctgttgc ccagggtgga gtgcagtggt acattcaagg  56640
ctcattgcag ccttcaccac ctgggttcag gtgatcctcc cacctcagcc tcttagacag  56700
ctgggactac aggcacgtgc caccacacct aattttttg cattttttgt agagacaggg  56760
tttcaccatg ttgcctaggc tggtcccaaa ctcctgggtt aaaatgatct gcccaccttg  56820
acttcccaga atgctgggat tacaggtatg agccaccatg ctgggccatt gttacatttt  56880
taatcaaaag atataccaac cagaggctgt tattcttgtt agttggaacc tgattagaaa  56940
gctctttaat ttgaaatatt gttcagtaat ccagtacagc atttaaatgc ctatagatga  57000
attatgctgc tgatcaaaat taggacactg agaattgtag ttagtaaatc tttaataaca  57060
atattttctc ttgtatttat atgtaacttt ttacatattc ttacgttata tatgttggga  57120
attataaaaa catacacatt gtcctgatca gtattatgtt acttgcaatg gaggttaaaa  57180
aaaaactgta acagtcaggc atggtggctc acgcctgtaa tcccagcact ctgggaggcc  57240
gaggcaggcg gatcacgagg tcaggagttc gagaccagcc tgaccaatat ggtgaaaccc  57300
cgtccctact aaaaatacaa aagttagcca ggcgtggtgg catgtgcctg taatcccagc  57360
tacccaggag gctgaggcag gagaattgct tgaacccggg aggtggaggt tgcagtgagc  57420
caaaatcacg ccattgcact ccagcttggg tgacagagtg aaactctgtc tcaaaaaaaa  57480
aaaaaaaaaa caccagtaac atacccactg ttattcagtt acatttggat tttaagtttg  57540
tttgattcta ggttttttct tttacagttc tttggtaatt atttgtatta aagcaaagtt  57600
acatttttgt agatctcatg tgccactgtg ttaaaacttt gcttagtaaa ttgtgaattt  57660
taaatctgtg ataactttca ctggaaaaat ttgaaactta ctacaaatat atattttttt  57720
taatatcagg cacagtctga tgaaaagtcg ctcattgcca agttgcacca acataatgtc  57780
tctcttcaac tgagtgaggc tactgctctt ggtaagttgg agtcaattac atctaaactg  57840
cagaagatgg aggcctacaa cttgcgctta gagcagaaac ttgatgaaaa agaacaggct  57900
ctctattatg ctcgtttgga gggaagaaac agagcaaaac atctgcgcca aacaattcag  57960
tctctacgac gacagtttag tggagcttta cccttggcac aacaggaaaa gttctccaaa  58020
acaatgattc aactacaaaa tgacaaactt aagataatgc aagaaatgaa aaattctcaa  58080
caagaacata gaaatatgga gaacaaaaca ttggagatgg aattaaaatt aaagggcctg  58140
gaagagttaa taagcacttt aaaggatacc aaaggagccc aaaaggtaaa catttaaact  58200
tgattttttt ttttaagaga cagtatcttg atctgtttcc caggctggag ttcagtggtg  58260
caaacatagc tggaactcct gggctcaagg gactctctag cctcagcctc ctgagtagtt  58320
gtagctggca gtacaggtgc acaccaccat acctacctaa tttttaaaa tttttaaatt  58380
tttttgtaga gacaaggtct cactttgtca cccaggctgg ccttgaactc ctggcttcaa  58440
gtaatcctcc tgctttggtc tctcaaaagt gctgagatta caggcatgag ccactgtgcc  58500
```

```
cagccaattt taaattcatt atcttcaaaa gagttacatg ataatttctt aatatatgcc  58560
tatatgaaaa atgcttaaga tacaaattcc aattatgatt cattaattta gattttataa  58620
cttagcagtg ttggctattt gaatgtctat tatacgtaaa aataaaatta ggcttttcta  58680
accaaagatt ttagtgggaa tgttcagatt gtataatagc aaagaatttt aattactata  58740
ggaaaattta tattaattaa acactaatta ttatatttaa acattgtagt agttatcagt  58800
tgatttctac tgttcataat tatctttgat ctacaagtag tgggcccaca tttactttta  58860
atatggttta atcttcattt agaaagaatt aaatgaaaaa taattatctt gcaactacat  58920
cctgttctct aggctagaaa catttaggat ttctgttttt gaaagtaata ccaaagttcc  58980
aatgacctgc ttatagtcag tgttcaataa acgtataaca aatgaaagtg aatattagtg  59040
atgtccattc caacataatt tgaagatttt tattgtaaaa tcccacatat ttgtagaaaa  59100
gtctatggaa atcctaaata agattttgtc atgtagtttg acaaaagata acattgtgtc  59160
ttattttatt ttagaatggc cattactttc aattaaaatc attatcatca atggaggaat  59220
gttatttgtt aatatagcat ttatatttgt gtatataaat tgtaaatctt aggtaatcaa  59280
ctggcatatg aaaatagaag aacttcgtct tcaagaactt aaactaaatc gggaattagt  59340
caaggataaa gaagaaataa aatatttgaa taacataatt tctgaatatg aacgtacaat  59400
cagcagtctt gaagaagaaa ttgtgcaaca gaacaaggtt ttattttata tttatttcat  59460
ttttttccct aagttttttt tttttttttt tttttttgag atggagtctc actctgtcgc  59520
ccagactgga gtgcagtggc gtgatctcgg ctcactgcaa gctctgcctc ccgggttcat  59580
gccattctcc tgcctcagcc tcccaagtag ctgggactac aggcacccgc caccgtgcct  59640
ggctaatttt ttgtattttt agtagagacg gggtttcacc atattagcca ggatggtctt  59700
gatctcctga cctcatgatc cgcccgcctc ggcctcccaa agtgctggga ttacaggcgt  59760
gagcccctaa gattttaaac aagaatattg cacaaatgac tatgttatcc ttctaattaa  59820
gtgcaccttc cattactaat tgattatata ataatttgtt ttttattttc taaactattc  59880
taaaaattca tatttattta gcttttataa cagtagtctt aatcttaaaa acggcaatac  59940
ataagcaacc tcatttggta agttaatttt tattttgata ttggttattt gacttttcac  60000
agttccacgt ttctactggc tctcactgat agagtaagaa gtcagcttct tatagaataa  60060
agtatatact tcagagacag atgaaattcg tcaaacatat gactgtctca gagattgttc  60120
cccctgctta aattgttctt accctagata cctttggtat ttacactgtc agtgcctgca  60180
ggtcttagct caaatgtctt accttatcag tgtatccttc accagccacc taatatacaa  60240
cagtaaatcc tactatccag attcctaaat agagattaat taacttaatt tttctccaaa  60300
gtgcttgtaa ccttctgacg tattacatac ttactggttt attattgact gtctttcctt  60360
cgccagaatg caagttccgt ggtgacacgg acttggtttt gtttactgcc atgtttgtat  60420
ttcctagaat gatgcttggc acataaatata tgtcatcaaa tatctttcgt atagctgaac  60480
ggatggatgg atggatggat ggatggatgg atagactgaa atccttactt cacatctgcc  60540
tttgtgatct tacacaagtt acttcacctc tctgagtttg tatttttttc cataaaagga  60600
aaataattac agtttcttca atgtgttgtg aggattagat aagaaaatat atataaaatg  60660
cctgttatgt gcctgatgtc ttcgtgtatg tgtctgacac aaattgtcct ttttttagtt  60720
tcatgaagaa agacaaatgg cctgggatca aagagaagtt gacctggaac gccaactaga  60780
catttttgac cgtcagcaaa atgaaatact aaatgcggca caaaaggtat gaatgattaa  60840
tcttgtttgt tactctgtag catagtctag agtgttaact cacagaaata tttcctgtat  60900
cagatgtaat tttaattgat gttatattgt atatttaaaa tataagaggg gtttaatcta  60960
tgttttatca tacagctgta aaaattaata gttactctca atgctgcaac tgctttttta  61020
aaaaacatac tatttcttaa tagtttgaag aagctacagg atcaatccct gaccctagtt  61080
tgccccttcc aaatcaactt gagatcgctc taaggaaaat taaggagaac attcgaataa  61140
ttctagaaac acgggcaact tgcaaatcac tagaagaggt aattagaaga atttgcattt  61200
tgattagtgt attatttggt atgtttgggg ggctttctaa ataatatttc tttatgaggg  61260
caatgcatag aatgatgaat ctattgctaa tttcactatt tttctattct cctataatgt  61320
ttctaatagc caataatgaa cagcagatat agttaatttg aattcactat ttaattatta  61380
gttggtacct ttcggtacac tgaatatgaa aggaaataaa aagcatttaa ttgtagttct  61440
atgagcaata tattctctta tatgatctct ttattcttac tttttggttt ttattttgaa  61500
gtgcatgtta cataatctat gaatcaattt tcagttcatt gcctttaatg catggttaaa  61560
gggttgaagg taaattagaa attactttct gttttaacct agatcttgaa tttgattagt  61620
aggtgatcaa atctgtcatc ttcattaaat tattcagaaa ataatgtaaa ctgaatgtgt  61680
tttcatttta gttttcatct aaataaactg caaatacatt taaaatatac ataaagaagt  61740
ttttcaagta aaactgtaca tttttaatca tttcaggaaa cgtagatttt cttcagtaat  61800
tttaagattt gtcatttatg tgaattgcca ttgaattact taatttaaaa tactcacctt  61860
aatcctcttg aagagtaaaa atttttctgt ttttttctct ttgttttaat aagctgcgga  61920
ttttatattc gtaatttatt gagttgggcc tctaaaattc cagttttgta cttaactgac  61980
ttatagatta gtctcctaat gctctgctag tcaatggacc aaaataaaag aaataattta  62040
ttacatattc ttcctaaatc tagtaccacc atacatgtat aattctaaac tgtaatatct  62100
caataaagta ccttaattaa attttatgtt catcataaca atgaagtttc tagcatatgt  62160
aatagtctta taaataagca tgcaaataac tgctgtcaat tagaattagt cagtttaacc  62220
ttattaagta tcaaatggct attgtacata tgatgtgaaa aataaagtga atttttttttg  62280
gctaataact aatctaaaat tcagatgaag cattttaaag ggaaaaagat actttaatga  62340
tttattataa tttaatcatt gcagaaacta aaagagaaag aatctgcttt aaggttagca  62400
gaacaaaata tactgtcaag agacaaagta atcaatgaac tgaggcttcg attgcctgcc  62460
actgcagaaa gagaaaagct catagctgag ctaggcagaa aagagatgga accaaaatct  62520
caccacacat tgaaaattgc tcatcaaacc attgcaaaca tgcaagcaag gttaaatcaa  62580
aaagaagaag tattaaagaa gtatcaacgt cttctagaaa aagccagaga ggtattttat  62640
tatattatga gttatgctgt tatccattag tttttttaag caaatgctaa atattatttt  62700
accctaaagt ggtatttctt ttcttgcttt caaatgattc tatttaagaa ttgttacttg  62760
catgtgattg gattacacct ctgtcagtaa aactggaagt ttgtgtacat gtatctttct  62820
attatacact gactaaacca cgagtagcta tcatggtgaa atcatatgat tttgaaaaat  62880
attttaattg agtttatagg tgaggattga ggcaataggg tggaatgaaa tatatcacac  62940
cggtaatcag tagaaatcag atttgttaga acttcgtggg ggaaagctaa catttaattt  63000
tttctagaag taagttaaaa gatgatagat acatgtcatt ctaatgttaa gaataaatta  63060
tgaactgagg ctgggcttgt caacttgaac attgtctgag gggacatgca taccagtcta  63120
gatacataca tatatggaga tactgtttct tcctcatctc aaaggaattt tagaagattg  63180
aagagaaaat atataaggtc ttcaaaatgt gaatttgttt taatcacaat ttaagatata  63240
```

```
gtttcgattt tctgtaaaac aggagcaaag agaaattgtg aagaaacatg aggaagacct  63300
tcatattctt catcacagat tagaactaca ggctgatagt tcactaaata aattcaaaca  63360
aacggcttgg gtaagattct aagaactttg ttccattctt tattgatttt tgtgaccatg  63420
taaattaaaa ttcagctctc ttcttttttg gaatggaagt taccctttttt gttgccaaaa  63480
taatcttctg aaaacatagc tctgatcatt cttcctcctg tagctcaccg ctgttcacaa  63540
aattatattt ataattctta gccatgtact caatctgcta tgaacctacc tgcctttctt  63600
ttcaaattct actcactgtg agtttagcta tatctaactt ccagaattca gctcatattt  63660
gcctcttttg accattctgt tccatatgta tgaaatgaca tgtctttcat cttttaatgt  63720
gtaaccttag catatttgag cattacctcg ttaattcggt caacacttat tgatctcctg  63780
ctacgtgcag acattttgct agctattgta aatacaaata ataaagtctg catttcctgt  63840
cttctttaag ccttcattgc ctattaaatc attacatttt agattagata ttatattttg  63900
atcatttgag gaaccaaatt aaaaatatgg aataagtatg gcattgaatt atacatgcct  63960
attgctaata tattcatatt ttataggatt taatgaaaca gtctcccact ccagttccta  64020
ccaacaagca ttttattcgt ctggctgaga tggaacagac agtagcagaa caagatgact  64080
ctctttcctc actcttggtc aaactaaaga aagtatcaca agatttggag agacaaagag  64140
aaatcactga attaaaagta aaagaatttg aaaatatcaa attacagtaa gtcttcgaaa  64200
tgtattgtaa aaataggcaa atgataagtg atataatgaa gataaacata agtgtttgct  64260
atgccaggca ctgttctaag acttttaagt atattgtctc atttttatcc tcaggactgc  64320
tggttacata tgttatcatt ttccccattt taaagagagg atatggcctc aggaatgctt  64380
aatagcatgt ctgggggtag atgggaaagc cataatttga aactagtcag tctgactcaa  64440
aagccaatac aaattctttt ccagaatctc atttttacct tctttgagcc tcagtttcat  64500
cttatttatt tatttttatt tttgagacaa ggtctggctc tatttcctag gctggagtgc  64560
agtgacataa tctcagctca ctgcaacctt gaccttccag gctcaaacca tcttcccacc  64620
tcagcctgca gagtagctgg cactacaggc aggtgccacc acacctgggt agttttttttg  64680
tatttttgta gagacaaggt ttctccatgt tgcccaggct ggtcttgaac tcgtgagctc  64740
aagtgatccg cccacttcgg cctcccaaag tgctgggatt acaggcctga gccattgcac  64800
ccagcctcat catctttaaa atggaaataa taatacttac cctggcccctt tcagggtggt  64860
tatatgaagg tcaaattata ccgtgtatga aagtaatttg aaaactgtaa aataacatac  64920
agatagaaaa cttttgatta cacacttata agagtgtctg tcatataata gagattctaa  64980
acattgttca accactttat cagaacgtag attttaaact caaaataggt ttatagttag  65040
gtagtttcta atcattataa tattatctct atgggcctaa attttattat ctgaaaaaac  65100
atgagaaaat tgaactgctt gacttataat tccatttcag ctctcaagcc cctgctagag  65160
tctttgattc tttactcact tattcaaatg cctctgacag aattaacact attttttgctt  65220
tgctaaggag ctgccactgt taagaaatta ctctctaaaa gaaagaaaat tggcaacagc  65280
atatgtgtat tttcagtctc ttttcctcac tctattaaat tttgtacaag agatgttatt  65340
tttggtctag taaatttctg tcatgttttg gagtataaaa ttacttgtgc ttttgcatct  65400
aatttgtggg tgtagaaaat cataatcttt tgaaatacct tatataatac atttttttgc  65460
cacaggaaat acttgaagtt attgttgtgt accttacgtc attttagtcc aaaattatac  65520
ttgtgttctc tgtgtgcata ttttgatatg tattaggaga ttatggatct gtgtgatttc  65580
ttaagtaaat cctgatattt tcacaatttg atgatgactc tttaaagtta gacttaagtt  65640
ttgccaaaag caagaagcct caaagagtaa catttgttca tgtcttaaca ctatctcccct  65700
cttattggtc agaatctcag tatggatgca gtgtccatat gcacaacaat atattaattc  65760
agtttaacag acttaatgct gaataagcaa taagattaat tgaattaact aaatcttttg  65820
atagtatcca cttccatata tatagttata gatataatgc tagtgaattt gaaccataaa  65880
caaattaata atacatgtga tttctgtgaa aatttatatt agtcttttca atatgtcaat  65940
atagggcagt atttctcaaa tatagaggat cagtttttca ccattgtccc tcttggggac  66000
atttggcgat gtctggagac atttttgatt gtcatggctc gggggtgcta ctggtatcca  66060
gtgggtagaa tcaaaagatg ctgctaaaca tcctatcatg cacaaggcag ccccaccacc  66120
aacaaagaat tatccagtca aaaatgttac tagtagtatg gttaggaaac tatcatatag  66180
aggaagcaat cacattttac aagagccata atatttaaaa tgccttttttg ttcattctct  66240
gtatatttga ctagagtcac aaaataactt gataagattg ttgccaaaaa tattagaaac  66300
tagaagaaaa atgtgttgtt aagtctaaga gtagttaaat gaaataaaga attattcttc  66360
tttggatttg gatgcctgca tcaagattta gattgtaagg atacttagga ctgaacattt  66420
gctctatatg aaatttgtat taatcaaggt atgaattgca gcaaccactc tattaattac  66480
atatgtttgg ccaggtgtgg tggctcacac ctgtaatccc agcaatttgg gatgccaaag  66540
cgggcttatc acctgaggtc atgcgttcaa actggcctgg ccaacatggt gaaaccccat  66600
ctctactaaa aatacaaaaa ttagctgggc ctgatggtgc acgcccgtag tcccagctac  66660
tcaggaagtt gaggcaaaaa aatcacttga atctgggagg cagaggttgc agtcagccga  66720
gattgcgctg ctgcactcca gcctgggtga cagagtgaga ctgggtctca aaaaaattaa  66780
aaattaaaaa acacacacac acatatgttt atttacatca ggcttcaaga aaaccatgaa  66840
gatgaagtga aaaaagtaaa agcggaagta gaggatttaa agtatcttct ggaccagtca  66900
caaaaggagt cacagtgttt aaaatctgaa cttcaggctc aaaaagaagc aaattcaaga  66960
gctccaacaa ctacaatgag aaatctagta gaacggctaa agagccaatt agccttgaag  67020
gagaaacaac agaaagtaag taacaacaga aaattatcaa catttaggaa aaatatgtgg  67080
tagattgctt ttagagaaga tttgtaaatt tataaaagat ggtagtataa atctccgtgt  67140
tgtaataaaa agtatgagct ttatcttatg ctgttaaaca aggtatttta gacaatgctg  67200
tttttgtggg cagatatagt ccaatttatc tttttatgtt ttcgtcaatc tgatttgtga  67260
attatctata tgaagttagg aaaaatctta atgtacatta caaaaatata atatatatta  67320
cattgtattt tcttttttttc tactggaatt ttatgctact gaggctattt ttaacaaatg  67380
aacaattttg aacaatttga gggattgagg gaagtatgat aatgacaaaa agggatgaaa  67440
aaagggggtc atagagatgt ttttgtgaga aggagttggt cagtgtattc tgatttatta  67500
gggttttttt tagtttatct cagatttgat ctatttaaat tgttttagaa gatgctggtg  67560
tttttctgtg ctagctatga aatttatggg taaactttaa gcctttccta gtccttttgt  67620
tgtctaccta aattcaatta atttcatatg gaaggatgta gtaagtgagt aatataaata  67680
tctaaaattg gatgtttgaa aacaaaacat acctgttttt tgtaatagct tgatttaatg  67740
ctgagttctc aaaatcatta ttaagatttt gaactttcac attcaatgtg gaaagaattg  67800
agtgtaatta caaaagattt atttgaaaaa gttgagttgt taatttgtga aatatgttcc  67860
attaaactca taatatttta gaaaaatagt aggaagtaat aaagcttgtt tattttttat  67920
atcatatatt catataaaat gtcagttttc ctttaaaaat tacatttttt ttttggttaa  67980
```

```
tttttaggca cttagtcggg cacttttaga actccgggca gaaatgacag cagctgctga  68040
agaacgtatt atttctgcaa cttctcaaaa agaggcccat ctcaatgttc aacaaatcgt  68100
tgatcgacat actagagagc taaaggtgaa catcaacacg tgttaatgta acaaaatttc  68160
tgataattcc tattggaaga gaattcacta tgatatatag taattttgtt gatgaatagg  68220
gaatttataa tgcactgttg gtggctagac atagacacac acatgcattt ttcaacaata  68280
agtctcttta tgatactcat ttactgatta tcatcttggg gattaggaaa ggataggcca  68340
ttatgaacta ctgtttctaa tgaaattaaa tttaagaaat attttactta ggattttttt  68400
taagacttta ttattttttt agagcaattt taggttcaca gcaaaattga gaggaaggta  68460
cagagatttc ctgtatatct cctaccctga aagtggtaca tttgttaaaa ttgatgaacc  68520
tatattgata catcataatc acccaaagtc caagtttacc tctattttag ctcttggtat  68580
tttacactct gtgtgtttag acaaatgtat aatgatatgt atccatcatt atagtattat  68640
acagggtatt ttcactgccc taaaaatctt ctgtgcctct cttcttcatt ccttcctctg  68700
cacctcacca aacccctggc aaccagtgat ctttttactg tctccatagt ttcacctttt  68760
ccagaatatg ttatagatgg aaacatacag tgtgtcccca tcattctcac cataggacag  68820
ctaggaactc ctttctagtg gcatacatat tgtctagtat tgtaagttac cctttttatat  68880
cttatctttg taaactaggt tagaaattac ttcaagtcag agatttgttc tgtactactc  68940
ttatgcttca tagtgtttaa aacgttgtca tatatattgt tatatacttg tttgtttaat  69000
taattcagcc aaaatgaaac gtgcatattt gataaaattt tgtttgtggg tgtttgttga  69060
agatgaattg ctttacacta gttttttttt tttttctcaa agtcgacttt tttcctcaag  69120
gtagacttga catgaatatg gaaaaatata tgtagtttgt ggttattttt tttctcttgt  69180
gtacttaaaa attcagactg aatttttctt ataatggtat attttctgtt ttatgttcct  69240
tttatcattg atacttcttg aagagtcatg aataatacct ttctttttct cttattagac  69300
acaagttgaa gatttaaatg aaaatctttt aaaattgaaa gaagcactta aaacaagtaa  69360
aaacagagaa aactcactaa ctgataattt gaatgactta aataatgaac tgcaaaagaa  69420
acaaaaagcc tataataaaa tacttagaga gaaagaggaa attgatcaag agaatgatga  69480
actgaaaagg caaattaaaa gactaaccag tggattacag gtaattttat atttaactct  69540
gataatgtct gatttacaat atagaggtag tagtttattt ctactttatc attttatcta  69600
tggtatttgt taaaactgac tttcaaatca ctttgattaa tgtaattaat ttcttttgtg  69660
acttctattg tgtttatagt tctagagtag catattagta tgttgtatta aaatgcagaa  69720
gcagctacca gattatctta tgtattaagt gtcatttaga aagtatggtc agtgatagct  69780
tcagaaagtt gctattatat aattgaaata tttactgtct attttgtttt acatttattt  69840
gtaaaaatat aaagttacat tttatttttt agggcaaacc cctgacagat aataaacaaa  69900
gtctaattga agaactccaa aggaaagtta aaaaactaga gaaccaatta gagggaaagg  69960
tggaggaagt agacctaaaa cctatgaaag aaaaggtatg tgaagaaaca tactgactta  70020
tatgcttaag gtagtgacag agtaagttaa atacatagct gattaacagt taatatactg  70080
ccttaatttg atgacctggc tgtattaatt ctgtattaat tttgaggact ataagcagta  70140
ttgaataacg tagaaaagtc taagtttctg ttctgtagga atttagagtc tacttgagga  70200
gatacctata atgtaactct tatttggaaa ttactacatc aatttcattc atctttctga  70260
cattagagta cctctgaagt tccttcacac cttaacatat tcaactgtgt atcatttctc  70320
tccaaagtaa tcatttacac aggttggtgc ttttgacttt tgggacagaa agatagacat  70380
tttaagatac cccactttga cccaaatagg tcctttttaa tccttcagga gactaggctg  70440
ttatttcaga tagcaaagtt atttggaata tcttcagtat ttgcagtaat aatcagtaac  70500
caatctgctc atagattaat tctgtgggag aaattgctta aaattttata gttcatagta  70560
aactgttttg taataaaaat tactgattga aataacccca aaaaaaacta aaattggcta  70620
aaatgcgtgt aattaaattt gttatggaca ataaattgga gataacttgt tggtaacatt  70680
caaaatatcg aaagtgaact gggaaatgtt gatgttagca gtaatatttg ccattgaaga  70740
aaatcagtat ggaggagcta tggttaggaa aatttttatt ataaaattta cccagaaaat  70800
atttaatgtc tataaaataa tttcaatcac atgaaaatgg aaaagaaaat tctgtcttta  70860
aaggcattga atagaaaata ggtaatggaa ttcaaatttc ttaatagagt atgctcccaa  70920
aattattttc tatgaaaatt cattaatgtc agtgtaattt attgacacta tttgcgtgga  70980
gtcacaacat gcttgctgtc agaagctttg ctggtgaaaa ctgtaagatc aaagtgtcct  71040
taatcttttg gatttccatc tttctaactc cctaattggg gataggcctg atcttatccc  71100
taaatgggga taggttagaa actggtatgt ttgttcctaa ctggtgtgtt tctataccag  71160
tttctaacct gattcctatc agaatgtttt aagagccttg tggctttgcc tggactcttc  71220
tatgctacag tttatttagt ttatttattc agtttattcc tccttaaagt gggaataata  71280
ctatctgtat tgccagtttc tcaggattat tttacataaa atgatatgat atgcggaagt  71340
cttttgtaag ccatcacatc catagcagta taagatatta ctactaacta gaaagagaaa  71400
acaggggtct atgcccagta ttaaaattgg cattcaggaa tctagtgaga atattttttc  71460
aggttcattg cttgggcatt tctaatttat actcaagaaa tgctttcata ttgtttggaa  71520
attttagtac ccttttctct gtaaacagaa tttgtagtct acctatgtaa caaaacccac  71580
ccctgtgcct tgcatttcat tctccttagc atttattact atcttaacat actagacatg  71640
tacttgtctt ttgttcatct tttttttttc tttttttatt agaccataaa ctttgatggc  71700
aggaactttg cctattttat ttattattgt attcccagca cctagaacaa tcgctggcac  71760
atagtagatg ctcagtattt gttgaatgaa tataaatttt taaatgttat aataatatta  71820
ttctgaaatc tatgcatacg aagcttttgg tacagaaaac atgaaaagag aactactgcc  71880
ttatcatcca gtcttcttcc ctcttctcat tcagtctaga acataacctg ttttggaaaa  71940
agttctcaaa ccatatgttt atcttgccct caaaccataa caacaatcaa tgcaaaagac  72000
ttctgtgacc cccagaatat gtggggattt ctccacatca gcaagcaagc agttggtttt  72060
gtagcagaca ccaactgggt gtcgtccaat tcaattcatc atctacctgg agatagtgtc  72120
agatcccaca gatatcttac ttcgatcaaa tcacaagtcc aggcctccgt gacttccgaa  72180
gttcccacat ccccagcccc cagctttggg tttgattaat ttcctggagt ggctcacaga  72240
actcagggaa acatttactt acatttacca gtttataata aaggttatta caaaggatac  72300
aggttaagag atgtgtaaga agagatatgg gggaaggggt gtggaccttc catgcctttc  72360
tggggtgcca ccttcctcta gaaacctcca catgttcagt tctccagaac ctctctgaac  72420
ccagtcctct tggtttttag ggaagcttca tgacatcagt atttcttctc ctagggtatg  72480
gggcaggacc ccctcgtatt agggttttaa gacccacagt cagaaaggca ggggaagatt  72540
acagtcctgc cttagggcag gtgaaaggag gatgggagaa ggtcagagag actcttttct  72600
gaggtgtgct cggaaggcct aacacactca atattataac taaagatgag gacaagggct  72660
atgagagtta taagccagga accatggaaa aaagcctata tgtaataaca ccacaatacc  72720
```

```
catggtacca ttcacgtttg ttgtttttct gtttttcaat tgttctttca gtcttggttc  72780
ccttaatctt aatttagcaa gtaatgccag gtgggataaa attgcccaaa cccaacaaag  72840
tactgtgtgc tgcaggatta tttaatgaca taccttatgt cccccactag tatttacatt  72900
tctgggagta cagaaaaatt cttgtacata tttcagaaaa aatgaaatta ataactatca  72960
accacttagt gaagttttta cttttttttt tgagatggag ttttattctt gtcacccagg  73020
ctggagtgca atggcgcaat ctcagctcac tgcaacctcc gcctcctggg ttcaagtgat  73080
tctcctgcat caacctccca agtagctggg attacaggtg cctggcacca cgactggcta  73140
atttttgaat ttttagtaaa gatggggttt caccatgttg gccaggctag tctcaaactc  73200
ctgacctcag gtgatctgcc cgccttggcc ccccaaagtg ctggattaca ggtatgagcc  73260
accacaccca gactgaagtt tttacatttt ttaaagggca cttattagct gaattaaata  73320
aggtaaaaaa ttgactagta ttagagacaa gaattggaga atatagttct ctagtattcg  73380
agaaagtcgt tttgatagga caactaatct tagtgagaat ttggctttat ttcatatttt  73440
tttaattttt tgagatgacg tcttactatg ttgccctggc tggtctttga actctgggct  73500
caaacaatct tcctgcctcg gcctcccaaa gtgctgagat tataagcatg agccatctcc  73560
ccaggaattt gactttaaac catggttctc aacccttca gattcaacat tccctttaat  73620
aaaaaatata atgtttcata atttcccctt tactattata attgaaatgc atagttaaca  73680
taaactctac ctacttacat aatttcaaaa atgtcattat gaatgtccta aatgaaatat  73740
atagggggaa cataaaagga atattcatat ttcaacatgt aaatgctttg gcatgactcc  73800
attggaaaat ataatgaact agtcatgtgc ttgcaccttc attaatgtga gttcaaagct  73860
acgattgcag actgacacaa atgtgttcta ttggcaactg atgggtcatg atggtattgc  73920
catttgtaat ttgatttcca aaatggtaaa caaattgttg gtgcagttct cagcaaaaca  73980
atgtctataa tcttacttt tataagactg ttgtattcct agaaaactta gtgtatagta  74040
aaaccattaa aaaattactt agtgtgaata tgttagttgg agataaattc ttagctcaga  74100
ccagtgtaag cagaattttt tactgtatta atatccagta gaacatttga aagttgttca  74160
gtgcatgaga ctattctgca ttggataggc tttctttggc tcctttatca tagttataat  74220
aaaccatgac acctacccct gaaatgccct aattcccttc cgtttctttt tcttttttct  74280
ttttagcact taaaactagc taacttacta caaaatagat ttagatttat ttcttgtttt  74340
gttatctgta tcgtttgctc ccttctcccc aatctatcta accaactagt ataaactaga  74400
tagtaagatt catgaagata cactttttta tctgatttta ttcatttgtt ctattcctat  74460
tgcctctaga gtagtacttg gcacatggtt agcactaaat aagtacctgt caaatgagtg  74520
aagtaatgtg cattgaagac ttgaaggggc tctgatgcta ggaaattgtc atgggataat  74580
agatgaggtt ggtcgtttgt acagaggatt cttgttagaa gcttactcta gtcatgattg  74640
tattagaatc ttcatttaaa ggctcctgaa gggtgttggc attagtcaga actgtctccc  74700
agaattttat ttgtcttgtg atagaataaa gcatagttag cctaaagagc agttttccta  74760
atagctcggc atgcccaaag attctaggag ttatacaggt tgaacatcta atccaaaaat  74820
ctgaaatgct ccaagataca aaattttttg agcaccaata tgatgccaca agtggaaaat  74880
tctgatgtga cctcatatga tgagtcacag tcaaaacaca gtcaaaactt tgtttcatgt  74940
acaaaattat taaaaaatat tgtataatac tacctccaag ctatgtgtag aaggtgtatg  75000
tgaaacataa gtgaattttg tgtttggact tgggacccat ccctaagata tctcattatg  75060
tatatgcaaa tattccaaaa atattttta aaaaaatcca aattctaaaa cacggctggt  75120
tccaagcgtt tcgtaaggga tactcaacct gtatagcaaa atgaacatat ttacatattc  75180
tctaggaaat attagtttac aatttttcta ggcaaattat aattgataaa tcataaagaa  75240
aatttaaaat aacactggta attttcctac ctccttcgtt attgttacag aatgctaaag  75300
aagaattaat taggtgggaa gaaggtaaaa agtggcaagc caaaatagaa ggaattcgaa  75360
acaagttaaa agagaaagag ggggaagtct ttactttaac aaagcagttg aatactttga  75420
aggatctttt tgccaagtga gtttaaatat cattataaaa ctaattatgt gtaaaatcct  75480
ttagtgacct ggaaattata tagctttatc atagttgata atatgagaaa tggtctagtt  75540
taaatgatca tttattatct atgatttact tactttttat tttctttaaa atctgtttta  75600
aatatattgt aacaattata gatggatttt cctgtgatct cgttgtaaat tagcttatga  75660
caaatatagg gtgttacaat tattgtaatt tggtttggta atgagtatgc aattgaaaag  75720
ccaaacactg aatggtatat ttcatgattc tatattaaat tccacagagc cgataaagag  75780
aaacttactt tgcagaggaa actaaaaaca actggcatga ctgttgatca ggttttggga  75840
atacgagctt tggagtcaga aaaagaattg gaagaattaa aaaagagaaa tcttgactta  75900
gaaaatgata tattgtatat gaggtaagct attatgtgga aatgtgccac ccattgtaat  75960
gaaaaactgg ttgaccccta gaaattgaaa taataaatgt gtgttgtctt aagcttgggt  76020
tatgttttct tttcccatgt gaattgagat attcctggtt cttcatatgc cacataattt  76080
tggtgtattt ttgatctttt gaatattata ttgtgagact ctggttcttg tttaaattct  76140
atgggaaaat gtagatactt ttgttttagc atgcaatcgg tctaattagg ttcaggccac  76200
aagttccaac ctcatttctt gggctgtggt tccatttttc aaagcctttt caatactctt  76260
cagatctgtc ctgcctgtgt acctcacaat aggtgatctg gtatgtgagc tatgtaccat  76320
tagttcagtt cttagaaact ttggtattct gattaggatc gatccataca tttgcagctc  76380
aagagtgagc ccagaagttc ataaacaact ttatagggtc cctttcttga gctcctccct  76440
ctttgccatc tctctgatac tttgtttccc tagggatttc catttggggc tttagttacc  76500
cagtgatgcc atgtacttca ggaattgcac acttctgcag ccaagcaagc aagaggagag  76560
tagaaagagg aagaaaaaaa cgacttttac cttaccctct tagtatcata gctctaccaa  76620
ttggagattt ccctcccaaa aaatattagc ttctgtgagt tcccattgca gcctctatta  76680
ccactgctat gggatggctt aagggttggg gcatgaaaga acagatagaa gaaaaaaaaa  76740
gtgaggtgtt ttcatattgt ctcttgagtg ttaaaagatt ccctttctct ttactcgagc  76800
tagaattaga aggtttacct ggagctctct ctgtcagtgc agacacccat cttcaggttt  76860
caaataatgt tgtcttcagg gcaggcagta acagaataaa agaaaaggta aattcatcac  76920
ctgtttgctg ctactttaag tcctggtatt ctattgtaat ctgccttcta ctcctttgca  76980
aagtcctcaa atggttgctc catgcattta ggagagagaa gattgaatgt atttactcca  77040
ttgtacctgg aaccagatgc ccttgccctg catcacccca tgtcatttct tagcagagcc  77100
tttgagattt ttgtgtgtgt gtgctttaca atctctttcc aagttatatc ttctgataca  77160
gtcatggtcg tgaaaagcaa aataaaatca tgtgttaaca tttaaaactt tttaatttta  77220
ttctgacaac agctaaaact atttaatctt ctgtttcgct catttcttcc aaggtaaact  77280
tcagttggtt ttacgtgatt tgctatttct tcttctttgc atttacaaat gatctgtgat  77340
catattactg atctttgtaa aggctaata tctacctgca acatttggat atgacagtat  77400
ttaccctttg taaatacaca ttttctattt atcttcaaaa attaccattc attagtctgt  77460
```

```
gttaatgtct gtttactatt gtgtcattat gaatgtgatg tgaacatacg aagttgaact  77520
tatttaaacg aacactctca tgagcttcta atccacattc cttccttttc cttctaagtt  77580
accatttctt aaaaatcttt tagaagtttc cttgataggg aaaacacaaa ttattgagga  77640
atttttcttt ctcttgacat ctgtttatag ttactctctt gttccagcag tggatatttc  77700
ccctccatgt ttttctttgt ctaaacatat gttcaaaaca aaacactttt attcttcttt  77760
gcaggtttta caaggatcaa cttttagttt tgaaacctgc tattactttt agaggccatt  77820
ttttttttct ctaataatgt gagttcatgc gggctgaagt aattggaata ctttatagaa  77880
aagattgaat ttgtcttctc tctgaactct agtttgaatt tctaaatttt atgaatcatc  77940
tagatattaa agaggagggg catatcaaag aggagaaccc tagcagagat aagaggcaag  78000
agtaaatgtt tcatgtatgg gtaagagtgg atttgtattt acctaagtaa aggtagaccc  78060
tggacaataa ggttggatag atgtggaggt ggcaaaccat ggagggtctt gtaggtcaag  78120
tggatgtttt tagacttgaa gtgttaaatt attatctgaa atcattaaga gtctttttag  78180
atccttgagc ttcttgagaa gaccatggat attatgcagt tattatataa tgttttaaaa  78240
tagtaagtat tttagtttaa ctgtcttatg taattccata taaatggatg catgttcttt  78300
aaaaatgtta atgtatttca gtaaatcaaa atatactttt tgactcatca tttaaaggag  78360
gccttcagtg aatgctctgt agaggattat tttataatac taattttgat atcctaattt  78420
atttgttata aagtttagaa ggtttgaaga atttaaaata tagtgttaat aaacacactg  78480
aacttttctt tttttatctt gtatttttat atagtacaac agaaaaaaga tgaaatgtga  78540
atagtaaaga gtctgtgatt gttgttcata gggcccacca agctcttcct cgagattctg  78600
ttgtagaaga tttacattta caaaatagat acctccaaga aaaacttcat gctttagaaa  78660
aacagttttc aaaggataca tattctaagc cttcagtaag tgtatatctt ttattatttt  78720
tttctttttt ccatgttaaa atgcatgaaa gtgaaatcaa cttcttttctt aatctggcca  78780
aaagcattac atctttctca ttaatagtaa tacagtaaat tcaactttta tttttaacag  78840
gtagtgatgt gtaataattt atttaatcct ttttaacata ataacagtaa acttaagatt  78900
cttaagcttt tcataaagct cataaatgat ttctagaaat tttaaatatg tagttatcat  78960
tatgtatttt gctgtagcag cagtatacag ttaaataaaa taggaaaaca tgttccaaga  79020
ctgttttcat tcaaatattt atgctatatt tttagcttat aaaaactcat taatcattaa  79080
tgtaaaatta tttgttggat tttttaaata tttagtgtat tatttttgtt tcttttttct  79140
ttccatgttt cttcattctt ccaccttaag cagaatcagg tgtgtgacac aactatgttt  79200
tctatccttg ttaccattat taataaatac aagggcatga tatttttcac aaaagaaaca  79260
ctttgttcag aaccaaaaaa gatcatggca acagtcagaa ttaaaaatgg taaaagacta  79320
ggtgccaaag atgacttaca taattgggta cctagaaata ttctatggta ttacagtaat  79380
gatgaaaaat acaaattaga acacatttta gatcctattg agttaaataa atcagagtca  79440
agaccaaaca ataaataaag tcaatttacg tcaacaaatg gtaagttggc agattttaac  79500
tccctttttg aaaatgaacc atgatcctaa ggttggtaaa attaatcaag aatgttgtca  79560
aaatgataaa gataaaaatg aggaagagaa taagataggc aagagtgaga aaggaaagag  79620
acacatagct gaaaatgtga gtcacaacaa ctacatagat ccgtagaatc tgctatggag  79680
gactgtgatt atgtgacagt tgctgatgcc gtggcttagt gagctgaggg tgatgcacag  79740
gcaggcgatg taactgatgc gtcagtccag ccaagaaagg acgcgtccct ggtttggcta  79800
cgtggccgtc ctttatttct ttgttaactg aattttctta tagtaagtag cttacgtaca  79860
tatatagtgc aaatgggaaa gtgtgtaaga tttagaaaaa gcattaacta ttagtaaact  79920
ttatcttaag ctctaacttt tgattagttc ctacaaaaat tagtgaatat gcattttcta  79980
atttagtgct tttttttttt ttacaattgg tgttcactta atgttatatt agataaatga  80040
atagcaaaaa taaggtactt tagagttgat tgttttgcct tacaaacttc taatccatcc  80100
agctgtattt agaagtaaga tctcactaca gcgaattata tcagtaaaat tttgttacag  80160
tgttgtgcag tgtcctaaga tgtatactaa gttccttcag tggctttttt tgccatgttt  80220
tataacagat aattttgtta taatgagaaa aggaaacttg gatgtgttgc tgtctatatt  80280
gtgttaggct caggcaggat gctgtggctt actcatttaa tcactttggg aggcaggggc  80340
aggaagattg cttgaggcca agagtttgag atcagcttgg gcagcatagc cagaccctgt  80400
ctctacaaaa aatttagaca gatgtggtgg aacacatttg tagtcctagc tattagggag  80460
gctgtggtgg gaggatcatt tgagcccagg agtttgatgt tacattgccc tattgcactc  80520
cagactgggc aacagagtga gacctgtctc taaaataata ataatgataa tgataaatgg  80580
tgttaggctc tgtgcctaag tatatttttc acataggctg ggtaaagtgg ctcatgcctg  80640
caatcccagc actttgggag gccaaggcag caggagcatt tgaggccagg agtcaaagac  80700
cagccttgag agaccccatc tctaccagaa aaaaaaaaaa aaagaaacaa ttagctgggt  80760
gtgattgtgc acacctgtag tcctagctac tcgggaggca gaggtgggca gatcacttga  80820
gcccaggagt ttgaggttat agtgagctaa gattgtgcca ctgcactcca gactgggcaa  80880
cagagcaaga ctgtctcaaa caaaaacaaa caaacaaaaa gcactttgca gaatatcagt  80940
ctaactctac agtttatgga ctttttatgt acgtactact tttggctagc ttacattgag  81000
atacagaata aaagtttgtt catagcattt atcgtttttt tctttatact gtccacctga  81060
gatattccag tcacctaagt catggaaaca tcaactaaaa ttaaatatct atgttaagag  81120
aaaatggctg aaagtgattt aattcataac actttttttc acatgctaat aaataagagt  81180
ttgagacttc cactaggcat tatctctaac tcctatccac taagaatttg attttaagta  81240
gttgatggct tttaaccgga ttattcttct gtaagagttt ggaagtctcg tgaagttcgt  81300
tatacaagaa ttctgtttac aagagagcat tacattagaa tttgtttttc agaaatttgg  81360
actatctcaa cgaataccttt tagttttatt atttcaaaat gcaagggaaa aaatgagcca  81420
taatcactaa tagtaactgc atcatatttt agtgagaaat gtgttaaaaa tatcctcatg  81480
tgagatcttc cttagataga attaccctct actctaatat ttaatatatt tttatatctac  81540
caatcagtga tattaatagg tgtttatcat ttgctgaatc aaataggtac aacagaagac  81600
aggaagtttg ggagatagaa gagctcaggg acaggaaatc acagatgtcc atatctgaaa  81660
taaccttaaa agttatcctg tctaatgcct tcacttataa actgtagtgg tagaatttgc  81720
ctagtattaa cctaatagtg gtagatttga atgtatactt gggctttctt attaagtgga  81780
aatgtattcc tgtgatttac atatatcaac aaaaatgttt gtcttctttt ttttgctacg  81840
acatatgtgc atgtgcacac acatctcctc aaacaaaaat cagatggaca catgcagtca  81900
ttggatctaa aagatgttat aaagttgtgt ataataggta ttttataata atatatttta  81960
agacccataa tgtcggtgga gtaactgact ttacagccca tcaagccaat agagagagaa  82020
aggagaaaaa aatgaaagtt gtgctgaata attaaaaaaa attatttcct atgatgctta  82080
taacagtcct atgaggtagg tggtattcta atttatagaa aaaatgcata gaaaaatata  82140
attaagcaca gttaaaaaaa ataaagttta gaatgagaag taacaacata aataatgacc  82200
```

caatgtagat tcaggtcaaa agaaatgaaa atataatatt aatggttttc aaagagggaa 82260
ccattacttt agctcaaaga atgaaggagg gctttccgaa ggagtaaaga attatggcag 82320
ttcttttgta gcctagtgta ttcatttgct aaggtggctg taacagacta ctacagattt 82380
ggtggcttaa acaatagaaa tttatggtct tagttctgga gacctagaag tccaaaatca 82440
agacatcagc agggttgatt tcctctgcac aatcagaggg aaagatcttt cccaatcctc 82500
tctccttggc ttataaatgt ccatgttttc cctgtttctt tttatcatct tccttctgta 82560
catgtctctg tgtctaaatc cccaaatttt ctcttttcat aaggatacca gtcacagtcg 82620
aatagggttt accctgaaat ctcattttaa cttgaatacc tctgtaaaga cccagtctcc 82680
aaataaagtc acattctgag gtactggaaa ttatgacttt aatatataaa tgtggagggt 82740
aaggggaaca cagttcaacc cataacggtt agataacaat cgtgctttat tttggactag 82800
taaaaccacc atagatcagt ttaaccatta tgaaattata catgaaggca ttatatgtat 82860
ggacattatt aagtcatact tgctttgctt ccattgtaat taaaacaaac catactacct 82920
ttgttctgca agttttgtat tctaacttat ttatttttgg ctttcaccag aacactccga 82980
ttttctcata ttcctttgag gaaaaaaagt taccttttga cagtattttc ttatccagta 83040
tgtcttttat ggcttttatt tattaaactt taaaaatatt cctaatttca tttccctgaa 83100
gatttcagga atagagtcag atgatcattg tcagagagaa caggagcttc agaaggaaaa 83160
cttgaagttg tcatctgaaa atattgaact gaaatttcag cttgaacaag caaataaaga 83220
tttgccaaga ttaaaggtga atttaatgtt ttttattagg aaatctaatg cctaaaactc 83280
cttccttagt tgttatgttt acttttatta gcttattaag aagtcaaaaa tgcatattcc 83340
taatatatca tggtgatggt atactttata catttgctct ttagcattta tttgttgaag 83400
gcctacttta tattaaacac tcctccagat gctgggaaac agcagtcaaa aaattcctta 83460
tactcatagg acttacgttc tagtggagaa gactgacaat aaacaagtca ctaaatagta 83520
tgtcatctga tgttagtgct aaggagagaa ataaagcatg attggtgtaa agagtatggg 83580
gagagagaag gggtgtaact gaaaatagag tagtaaggga ggtcttcctt aataagatga 83640
tatatgaaca gagagctaag gaggggtaaa ggaagtgagt catacagata ctagaaaaat 83700
aattacagac aacagaaata gcaagttcag atgtcctaag gtgggaggat gcgtggtata 83760
tttcattaaa aattatcaca ctgtaaaata taagaataat ttgtttcttt tagaaatttt 83820
actttattct gatattaata atgatttttt aatctttggt tttccaagtc ttaccctatt 83880
tatgggaatc tttttttct tttggctagc taattgcttc agttttgttt tctaatctag 83940
aatgttagca atctgttaat tccactggta atgatatagt taagctatgt cttgcttctc 84000
acactttatt tatttattta ctcagggcac taatctgcca ttttttcgca cttttttcc 84060
tttttttttt ttttggtact gcttcttatt ctggttttta cattgataga accaatgtta 84120
gacgttcatt tgccttttgc tgtgtatatt tgggtaagga tctatatgtg caatatatgg 84180
gacagttaaa atcagaattc taaatttgta ttattgcatc aggcaataat gtgggaaata 84240
ccttgacatt tcatatacac aatattcttg tattaattta acgtcttagt tcaaaatctt 84300
ccttgttaat atagagaccc tattatttgg tttggcaata cagttgaaga gattgatggt 84360
tcttatgaat tgtttgcctt ttcttttcaa tggctgtagc tatgttaaat tattacatgt 84420
ttgcttgtta tctttcagaa tcaagtcaga gatttgaagg aaatgtgtga atttcttaag 84480
aaagaaaaag cagaagttca gcggaaactt ggccatgtta gaggggtatg tgagaattta 84540
ccatacattt gttttggttt cagcagtgat aagccagaaa tgaaaagttt agatatgttg 84600
taaaagtact gatatgcctc tacaagtgcc ctgtagtttc agtgtttatt ctgcatctgt 84660
aatataaaac agtaagcatt tctatgtgtc tcaaagtatt ttatcatctg ttatacctta 84720
catactttca tctctctttt tattgaatat gcctccatac cttgaaaaca tttaacttcc 84780
aggaatcctt ttgtttatgg aggtaactgc taactggtcc ttggtccaat gctgccattt 84840
tgtaaccatt tgttatgata tcttcccagc ttggtataat gttttataat tacattgttc 84900
ctccccctct ttttttgtgt tcttgtaatt ttctccctat gttattttgt attcatttta 84960
tataatgaat aaatgttgct tatgaggtca aggccaaaga cttaagctcc tgttgatttc 85020
atgttgctga gtgtcataaa tggaagcaat cataatgcag agtcattctg gtagtaatat 85080
taaatatatg atggattcag tgaaaatatt atgtgttatt agaaaaatat tcagaacagg 85140
ccgggggcag tggctcacac ctgtaatccc agcaatttgg gaggccgagg cgggcagatc 85200
actggaagtc aggagttcaa gaccagcctg gccgacatgg tgaaacccca tctctactaa 85260
aaatatgaaa attagctggg catggtggct catgcctgta atcctagcta ctcaggaggt 85320
tgaggcagga gaattgcttg aacctggcag gcggaggtta cagtgagcca tggtcacaca 85380
actgtactcc agcctgggcg acagagcgag actccatctt ttaaaacaaa aaaaaaaaag 85440
gaaaaatatt cagaacagta tcttgctggc agcaacattt gtttcatcaa tgaaaatatg 85500
tgttaatttg accttttcta tctaagttaa ttatgaaagt gcatactaaa atgatgtaaa 85560
agtttatatt tcaggattat tcttattcat ggatgattaa ctaaaatgca aaaagaaatt 85620
aagcatactg tttggctaaa ctgttaaaaa ttattttat tttaaatgat aagcagttaa 85680
acttattaag tgatgactca tctctgctga tatatttatg caaggttttt tatttcagat 85740
aactcttcta tttatattaa acagaaactg tatttctaag caatagcatt tcttagagaa 85800
aattgcctct attatgttgc aattaaaatt taattactca tgagctcttt aaagacacaa 85860
tttctcttgt gtggttttat ttcatataaa gaaaaactct gatatactgg agagaacatt 85920
agctaaatag actatttaga cttaatcatt ttgatcagac atcaaggcta gactatttaa 85980
gctgttactt attagctgca tgattttagg aatgtcaaat ttcctaagtc ttggttttct 86040
tgtatttaaa atggaaatta taattcctat ctcatagaat tgttttaagg atgaattgaa 86100
ttaatacagt tttgacttca aatattagga attattgagt ataataagcc tgttgtattg 86160
ttggtacttc gtattatact tactaaaata tttgattaaa gatttaacat attctttcgt 86220
agtctggtag aagtggaaag acaatcccag aactggaaaa aaccattggt ttaatgaaaa 86280
aagtagttga aaaagtccag agagaaaatg aacagttgaa aaaagcatca ggaatattga 86340
ctagtgaaaa aatggctaat attgagcagg aaaatgaaaa attgaaggta attttttta 86400
atgtgatcat ttttagggga atattttacg ttttgttact atttaggaaa atttcaaata 86460
tgctcattac tatataaaat ggctttaatg aatacaatac atattttata aatatagaaa 86520
aaaacttatg agaggcaagg ctaagggtta tagagtaggt ctacctgatc tttcttgtta 86580
tttcaagacc aatacttttc acttttctct ctgacagcat agattaatta cctgtgtctc 86640
tctttttttt ttcttttgag atggagtact gctttgtcac ccaggctgga atgcagtggt 86700
gcaatcttga ctcactgcaa gctctgcctc ccgggttcat gccattctcc tgcctcagcc 86760
tcccccagta gctgggacta caggtgccca ccaccacgcc tggctaactt ttcgtatttt 86820
tagtagagat ggggtttcac catgttaacc aggactgtct cgatctcctg acctcgtgat 86880
ccgcccactg cggcctctgt gtctctttgt gaaaatacag atgcccaagc tcccatccct 86940

```
gaaattgatt taattatttt agggtgggtc ctgacacaga tatgtatgtt gttgttattt  87000
taagtcatca atttattcta atatgtagcc aacgttggga acttcgttct cactaatatt  87060
caaatgaaga ctttaattct aatcatatca aatatggttt ctaaaactac tttgaagatt  87120
tatgagttta taagattatc ttttatttcc ttgttttgat aatgtatact ttttattttg  87180
tttgtttttt tactaggctg aattagaaaa acttaaagct catcttgggc atcagttgag  87240
catgcactat gaatccaaga ccaaaggcac agaaaaaatt attgctgaaa atgaaaggct  87300
tcgtaaagaa cttaaaaaag tatgactttt atgactgatt ataacttttg atttttattt  87360
tacttaatac ctcttggaaa aactggaagt agatccttga tgagagtgtc tgtaaaggta  87420
gatattaaga gattgaggaa ttgtgtttct atgcctgctg tcatcacatt ccaccatgaa  87480
aaacattgat aataaaagtt aatacattta ggctgggcac ggtggctcac gcctgtaatc  87540
ccagcacttt gggaggccaa ggcgggtgga tcacgaggtc aggagatcga gaccatcctg  87600
gctaacacgg tgaaaccccg tctctactaa aaatacaaaa aattagccgg gcgtggtggc  87660
gggcgcctgt agtcccagct actcgggaag ctgaggcagg agaatcgctt gaacccggga  87720
ggcagaggtt gcagtgagcc gagatcgcac cactacactc cagcctgggc aacagagcga  87780
gactccatct caaacaaaca aaaaaaagaa atgatctacg ttgcttacac ataccttatg  87840
cttatagcta ggtctcgtaa gcattaggaa gtcaaaacaa agaatctttt acatgtgtaa  87900
aggtataaac tatcccattt ttctaaaaat atagaggaac aaagtgtcaa atttaaagta  87960
atcactagta actaaatata ttcctctgac ctcattttcg tgatctgttg ttctaattat  88020
tattggccat attgctgctt taaaggagag atgttgaatt tgttgaaatt ttaatcagca  88080
tttagagccc caggttattt ttgttttcca atttgtaatg ataattttga atacactgaa  88140
tctatgagaa cagtattatg ttttctcata aaatactaat tagcatttaa tgataggaaa  88200
ctgatgctgc agagaaatta cggatagcaa agaataattt agagatatta aatgagaaga  88260
tgacagttca actagaagag actggtaaga gattgcagtt tgcagaaagc agaggtccac  88320
agcttgaagg tgctgacagt aagagctgga aatccattgt ggttacaagg taggaacaga  88380
gttttaaact tgtacaaagt ttaatcattt caaattttgg cattgtttta aaagacaaca  88440
ctattctgga taacctggtt tcttcctgat gaacagttgg tttggttgtt gttttaacat  88500
aatacttttt ttctgttgta gtattgttgg agactttttc ttccttgaaa tgtttaactt  88560
gtttaacctt gtttgggtgg cagggcatgg aacagtgtag agctggggct gggcgaagga  88620
gttggagctg tgtgtgcgtc atgaagctgt catcagctat gagcctgggc tgaggctgct  88680
cagcttctcc tgggtgctat ttttctccaa ctgcagcttc agcttcttga ttgtataatt  88740
tgcttcctca agtatgagcc aggaataatt gagctgtctt gtcacaatgt gtggcatact  88800
ggatctaggc tgtgctgcaa tgcttttaga gttatatcct gggcaacttt ctcttcagat  88860
agccccaaga gatgaattca gcaccagctt tgatgtttta ctagcttctg ctttctggta  88920
cttgattttc tcccaccccg aacacatggg attccaacct gtgaaactaa tttttgtggc  88980
tatgaaagag gtagtggtag tttatgagta aacattcagt ctgttgccac tatcatcatg  89040
tgtggttcat catgactgtg atgagtaggt aaaaggctct ttgtgtcatt ctcatttcca  89100
attttaagca gctgcttcaa ggagtctgga agtcattgac cagtgggatc ctgcctgtgt  89160
cttttcccat taaagccatc ctgtatgaag tggtatcctt taccatctag cacatctgcc  89220
gcccccattt caaaaggcat actcatcttt atctcaacat tctcatacag ttccttatgt  89280
ccatgcacct ccaatgtccc ctttgatgtc tttgaggttt tcatcttcca tgtctgctat  89340
ttggaatggt cttgatggga ggcaagatag tgatcactac aactaggatg ggagtcttag  89400
taccgtgagg ctacagcaag tcccacagag ggcctgctgc actgtacttg cctctgtcaa  89460
ccaagtctaa ggagaaagat taagcaggca tattaaagga cagcccagat ggacatgaag  89520
tcctggagga ggccttggtt cctgtcctaa tactaaacct agagtaccca gaatccacac  89580
ttctccactc tagctctcac ttttcccatc tacacactgg gaaaaattat tctgtcagaa  89640
agccagtgtc aaggtgagaa caaataacaa atgtgatgat atggagtggg agaaggggtc  89700
tcttctactg tcttattgga ccctagcagt ggctctgagc cagcagtcct gtcagttgat  89760
ttcttggtcg ttcctttgtt ttcttctata atcacatgtg gactcagaat gaattttgag  89820
ttactctgaa atctatttat tcaacagata tttacttagt acctcctatt gccagactct  89880
gctttatgtt ggatattatt ttttaaaagc ccaccttgcc tagatttcct caaaggacca  89940
ggtggcttcc ctggttttga aagaccctaa ttcttactat gatcttaagt aaattatatc  90000
ctttctgtgg gctcaagttc tttctaagag ggctctttgg ggctacaaaa gaaattgtta  90060
gtgcaaaaag agtttataag gtttataaat ggttagtaga ggtgatgatg atatttaacc  90120
ataattgaag atgactttgc attttagatc atatacgtgt ttttcgtctg agaacgatac  90180
aggtcactga gcataccata agccttcagt aaatcatttg cagaagacat tgcagaagac  90240
ataagtctaa gtagaaatct cttgacagag agaaggctcg ttttgatcct tgacctcaaa  90300
tttaggttcc ctaaatccat taaaaaagag aaagaaaaag aaaaaaagtt actaaagttt  90360
aaatctggga ggattatata cccttctcaa taaagcagtt tagagagatc tcttttggga  90420
cccatgacac aggtcttgct catgctgaca tctttatagt tgctttatta tttattcaac  90480
aaacttagta acacgtattc tatgtcaggc cttttcctga ctactgggac aaaccagggt  90540
gatgtggggg ctgttttaga tagggtgatc agaggaggcc tctctgtttg ggtggctttt  90600
gaatagaaaa ttagatgaag tgaaggagta agcttctgat atttcactgt ttacttgtgg  90660
tagatctgtg ataatctctg tcaggttaaa aacattccct tctaatctaa gtttctaaga  90720
tctatcaaaa gctgtttgaa tatatttaga caatcataat tttcctttct tgtattatcc  90780
tagcagattt tgttgccaaa gctatactgg ccattttaac ttagaatgca gtctttctat  90840
tcatttctct ggaaaagttt ggatattgta agcattattt ttctttaggt atgatgaacc  90900
tgcagaactg tttggttcaa ttatgaattt ttttttctg gagtctgtat ttttttgaac  90960
tattaatcat ttctttaatg attataaatc tattcagatt tttacaagct ttatccctct  91020
cccatcatac actattttc ttacccatgc ttttgcacaa tttttcctc tcccttagtg  91080
ttttcctacc tagatacctc ctatgtgtgt ctgtgtatgt gagaaaagct ttttatttgc  91140
catctttata tttctaagaa tatctagtaa tacagaattt tatattctga agaattttac  91200
tttgcatttt cttattttgt gattgaaaaa aggtattaat tttaaaatgg tcaaatcagg  91260
ctccatcctt ggaaaatacc caaatccttt attttgattg ggccatctgt taattaggga  91320
taccttatct cttgccacca ctttttaatg ctaaataaat atgtagctaa aactttgact  91380
agaagaaaca gtaaaataag atattcttgc ttatttttag tacagttatt tgaactgact  91440
tttaaatcag tgacataaat tatttgccat gtctatactt tttttcctta tacttttaga  91500
atgtatgaaa ccaagttaaa agaattggaa actgatattg ccaaaaaaaa tcaaagcatt  91560
actgacctta aacagcttgt aaaagaagca acagagagag aacaaaaagt taacaaatac  91620
aatgaagacc ttgaacaaca ggtaagtaac gtaatttttc tttacatgat aaaataatgc  91680
```

```
ataatatcgc aagatgttcc ttgcattgtc ttatatagat aaaaatggac tctattaaga  91740
agacccatct aactgaaggg caccccattc acccatttgc ttaagccaga aactttggat  91800
catcaacgac ttcattcttt tcattctcca cattttctat cattaaatca tgtcagctct  91860
attttcaaac tatatcctaa atatgaccac ttcttggtat cttgagacat cactaccagt  91920
cttgtccaag ctattgtttt atacctgaat aactgcaata atttccaagc tggtatctca  91980
gcttccactc ttggattatt tcaccctatt tctatttctg ggctgtctcc acacagttgc  92040
caggtaaccc ttttaaaaca taaagcacat cacaaagcac aaagtcctat cctcagaatc  92100
ttccagtggt tctccatcac cctaaaataa aacttaaaag ttcttttcat atcccaaaac  92160
aacatatgag gtctggcacc cagttttctt cccaatctca tcttctacta cttttccctt  92220
catttcattc acaatgtttt aaccacagta accttcttc agtactttaa acaatccaaa  92280
ctcgtttaag cgtcaagtcc ttatacttgt ttcctttgtt tagaatactg ttcacccaaa  92340
tattctcata gcttgctccc agacttcatg tctctgctga aatagaggct ccttagagag  92400
accttcccta accctaaccc taaccctata ctacttgcca tcactcttta tcctcttacc  92460
ctggattatt ttttcttgat agctcttcct accatctggc actatattac atcatatcat  92520
attaaacaca cattctttgt gcttccccac taaacaagga ccatgcaaga tggaacattg  92580
ccattttgtt cactgctgtt agcctctgtg cctaggacaa tgccagttat gcagtagtta  92640
ctcaatactt gttgaatgaa tggtgaatag aacatagaaa tttgcctatg cgtgcttttg  92700
aaaaccatat tttaatatta cgctttgtta aaaatgtgta tctttataaa tcctcatatt  92760
tccatggcaa accttatctt ctaactttc attgtcctca aagattaaga ttcttaaaca  92820
tgttcctgaa ggtgctgaga cagagcaagg ccttaaacgg gagcttcaag ttcttaggta  92880
catcatgtat tcatatgact actttgtttt tttctttaaa aaaaaaatta ttagtttta  92940
tatactccga attgctacaa ctagagacaa gcatttttcg actttactgc ctaacaggct  93000
tattaggtcc ttatttcttc cctctaatgc taatcactct ttttcataat acacactaga  93060
aaaaaaggat aaacccaact ctaagtttcc agtttgtaat ttagtttaaa cttttctaag  93120
agcatagaat gagttaaacc ttagcttccc agaggaaaat actaatgaaa gagaacaagt  93180
aattttttta ctttcagggg tctctgtagc ctgctttcat taagctcctc ttataacgaa  93240
accacacttg caaatgccat caggtcagat attaagaaaa acgtgaaggc ttttgtattc  93300
caggcttttt gtttgagaat ggtgacattg tagcattgag agtaaatgtt tacttcgata  93360
aaggctagct tgttctgatt actgtacatc actagttcat aagaaatgcc catatatttt  93420
atgaagcaat atctgcttta ttttttttaac acattatcat tgtgttctag attagctaat  93480
catcagctgg ataaagagaa agcagaatta atccatcaga tagaagctaa caaggaccaa  93540
agtggagctg aaagcaccat acctggtaat gtattttaaa aaacatgtta gctaccccca  93600
agtttttgaa tttgggtttg ccttttttttt tttttttgg ctcagatttc tgatcattgt  93660
ctccctgtaa aatcgaattc ctgataagct ttgggtcttt tgtctctctg tgctattaat  93720
ataaaaatat tcccattttt ctctttgtgt tgtttatact atagagtagc aagtacccaa  93780
gtgttcttct ctttgttctc catctgggtg ttacagattt aatcacaata cagtgctaag  93840
caatgaatac taaatctgtt gcttccagtt tctaagtata ggctctttca agtcctctga  93900
acatttttaa aaactgcaaa taagtaaata ctgcctatat ttttttccgt ttacaaagta  93960
aaaagaaaat ctttctgctc ccttccattc ccattcaaaa gtgattacta atcattcctc  94020
attcctgcat atacatacac acatatttttg tatacatata tatcacacat atgcatacat  94080
gtgtttgtat gttcatatgt acaatgtaca tatcctcatt atttgtggat tctgtatttt  94140
ctaaatcacc tcctcactaa agtgtgtatg taatcccaaa tcaacactcg cagcacattt  94200
gcaaacatcc acagagcctt ggaaagtttg aataatccaa cctacatgtc cccagcagaa  94260
gtccaacaag gcagtgctca gtatcctcat ttcagttttc atagagaaat gagcagagga  94320
tggagacagt agagggcagc acagcatagt gcaagaagct gtggctctgg ggcctggtgg  94380
aagggatttg aatcccaatt ctgaggcttg ttactgctct agccttagga gagtcatgta  94440
acacttctga atcttgtttt cttatgtaaa taaatagaat ttaccaggat gagttatctt  94500
taggatttaa gattatcatc tgtgtgagat atgtaggtgt atgtatatat atgcgtgtat  94560
gtatatatat gcgtgtatgt atatatatgc atgtctgtac atatttcccg tagcagcagt  94620
ggtttgatat tcactaattg ggctaacttt atagaccaaa actactatgg atagagaata  94680
ctttgtttgc atttacgtat atatattttc ttggcaagta acataaaatt gaactaatac  94740
tatacacatt tctagcatat ttgcctttaa cagtttatca tggacatctt ttgaggtctg  94800
ttcataaatt atctcatcca tttaataatt ccatagtgta ttattgcatg tataagcaca  94860
tcgaaccatt tatgttttga tggatattta gtttgcttcc aagtttctgc ttctataaaa  94920
tatgattaat ctattgacct aattatgcca ttgtgatagg atgatagaga tgccattctc  94980
tccaaaggat tataccaatt tatatctgaa ctatctttga ctatctcttg tagcttttttc  95040
agtatgctat gtagtcctat tactaatttg taataaaagc catcatgtgt gagttgtact  95100
agacactatg ctaattgcct tacaagcatt ctatatttac aaccatatat gataggtatt  95160
actgtctcca ttttatgtga taaacaaatt caaagtggtt aagtaaccat tccctaagcc  95220
agctaggaaa tagaggcagg attaaaatct aaatgtatga aactccacag ctccttggca  95280
ttcctagtcc ttaacccgct atgctatgct acgtcttggt aactaaaagt acatattaaa  95340
tactctcaaa atatgtctca tagcagccag cttggtatgt acactagaca cagtattaat  95400
gctgttgatg tgaggaaaat tttataattt tccttccatc catatactaa ccaggcccaa  95460
cagtgcttag cttctgagat cagagatcag gtgcatgtgc attaagggtc atatggccat  95520
agatagttct ctaatctttc cattcctcag tttcttaagg gaatttctga accctcaaaa  95580
ttccttattt cctaagtaga cagattacct gtcatttttc aaagattaag gcttaagatc  95640
aaaccagaac tgttttggaa attctaaatc actgtctata taaatggcaa gataactttt  95700
aagatattta taccaagccc agtacagtag cacaccacac ctgtaatccc agcactttgg  95760
gaggctgaag tgggtggatc acatgaggtc aggagttcga gaccactctg gccaacatgg  95820
tgaaaccctg tctctactaa aaatataaaa attagccagg catggtggca cttgcctgtt  95880
atcccagcta caagggaggc taaggcagga gaatcgcttt aacctgggag gcagtggttg  95940
ttgcagtgag ccaagattgc accactgcac tctagcctgg gcgacagagt gagactgtct  96000
caaaaaaaaa aaaaaaaaaa aagatacttg tcccagccat gaaaatgttt gctgcccctt  96060
actttcgcaa acttttagta ttttattatt tttcaatggc tgtaaaatat gacttattaa  96120
atgtagtata atataaagaa aagagatatc tagcaaagat agcattaaag caaaaatcct  96180
atttgcctgc tgataaagtt agaggtgtta acttggaggg tgaatccaat aaattagaac  96240
ttttgtgcta tatttggaga cttttgtttt cctaccaaag tatcagggct atgtcttact  96300
tatctttgta ttacacagcc tgcatgacac gttttgcaca tagtaattgc acagtaaatg  96360
tgtaataacc tacatggaat agccagtgtt gtgttggata gcgggagcat ttggctagct  96420
```

-continued

```
tatggttata gtcccttacc caacagtctg cttttcttct gttgtacttt tagtacctaa  96480
caagtttccc tggctttagg attttttcca tgtaaaattt ctatcatgtg aagaaaaaat  96540
aacttggcct acacttctaa tacctagcac atacctcttt ctgcctgcta tgaaattata  96600
atacttgatg gagggaggca gcattaagtg tttacatcct gaagtatttc agccataaca  96660
tccagtgttt tccaggttct aggtttcata aaatgtatct ctgttctcta gaacaaatcc  96720
attaccttga actcattcgt agtgggaaaa agctgagtct aatttgtatg actttttcaa  96780
cagatgctga tcaactaaag gaaaaaataa aagatctaga gacacagctc aaaatgtcag  96840
atctagaaaa gcagcatttg aaggtaatat ttaattatat tttagtatcg ttttgtgaaa  96900
acagctgttg aaaactattt tcattaccat ctttaactac gtatcctaaa aaattcagta  96960
ataacatctt atatttgacc tttatattgc aaagttaatt atgttcatct gactattcct  97020
aacatattag agttaacaaa aaattcagac tcaacatagg attaagtagt aaatttattt  97080
tttaattgta acaaatatat gccattagta tgttcttaag ttttgggtca cattggcaac  97140
agtgtcttta ttttttttt gaaattcttt tcaggaatcc taaggttata gttcccttaa  97200
aaaaatattt gctgttttac ctcttttaag actgtaaaca ggacaaaaag gcatggatat  97260
gagaattagc tagtgatcac tggctattct aaatagtcac taaggcttga attgtctctt  97320
caccagatgc ctgtcagaag tcccaaaggt ttccctgatc atattaataa ctttataaaa  97380
aattgatcat tattcattaa atattagata ttagtaagga aaatataaat gaagtctaaa  97440
ccaaaactct taaccagact aacttcaatg ttatgaatca caaaatcttt ttgattgatt  97500
gctctattga caagctctta tatgctttta gagaaagatt aagtcccatt ataagagatg  97560
ataaatttta gtcaaagact agaacacaac ttacagaata cataactgga cttgacagtt  97620
aacaacttag ttatttacac tgtacaatgg aacaaagaaa aatcttaatt cttctgcctt  97680
tattgctgta tttgaccatt caggaatact ttggctttca tatttacaat taaatctcct  97740
tgttcaaacg taaaatatgt atatttccta tatgcaactt ttaaagataa tgtttccatt  97800
aggaggaaat aaagaagctg aaaaaagaac tggaaaattt tgatccttca tttttgaag   97860
aaattgaaga tcttaagtat aattacaagg aagaagtgaa gaagaatatt ctcttagaag  97920
agaaggtaaa aaaactttca gaacaattgg gagttgaatt aactagccct gttgctgctt  97980
ctgaagagtt tgaagatgaa gaagaaagtc ctgttaattt ccccatttac taaaggtcac  98040
ctataaactt tgtttcattt aactatttat taactttata agttaaatat acttggaaat  98100
aagcagttct ccgaactgta gtatttcctt ctcactacct tgtaccttta tacttagatt  98160
ggaattctta ataaataaaa ttatatgaaa ttttcaactt attataaaag tatatacttg  98220
aagacttgtt acagccatca aataggcagt gagctctggt gaatttctct acattcataa  98280
tgctttaagt tttttaaaga atatgagggt aaattcagca attttaagat ttaaaattgg  98340
agtttatata tacttattta tacatgtgtt aagattctca aatcctatga tatatacaca  98400
gatgtagaca tacacacata taggttatga ggttgagccg tatgttttgt taaatatcta  98460
gcaaaattaa attgagctta aactatttaa ttttgaaaat tagtgacatt aaattgttgt  98520
ctttaaatta ccactcagtt atagtgaaga gaatccagcc tttgtccaag cttaggagct  98580
tactattact tatgtttta tggctagaga ttaaaattaa tttgctggtt tttaataaaa   98640
ttttgaatag gtacttgaaa ctggaaaatt catttcttca caaatggtag aaaacatatt  98700
gatgtttcat aatgaacaga aaccttgaga tatttttaaa tatggtagaa tattcaagat  98760
tagaatataa tgataaacta attttatttg cattttatac atcaaatatt atatctttga  98820
gtctaacaaa tttctgatta tctattttta aaaaatgatt aaacaaacac ttaatatcaa  98880
aggcagagtc acatttgttc aggttcatgt tgataataac tggtcttgaa ttcatgtaag  98940
tatctggaat tggccagcat aagccaagat gatggcgatg gacctggaaa gagaaaaaag  99000
gtattagctt tagcatacag atactatctt cattcactta gaaatatttg agtgcccact  99060
gtctgccagg tactgggtaa gactccactt tatcttactg ttttttttt tatagctggt   99120
cttctcctga catattacat atttgtttat tgtctatctt ccccattaga atgtgagctt  99180
catgaaggca gacaccttgt tttgttgact gtgtatgtcc agcacctgga aacatgccag  99240
gaacattatc aggggctcca taaaatgtta tgaatcatag agcctgttgc tgagtacaga  99300
ctagctacct gaaaaatgtg ggcaaggagg cattctaatt gaaaggaatg ttatatgata  99360
gaatggagtt ttttgctcta attgcaatca tgtaaatatg gttacagcaa acacagtgtg  99420
agtgtgtttg cgggggcaga ggtggagagc agttctggga aattaagtag gggccagatc  99480
atgaatgttt aatgtaactg aacagattta tgcaggaaag taatatgctc attcatttgt  99540
gaagaatgga gaggacaggg ctaaaactga aagatactat ttttggaggg tgatatgata  99600
gttaaagcat gaatcttggc ttaaattaaa attaacagtt gggaagaagt acatagatta  99660
gaactgttag gaattgataa ctggatgtat gaagtaatga aaagaggggt taaaattaat  99720
atccaagttt ttacttcagt gaattatgtg gactcagaga gttacaacta ggcccagttt  99780
tgaatattat gaatttcagg tacctgtgag aaatcaaaca gacaagtcca ggagacagaa  99840
agggaacaaa gtataagata attcattctg tatatatcaa ctgctacctt ggcactcttt  99900
ttactcaaca gattctacac tcaagtctgg gagatgctga gttaagttag tacaagatgt  99960
ctctgagagc actactgtgc aacatgaatt tccacgcagg ggatatatag ttatcacttt  100020
aattctgaag cacacctgtt atgatcgatg ccccacacaa tacacactgg gaagcactgt  100080
tttacctctt aaaaaatggt ggtacatggg atgagaaaat taaatttctt tactgcaaat  100140
aagaattgct gccatttgta gagagaattt tagtgtcact tctactctat tgtaggaata  100200
taag                                                               100204
```

TRANS-SPLICING MOLECULES

CROSS-REFERENCE TO RELATED APPLICATIONS

The instant application claims the benefit of priority to U.S. provisional application Ser. Nos. 62/658,658 and 62/658,667, both of which were filed on Apr. 17, 2018, the contents of both of which are herein incorporated by reference in their entirety.

SEQUENCE LISTING

The instant application contains a Sequence Listing which has been submitted electronically in XML format and is hereby incorporated by reference in its entirety. Said XML copy, created on May 2, 2024, is named 51502-016003_Sequence_Listing_5_2_24.xml and is 547,649 bytes in size.

FIELD OF THE INVENTION

In general, the invention features ABCA4 and CEP290 trans-splicing molecules.

BACKGROUND

Stargardt Disease is a progressive ocular disease characterized by loss of central and color vision, which can occur rapidly or over the course of multiple years. Peripheral vision generally remains intact. Various mutations along the length of the ABCA4 gene can cause Stargardt Disease. Treatments currently in development for Stargardt Disease include lentiviral delivery of ABCA4, chemically modified variants of vitamin A, and retinal pigment epithelial cell therapy.

Leber congenital amourosis 10 (LCA 10) is a condition characterized by severe visual impairment beginning in infancy. The loss of vision is associated with photoreceptor death due to ciliary defects. The most common known mutation associated with LCA 10 is a point mutation in which an adenine is replaced with a guanine at nucleotide 1,655 of intron 26 of the CEP290 gene, which results in a splice defect in which a cryptic stop codon is spliced between exons 26 and 27. This autosomal recessive mutation causes the production of a nonfunctional centrosomal protein, causing the blindness characteristic of LCA 10.

Adeno-associated viral (AAV) vector-mediated gene therapy has a proven safety profile in humans and represents a promising approach for treating a variety of genetic defects. However, AAV vectors can have limitations dictated by viral biology, such as packaging size constraints that can hinder delivery of large nucleic acid molecules, such as those necessary to replace the ABCA4 gene or the CEP290 gene. Thus, there is a need in the field for compositions and methods for correcting mutations in ABCA4 and CEP290.

SUMMARY

The present invention relates to nucleic acid trans-splicing molecules, and methods of use thereof for correcting mutations in the ABCA4 gene or the CEP290 gene. The compositions and methods provided herein can be useful in the treatment or prevention of diseases associated with mutations in ABCA4, such as Stargardt Disease (e.g., Stargardt Disease 1) or mutations in CEP290, such as LCA (e.g., LCA10).

ABCA4

In a first aspect, the invention features ABCA4 trans-splicing molecules. For example, the invention provides a nucleic acid trans-splicing molecule comprising, operatively linked in either a 3'-to-5' direction or a 5'-to-3' direction: (a) a binding domain configured to bind a target ABCA4 intron selected from the group consisting of introns 19, 22, 23, or 24; (b) a splicing domain configured to mediate trans-splicing; and (c) a coding domain comprising a functional ABCA4 exon; wherein the nucleic acid trans-splicing molecule is configured to trans-splice the coding domain to an endogenous ABCA4 exon adjacent to the target ABCA4 intron, thereby replacing the endogenous ABCA4 exon with the functional ABCA4 exon and correcting a mutation in ABCA4.

In some embodiments, the binding domain binds to the target ABCA4 intron 3' to the mutation, and wherein the mutation is in any one of ABCA4 exons 1-24 or introns 1-24. In some embodiments, the target ABCA4 intron is intron 19, the mutation is in any one of ABCA4 exons 1-19 or introns 1-19, and the coding domain comprises ABCA4 exons 1-19. In some embodiments, the binding domain is configured to bind intron 19 at a binding site comprising any one or more of nucleotides 990 to 2,174 of SEQ ID NO: 25 (e.g., any one or more of nucleotides 1,670 to 2,174 of SEQ ID NO: 25, e.g., any one or more of nucleotides 1,810 to 2,000 of SEQ ID NO: 25, e.g., any one or more of nucleotides 1,870 to 2,000 of SEQ ID NO: 25, e.g., any one or more of nucleotides 1,920 to 2,000 of SEQ ID NO: 25.

In some embodiments, the target ABCA4 intron is intron 23, the mutation is in any one of ABCA4 exons 1-23 or introns 1-23, and/or the coding domain comprises ABCA4 exons 1-23. In some embodiments, the binding domain is configured to bind intron 23 at a binding site comprising any one or more of nucleotides 80 to 570 or nucleotides 720 to 1,081 of SEQ ID NO: 29.

In some embodiments, the binding domain is configured to bind ABCA4 intron 23 at a binding site comprising any one or more of nucleotides 261 to 410 of SEQ ID NO: 29 (e.g., from 1 to 200, from 6 to 150, from 12 to 100, or from 20 to 80 nucleotides of a binding site within or encompassing nucleotides 261 to 410 of SEQ ID NO: 29, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 261 to 410 of SEQ ID NO: 29, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 261 to 410 of SEQ ID NO: 29). For example, in particular embodiments, the binding site comprises six or more of nucleotides 261 to 410 of SEQ ID NO: 29. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 261 to 410 of SEQ ID NO: 29, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind ABCA4 intron 23 at a binding site comprising any one or more of nucleotides 801 to 950 of SEQ ID NO: 29 (e.g., from 1 to 200, from 6 to 150, from 12 to 100, or from 20 to 80 nucleotides of a binding site within or encompassing nucleotides 801 to 950 of SEQ ID NO: 29, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 801 to 950 of SEQ ID NO: 29, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 801 to 950 of SEQ ID NO: 29). For example, in particular embodiments, the binding site comprises six or more of nucleotides 801 to 950 of SEQ ID NO: 29. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 801 to 950 of SEQ ID NO: 29, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind ABCA4 intron 23 at a binding site comprising any one or more of nucleotides 841 to 990 of SEQ ID NO: 29 (e.g., from 1 to 200, from 6 to 150, from 12 to 100, or from 20 to 80 nucleotides of a binding site within or encompassing nucleotides 841 to 990 of SEQ ID NO: 29, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 841 to 990 of SEQ ID NO: 29, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 841 to 990 of SEQ ID NO: 29). For example, in particular embodiments, the binding site comprises six or more of nucleotides 841 to 990 of SEQ ID NO: 29. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 841 to 990 of SEQ ID NO: 29, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In other embodiments, the target ABCA4 intron is intron 24, the mutation is in any one of ABCA4 exons 1-24 or introns 1-24, and the coding domain comprises ABCA4 exons 1-24. In some embodiments, the binding domain is configured to bind intron 24 at a binding site comprising any one or more of nucleotides 600 to 1,250 or nucleotides 1,490 to 2,660 of SEQ ID NO: 30. In other embodiments, the binding site comprises any one or more of nucleotides 1,000 to 1,200 of SEQ ID NO: 30.

In some embodiments, the binding domain binds to the target ABCA4 intron 5' to the mutation, and wherein the mutation is in any one of ABCA4 exons 23-50 or introns 22-49. For example, in some embodiments, the target ABCA4 intron is intron 23, the mutation is in any one of ABCA4 exons 24-50 or introns 23-49, and the coding domain comprises ABCA4 exons 24-50. In some embodiments, the binding domain is configured to bind intron 23 at a binding site comprising any one or more of nucleotides 80 to 1,081 of SEQ ID NO: 29. In some embodiments, the binding site comprises any one or more of nucleotides 230 to 1,081 of SEQ ID NO: 29, e.g., any one or more of nucleotides 250 to 400 of SEQ ID NO: 29 or any one or more of nucleotides 690 to 850 of SEQ ID NO: 29.

In some embodiments, the target ABCA4 intron is intron 24, the mutation is in any one of ABCA4 exons 25-50 or introns 24-49, and the coding domain comprises ABCA4 exons 25-50. In some embodiments, the binding domain is configured to bind intron 24 at a binding site comprising any one or more of nucleotides 1 to 250, nucleotides 300 to 2,100, or nucleotides 2,200 to 2,692 of SEQ ID NO: 30. In some embodiments, the binding site comprises any one or more of nucleotides 360 to 610 of SEQ ID NO: 30. In other embodiments, the binding site comprises any one or more of nucleotides 750 to 1,110 of SEQ ID NO: 30.

In another aspect, the invention features a nucleic acid trans-splicing molecule comprising, operatively linked in a 5'-to-3' direction: (a) a binding domain configured to bind ABCA4 intron 22 at a binding site comprising any one or more of nucleotides 60 to 570, 600 to 800, or 900 to 1,350 of SEQ ID NO: 28; (b) a splicing domain configured to mediate trans-splicing; and (c) a coding domain comprising functional ABCA4 exons 23-50; wherein the nucleic acid trans-splicing molecule is configured to trans-splice the coding domain to endogenous ABCA4 exon 22, thereby replacing endogenous ABCA4 exons 23-50 with the functional ABCA4 exons 23-50. In some embodiments, the binding site comprises any one or more of nucleotides 70-250 of SEQ ID NO: 28.

In yet another aspect, the invention features a nucleic acid trans-splicing molecule comprising, operatively linked in a 3'-to-5' direction: (a) a binding domain configured to bind ABCA4 intron 22 at a binding site comprising any one or more of nucleotides 1 to 510 or 880 to 1,350 of SEQ ID NO: 28; (b) a splicing domain configured to mediate trans-splicing; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In some embodiments, the binding domain is configured to bind ABCA4 intron 22 at a binding site comprising any one or more of nucleotides 1041 to 1190 of SEQ ID NO: 28 (e.g., from 1 to 200, from 6 to 150, from 12 to 100, or from 20 to 80 nucleotides of a binding site within or encompassing nucleotides 1041 to 1190 of SEQ ID NO: 28, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 1041 to 1190 of SEQ ID NO: 28, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 1041 to 1190 of SEQ ID NO: 28). In particular embodiments, the binding site comprises six or more of nucleotides 1041 to 1190 of SEQ ID NO: 28. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 1041 to 1190 of SEQ ID NO: 28, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind any one or more of nucleotides 1171 to 1320 of SEQ ID NO: 28 (e.g., from 1 to 200, from 6 to 150, from 12 to 100, or from 20 to 80 nucleotides of a binding site within or encompassing nucleotides 1171 to 1320 of SEQ ID NO: 28, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 1171 to 1320 of SEQ ID NO: 28, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 1171 to 1320 of SEQ ID NO: 28). In particular embodiments, the binding site comprises six or more of nucleotides 1171 to 1320 of SEQ ID NO: 28. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 1171 to 1320 of SEQ ID NO: 28, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In some embodiments, the binding domain is configured to bind any one or more of nucleotides 1201 to 1350 of SEQ ID NO: 28 (e.g., from 1 to 200, from 6 to 150, from 12 to 100, or from 20 to 80 nucleotides of a binding site within or encompassing nucleotides 1201 to 1350 of SEQ ID NO: 28, e.g., from 1 to 6, from 6 to 12, from 12 to 18, from 18 to 24, from 24 to 50, from 50 to 100, from 100 to 150, or from 150 to 200 nucleotides of a binding site within or encompassing nucleotides 1201 to 1350 of SEQ ID NO: 28, e.g., at least one, at least two, at least three, at least four, at least five, at least six, at least seven, at least eight, at least nine, at least 10, at least 12, at least 15, at least 20, at least 25, at least 30, at least 40, at least 50, at least 60, at least 70, at least 80, at least 90, at least 100, at least 120, at least 150, or at least 200 nucleotides of a binding site within or encompassing nucleotides 1201 to 1350 of SEQ ID NO: 28). In particular embodiments, the binding site comprises six or more of nucleotides 1201 to 1350 of SEQ ID NO: 28. In some embodiments, the binding domain comprises six or more consecutive nucleic acid residues that are complementary to (e.g., antisense to) the six or more nucleotides of the binding site. In some embodiments, the binding domain comprises a set of consecutive nucleic acid residues that are complementary to a corresponding set of complementary nucleotides of an ABCA4 binding site having one or more of nucleotides 1201 to 1350 of SEQ ID NO: 28, wherein the set of consecutive nucleic acid residues of the binding domain is from 6 to 500 residues in length (e.g., from 8 to 400, from 12 to 300, from 16 to 200, from 24 to 280, or from 50 to 150 residues in length, e.g., from 100 to 200, from 6 to 10, from 10 to 20, from 20 to 30, from 30 to 40, from 40 to 50, from 50 to 80, from 80 to 100, from 100 to 120, from 120 to 150, from 150 to 200, or from 200 to 300 residues in length, e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, or more residues in length).

In any of the preceding embodiments, the binding domain can be 20-1,000 nucleotides in length (e.g., 25-900 nucleotides in length, 30-800 nucleotides in length, 40-700 nucleotides in length, 50-600 nucleotides in length, 75-500 nucleotides in length, 100-400 nucleotides in length, 125-200 nucleotides in length, or about 150 nucleotides in length, e.g., 20-30 nucleotides in length, 30-40 nucleotides in length, 40-50 nucleotides in length, 50-75 nucleotides in length, 75-100 nucleotides in length, 125-150 nucleotides in length, 150-175 nucleotides in length, 175-200 nucleotides in length, 200-250 nucleotides in length, 250-500 nucleotides in length, 500-750 nucleotides in length, or 750-1,000 nucleotides in length).

In some embodiments, the coding domain is a cDNA sequence. In some embodiments, the coding domain comprises a naturally-occurring sequence. In other embodiments, the coding domain includes a codon-optimized sequence. In some embodiments, the trans-splicing molecule includes an artificial intron that comprises a spacer sequence.

In some embodiments of any of the preceding methods, the nucleic acid trans-splicing molecule is from 3,000 to 4,000 nucleotides in length (e.g., 3,100-3,900 nucleotides in length, 3,200-3,800 nucleotides in length, 3,300-3,700 nucleotides in length, 3,400-3,600 nucleotides in length, or about 3,500 nucleotides in length, e.g., 3,000-3,100 nucleotides in length, 3,100-3,200 nucleotides in length, 3,200-3,300 nucleotides in length, 3,300-3,400 nucleotides in length, 3,400-3,500 nucleotides in length, 3,500-3,600 nucleotides in length, 3,600-3,700 nucleotides in length, 3,800-3,900 nucleotides in length, or 3,900-4,000 nucleotides in length).

In some embodiments, the mutation in the ABCA4 gene is associated with Stargardt Disease. In some embodiments, the mutation in the ABCA4 gene associated with Stargardt Disease is expressed in a photoreceptor cell.

In another aspect, provided herein is a nucleic acid trans-splicing molecule comprising, operatively linked in a 3'-to-5' direction: (a) a binding domain configured to bind ABCA4 intron 23 at a binding site comprising six or more of nucleotides 261 to 410 of SEQ ID NO: 29, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-23; wherein the nucleic acid trans-splicing molecule is configured to trans-splice the coding domain to endogenous ABCA4 exon 24, thereby replacing endogenous ABCA4 exons 1-23 with the functional ABCA4 exons 1-23.

In another aspect, the invention provides a nucleic acid trans-splicing molecule comprising, operatively linked in a 3'-to-5' direction: (a) a binding domain configured to bind ABCA4 intron 23 at a binding site comprising six or more of nucleotides 801 to 950 of SEQ ID NO: 29, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-23; wherein the nucleic acid trans-splicing molecule is configured to trans-splice the coding domain to endogenous ABCA4 exon 24, thereby replacing endogenous ABCA4 exons 1-23 with the functional ABCA4 exons 1-23.

In another aspect, provided herein is a nucleic acid trans-splicing molecule comprising, operatively linked in a 3'-to-5' direction: (a) a binding domain configured to bind ABCA4 intron 23 at a binding site comprising six or more of nucleotides 841 to 990 of SEQ ID NO: 29, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-23; wherein the nucleic acid trans-splicing molecule is configured to trans-splice the coding domain to endogenous ABCA4 exon 24, thereby replacing endogenous ABCA4 exons 1-23 with the functional ABCA4 exons 1-23.

In another aspect, the invention provides a nucleic acid trans-splicing molecule comprising, operatively linked in a 3'-to-5' direction: (a) a binding domain configured to bind ABCA4 intron 22 at a binding site comprising six or more of nucleotides 1041 to 1190 of SEQ ID NO: 28, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In another aspect, the invention features a nucleic acid trans-splicing molecule comprising, operatively linked in a 3'-to-5' direction: (a) a binding domain configured to bind ABCA4 intron 22 at a binding site comprising six or more of nucleotides 1171 to 1320 of SEQ ID NO: 28, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In yet another aspect, provided herein is a nucleic acid trans-splicing molecule comprising, operatively linked in a 3'-to-5' direction: (a) a binding domain configured to bind ABCA4 intron 22 at a binding site comprising six or more of nucleotides 1201 to 1350 of SEQ ID NO: 28, wherein the binding domain comprises six or more consecutive nucleic acid residues that are complementary to the six or more nucleotides of the binding site; (b) an artificial intron comprising a splicing domain; and (c) a coding domain comprising functional ABCA4 exons 1-22; wherein the nucleic acid trans-splicing molecule is configured to trans-splice the coding domain to endogenous ABCA4 exon 23, thereby replacing endogenous ABCA4 exons 1-22 with the functional ABCA4 exons 1-22.

In another aspect, the invention features a proviral plasmid including the nucleic acid trans-splicing molecule of any of the preceding embodiments.

In yet another aspect, the invention features an adeno-associated virus (AAV) comprising the nucleic acid molecule of any of the preceding embodiments. In some embodiments, the AAV preferentially targets a photoreceptor cell. In some embodiments, the AAV comprises an AAV5 capsid protein, an AAV8 capsid protein, an AAV8(b) capsid protein, or an AAV9 capsid protein.

In another aspect, the invention features a pharmaceutical composition comprising the nucleic acid trans-splicing molecule, the proviral plasmid, or the AAV of any of the preceding aspects.

In another aspect, provided herein is a pharmaceutical composition having any of the 5' nucleic acid trans-splicing molecules of any the preceding embodiments and a 3' nucleic acid trans-splicing molecule of any of the preceding embodiments.

In yet another aspect, the invention features a method of correcting a mutation in an ABCA4 gene in a target cell of a subject by administering to the subject the pharmaceutical composition of any of the preceding aspects.

In another aspect, provided herein is a method of correcting a mutation in any one or more of ABCA4 exons 1-24 in a subject in need thereof by administering to the subject a pharmaceutical composition having the nucleic acid trans-splicing molecule of any of the preceding embodiments. In particular embodiments, the mutated ABCA4 exon to be corrected by an ABCA4 trans-splicing molecule of the invention is exon 2. Additionally or alternatively, the mutated ABCA4 exon to be corrected by an ABCA4 trans-splicing molecule of the invention is exon 3. Additionally or alternatively, the mutated ABCA4 exon to be corrected by an ABCA4 trans-splicing molecule of the invention is exon 4.

In another aspect, the invention includes a method of correcting a mutation in any one or more of ABCA4 exons 23-50 in a subject in need thereof by administering to the subject a pharmaceutical composition comprising the nucleic acid trans-splicing molecule of any of the preceding embodiments.

In another aspect, the invention features a method of correcting a mutation in any one of ABCA4 exons 1-24 and a second mutation in any one of exons 23-50 in a subject in need thereof, the method comprising administering to the subject the pharmaceutical composition having a 5' nucleic acid trans-splicing molecules of any the preceding embodiments and a 3' nucleic acid trans-splicing molecule of any of the preceding embodiments.

In yet another embodiment, the invention features a method of treating a subject having a disorder associated with a mutation in ABCA4, the method comprising administering to the subject the any of the preceding pharmaceutical compositions. In some embodiments, a subject having a disorder associated with a mutation in any one or more of ABCA4 exons 1-24 or introns 1-24 is treated by administering a pharmaceutical composition comprising the nucleic acid trans-splicing molecule of any of the preceding embodiments. In some embodiments, a subject having a disorder associated with a mutation in any one or more of ABCA4 exons 23-50 or introns 22-49 is treated by administering a pharmaceutical composition comprising the nucleic acid trans-splicing molecule of any of the preceding embodiments.

In another aspect, the invention features a method of treating a subject having a disorder associated with a first mutation in any one of ABCA4 exons 1-24 and a second mutation in any one of exons 23-50 by administering to the subject the pharmaceutical composition having a 5' nucleic acid trans-splicing molecules of any the preceding embodiments and a 3' nucleic acid trans-splicing molecule of any of the preceding embodiments.

In any of the preceding methods, the subject may have Stargardt Disease. In some embodiments, the composition is administered by subretinal injection, intravitreal injection, or intravenous injection.

In some embodiments of any of the preceding methods, the subject exhibits at least 1% increase in ABCA4 protein expression after administration (e.g., a 1-5% increase, a 5-10%, a 10-15% increase, a 15-20% increase, a 20-25% increase, a 25-50% increase, or a 50-100% increase in ABCA4 protein expression after administration, e.g., relative to an ABCA4 protein expression in the same subject prior to administration, or relative to a reference sample, reference subject, or a reference group of subjects).

CEP290

In another aspect, the invention features CEP290 trans-splicing molecules. For example, the invention provides a nucleic acid trans-splicing molecule comprising, operatively linked in a 3'-to-5' direction: (a) a binding domain configured to bind CEP290 intron 26 at a binding site comprising any one or more of nucleotides 4,800 to 5,838 of SEQ ID NO: 85; (b) a splicing domain configured to mediate trans-splicing; and (c) a coding domain comprising functional CEP290 exons 2-26; wherein the nucleic acid trans-splicing molecule is configured to trans-splice the coding domain to endogenous CEP290 exon 27, thereby replacing endogenous CEP290 exons 2-26 with the functional CEP290 exons 2-26 and correcting the pathogenic point mutation. In some embodiments, the pathogenic point mutation is an A-to-G mutation at nucleotide 1,655 of SEQ ID NO: 85.

In some embodiments, the binding site comprises any one or more of nucleotides 4,980 to 5,838 of SEQ ID NO: 85. In some embodiments, the binding site comprises any one or more of nucleotides 5,348 to 5,838 of SEQ ID NO: 85. In some embodiments, the binding site comprises any one or more of nucleotides 5,348 to 5,700 of SEQ ID NO: 85. In some embodiments, the binding site comprises any one or more of nucleotides 5,400 to 5,600 of SEQ ID NO: 85. In some embodiments, the binding site comprises any one or more of nucleotides 5,460 to 5,560 of SEQ ID NO: 85. In some embodiments, the binding site comprises nucleotide 5,500 of SEQ ID NO: 85.

In another aspect, the invention features a nucleic acid trans-splicing molecule comprising, operatively linked in a 3'-to-5' direction: (a) a binding domain configured to bind CEP290 at any one of target introns 27, 28, 29, or 30; (b) a splicing domain configured to mediate trans-splicing; and (c) a coding domain comprising functional CEP290 exons 5' to the target intron; wherein the nucleic acid trans-splicing molecule is configured to trans-splice the coding domain to endogenous CEP290, thereby replacing endogenous CEP290 exons 5' to the target intron with the functional CEP290 exons and correcting the pathogenic point mutation. In some embodiments, the pathogenic point mutation is an A-to-G mutation at nucleotide 1,655 of SEQ ID NO: 85.

In some embodiments, the target intron is intron 27, the coding domain comprising functional CEP290 exons 2-27, and the nucleic acid trans-splicing molecule is configured to replace endogenous CEP290 exons 2-27 with the functional CEP290 exons 2-27. In some embodiments, the binding domain is configured to bind intron 27 at a binding site comprising any one or more of nucleotides 120 to 680, nucleotides 710 to 2,200, or nucleotides 2,670 to 2,910 of SEQ ID NO: 86. In some embodiments, the binding site comprises any one or more of nucleotides 790 to 2,100 of SEQ ID NO: 86, e.g., any one or more of nucleotides 1,020 to 1,630 of SEQ ID NO: 86. In other embodiments, the binding site comprises any one or more of nucleotides 1,670 to 2,000 of SEQ ID NO: 86.

In some embodiments, the target intron is intron 28, the coding domain comprising functional CEP290 exons 2-28, and the nucleic acid trans-splicing molecule is configured to replace endogenous CEP290 exons 2-28 with the functional CEP290 exons 2-28. In some embodiments, the binding domain is configured to bind intron 28 at a binding site comprising any one or more of nucleotides 1 to 390, nucleotides 410 to 560, or nucleotides 730 to 937 of SEQ ID NO: 87. In some embodiments, the binding site comprises any one or more of nucleotides 1 to 200 of SEQ ID NO: 87. In other embodiments, the binding site comprises any one or more of nucleotides 720 to 900 of SEQ ID NO: 87.

In some embodiments, the target intron is intron 29, the coding domain comprising functional CEP290 exons 2-29, and the nucleic acid trans-splicing molecule is configured to replace endogenous CEP290 exons 2-29 with the functional CEP290 exons 2-29. In some embodiments, the binding domain is configured to bind intron 29 at a binding site comprising any one or more of nucleotides 1 to 600, nucleotides 720 to 940, or nucleotides 1,370 to 1,790 of SEQ ID NO: 88.

In some embodiments, the target intron is intron 30, the coding domain comprising functional CEP290 exons 2-30, and the nucleic acid trans-splicing molecule is configured to replace endogenous CEP290 exons 2-30 with the functional CEP290 exons 2-30. In some embodiments, the binding domain is configured to bind intron 29 at a binding site comprising any one or more of nucleotides 880 to 1,240 of SEQ ID NO: 89, e.g., any one or more of nucleotides 950 to 1,240 of SEQ ID NO: 89, e.g., any one or more of nucleotides 1,060 to 1,240 of SEQ ID NO: 89.

In any of the preceding embodiments, the binding domain is 20-1,000 nucleotides in length (e.g., 25-900 nucleotides in length, 30-800 nucleotides in length, 40-700 nucleotides in length, 50-600 nucleotides in length, 75-500 nucleotides in length, 100-400 nucleotides in length, 125-200 nucleotides in length, or about 150 nucleotides in length, e.g., 20-30 nucleotides in length, 30-40 nucleotides in length, 40-50 nucleotides in length, 50-75 nucleotides in length, 75-100 nucleotides in length, 125-150 nucleotides in length, 150-175 nucleotides in length, 175-200 nucleotides in length, 200-250 nucleotides in length, 250-500 nucleotides in length, 500-750 nucleotides in length, or 750-1,000 nucleotides in length).

In some embodiments, the coding domain is a cDNA sequence. In some embodiments, the coding domain is a naturally-occurring sequence. In other embodiments, the coding domain is a codon-optimized sequence.

In some embodiments, an artificial intron comprises an artificial intron and a spacer sequence.

In any of the preceding embodiments, the nucleic acid trans-splicing molecule may be 3,000 to 4,000 nucleotides in length.

In any of the preceding embodiments, the mutated CEP290 exon may be associated with LCA 10. In some embodiments, the mutated CEP290 exon associated with LCA 10 is expressed in a photoreceptor cell.

In another aspect of the invention, provided herein is a proviral plasmid comprising the nucleic acid trans-splicing molecule of any of the preceding aspects.

In yet another aspect, the invention provides an adeno-associated virus (AAV) comprising the nucleic acid molecule of any of the preceding aspects. In some embodiments, the AAV preferentially targets a photoreceptor cell. In some embodiments, the AAV comprises an AAV5 capsid protein, an AAV8 capsid protein, an AAV8(b) capsid protein, or an AAV9 capsid protein.

In another aspect, the invention features a pharmaceutical composition comprising the nucleic acid trans-splicing molecule, the proviral plasmid, or the AAV of any of the preceding aspects.

In another aspect, featured herein are methods of correcting a pathogenic point mutation in CEP290 intron 26 in a target cell of a subject, the methods comprising administering to the subject the nucleic acid trans-splicing molecule, the proviral plasmid, the AAV, or the pharmaceutical composition of any of the preceding aspects. In some embodiments, the subject has LCA 10.

In yet another aspect, the invention provides a method of treating a subject having LCA 10 caused by a pathogenic point mutation in CEP290 intron 26, the method comprising administering to the subject the nucleic acid trans-splicing molecule, the proviral plasmid, the AAV, or the pharmaceutical composition of any of the preceding aspects.

In any of the preceding methods, the pathogenic point mutation may be an A-to-G mutation at nucleotide 1,655 of CEP290 intron 26 (SEQ ID NO: 85). In some embodiments, the nucleic acid trans-splicing molecule, the proviral plasmid, the AAV, or the pharmaceutical composition is administered by subretinal injection, intravitreal injection, or intravenous injection.

In another aspect, the invention provides a kit comprising any one or more of the aforementioned nucleic acid trans-splicing molecules, proviral plasmids, AAVs, or pharmaceutical compositions, wherein the kit further includes instructions for using the one or more nucleic acid trans-splicing molecules, proviral plasmids, AAVs, or pharmaceutical compositions for correcting a mutation in a CEP290 gene of a subject (e.g., a mutation associated with a disorder, such as LCA 10).

BRIEF DESCRIPTION OF THE DRAWINGS

FIGS. 12A and 12B show site-specific guides (FIG. 12A) that were designed to insert the CAG promotor and a puromycin selectable marker using homology arms (FIG. 12B).

FIG. 14A shows RNA expression and FIG. 14B shows protein expression of the cell lines. Membrane preparations of the indicated cells lines were probed for ABCA4 protein using a rabbit polyclonal antibody to ABCA4 (Abcam, ab72955). Exposure time is 23 seconds. 293 cells are the parental cell that does not express ABCA4. The top band is non-specific background present in all cells.

FIG. 18 is a set of tables showing that the mutation analyses from FIGS. 17A and 17B confirmed that exons 3 and 4 were targeted and interrupted in alleles in the 17+06 and 17+21 cell lines.

FIG. 19A shows a generic trans-splicing molecule including a codon optimized exon (or set of exons), a binding domain that hybridizes to a target RNA, and an artificial intron linker. FIG. 19B shows various trans-splicing molecules that target particular regions within introns 22 and 23 of ABCA4.

FIGS. 20A and 20B show protein and RNA levels, respectively, of intron 22 trans-splicing reactions, and FIGS. 20C and 20D show protein and RNA levels, respectively, of intron 23 trans-splicing reactions.

DETAILED DESCRIPTION

Figure 1:
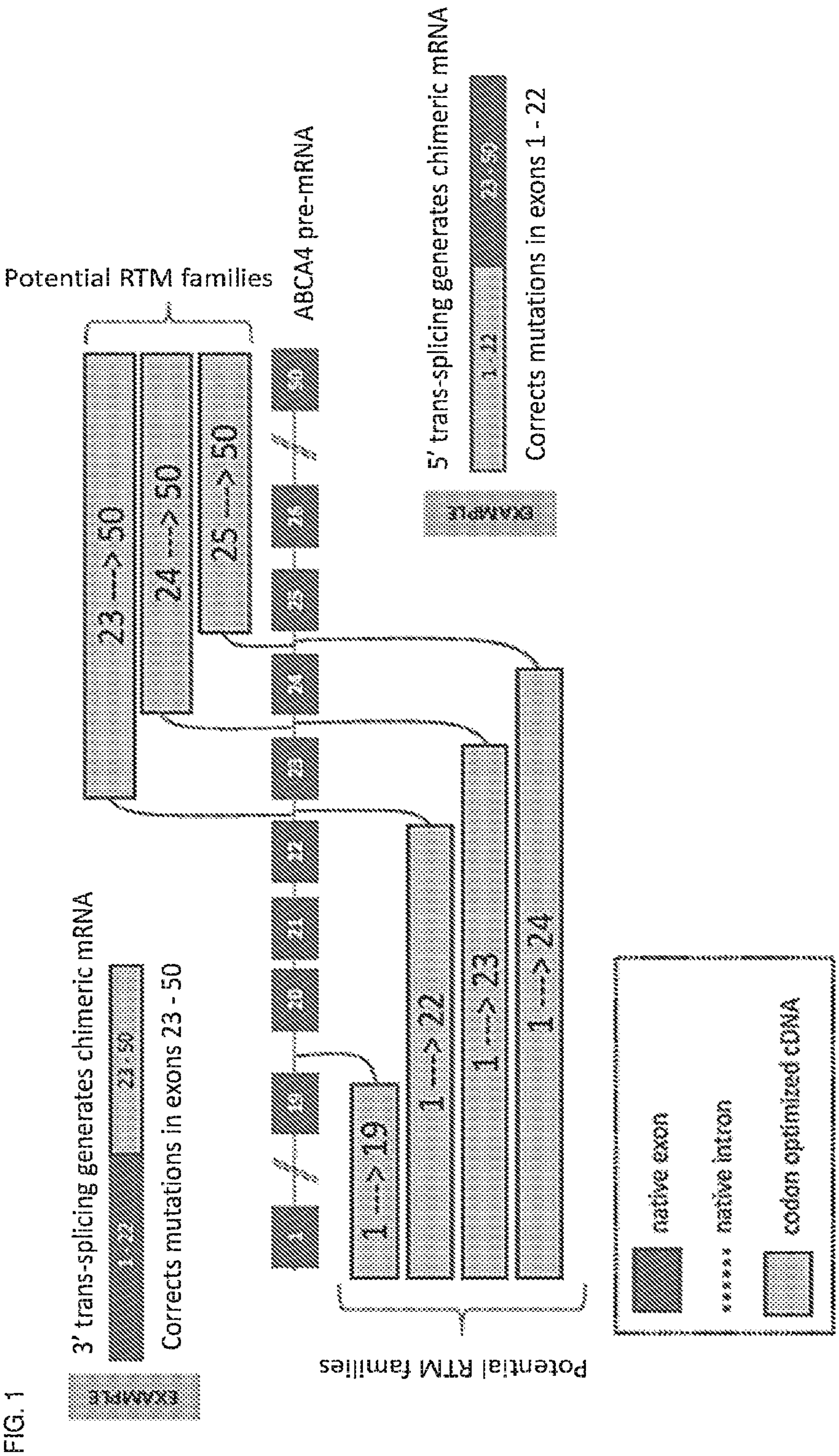
FIG. 1 is a schematic drawing of several exemplary nucleic acid trans-splicing molecules for correcting a mutated ABCA4 exon with a functional ABCA4 exon. Dark shaded boxes represent native ABCA4 exons. Dashed lines joining the dark shaded boxes represent native introns. Light shaded boxes with dark borders represent functional ABCA4 exons within a nucleic acid trans-splicing molecule. A splicing domain, represented by a curved line, is attached to one end of each of the functional ABCA4 exons and leads to an intron of the ABCA4 pre-mRNA.

The compositions and methods described herein involve trans-splicing molecules (e.g., pre-mRNA trans-splicing molecules delivered by adeno-associated virus (AAV)) for treating diseases or disorders caused by a mutation in the ABCA4 gene. The methods and compositions described herein employ pre-mRNA trans-splicing as a gene therapy (e.g., ex vivo and in vivo gene therapy) for the treatment of diseases caused by an ABCA4 mutation, such as Stargardt Disease (e.g., Stargardt Disease 1).

Alternatively, compositions and methods described herein involve trans-splicing molecules (e.g., pre-mRNA trans-splicing molecules delivered by adeno-associated virus (AAV)) for treating diseases or disorders caused by a mutation in the CEP290 gene, such as LCA 10. These methods employ pre-mRNA trans-splicing as a gene therapy (e.g., ex vivo and in vivo gene therapy) for the treatment of diseases caused by a CEP290 mutation, such as LCA 10.

The trans-splicing molecules and methods of use thereof exemplified herein provide several advantages over conventional therapies. First, the use of the trans-splicing molecule delivery by AAV provides efficient and specific delivery of a gene therapy to photoreceptors, while overcoming difficulties associated with the packaging limit of AAV. Second, these compositions and methods permit correction of the genetic defect at the source. Additionally, the compositions and methods provided herein are useful to treat any type of mutation in ABCA4 (or other large cDNAs/transgene cassettes). Correction of the defect in photoreceptors provides secondary rescue to retinal pigment epithelium cells. Further, the present methods and compositions are generally immunologically benign. The use of subretinal delivery and other features renders the effect specific to target cells, such as photoreceptors, so that toxicity due to off-target splicing is reduced. Further, unlike nucleases, trans-splicing does not require genomic alterations. Finally, RNA repair does not require cell division, whereas DNA repair methodologies (such as CRISPR-Cas9 or zinc fingers) have a requirement for the cell to go through mitosis for homology directed repair to occur, which is a disadvantage in post-mitotic tissues like the retina.

I. Definitions

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. In the event of any conflicting definitions between those set forth herein and those of a referenced publication, the definition provided herein shall control.

A "nucleic acid trans-splicing molecule" or "trans-splicing molecule" has three main elements: (a) a binding domain that confers specificity by tethering the trans-splicing molecule to its target gene (e.g., pre-mRNA); (b) a splicing domain (e.g., a splicing domain having a 3' or 5' splice site); and (c) a coding sequence configured to be trans-spliced onto the target gene, which can replace one or more exons in the target gene (e.g., one or more mutated exons). A "pre-mRNA trans-splicing molecule" or "RTM" refers to a nucleic acid trans-splicing molecule that targets pre-mRNA. In some embodiments, a trans-splicing molecule, such as an RTM, can include cDNA, e.g., as part of a functional exon (e.g., a functional ABCA4 or CEP290 exon, e.g., a codon-optimized exon) for replacement or correction of a mutated ABCA4 exon or CEP290).

By "trans-splicing" is meant joining of a nucleic acid molecule containing one or more exons (e.g., exogenous exons, e.g., exons that are part of a coding domain of a trans-splicing molecule) to a first portion of a separate RNA molecule (e.g., a pre-mRNA molecule, e.g., an endogenous pre-mRNA molecule) by replacing a second portion of the RNA molecule through a spliceosome-mediated mechanism.

"Binding" between a binding domain and a target intron, as used herein, refers to hydrogen bonding between the binding domain and the target intron in a degree sufficient to mediate trans-splicing by bringing the trans-splicing molecule into association with the target gene (e.g., pre-mRNA). In some embodiments, the hydrogen bonds between the binding domain and the target intron are between nucleotide bases that are complementary to and in antisense orientation from one another (e.g., hybridized to one another).

As used herein, an "artificial intron" refers to a nucleic acid sequence that links (directly or indirectly) a binding domain to a coding domain. An artificial intron includes a splicing domain and may further include one or more spacer sequences and/or other regulatory elements.

A "splicing domain," as used herein, refers to a nucleic acid sequence having motifs that are recognized by the spliceosome and mediate trans-splicing. A splicing domain includes a splice site (e.g., a single splice site, i.e., one and only one splice site), which can be a 3' splice site or a 5' splice site. A splicing domain may include other regulatory elements. For example, in some embodiments, a splicing domain includes splicing enhancers (e.g., exonic splicing enhancers (ESE) or intronic splicing enhancers (ISE)). In some embodiments, a splicing domain includes a branch point (e.g., a strong conserved branch point) or branch site sequence and/or a polypyrimidine tract (PPT). In some embodiments, a splicing domain of a 5' trans-splicing molecule does not contain the branch point or PPT, but comprises a 5' splice acceptor or a 3' splice donor.

As used herein, a "mutation" refers to any aberrant nucleic acid sequence that causes a defective protein product (e.g., a non-functional protein product, a protein product having reduced function, a protein product having aberrant function, and/or a protein product that is produced in less than normal or greater than normal quantities). Mutations include base pair mutations (e.g., single nucleotide polymorphisms), missense mutations, frameshift mutations, deletions, insertions, and splice mutations. In some embodiments, a mutation refers to a nucleic acid sequence that is different in one or more portions of its sequence than a corresponding wildtype nucleic acid sequence or functional variant thereof. In some embodiments, a mutation refers to a nucleic acid sequence that encodes a protein having an amino acid sequence that is different than a corresponding wildtype protein or functional variant thereof. A "mutated exon" (e.g., a mutated ABCA4 exon) refers to an exon containing a mutation or an exon sequence that reflects a mutation in a different region, such as a cryptic exon resulting from a mutation in an intron.

As used herein, the term "ABCA4" refers to a polynucleotide (e.g., RNA (e.g., pre-mRNA or mRNA) or DNA) that encodes retinal-specific ATP-binding cassette transporter. An exemplary pre-mRNA sequence of a functional human ABCA4 gene is given by SEQ ID NO: 6. An exemplary genomic DNA sequence of a functional (wildtype) human ABCA4 gene is given by NCBI Reference Sequence: NG_009073. The amino acid sequence of an exemplary ABCA4 protein is given by Protein Accession No. P78363.

Exons and introns of ABCA4 are identified herein as set forth in Table 1, below, which can be mapped onto the ABCA4 pre-mRNA molecule of SEQ ID NO: 6. Each exon and intron of ABCA4 are identified herein according to the reference number in the first (left-hand) column. The size of each exon and intron (base pairs; bp) are indicated in the second and third columns. The fourth column indicates the length of a cDNA molecule corresponding to exons 5' to the corresponding intron number. The fifth column indicates the length of a cDNA molecule corresponding to mRNA 3' to the corresponding intron number.

TABLE 1

ABCA4 exon and intron summary

| Exon/Intron Number | Exon Size | Intron Size | 5' cDNA | 3' cDNA |
|---|---|---|---|---|
| 1 | 153 | 7,913 | 66 | 6,822 |
| 2 | 94 | 1,393 | 160 | 6,756 |
| 3 | 142 | 2,721 | 302 | 6,662 |
| 4 | 140 | 5,434 | 442 | 6,520 |
| 5 | 128 | 4,023 | 570 | 6,380 |

TABLE 1-continued

ABCA4 exon and intron summary

| Exon/Intron Number | Exon Size | Intron Size | 5' cDNA | 3' cDNA |
|---|---|---|---|---|
| 6 | 198 | 15,352 | 768 | 6,252 |
| 7 | 90 | 2,633 | 858 | 6,054 |
| 8 | 241 | 1,016 | 1,099 | 5,964 |
| 9 | 140 | 615 | 1,239 | 5,723 |
| 10 | 117 | 702 | 1,356 | 5,583 |
| 11 | 198 | 14,372 | 1,554 | 5,466 |
| 12 | 206 | 358 | 1,760 | 5,268 |
| 13 | 177 | 1,817 | 1,937 | 5,062 |
| 14 | 223 | 3,714 | 2,160 | 4,885 |
| 15 | 222 | 1,285 | 2,382 | 4,662 |
| 16 | 205 | 3,412 | 2,587 | 4,440 |
| 17 | 66 | 2,675 | 2,653 | 4,235 |
| 18 | 90 | 1,774 | 2,743 | 4,169 |
| 19 | 175 | 2,174 | 2,918 | 4,079 |
| 20 | 132 | 1,137 | 3,050 | 3,904 |
| 21 | 140 | 437 | 3,190 | 3,772 |
| 22 | 138 | 1,358 | 3,328 | 3,632 |
| 23 | 194 | 1,081 | 3,522 | 3,494 |
| 24 | 85 | 2,692 | 3,607 | 3,300 |
| 25 | 206 | 356 | 3,813 | 3,215 |
| 26 | 49 | 4,696 | 3,862 | 3,009 |
| 27 | 266 | 657 | 4,128 | 2,960 |
| 28 | 125 | 469 | 4,253 | 2,694 |
| 29 | 99 | 796 | 4,352 | 2,569 |
| 30 | 187 | 4,396 | 4,539 | 2,470 |
| 31 | 95 | 1,535 | 4,634 | 2,283 |
| 32 | 33 | 1,434 | 4,667 | 2,188 |
| 33 | 106 | 131 | 4,773 | 2,155 |
| 34 | 75 | 230 | 4,848 | 2,049 |
| 35 | 170 | 1,480 | 5,018 | 1,974 |
| 36 | 178 | 3,727 | 5,196 | 1,804 |
| 37 | 116 | 1,048 | 5,312 | 1,626 |
| 38 | 148 | 3,157 | 5,460 | 1,510 |
| 39 | 124 | 332 | 5,584 | 1,362 |
| 40 | 130 | 1,928 | 5,714 | 1,238 |
| 41 | 121 | 453 | 5,835 | 1,108 |
| 42 | 63 | 494 | 5,898 | 987 |
| 43 | 107 | 2,051 | 6,005 | 924 |
| 44 | 142 | 3,448 | 6,147 | 817 |
| 45 | 135 | 752 | 6,282 | 675 |
| 46 | 104 | 73 | 6,386 | 540 |
| 47 | 93 | 2,725 | 6,479 | 436 |
| 48 | 250 | 1,665 | 6,729 | 343 |
| 49 | 87 | 2,866 | 6,816 | 93 |
| 50 | 406 | | 6,822 | 6 |

As used herein, a "target ABCA4 intron" refers to one of the 49 ABCA4 introns identified in Table 1, above. Nucleic acid sequence identifiers for each ABCA4 intron sequence are provided in Table 2, below. It will be understood that the scope of the term "target ABCA4 intron" encompasses variants of ABCA4 introns provided herein, such as intron sequences having 90-100% homology with the sequences provided herein (e.g., 90%, 91%, 92%, 93%, 94%, 95%, 96%, 97%, 98%, 99%, or 100% homology with the sequences provided herein), where the location of the variant intron on the ABCA4 gene corresponds with that provided herein (e.g., in relation to its adjacent exons as set forth in Table 1).

TABLE 2

ABCA4 intron sequences

| Intron Number | Sequence |
|---|---|
| 1 | SEQ ID NO: 7 |
| 2 | SEQ ID NO: 8 |
| 3 | SEQ ID NO: 9 |
| 4 | SEQ ID NO: 10 |

TABLE 2-continued

| ABCA4 intron sequences | |
|---|---|
| Intron Number | Sequence |
| 5 | SEQ ID NO: 11 |
| 6 | SEQ ID NO: 12 |
| 7 | SEQ ID NO: 13 |
| 8 | SEQ ID NO: 14 |
| 9 | SEQ ID NO: 15 |
| 10 | SEQ ID NO: 16 |
| 11 | SEQ ID NO: 17 |
| 12 | SEQ ID NO: 18 |
| 13 | SEQ ID NO: 19 |
| 14 | SEQ ID NO: 20 |
| 15 | SEQ ID NO: 21 |
| 16 | SEQ ID NO: 22 |
| 17 | SEQ ID NO: 23 |
| 18 | SEQ ID NO: 24 |
| 19 | SEQ ID NO: 25 |
| 20 | SEQ ID NO: 26 |
| 21 | SEQ ID NO: 27 |
| 22 | SEQ ID NO: 28 |
| 23 | SEQ ID NO: 29 |
| 24 | SEQ ID NO: 30 |
| 25 | SEQ ID NO: 31 |
| 26 | SEQ ID NO: 32 |
| 27 | SEQ ID NO: 33 |
| 28 | SEQ ID NO: 34 |
| 29 | SEQ ID NO: 35 |
| 30 | SEQ ID NO: 36 |
| 31 | SEQ ID NO: 37 |
| 32 | SEQ ID NO: 38 |
| 33 | SEQ ID NO: 39 |
| 34 | SEQ ID NO: 40 |
| 35 | SEQ ID NO: 41 |
| 36 | SEQ ID NO: 42 |
| 37 | SEQ ID NO: 43 |
| 38 | SEQ ID NO: 44 |
| 39 | SEQ ID NO: 45 |
| 40 | SEQ ID NO: 46 |
| 41 | SEQ ID NO: 47 |
| 42 | SEQ ID NO: 48 |
| 43 | SEQ ID NO: 49 |
| 44 | SEQ ID NO: 50 |
| 45 | SEQ ID NO: 51 |
| 46 | SEQ ID NO: 52 |
| 47 | SEQ ID NO: 53 |
| 48 | SEQ ID NO: 54 |
| 49 | SEQ ID NO: 55 |

As used herein, the term "CEP290" refers to a polynucleotide (e.g., RNA (e.g., pre-mRNA or mRNA) or DNA) that encodes the centrosomal protein 290. An exemplary pre-mRNA sequence of a functional human CEP290 gene is given by SEQ ID NO: 113. An exemplary genomic DNA sequence of a functional (wildtype) human CEP290 gene is given by NCBI Reference Sequence: NG_008417. The amino acid sequence of an exemplary human centrosomal protein 290 protein is given by Protein Accession No. O15078.

Exons and introns of CEP290 are identified herein as set forth in Table 3, below, which can be mapped onto the CEP290 pre-mRNA molecule of SEQ ID NO: 112. Each exon and intron of CEP290 are identified herein according to the reference number in the first (left-hand) column. The size of each exon and intron (base pairs; bp) are indicated in the second and third columns. The fourth column indicates the length of a cDNA molecule corresponding to exons 5' to the corresponding intron number. The fifth column indicates the length of a cDNA molecule corresponding to mRNA 3' to the corresponding intron number.

TABLE 3

| CEP290 exon and intron summary | | | | |
|---|---|---|---|---|
| Exon/Intron Number | Exon size | Intron size | 5' cDNA | 3' cDNA |
| 1 | 317 | 565 | N/A | 7440 |
| 2 | 129 | 172 | 102 | 7338 |
| 3 | 78 | 1391 | 180 | 7260 |
| 4 | 70 | 303 | 250 | 7190 |
| 5 | 47 | 2358 | 297 | 7143 |
| 6 | 144 | 5424 | 441 | 6999 |
| 7 | 54 | 599 | 495 | 6945 |
| 8 | 21 | 124 | 516 | 6924 |
| 9 | 153 | 391 | 669 | 6771 |
| 10 | 183 | 658 | 852 | 6588 |
| 11 | 90 | 2507 | 942 | 6498 |
| 12 | 123 | 946 | 1065 | 6375 |
| 13 | 124 | 4079 | 1189 | 6251 |
| 14 | 170 | 720 | 1359 | 6081 |
| 15 | 163 | 1370 | 1522 | 5918 |
| 16 | 101 | 72 | 1623 | 5817 |
| 17 | 88 | 1337 | 1711 | 5729 |
| 18 | 113 | 1850 | 1824 | 5616 |
| 19 | 85 | 535 | 1909 | 5531 |
| 20 | 143 | 2561 | 2052 | 5388 |
| 21 | 165 | 342 | 2217 | 5223 |
| 22 | 150 | 2020 | 2367 | 5073 |
| 23 | 116 | 1967 | 2483 | 4957 |
| 24 | 103 | 90 | 2586 | 4854 |
| 25 | 231 | 3663 | 2817 | 4623 |
| 26 | 174 | 5838 | 2991 | 4449 |
| 27 | 112 | 2912 | 3103 | 4337 |
| 28 | 206 | 937 | 3309 | 4131 |
| 29 | 152 | 1841 | 3461 | 3979 |
| 30 | 112 | 1240 | 3573 | 3867 |
| 31 | 456 | 1087 | 4029 | 3411 |
| 32 | 165 | 1281 | 4194 | 3246 |
| 33 | 108 | 217 | 4302 | 3138 |
| 34 | 135 | 1186 | 4437 | 3003 |
| 35 | 267 | 631 | 4704 | 2736 |
| 36 | 108 | 616 | 4812 | 2628 |
| 37 | 200 | 2635 | 5012 | 2428 |
| 38 | 214 | 952 | 5226 | 2214 |
| 39 | 138 | 1173 | 5364 | 2076 |
| 40 | 222 | 352 | 5586 | 1854 |
| 41 | 123 | 5295 | 5709 | 1731 |
| 42 | 146 | 331 | 5855 | 1585 |
| 43 | 156 | 2648 | 6011 | 1429 |
| 44 | 124 | 4406 | 6135 | 1305 |
| 45 | 135 | 1202 | 6270 | 1170 |
| 46 | 87 | 1697 | 6357 | 1083 |
| 47 | 165 | 809 | 6522 | 918 |
| 48 | 123 | 877 | 6645 | 795 |
| 49 | 173 | 3130 | 6818 | 622 |
| 50 | 142 | 1162 | 6960 | 480 |
| 51 | 74 | 593 | 7034 | 406 |
| 52 | 95 | 3218 | 7129 | 311 |
| 53 | 80 | 939 | 7209 | 231 |
| 54 | 395 | N/A | 7440 | N/A |

As used herein, a "target CEP290 intron" refers to one of the 53 CEP290 introns identified in Table 3, above. Nucleic acid sequence identifiers for each CEP290 intron sequence are provided in Table 4, below. It will be understood that the scope of the term "target CEP290 intron" encompasses variants of CEP290 introns provided herein, such as intron sequences having 90-100% homology with the sequences provided herein (e.g., 90%, 91%, 92%, 93%, 94%, 95%, 96%, 97%, 98%, 99%, or 100% homology with the sequences provided herein), where the location of the variant intron on the CEP290 gene corresponds with that provided herein (e.g., in relation to its adjacent exons as set forth in Table 3).

TABLE 4

| CEP290 intron sequences | |
|---|---|
| Intron Number | Sequence |
| 1 | SEQ ID NO: 60 |
| 2 | SEQ ID NO: 61 |
| 3 | SEQ ID NO: 62 |
| 4 | SEQ ID NO: 63 |
| 5 | SEQ ID NO: 64 |
| 6 | SEQ ID NO: 65 |
| 7 | SEQ ID NO: 66 |
| 8 | SEQ ID NO: 67 |
| 9 | SEQ ID NO: 68 |
| 10 | SEQ ID NO: 69 |
| 11 | SEQ ID NO: 70 |
| 12 | SEQ ID NO: 71 |
| 13 | SEQ ID NO: 72 |
| 14 | SEQ ID NO: 73 |
| 15 | SEQ ID NO: 74 |
| 16 | SEQ ID NO: 75 |
| 17 | SEQ ID NO: 76 |
| 18 | SEQ ID NO: 77 |
| 19 | SEQ ID NO: 78 |
| 20 | SEQ ID NO: 79 |
| 21 | SEQ ID NO: 80 |
| 22 | SEQ ID NO: 81 |
| 23 | SEQ ID NO: 82 |
| 24 | SEQ ID NO: 83 |
| 25 | SEQ ID NO: 84 |
| 26 | SEQ ID NO: 85 |
| 27 | SEQ ID NO: 86 |
| 28 | SEQ ID NO: 87 |
| 29 | SEQ ID NO: 88 |
| 30 | SEQ ID NO: 89 |
| 31 | SEQ ID NO: 90 |
| 32 | SEQ ID NO: 91 |
| 33 | SEQ ID NO: 92 |
| 34 | SEQ ID NO: 93 |
| 35 | SEQ ID NO: 94 |
| 36 | SEQ ID NO: 95 |
| 37 | SEQ ID NO: 96 |
| 38 | SEQ ID NO: 97 |
| 39 | SEQ ID NO: 98 |
| 40 | SEQ ID NO: 99 |
| 41 | SEQ ID NO: 100 |
| 42 | SEQ ID NO: 101 |
| 43 | SEQ ID NO: 102 |
| 44 | SEQ ID NO: 103 |
| 45 | SEQ ID NO: 104 |
| 46 | SEQ ID NO: 105 |
| 47 | SEQ ID NO: 106 |
| 48 | SEQ ID NO: 107 |
| 49 | SEQ ID NO: 108 |
| 50 | SEQ ID NO: 109 |
| 51 | SEQ ID NO: 110 |
| 52 | SEQ ID NO: 111 |
| 53 | SEQ ID NO: 112 |

As used herein, the term "subject" includes any mammal in need of these methods of treatment or prophylaxis, including humans. Other mammals in need of such treatment or prophylaxis include dogs, cats, or other domesticated animals, horses, livestock, laboratory animals, including non-human primates, etc. The subject may be male or female. In one embodiment, the subject has a disease or disorder caused by a mutation in the ABCA4 gene (e.g., Stargardt Disease, e.g., Stargardt Disease 1) or the CEP290 gene (e.g., an autosomal recessive disorder, such as LCA 10). In another embodiment, the subject is at risk of developing a disease or disorder caused by a mutation in the ABCA4 gene or the CEP290 gene. In another embodiment, the subject has shown clinical signs of a disease or disorder caused by a mutation in the ABCA4 gene (such as Stargardt Disease) or the CEP290 gene (such as LCA 10). The subject may be any age during which treatment or prophylactic therapy may be beneficial. For example, in some embodiments, the subject is 0-5 years of age, 5-10 years of age, 10-20 years of age, 20-30 years of age, 30-50 years of age, 50-70 years of age, or more than 70 years of age. In another embodiment, the subject is 12 months of age or older, 18 months of age or older, 2 years of age or older, 3 years of age or older, 4 years of age or older, 5 years of age or older, 6 years of age or older, 7 years of age or older, 8 years of age or older, 9 years of age or older, or 10 years of age or older. In another embodiment, the subject has viable retinal cells.

As used herein, the terms "disorder associated with a mutation" or "mutation associated with a disorder" refer to a correlation between a disorder and a mutation. In some embodiments, a disorder associated with a mutation is known or suspected to be wholly or partially, or directly or indirectly, caused by the mutation. For example, a subject having the mutation may be at risk of developing the disorder, and the risk may additionally depend on other factors, such as other (e.g., independent) mutations (e.g., in the same or a different gone), or environmental factors.

As used herein, the term "treatment," or a grammatical derivation thereof, is defined as reducing the progression of a disease, reducing the severity of a disease symptom, retarding progression of a disease symptom, removing a disease symptom, or delaying onset of a disease.

As used herein, the term "prevention" of a disorder, or a grammatical derivation thereof, is defined as reducing the risk of onset of a disease, e.g., as a prophylactic therapy for a subject who is at risk of developing a disorder associated with a mutation. A subject can be characterized as "at risk" of developing a disorder by identifying a mutation associated with the disorder, according to any suitable method known in the art or described herein. In some embodiment, a subject who is at risk of developing a disorder has one or more ABCA4 or CEP290 mutations associated with the disorder. Additionally or alternatively, a subject can be characterized as "at risk" of developing a disorder if the subject has a family history of the disorder.

Treating or preventing a disorder in a subject can be performed by directly administering the trans-splicing molecule (e.g., within an AAV vector or AAV particle) to the subject. Alternatively, host cells containing the trans-splicing molecule may be administered to the subject.

The term "administering," or a grammatical derivation thereof, as used in the methods described herein, refers to delivering the composition, or an ex vivo-treated cell, to the subject in need thereof, e.g., having a mutation or defect in the targeted gene. For example, in one embodiment in which ocular cells are targeted, the method involves delivering the composition by subretinal injection to the photoreceptor cells or other ocular cells. In another embodiment, intravitreal injection to ocular cells or injection via the palpebral vein to ocular cells may be employed. In another embodiment, the composition is administered intravenously. Still other methods of administration may be selected by one of skill in the art, in view of this disclosure.

Codon optimization refers to modifying a nucleic acid sequence to change individual nucleic acids without any resulting change in the encoded amino acid. Sequences modified in this way are referred to herein as "codon-optimized." This process may be performed on any of the sequences described in this specification to enhance expression or stability. Codon optimization may be performed in a manner such as that described in, e.g., U.S. Pat. Nos. 7,561,972, 7,561,973, and 7,888,112, each of which is incorporated herein by reference in its entirety. The sequence surrounding the translational start site can be converted to a consensus Kozak sequence according to known methods. See, e.g., Kozak et al, Nucleic Acids Res. 15 (20): 8125-8148, incorporated herein by reference in its entirety.

The term "homologous" refers to the degree of identity between sequences of two nucleic acid sequences. The homology of homologous sequences is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (*Nucleic Acid Res.,* 1994, 22 (22): 4673 4680). Commonly available sequence analysis software, such as, Vector NTI, GENETYX, BLAST, or analysis tools provided by public databases may also be used.

The term "pharmaceutically acceptable" means safe for administration to a mammal, such as a human. In some embodiments, a pharmaceutically acceptable composition is approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which a therapeutic molecule (e.g., a trans-splicing molecule or a trans-splicing molecule including a vector or cell of the present invention) is administered. Examples of suitable pharmaceutical carriers are described in "Remington's Pharmaceutical Sciences," Mack Publishing Co., Easton, PA., $2^{nd}$ edition, 2005.

The terms "a" and "an" mean "one or more of." For example, "a gene" is understood to represent one or more such genes. As such, the terms "a" and "an," "one or more of a (or an)," and "at least one of a (or an)" are used interchangeably herein.

As used herein, the term "about" refers to a value within ±10% variability from the reference value, unless otherwise specified.

II. Trans-Splicing Molecules

Provided herein are ABCA4 trans-splicing molecules and CEP290 trans-splicing molecules.

ABCA4 Trans-Splicing Molecules

The present invention features nucleic acid trans-splicing molecules useful for treating diseases and disorders associated with a mutation in an ABCA4 gene by replacing one or more exons in the ABCA4 gene (e.g., an ABCA4 gone having a mutated ABCA4 exon). In some embodiments, the nucleic acid trans-splicing molecule is a pre-RNA trans-splicing molecule (RTM). The design of the trans-splicing molecule permits replacement of the defective or mutated portion of the pre-mRNA exon(s) with a nucleic acid sequence, e.g., the exon(s) having a functional (e.g., normal) sequence without the mutation. The functional sequence can be a wild-type, naturally-occurring sequence or a corrected sequence with some other modification, e.g., codon optimization.

In one embodiment, a trans-splicing molecule is configured to correct one or more mutations located on a 3' portion of the ABCA4 gene. In one embodiment, a trans-splicing molecule is configured to correct one or more mutations located on a 5' portion of the ABCA4 gene. The trans-splicing molecules provided herein function to repair the defective gene in the target cell of a subject by replacing the defective pre-mRNA gene sequence and removing the defective portion of the target pre-mRNA, yielding a functional ABCA4 gene capable of transcribing a functional gene product in the cell.

The invention provides trans-splicing molecules having a binding domain configured to bind a target ABCA4 intron, a splicing domain configured to mediate trans-splicing, and a coding domain having one or more functional ABCA4 exons. In a 5' trans-splicing molecule, the coding domain, splice site, and binding domain are operatively linked in a 5'-to-3' direction, such that the trans-splicing molecule is configured to replace the 5' end of the endogenous gene with the coding domain, which includes a functional ABCA4 exon to replace the mutated ABCA4 exon. Conversely, in a 3' trans-splicing molecule, the coding domain, splice site, and binding domain are operatively linked in a 3'-to-5' direction, such that the trans-splicing molecule is configured to replace the 3' end of the endogenous gene with the coding domain, which includes a functional ABCA4 exon to replace the mutated ABCA4 exon. In some embodiments, the splicing domain resides within an artificial intron, which links the binding domain to the coding domain. The artificial intron may include additional components, such as a spacer.

In some embodiments, the trans-splicing molecule or coding domain thereof is up to 4,700 nucleotide bases in length (e.g., from 200 to 300 nucleotide bases in length, from 300 to 400 nucleotide bases in length, from 400 to 500 nucleotide bases in length, from 500 to 600 nucleotide bases in length, from 600 to 700 nucleotide bases in length, from 700 to 800 nucleotide bases in length, form 800 to 900 nucleotide bases in length, from 900 to 1,000 nucleotide bases in length, from 1,000 to 1,500 nucleotide bases in length, from 1,500 to 2,000 nucleotide bases in length, from 2,000 to 2,500 nucleotide bases in length, from 2,500 to 3,000 nucleotide bases in length, or from 3,000 to 4,000 nucleotide bases in length, e.g., from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length, e.g., about 2,918 nucleotide bases in length, about 3,328 nucleotide bases in length, about 3,522 nucleotide bases in length, about 3,607 nucleotide bases in length, about 3,632 nucleotide bases in length, about 3,494 nucleotide bases in length, or about 3,300 nucleotide bases in length).

Due to the large size of the ABCA4 gene and the size constraints of AAV delivery, a single trans-splicing molecule configured for packaging within an AAV vector may not span all mutations in an ABCA4 gene that may be associated with a disorder and thereby may not correct mutations along the length of the entire ABCA4 gene. Accordingly, the trans-splicing molecules of the invention can be adapted as part of methods described below to correct multiple mutations spanning the entire length of the ABCA4 gene.

An ABCA4 gene targeted by a trans-splicing molecule described herein contains one or multiple mutations that are associated with (e.g., cause, or are correlated with) a disease, such as a Stargardt Disease (e.g., Stargardt Disease 1). An exemplary DNA sequence of a functional (wildtype) human ABCA4 gene is given by the NCBI Reference Sequence:

NG_009073. The amino acid sequence of an exemplary protein retinal-specific ATP-binding cassette transporter expressed by ABCA4 is given by Protein Accession No. P78363.

In addition to these published sequences, all corrections later obtained or naturally occurring conservative and non-disease-causing variants sequences that occur in the human or other mammalian population are also included. Additional conservative nucleotide replacements or those causing codon optimizations are also included. The sequences as provided by the database accession numbers may also be used to search for homologous sequences in the same or another mammalian organism.

It is anticipated that the ABCA4 nucleic acid sequences and resulting protein truncates or amino acid fragments may tolerate certain minor modifications at the nucleic acid level to include, for example, modifications to the nucleotide bases which are silent, e.g., preference codons. In other embodiments, nucleic acid base modifications which change the amino acids, e.g., to improve expression of the resulting peptide/protein (for example, codon optimization) are anticipated. Also included as likely modification of fragments are allelic variations, caused by the natural degeneracy of the genetic code.

Also included as modifications of ABCA4 genes are analogs, or modified versions, of the encoded protein fragments provided herein. Typically, such analogs differ from the specifically identified proteins by only one to four codon changes. Conservative replacements are those that take place within a family of amino acids that are related in their side chains and chemical properties.

The nucleic acid sequence of a functional ABCA4 gene may be derived from any mammal which natively expresses functional retinal-specific ATP-binding cassette transporter, or homolog thereof. In other embodiments, certain modifications are made to the ABCA4 gene sequence in order to enhance expression in the target cell. Such modifications include codon optimization.

In some embodiments, the disorder associated with a mutation in ABCA4 is an autosomal recessive disease, for example, Stargardt Disease. In certain instances involving a subject having an autosomal recessive disorder, the subject has a mutation in ABCA4 on both alleles. Compositions comprising trans-splicing molecules can correct the mutations on both alleles, regardless of the location of the mutation within the ABCA4 gene. For instance, for a subject having a mutated ABCA4 exon 1 on a first allele and a mutated ABCA4 exon 30 on a second allele, provided herein is a composition having a 5' trans-splicing molecule to replace the mutated ABCA4 exon 1 and a 3' trans-splicing molecule to replace the mutated ABCA4 exon 30. In such embodiments, the two trans-splicing molecules can be co-delivered as part of the same AAV vector or delivered in separate AAV vectors (e.g., in the case in which both trans-splicing molecules exceed the packaging limit of AAV).

Alternatively, in embodiments in which two or more mutations are located on a portion of the ABCA4 gene that can be replaced by the same trans-splicing molecule, a single trans-splicing molecule having a coding region containing a functional ABCA4 exon can replace the one or more exons containing the mutations. Mutations in particular ABCA4 exons are also listed in International Patent Publication No. WO 2017/087900, incorporated herein by reference.

ABCA4 Coding Domains

In some embodiments, the coding domain of a 5' trans-splicing molecule includes all ABCA4 exons (e.g., functional ABCA4 exons) that are 5' to the target ABCA4 intron. For example, in embodiments in which a 5' trans-splicing molecule targets ABCA4 intron 19, the coding domain includes functional ABCA4 exons 1-19. In such embodiments featuring a 5' trans-splicing molecule having a coding domain including functional ABCA4 exons 1-19, the coding domain is about 2918 bp in length. In embodiments in which a 5' trans-splicing molecule targets ABCA4 intron 22, the coding domain includes functional ABCA4 exons 1-22. In such embodiments featuring a 5' trans-splicing molecule having a coding domain including functional ABCA4 exons 1-22, the coding domain is about 3,328 bp in length. In embodiments in which a 5' trans-splicing molecule targets ABCA4 intron 23, the coding domain includes functional ABCA4 exons 1-23. In such embodiments featuring a 5' trans-splicing molecule having a coding domain including functional ABCA4 exons 1-23, the coding domain is about 3,522 bp in length. In embodiments in which a 5' trans-splicing molecule targets ABCA4 intron 24, the coding domain includes functional ABCA4 exons 1-24. In such embodiments featuring a 5' trans-splicing molecule having a coding domain including functional ABCA4 exons 1-24, the coding domain is about 3,607 bp in length. The aforementioned embodiments of 5' ABCA4-targeting trans-splicing molecules are illustrated at the lower left-hand portion of FIG. 1.

In some embodiments, the coding domain of a 3' trans-splicing molecule includes any one or more of ABCA4 exons 20-50. For example, in embodiments in which a 3' trans-splicing molecule targets ABCA4 intron 22, the coding domain includes functional ABCA4 exons 23-50. In such embodiments featuring a 3' trans-splicing molecule having a coding domain including functional ABCA4 exons 23-50, the coding domain is about 3,632 bp in length. In embodiments in which a 3' trans-splicing molecule targets ABCA4 intron 23, the coding domain includes functional ABCA4 exons 24-50. In such embodiments featuring a 3' trans-splicing molecule having a coding domain including functional ABCA4 exons 24-50, the coding domain is about 3,494 bp in length. In embodiments in which a 3' trans-splicing molecule targets ABCA4 intron 24, the coding domain includes functional ABCA4 exons 25-50. In such embodiments featuring a 3' trans-splicing molecule having a coding domain including functional ABCA4 exons 25-50, the coding domain is about 3,300 bp in length. The aforementioned embodiments of 3' ABCA4-targeting trans-splicing molecules are illustrated at the upper right-hand portion of FIG. 1.

In some embodiments, the coding domain includes 1, 2, 3, 4, 5, 6, 7, 8, 9, 10, 11, 12, 13, 14, 15, 16, 17, 18, 19, 20, 21, 22, 23, 24, 25, 26, 27, or 28 functional ABCA4 exons.

In some instances, both mutations occur in the 5' portion of the target gene, and a 5' trans-splicing molecule is selected to correct both mutations. In one embodiment, the binding domain binds to intron 19, and the coding domain includes functional ABCA4 exons 1-19. In one embodiment, the binding domain binds to intron 22, and the coding domain includes functional ABCA4 exons 1-22. In one embodiment, the binding domain binds to intron 23, and the coding domain includes functional ABCA4 exons 1-23. In one embodiment, the binding domain binds to intron 24, and the coding domain includes functional ABCA4 exons 1-24. Alternatively, in instances in which both mutations occur on the 3' portion of the target gene, a 3' trans-splicing molecule is selected to correct both mutations. In one embodiment, the binding domain binds to intron 22, and the coding domain includes functional ABCA4 exons 23-50. In one embodiment, the binding domain binds to intron 23, and the coding domain includes functional ABCA4 exons 24-50. In one embodiment, the binding domain binds to intron 24, and the coding domain includes functional ABCA4 exons 25-50.

As one example, a 3' pre-mRNA ABCA4 trans-splicing molecule operates as follows: A chimeric mRNA is created through a trans-splicing reaction mediated by the spliceosome between the 5' splice site of the endogenous target pre-mRNA and the 3' splice site of the trans-splicing molecule. The trans-splicing molecule binds through specific base pairing to a target ABCA4 intron of the endogenous target pre-mRNA and replaces the whole 3' sequence of the endogenous ABCA4 gene upstream of the targeted intron with the coding domain having a functional ABCA4 exon sequence of the trans-splicing molecule.

A 3' trans-splicing molecule includes a binding domain which binds to the target ABCA4 intron 5' to the mutation or defect, an artificial intron comprising optional spacer and a 3' splice site, and a coding domain that encodes all exons of the ocular target gene that are 3' to the binding of the binding domain to the target. A 5' trans-splicing molecule includes a binding domain binds to the target ABCA4 intron 3' to the mutation or defect, a 5' splice site, an optional spacer and a coding domain that encodes all exons of the ocular target gene that are 5' to the binding of the binding domain to the target.

In some embodiments, the coding domain includes a complementary DNA (cDNA) sequence. For example, one or more functional ABCA4 exons within the coding domain can be a cDNA sequence. In some embodiments, the entire coding domain is a cDNA sequence. Additionally or alternatively, all or a portion of the coding domain, or one or more functional ABCA4 exons thereof, can be a naturally-occurring sequence (e.g., a sequence having 90%, 91%, 92%, 93%, 94%, 95%, 96%, 97%, 98%, 99%, or 100% sequence identity with an endogenous ABCA4 exon).

In some embodiments, all or a portion of the coding domain, or one or more functional ABCA4 exons thereof, is a codon-optimized sequence in which a nucleic acid sequence has been modified, e.g., to enhance expression or stability, without resulting in a change in the encoded amino acid. Codon optimization may be performed in a manner such as that described in, e.g., U.S. Pat. Nos. 7,561,972, 7,561,973, and 7,888,112, each of which is incorporated herein by reference in its entirety. For delivery via a recombinant AAV, as described herein, in one embodiment, the coding domain can be a nucleic acid sequence of up to 4,000 nucleotide bases in length (e.g., from 3,000 to 4,000 nucleotide bases in length, from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length).

ABCA4 Binding Domains

Trans-splicing molecules of the invention feature a binding domain configured to bind a target ABCA4 intron. In one embodiment, the binding domain is a nucleic acid sequence complementary to a sequence of the target ABCA4 pre-mRNA (e.g., a target ABCA4 intron) to suppress endogenous target cis-splicing while enhancing trans-splicing between the trans-spicing molecule and the target ABCA4 pre-mRNA, e.g., to create a chimeric molecule having a portion of endogenous ABCA4 mRNA and the coding domain having one or more functional ABCA4 exons. In some embodiments, the binding domain is in an antisense orientation to a sequence of the target ABCA4 intron.

A 5' trans-splicing molecule will generally bind the target ABCA4 intron 3' to the mutation, while a 3' trans-splicing molecule will generally bind the target ABCA4 intron 5' to the mutation. In one embodiment, the binding domain comprises a part of a sequence complementary to the target ABCA4 intron. In one embodiment herein, the binding domain is a nucleic acid sequence complementary to the intron closest to (i.e., adjacent to) the exon sequence that is being corrected.

In another embodiment, the binding domain is targeted to an intron sequence in close proximity to the 3' or 5' splice signals of a target intron. In still another embodiment, a binding domain sequence can bind to the target intron in addition to part of an adjacent exon.

Thus, in some instances, the binding domain binds specifically to the mutated endogenous target pre-mRNA to anchor the coding domain of the trans-splicing molecule to the pre-mRNA to permit trans-splicing to occur at the correct position in the target ABCA4 gene. The spliceosome processing machinery of the nucleus may then mediate successful trans-splicing of the corrected exon for the mutated exon causing the disease.

In certain embodiments, the trans-splicing molecules feature binding domains that contain sequences on the target pre-mRNA that bind in more than one place. The binding domain may contain any number of nucleotides necessary to stably bind to the target pro-mRNA to permit trans-splicing to occur with the coding domain. In one embodiment, the binding domains are selected using mFOLD structural analysis for accessible loops (Zuker, *Nucleic Acids Res.* 2003, 31 (13): 3406-3415).

Suitable target binding domains can be from 10 to 500 nucleotides in length. In some embodiments, the binding domain is from 20 to 400 nucleotides in length. In some embodiments, the binding domain is from 50 to 300 nucleotides in length. In some embodiments, the binding domain is from 100 to 200 nucleotides in length. In some embodiments, the binding domain is from 10-20 nucleotides in length (e.g., 10, 11, 12, 13, 14, 15, 16, 17, 18, 19, or 20 nucleotides in length), 20-30 nucleotides in length (e.g., 20, 21, 22, 23, 24, 25, 26, 27, 28, 29, or 30 nucleotides in length), 30-40 nucleotides in length (e.g., 30, 31, 32, 33, 34, 35, 36, 37, 38, 39, or 40 nucleotides in length), 40-50 nucleotides in length (e.g., 40, 41, 42, 43, 44, 45, 46, 47, 48, 49, 50 nucleotides in length), 50-60 nucleotides in length (e.g., 50, 51, 52, 53, 54, 55, 56, 57, 58, 59, or 60 nucleotides in length), 60-70 nucleotides in length (e.g., 60, 61, 62, 63, 64, 65, 66, 67, 68, 69, or 70 nucleotides in length), 70-80 nucleotides in length (e.g., 70, 71, 72, 73, 74, 75, 76, 77, 78, 79, or 80 nucleotides in length), 80-90 nucleotides in length (e.g., 80, 81, 82, 83, 84, 85, 86, 87, 88, 89, or 90 nucleotides in length), 90-100 nucleotides in length (e.g., 90, 91, 92, 93, 94, 95, 96, 97, 98, 99, or 100 nucleotides in length), 100-110 nucleotides in length (e.g., 100, 101, 102, 103, 104, 105, 106, 107, 108, 109, or 110 nucleotides in length), 110-120 nucleotides in length (e.g., 110, 111, 112, 113, 114, 115, 116, 117, 118, 119, or 120 nucleotides in length), 120-130 nucleotides in length (e.g., 120, 121, 122, 123, 124, 125, 126, 127, 128, 129, or 130 nucleotides in length), 130-140 nucleotides in length (e.g., 130, 131, 132, 133, 134, 135, 136, 137, 138, 139, or 140 nucleotides in length), 140-150 nucleotides in length (e.g., 140, 141, 142, 143, 144, 145, 146, 147, 148, 149, or 150 nucleotides in length), 150-160 nucleotides in length (e.g., 150, 151, 152, 153, 154, 155, 156, 157, 158, 159, or 160 nucleotides in length), 160-170 nucleotides in length (e.g., 160, 161, 162, 163, 164, 165, 166, 167, 168, 169, or 170 nucleotides in length), 170-180 nucleotides in length (e.g., 170, 171, 172, 173, 174, 175, 176, 177, 178, 179, or 180 nucleotides in length), 180-190 nucleotides in length (e.g., 180, 181, 182, 183, 184, 185, 186, 187, 188, 189, or 190 nucleotides in length), 190-200 nucleotides in length (e.g., 190, 191, 192, 193, 194, 195, 196, 197, 198, 199, or 200 nucleotides in length), 200-210 nucleotides in length, 210-220 nucleotides in length, 220-230 nucleotides in length, 230-240 nucleotides in length, 240-250 nucleotides in length, 250-260 nucleotides in length, 260-270 nucleotides in length, 270-280 nucleotides in length, 280-290 nucleotides in length, 290-300 nucleotides in length, 300-350 nucleotides in length, 350-400 nucleotides in length, 400-450 nucleotides in length, or 450-500 nucleotides in length. In some embodiments, the binding domain is about 150 nucleotides in length. In another embodiment, the target binding domains may include a nucleic acid sequence up to 750 nucleotides in length. In another embodiment, the target binding domains may include a nucleic acid sequence up to 1000 nucleotides in length. In another embodiment, the target binding domains may include a nucleic acid sequence up to 2000 nucleotides or more in length.

In some embodiments, the specificity of the trans-splicing molecule may be increased by increasing the length of the target binding domain. Other lengths may be used depending upon the lengths of the other components of the trans-splicing molecule.

The binding domain may be from 80% to 100% complementary to the target intron to be able to hybridize stably with the target intron. For example, in some embodiments, the binding domain is 80%, 81%, 82%, 83%, 84%, 85%, 86%, 87%, 88%, 89%, 90%, 91%, 92%, 93%, 94%, 95%, 96%, 97%, 98%, 99%, or 100% complimentary to the target intron. The degree of complementarity is selected by one of skill in the art based on the need to keep the trans-splicing molecule and the nucleic acid construct containing the necessary sequences for expression and for inclusion in the rAAV within a 3,000 or up to 4,000 nucleotide base limit. The selection of this sequence and strength of hybridization depends on the complementarity and the length of the nucleic acid.

Any of the aforementioned binding domains may bind to a binding site within intron 19 (SEQ ID NO: 25), intron 22 (SEQ ID NO: 28) intron 23 (SEQ ID NO: 29), or intron 24 (SEQ ID NO: 30).

In certain instances of the invention, the trans-splicing molecule is a 5' trans-splicing molecule and features a binding domain that binds to intron 19 of ABCA4 (SEQ ID NO: 25) and includes a coding domain having functional ABCA4 exons 1-19. In some embodiments, the binding site comprises any one or more of nucleotides 990 to 2,174 of SEQ ID NO: 25 (e.g., any one or more of nucleotides 1,670 to 2,174 of SEQ ID NO: 25, any one or more of nucleotides 1,810 to 2,000 of SEQ ID NO: 25, any one or more of nucleotides 1,870 to 2,000 of SEQ ID NO: 25, or any one or more of nucleotides 1,920 to 2,000 of SEQ ID NO: 25).

In some embodiments, the trans-splicing molecule is a 5' trans-splicing molecule and features a binding domain that binds to intron 22 of ABCA4 (SEQ ID NO: 28) and includes a coding domain having functional ABCA4 exons 1-22. In some embodiments, the binding site comprises any one or more of nucleotides 60 to 570, nucleotides 600 to 800, or nucleotides 900 to 1,350 of SEQ ID NO: 28 (e.g., any one or more of nucleotides 70 to 250 of SEQ ID NO: 28).

Alternatively, the trans-splicing molecule can be a 3' trans-splicing molecule and can feature a binding domain that binds to intron 22 of ABCA4 (SEQ ID NO: 28). This trans-splicing molecules may include a coding domain having functional ABCA4 exons 23-50. In some embodiments, the binding site comprises any one or more of nucleotides 1 to 510 or 880 to 1,350 of SEQ ID NO: 28.

In other embodiments, the trans-splicing molecule is a 5' trans-splicing molecule and features a binding domain that binds to intron 23 of ABCA4 (SEQ ID NO: 29) and includes a coding domain having functional ABCA4 exons 1-23. In some embodiments, the binding site comprises any one or more of nucleotides 80 to 570 or 720 to 1,081 of SEQ ID NO: 29.

Alternatively, the trans-splicing molecule can be a 3' trans-splicing molecule and can feature a binding domain that binds to intron 23 of ABCA4 (SEQ ID NO: 29) and a coding domain having functional ABCA4 exons 24-50. In some embodiments, the binding site comprises any one or more of nucleotides 80 to 1,081 of SEQ ID NO: 29 (e.g., any one or more of nucleotides 230 to 1,081 of SEQ ID NO: 29, any one or more of nucleotides 250 to 400 of SEQ ID NO: 29, or any one or more of nucleotides 690 to 850 of SEQ ID NO: 29).

In some embodiments, the trans-splicing molecule is a 5' trans-splicing molecule and features a binding domain that binds to intron 24 of ABCA4 (SEQ ID NO: 30) and includes a coding domain having functional ABCA4 exons 1-24. In some embodiments, the binding site comprises any one or more of nucleotides 600 to 1,250 or 1,490 to 2,660 of SEQ ID NO: 30 (e.g., any one or more of nucleotides 1,000 to 1,200 of SEQ ID NO: 30).

In other embodiments, the trans-splicing molecule is a 3' trans-splicing molecule and features a binding domain that binds to intron 24 of ABCA4 (SEQ ID NO: 30) and includes a coding domain having functional ABCA4 exons 25-50. In some embodiments, the binding site comprises any one or more of nucleotides 1 to 250, nucleotides 300 to 2,100, or nucleotides 2,200 to 2,692 of SEQ ID NO: 30 (e.g., any one or more of nucleotides 360 to 610 of SEQ ID NO: 30 or any one or more of nucleotides 750 to 1,110 of SEQ ID NO: 30).

CEP290 Trans-Splicing Molecules

The present invention features nucleic acid trans-splicing molecules useful for treating diseases and disorders associated with a mutation in a CEP290 gene by replacing one or more exons in the CEP290 gene (e.g., a CEP290 gene having a mutation in intron 26). In some embodiments, the nucleic acid trans-splicing molecule is a pre-RNA trans-splicing molecule (RTM). The design of the trans-splicing molecule permits replacement of the defective or mutated portion of the pre-mRNA with a nucleic acid sequence, e.g., the exon(s) having a functional (e.g., normal) sequence without the mutation. The functional sequence can be a wild-type, naturally-occurring sequence or a corrected sequence with some other modification, e.g., codon optimization.

In one embodiment, a trans-splicing molecule is configured to correct one or more mutations located on a 5' portion of the CEP290 gene. The trans-splicing molecules provided herein function to repair the defective gene in the target cell of a subject by replacing the defective pre-mRNA gene sequence, yielding a functional CEP290 gone capable of transcribing a functional gene product in the cell.

The invention provides trans-splicing molecules having a binding domain configured to bind a target CEP290 intron, a splicing domain configured to mediate trans-splicing, and a coding domain having one or more functional CEP290 exons. In a 5' trans-splicing molecule, the coding domain, splice site, and binding domain are operatively linked in a 5'-to-3' direction, such that the trans-splicing molecule is configured to replace the 5' end of the endogenous gene with the coding domain, which includes a functional CEP290 exon to corrected the mutated CEP290 pre-mRNA. In some embodiments, the splicing domain resides within an artificial intron, which links the binding domain to the coding domain. The artificial intron may include additional components, such as a spacer.

In some embodiments, the trans-splicing molecule is up to 4,700 nucleotide bases in length (e.g., from 3,000 to 4,000 nucleotide bases in length, from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length, e.g., about 2,991 nucleotide bases in length, about 3,103 nucleotide bases in length, about 3,309 nucleotide bases in length, about 3,461 nucleotide bases in length, or about 3,573 nucleotide bases in length).

A CEP290 gene targeted by a trans-splicing molecule described herein contains one or multiple mutations that are associated with (e.g., cause, or are correlated with) a disease, such as Leber congenital amourosis (e.g., LCA 10). An exemplary DNA sequence of a functional (wildtype) human CEP290 gene is given by the NCBI Reference Sequence: NG_008417. The amino acid sequence of an exemplary centrosomal protein 290 is given by Protein Accession No. O15078.

In addition to these published sequences, all corrections later obtained or naturally occurring conservative and non-disease-causing variants sequences that occur in the human or other mammalian population are also included. Additional conservative nucleotide replacements or those causing codon optimizations are also included. The sequences as provided by the database accession numbers may also be used to search for homologous sequences in the same or another mammalian organism.

It is anticipated that the CEP290 nucleic acid sequences and resulting protein truncates or amino acid fragments may tolerate certain minor modifications at the nucleic acid level to include, for example, modifications to the nucleotide bases which are silent, e.g., preference codons. In other embodiments, nucleic acid base modifications which change the amino acids, e.g., to improve expression of the resulting peptide/protein (for example, codon optimization) are anticipated. Also included as likely modification of fragments are allelic variations, caused by the natural degeneracy of the genetic code.

Also included as modifications of CEP290 genes are analogs, or modified versions, of the encoded protein fragments provided herein. Typically, such analogs differ from the specifically identified proteins by only one to four codon changes. Conservative replacements are those that take place within a family of amino acids that are related in their side chains and chemical properties.

The nucleic acid sequence of a functional CEP290 gone may be derived from any mammal which natively expresses functional centrosomal protein 290, or homolog thereof. In other embodiments, certain modifications are made to the CEP290 gene sequence in order to enhance expression in the target cell. Such modifications include codon optimization.

CEP290 mutations can be found on the CCHMC Molecular Genetics Laboratory Mutation Database, LOVD v.2.0. Mutations in particular CEP290 exons are also listed in International Patent Publication No. WO 2017/087900, incorporated herein by reference. Table 3, above, provides information regarding the size and position of each exon and intron of CEP290.

In some embodiments, the disorder associated with a mutation in CEP290 is an autosomal recessive disease, for example, LCA 10.

Coding Domains

Figure 21:
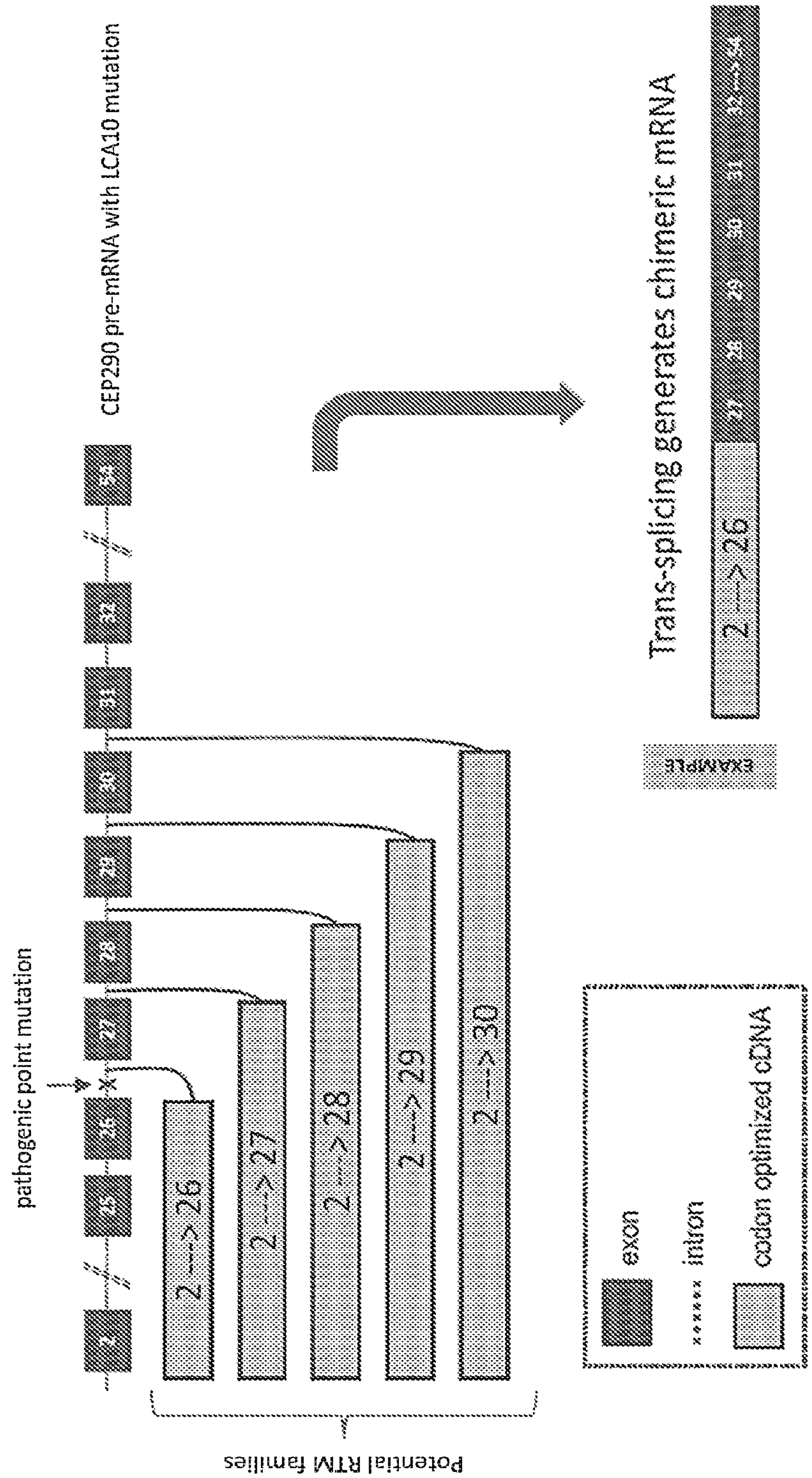
FIG. 21 is a schematic drawing of several exemplary nucleic acid trans-splicing molecules for correcting a mutation in CEP290 intron 26 with a functional 5' portion of the CEP290 gene. Dark shaded boxes represent native CEP290 exons. Dashed lines joining the dark shaded boxes represent native introns. Light shaded boxes with dark borders represent functional CEP290 exons within a nucleic acid trans-splicing molecule. A splicing domain, represented by a curved line, is attached to one end of each of the functional CEP290 exon sequences and leads to an intron of the CEP290 pre-mRNA.

In some embodiments, the coding domain of a 5' trans-splicing molecule includes all CEP290 exons (e.g., functional CEP290 exons) that are 5' to the target CEP290 intron. For example, in embodiments in which a 5' trans-splicing molecule targets CEP290 intron 26, the coding domain includes functional CEP290 exons 2-26. In such embodiments featuring a 5' trans-splicing molecule having a coding domain including functional CEP290 exons 2-26, the coding domain is about 2,991 bp in length. In embodiments in which a 5' trans-splicing molecule targets CEP290 intron 27, the coding domain includes functional CEP290 exons 2-27. In such embodiments featuring a 5' trans-splicing molecule having a coding domain including functional CEP290 exons 2-27, the coding domain is about 3, 103 bp in length. In embodiments in which a 5' trans-splicing molecule targets CEP290 intron 28, the coding domain includes functional CEP290 exons 2-28. In such embodiments featuring a 5' trans-splicing molecule having a coding domain including functional CEP290 exons 2-28, the coding domain is about 3,309 bp in length. In embodiments in which a 5' trans-splicing molecule targets CEP290 intron 29, the coding domain includes functional CEP290 exons 2-29. In such embodiments featuring a 5' trans-splicing molecule having a coding domain including functional CEP290 exons 2-29, the coding domain is about 3,461 bp in length. In embodiments in which a 5' trans-splicing molecule targets CEP290 intron 30, the coding domain includes functional CEP290 exons 2-30. In such embodiments featuring a 5' trans-splicing molecule having a coding domain including functional CEP290 exons 2-30, the coding domain is about 3,573 bp in length. The aforementioned embodiments of 5' CEP290-targeting trans-splicing molecules are illustrated in FIG. 21.

In some embodiments, the coding domain includes 25, 26, 27, 28, or 29 functional CEP290 exons.

In some embodiments, the coding domain includes a complementary DNA (cDNA) sequence. For example, one or more functional CEP290 exons within the coding domain can be a cDNA sequence. In some embodiments, the entire coding domain is a cDNA sequence. Additionally or alternatively, all or a portion of the coding domain, or one or more functional CEP290 exons thereof, can be a naturally-occurring sequence (e.g., a sequence having 90%, 91%, 92%, 93%, 94%, 95%, 96%, 97%, 98%, 99%, or 100% sequence identity with an endogenous CEP290 exon).

In some embodiments, all or a portion of the coding domain, or one or more functional CEP290 exons thereof, is a codon-optimized sequence in which a nucleic acid sequence has been modified, e.g., to enhance expression or stability, without resulting in a change in the encoded amino acid. Codon optimization may be performed in a manner such as that described in, e.g., U.S. Pat. Nos. 7,561,972, 7,561,973, and 7,888,112, each of which is incorporated herein by reference in its entirety. For delivery via a recombinant AAV, as described herein, in one embodiment, the coding domain can be a nucleic acid sequence of up to 4,000 nucleotide bases in length (e.g., from 3,000 to 4,000 nucleotide bases in length, from 3,100 to 3,800 nucleotide bases in length, from 3,200 to 3,700 nucleotide bases in length, or from 3,300 to 3,500 nucleotide bases in length, e.g., from 3,000 to 3,100 nucleotide bases in length, from 3,100 to 3,200 nucleotide bases in length, from 3,200 to 3,300 nucleotide bases in length, from 3,300 to 3,400 nucleotide bases in length, from 3,400 to 3,500 nucleotide bases in length, from 3,500 to 3,600 nucleotide bases in length, from 3,600 to 3,700 nucleotide bases in length, from 3,700 to 3,800 nucleotide bases in length, from 3,800 to 3,900 nucleotide bases in length, or from 3,900 to 4,000 nucleotide bases in length, e.g., about 3,108 nucleotide bases in length, about 3,285 nucleotide bases in length, about 3,375 nucleotide bases in length, about 3,503 nucleotide bases in length, about 3,630 nucleotide bases in length, about 3,540 nucleotide bases in length, about 3,363 nucleotide bases in length, about 3,273 nucleotide bases in length, about 3,145 nucleotide bases in length, or about 3,018 nucleotide bases in length).

Binding Domains

Trans-splicing molecules of the invention feature a binding domain configured to bind a target CEP290 intron. In one embodiment, the binding domain is a nucleic acid sequence complementary to a sequence of the target CEP290 pre-mRNA (e.g., a target CEP290 intron) to suppress endogenous target cis-splicing while enhancing trans-splicing between the trans-spicing molecule and the target CEP290 pre-mRNA, e.g., to create a chimeric molecule having a portion of endogenous CEP290 mRNA and the coding domain having one or more functional CEP290 exons. In some embodiments, the binding domain is in an antisense orientation to a sequence of the target CEP290 intron.

A 5' trans-splicing molecule will generally bind the target CEP290 intron 3' to the mutation. In one embodiment, the binding domain comprises a part of a sequence complementary to the target CEP290 intron.

In another embodiment, the binding domain is targeted to an intron sequence in close proximity to the 3' or 5' splice signals of a target intron. In still another embodiment, a binding domain sequence can bind to the target intron in addition to part of an adjacent exon.

Thus, in some instances, the binding domain binds specifically to the mutated endogenous target pre-mRNA to anchor the coding domain of the trans-splicing molecule to the pre-mRNA to permit trans-splicing to occur at the correct position in the target CEP290 gene. The spliceosome processing machinery of the nucleus may then mediate successful trans-splicing of the corrected exon for the mutated exon causing the disease.

In certain embodiments, the trans-splicing molecules feature binding domains that contain sequences on the target pre-mRNA that bind in more than one place. The binding domain may contain any number of nucleotides necessary to stably bind to the target pre-mRNA to permit trans-splicing to occur with the coding domain. In one embodiment, the binding domains are selected using mFOLD structural analysis for accessible loops (Zuker, *Nucleic Acids Res.* 2003, 31 (13): 3406-3415).

Suitable target binding domains can be from 10 to 500 nucleotides in length. In some embodiments, the binding domain is from 20 to 400 nucleotides in length. In some embodiments, the binding domain is from 50 to 300 nucleotides in length. In some embodiments, the binding domain is from 100 to 200 nucleotides in length. In some embodiments, the binding domain is from 10-20 nucleotides in length (e.g., 10, 11, 12, 13, 14, 15, 16, 17, 18, 19, or 20 nucleotides in length), 20-30 nucleotides in length (e.g., 20, 21, 22, 23, 24, 25, 26, 27, 28, 29, or 30 nucleotides in length), 30-40 nucleotides in length (e.g., 30, 31, 32, 33, 34, 35, 36, 37, 38, 39, or 40 nucleotides in length), 40-50 nucleotides in length (e.g., 40, 41, 42, 43, 44, 45, 46, 47, 48, 49, 50 nucleotides in length), 50-60 nucleotides in length (e.g., 50, 51, 52, 53, 54, 55, 56, 57, 58, 59, or 60 nucleotides in length), 60-70 nucleotides in length (e.g., 60, 61, 62, 63, 64, 65, 66, 67, 68, 69, or 70 nucleotides in length), 70-80 nucleotides in length (e.g., 70, 71, 72, 73, 74, 75, 76, 77, 78, 79, or 80 nucleotides in length), 80-90 nucleotides in length (e.g., 80, 81, 82, 83, 84, 85, 86, 87, 88, 89, or 90 nucleotides in length), 90-100 nucleotides in length (e.g., 90, 91, 92, 93, 94, 95, 96, 97, 98, 99, or 100 nucleotides in length), 100-110 nucleotides in length (e.g., 100, 101, 102, 103, 104, 105, 106, 107, 108, 109, or 110 nucleotides in length), 110-120 nucleotides in length (e.g., 110, 111, 112, 113, 114, 115, 116, 117, 118, 119, or 120 nucleotides in length), 120-130 nucleotides in length (e.g., 120, 121, 122, 123, 124, 125, 126, 127, 128, 129, or 130 nucleotides in length), 130-140 nucleotides in length (e.g., 130, 131, 132, 133, 134, 135, 136, 137, 138, 139, or 140 nucleotides in length), 140-150 nucleotides in length (e.g., 140, 141, 142, 143, 144, 145, 146, 147, 148, 149, or 150 nucleotides in length), 150-160 nucleotides in length (e.g., 150, 151, 152, 153, 154, 155, 156, 157, 158, 159, or 160 nucleotides in length), 160-170 nucleotides in length (e.g., 160, 161, 162, 163, 164, 165, 166, 167, 168, 169, or 170 nucleotides in length), 170-180 nucleotides in length (e.g., 170, 171, 172, 173, 174, 175, 176, 177, 178, 179, or 180 nucleotides in length), 180-190 nucleotides in length (e.g., 180, 181, 182, 183, 184, 185, 186, 187, 188, 189, or 190 nucleotides in length), 190-200 nucleotides in length (e.g., 190, 191, 192, 193, 194, 195, 196, 197, 198, 199, or 200 nucleotides in length), 200-210 nucleotides in length, 210-220 nucleotides in length, 220-230 nucleotides in length, 230-240 nucleotides in length, 240-250 nucleotides in length, 250-260 nucleotides in length, 260-270 nucleotides in length, 270-280 nucleotides in length, 280-290 nucleotides in length, 290-300 nucleotides in length, 300-350 nucleotides in length, 350-400 nucleotides in length, 400-450 nucleotides in length, or 450-500 nucleotides in length. In some embodiments, the binding domain is about 150 nucleotides in length. In another embodiment, the target binding domains may include a nucleic acid sequence up to 750 nucleotides in length. In another embodiment, the target binding domains may include a nucleic acid sequence up to 1000 nucleotides in length. In another embodiment, the target binding domains may include a nucleic acid sequence up to 2000 nucleotides or more in length.

In some embodiments, the specificity of the trans-splicing molecule may be increased by increasing the length of the target binding domain. Other lengths may be used depending upon the lengths of the other components of the trans-splicing molecule.

The binding domain may be from 80% to 100% complementary to the target intron to be able to hybridize stably with the target intron. For example, in some embodiments, the binding domain is 80%, 81%, 82%, 83%, 84%, 85%, 86%, 87%, 88%, 89%, 90%, 91%, 92%, 93%, 94%, 95%, 96%, 97%, 98%, 99%, or 100% complimentary to the target intron. The degree of complementarity is selected by one of skill in the art based on the need to keep the trans-splicing molecule and the nucleic acid construct containing the necessary sequences for expression and for inclusion in the rAAV within a 3,000 or up to 4,000 nucleotide base limit. The selection of this sequence and strength of hybridization depends on the complementarity and the length of the nucleic acid.

Any of the aforementioned binding domains may bind to a binding site within intron 26 (SEQ ID NO: 85; e.g., at or 3' to a mutation, e.g., a substitution mutation at nucleotide 1,655 of intron 26), intron 27 (SEQ ID NO: 86), intron 28 (SEQ ID NO: 87), intron 29 (SEQ ID NO: 88), or intron 30 (SEQ ID NO: 89).

In certain instances of the invention, the trans-splicing molecule features a binding domain that binds to intron 26 of CEP290 (SEQ ID NO: 85) and includes a coding domain having functional CEP290 exons 2-26. In some embodiments, the binding site comprises any one or more of nucleotides 4,980 to 5,383 of SEQ ID NO: 85. In one embodiment, the binding site comprises any one or more of nucleotides 5,348 to 5,838 of SEQ ID NO: 85 (e.g., any one or more of nucleotides 5,348 to 5,700 of SEQ ID NO: 85, e.g., any one or more of nucleotides 5,400 to 5,600 of SEQ ID NO: 85, e.g., any one or more of nucleotides 5,460 to 5,560 of SEQ ID NO: 85, e.g., at least nucleotide 5,500 of SEQ ID NO: 85).

In other embodiments, the trans-splicing molecule features a binding domain that binds to intron 27 of CEP290 (SEQ ID NO: 86) and includes a coding domain having functional CEP290 exons 2-27. In some embodiments, the binding site comprises any one or more of nucleotides 120 to 680, nucleotides 710 to 2,200, or nucleotides 2,670 to 2,910 of SEQ ID NO: 86. In some embodiments, the binding site comprises any one or more of nucleotides 790 to 2,100 of SEQ ID NO: 86, e.g., any one or more of nucleotides 1,020 to 1,630 of SEQ ID NO: 86. In other embodiments, the binding site comprises any one or more of nucleotides 1,670 to 2,000 of SEQ ID NO: 86.

In some embodiments, the trans-splicing molecule features a binding domain that binds to intron 28 of CEP290 (SEQ ID NO: 87) and includes a coding domain having functional CEP290 exons 2-28. In some embodiments, the binding site comprises any one or more of nucleotides 1 to 390, nucleotides 410 to 560, or nucleotides 730 to 937 of SEQ ID NO: 87. In some embodiments, the binding site comprises any one or more of nucleotides 1 to 200 of SEQ ID NO: 87. In other embodiments, the binding site comprises any one or more of nucleotides 720 to 900 of SEQ ID NO: 87.

In some embodiments, the trans-splicing molecule features a binding domain that binds to intron 29 of CEP290 (SEQ ID NO: 88) and includes a coding domain having functional CEP290 exons 2-29. In some embodiments, the binding site comprises any one or more of nucleotides 1 to 600, nucleotides 720 to 940, or nucleotides 1,370 to 1,790 of SEQ ID NO: 88.

In other embodiments, the trans-splicing molecule features a binding domain that binds to intron 30 of CEP290 (SEQ ID NO: 89) and includes a coding domain having functional CEP290 exons 2-30. In some embodiments, the binding site comprises any one or more of nucleotides 880 to 1,240 of SEQ ID NO: 89, e.g., any one or more of nucleotides 950 to 1,240 of SEQ ID NO: 89, e.g., any one or more of nucleotides 1,060 to 1,240 of SEQ ID NO: 89.

Splicing Domains

The following splicing domains can be used in any of the trans-splicing molecules of the invention (e.g., any of the ABCA4 trans-splicing molecules or CEP290 trans-splicing molecules described herein).

The splicing domain can include a splice site, a branch point, and/or a PPT tract to mediate trans-splicing. In some embodiments, a splicing domain has a single splice site, which denotes that the splice site enables trans-splicing, but not cis-splicing, due to the lack of a corresponding splice site. In some embodiments, the splicing domains of the 3' trans-splicing molecule include a strong conserved branch point or branch site sequence, a polypyrimidine tract (PPT), and a 3' splice acceptor (AG or YAG) site and/or a 5' splice donor site. The splicing domains of the 5' trans-splicing molecule do not contain the branch point or PPT, but comprise a 5' splice acceptor/or 3' splice donor splice site.

Splicing domains may be selected by one of skill in the art according to known methods and principles. The splicing domain provides essential consensus motifs that are recognized by the spliceosome. The use of branch point and PPT follows consensus sequences required for performance of the two phosphoryl transfer reaction involved in trans-splicing. In one embodiment a branch point consensus sequence in mammals is YNYURAC (Y=pyrimidine; N=any nucleotide). A polypyrimidine tract is located between the branch point and the splice site acceptor and is important for different branch point utilization and 3' splice site recognition. Consensus sequences for the 5' splice donor site and the 3' splice region used in RNA splicing are well known in the art. In addition, modified consensus sequences that maintain the ability to function as 5' donor splice sites and 3' splice regions may be used. Briefly, in one embodiment, the 5' splice site consensus sequence is the nucleic acid sequence AG/GURAGU (where / indicates the splice site). In another embodiment the endogenous splice sites that correspond to the exon proximal to the splice site can be employed to maintain any splicing regulatory signals.

In one embodiment, a suitable 5' splice site with spacer is: 5'-GTA AGA GAG CTC GTT GCG ATA TTA T-3' (SEQ ID NO: 1). In one embodiment, a suitable 5' splice site is AGGT.

In one embodiment, a suitable 3' trans-splicing molecule branch site is 5'-TACTAAC-3'. In one embodiment, a suitable 3' splice site is: 5'-TAC TAA CTG GTA CCT CTT CTT TTT TTT CTG CAG-3' (SEQ ID NO: 2) or 5'-CAGGT-3'. In one embodiment, a suitable 3' trans-splicing molecule PPT is: 5'-TGG TAC CTC TTC TTT TTT TTC TG-3' (SEQ ID NO: 3).

Additional Components or Modifications

In some embodiments of any of the trans-splicing molecules of the invention (e.g., any of the ABCA4 trans-splicing molecules or CEP290 trans-splicing molecules described herein), the splicing domain is included as part of an artificial intron, which may include one or more additional components. For example, a spacer region may be included within an artificial intron to separate the splicing domain from the target binding domain in the trans-splicing molecule. The spacer region may be designed to include features such as (i) stop codons which would function to block translation of any unspliced trans-splicing molecule and/or (ii) sequences that enhance trans-splicing to the target pre-mRNA. The spacer may be between 3 to 25 nucleotides or more depending upon the lengths of the other components of the trans-splicing molecule and the rAAV limitations. In one embodiment, a suitable 5' trans-splicing molecule spacer is AGA TCT CGT TGC GAT ATT AT (SEQ ID NO: 4). In one embodiment, a suitable 3' spacer is: 5'-GAG AAC ATT ATT ATA GCG TTG CTC GAG-3' (SEQ ID NO: 5).

Still other optional components of the trans-splicing molecules (e.g., as part of artificial introns) include mini introns, and intronic or exonic enhancers (e.g., intronic splice enhancers, e.g., downstream intronic splice enhancers) or silencers that would regulate the trans-splicing.

In another embodiment, the trans-splicing molecule further comprises (e.g., as part of an artificial intron) at least one safety sequence incorporated into the spacer, binding domain, or elsewhere in the trans-splicing molecule to prevent nonspecific trans-splicing. This is a region of the trans-splicing molecule that covers elements of the 3' and/or 5' splice site of the trans-splicing molecule by relatively weak complementarity, preventing non-specific trans-splicing. The trans-splicing molecule is designed in such a way that upon hybridization of the binding/targeting portion(s) of the trans-splicing molecule, the 3' or 5' splice site is uncovered and becomes fully active. Such safety sequences comprise a complementary stretch of cis-sequence (or could be a second, separate, strand of nucleic acid) which binds to one or both sides of the trans-splicing molecule branch point, pyrimidine tract, 3' splice site and/or 5' splice site (splicing elements), or could bind to parts of the splicing elements themselves. The binding of the safety sequence may be disrupted by the binding of the target binding region of the trans-splicing molecule to the target pre-mRNA, thus exposing and activating the splicing elements (making them available to trans-splice into the target pre-mRNA). In another embodiment, the trans-splicing molecule has 3' UTR sequences or ribozyme sequences added to the 3' or 5' end.

In an embodiment, splicing enhancers such as, for example, sequences referred to as exonic splicing enhancers may also be included in the structure of an artificial intron. Additional features can be added to the artificial intron, such as polyadenylation signals to modify RNA expression/stability, or 5' splice sequences to enhance splicing, additional binding regions, safety-self complementary regions, additional splice sites, or protective groups to modulate the stability of the molecule and prevent degradation. In addition, stop codons may be included in the trans-splicing molecule (e.g., as part of the artificial intron) structure to prevent translation of unspliced trans-splicing molecules. Additional elements, such as a 3' hairpin structure, circularized RNA, nucleotide base modification, or synthetic analogs can be incorporated into trans-splicing molecules to promote or facilitate nuclear localization and spliceosomal incorporation, and intra-cellular stability.

In some embodiments, binding of a trans-splicing molecule to the target pro-mRNA is mediated by complementarity (i.e. based on base-pairing characteristics of nucleic acids), triple helix formation, or protein-nucleic acid interaction (as described in documents cited herein). In one embodiment, the nucleic acid trans-splicing molecule includes DNA, RNA, or DNA/RNA hybrid molecules, wherein the DNA or RNA is either single or double stranded. Also included herein are RNAs or DNAs, which can hybridize to one of the aforementioned RNAs or DNAs, preferably under stringent conditions, for example, at 60° C. in 2.5× SSC buffer and several washes at 37° C. at a lower buffer concentration, for example, 0.5× SSC buffer. These nucleic acids can encode proteins exhibiting lipid phosphate phosphatase activity and/or association with plasma membranes. When trans-splicing molecules are synthesized in vitro, such trans-splicing molecules can be modified at the base moiety, sugar moiety, or phosphate backbone, for example, to improve stability of the molecule, hybridization to the target mRNA, transport into the cell, stability in the cells to enzymatic cleavage, etc. For example, modification of a trans-splicing molecule to reduce the overall charge can enhance the cellular uptake of the molecule. In addition modifications can be made to reduce susceptibility to nuclease or chemical degradation. The nucleic acid molecules may be synthesized in such a way as to be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing intracellular stability and half-life (see also above for oligonucleotides). Possible modifications are known to the art. Modifications, which may be made to the structure of synthetic trans-splicing molecules include backbone modifications.

III. Recombinant AAV Molecules

Any suitable nucleic acid vector may be used in conjunction with the present compositions and methods to design and assemble the components of the trans-splicing molecule and a recombinant adeno-associated virus (AAV). In one embodiment, the vector is a recombinant AAV carrying the trans-splicing molecule and driven by a promoter that expresses a trans-splicing molecule in selected cells of a subject. Methods for assembly of the recombinant vectors are known in the art. See, e.g., Ausubel et al., *Current Protocols in Molecular Biology*, John Wiley & Sons, New York, 1989; Kay, M. A. et al., *Nat. Medic,* 2001, 7 (I): 33-40; and Walther W. and Stein U., *Drugs* 2000, 60 (2): 249-71.

In certain embodiments described herein, the trans-splicing molecule carrying the ABCA4 gene binding and coding domains is delivered to the selected cells, e.g., photoreceptor cells, in need of treatment by means of an AAV vector. More than 30 naturally occurring serotypes of AAV are available. Many natural variants in the AAV capsid exist, allowing identification and use of an AAV with properties specifically suited for ocular cells. AAV viruses may be engineered by conventional molecular biology techniques, making it possible to optimize these particles for cell specific delivery of the trans-splicing molecule nucleic acid sequences, for minimizing immunogenicity, for tuning stability and particle lifetime, for efficient degradation, for accurate delivery to the nucleus, etc.

The expression of the trans-splicing molecules described herein can be achieved in the selected cells through delivery by recombinantly engineered AAVs or artificial AAVs that contain sequences encoding the desired trans-splicing molecule. The use of AAVs is a common mode of exogenous delivery of DNA as it is relatively non-toxic, provides efficient gene transfer, and can be easily optimized for specific purposes. Among the well-characterized serotypes of AAVs isolated from human or non-human primates, human serotype 2 has been widely used for efficient gene transfer experiments in different target tissues and animal models. Other AAV serotypes include, but are not limited to, AAV1, AAV3, AAV4, AAV5, AAV6, AAV7, AAV8, and AAV9. Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9 or other known and unknown AAV serotypes. In one embodiment, the ITRs are from AAV2. These ITRs or other AAV components may be readily isolated using techniques available to those of skill in the art from an AAV serotype. Such AAV may be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank, PubMed, or the like.

Desirable AAV fragments for assembly into vectors include the cap proteins, including the vp1, vp2, vp3, and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is utilized with the ITRs from an AAV having a different capsid protein, are useful in the invention. In one embodiment, the AAV is AAV2/5 (i.e., an AAV having AAV2 ITRs and an AAV5 capsid). In another embodiment, the AAV is AAV2/8 (i.e., an AAV having AAV2 ITRs and an AAV8 capsid). In one embodiment, the AAV includes an AAV8 capsid. Such AAV8 capsid includes the amino acid sequence found under NCBI Reference Sequence: YP_077180.1 (SEQ ID NO: 56). In another embodiment, the AAV8 capsid includes a capsid encoded by nt 2121 to 4337 of GenBank accession: AF513852.1 (SEQ ID NO: 57).

In one embodiment, the AAV includes a capsid sequence derived from AAV8. In some embodiments, the AAV derived from AAV8 is AAV8(b), described in U.S. Pat. No. 9,567,376, which is incorporated herein by reference in its entirety. AAV(b) (SEQ ID NO: 58) comprises the amino acid sequence of Pro-Glu-Arg-Thr-Ala-Met-Ser-Leu-Pro at amino acid positions 587-595 as compared to wildtype AAV8. In another embodiment, the AAV8(b) capsid is encoded by SEQ ID NO: 59.

In one embodiment, the vectors useful in compositions and methods described herein contain, at a minimum, sequences encoding a selected AAV serotype capsid, e.g., an AAV2 capsid, or a fragment thereof. In another embodiment, useful vectors contain, at a minimum, sequences encoding a selected AAV serotype rep protein, e.g., AAV2 rep protein, or a fragment thereof. Optionally, such vectors may contain both AAV cap and rep proteins. In vectors in which both AAV rep and cap are provided, the AAV rep and AAV cap sequences can both be of one serotype origin, e.g., an AAV2 origin.

Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector described in U.S. Pat. No. 7,282,199, which is incorporated by reference herein.

A suitable recombinant AAV (rAAV) is generated by culturing a host cell which contains a nucleic acid sequence encoding an AAV serotype capsid protein, or fragment thereof, as defined herein; a functional rep gene; a minigene composed of, e.g., AAV ITRs and the trans-splicing molecule nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

In one embodiment, the AAV includes a promoter (or a functional fragment of a promoter). The selection of the promoter to be employed in the rAAV may be made from among a wide number of constitutive or inducible promoters that can express the selected transgene in the desired target cell. See, e.g., the list of promoters identified in International Patent Publication No. WO 2014/012482, incorporated by reference herein. In one embodiment, the promoter is cell-specific. The term "cell-specific" means that the particular promoter selected for the recombinant vector can direct expression of the selected transgene in a particular cell type. In one embodiment, the promoter is specific for expression of the transgene in photoreceptor cells. In another embodiment, the promoter is specific for expression in the rods and/or cones. In another embodiment, the promoter is specific for expression of the transgene in retinal pigment epithelium (RPE) cells. In another embodiment, the promoter is specific for expression of the transgene in ganglion cells. In another embodiment, the promoter is specific for expression of the transgene in Mueller cells. In another embodiment, the promoter is specific for expression of the transgene in bipolar cells. In another embodiment, the promoter is specific for expression of the transgene in horizontal cells. In another embodiment, the promoter is specific for expression of the transgene in amacrine cells. In another embodiment, the transgene is expressed in any of the above noted cells.

In another embodiment, the promoter is the native promoter for the target gone to be expressed. Useful promoters include, without limitation, a rod opsin promoter, a red-green opsin promoter, a blue opsin promoter, a cGMP-phosphodiesterase promoter, a mouse opsin promoter, a rhodopsin promoter, an alpha-subunit of cone transducing, a beta phosphodiesterase (PDE) promoter, a retinitis pigmentosa promoter, a NXNL2/NXNL 1 promoter, the RPE65 promoter, the retinal degeneration slow/peripherin 2 (Rds/perph2) promoter, and the VMD2 promoter.

Other conventional regulatory sequences contained in the mini-gene or rAAV are also disclosed in documents such as WO 2014/124282 and others cited and incorporated by reference herein. One of skill in the art may make a selection among these, and other, expression control sequences without departing from the scope described herein An AAV minigene may include the trans-splicing molecule described herein and its regulatory sequences, and 5' and 3' AAV ITRs. In one embodiment, the ITRs of AAV serotype 2 are used. In another embodiment, the ITRs of AAV serotype 5 or 8 are used. However, ITRs from other suitable serotypes may be selected. In some embodiments, the minigene is packaged into a capsid protein and delivered to a selected host cell.

The minigene, rep sequences, cap sequences, and helper functions required for producing the rAAV may be delivered to the packaging host cell in the form of any genetic element which transfers the sequences carried thereon. The selected genetic element may be delivered by any suitable method, including those described herein. The methods used to construct any embodiment described herein are known to those with skill in nucleic acid manipulation and include genetic engineering, recombinant engineering, and synthetic techniques. See, e.g., Sambrook et al., *Molecular Cloning: A Laboratory Manual*, Cold Spring Harbor Press, Cold Spring Harbor, NY. Similarly, methods of generating rAAV virions are well known and the selection of a suitable method is not a limitation on the present invention. See, e.g., K. Fisher et al., *J. Virol.*, 1993 70:520-532 and U.S. Pat. No. 5,478,745, each of which is incorporated by reference herein.

In another embodiment, the trans-splicing molecule minigene is prepared in a proviral plasmid, such as those disclosed in International Patent Publication No. WO 2012/158757, incorporated herein by reference. Such a proviral plasmid contains a modular recombinant AAV genome comprising in operative association comprising: a wildtype 5' AAV2 ITR sequence flanked by unique restriction sites that permit ready removal or replacement of said ITR; a promoter comprising a 49-nucleic acid cytomegalovirus sequence upstream of a cytomegalovirus (CMV)-chicken beta actin sequence, or a photoreceptor-specific promotor/enhancer, the promoter flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. The trans-splicing molecule described herein can be inserted into the site of a multi-cloning poly linker, wherein the trans-splicing molecule is operatively linked to, and under the regulatory control of, the promoter. A bovine growth hormone polyadenylation sequence flanked by unique restriction sites that permit ready removal or replacement of said polyA sequence; and a wildtype 3' AAV2 ITR sequence flanked by unique restriction sites that permit ready removal or replacement of the 3' ITR; are also part of this plasmid. The plasmid backbone comprises the elements necessary for replication in bacterial cells, e.g., a kanamycin resistance gene, and is itself flanked by transcriptional terminator/insulator sequences.

In one embodiment, a proviral plasmid comprises: (a) a modular recombinant AAV genome comprising in operative association comprising: (i) a wildtype 5' AAV2 ITR sequence flanked by unique restriction sites that permit ready removal or replacement of said ITR; (ii) a promoter comprising (A) a 49-nucleic acid CMV sequence upstream of a CMV-chicken beta actin sequence; (b) a photoreceptor-specific promoter/enhancer; or (c) a neuronal cell-specific promoter/enhancer. The promoter is flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. Also part of this proviral plasmid is a multi-cloning polylinker sequence that permits insertion of a trans-splicing molecule sequence including any of those described herein, wherein the trans-splicing molecule is operatively linked to, and under the regulatory control of, the promoter; a bovine growth hormone polyadenylation sequence flanked by unique restriction sites that permit ready removal or replacement of said polyA sequence; and a wildtype 3' AAV2 ITR sequence flanked by unique restriction sites that permit ready removal or replacement of the 3' ITR. The proviral plasmid also contains a plasmid backbone comprising the elements necessary for replication in bacterial cells, and further comprising a kanamycin resistance gene, said plasmid backbone flanked by transcriptional terminator/insulator sequences. The proviral plasmid described herein may also contain in the plasmid backbone a non-coding lambda phage 5.1 kb stuffer sequence to increase backbone length and prevent reverse packaging of non-functional AAV genomes.

In some embodiments, a proviral plasmid contains multiple copies of a trans-splicing molecule. For example, the present invention features trans-splicing molecules that are less than half the packaging limit for AAV and can therefore be repeated once, twice, three times, four times, five times, six times, seven times, eight times, nine times, 10 times, 11 times, 12 times, 13 times, 14 times, 15 times, 16 times, 17 times, 18 times, 19 times, 20 times, or more on a single proviral plasmid.

In yet a further aspect, the promoter of the proviral plasmid is modified to reduce the size of the promoter to permit larger trans-splicing molecule sequences to be inserted in the rAAV. In one embodiment, the CMV/CBA hybrid promoter, which normally includes a non-coding exon and intron totaling about 1,000 base pairs, is replaced with a 130-base pair chimeric intron, as described in International Patent Publication No. WO 2017/087900, which is incorporated herein by reference in its entirety.

These proviral plasmids are then employed in currently conventional packaging methodologies to generate a recombinant virus expressing the trans-splicing molecule transgene carried by the proviral plasmids. Suitable production cell lines are readily selected by one of skill in the art. For example, a suitable host cell can be selected from any biological organism, including prokaryotic (e.g., bacterial) cells, and eukaryotic cells, including, insect cells, yeast cells and mammalian cells. Briefly, the proviral plasmid is transfected into a selected packaging cell, where it may exist transiently. Alternatively, the minigene or gene expression cassette with its flanking ITRs is stably integrated into the genome of the host cell, either chromosomally or as an episome. Suitable transfection techniques are known and may readily be utilized to deliver the recombinant AAV genome to the host cell. Typically, the proviral plasmids are cultured in the host cells which express the cap and/or rep proteins. In the host cells, the minigene consisting of the trans-splicing molecule with flanking AAV ITRs is rescued and packaged into the capsid protein or envelope protein to form an infectious viral particle. Thus, a recombinant AAV infectious particle is produced by culturing a packaging cell carrying the proviral plasmid in the presence of sufficient viral sequences to permit packaging of the gene expression cassette viral genome into an infectious AAV envelope or capsid.

IV. Pharmaceutical Compositions and Kits

Provided herein are pharmaceutical compositions including a nucleic acid trans-splicing molecule, a proviral plasmid, or a rAAV comprising the nucleic acid trans-splicing molecule described herein. In some embodiments, the pharmaceutical composition includes any of the 5' trans-splicing molecules described herein. In other embodiments, the pharmaceutical composition includes any of the 3' trans-splicing molecules described herein. In some embodiments, the pharmaceutical composition includes a 5' trans-splicing molecule and a 3' trans-splicing molecule, e.g., wherein the 5' trans-splicing molecule and the 3' trans-splicing molecule together contain functional ABCA4 exons 1-50 and bind the same target ABCA4 intron.

The pharmaceutical compositions described herein may be assessed for contamination by conventional methods and then formulated into a pharmaceutical composition intended for a suitable route of administration. Still other compositions containing the trans-splicing molecule, e.g., naked DNA or as protein, may be formulated similarly with a suitable carrier. Such formulation involves the use of a pharmaceutically and/or physiologically acceptable vehicle or carrier, particularly directed for administration to the target cell. In one embodiment, carriers suitable for administration to the target cells include buffered saline, an isotonic sodium chloride solution, or other buffers, e.g., HEPES, to maintain pH at appropriate physiological levels, and, optionally, other medicinal agents, pharmaceutical agents, stabilizing agents, buffers, carriers, adjuvants, diluents, etc.

In some embodiments, the carrier is a liquid for injection. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In other embodiments, compositions containing trans-splicing molecules described herein include a surfactant. Useful surfactants, such as Pluronic F68 (Poloxamer 188, also known as LUTROL® F68) may be included as they prevent AAV from sticking to inert surfaces and thus ensure delivery of the desired dose. As an example, one illustrative composition designed for the treatment of the ocular diseases described herein comprises a recombinant adeno-associated vector carrying a nucleic acid sequence encoding 3' trans-splicing molecule as described herein, under the control of regulatory sequences which express the trans-splicing molecule in an ocular cell of a mammalian subject, and a pharmaceutically acceptable carrier. The carrier is isotonic sodium chloride solution and includes a surfactant Pluronic F68. In one embodiment, the trans-splicing molecule is any of those described herein.

In yet another exemplary embodiment, the composition comprises a recombinant AAV2/5 pseudotyped adeno-associated virus carrying a 3' or 5' trans-splicing molecule for ABCA4 gene replacement, the nucleic acid sequence under the control of promoter which directs expression of the trans-splicing molecule in said photoreceptor cells, wherein the composition is formulated with a carrier and additional components suitable for subretinal injection. In still another embodiment, the composition or components for production or assembly of this composition, including carriers, rAAV particles, surfactants, and/or the components for generating the rAAV, as well as suitable laboratory hardware to prepare the composition, may be incorporated into a kit.

In some instances, the composition comprises a recombinant AAV2/5 pseudotyped adeno-associated virus carrying a 5' trans-splicing molecule for CEP290 gene replacement, the nucleic acid sequence under the control of promoter which directs expression of the trans-splicing molecule in said photoreceptor cells, wherein the composition is formulated with a carrier and additional components suitable for subretinal injection. In still another embodiment, the composition or components for production or assembly of this composition, including carriers, rAAV particles, surfactants, and/or the components for generating the rAAV, as well as suitable laboratory hardware to prepare the composition, may be incorporated into a kit.

Additionally provided herein are kits containing a first pharmaceutical composition comprising a 5' trans-splicing molecule and a second pharmaceutical composition comprising a 3' trans-splicing molecule, e.g., wherein the 5' trans-splicing molecule and the 3' trans-splicing molecule together contain functional ABCA4 exons 1-50 and bind the same target ABCA4 intron (e.g., wherein the trans-splicing molecules are packaged in any AAV vectors described herein). In some embodiments, the kit includes instructions for mixing the two pharmaceutical compositions prior to administration.

Additionally provided herein are kits containing a first pharmaceutical composition comprising a 5' trans-splicing molecule to bind a target CEP290 intron.

V. Methods

The compositions described above involving ABCA4 trans-splicing are useful in methods of treating diseases or disorders caused by a mutation in the ABCA4 gene, such as a Stargardt Disease (e.g., Stargardt Disease 1) including delaying or ameliorating symptoms associated with the disease described herein. Such methods involve contacting a target ABCA4 gene (e.g., ABCA4 pre-mRNA) with a trans-splicing molecule as described herein (e.g., one or more of a 3'trans-splicing molecule, 5' trans-splicing molecule, or both 3' and 5' trans-splicing molecule as described herein), under conditions in which a coding domain of the trans-splicing molecule is spliced to the target ABCA4 gene to replace a part of the targeted gene carrying one or more defects or mutations, with a functional (i.e., healthy), or normal or wildtype or corrected mRNA of the targeted gene, in order to correct expression of ABCA4 in the target cell. Thus, the methods and compositions are used to treat the ocular diseases/pathologies associated with the specific mutations and/or gene expression.

In one embodiment, the contacting involves direct administration to the affected subject. In another embodiment, the contacting may occur ex vivo to the cultured cell and the treated ocular cell reimplanted in the subject. In one embodiment, the method involves administering a rAAV carrying a 3' trans-splicing molecule. In another embodiment, the method involves administering a rAAV carrying a 5' trans-splicing molecule. In still another embodiment, the method involves administering a mixture of rAAV carrying a 3' trans-splicing molecule and rAAV carrying a 5' trans-splicing molecule. These methods comprise administering to a subject in need thereof an effective concentration of a composition of any of those described herein.

In some embodiments, the methods include selecting one or more trans-splicing molecules for treating a subject having a disorder associated with a mutation in ABCA4, such as Stargardt Disease (e.g., Stargardt Disease 1). Such selection can be based on the genotype of the subject. In some embodiments, a disorder associated with ABCA4 may be an autosomal recessive disorder. In some instances, the subject is homozygous or compound heterozygous for the mutation in ABCA4. Methods of screening for and identifying particular mutations in ABCA4 are known in the art.

In other instances, the compositions described above involving CEP290 trans-splicing are useful in methods of treating diseases or disorders caused by a mutation in the CEP290 gene, such as Leber congenital amourosis (e.g., LCA 10) including delaying or ameliorating symptoms associated with the disease described herein. Such methods involve contacting a target CEP290 gene (e.g., CEP290 pre-mRNA) with a trans-splicing molecule as described herein (e.g., a 5' trans-splicing molecule), under conditions in which a coding domain of the trans-splicing molecule is spliced to the target CEP290 gene to replace a part of the targeted gene carrying one or more defects or mutations, with a functional (i.e., healthy), or normal or wildtype or corrected mRNA of the targeted gene, in order to correct expression of CEP290 in the target cell. Thus, the methods and compositions are used to treat the ocular diseases/pathologies associated with the specific mutations and/or gene expression. Methods of the invention include correcting a pathogenic point mutation in intron 26 (e.g., at nucleotide 1,655 of intron 26) of CEP290 by administering a 5' trans-splicing molecule (e.g., any of the 5' trans-splicing molecules described herein), or a pharmaceutical composition thereof. Thus, the invention provides methods of treating a subject having a disease or disorder associated with a mutation in CEP290 (e.g., a disease or disorder associated with a mutation in intron 26 of CEP290, e.g., at nucleotide 1,655 of intron 26) by administering a trans-splicing molecule described herein. Any of the aforementioned trans-splicing molecules can be included in a pharmaceutical composition (e.g., a single pharmaceutical composition including both molecules, either pre-prepared or admixed prior to administration, e.g., as part of a kit).

In one embodiment, the contacting involves direct administration to the affected subject. In another embodiment, the contacting may occur ex vivo to the cultured cell and the treated ocular cell reimplanted in the subject. In one embodiment, the method involves administering a rAAV carrying a 5' trans-splicing molecule. These methods comprise administering to a subject in need thereof an effective concentration of a composition of any of those described herein.

In some embodiments, the methods include selecting one or more trans-splicing molecules for treating a subject having a disorder associated with a mutation in CEP290, such as LCA 10. Such selection can be based on the genotype of the subject. In some embodiments, a disorder associated with CEP290 may be an autosomal recessive disorder. In some instances, the subject is homozygous or compound heterozygous for the mutation in CEP290. Methods of screening for and identifying particular mutations in CEP290 are known in the art.

Single Trans-Splicing Molecules for Correcting a Single Mutation

Methods of the invention include selecting a single trans-splicing molecule based on the location of a single mutation in ABCA4 (e.g., a mutation of one allele of the subject). In some instances in the context of autosomal recessive mutations, correction of just one of two mutations can be sufficient to restore functional protein activity, for example, wherein the second allele has a mutation on the opposite portion of the ABCA4 gene, out of range of a single AAV-delivered trans-splicing molecule configured to correct the first mutation.

Thus, in some embodiments, methods of the invention include selecting a single trans-splicing molecule to correct a single mutation on the 5' portion of the target gene, e.g., without regard to the location of the mutation in the other allele. In one embodiment, the mutated exon is exon 1, the target intron is intron 19, 22, 23, or 24, and the coding domain includes a functional ABCA4 exon 1. In one embodiment, exon 1 or exon 2 is mutated, the target intron is intron 19, 22, 23, or 24, and the coding domain includes functional ABCA4 exons 1 and 2. In one embodiment, one of exons 1, 2, and 3 is mutated, the target intron is intron 19, 22, 23, or 24, and the coding domain includes functional ABCA4 exons 1-3. In one embodiment, one of exons 1, 2, 3, and 4 is mutated, the target intron is intron 19, 22, 23, or 24, and the coding domain includes functional ABCA4 exons 1-4. In one embodiment, one of exons 1, 2, 3, 4, and 5 is mutated, the target intron is intron 19, 22, 23, or 24, and the coding domain includes functional ABCA4 exons 1-5. In one embodiment, one of exons 1, 2, 3, 4, 5, and 6 is mutated, the target intron is intron 19, 22, 23, or 24, and the coding domain includes functional ABCA4 exons 1-6. In one embodiment, one of exons 1, 2, 3, 4, 5, 6, or 7 is mutated, the target intron is intron 19, 22, 23, or 24, and the coding domain includes functional ABCA4 exons 1-7. In one embodiment, one of exons 1, 2, 3, 4, 5, 6, 7, or 8 is mutated, the target intron is intron 19, 22, 23, or 24, and the coding domain includes functional ABCA4 exons 1-8. In one embodiment, one of exons 1, 2, 3, 4, 5, 6, 7, 8, or 9 is mutated, the target intron is intron 19, 22, 23, or 24, and the coding domain includes functional ABCA4 exons 1-9. In one embodiment, one of exons 1, 2, 3, 4, 5, 6, 7, 8, 9, or 10 is mutated, the target intron is intron 19, 22, 23, or 24, and the coding domain includes functional ABCA4 exons 1-10. In one embodiment, one of exons 1, 2, 3, 4, 5, 6, 7, 8, 9, 10, or 11 is mutated, the target intron is intron 19, 22, 23, or 24, and the coding domain includes functional ABCA4 exons 1-11. In one embodiment, one of exons 1, 2, 3, 4, 5, 6, 7, 8, 9, 10, 11, or 12 is mutated, the target intron is intron 19, 22, 23, or 24, and the coding domain includes functional ABCA4 exons 1-12. In one embodiment, one of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In one embodiment, one of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In one embodiment, one of exons 1, 2, 3, 4, 5, 6, 7, 8, 9, 10, 11, 12, 13, or 14 is mutated, the target intron is intron 19, 22, 23, or 24, and the coding domain includes functional ABCA4 exons 1-14. In one embodiment, one of exons 1, 2, 3, 4, 5, 6, 7, 8, 9, 10, 11, 12, 13, 14, or 15 is mutated, the target intron is intron 19, 22, 23, or 24, and the coding domain includes functional ABCA4 exons 1-15. In one embodiment, one of exons 1, 2, 3, 4, 5, 6, 7, 8, 9, 10, 11, 12, 13, 14, 15, or 16 is mutated, the target intron is intron 19, 22, 23, or 24, and the coding domain includes functional ABCA4 exons 1-16. In one embodiment, one of exons 1, 2, 3, 4, 5, 6, 7, 8, 9, 10, 11, 12, 13, 14, 15, 16, or 17 is mutated, the target intron is intron 19, 22, 23, or 24, and the coding domain includes functional ABCA4 exons 1-17. In one embodiment, one of exons 1, 2, 3, 4, 5, 6, 7, 8, 9, 10, 11, 12, 13, 14, 15, 16, 17, or 18 is mutated, the target intron is intron 19, 22, 23, or 24, and the coding domain includes functional ABCA4 exons 1-18. In one embodiment, one of exons 1, 2, 3, 4, 5, 6, 7, 8, 9, 10, 11, 12, 13, 14, 15, 16, 17, 18, or 19 is mutated, the target intron is intron 19, 22, 23, or 24, and the coding domain includes functional ABCA4 exons 1-19. In one embodiment, one of exons 1, 2, 3, 4, 5, 6, 7, 8, 9, 10, 11, 12, 13, 14, 15, 16, 17, 18, 19, or 20 is mutated, the target intron is intron 22, 23, or 24, and the coding domain includes functional ABCA4 exons 1-20. In one embodiment, one of exons 1, 2, 3, 4, 5, 6, 7, 8, 9, 10, 11, 12, 13, 14, 15, 16, 17, 18, 19, 20, or 21 is mutated, the target intron is intron 22, 23, or 24, and the coding domain includes functional ABCA4 exons 1-21. In one embodiment, one of exons 1, 2, 3, 4, 5, 6, 7, 8, 9, 10, 11, 12, 13, 14, 15, 16, 17, 18, 19, 20, 21, or 22 is mutated, the target intron is intron 22, 23, or 24, and the coding domain includes functional ABCA4 exons 1-22. In one embodiment, one of exons 1, 2, 3, 4, 5, 6, 7, 8, 9, 10, 11, 12, 13, 14, 15, 16, 17, 18, 19, 20, 21, 22, or 23 is mutated, the target intron is intron 23 or 24, and the coding domain includes functional ABCA4 exons 1-23. In one embodiment, one of exons 1, 2, 3, 4, 5, 6, 7, 8, 9, 10, 11, 12, 13, 14, 15, 16, 17, 18, 19, 20, 21, 22, 23, or 24 is mutated, the target intron is intron 24, and the coding domain includes functional ABCA4 exons 1-24.

Alternatively, in instances in which a mutation is on the 3' portion of the target gene, a 3' trans-splicing molecule is selected to correct the mutation, e.g., without regard to the location of the mutation on the other allele. In one embodiment, one of exons 23, 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, and the coding domain includes functional ABCA4 exons 23-50. In one embodiment, one of exons 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22 or 23, and the coding domain includes functional ABCA4 exons 24-50. In one embodiment, one of exons 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 25-50. In one embodiment, one of exons 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 26-50. In one embodiment, one of exons 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 27-50. In one embodiment, one of exons 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 28-50. In one embodiment, one of exons 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 29-50. In one embodiment, one of exons 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 30-50. In one embodiment, one of exons 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 31-50. In one embodiment, one of exons 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 32-50. In one embodiment, one of exons 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 33-50. In one embodiment, one of exons 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 34-50. In one embodiment, one of exons 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 35-50. In one embodiment, one of exons 36, 37, 38, 39, 40, 41, 42, 43, 44, 45, 46, 47, 48, 49, or 50 is mutated, the target intron is intron 22, 23, or 24, and the coding domain includes functional ABCA4 exons 36-50. In one embodiment, one of exons 37, 38, 39, 40, 41, 42, 43, 44, 45, 46, 47, 48, 49, or 50 is mutated, the target intron is intron 22, 23, or 24, and the coding domain includes functional ABCA4 exons 37-50. In one embodiment, one of exons 38, 39, 40, 41, 42, 43, 44, 45, 46, 47, 48, 49, or 50 is mutated, the target intron is intron 22, 23, or 24, and the coding domain includes functional ABCA4 exons 38-50. In one embodiment, one of exons 39, 40, 41, 42, 43, 44, 45, 46, 47, 48, 49, or 50 is mutated, the target intron is intron 22, 23, or 24, and the coding domain includes functional ABCA4 exons 39-50. In one embodiment, one of exons 40, 41, 42, 43, 44, 45, 46, 47, 48, 49, or 50 is mutated, the target intron is intron 22, 23, or 24, and the coding domain includes functional ABCA4 exons 40-50. In one embodiment, one of exons 41, 42, 43, 44, 45, 46, 47, 48, 49, or 50 is mutated, the target intron is intron 22, 23, or 24, and the coding domain includes functional ABCA4 exons 41-50. In one embodiment, one of exons 42, 43, 44, 45, 46, 47, 48, 49, or 50 is mutated, the target intron is intron 22, 23, or 24, and the coding domain includes functional ABCA4 exons 42-50. In one embodiment, one of exons 43, 44, 45, 46, 47, 48, 49, or 50 is mutated, the target intron is intron 22, 23, or 24, and the coding domain includes functional ABCA4 exons 43-50. In one embodiment, one of exons 44, 45, 46, 47, 48, 49, or 50 is mutated, the target intron is intron 22, 23, or 24, and the coding domain includes functional ABCA4 exons 44-50. In one embodiment, one of exons 45, 46, 47, 48, 49, or 50 is mutated, the target intron is intron 22, 23, or 24, and the coding domain includes functional ABCA4 exons 45-50. In one embodiment, one of exons 46, 47, 48, 49, or 50 is mutated, the target intron is intron 22, 23, or 24, and the coding domain includes functional ABCA4 exons 46-50. In one embodiment, one of exons 47, 48, 49, or 50 is mutated, the target intron is intron 22, 23, or 24, and the coding domain includes functional ABCA4 exons 47-50. In one embodiment, one of exons 48, 49, or 50 is mutated, the target intron is intron 22, 23, or 24, and the coding domain includes functional ABCA4 exons 48-50. In one embodiment, one of exons 49 or 50 is mutated, the target intron is intron 22, 23, or 24, and the coding domain includes functional ABCA4 exons 49 or 50. In one embodiment, exon 50 is mutated, the target intron is intron 22, 23, or 24, and the coding domain includes functional ABCA4 exon 50.

Single Trans-Splicing Molecules for Correcting Multiple Mutations

Methods of the invention include selecting a single trans-splicing molecule based on the location of a mutation in ABCA4 in each allele of the subject, when two mutations are either on a 5' portion of the gene or the 3' portion of the gene, such that a single trans-splicing molecule capable of being packaged in an AAV vector is capable of spanning both mutations, thereby correcting both mutations.

For example, in instances in which both mutations occur on the 5' portion of the target gene, a 5' trans-splicing molecule is selected to correct both mutations. In one embodiment, the mutated exon is exon 1 (i.e., both mutations are in exon 1), the target intron is intron 19, 22, 23, or 24, and the coding domain includes a functional ABCA4 exon 1. In one embodiment, exon 1 and/or exon 2 are mutated, the target intron is intron 19, 22, 23, or 24, and the coding domain includes functional ABCA4 exons 1 and 2. In one embodiment, one or two of exons 1, 2, and 3 is mutated, the target intron is intron 19, 22, 23, or 24, and the coding domain includes functional ABCA4 exons 1-3. In one embodiment, one or two of exons 1, 2, 3, and 4 is mutated, the target intron is intron 19, 22, 23, or 24, and the coding domain includes functional ABCA4 exons 1-4. In one embodiment, one or two of exons 1, 2, 3, 4, and 5 is mutated, the target intron is intron 19, 22, 23, or 24, and the coding domain includes functional ABCA4 exons 1-5. In one embodiment, one or two of exons 1, 2, 3, 4, 5, and 6 is mutated, the target intron is intron 19, 22, 23, or 24, and the coding domain includes functional ABCA4 exons 1-6. In one embodiment, one or two of exons 1, 2, 3, 4, 5, 6, or 7 is mutated, the target intron is intron 19, 22, 23, or 24, and the coding domain includes functional ABCA4 exons 1-7. In one embodiment, one or two of exons 1, 2, 3, 4, 5, 6, 7, or 8 is mutated, the target intron is intron 19, 22, 23, or 24, and the coding domain includes functional ABCA4 exons 1-8. In one embodiment, one or two of exons 1, 2, 3, 4, 5, 6, 7, 8, or 9 is mutated, the target intron is intron 19, 22, 23, or 24, and the coding domain includes functional ABCA4 exons 1-9. In one embodiment, one or two of exons 1, 2, 3, 4, 5, 6, 7, 8, 9, or 10 is mutated, the target intron is intron 19, 22, 23, or 24, and the coding domain includes functional ABCA4 exons 1-10. In one embodiment, one or two of exons 1, 2, 3, 4, 5, 6, 7, 8, 9, 10, or 11 is mutated, the target intron is intron 19, 22, 23, or 24, and the coding domain includes functional ABCA4 exons 1-11. In one embodiment, one or two of exons 1, 2, 3, 4, 5, 6, 7, 8, 9, 10, 11, or 12 is mutated, the target intron is intron 19, 22, 23, or 24, and the coding domain includes functional ABCA4 exons 1-12. In one embodiment, one or two of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In ono embodiment, one or two of exons 1, 2, 3, 4, 5, 6, 7, 8, 9, 10, 11, 12, or 13 is mutated, the target intron is intron 19, 22, 23, or 24, and the coding domain includes functional ABCA4 exons 1-13. In one embodiment, one or two of exons 1, 2, 3, 4, 5, 6, 7, 8, 9, 10, 11, 12, 13, or 14 is mutated, the target intron is intron 19, 22, 23, or 24, and the coding domain includes functional ABCA4 exons 1-14. In one embodiment, one or two of exons 1, 2, 3, 4, 5, 6, 7, 8, 9, 10, 11, 12, 13, 14, or 15 is mutated, the target intron is intron 19, 22, 23, or 24, and the coding domain includes functional ABCA4 exons 1-15. In one embodiment, one or two of exons 1, 2, 3, 4, 5, 6, 7, 8, 9, 10, 11, 12, 13, 14, 15, or 16 is mutated, the target intron is intron 19, 22, 23, or 24, and the coding domain includes functional ABCA4 exons 1-16. In one embodiment, one or two of exons 1, 2, 3, 4, 5, 6, 7, 8, 9, 10, 11, 12, 13, 14, 15, 16, or 17 is mutated, the target intron is intron 19, 22, 23, or 24, and the coding domain includes functional ABCA4 exons 1-17. In one embodiment, one or two of exons 1, 2, 3, 4, 5, 6, 7, 8, 9, 10, 11, 12, 13, 14, 15, 16, 17, or 18 is mutated, the target intron is intron 19, 22, 23, or 24, and the coding domain includes functional ABCA4 exons 1-18. In one embodiment, one or two of exons 1, 2, 3, 4, 5, 6, 7, 8, 9, 10, 11, 12, 13, 14, 15, 16, 17, 18, or 19 is mutated, the target intron is intron 19, 22, 23, or 24, and the coding domain includes functional ABCA4 exons 1-19. In one embodiment, one or two of exons 1, 2, 3, 4, 5, 6, 7, 8, 9, 10, 11, 12, 13, 14, 15, 16, 17, 18, 19, or 20 is mutated, the target intron is intron 22, 23, or 24, and the coding domain includes functional ABCA4 exons 1-20. In one embodiment, one or two of exons 1, 2, 3, 4, 5, 6, 7, 8, 9, 10, 11, 12, 13, 14, 15, 16, 17, 18, 19, 20, or 21 is mutated, the target intron is intron 22, 23, or 24, and the coding domain includes functional ABCA4 exons 1-21. In one embodiment, one or two of exons 1, 2, 3, 4, 5, 6, 7, 8, 9, 10, 11, 12, 13, 14, 15, 16, 17, 18, 19, 20, 21, or 22 is mutated, the target intron is intron 22, 23, or 24, and the coding domain includes functional ABCA4 exons 1-22. In one embodiment, one or two of exons 1, 2, 3, 4, 5, 6, 7, 8, 9, 10, 11, 12, 13, 14, 15, 16, 17, 18, 19, 20, 21, 22, or 23 is mutated, the target intron is intron 23 or 24, and the coding domain includes functional ABCA4 exons 1-23. In one embodiment, one or two of exons 1, 2, 3, 4, 5, 6, 7, 8, 9, 10, 11, 12, 13, 14, 15, 16, 17, 18, 19, 20, 21, 22, 23, or 24 is mutated, the target intron is intron 24, and the coding domain includes functional ABCA4 exons 1-24.

Alternatively, in instances in which both mutations occur on the 3' portion of the target gene, a 3' trans-splicing molecule is selected to correct both mutations. In one embodiment, one or two of exons 23, 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, and the coding domain includes functional ABCA4 exons 23-50. In one embodiment, one or two of exons 24, 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22 or 23, and the coding domain includes functional ABCA4 exons 24-50. In one embodiment, one or two of exons 25, 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 25-50. In one embodiment, one or two of exons 26, 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 26-50. In one embodiment, one or two of exons 27, 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 27-50. In one embodiment, one or two of exons 28, 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 28-50. In one embodiment, one or two of exons 29, 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 29-50. In one embodiment, one or two of exons 30, 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 30-50. In one embodiment, one or two of exons 31, 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 31-50. In one embodiment, one or two of exons 32, 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 32-50. In one embodiment, one or two of exons 33, 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 33-50. In one embodiment, one or two of exons 34, 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 34-50. In one embodiment, one or two of exons 35, 36, 37, 38, 39, 40, 41, 42, 43, 44, 45, 46, 47, 48, 49, or 50 is mutated, the target intron is intron 22, 23, or 24, and the coding domain includes functional ABCA4 exons 35-50. In one embodiment, one or two of exons 36, 37, 38, 39, 40, 41, 42, 43, 44, 45, 46, 47, 48, 49, or 50 is mutated, the target intron is intron 22, 23, or 24, and the coding domain includes functional ABCA4 exons 36-50. In one embodiment, one or two of exons 37, 38, 39, 40, 41, 42, 43, 44, 45, 46, 47, 48, 49, or 50 is mutated, the target intron is intron 22, 23, or 24, and the coding domain includes functional ABCA4 exons 37-50. In one embodiment, one or two of exons 38, 39, 40, 41, 42, 43, 44, 45, 46, 47, 48, 49, or 50 is mutated, the target intron is intron 22, 23, or 24, and the coding domain includes functional ABCA4 exons 38-50. In one embodiment, one or two of exons 39, 40, 41, 42, 43, 44, 45, 46, 47, 48, 49, or 50 is mutated, the target intron is intron 22, 23, or 24, and the coding domain includes functional ABCA4 exons 39-50. In one embodiment, one or two of exons 40, 41, 42, 43, 44, 45, 46, 47, 48, 49, or 50 is mutated, the target intron is intron 22, 23, or 24, and the coding domain includes functional ABCA4 exons 40-50. In one embodiment, one or two of exons 41, 42, 43, 44, 45, 46, 47, 48, 49, or 50 is mutated, the target intron is intron 22, 23, or 24, and the coding domain includes functional ABCA4 exons 41-50. In one embodiment, one or two of exons 42, 43, 44, 45, 46, 47, 48, 49, or 50 is mutated, the target intron is intron 22, 23, or 24, and the coding domain includes functional ABCA4 exons 42-50. In one embodiment, one or two of exons 43, 44, 45, 46, 47, 48, 49, or 50 is mutated, the target intron is intron 22, 23, or 24, and the coding domain includes functional ABCA4 exons 43-50. In one embodiment, one or two of exons 44, 45, 46, 47, 48, 49, or 50 is mutated, the target intron is intron 22, 23, or 24, and the coding domain includes functional ABCA4 exons 44-50. In one embodiment, one or two of exons 45, 46, 47, 48, 49, or 50 is mutated, the target intron is intron 22, 23, or 24, and the coding domain includes functional ABCA4 exons 45-50. In one embodiment, one or two of exons 46, 47, 48, 49, or 50 is mutated, the target intron is intron 22, 23, or 24, and the coding domain includes functional ABCA4 exons 46-50. In one embodiment, one or two of exons 47, 48, 49, or 50 is mutated, the target intron is intron 22, 23, or 24, and the coding domain includes functional ABCA4 exons 47-50. In one embodiment, one or two of exons 48, 49, or 50 is mutated, the target intron is intron 22, 23, or 24, and the coding domain includes functional ABCA4 exons 48-50. In one embodiment, one or two of exons 49 or 50 is mutated, the target intron is intron 22, 23, or 24, and the coding domain includes functional ABCA4 exons 49 or 50. In one embodiment, exon 50 is mutated, the target intron is intron 22, 23, or 24, and the coding domain includes functional ABCA4 exon 50.

Two Trans-Splicing Molecules for Correcting Multiple Mutations

Additionally, provided herein are methods of correcting multiple mutations within an ABCA4 gene using two trans-splicing molecules—a 5' trans-splicing molecule and a 3' trans-splicing molecule. In some embodiments, the entire ABCA4 gene is replaced upon binding of both trans-splicing molecules, for example, where the 5' trans-splicing molecule and the 3' trans-splicing molecule bind the same target ABCA4 intron and replace the exons upstream and downstream, respectively, of the target intron.

For example, in some embodiments of the invention, a 5' trans-splicing molecule and a 3' trans-splicing molecule each bind target ABCA4 intron 22; the 5' trans-splicing molecule replaces endogenous exons 1-22 with functional exons 1-22; and the 3' trans-splicing molecule replaces endogenous exons 23-50 with functional exons 23-50. In other embodiments, a 5' trans-splicing molecule and a 3' trans-splicing molecule each bind target ABCA4 intron 23; the 5' trans-splicing molecule replaces endogenous exons 1-23 with functional exons 1-23; and the 3' trans-splicing molecule replaces endogenous exons 24-50 with functional exons 24-50. In other embodiments, a 5' trans-splicing molecule and a 3' trans-splicing molecule each bind target ABCA4 intron 24; the 5' trans-splicing molecule replaces endogenous exons 1-24 with functional exons 1-24; and the 3' trans-splicing molecule replaces endogenous exons 25-50 with functional exons 25-50. Any of the aforementioned combinations of 5' and 3' trans-splicing molecules can be included in a pharmaceutical composition (e.g., a single pharmaceutical composition including both molecules, either pre-prepared or admixed prior to administration, e.g., as part of a kit).

Dosing, Monitoring, and Combination Therapies

An effective concentration of a recombinant adeno-associated virus carrying a trans-splicing molecule as described herein ranges between about $10^8$ and $10^{13}$ vector genomes per milliliter (vg/mL). The rAAV infectious units are measured as described in McLaughlin et al., *J. Virol.* 1988, 62:1963. In one embodiment, the concentration ranges between $10^9$ and $10^{13}$ vg/mL. In another embodiment, the effective concentration is about $1.5\times10^{11}$ vg/mL. In one embodiment, the effective concentration is about $1.5\times10^{10}$ vg/mL. In another embodiment, the effective concentration is about $2.8\times10^{11}$ vg/mL. In another embodiment, the effective concentration is about $5\times10^{11}$ vg/mL. In yet another embodiment, the effective concentration is about $1.5\times10^{12}$ vg/mL. In another embodiment, the effective concentration is about $1.5\times10^{13}$ vg/mL.

It is desirable that the lowest effective dosage (total genome copies delivered) of virus be utilized in order to reduce the risk of undesirable effects, such as toxicity, and other issues related to administration to the eye, e.g., retinal dysplasia and detachment. An effective dosage of a recombinant adeno-associated virus carrying a trans-splicing molecule as described herein ranges between about $10^8$ and $10^{13}$ vector genomes (vg) per dose (i.e., per injection). In one embodiment, the dosage ranges between $10^9$ and $10^{13}$ vg. In another embodiment, the effective dosage is about $1.5\times10^{11}$ vg. In another embodiment, the effective dosage is about $5\times10^{11}$ vg. In one embodiment, the effective dosage is about $1.5\times10^{10}$ vg. In another embodiment, the effective dosage is about $2.8\times10^{11}$ vg. In yet another embodiment, the effective dosage is about $1.5\times10^{12}$ vg. In another embodiment, the effective concentration is about $1.5\times10^{13}$ vg. Still other dosages in these ranges or in other units may be selected by the attending physician, taking into account the physical state of the subject being treated, including the age of the subject; the composition being administered, and the particular disorder; the targeted cell and the degree to which the disorder, if progressive, has developed.

The composition may be delivered in a volume of from about 50 μL to about 1 mL, including all numbers within the range, depending on the size of the area to be treated, the viral titer used, the route of administration, and the desired effect of the method. In one embodiment, the volume is about 50 μL. In another embodiment, the volume is about 70 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 250 μL. In another embodiment, the volume is about 300 μL. In another embodiment, the volume is about 350 μL. In another embodiment, the volume is about 400 μL In another embodiment, the volume is about 450 μL. In another embodiment, the volume is about 500 μL. In another embodiment, the volume is about 600 μL. In another embodiment, the volume is about 750 μL. In another embodiment, the volume is about 850 μL. In another embodiment, the volume is about 1,000 μL.

In one embodiment, the volume and concentration of the rAAV composition is selected so that only certain anatomical regions having target cells are impacted. In another embodiment, the volume and/or concentration of the rAAV composition is a greater amount, in order reach larger portions of the eye. Similarly dosages are adjusted for administration to other organs.

In another embodiment, the invention provides a method to prevent, or arrest photoreceptor function loss, or increase photoreceptor function in the subject. The composition may be administered before or after disease onset. For example, photoreceptor function may be assessed using the functional studies, e.g., ERG or perimetry, which are conventional in the art. As used herein "photoreceptor function loss" means a decrease in photoreceptor function as compared to a normal, non-diseased eye or the same eye at an earlier time point. As used herein, "increase photoreceptor function" means to improve the function of the photoreceptors or increase the number or percentage of functional photoreceptors as compared to a diseased eye (having the same ocular disease), the same eye at an earlier time point, a non-treated portion of the same eye, or the contralateral eye of the same subject.

For each of the described methods, the treatment may be used to prevent the occurrence of further damage or to rescue tissue having mild or advanced disease. As used herein, the term "rescue" means to prevent progression of the disease, prevent spread of damage to uninjured cells or to improve damage in injured cells.

Thus, in one embodiment, the composition is administered before disease onset. In another embodiment, the composition is administered prior to the development of symptoms. In another embodiment, the composition is administered after development of symptoms. In yet another embodiment, the composition is administered when less than 90% of the target cells are functioning or remaining, e.g., as compared to a reference tissue. In yet another embodiment, the composition is administered when more than 10% of the target cells are functioning or remaining, e.g., as compared to a reference tissue. In yet another embodiment, the composition is administered when more than 20% of the target cells are functioning or remaining. In yet another embodiment, the composition is administered when more than 30% of the target cells are functioning or remaining.

In yet another embodiment, any of the above described methods is performed in combination with another, or secondary, therapy. The therapy may be any now known, or as yet unknown, therapy which helps prevent, arrest or ameliorate these mutations or defects or any of the effects associated therewith. The secondary therapy can be administered before, concurrent with, or after administration of the trans-splicing molecules described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In another embodiment, the method includes performing functional and imaging studies to determine the efficacy of the treatment. These studios include electroretinography (ERG) and in vivo retinal imaging, as described in U.S. Pat. No. 8,147,823; in International Patent Publication Nos. WO 2014/011210 or WO 2014/124282, incorporated herein by reference. In addition visual field studies, perimetry and microperimetry, mobility testing, visual acuity, and/or color vision testing may be performed.

In certain embodiments, it is desirable to perform non-invasive retinal imaging and functional studies to identify areas of retained photoreceptors to be targeted for therapy. In these embodiments, clinical diagnostic tests are employed to determine the precise location(s) for one or more subretinal injection(s). These tests may include ERG, perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. In view of the imaging and functional studies, in some embodiments one or more injections are performed in the same eye in order to target different areas of retained photoreceptors.

For use in these methods, the volume and viral titer of each injection is determined individually, and may be the same or different from other injections performed in the same, or contralateral, eye. In another embodiment, a single, larger volume injection is made in order to treat the entire eye. The dosages, administrations, and regimens may be determined by the attending physician given the teachings of this disclosure.

EXAMPLES

The invention is based, at least in part, on Applicant's discovery that particular introns of ABCA4, and specific regions within those introns, provide highly efficient binding sites for binding domains of trans-splicing molecules and efficiently mediate trans-splicing. Applicant has generated a series of mock trans-splicing molecules having 150-mer binding domains designed to hybridize to a corresponding series of 150-base pair binding site sequences of (i) ABCA4 introns of interest (introns 19 and 22-24) and (ii) CEP290 introns of interest (introns 26-30). Each binding domain in the ABCA4 series and the CEP290 series was designed to overlap by 140 nucleotides, enabling scanning of each intron by 10 nucleotides between each sequential test binding domain. Trans-splicing efficiency was quantified for each binding domain across each of ABCA4 introns 19 and 22-24 and CEP290 introns 26-30. ABCA4 screening is described in Example 1, and results are shown in FIGS. 1-8. CEP290 screening is described in Example 2, and results are shown in FIGS. 21-26.

Example 1. ABCA4

This Example describes development of ABCA4 trans-splicing molecules, for example, by screening for effective binding sites within particular ABCA4 introns, developing an ABCA4 cell line for testing trans-splicing molecules, and testing various ABCA4 trans-splicing molecules for restoration of ABCA4 protein expression.

Binding Site Screening

Figure 2:
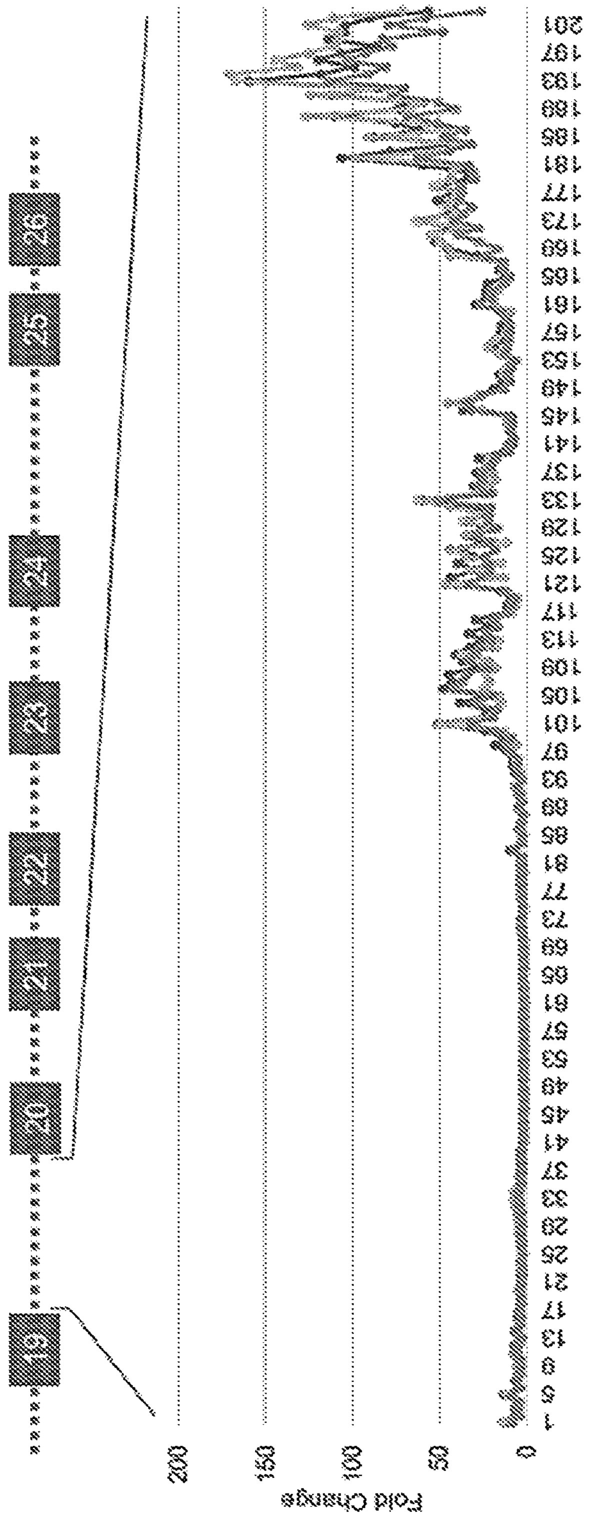
FIG. 2 is a graph showing trans-splicing efficiency (relative fold change) conferred by 150-mer binding domains across ABCA4 intron 19 (SEQ ID NO: 25) in ten-nucleotide intervals using 5' trans-splicing molecules. X axis labels indicate the number of each binding site starting from the 5' end of the intron (i.e., the first nucleotide of the intron sequence).

Screening of a series of binding domains configured to bind ABCA4 intron 19 (SEQ ID NO: 25) at sequential bindings sites revealed a region at the 3' portion of ABCA4 intron 19 that was preferentially efficient at trans-splicing of a 5' trans-splicing molecule—a region from nucleotides 990 to 2, 174 of intron 19 (FIG. 2). Binding sites within the range of nucleotides from 1,670 to 2,174, from 1,810 to 2,000, from 1,870 to 2,000, or from 1,920 to 2,000 were revealed as particularly highly efficient at mediating 5' trans-splicing at intron 19.

Figure 3:
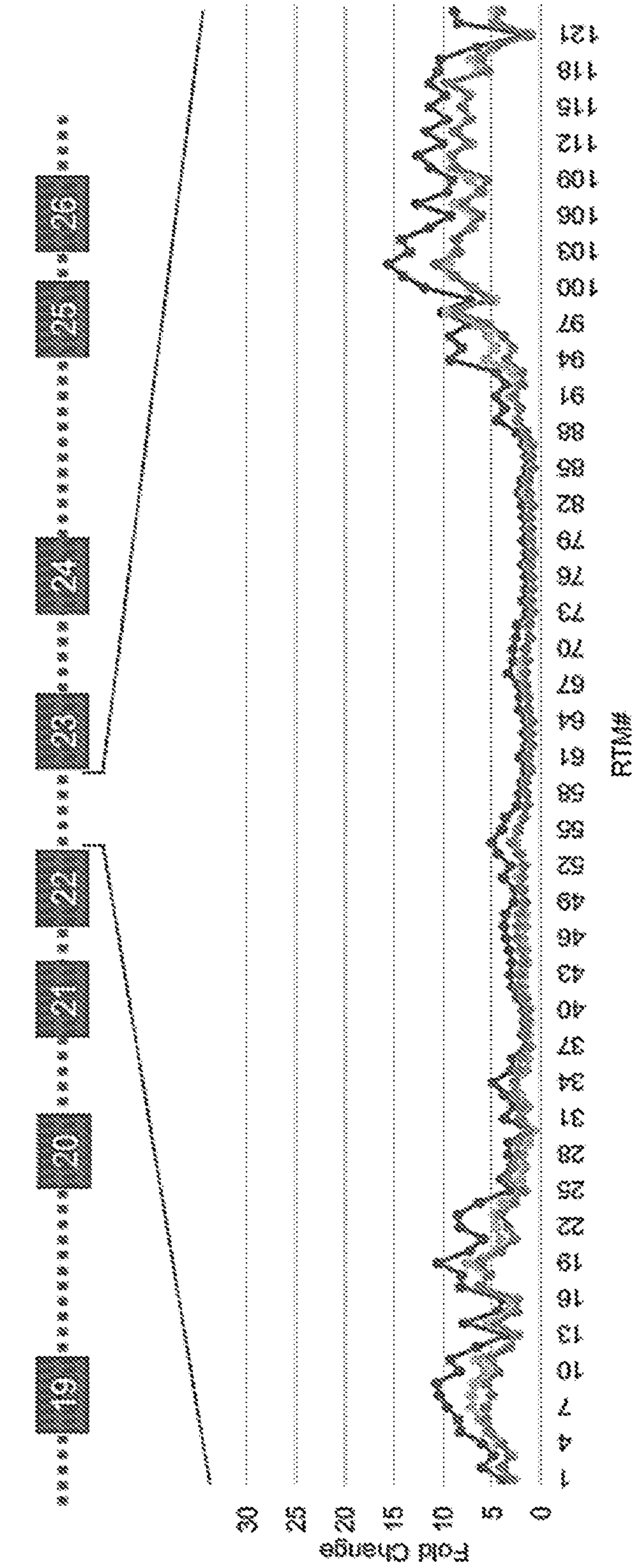
FIG. 3 is a graph showing trans-splicing efficiency (relative fold change) conferred by 150-mer binding domains across ABCA4 intron 22 (SEQ ID NO: 28) in ton-nucleotide intervals using 5' trans-splicing molecules. X axis labels indicate the number of each binding site starting from the 5' end of the intron (i.e., the first nucleotide of the intron sequence).

Suitable binding sites for 5' trans-splicing molecules within intron 22 were similarly identified (FIG. 3). Binding sites within the ranges of nucleotides 1 to 150 or nucleotides 880 to 1,350 of intron 22 were especially efficient, relative to the remainder of the intron.

Figure 4:
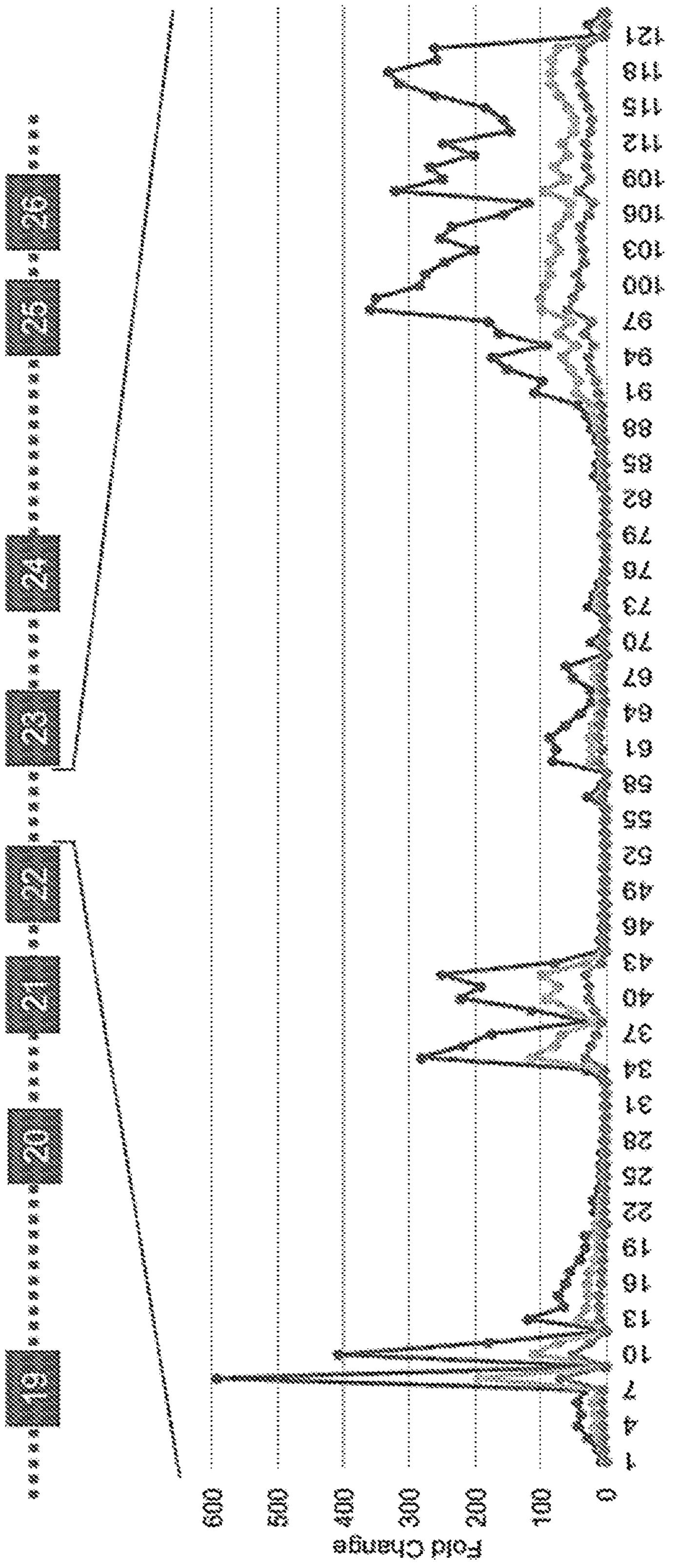
FIG. 4 is a graph showing trans-splicing efficiency (relative fold change) conferred by 150-mer binding domains across ABCA4 intron 22 (SEQ ID NO: 28) in ten-nucleotide intervals using 3' trans-splicing molecules. X axis labels indicate the number of each binding site starting from the 5' end of the intron (i.e., the first nucleotide of the intron sequence).

FIG. 4 shows results of an analogous screen for ABCA4 intron 22 (SEQ ID NO: 28) for a 3' trans-splicing molecule. Binding sites having nucleotides 60 to 570, nucleotides 600 to 800, or nucleotides 900 to 1,350 were identified as preferentially suitable for trans-splicing of a 3' trans-splicing molecule. In particular, binding domains targeted to binding sites within the range of nucleotides 70 to 250 were highly efficient at 3' trans-splicing.

Figure 5:
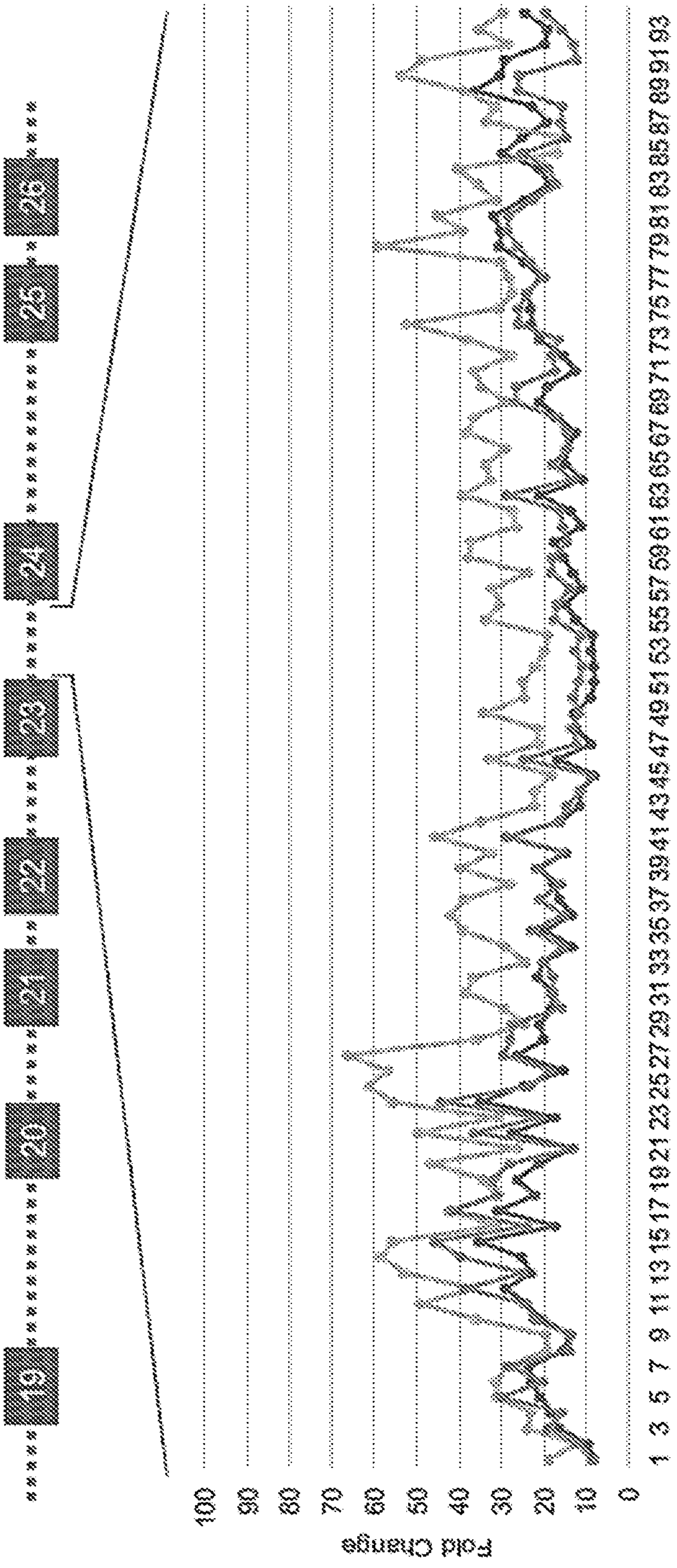
FIG. 5 is a graph showing trans-splicing efficiency (relative fold change) conferred by 150-mer binding domains across ABCA4 intron 23 (SEQ ID NO: 29) in ten-nucleotide intervals using 5' trans-splicing molecules. X axis labels indicate the number of each binding site starting from the 5' end of the intron (i.e., the first nucleotide of the intron sequence).
Figure 6:
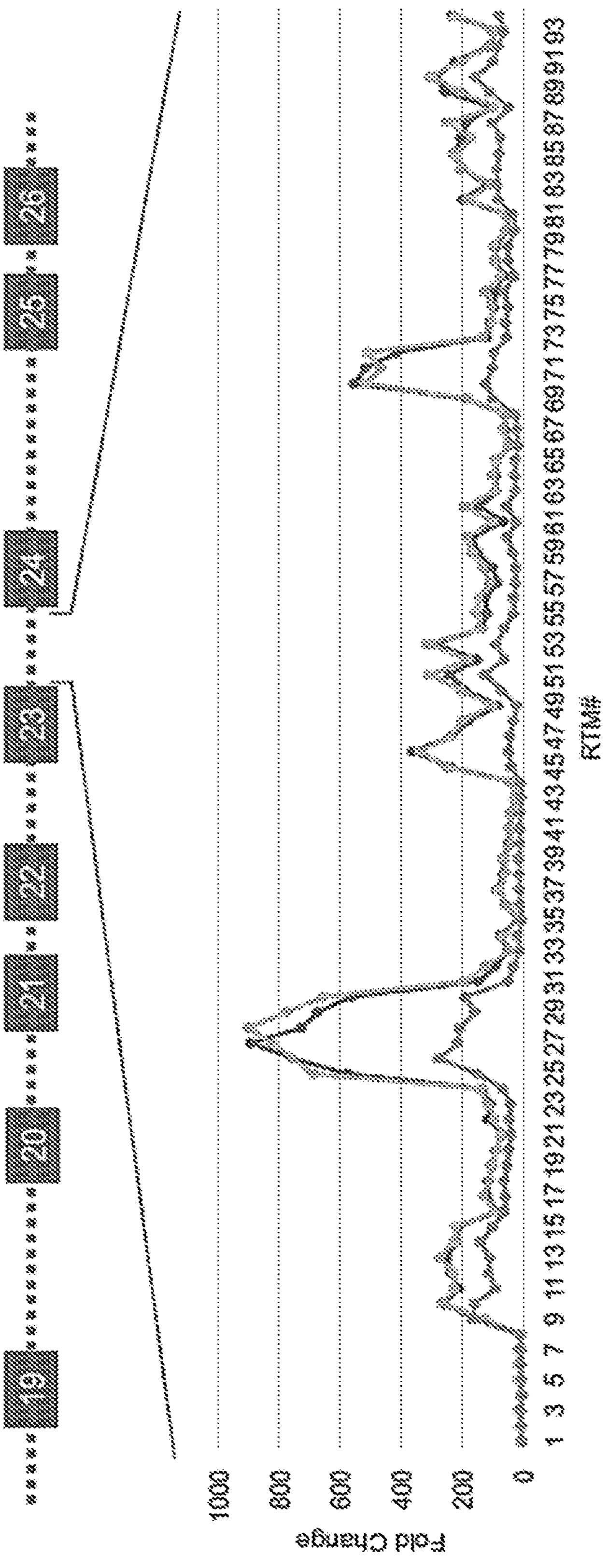
FIG. 6 is a graph showing trans-splicing efficiency (relative fold change) conferred by 150-mer binding domains across ABCA4 intron 23 (SEQ ID NO: 29) in ten-nucleotide intervals using 3' trans-splicing molecules. X axis labels indicate the number of each binding site starting from the 5' end of the intron (i.e., the first nucleotide of the intron sequence).

Within intron 23, relatively efficient binding sites for 5' trans-splicing molecules were identified as those within the ranges of nucleotides 80 to 570 or nucleotides 720 to 1,081 of SEQ ID NO: 29 (FIG. 5). For 3' trans-splicing molecules, binding sites with particularly good efficiency included those within nucleotides 80 to 1,081 of SEQ ID NO: 29 (e.g., nucleotides 230 to 1,081 of SEQ ID NO: 29, nucleotides 250 to 400 of SEQ ID NO: 29, or nucleotides 690 to 850 of SEQ ID NO: 29), as shown in FIG. 6.

Figure 7:
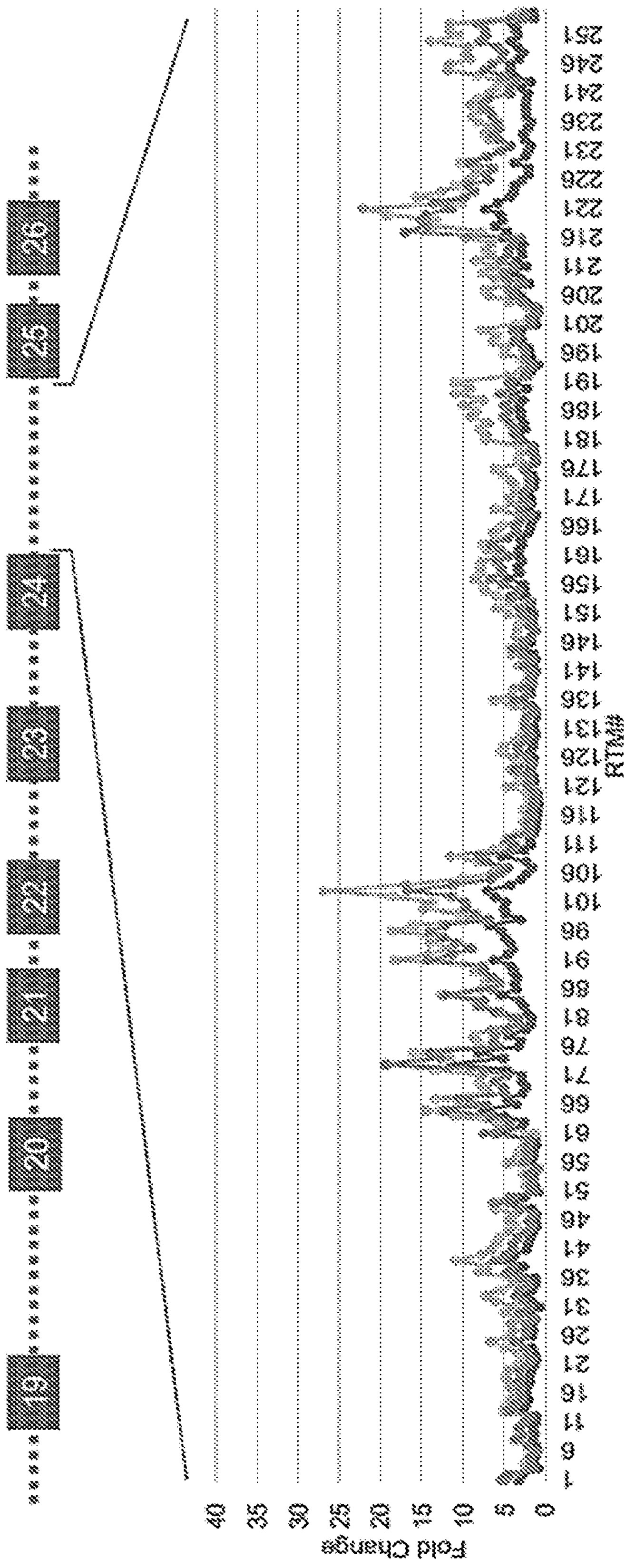
FIG. 7 is a graph showing trans-splicing efficiency (relative fold change) conferred by 150-mer binding domains across ABCA4 intron 24 (SEQ ID NO: 30) in ten-nucleotide intervals using 5' trans-splicing molecules. X axis labels indicate the number of each binding site starting from the 5' end of the intron (i.e., the first nucleotide of the intron sequence).
Figure 8:
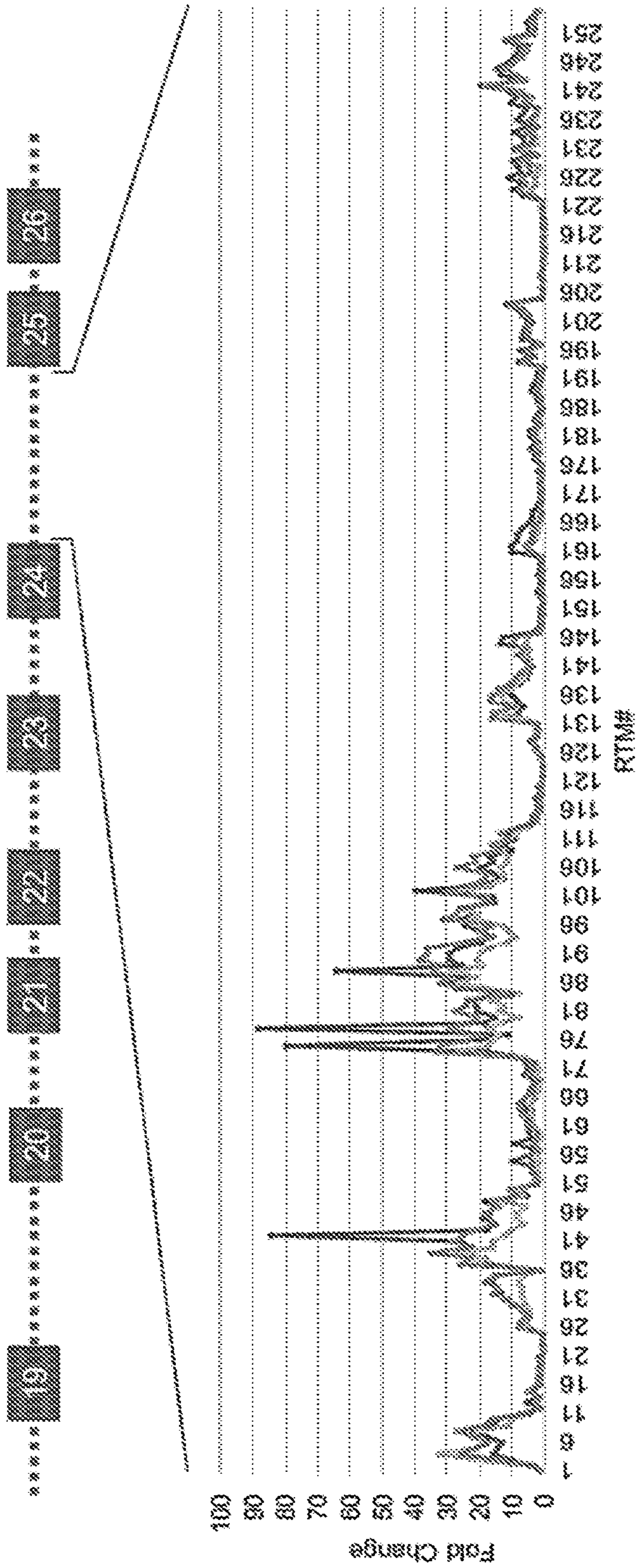
FIG. 8 is a graph showing trans-splicing efficiency (relative fold change) conferred by 150-mer binding domains across ABCA4 intron 24 (SEQ ID NO: 30) in ten-nucleotide intervals using 3' trans-splicing molecules. X axis labels indicate the number of each binding site starting from the 5' end of the intron (i.e., the first nucleotide of the intron sequence).

An analogous screening at intron 24 of ABCA4 (SEQ ID NO: 30) revealed that binding sites within the ranges of nucleotides 600 to 1,250 or nucleotides 1,490 to 2,660 were efficient at 5' trans-splicing (FIG. 7). In particular, binding sites within the range of nucleotides 1,000 to 1,200 exhibited the greatest 5' trans-splicing efficiency. FIG. 8 shows the results of a screening of 3' trans-splicing efficiency, which revealed that binding sites within the range of nucleotides 1 to 250, nucleotides 300 to 2,000, or nucleotides 2,200 to 2,692 (in particular, binding sites within the range of nucleotides or nucleotides 750 to 1,110) were most efficient.

ABCA4 Cell Lines

First, cell lines expressing ABCA4 were generated. The ABCA4 gene is only known to be expressed in living photoreceptors in the retina, and full-length ABCA4 pre-mRNA and protein are not generally detectable in cultured cells in vitro. Therefore, to test trans-splicing strategies for ABCA4, cells were engineered to express ABCA4 from its native genomic locus on chromosome 1 (1p22.1). Two strategies were pursued. In the first case, stable cell lines were derived to express site-specific (upstream of the ABCA4 transcriptional start site) DNA-binding TALENs that were fused to the VP64 viral trans-activator. In the second case, a constitutive eukaryotic promotor was directly inserted (using CRISPR/Cas9) into the genomic locus immediately upstream of the ABCA4 transcriptional start site. The results in both cases were stable cell lines that robustly expressed ABCA4 pre-mRNA and protein.

TALEN Cell Lines

Figure 9:
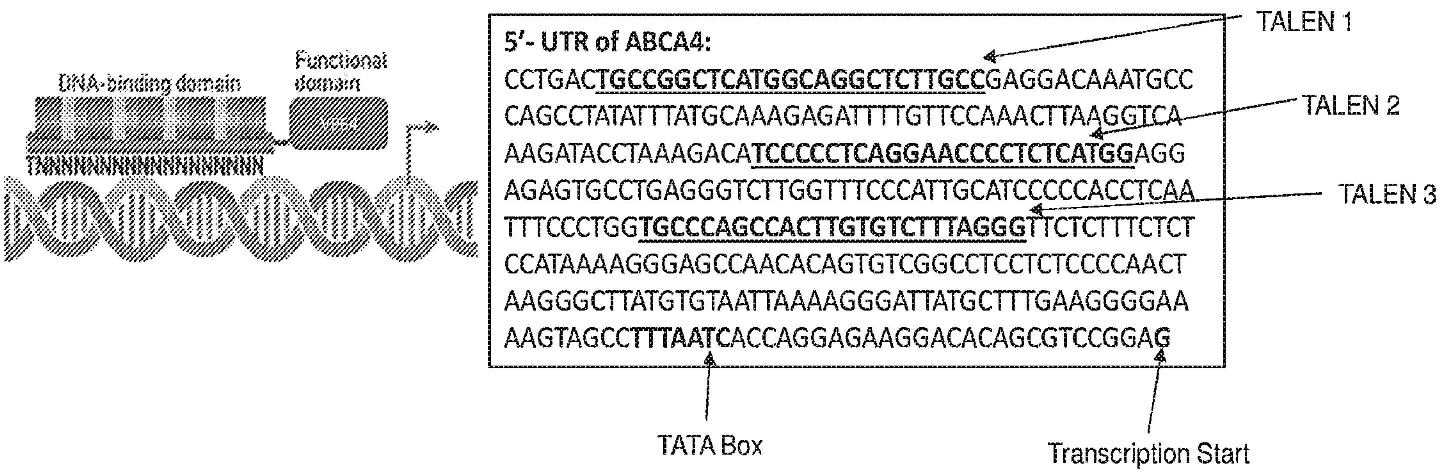
FIG. 9 is a schematic drawing showing a TALEN protein consisting of a DNA binding domain linked to a transcription activation domain. A VP64 transcription activation domain is shown. The right panel shows a portion of the 5' untranslated region (5'-UTR) of ABCA4. The TATA box and the putative transcription start site are shown. The sequences targeted the by the three different DNA binding domains of TALENs are also shown. TALEN 1 binds to the first underlined sequence, TALEN 2 binds to the second underlined sequence, and TALEN 3 binds to the third underlined sequence, as indicated.
Figure 10:
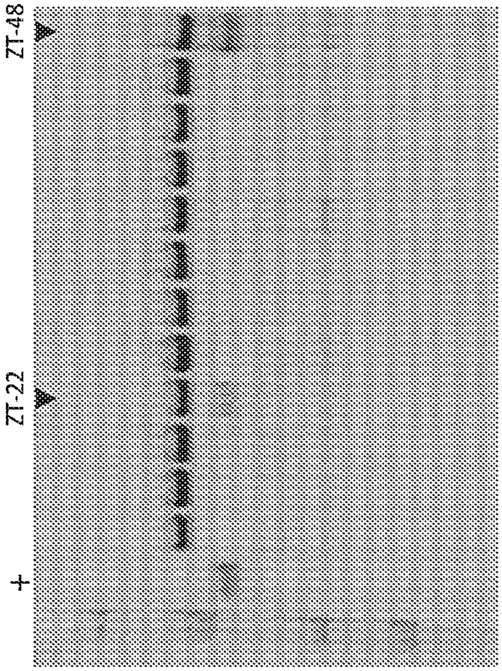
FIG. 10 is a gel showing 293T cells were transfected with TALEN constructs designed to induce endogenous ABCA4 expression. All three TALENS from FIG. 9 were stably introduced into 293 cells and single cell clones were picked and analyzed by western blot. The positive control (+) indicates cells transfected with a plasmid expressing an ABCA4 cDNA. Cell lysates were made 48 hours after transfection and the membrane fractions were examined for ABCA4 expression using antibody ab72955 (Abcam). Clones ZT-22 and ZT-48 showed ABCA4 protein expression.

TALENs targeted to specific domains upstream of the ABCA4 transcriptional start site were designed and fused to a VP-64 trans-activator sequence (FIG. 9). This combination of three TALENs were transfected into 293 cells and stable single cell clones were derived. Two clones were shown to direct expression of ABCA4 protein (FIG. 10).

CAG Promoter Cell Lines

Figure 11:
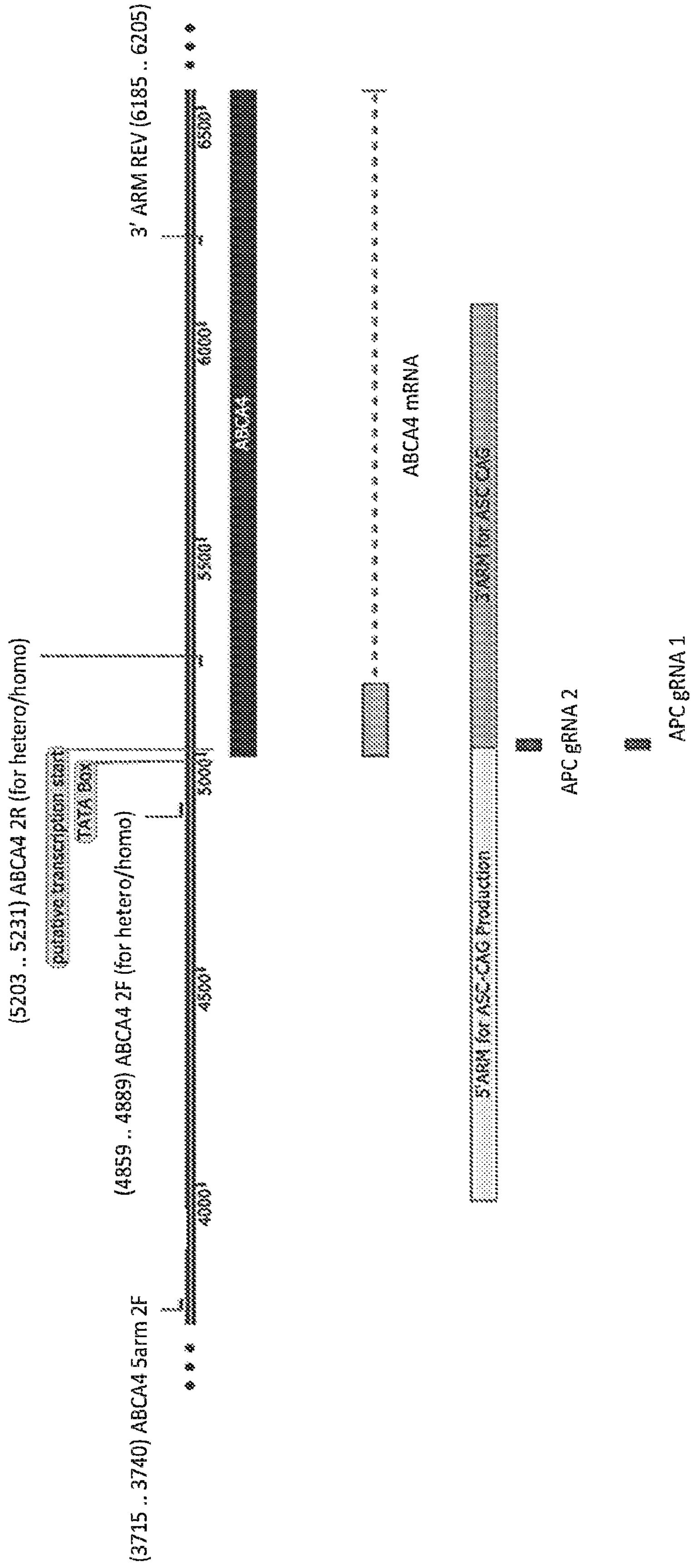
FIG. 11 is a schematic drawing showing a CAG promoter cell line.
Figure 12B:
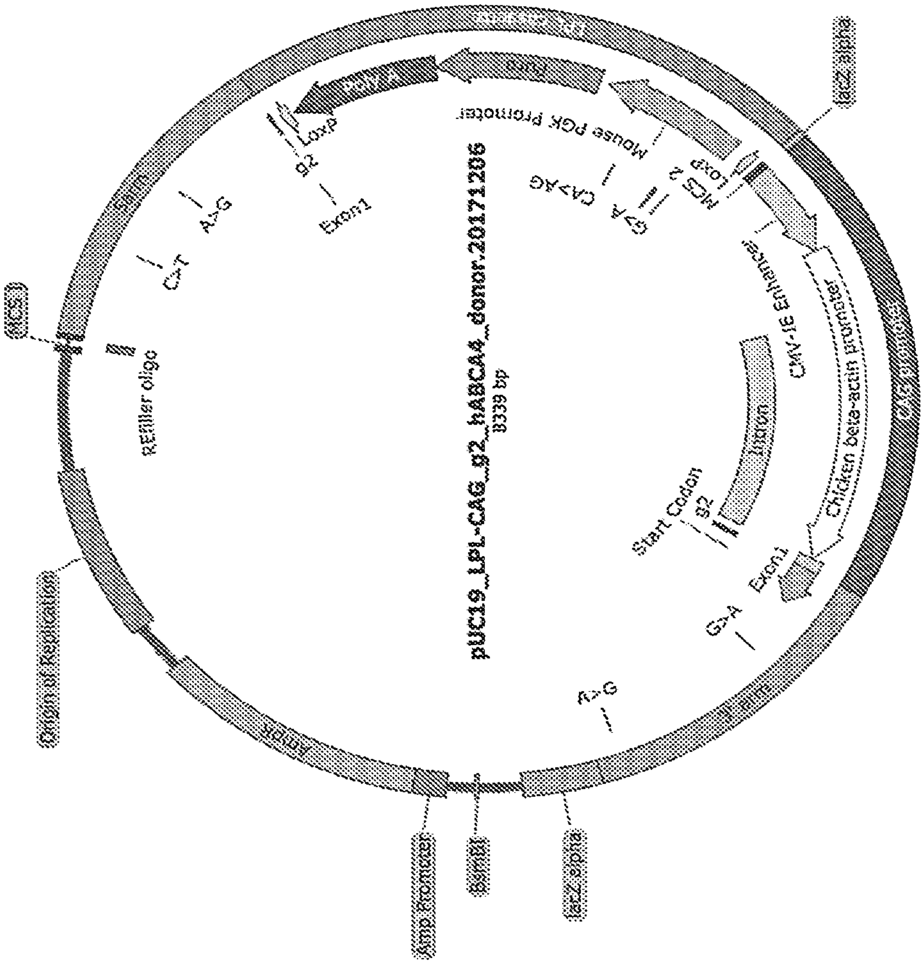
Figure 13:
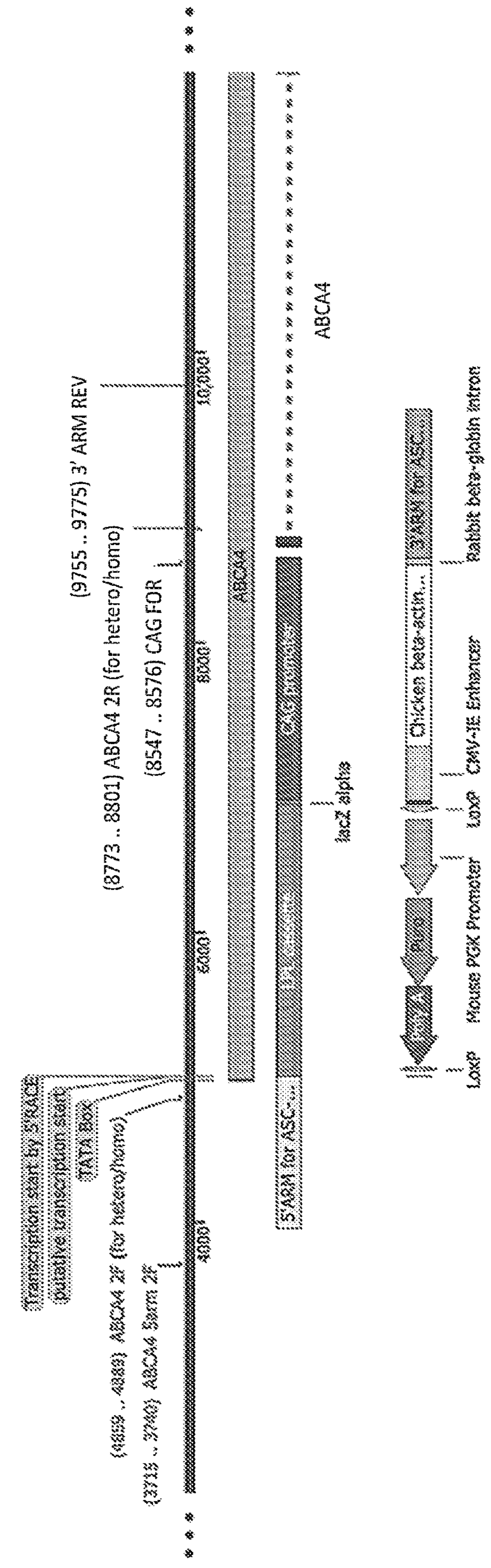
FIG. 13 is a schematic drawing showing a CAG promoter cell line.
Figure 14A:
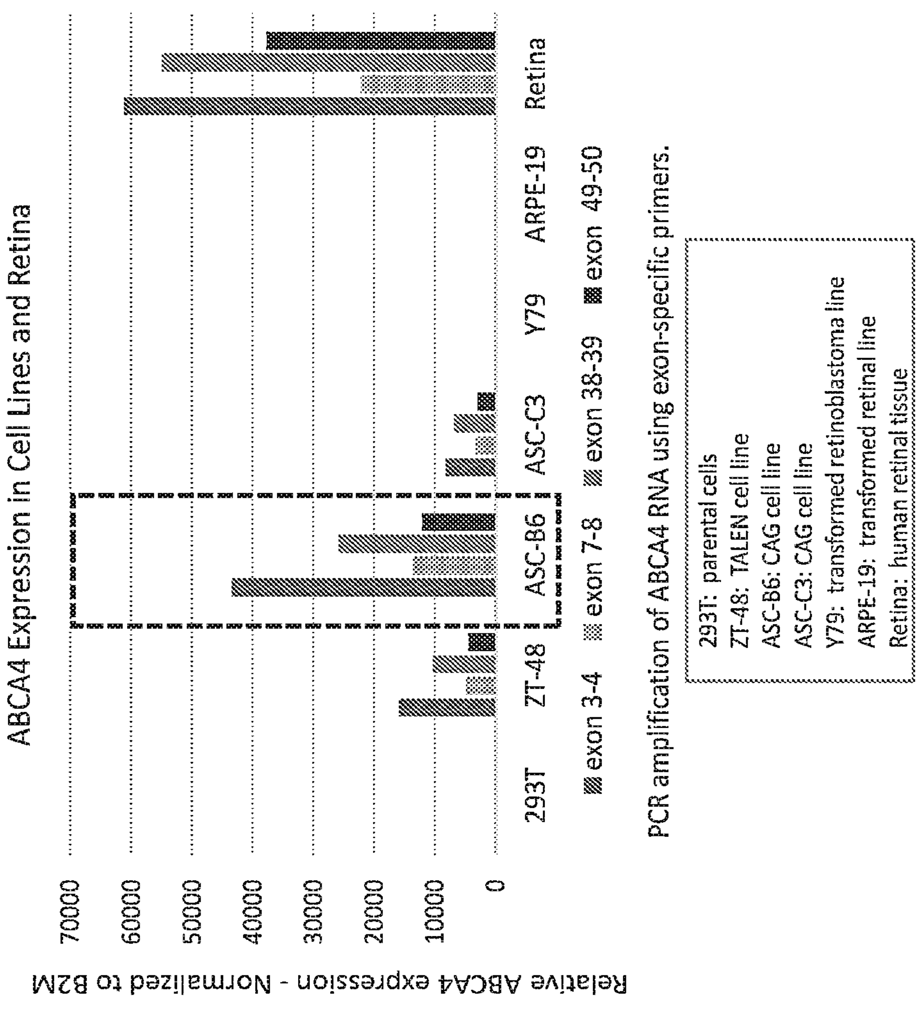
FIGS. 14A and 14B are a graph and a gel, respectively, showing expression results from several clonal lines that were selected for further analyses.
Figure 14B:
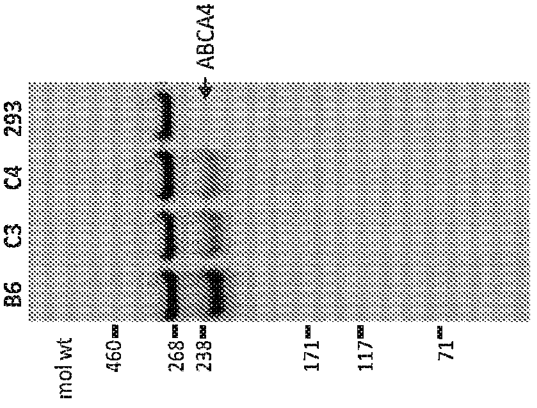

The general strategy for deriving CAG promoter cell lines is outlined in FIGS. 11-13. Site-specific guides (FIG. 12A) were designed to insert the CAG promoter and a puromycin selectable marker using homology arms (FIG. 12B). Puromycin resistant cells were cloned and analyzed by PCR for the desired insertion. Several clonal lines were selected for further analyses. RNA and protein expression for two lines (B6 and C3) are shown in FIGS. 14A and 14B. Both lines clearly contained the promoter insertion, as demonstrated by RNA and protein analyses.

ABCA4 Knockout Cell Lines

Figure 15:
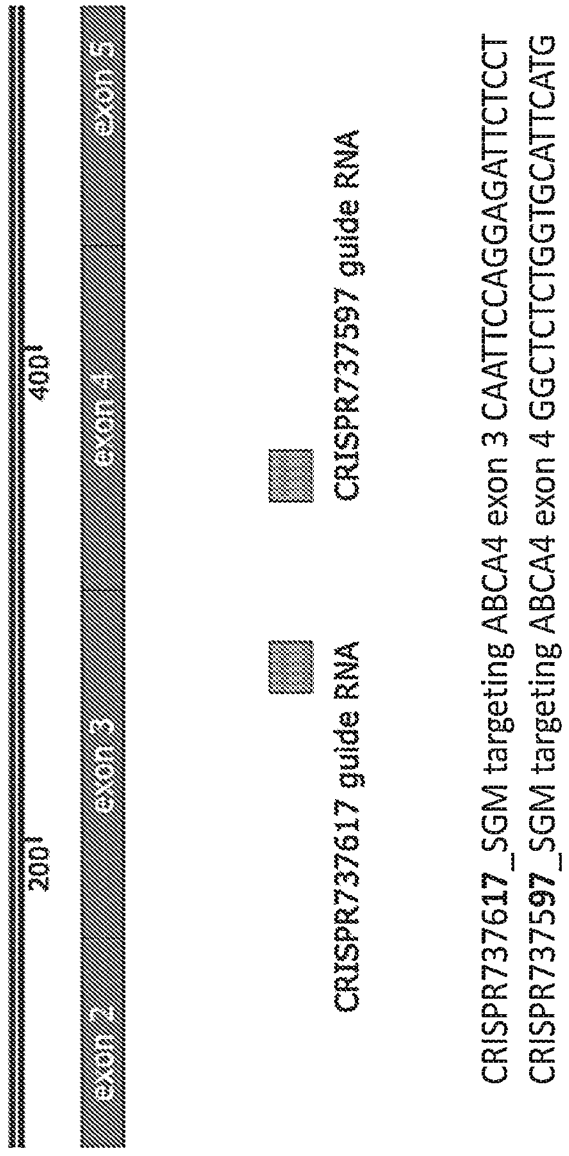
FIG. 15 is a schematic drawing showing CRISPR guide RNA for targeting exons 3 and 4.

Once stable ABCA4 expression was established in cultured cells, knock-outs of ABCA4 expression were generated for testing of ABCA4 trans-splicing molecules designed to restore ABCA4 protein expression. In general, guide RNA and Cas9 protein were co-transfected in B6 cells (CAG-promotor knocked into ABCA4 locus and mediating ABCA4 expression). After nine days, a second transfection with guide RNA and Cas9 protein was performed. The basic design targeting exons 3 and 4 is shown in FIG. 15. Single cells were plated by limiting dilution and once grown, evaluated for protein expression of ABCA4 by Western blot.

Figure 16:
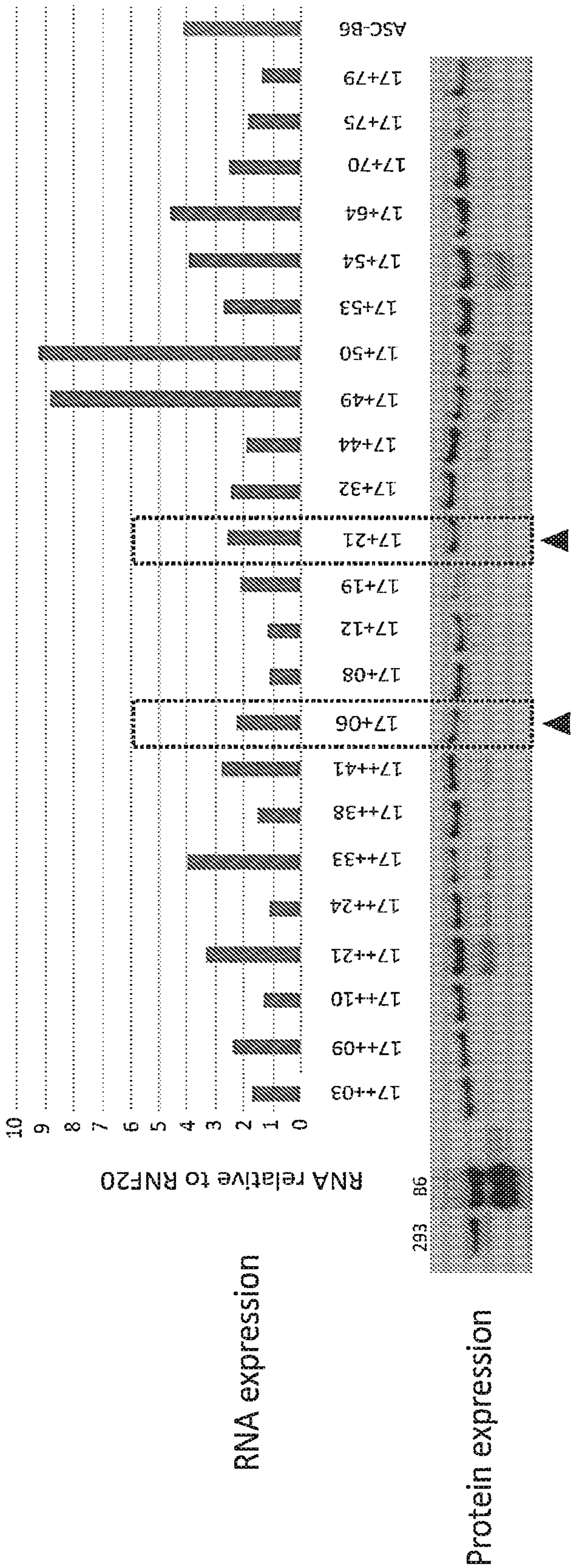
FIG. 16 is a graph showing RNA expression and a gel showing protein profiles of single cell clones derived after treatment with CRISPR/Cas9, as depicted in FIG. 15.
Figure 17A:
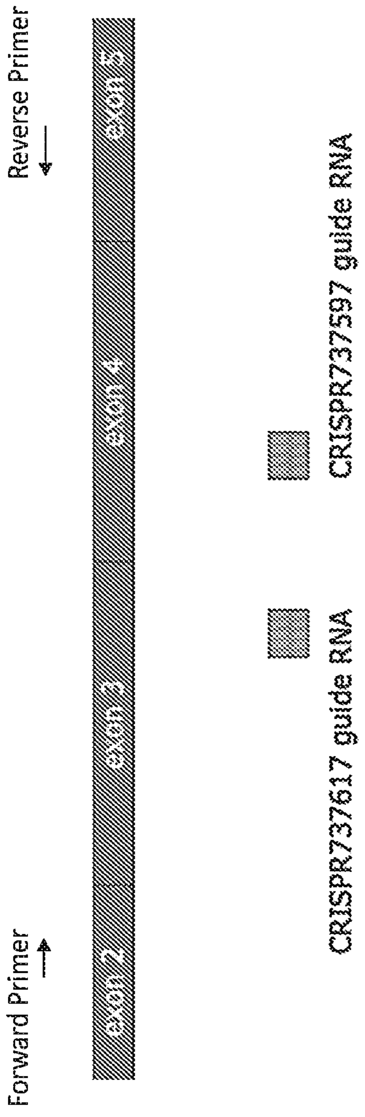
FIGS. 17A and 17B are schematic drawings showing PCR for mutation analyses on cDNA (FIG. 17A) and PCR for genotyping on cDNA (FIG. 17B), confirming that exons 3 and 4 were targeted and interrupted.
Figure 17B:
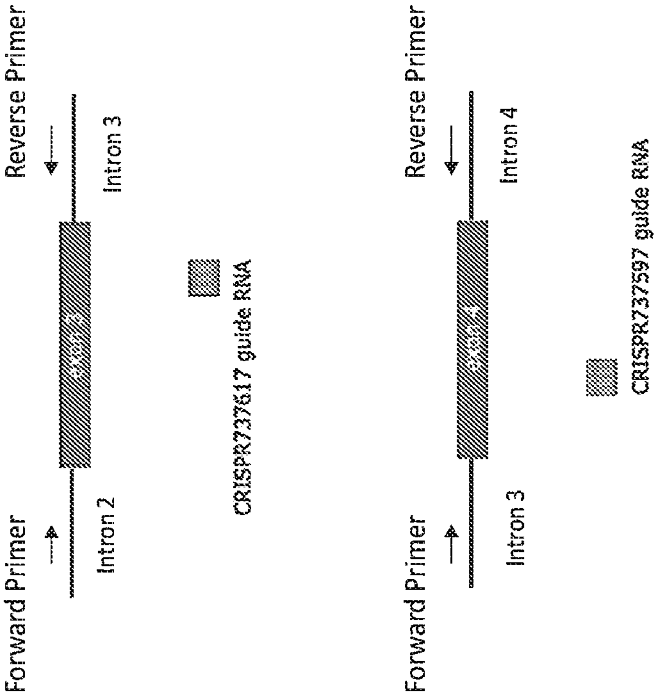

FIG. 16 shows the RNA and protein profiles of single cell clones derived after treatment with CRISPR/Cas9, as depicted in FIG. 15. There were varying degrees of RNA and protein ablation. Clones 17+06 and 17+21 were chosen because they exhibited complete ABCA4 protein knockout. Mutation analyses (FIGS. 17A-17B and 18) confirmed that exons 3 and 4 were targeted and interrupted.

ABCA4 Trans-Splicing-Mediated Protein Restoration

Eight trans-splicing molecules were selected based on the high-throughput binding site screening described above. Methods and results of these studies are described below

Methods

For Western blot assays, 17+06 or 17+21 cells were seeded at a density of $10^6$ cells per well in each well of twelve-well plates. Individual wells were transfected with 1 μg of plasmid ($RTM_x$). At 48 hours, cells were harvested, and membrane preparations were processed for analysis by standard western blotting using Mem-PER Plus Membrane Protein Extraction Kit (Thermo Fisher 89842) according to the manufacturer's protocol with addition of 1× HALT™ Protease and Phosphatase Inhibitor Cocktail (Thermo Fisher 78440) in all buffers. RNA was also processed for analysis as described below. Membrane lysates were denatured with 4× Laemmli Sample Buffer (Biorad 161-0737) including 10% reducing agent TCEP 0.5 M (Sigma 646547) for 30 minutes at room temperature. Samples were run on NuPage Precast 3-8% Tris-Acetate gels (Thermo Fisher) and proteins were transferred using the iBlot 2 Mini PVDF Transfer Packs—run at 25V 10 minutes with iBlot 2. The primary antibody for ABCA4 was Abcam ab72955, rabbit polyclonal (@1:2500 dilution). The secondary antibody was anti-rabbit (@1:5000 dilution). Blots were exposed for various times, depending on strength of signal.

For qPCR for RNA samples, RNA was harvested as described above for qPCR analysis using RNeasy Plus Mini kit (Qiagen). cDNA was synthesized from 400 ng RNA in 20 μl reaction with SuperScript IV VILO Master Mix (Thermo 11756500; diluted 1:4 in water). Native ABCA4 (Thermo commercial assay Hs00979594_m1) spans exons 49-50. For the housekeeper gene as a control, an RNF20 assay was used (Thermo commercial assay Hs00219623_m1). Chimeric ABCA4 codon optimized exon 22—native exon 23—qPCR primers and probes were the following:

```
Probe (FAM) 063_ABCA4 co22n23_P1:
CGTGGACCCTTACAGCAGAAG

Forward Primer 064_ABCA4 co22n23_F1:
GATCCTGGATGAGCCTAC

Reverse Primer 065_ABCA4 co22n23_R1:
GGACATGATGATGGTTCTG
```

Duplex with RNF20 assay qPCR primers and probes were the following:

```
Probe (VIC) 088_RNF20_P2:
CAGCGACTCAACCGACACTT

Forward primer 091_RNF20_F2:
GCAGTGGGATATTGACAA

Reverse primer 099_RNF20_R5:
CGAGCATTGATAGTGATTG
```

The PCT reaction was run using QuantiFast 2× qPCR Mastermix.

Results

Figure 19B:
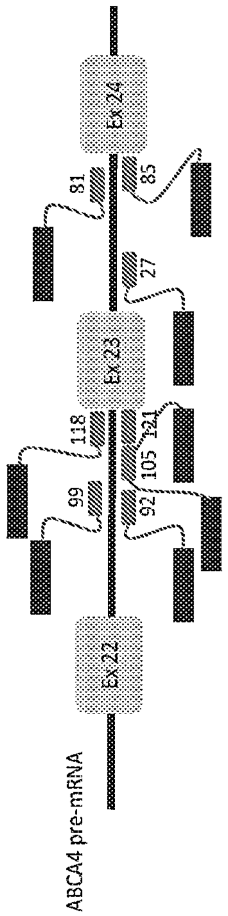
FIGS. 19A and 19B are schematic drawings of trans-splicing molecules targeting ABCA4 pre-mRNA.
Figure 19A:
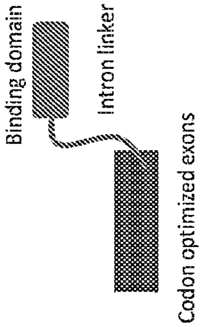

Trans-splicing molecules binding to introns 19, 22, 23, and 24 were tested. No protein restoration was observed in trans-splicing molecules binding to introns 19 and 24 (data not shown), but trans-splicing molecules binding to introns 22 and 23 yielded restoration of ABCA4 protein and RNA expression (FIGS. 19A and 19B), as discussed below.

Figure 20B:
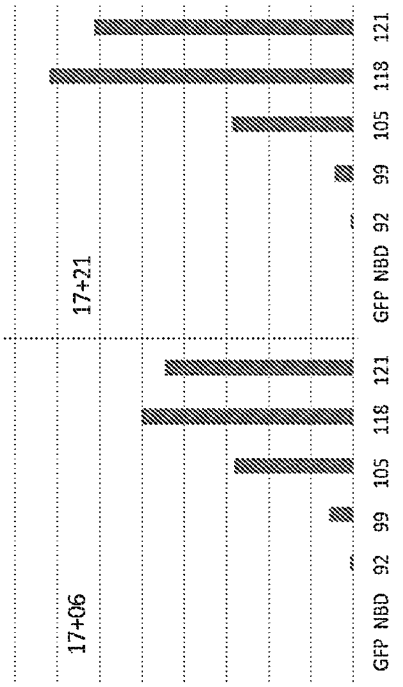
FIGS. 20A-20D are gels (FIGS. 20A and 20C) and graphs (FIGS. 20B and 20D) showing results from trans-splicing reactions.
Figure 20A:
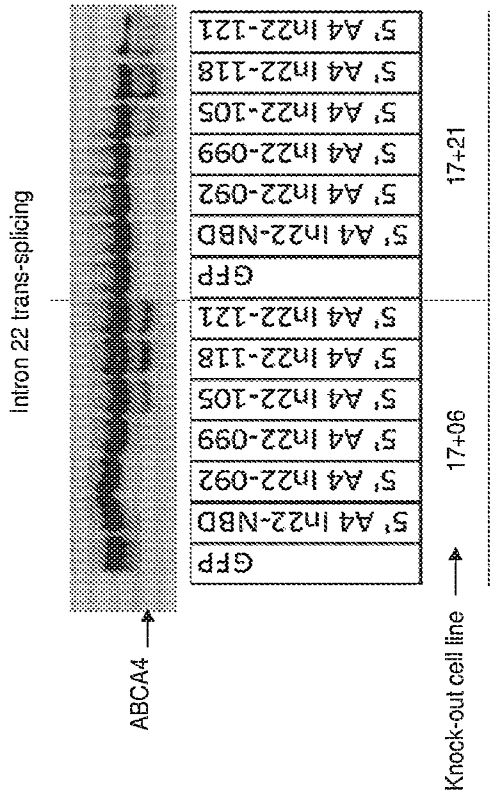

FIG. 20A is a western blot showing ABCA4 protein expression attributed to trans-splicing reactions from two different cell lines (17+06 and 17+21) with a mock GFP control or 5'A4In22 tethered to five different binding domains (No binding domain (NBD) control, 92, 99, 105, 118, and 121, numbering corresponding to FIG. 3 RTM #, where binding domain 92 binds nucleotides 911-1060 of intron 22, binding domain 99 binds nucleotides 981-1130 of intron 22, binding domain 105 binds nucleotides 1041-1190 of intron 22, binding domain 118 binds nucleotides 1171-1320 of intron 22, and binding domain 121 binds nucleotides 1201-1350 of intron 22 (following to the 10-base shift interval of 150-mers across intron 22, described above)). Four of these intron-22 binding constructs, 99, 105, 118, and 121 yielded protein restoration, with 105, 118, and 121 showing particularly enhanced restoration and 118 showing the greatest amount of protein expressed in both cell lines. mRNA expression profiles showed a similar pattern, with the 118 construct yielding the greatest levels of ABCA4 mRNA in both cell lines (FIG. 20B). Units are relative to the RNF20 housekeeping gene.

Figure 20D:
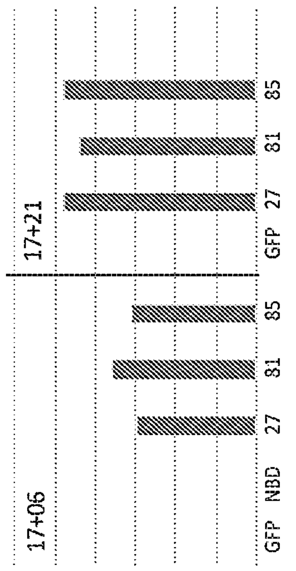
Figure 20C:
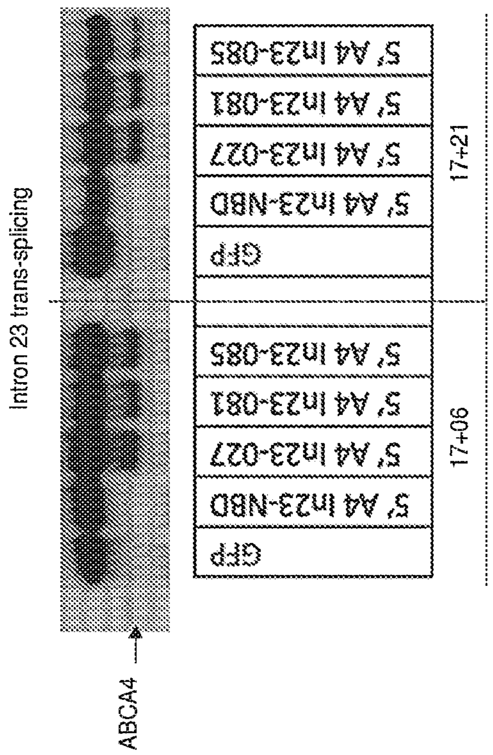

FIG. 20C is a western blot showing ABCA4 protein expression attributed to trans-splicing reactions from two different cell lines (17+06 and 17+21) with a mock GFP control or 5'A4In23 tethered to three different binding domains (NBD control, 27, 81, and 85, numbering corresponding to FIG. 5 RTM #, where binding domain 27 binds nucleotides 261-410 of intron 23, binding domain 81 binds to 801-950 of intron 23, and binding domain 85 binds 841-990 of intron 23 (following to the 10-base shift interval of 150-mers across intron 23, described above)). All three intron 23-binding constructs yielded trans-splicing as indicated by the amount of protein expressed in both cell lines. mRNA expression profiles yielded similar results, with all three constructs yielding robust ABCA4 mRNA expression in both cell lines (FIG. 20D). Units are relative to the RNF20 housekeeping gene.

Together, the ABCA4 protein and RNA expression data obtained for intron 22- and 23-binding trans-splicing molecules correlate with the binding domain screen described above. In particular, intron 22-binding constructs 105, 118, and 121 and intron 23-binding constructs 27, 81, and 85 were predicted to bind with high efficiency (FIGS. 3 and 5), and the present ABCA4 protein restoration data indicate that the ABCA4 intron regions containing the binding sites of these constructs are amenable to binding to ABCA4 trans-splicing molecules to confer protein and RNA restoration. In the present examples, 10-20% protein expression was restored, with restoration being comparable between intron 22- and 23-binding trans-splicing molecules. Importantly, because ABCA4-related diseases (such as Stargardt Disease) are recessive, asymptomatic carriers of the disease likely express less-than normal ABCA4, and, without wishing to be bound by theory, partial protein restoration, as shown here, is likely to confer a meaningful clinical benefit.

Example 2. CEP290

Figure 22:
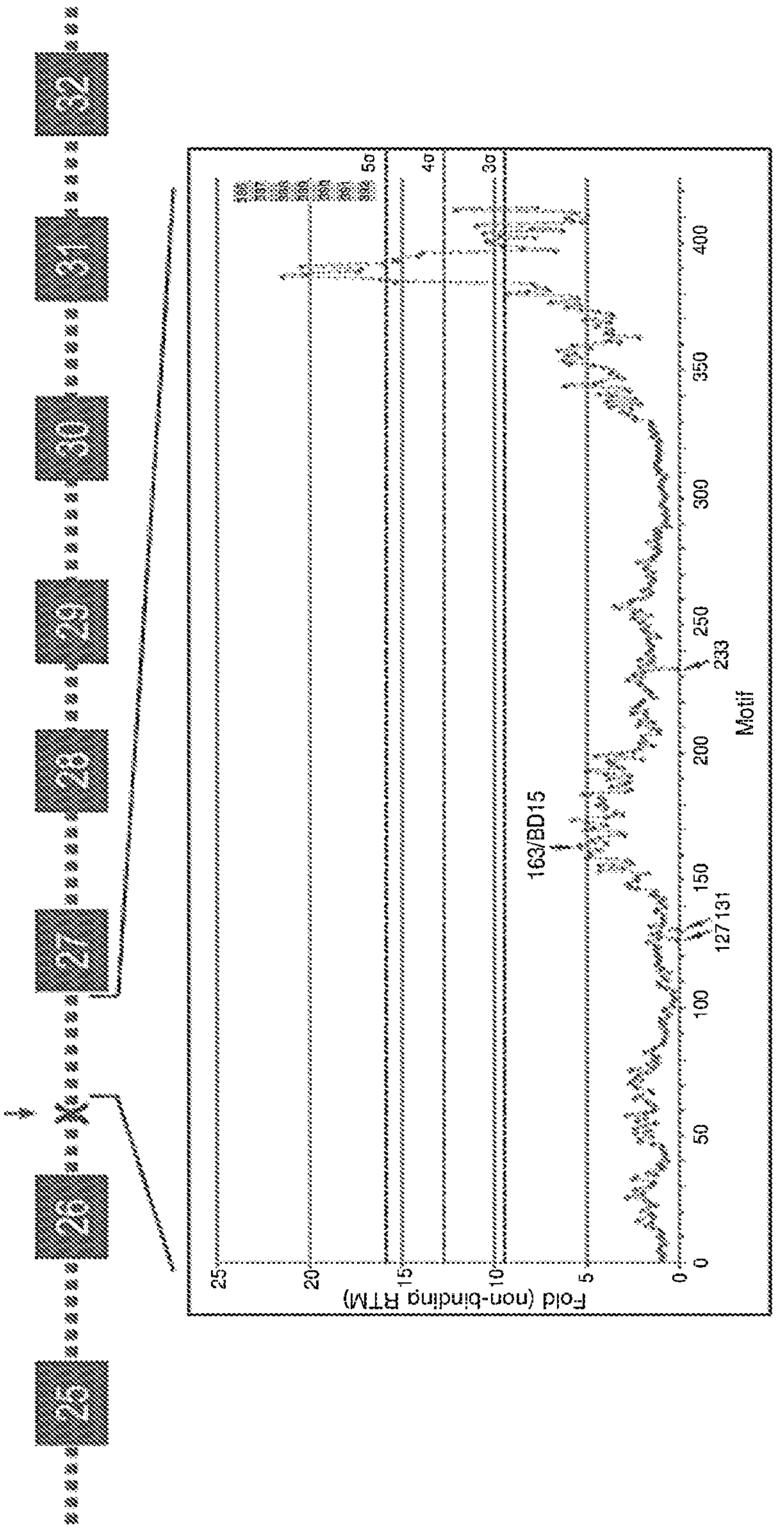
FIG. 22 is a graph showing trans-splicing efficiency (relative fold change) conferred by 150-mer binding domains across CEP290 intron 26 (SEQ ID NO: 85) in ten-nucleotide intervals. X axis labels indicate "motif number," of the number of each binding site starting from the 5' end of the intron (i.e., the first nucleotide of the intron sequence).

Screening a series of binding domains configured to bind CEP290 intron 26 (SEQ ID NO: 85) at sequential binding sites revealed a region at the 3' portion of CEP290 intron 26 that was preferentially amenable to trans-splicing of a 5' trans-splicing molecule—a region from nucleotides 4,980 to 5,838 of intron 26 (FIG. 22). Binding sites within the range of nucleotides from 5,348 to 5,838, from 5,348 to 5,700, from 5,400 to 5,600, from 5,460 to 5,560, or 5,500 were revealed as particularly highly efficient at mediating trans-splicing.

Figure 23:
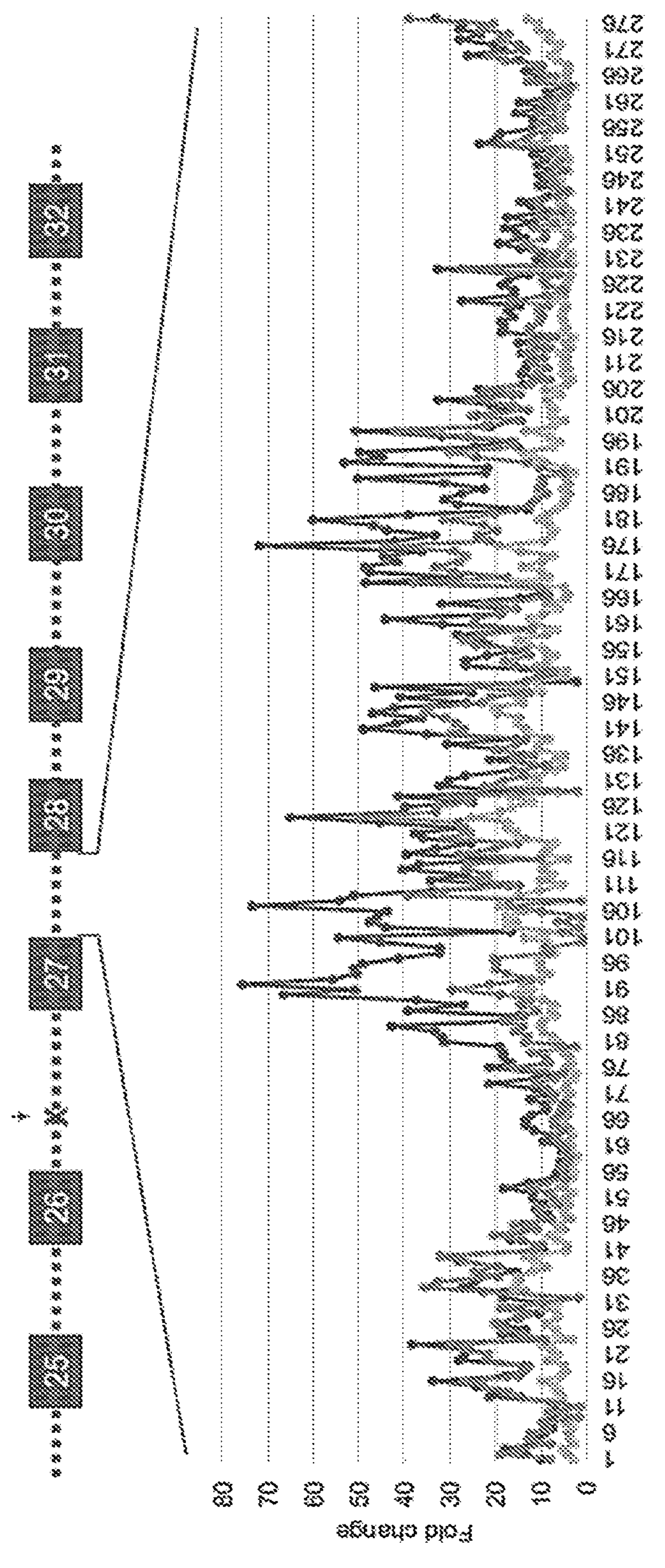
FIG. 23 is a graph showing trans-splicing efficiency (relative fold change) conferred by 150-mer binding domains across CEP290 intron 27 (SEQ ID NO: 86) in ten-nucleotide intervals. Each of the three lines represents an independent experiment. X axis labels indicate "motif number," of the number of each binding site starting from the 5' end of the intron (i.e., the first nucleotide of the intron sequence).

FIG. 23 shows results of a similar screen for CEP290 intron 27 (SEQ ID NO: 86). Binding sites having nucleotides 120 to 680, 710 to 2,200, 2,670 to 2,910 were identified as preferentially suitable for trans-splicing of a 5' trans-splicing molecule. In particular, binding domains targeted to binding sites within the ranges of nucleotides 790 to 2,100, nucleotides 1,020 to 1,630, or nucleotides 1,670 to 2,000 were highly efficient at trans-splicing.

Figure 24:
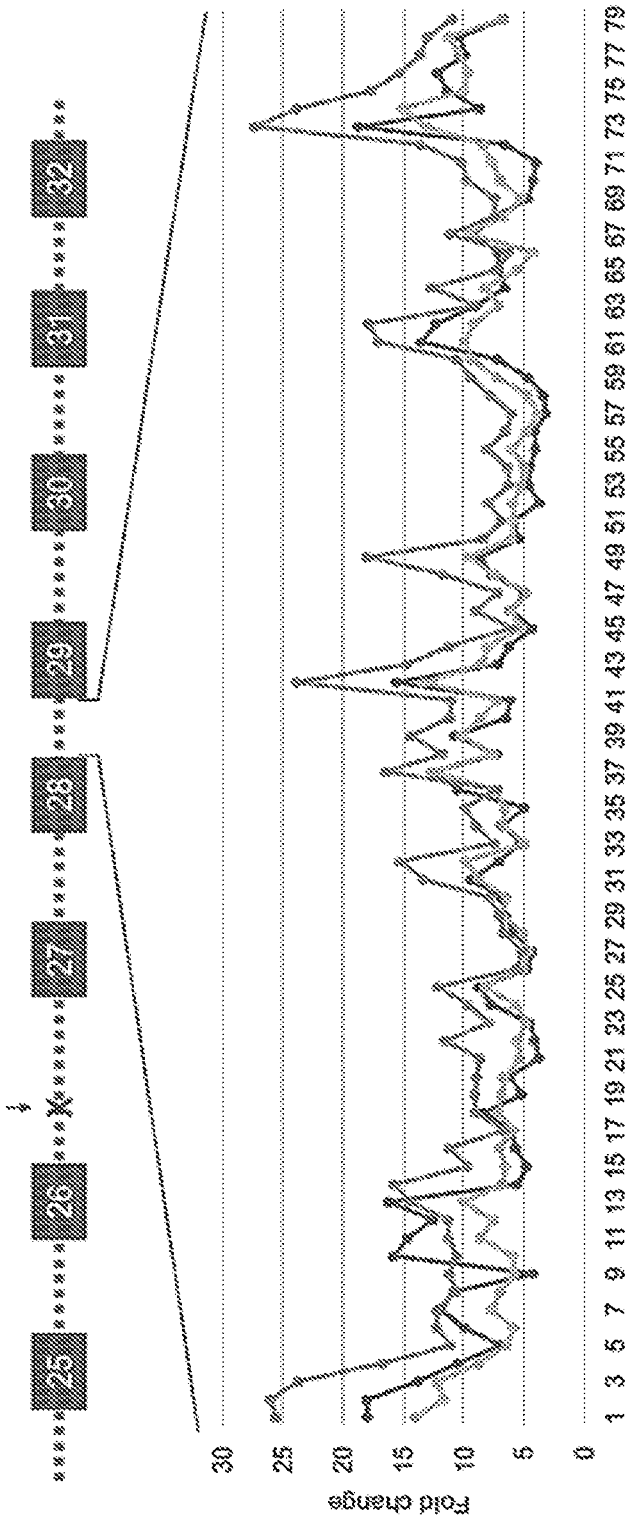
FIG. 24 is a graph showing trans-splicing efficiency (relative fold change) conferred by 150-mer binding domains across CEP290 intron 28 (SEQ ID NO: 87) in ten-nucleotide intervals. Each of the three lines represents an independent experiment. X axis labels indicate "motif number," of the number of each binding site starting from the 5' end of the intron (i.e., the first nucleotide of the intron sequence).

At intron 27 (SEQ ID NO: 87), binding sites within the ranges of nucleotides 1 to 390 (e.g., nucleotides 1 to 200), nucleotides 410 to 560, or nucleotides 720 to 937 were identified as having relatively high efficiency of trans-splicing (FIG. 24).

Figure 25:
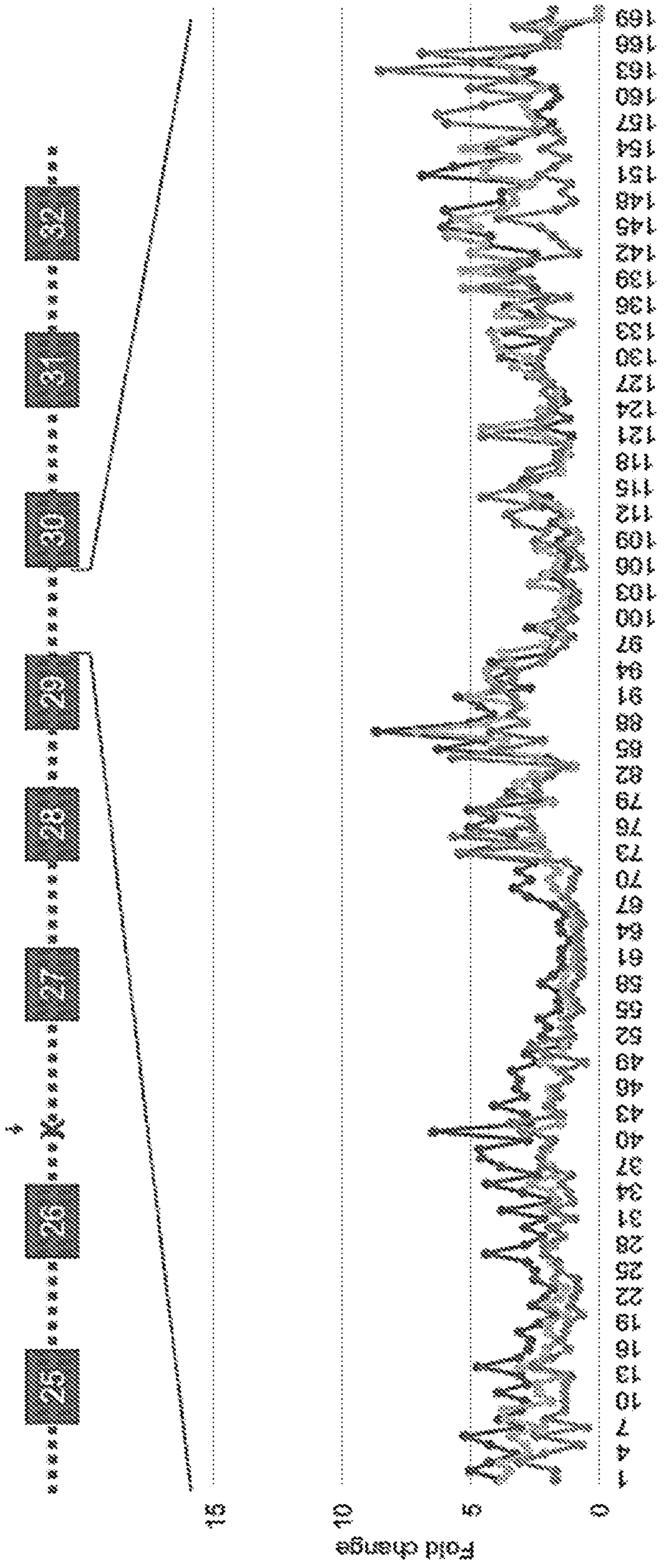
FIG. 25 is a graph showing trans-splicing efficiency (relative fold change) conferred by 150-mer binding domains across CEP290 intron 29 (SEQ ID NO: 88) in ten-nucleotide intervals. Each of the three lines represents an independent experiment. X axis labels indicate "motif number," of the number of each binding site starting from the 5' end of the intron (i.e., the first nucleotide of the intron sequence).

Intron 28 (SEQ ID NO: 88) was similarly characterized and shown to possess relatively efficient binding sites within nucleotides 1 to 600, nucleotides 720 to 940, or nucleotides 1,370 to 1,790 (FIG. 25).

Figure 26:
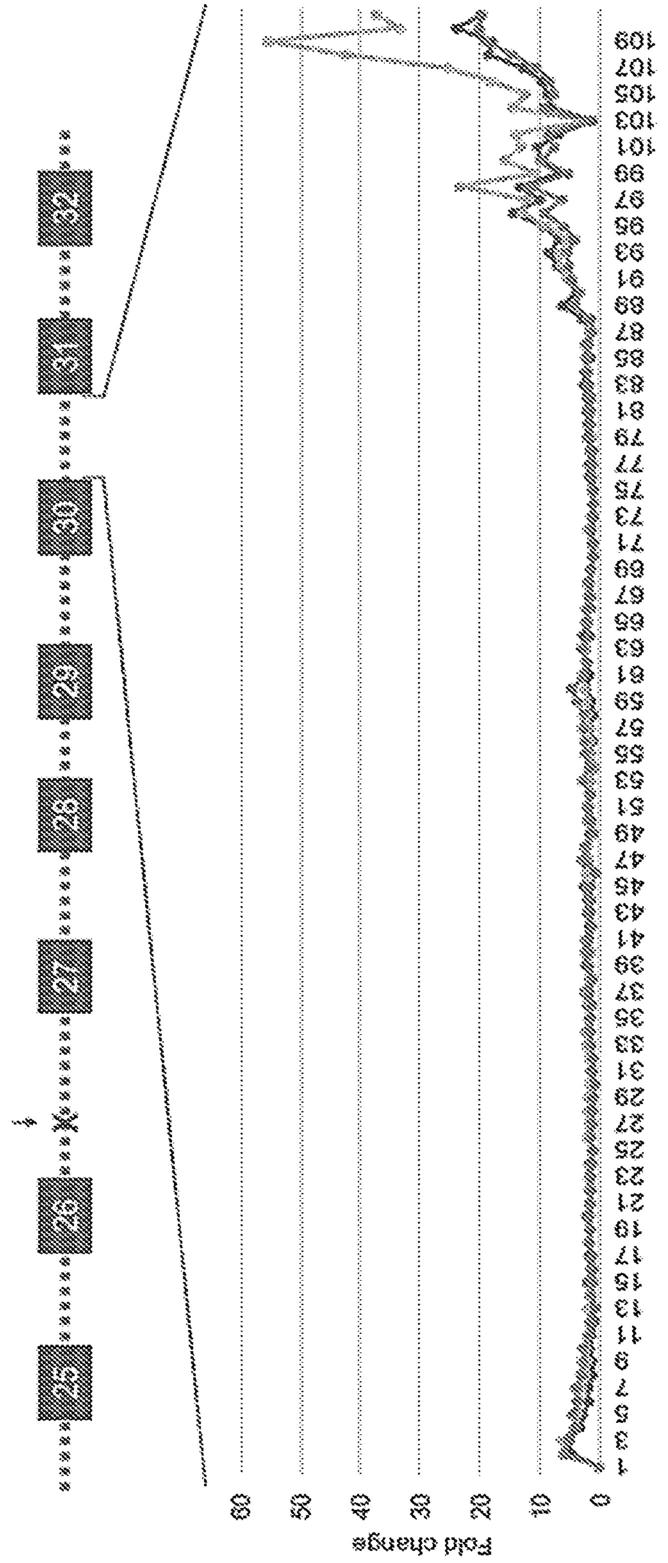
FIG. 26 is a graph showing trans-splicing efficiency (relative fold change) conferred by 150-mer binding domains across CEP290 intron 30 (SEQ ID NO: 89) in ten-nucleotide intervals. Each of the three lines represents an independent experiment. X axis labels indicate "motif number," of the number of each binding site starting from the 5' end of the intron (i.e., the first nucleotide of the intron sequence).

At intron 29 (SEQ ID NO: 89), the 3' portion of the intron was significantly more efficient at mediating 5' trans-splicing relative to the remainder of the intron (FIG. 26). In particular, binding domains targeting binding sites within the range of nucleotides 95 to 1,240, e.g., nucleotides 1,060 to 1,240, exhibited the greatest trans-splicing efficiency.

What is claimed is:

1. A nucleic acid trans-splicing molecule comprising, operatively linked in a 5'-to-3' direction:

(a) a binding domain, wherein the binding domain comprises a sequence ranging from 50-300 nucleotides in length and is configured to bind ABCA4 intron 22 at a binding site within nucleotides 60 to 570, 600 to 800, or 900 to 1,350 of SEQ ID NO: 28;

(b) a splicing domain configured to mediate trans-splicing; and (c) a coding domain comprising functional ABCA4 exons 23-50;

wherein the nucleic acid trans-splicing molecule is configured to trans-splice the coding domain to endogenous ABCA4 exon 22, thereby replacing endogenous ABCA4 exons 23-50 with the functional ABCA4 exons 23-50.

2. The nucleic acid trans-splicing molecule of claim 1, wherein the binding site is within nucleotides 60 to 570 of SEQ ID NO: 28.

3. The nucleic acid trans-splicing molecule of claim 2, wherein the binding site is within nucleotides 70-250 of SEQ ID NO: 28.

4. The nucleic acid trans-splicing molecule of claim 1, wherein the binding site is within nucleotides 900 to 1,350 of SEQ ID NO: 28.

5. The nucleic acid trans-splicing molecule of claim 1, wherein the binding site comprises:

(a) six or more of nucleotides 60 to 570 of SEQ ID NO: 28;

(b) six or more of nucleotides 600 to 800 of SEQ ID NO: 28; or (c) six or more of nucleotides 900 to 1,350 of SEQ ID NO: 28.

6. The nucleic acid trans-splicing molecule of claim 5, wherein the binding domain comprises six or more consecutive nucleic acid residues that are complementary to the six or more nucleotides of the binding site.

7. The nucleic acid trans-splicing molecule of claim 1, wherein the binding domain comprises a sequence ranging from 50-75 nucleotides in length, 75-100 nucleotides in length, 125-150 nucleotides in length, 150-175 nucleotides in length, 175-200 nucleotides in length, 200-250 nucleotides in length, 100-200 nucleotides in length, or 150 nucleotides in length.

8. The nucleic acid trans-splicing molecule of claim 1, wherein the binding domain comprises at least 10, at least 12, at least 15, at least 20, at least 25, at least 30, at least 40, at least 50, at least 60, at least 70, at least 80, at least 90, at least 100, at least 120, at least 150, or at least 200 consecutive nucleotides that are complementary to the binding site.

9. The nucleic acid trans-splicing molecule of claim 1, wherein the binding domain is 80% to 100% complementary to the binding site.

10. The nucleic acid trans-splicing molecule of claim 1, wherein:

(i) the binding domain is 100-200 nucleotides in length;

(ii) the coding domain is a cDNA sequence;

(iii) the coding domain comprises a naturally-occurring sequence;

(iv) the coding domain comprises a codon-optimized sequence;

(v) an artificial intron comprises a spacer sequence;

(vi) the trans-splicing molecule is from 3,000 to 4,000 nucleotides in length;

(vii) the mutation in the ABCA4 gene is associated with Stargardt Disease; and/or (viii) the mutation is expressed in a photoreceptor cell.

11. A proviral plasmid comprising the nucleic acid trans-splicing molecule of claim 1.

12. An adeno-associated virus (AAV) comprising the nucleic acid trans-splicing molecule of claim 1.

13. The AAV of claim 12, wherein the AAV preferentially targets a photoreceptor cell.

14. The AAV of claim 12, wherein the AAV comprises an AAV5 capsid protein, an AAV8 capsid protein, an AAV8 (b) capsid protein, or an AAV9 capsid protein.

15. The AAV of claim 12, comprising an assembled capsid having packaged therein a vector genome comprising an AAV 5' ITR, the nucleic acid trans-splicing molecule under the operative control of regulatory sequences, and an AAV 3' ITR.

16. A pharmaceutical composition comprising the nucleic acid trans-splicing molecule of claim 1, or a proviral plasmid thereof, or an AAV plasmid thereof.

17. A method of correcting a mutation in an ABCA4 gene in a target cell of a subject, the method comprising administering to the subject the pharmaceutical composition of claim 16.

18. A method of correcting a mutation in any one or more of ABCA4 exons 23-50 in a subject in need thereof, the method comprising administering to the subject the pharmaceutical composition of claim 16.

19. The method of claim 17, wherein the subject has Stargardt Disease.

20. The method of claim 17, wherein the composition is administered by subretinal injection, intravitreal injection, or intravenous injection.

21. A method of treating a subject having a disorder associated with a mutation in ABCA4, the method comprising administering to the subject the pharmaceutical composition of claim 16.

* * * * *